(12) United States Patent
Baque et al.

(10) Patent No.: US 6,603,005 B2
(45) Date of Patent: Aug. 5, 2003

(54) HETEROCYCLYLALKYLPIPERIDINE DERIVATIVES, THEIR PREPARATION AND COMPOSITIONS CONTAINING THEM

(75) Inventors: Eric Baque, Gif sur Yvette (FR); Jean-Christophe Carry, Saint Maur des Fosses (FR); Youssef El-Ahmad, Creteil (FR); Michel Evers, La Queue en Brie (FR); Philippe Hubert, Maisons-Alfort (FR); Jean-Luc Malleron, Marcoussis (FR); Serge Mignani, Chatenay-Malabry (FR); Guy Pantel, La Queue en Brie (FR); Michel Tabart, La Norville (FR); Fabrice Viviani, Louvres (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/987,386

(22) Filed: Nov. 14, 2001

(65) Prior Publication Data
US 2002/0111492 A1 Aug. 15, 2002

Related U.S. Application Data

(60) Provisional application No. 60/225,145, filed on Dec. 14, 2000.

(30) Foreign Application Priority Data

Nov. 15, 2000 (FR) .............................. 00 14738

(51) Int. Cl.$^7$ .................... C07D 471/02; C07D 215/12; A61K 31/44; A61K 31/47
(52) U.S. Cl. ................ 546/176; 546/122; 546/123; 514/300; 514/314
(58) Field of Search ................ 514/314, 300; 546/176, 122, 123

(56) References Cited

FOREIGN PATENT DOCUMENTS

| WO | WO 99/37635 | 7/1999 |
|----|-------------|--------|
| WO | WO 00/43383 | 7/2000 |

*Primary Examiner*—D. Margaret Seaman
(74) *Attorney, Agent, or Firm*—Finnegan, Henderson, Farabow, Garrett & Dunner LLP

(57) ABSTRACT

Heterocyclylalkylpiperidine derivatives of general formula (I)

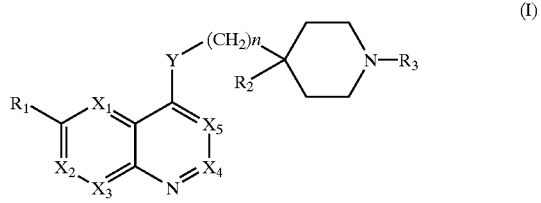

in their enantiomeric or diastereoisomeric forms or mixtures of these forms, and/or, where appropriate, in their syn or anti form or a mixture thereof, as well as any salt thereof.

20 Claims, No Drawings

HETEROCYCLYLALKYLPIPERIDINE DERIVATIVES, THEIR PREPARATION AND COMPOSITIONS CONTAINING THEM

The present application claims priority of U.S. Provisional Application No. 60/255,145, filed Dec. 14, 2000, and of French Patent Application No. FR 00 14738, filed Nov. 15, 2000, all of which are specifically incorporated by reference herein.

The present invention relates to heterocyclylalkyl-piperidine derivatives of general formula:

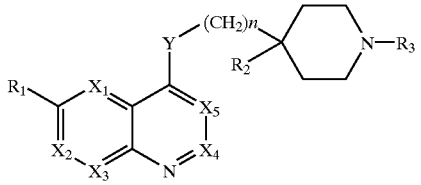

(I)

which are active as antimicrobial agents. The invention also relates to their preparation and to compositions containing them.

Patent applications WO 99/37635 and WO 00/43383 disclose antimicrobial quinolylpropylpiperidine derivatives of general formula:

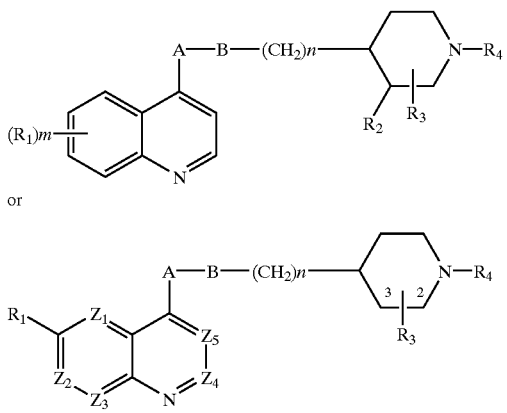

in which the radical $R_1$ is especially (C1-6) alkoxy, $R_2$ is hydrogen, $R_3$ is in position -2 or -3 and represents (C1-6) alkyl which may optionally be substituted with from 1 to 3 substituents chosen from thiol, halogen, alkylthio, trifluoromethyl, carboxyl, alkyloxycarbonyl, alkylcarbonyl, alkenyloxycarbonyl, alkenylcarbonyl, hydroxyl optionally substituted with alkyl, etc., $R_4$ is a group —$CH_2$—$R_5$ for which $R_5$ is selected from alkyl, hydroxyalkyl, alkenyl, alkynyl, tetrahydrofuryl, optionally substituted phenylalkyl, optionally substituted phenylalkenyl, optionally substituted heteroarylalkyl, optionally substituted heteroaryl, etc., n is 0 to 2, m is 1 or 2 and A and B are especially oxygen, sulfur, sulfinyl, sulfonyl, $NR_{11}$, $CR_6R_7$ for which $R_6$ and $R_7$ represent H, thiol, alkylthio, halo, trifluoromethyl, alkenyl, alkenylcarbonyl, hydroxyl, amino, and $Z_1$ to $Z_5$ are N or $CR_{1a}$, etc.

These products show antimicrobial activity. However, no derivative disubstituted in position -4 of the piperidine had been synthesized hitherto and consequently no biological activity had been discovered for such products either.

Since slight modifications to the structures already known can result in large variations in activity, it was not obvious that derivatives disubstituted in position -4 of the piperidine would also have antibacterial activity.

European patent application EP 30044 discloses quinoline derivatives which are useful as cardiovascular agents, corresponding to the general formula:

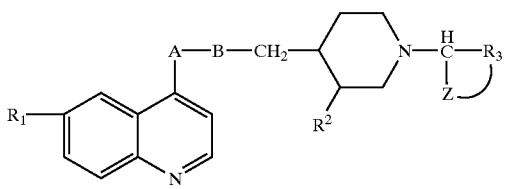

in which $R_1$ is especially alkyloxy, A-B is —$CH_2$—$CH_2$—, —CHOH—$CH_2$—, —$CH_2$—CHOH—, —$CH_2$—CO— or —CO—$CH_2$—, $R_1$ is H, OH or alkyloxy, $R_2$ is ethyl or vinyl, $R_3$ is especially alkyl, hydroxyalkyl, cycloalkyl, hydroxyl, alkenyl, alkynyl, tetrahydrofuryl, phenylalkyl, optionally substituted diphenylalkyl, optionally substituted phenylalkenyl, optionally substituted benzoyl or benzoylalkyl, optionally substituted heteroaryl or heteroarylalkyl, and Z is H or alkyl or forms with $R_3$ a cycloalkyl radical.

It has now been found, and this forms the subject of the present invention, that the products of general formula (I) for which:

$X_1$, $X_2$, $X_3$, $X_4$ and $X_5$ represent, respectively, >C—$R'_1$ to >C—$R'_5$, or alternatively not more than one of them represents a nitrogen atom, $R_1$, $R'_1$, $R'_2$, $R'_3$, $R'_4$ and $R'_5$ are identical or different and represent a hydrogen or halogen atom or an alkyl, cycloalkyl, phenyl, phenylthio, mono- or bicyclic aromatic heterocyclyl or heterocyclylthio, hydroxyl, alkyloxy, trifluoromethoxy, alkylthio, trifluoromethylthio, cycloalkyloxy, cycloalkylthio, cyano, carboxyl, alkyloxycarbonyl, cycloalkyloxycarbonyl, —NRaRb or —CONRaRb radical (for which Ra and Rb can represent hydrogen, alkyl, cycloalkyl, phenyl, mono- or bicyclic aromatic heterocyclyl or Ra and Rb form, together with the nitrogen atom to which they are attached, a 5- or 6-membered heterocycle which can optionally contain another heteroatom chosen from O, S, and N and, where appropriate, bearing an alkyl, phenyl or mono- or bicyclic aromatic heterocyclyl substituent on the nitrogen atom or, where appropriate, the sulfur atom of which is oxidized in the form of sulfinyl or sulfonyl), or represent a methylene radical substituted with fluoro, hydroxyl, alkyloxy, alkylthio, cycloalkyloxy, cycloalkylthio, phenyl, mono- or bicyclic aromatic heterocyclyl, carboxyl, alkyloxycarbonyl, cycloalkyloxycarbonyl, —NRaRb or —CONRaRb for which Ra and Rb are defined as above, or represent phenoxy, heterocyclyloxy, benzyloxy, heterocyclylmethyloxy, or alternatively $R_1$ can also represent difluoromethoxy, or a radical of structure —$C_mF_{2m+1}$, —$SC_mF_{2m+1}$ or —$OC_mF_{2m+1}$ for which m is an integer from 1 to 6, or alternatively $R'_5$ can also represent trifluoroacetyl, $R_2$ represents carboxyl, alkyloxycarbonyl, cycloalkyloxycarbonyl, cyano, —CONRaRb (for which Ra and Rb represent, respectively, hydrogen, alkyl, cycloalkyl, phenyl, mono- or bicyclic aromatic heterocyclyl, or Ra or Rb represents hydroxyl, alkyloxy, cycloalkyloxy, or Ra and Rb form, together with the nitrogen atom to which they are attached, a 5- or 6-membered heterocycle which can optionally contain another heteroatom chosen from O, S and N and, where appropriate, bearing an alkyl, phenyl or mono- or bicyclic aromatic heterocyclyl substituent on the nitrogen atom or, where appropriate, the sulfur atom of which is oxidized in the form of sulfinyl or sulfonyl), or $R_2$ represents hydroxymethyl, alkyl containing 1 or 2 carbon atoms substituted with carboxyl, alkyloxycarbonyl, cycloalkyloxycarbonyl, cyano or —CONRaRb for which Ra and Rb are defined as above, or $R_2$ represents a radical of structure —$CF_2$—Rc, —$C(CH_3)_2$—Rc, —CO—Rc, —CHOH—Rc, —C(cycloalkyl)-Rc, or —CH═CH—Rc for which Rc is carboxyl, alkyloxycarbonyl, cycloalkyloxycarbonyl, or —CONRaRb for which Ra and Rb are defined as above, $R_3$ represents a phenyl, mono- or bicyclic aromatic heterocyclyl or alk-$R°_3$ radical for which alk is an alkyl radical and $R°_3$ represents hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)$_2$, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)$_2$, phenylalkyloxy, phenylalkylthio, phenylalkylsulfinyl, phenylalkylsulfonyl, phenylalkylamino, N-alkyl-N-phenylaminoalkyl, N-cycloalkyl-N-phenylalkylamino, benzoyl, mono- or bicyclic aromatic heterocyclyl, heterocyclyloxy, heterocyclylthio, heterocyclylsulfinyl, heterocyclylsulfonyl, heterocyclylamino, N-alkyl-N-heterocyclylamino, N-cycloalkyl-N-heterocyclylamino, heterocyclylcarbonyl, heterocyclylalkyloxy, heterocyclylalkylthio, heterocyclylalkylsulfinyl, heterocyclylalkylsulfonyl, heterocyclylalkylamino, N-alkyl-N-heterocyclylaminoalkyl, N-cycloalkyl-N-heterocyclylaminoalkyl, (the heterocyclyl portions mentioned above being mono- or bicyclic aromatic), carboxyl, alkyloxycarbonyl, —NRaRb or —CO—NRaRb for which Ra and Rb are defined as above in the definition of $R_2$, or alternatively $R°_3$ represents —CR'b═CR'c-R'a for which R'a represents phenyl, phenylalkyl, heterocyclyl or heterocyclylalkyl in which the heterocyclyl portion is mono- or bicyclic aromatic, phenoxyalkyl, phenylthioalkyl, phenylsulfinylalkyl, phenylsulfonylalkyl, phenylaminoalkyl, N-alkyl-N-phenylaminoalkyl, heterocyclyloxyalkyl, heterocyclylthioalkyl, heterocyclylsulfinylalkyl, heterocyclylsulfonylalkyl, heterocyclylaminoalkyl, N-alkyl-N-heterocyclylaminoalkyl, heterocyclylthio, heterocyclylsulfinyl, heterocyclylsulfonyl, (the heterocyclyl portions mentioned above being mono- or bicyclic aromatic), phenylthio, phenylsulfinyl, phenylsulfonyl, and for which R'b and R'c represent hydrogen, alkyl or cycloalkyl, or alternatively $R°_3$ represents a radical —C≡C—Rd for which Rd is alkyl, phenyl, phenylalkyl, phenoxyalkyl, phenylthioalkyl, N-alkyl-N-phenylaminoalkyl, mono- or bicyclic aromatic heterocyclyl, heterocyclylalkyl, heterocyclyloxyalkyl, heterocyclylthioalkyl, heterocyclylaminoalkyl, N-alkyl-N-heterocyclylaminoalkyl, (the heterocyclyl portions mentioned above being mono- or bicyclic aromatic), or alternatively $R°_3$ represents a —$CF_2$-phenyl or mono- or bicyclic aromatic —$CF_2$-heterocyclyl radical, Y represents a radical >CH—Re for which Re is hydrogen, fluoro, hydroxyl, alkyloxy, cycloalkyloxy, carboxyl, alkyloxycarbonyl, cycloalkyloxycarbonyl, —NRaRb or —CO—NRaRb for which Ra and Rb are defined as above for $R_2$ or one represents a hydrogen atom and the other represents an alkyloxycarbonyl, acyl, cycloalkylcarbonyl, benzoyl or heterocyclylcarbonyl radical in which the heterocyclyl portion is mono- or bicyclic aromatic, or alternatively Y represents a difluoromethylene, carbonyl, hydroxyiminomethylene, alkyloxyiminomethylene or cycloalkyloxyiminomethylene radical or a 1,1-cycloalkylene radical containing 3 to 6 carbon atoms; and n is an integer from 0 to 4;

it being understood that the phenyl, benzyl, benzoyl or heterocyclyl radicals or portions mentioned above may optionally be substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are defined as above, phenyl, hydroxyalkyl, alkylthioalkyl, alkylsulfinylalkyl and alkylsulfonylalkyl, in their enantiomeric or diastereoisomeric forms or mixtures of these forms, and/or, where appropriate, in their syn or anti form or a mixture thereof, as well as the salts thereof, are powerful antibacterial agents.

It is understood that the alkyl or acyl radicals and portions contain (except where especially mentioned) 1 to 10 carbon atoms in a straight or branched chain and that the cycloalkyl radicals contain 3 to 6 carbon atoms.

It is also understood that the radicals which represent or bear a halogen atom represent a halogen chosen from fluorine, chlorine, bromine and iodine, wherein fluorine is an embodiment of particular interest.

In the above general formula, when the radicals represent or bear a mono- or bicyclic aromatic heterocyclyl substituent, this substituent contains 5 to 10 chain members and may be chosen (in a nonlimiting manner) from thienyl, furyl, pyrrolyl, imidazolyl, thiazolyl, oxazolyl, thiadiazolyl, oxadiazolyl, tetrazolyl, pyridyl, pyridazinyl, pyrazinyl, pyrimidinyl, indolyl, benzothienyl, benzofuryl indazolyl, benzothiazolyl, naphthyridinyl, quinolyl, isoquinolyl, cinnolyl, quinazolyl, quinoxalyl, benzoxazolyl and benzimidazolyl which may optionally be substituted with the substituents listed above.

According to the invention, the products of general formula (I) may be obtained by coupling the chain $R_3$ with the heterocyclylalkylpiperidine derivative of general formula:

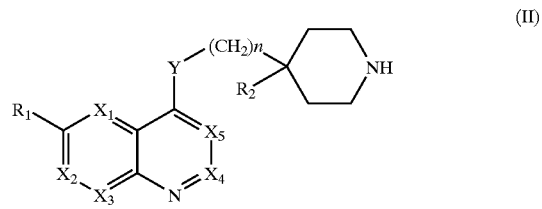

(II)

in which $X_1$, $X_2$, $X_3$, $X_4$, $X_5$, $R_1$, $R_2$, Y and n are defined as above, and $R_2$ is protected when it bears a carboxyl or amino radical, optionally followed by removal of the acid-protecting or amine-protecting radical, optional separation of the enantiomeric or diastereoisomeric forms and/or, where appropriate, of the syn or anti forms and optional conversion of the product obtained into a salt.

The coupling of the chain $R_3$ with the piperidine is advantageously carried out by the action of a derivative of general formula (IIa):

$R_3$—X (IIa)

in which $R_3$ is defined as above and X represents a halogen atom, a methylsulfonyl radical, a trifluoromethylsulfonyl radical or a p-toluenesulfonyl radical, working in anhydrous medium, which is optionally inert (for example nitrogen or argon) in an organic solvent such as an amide (for example dimethylformamide), a ketone (for example acetone) or a nitrile (for example acetonitrile) in the presence of a base such as an organonitrogen base (for example triethylamine) or a mineral base (alkaline carbonate, for example potassium carbonate) at a temperature of between 20° C. and the reflux temperature of the solvent. It is understood that the nitrogen atom of the piperidine in the derivative of general formula (II) is optionally protected according to the usual methods which do not affect the rest of the molecule or the reaction; for example, the protection is carried out by a protecting radical chosen from t-butoxycarbonyl and benzyloxycarbonyl.

In one embodiment of the invention, a derivative of general formula (IIa) for which X is a bromine or iodine atom is reacted.

When $R_3$ is a phenyl radical, it is also possible to act on the iodo or bromo derivative $R_3$-X in the presence of a palladium catalyst according to the method described in *J. Org. Chem.*, 6066 (1997) or *Tet. Lett.*, 6359 (1997). The palladium catalyst may be chosen from tris(dibenzylideneacetone)dipalladium, and palladium diacetate with a ligand such as 2,2'-bis(diphenylphosphino)-1,1'-binaphthyl or 2-(di-t-butylphosphino)biphenyl, for example, a base such as sodium tert-butoxide or cesium carbonate in a solvent such as tetrahydrofuran, tetraglyme or toluene, optionally in the presence of a crown ether such as 18-C-6 (1,4,7,10,13,16-hexaoxacyclooctadecane). The reaction is carried out at a temperature of between 20° C. and 110° C.

When $R_3$ represents a radical -alk-$R°_3$ for which alk is an alkyl radical and $R°_3$ represents —C≡C—Rd in which Rd is phenyl, phenylalkyl, heterocyclyl or mono- or bicyclic aromatic heterocyclylalkyl, optionally one may couple an alkynyl halide: HC≡C-alk-X for which alk is defined as above and X is a halogen atom, and then may substitute the chain with a phenyl, phenylalkyl, heterocyclyl or heterocyclylalkyl radical.

In this alternative, the addition of the alkynyl chain is carried out using an alkynyl halide HC≡C-alk-X for which X is optionally a bromine atom, under the conditions listed above for the coupling of the chain $R_3$, in the presence or absence of an alkali metal iodide such as, for example, potassium iodide or sodium iodide.

The substitution with a phenyl or heterocyclyl radical is carried out by the action of a halide derived from the cyclic radical to be substituted, in the presence of triethylamine, in anhydrous medium in a solvent such as an amide (for example dimethylformamide) or a nitrile (for example acetonitrile) and in the presence of a palladium salt such as, for example, tetrakis(triphenylphosphine)palladium and cuprous iodide, at a temperature of between 20° C. and the reflux temperature of the solvent.

The substitution with a phenylalkyl or heterocyclylalkyl radical is carried out by the action of the corresponding halide, in basic medium, for example in the presence of potassium hydride or sodium hydride or n-butyllithium, in a solvent such as an ether (tetrahydrofuran) or an amide (dimethylformamide) at a temperature of between −60° C. and the boiling point of the reaction medium.

It is understood that, if the alkyl radicals represented by $R_3$ bear carboxyl or amino substituents, these substituents are protected beforehand then freed after the reaction. The process is performed according to the usual methods which do not affect the rest of the molecule, in particular according to the methods described by T. W. Greene and P. G. M. Wuts, *Protective Groups in Organic Synthesis* ($2^{nd}$ edition), A. Wiley—Interscience Publication (1991), or by McOmie, *Protective Groups in Organic Chemistry*, Plenum Press (1973).

The protected carboxyl radical borne by $R_2$ may be chosen from readily hydrolyzable esters. Examples are the methyl, benzyl, and tert-butyl esters, or the phenyl propyl or allyl esters. The protection of the carboxyl radical is optionally carried out at the same time as the reaction.

Where appropriate, the amino radical is protected using the usual protecting radicals mentioned in the above references.

These protecting radicals are installed and removed according to the usual methods, mentioned above for $R_3$.

When $R_3$ represents a radical-alk-$R°_3$ for which alk is an alkyl radical and $R°_3$ represents a phenoxy, phenylthio, phenylamino, heterocyclyloxy, heterocyclylthio or heterocyclylamino radical in which the heterocyclyl portion is aromatic, optionally the chain may be constructed step by step, by first condensing a chain HO-alk-X, for which X is a halogen atom (optionally iodine), under the conditions described above for the reaction of the product of general formula (IIa), and then by converting the hydroxyalkyl chain into a haloalkyl, methanesulfonylalkyl or p-toluenesulfonylalkyl chain, and finally by reacting, in basic medium, an aromatic derivative of structure Ar—ZH for which AR is an aromatic phenyl or heterocyclyl radical and Z is a sulfur, oxygen or nitrogen atom.

The conversion of the hydroxylated chain into a haloalkyl or p-toluenesulfonyl chain is carried out according to the usual methods of halogenation or sulfonylation, especially by reacting a halogenating agent, for instance, thionyl chloride, halophosphorus derivatives: for example phosphorus trichloride or tribromide or a sulfonylating agent such as, for example, methanesulfonyl chloride, p-toluenesulfonyl chloride or trifluoromethanesulfonic anhydride. The reaction is carried out in an organic solvent, for instance a chlorinated solvent (for example dichloromethane or chloroform), at a temperature of between 0° C. and 60° C. In certain cases, it may be advantageous to work in the presence of a base, for instance pyridine or triethylamine.

The reaction of the aromatic derivative Ar—ZH is advantageously carried out as described above for the action of the derivative of general formula (IIa), in the presence of a base, for example such as a nitrogenous base, in an organic solvent such as an amide (for example dimethylformamide), a ketone (for example acetone) or a nitrile (for example acetonitrile), in the presence of a base such as a nitrogenous organic base (for example triethylamine) or a mineral base (alkali metal carbonate: for example potassium carbonate) at a temperature of between 20° C. and the reflux temperature of the reaction mixture. It may be advantageous to work in the presence of potassium iodide.

According to the invention, the heterocyclylalkylpiperidine derivatives of general formula (II) may be prepared according to the coupling method described below, and then where appropriate converted according to one of the methods ①  to ⑨ below, via a subsequent operation starting with one of the derivatives of general formula (II) already obtained, to prepare the derivatives corresponding to the various alternatives of Y and/or of $R_1$, $R'_1$, $R'_2$, $R'_3$, $R'_4$ or $R'_5$.

It is understood that when carboxylic acid radicals are present on the molecule, these radicals are protected beforehand and then freed after the reaction according to the usual methods which do not affect the rest of the molecule, especially according to the methods mentioned in the references cited above. It is also understood that, prior to the reactions which may interfere with the amine of the piperidine in the derivative of general formula (II), this amine is protected, and then freed after the reaction. The protection is carried out according to the usual methods, as specified above, especially via a t-butoxycarbonyl or benzyloxycarbonyl radical.

According to the invention, the preparation of the products of general formula (II) for which Re in Y is a hydrogen atom is carried out by coupling a heterocyclic derivative of general formula:

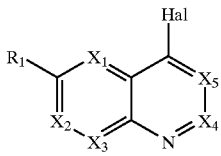

(III)

in which $R_1$, $X_1$, $X_2$, $X_3$, $X_4$ and $X_5$ are defined as above and Hal represents a halogen atom, with a piperidine derivative of general formula:

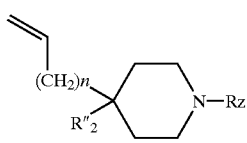

(IV)

in which Rz is a protecting radical and $R''_2$ is defined as above or represents a protected radical if $R_2$ represents or bears a carboxylic acid function, followed by removal of the protecting radicals and/or followed by conversion, via a subsequent operation, of the substituents of the bicycle of the heterocyclylalkylpiperidine derivative of general formula (II) thus obtained, to give the expected derivative bearing the radical $R_1$, $R'_1$, $R'_2$, $R'_3$, $R'_4$, or $R'_5$, and, where appropriate, removal of the protecting radical(s) still present on the molecule.

The radical Rz may be any protecting group for the nitrogen atom which is compatible with the reaction (for example t-butyloxycarbonyl or benzyloxycarbonyl). The protecting groups for the acid functions are chosen from the usual groups whose installation and removal do not affect the rest of the molecule, especially those mentioned in the references cited above.

The reaction is carried out by the successive action of an organoborane (for example 9-borabicyclo-[3.3.1]nonane) in a solvent such as an ether (for example tetrahydrofuran or dioxane) at a temperature of between −20° C. and 20° C., and then of the bicyclic derivative of general formula (III) wherein Hal optionally represents a bromine or iodine atom or a chlorine atom, by analogy with the methods described by Suzuki et al., *Pure and Appl. Chem.*, 57, 1749 (1985). The reaction is generally carried out in the presence of a palladium salt (for example diphenylphosphinoferrocene-palladium chloride) and of a base such as potassium phosphate, at a temperature of between 20° C. and the reflux temperature of the solvent.

① The heterocyclylalkylpiperidines of general formula (II) for which Re in Y represents a hydroxyl radical may be prepared by oxidation in basic medium of the corresponding heterocyclylalkylpiperidine derivative of general formula (II) for which Re in Y is a hydrogen atom. The oxidation is carried out by the action of oxygen, optionally in an inert solvent such as dimethyl sulfoxide in the presence of tert-butanol and of a base such as potassium tert-butoxide or sodium tert-butoxide at a temperature of between 0° C. and 100° C.

The heterocyclylalkylpiperidine derivative for which Re in Y is a fluorine atom is prepared by fluorination starting with a derivative for which Re is hydroxyl. The reaction is carried out in the presence of a sulfur fluoride [for example in the presence of an aminosulfur trifluoride (diethylaminosulfur trifluoride (*Tetrahedron*, 44, 2875 (1988), bis(2-methoxyethyl)aminosulfur trifluoride (Deoxofluor®), or morpholinosulfur trifluoride, for example) or alternatively in the presence of sulfur tetrafluoride (*J. Org. Chem.*, 40, 3808 (1975); alternatively, the fluorination reaction can also be carried out using a fluorinating agent such as hexafluoropropyldiethylamine (JP 2 039 546) or N-(2-chloro-1,1,2-trifluoroethyl)diethylamine. The process is performed in an organic solvent such as a chlorinated solvent (for example dichloromethane, dichloroethane or chloroform), or in an ether (for example tetrahydrofuran or dioxane), at a temperature of between −78° C. and 40° C., or optionally between 0° C. and 30° C. It is advantageous to work in inert medium (especially argon or nitrogen).

The heterocyclylalkylpiperidine derivative of general formula (II) for which Re in Y is an alkyloxy or cycloalkyloxy radical is prepared by the action of an alkyl or cycloalkyl halide on the corresponding derivative of general formula (II) for which Re is hydroxyl. The reaction is generally carried out using the bromide or chloride, in an inert solvent such as N,N-dimethylformamide or dimethyl sulfoxide, in the presence of an acid acceptor such as a trialkylamine (for example triethylamine) or an alkali metal hydride (for example sodium hydride), at a temperature of between 20° C. and 100° C.

The heterocyclylalkylpiperidine derivative of general formula (II) for which Y is a carbonyl radical may be prepared by oxidation of the corresponding derivative of general formula (II) for which Re in Y is a hydroxyl radical. This oxidation is carried out, for example, using potassium permanganate optionally in a solution of sodium hydroxide (for example 3N sodium hydroxide), at a temperature of between −20° C. and 20° C., or alternatively by the action of oxalyl chloride in the presence of dimethyl sulfoxide, followed by the addition of an amine such as triethylamine, in an inert solvent such as dichloromethane or dimethyl sulfoxide, at a temperature of between −60° C. and 20° C., by analogy with the method described by D. Swern et al., *J. Org. Chem.*, 44, 4148 (1979).

The heterocyclylalkylpiperidine derivative of general formula (II) for which Y is a difluoromethylene radical may be prepared by dihalogenation of the product of general formula (II) for which Y is carbonyl, under conditions analogous to those of the fluorination described above.

The heterocyclylalkylpiperidine derivative of general formula (II) for which Y is a hydroxyiminomethylene radical may be prepared by the action of hydroxylamine on a derivative of general formula (II) for which Y is a carbonyl radical. The reaction is generally carried out in an inert solvent such as an alcohol (methanol or ethanol) and optionally in the presence of sodium hydroxide (for example 1N sodium hydroxide), at a temperature of between 0° C. and the boiling point of the reaction mixture.

The heterocyclylalkylpiperidine derivative of general formula (II) for which Y is an alkyloxyiminomethylene or cycloalkyloxyiminomethylene radical may be prepared by the action of an alkyl or cycloalkyl halide on the corresponding derivative of general formula (II) for which Y is hydroxyiminomethylene. The reaction is generally carried out in an inert solvent such as N,N-dimethylformamide or dimethyl sulfoxide, in the presence of an acid acceptor such as a trialkylamine (for example triethylamine) or an alkali metal hydride (for example sodium hydride), at a temperature of between 20° C. and 100° C. A bromide is one example of interest in the present invention.

The heterocyclylalkylpiperidine derivative of general formula (II) for which Re in Y is a radical —NRaRb may be prepared from the corresponding tosyloxy derivative by the action of an amine HNRaRb (or, where appropriate, of ammonia when Re is —NH$_2$) in an inert solvent such as N,N-dimethylformamide or dimethyl sulfoxide, at a temperature of between 20° C. and the boiling point of the reaction mixture. When ammonia is reacted, the process is optionally performed under pressure (2 to 20 atmospheres) at a temperature of between 20° C. and 100° C. When the process is performed using an amine HNRaRb, the reaction is optionally carried out in the presence of a base such as a trialkylamine (for example triethylamine), pyridine or an alkali metal hydride (for example sodium hydride).

The derivative for which Re in Y is tosyloxy is obtained from the product of general formula (II) for which Re in Y is hydroxyl, by the action of tosyl chloride in pyridine, at a temperature of between −10° C. and 20° C.

The heterocyclylalkylpiperidine derivative of general formula (II) for which Re in Y is a carboxyl radical may be prepared by the action of an alkaline cyanide on the corresponding tosyloxy derivative, in an organic solvent such as dimethylformamide or dimethyl sulfoxide or in aqueous-organic medium, for example a water-alcohol mixture, at a temperature of between 0° C. and the boiling point of the reaction mixture, followed by hydrolysis of the nitrile obtained by the action of a strong acid such as hydrochloric acid, and optionally of a lower aliphatic alcohol, at a temperature of between 0° C. and the boiling point of the reaction mixture. Sodium cyanide or potassium cyanide are both options according to the present invention.

The heterocyclylalkylpiperidine derivative of general formula (II) for which Re in Y is an alkyloxycarbonyl or cycloalkyloxycarbonyl or —CO—NRaRb radical may be prepared by the action, respectively, of the alcohol or of the corresponding amine on the derivative of general formula (II) for which Re in Y is a carboxyl radical. The reaction is carried out in the presence of a coupling agent such as a carbodiimide (for example N,N'-dicyclohexylcarbodiimide) or N,N'-carbonyldiimidazole, in an inert solvent such as an ether (for example tetrahydrofuran or dioxane), an amide (N,N-dimethylformamide), a chlorinated solvent (for example methylene chloride, 1,2-dichloroethane or chloroform) or dimethyl sulfoxide, at a temperature of between 0° C. and the reflux temperature of the reaction mixture.

② The heterocyclylalkylpiperidine derivative of general formula (II) for which Y is a 1,1-cycloalkylene radical may be prepared by the action, in basic medium, of a product of structure Hal-Alk-Hal for which Alk is an alkylene radical corresponding to the expected cycloalkylene, on a heterocyclylalkylpiperidine derivative for which Re in Y is a hydrogen atom. The reaction is generally carried out in an inert solvent such as N,N-dimethylformamide or dimethyl sulfoxide, in the presence of an acid acceptor such as an alkali metal hydride (for example sodium hydride), at a temperature of between 20° C. and 100° C.

③ The heterocyclylalkylpiperidine derivatives of general formula (II) for which one from among $R_1$, $R'_1$, $R'_2$, $R'_3$, $R'_4$ and $R'_5$ represents an alkyl, cycloalkyl, phenyl, heterocyclyl, benzyl or heterocyclylmethyl radical may be prepared by the action of a boron derivative of structure $R'_iB(OH)_2$ ($R'i$ meaning one of the substituents $R_1$, $R'_1$, $R'_2$, $R'_3$, $R'_4$ or $R'_5$) or of 9-alkyl-(or 9-cycloalkyl)-9-borabicyclo[3.3.1]nonane structure on a derivative of general formula (II) for which the substituent $R'_i$ is a bromine, iodine or chlorine atom, by analogy with the methods described by F. Diederich and P. J. Stang, *Metal Catalysed Cross-coupling Reactions*, Wiley-VCH, (1997) in the presence of a palladium salt (for example tetrakis(triphenylphosphine) or diphenylphosphinoferrocenepalladium chloride) and of a base such as potassium phosphate, in an inert solvent such as an amide (for example N,N-dimethylformamide), an ether (for example tetrahydrofuran) or a nitrile (for example acetonitrile), at a temperature of between 20° C. and the reflux temperature of the reaction mixture.

④ The heterocyclylalkylpiperidine derivatives of general formula (II) for which one from among $R_1$, $R'_1$, $R'_2$, $R'_3$, $R'_4$ and $R'_5$ represents a radical —NRaRb may be prepared by the action of an amine HNRaRb on a derivative of general formula (II) for which the substituent $R'_i$ ($R'i$ meaning one of the substituents $R_1$ $R'_1$, $R'_2$, $R'_3$, $R'_4$ or $R'_5$) is a bromine, iodine or chlorine atom, by analogy with the methods described in *J. Org. Chem.*, 6066 (1997) and *Tetrahedron Lett.*, 6359 (1997) in the presence of a palladium catalyst, under conditions similar to those described for the reaction of the halo derivative of formula (III) with the derivative of general formula (II).

When Ra and Rb represent hydrogen atoms, the amino derivative obtained may be converted into a fluoro derivative by the action of an alkaline nitrite (for example sodium nitrite) in acidic medium (tetrafluoroboric acid or hexafluorophosphoric acid) in water at a temperature of between −10° C. and 20° C., to prepare a diazonium tetrafluoroborate or hexafluorophosphate, followed by pyrolysis of the product obtained according to the Baz-Schieman reaction, *Org. Synth., Coll* 5, 133 (1973).

⑤ The heterocyclylalkylpiperidine derivatives of general formula (II) for which $R_1$, $R'_1$, $R'_2$, $R'_3$, $R'_4$ or $R'_5$ represents an alkyloxy, alkylthio, cycloalkyloxy, cycloalkylthio, benzyloxy or heterocyclylmethyloxy radical, may be prepared by the action of the alcohol or of the corresponding thiol on the heterocyclylalkylpiperidine derivative for which one of the radicals $R'_i$ is a bromine, iodine or chlorine atom. The reaction is generally carried out in an inert solvent such as an ether (for example tetrahydrofuran or dioxane), an amide (for example N,N-dimethylformamide) or dimethyl sulfoxide, in the presence of an acid acceptor such as a trialkylamine (for example triethylamine), an alkali metal hydride (for example sodium hydride), methyllithium or n-butyllithium, at a temperature of between 0° C. and the reflux temperature of the reaction mixture.

The heterocyclylalkylpiperidine derivatives of general formula (II) for which $R_1$, $R'_1$, $R'_2$, $R'_3$, $R'_4$ or $R'_5$ represents a hydroxyl radical may be prepared from the corresponding derivative for which one of the radicals R'i is methoxy by the action of a strong acid such as hydrobromic acid, at a temperature of between 20° C. and the reflux temperature of the reaction mixture.

The heterocyclylalkylpiperidine derivatives of general formula (II) for which $R_1$, $R'_1$, $R'_2$, $R'_3$, $R'_4$ or $R'_5$ represents a trifluoromethoxy radical may be obtained by analogy with the method described by Sun W. Y. *Synlett.*, 11, 1279 (1997) to prepare a derivative for which $R'_i$ is an —O—CS—SCH$_3$ radical, starting with the corresponding hydroxyl derivative; this radical is converted into a trifluoromethyl radical by applying the methods described by Kuroboshi M. et al., *Tetrahedron Lett.*, 33(29), 4173 (1992) in the presence of 1,3-dibromo-5,5-dimethylhydantoin in an HF-pyridine complex at a temperature of between 0° C. and 20° C.

The heterocyclylalkylpiperidine derivatives of general formula (II) for which $R_1$, $R'_1$, $R'_2$, $R'_3$, $R'_4$ or $R'_5$ represents an alkyloxy, cycloalkyloxy, phenoxy, benzyloxy, heterocyclyloxy or heterocyclylmethyloxy radical may be obtained by the action of the corresponding halo derivative on the derivative of general formula (II) for which the R'i to be modified is hydroxyl. The process is optionally performed using the bromo derivative, in an inert solvent such as an ether (for example tetrahydrofuran or dioxane), an amide (for example N,N-dimethylformamide) or dimethyl sulfoxide, in the presence of an acid acceptor such as a trialkylamine (for example triethylamine), an alkali metal hydride (for example sodium hydride), methyllithium or N-butyllithium, optionally in the presence of a palladium salt (by analogy with the methods described in *J. Am. Chem. Soc.*, 4369 (1999); *Tetrahedron Lett.*, 8005 (1997); *Angew. Chem. Int. Ed. Engl.*, 2047 (1998)), at a temperature of between 0° C. and the reflux temperature of the reaction mixture.

⑥ The heterocyclylalkylpiperidine derivatives of general formula (II) for which $R_1$ represents a trifluoromethyl radical may be prepared by the action of a trifluoromethylating agent (especially a bromo derivative Br—$CF_3$ or an iodo derivative I—$CF_3$) on the heterocyclylalkylpiperidine derivative for which one of the radicals $R_1$ is a bromine, iodine or chlorine atom, in the presence of copper or a copper(I) salt such as CuI, in a solvent such as dimethylformamide, between 20° C. and 150° C., by analogy with *J. C. S. Chem. Commun.*, 1, 53 (1992) or *Chem. Commun.*, 18, 1389 (1993).

⑦ The heterocyclylalkylpiperidine derivatives of general formula (II) for which $R_1$, $R'_1$, $R'_2$, $R'_3$, $R'_4$ or $R'_5$ represents an alkylthio, cycloalkylthio, trifluoromethylthio, phenylthio or heterocyclylthio radical may be obtained by the action of the corresponding halo derivative on the heterocyclylalkylpiperidine derivative bearing a mercapto substituent. In one embodiment of the present invention, the process is performed using the bromo derivative, under the conditions described above for the action of a halo derivative on an alcohol, at a temperature of between 20° C. and the reflux temperature of the reaction mixture. In the case of the trifluoromethylthio radical, the process is performed by analogy with the method described in *Tet. Lett.*, 33(44), 6677 (1992).

The mercapto derivative of the heterocyclylalkylpiperidine of general formula (II) may be obtained from the heterocyclylalkylpiperidine derivative for which one of the radicals R'i is a bromine, iodine or chlorine atom (in one embodiment of interest, a bromine atom) by analogy with the methods described by Q. L. Zhou et al., *Tetrahedron*, 15, 4467 (1994); C. Bieniauz et al., *Tetrahedron Letters*, 34, 6, 939 (1993) and E. D. Amstuts, *J. Am. Chem. Soc.*, 68, 498 (1946). The reaction is carried out, for example, in the presence of $Na_3PO_3S$ or $Na_2S$ in an inert solvent such as an alcohol (for example methanol or ethanol), optionally in the presence of water, at a temperature of between 20° C. and the reflux temperature of the reaction mixture.

⑧ The heterocyclylalkylpiperidine derivatives of general formula (II) for which $R_1$, $R'_1$, $R'_2$, $R'_3$, $R'_4$ or $R'_5$ represents a cyano radical may be obtained from the corresponding derivative for which one of the radicals $R'_i$ is a halogen atom, optionally a bromine or iodine atom, by applying the methods described by Halley F. et al., *Synth. Comm.*, 27(7), 1199 (1997) and Tschaen D. M. et al., *J. Org. Chem.*, 60(14), 4324 (1995), in the presence of CuCN, or KCN and optionally in the presence of a catalyst.

The heterocyclylalkylpiperidine derivatives of general formula (II) for which $R_1$, $R'_1$, $R'_2$, $R'_3$, $R'_4$ or $R'_5$ represents a carboxyl, alkyloxycarbonyl, cycloalkyloxycarbonyl or —CO—$NRaRb$ radical may be prepared from the cyano derivative, according to the usual methods for conversion into an acid, an ester and an amide, which do not affect the rest of the molecule, and some of the implementation conditions of which have been recalled above. In particular, in the presence of a carbodiimide (N,N'-dicyclohexylcarbodiimide) or N,N'-carbonyldiimidazole, in an ether (tetrahydrofuran or dioxane), an amide (N,N-dimethylformamide) or a chlorinated solvent (methylene chloride, 1,2-dichloroethane or chloroform), at a temperature of between 0° C. and the reflux temperature of the reaction mixture.

⑨ The heterocyclylalkylpiperidine derivatives of general formula (II) for which $R_1$, $R'_1$, $R'_2$, $R'_3$, $R'_4$ or $R'_5$ represents a hydroxymethyl radical may be obtained by reducing a heterocyclylalkylpiperidine derivative of general formula (II) for which one of the radicals R'i represents a carboxyl radical, using a reducing agent such as, for example, lithium aluminum hydride or a borohydride, in an inert solvent such as an ether (for example tetrahydrofuran or dioxane) or a chlorinated solvent (for example methylene chloride, 1,2-dichloroethane or chloroform), at a temperature of between 0° C. and the reflux temperature of the reaction mixture.

The heterocyclylalkylpiperidine derivatives of general formula (II) for which $R_1$, $R'_1$, $R'_2$, $R'_3$, $R'_4$ or $R'_5$ represents an alkyloxymethyl or cycloalkyloxymethyl radical may be obtained by the action of the corresponding halo derivative (optionally the bromo derivative) on the corresponding heterocyclyl-alkylpiperidine derivative for which the radical $R'_i$ represents a hydroxymethyl radical. The reaction is generally carried out in an inert solvent such as an ether (for example tetrahydrofuran or dioxane), an amide (for example N,N-dimethylformamide) or dimethyl sulfoxide, in the presence of an acid acceptor such as a trialkylamine (for example triethylamine) or an alkali metal hydride (for example sodium hydride), at a temperature of between 20° C. and 100° C.

The heterocyclylalkylpiperidine derivatives of general formula (II) for which $R_1$, $R'_1$, $R'_2$, $R'_3$, $R'_4$ or $R'_5$ represents a fluoromethyl radical may be obtained by the action of a fluorinating agent on the heterocyclylalkylpiperidine derivative for which the corresponding radical $R'_i$ represents a hydroxymethyl radical. The reaction may be carried out under the fluorinating conditions described above for the installation of a radical Re meaning fluorine.

The heterocyclylalkylpiperidine derivatives of general formula (II) for which $R_1$, $R'_1$, $R'_2$, $R'_3$, $R'_4$ or $R'_5$ represents an alkylthiomethyl or cycloalkylthiomethyl radical may be obtained by the action of the corresponding thiol on a heterocyclylalkylpiperidine derivative for which the radical $R'_i$ to be modified is halomethyl (wherein halogens according to one aspect of the invention are a bromine or a chlorine atom). The reaction is generally carried out in an inert solvent such as an ether (for example tetrahydrofuran or dioxane), an amide (for example N,N-dimethylformamide) or dimethyl sulfoxide, in the presence of an acid acceptor such as a trialkylamine (for example triethylamine) or an alkali metal hydride (for example sodium hydride), at a temperature of between 20° C. and the reflux temperature of the reaction mixture.

The heterocyclylalkylpiperidine derivatives bearing a halomethyl radical $R'_i$ are prepared from the corresponding derivative for which $R'_i$ is a hydroxymethyl radical by the action of a halogenating agent (halophosphorus derivative or thionyl chloride). The reaction is optionally carried out in an inert solvent such as dichloromethane, at a temperature of between 0° C. and 60° C., optionally in the presence of a base such as pyridine.

The heterocyclylalkylpiperidine derivatives of general formula (II) for which $R_1$, $R'_1$, $R'_2$, $R'_3$, $R'_4$, or $R'_5$ represents a radical —$CH_2$—NRaRb may be obtained by the action of an amine HNRaRb on a heterocyclylalkylpiperidine derivative for which the radical $R'_i$ to be modified is halomethyl (the halogen optionally being a bromine or chlorine atom). The reaction is carried out in an inert solvent such as an ether (for example tetrahydrofuran or dioxane), an amide (for example N,N-dimethylformamide) or dimethyl sulfoxide, in the presence of an acid acceptor such as a trialkylamine (for example triethylamine) or an alkali metal hydride (for example sodium hydride), at a temperature of between 20° C. and the reflux temperature of the reaction mixture. The halomethyl derivative is prepared as described above.

The heterocyclylalkylpiperidine derivatives of general formula (II) for which $R_1$, $R'_1$, $R'_2$, $R'_3$, $R'_4$, or $R'_5$ represents a carboxymethyl radical may be obtained by the action of an alkaline cyanide on a heterocyclylalkylpiperidine derivative for which the radical $R'_i$ to be modified is halomethyl (the halogen optionally being a bromine or chlorine atom), followed by hydrolysis of the nitrile. The reaction is carried out using sodium cyanide or potassium cyanide in an organic solvent such as dimethyl sulfoxide or dimethylformamide, or in a water-alcohol mixture, at a temperature of between 0° C. and the boiling point of the reaction mixture, followed by the action of a strong acid such as hydrochloric acid, optionally in the presence of a lower aliphatic alcohol, at a temperature of between 0° C. and the boiling point of the reaction mixture.

The heterocyclylalkylpiperidine derivatives of general formula (II) for which $R_1$, $R'_1$, $R'_2$, $R'_3$, $R'_4$, or $R'_5$ represents an alkyloxycarbonylmethyl, cycloalkyloxycarbonylmethyl or —$CH_2$—CO—NRaRb radical may be obtained from the corresponding acid according to the usual methods for converting an acid to an ester or amide which do not affect the rest of the molecule, especially in the presence of a coupling agent such as a carbodiimide as described above.

The heterocyclic derivatives of general formula (III) for which Hal is a bromine atom, $R_1$ is defined as above, $X_1$ to $X_4$ represent, respectively, >C—$R'_1$ to >C—$R'_4$ and $X_5$ represents >CH, may be prepared by brominating the corresponding 4-hydroxyquinolines using a brominating agent such as phosphorus oxitribromide or thionyl bromide without a solvent, at a temperature of between 20° C. and 115° C.

The 4-hydroxyquinolines may be prepared by decarboxylating the corresponding 3-carboxy-4-hydroxyquinolines, working in a solvent such as diphenyl ether at a temperature of between 100° C. and 260° C.

The 3-carboxy-4-hydroxyquinolines may be prepared by analogy with the method described in European patent application EP-A-0 379 412, starting with the desired aniline derivative.

The heterocyclic derivatives of general formula (III) for which Hal is a bromine atom, $R_1$ is defined as above, $X_1$ to $X_4$ represent, respectively, >C—$R'_1$ to >C—$R'_4$ and Xs represents >C—Cl, may be prepared by brominating the corresponding 3-chloro-4-hydroxyquinoline. The bromination is generally carried out with triphenylphosphine dibromide in acetonitrile at a temperature of between 20° C. and 85° C.

The 3-chloro-4-hydroxyquinolines may be prepared by chlorinating a 4-hydroxyquinoline. The chlorination is carried out, for example, using N-chlorosuccinimide in a solvent such as acetic acid, at a temperature of between 20° C. and 100° C.

The heterocyclic derivatives of general formula (III) for which Hal is a bromine atom, $R_1$ is defined as above, $X_1$ to $X_4$ represent, respectively, >C—$R'_1$ to >C—$R'_4$ and $X_5$ represents >C—$COCF_3$ may be prepared by analogy with the preparation of the derivatives for which $X_5$ represents >CH, by brominating the corresponding 4-hydroxy-3-fluoroacetylquinoline derivative. The reaction is carried out without a solvent, using a brominating agent such as phosphorus oxytribromide, at a temperature of between 20° C. and 115° C. The 4-hydroxy-3-trifluoroacetylquinoline may be prepared by analogy with the method described for the preparation of 3-carboxy-4-hydroxyquinoline.

The heterocyclic derivatives of general formula (III) for which Hal is an iodine atom, $R_1$ is a methoxy radical, $X_1$ to $X_4$ represent, respectively, >C—$R'_1$ to >C—$R'_4$ and $X_5$ represents >C—F, may be prepared by analogy with the studies of E. Arzel et al., *Tetrahedron*, 55, 12149–12156 (1999) starting with 3-fluoro-6-methoxyquinoline, by the successive action of a base and then iodine. For example, lithium diisopropylamide in a solvent such as an ether (tetrahydrofuran) at a temperature of between −80° C. and 20° C. is used.

The 3-fluoro-6-methoxyquinoline may be obtained by pyrolysis of 6-methoxyquinoline diazonium 3-tetrafluoroborate or 3-hexafluorophosphate according to the Balz-Schieman reaction, *Org. Synth., Coll* 5, 133 (1973), at a temperature of between 100° C. and 240° C. 6-Methoxyquinoline diazonium 3-tetrafluoroborate or 6-methoxyquinoline diazonium 3-hexafluorophosphate may be obtained from 3-amino-6-methoxyquinoline by the action of an alkaline nitrite (for example sodium nitrite) in acidic medium (tetrafluoroboric acid or hexafluorophosphoric acid) in a solvent such as water at a temperature of between −10° C. and +20° C., by analogy with the studies of A. Roe et al., *J. Am. Chem. Soc.*, 71, 1785–86 (1949) or by the action of an alkyl nitrite (such as, for example, isoamyl nitrite) and of the trifluoroborate/diethyl ether complex in a solvent such as an ether (for example tetrahydrofuran) at a temperature of between −10° C. and +10° C.

3-Amino-6-methoxyquinoline is prepared as described by N. Heindel, *J. Med. Chem.* 13, 760 (1970).

The heterocyclic derivatives of general formula (III) for which Hal is a bromine atom, $R_1$ is defined as above, $X_2$ to $X_4$ represent, respectively, >C—$R'_2$ to >C—$R'_4$ and $X_1$ represents a nitrogen atom or alternatively $X_1$, $X_3$, and $X_4$ represent, respectively, >C—$R'_1$, >C—$R'_3$, and >C—$R'_4$ and $X_2$ represents a nitrogen atom, and $X_5$ represents >CH or >C—Cl, may be prepared by analogy with the methods described above when $X_1$ to $X_4$ represent, respectively, >C—$R'_1$ to >C—$R'_4$ or according to the syntheses described by Adams J. T. et al., *J. Am. Chem. Soc.*, 68, 1317 (1946) for the 1,5-naphthyridines and S. Radl et al., *Collect. Czech. Chem. Commun.*, 56, 2420 (1991) for the 1,7-naphthyridines, starting with 3-aminopyridines.

The hydroxynaphthyridine required to carry out the reaction is also prepared by analogy with the methods described above for the hydroxyquinolines, but starting with 3-aminopyridine or its substituted derivatives. The 3-aminopyridine derivatives may be obtained by adaptation of the methods described in "The Chemistry of Heterocyclic Compounds", Vol. 14, *Pyridine and its Derivatives, Supplement Part III*, page 41. Ed. R. A. Abramovitch, Interscience Publication.

The heterocyclic derivatives of general formula (III) for which Hal is a bromine atom, $R_1$ is defined as above, $X_1$, $X_2$, and $X_4$ represent, respectively, >C—$R'_1$, >C—$R'_2$, and >C—$R'_4$, $X_3$ represents a nitrogen atom and $X_5$ represents >CH or >C—Cl, may be prepared by analogy with the methods described above when $X_1$ to $X_4$ represent respectively, >C—$R'_1$ to >C—$R'_4$ or according to the syntheses described by D. Heber et al., *Arzneim-Forsch*, 44, 809 (1994) starting with 2-aminopyridines or substituted derivatives thereof.

The 2-aminopyridines may be obtained by applying or adapting the methods described in "The Chemistry of Heterocyclic Compounds", Vol. 14, *Pyridine and its Derivatives, Supplement Part III*, page 41, Ed. R. A. Abramovitch, Interscience Publication.

The derivatives of general formula (III) for which Hal is a bromine atom, $R_1$ is defined as above and $X_5$ represents a nitrogen atom may be obtained from 2-amino-benzenamides as described in *J. Am. Chem. Soc.*, 69, 184 (1947). 2-Aminobenzenamide is cyclized in the presence of an alkyl orthoformate such as ethyl orthoformate in a solvent such as diethylene glycol at a temperature of between 105° C. and 120° C. to give 4-hydroxyquinazoline, which is brominated as described above. The 2-aminobenzenamide is obtained from the corresponding aniline by applying or adapting the methods described by V. Snieckus, *Chem. Rev.*, 90, 879 (1990) and *Pure Appl. Chem.*, 62, 2047 (1990).

The heterocyclic derivatives of general formula (III) for which Hal is a bromine atom, $R_1$ is defined as above and $X_4$ is a nitrogen atom may be obtained from 2-acetylaniline as described in *Synth. Commun.*, 19, 3087 (1989). The 4-hydroxycinnoline obtained is brominated under the conditions described above. The 2-acetylanilines are obtained from the corresponding aniline by applying the methods cited above for 2-aminobenzenamide.

The piperidine derivatives of general formula (IV) for which n=0 and $R''_2$ represents carboxyl may be prepared from the corresponding piperidine derivative of general formula:

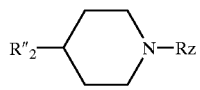

(V)

in which $R''_2$ defined as above is protected beforehand and Rz is defined as above, by analogy with the studies of Koppel, *J. Chem. Soc. Chem. Commun.*, 473 (1975) by reaction between the piperidine derivative and vinyl phenyl sulfoxide in the presence of a base (for example sodium hydride, lithium diisopropylamide or lithium hexamethyldisyliylamide) in a solvent such as an ether (for example tetrahydrofuran) at a temperature of between 0° C. and 100° C. The intermediate adduct obtained is then thermolyzed at between 60° C. and 150° C. in an inert solvent (for example chloroform, tetrahydrofuran, toluene or xylene). Rz is advantageously a protecting group for the nitrogen atom such as, for example, t-butyloxycarbonyl.

The piperidine derivatives of general formula (IV) for which n=1 or 2 and $R''_2$ represents carboxyl may be prepared from the corresponding piperidine derivative of general formula (V) for which $R''_2$ is protected beforehand, according to or by analogy with the methods described below in the examples. In particular, the process is performed by the successive action of a base such as, for example, lithium diisopropylamide or n-butyllithium, in a solvent such as an ether (for example tetrahydrofuran) at a temperature of between −80° C. and 0° C., and then of an alkenyl halide (allyl halide or 1-halo-3-butene).

The piperidine derivatives of general formula (IV) for which n is defined as above and $R''_2$ is alkyloxycarbonyl, cycloalkyloxycarbonyl, —CO—NRaRb, alkyloxycarbonylmethyl, alkyloxycarbonylethyl, cycloalkyloxycarbonylmethyl, cycloalkyloxycarbonylethyl, —$CH_2$—CONRaRb, or —$(CH_2)_2$—CONRaRb or for which Rc in $R_2$ represents alkyloxycarbonyl, cycloalkyloxycarbonyl or —CO—NRaRb may be prepared from the corresponding carboxylic acid derivative, according to the usual methods for converting into ester or amide which do not affect the rest of the molecule. The esters are prepared in the presence of a coupling agent such as a carbodiimide (for example (N,N'-dicyclocarbodiimide) or N,N'-carbonyldiimidazole in an ether (for example tetrahydrofuran or dioxane), an amide (for example dimethylformamide) or a chlorinated solvent (for example dichloromethane, 1,2-dichloroethane or chloroform), at a temperature of between 0° C. and the reflux temperature of the reaction mixture. The amides are prepared by the action of the corresponding amine under conditions identical to those described above. In particular also, when it involves the preparation of a derivative for which Rc in $R''_2$ is an ester, by analogy with the methods described by Saha et al., *J. Chem. Soc. Perkin I*, 505 (1985), by the action of a diazoalkane (for example diazomethane) in an ether (for example diethyl ether) at a temperature of between −10° C. and 5° C.

The piperidine derivatives of general formula (IV) for which n is defined as above and $R''_2$ represents cyano, —$CH_2$—CN, or —$(CH_2)_2$—CN may be prepared from the corresponding amides by the action of a dehydrating agent, by adapting the method described by Bieron et al., Zabicky "*The Chemistry of Amides*," Wiley, pp. 274–283 (1970). The reaction is carried out in the presence of phosphorus pentoxide or phosphorus oxychloride with or without solvent, at a temperature of between 20° C. and the reflux temperature of the reaction mixture.

The piperidine derivatives of general formula (IV) for which n is defined as above and $R''_2$ represents hydroxymethyl, cyanomethyl or carboxymethyl may be prepared from the piperidine derivative of general formula:

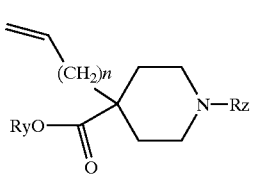

(VI)

in which Rz and n are defined as above, and Ry represents a readily hydrolyzable protecting radical, in particular, by the action of a hydride (for example lithium aluminum hydride or diisobutylaluminum hydride) in a solvent such as an ether (for example tetrahydrofuran) at a temperature of between 20° C. and 60° C. to prepare the piperidine derivative for which $R''_2$ is hydroxymethyl, followed by converting the hydroxymethyl radical into a cyanomethyl radical and then a carboxymethyl radical according to the usual methods which do not affect the rest of the molecule.

When Ry represents a readily hydrolyzable radical, it may be chosen especially from alkyl (1 to 4 carbon atoms in a straight or branched chain), benzyl, cycloalkyl, phenylpropyl, and allyl.

The conversion into acid may be carried out in particular from the latter compound, by the action of a halogenating agent such as, for example, thionylchloride or phosphorus trichloride or tribromide or by the action of an alkanesulfonyl chloride (for example methanesulfonyl chloride or p-toluenesulfonyl chloride) in an inert solvent (for example dichloromethane), followed by the action of an alkaline cyanide (for example potassium cyanide or sodium cyanide) and hydrolysis. The halogenation reaction is carried out in a chlorinated solvent (for example dichloromethane or chloroform), at a temperature of between 0° C. and the reflux temperature of the reaction mixture. The reaction of the alkaline cyanide may be carried out in dimethyl sulfoxide, an amide (for example dimethylformamide), a ketone (for example acetone), an ether (for example tetrahydrofuran) or an alcohol (for example methanol or ethanol), at a temperature of between 20° C. and the reflux temperature of the reaction mixture. The nitrile is hydrolyzed according to the conventional methods which do not affect the rest of the molecule, especially by the action of hydrochloric acid in methanolic medium, at a temperature of between 20° C. and 70° C., followed by saponification of the ester obtained (for example with sodium hydroxide in a mixture of dioxane and water), or directly by the action of aqueous sulfuric acid at a temperature of between 50° C. and 80° C.

The piperidine derivatives of general formula (IV) for which n and Rz are defined as above and $R''_2$ represents a 2-carboxyethyl radical may be prepared from the derivative of general formula (IV) for which $R'_2$ represents a hydroxymethyl radical via the halo derivative (prepared as described above) and then coupling with the sodium salt of diethyl malonate followed by acidic hydrolysis in aqueous medium of the product obtained.

The piperidine derivatives of general formula (IV) for which n and Rz are defined as above and $R''_2$ represents carboxyhydroxymethyl or carboxycarbonyl may be prepared by homologation of the piperidine derivative of general formula:

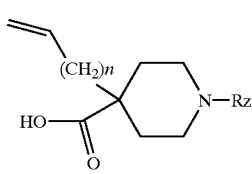

(VII)

in which Rz and n are defined as above, by applying or adapting the methods described by M. Mizuno et al., *Tetrahedron Lett.* 39, 9209 (1998). The reaction is carried out by the action of a dialkyl phosphorocyanidate (for example diethyl phosphorocyanidate) in the presence of an organic base (for example triethylamine) in an ether (for example tetrahydrofuran) at a temperature of between −50° C. and 10° C. The intermediate dicyanophosphate obtained is then hydrolyzed in acidic medium (for example concentrated hydrochloric acid) in a polar solvent (for example water) at the reflux temperature of the reaction mixture. The derivatives for which $R''_2$ is carboxycarbonyl are obtained by oxidation of the corresponding ester, by adapting the methods described by Burhardt et al., *Tetrahedron Lett.*, 29, 3433 (1988) followed by hydrolysis of the product obtained. In particular by the action of an oxidizing agent such as triacetoxy-1,1-dihydro-1,2-benziodoxol-3(1H)one in a solvent such as a nitrile or a chlorinated derivative (for example acetonitrile or dichloromethane) at a temperature of between 0° C. and 40° C., followed by hydrolysis by the action of a base (for example sodium hydroxide) in an aqueous-alcoholic solvent (for example water-methanol) at a temperature of between 20° C. and the reflux temperature of the reaction mixture.

The piperidine derivatives of general formula (IV) for which n and Rz are defined as above and $R''_2$ represents —$CF_2$—Rc may be prepared by the action of a fluorinating agent on a piperidine derivative of general formula (IV) for which $R''_2$ is a radical —CO—Rc, Rc being an ester, by analogy with the methods described by M. Parisi et al., *J. Org. Chem.*, 60, 5174 (1995), optionally followed by hydrolysis of the ester if it is desired to obtain a piperidine derivative for which Rc is carboxyl. The fluorinating conditions are similar to those described above for the preparation of derivatives for which Re in Y is a fluorine atom. The hydrolysis is carried out by the action of a base in an aqueous-alcoholic solvent under the conditions described above.

The piperidine derivatives of general formula (IV) for which n and Rz are defined as above and $R''_2$ represents a radical —CH=CH—Rc may be prepared by oxidation to aldehyde of the derivative of general formula (IV) for which $R''_2$ represents a hydroxymethyl radical by adapting the methods described in *Org. Synth. Coll.*, Vol. II, p. 541, *Coll.* Vol. 5,p. 242, followed by conversion to a derivative for which $R''_2$ is —CH=CH—Rc in which Rc is an ester, by applying the Wittig method optionally followed by hydrolysis of the ester obtained to an acid. The oxidation is carried out by the action of an oxidizing agent (for example potassium dichromate) in acidic medium (for example sulfuric acid) in a polar solvent (for example water) or chromium oxide in the presence of a base (for example pyridine) in a chlorinated solvent (for example dichloromethane) at a temperature of between 0° C. and 20° C. The conversion to an unsaturated derivative is carried out by adapting the methods described by Johnson in "*Ylid Chemistry*," Academic Press (1966) by the action of a phosphorus ylid (for example carbethoxymethylene-triphenylphosphorane) in a hydrocarbon (for example toluene) at a temperature of between 60° C. and the reflux temperature of the reaction mixture. The hydrolysis is carried out according to the methods described above.

The piperidine derivatives of general formula (IV) for which n and Rz are defined as above and $R''_2$ represents a radical $C(CH_3)_2Rc$ or —C(cycloalk)Rc may be prepared from a derivative of general formula (IV) for which $R''_2$ is an ester of the acid for which $R''_2$ is —$CH_2COOH$ by adapting the methods described by Ashutosh et al., *Tetrahedron Lett.*, 40, 4733 (1999) and Sauers, *J. Org. Chem.*, 57, 671 (1992) optionally followed by hydrolysis of the ester obtained. The reaction is carried out in particular by the successive action of an amide (for example lithium diisopropylamide) followed by a methyl halide (for example methyl iodide) or a derivative of formula Hal-Alk-Hal (Hal in one embodiment being a bromine atom) in a polar solvent (for example hexamethylphosphorotriamide) at a temperature of between 0° C. and 60° C.

It is understood that the processes listed above for the preparation of the piperidine derivatives of general formula (IV) may also be applied to the derivatives of general formula (II) if optionally first one couples the piperidine with the heterocyclic derivative of general formula (III) and then converts the radical $R_2$ under the conditions described above.

It is also understood that the methods described below in the examples also form part of the present invention.

It is understood that the derivatives of general formulae (I) and (II) may exist in enantiomeric or diastereoisomeric forms or in syn or anti form. The enantiomeric or diastereoisomeric and syn or anti forms and the mixtures thereof also fall within the context of the present invention. These forms may be separated according to the usual methods, especially by chromatography on silica or by high performance liquid chromatography (HPLC).

The heterocyclylalkylpiperidine derivatives of general formula (I) may be purified, where appropriate, by physical methods such as crystallization or chromatography.

The heterocyclylalkylpiperidine derivatives of general formula (I) may, where appropriate, be converted into addition salts with acids, by the known methods. It is understood that these salts also fall within the context of the present invention.

As examples of addition salts with pharmaceutically acceptable acids, mention may be made of the salts formed with mineral acids (hydrochlorides, hydrobromides, sulfates, nitrates and phosphates) or with organic acids (succinates, fumarates, tartrates, acetates, propionates, maleates, citrates, methanesulfonates, ethanesulfonates, phenylsulfonates, p-toluenesulfonates, isethionates, naphthylsulfonates or camphorsulfonates, or with substitution derivatives of these compounds).

Some of the heterocyclylalkylpiperidine derivatives of general formula (I) bearing a carboxyl radical may be converted into metal salts or into addition salts with nitrogen bases according to the methods that are known per se. These salts also fall within the context of the present invention. The salts may be obtained by the action of a metallic base (for example an alkali metal or alkaline-earth metal), ammonia or an amine, on a product according to the invention, in a suitable solvent such as an alcohol, an ether or water, or by exchange reaction with a salt of an organic acid. The salt formed precipitates after optional concentration of the solution, and is separated out by filtration, settling or freeze-drying.

Examples of pharmaceutically acceptable salts which may be mentioned are the salts with alkali metals (sodium, potassium or lithium) or with alkaline-earth metals (magnesium or calcium), the ammonium salts or the salts of nitrogen bases (ethanolamine, diethanolamine, trimethylamine, triethylamine, methylamine, propylamine, diisopropylamine, N-N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The heterocyclylalkylpiperidine derivatives according to the invention are particularly advantageous antibacterial agents.

In vitro, the heterocyclylalkylpiperidine derivatives according to the invention have been found to be active on gram-positive microorganisms at concentrations of between 0.03 µg/ml and 4 µg/ml on meticillin-resistant *Staphylococcus aureus* AS5155, and also, for most of them, at concentrations of between 0.03 µg/ml and 8 µg/ml on *Streptococcus pneumoniae* 6254-01; they have also been found to be active on gram-negative microorganisms such as, for example, and in a nonlimiting manner, on *Moraxella catarrhalis* IPA 152, at concentrations of between 0.12 µg/ml and 64 µg/ml. In vivo, they have been found to be active on experimental infections of mice with *Staphylococcus aureus* IP8203, either subcutaneously at doses of between 18 mg/kg and 150 mg/kg ($DC_{50}$), or orally at doses of between 20 mg/kg and 150 mg/kg.

Finally, the products according to the invention are particularly advantageous on account of their low toxicity. None of the products has shown any toxicity subcutaneously at the dose of 100 mg/kg in mice (two administrations).

In the general formula (I), the products for which $X_1$, $X_2$, $X_3$, $X_4$ and $X_5$ represent, respectively, >C—R'$_1$ to >C—R'$_5$, or alternatively not more than one of them represents a nitrogen atom, $R_1$, R'$_1$, R'$_2$, R'$_3$, R'$_4$ and R'$_5$ are identical or different and represent a hydrogen or halogen atom or an alkyl or alkyloxy radical, or represent a methylene radical substituted with alkyloxy, $R_2$ represents carboxyl, alkyloxycarbonyl or —CONRaRb (for which Ra represents a hydrogen atom and Rb represents a hydrogen atom or a hydroxyl radical) or $R_2$ represents hydroxymethyl, alkyl containing 1 or 2 carbon atoms substituted with carboxyl or alkyloxycarbonyl, $R_3$ represents a radical alk-R°$_3$ for which alk is an alkyl radical and R°$_3$ represents hydrogen, cycloalkyl, cycloalkylthio, phenyl, phenoxy, phenylthio, phenylamino, heterocyclyloxy or heterocyclylthio or alternatively R°$_3$ represents —CR'b=CR'c-R'a for which R'a represents phenyl, and for which R'b and R'c represent hydrogen, Y represents a radical >CH—Re for which Re is hydrogen, fluoro or hydroxyl, n is an integer from 2 to 3, it being understood that the phenyl or heterocyclyl radicals or portions mentioned above may be optionally substituted on the ring with 1 to 4 halogens.

Of special interest are the heterocyclylalkyl piperidine derivatives of general formula (I) mentioned below:

4-[3-(3-Chloro-6-methoxyquinolin-4-yl)propyl]-1-[2-(thien-2-yl)thioethyl]piperidine-4-carboxylic acid 4-[3-(3-Chloro-6-methoxyquinolin-4-yl)propyl]-1-[2-(3,5-difluorophenoxy)ethyl]piperidine-4-carboxylic acid 4-[3-(3-Chloro-6-methoxyquinolin-4-yl)propyl]-1-(2-thiazol-2-thioethyl)piperidine-4-carboxylic acid 1-(2-Cyclopentylthioethyl)-4-[3-(3-fluoro-6-methoxyquinolin-4-yl)propyl]piperidine-4-carboxylic acid 4-[3-(3-Fluoro-6-methoxyquinolin-4-yl)propyl]-1-(3-phenylallyl)piperidine-4-carboxylic acid and also the salts thereof.

Among the products according to the invention that may be mentioned are the heterocyclylalkylpiperidine derivatives of general formula (I), the names of which follow:

4-[3-(3-Chloro-6-methoxyquinolin-4-yl)propyl]-1-heptylpiperidine-4-carboxylic acid 4-[3-(3-Chloro-6-methoxyquinolin-4-yl)propyl]-1-[4-phenylbutyl]piperidine-4-carboxylic acid 4-[3-(3-Chloro-6-methoxyquinolin-4-yl)propyl]-1-[4-(2-fluorophenyl)propyl]piperidine-4-carboxylic acid 4-[3-(3-Chloro-6-methoxyquinolin-4-yl)propyl]-1-[4-(3-fluorophenyl)propyl]piperidine-4-carboxylic acid 4-[3-(3-Chloro-6-methoxyquinolin-4-yl)propyl]-1-[3-(4-fluorophenyl)propyl]piperidine-4-carboxylic acid 4-[3-(3-Chloro-6-methoxyquinolin-4-yl)propyl]-1-[4-(4-fluorophenyl)butyl]piperidine-4-carboxylic acid 4-[3-(3-Chloro-6-methoxyquinolin-4-yl)propyl]-1-[3-(2,3-difluorophenyl)propyl]piperidine-4-carboxylic acid 4-[3-(3-Chloro-6-methoxyquinolin-4-yl)propyl]-1-[4-(2,3-difluorophenyl)propyl]piperidine-4-carboxylic acid 4-[3-(3-Chloro-6-methoxyquinolin-4-yl)propyl]-1-[3-(2,6-difluorophenyl)propyl]piperidine-4-carboxylic acid 4-[3-(3-Chloro-6-methoxyquinolin-4-yl)propyl]-1-[4-(2,6-difluorophenyl)propyl]piperidine-4-carboxylic acid 4-[3-(3-Chloro-6-methoxyquinolin-4-yl)propyl]-1-[3-(3,5-difluorophenyl)propyl]piperidine-4-carboxylic acid 4-[3-(3-Chloro-6-methoxyquinolin-4-yl)propyl]-1-[3-(2,3,5-trifluorophenyl)propyl]piperidine-4-carboxylic acid 4-[3-(3-Chloro-6-methoxyquinolin-4-yl)propyl]-1-[3-(2,4,6-trifluorophenyl)propyl]piperidine-4-carboxylic acid 4-[3-(3-Chloro-6-methoxyquinolin-4-yl)propyl]-1-[3-(3,4,5-trifluorophenyl)propyl]piperidine-4-carboxylic acid 4-[3-(3-Chloro-6-methoxyquinolin-4-yl)propyl]-1-[3-phenylthiopropyl]piperidine-4-carboxylic acid 4-[3-(3-Chloro-6-methoxyquinolin-4-yl)propyl]-1-[3-(2-fluorophenylthio)propyl]piperidine-4-carboxylic acid 4-[3-(3-Chloro-6-methoxyquinolin-4-yl)propyl]-1-[3-(3-fluorophenylthio)propyl]piperidine-4-carboxylic acid 4-[3-(3-Chloro-6-methoxyquinolin-4-yl)propyl]-1-[2-(4-fluorophenylthio)ethyl]piperidine-4-carboxylic acid 4-[3-(3-Chloro-6-methoxyquinolin-4-yl)propyl]-1-[3-(4-fluorophenylthio)propyl]piperidine-4-carboxylic acid 4-[3-(3-Chloro-6-methoxyquinolin-4-yl)propyl]-1-[2-(2,3-difluorophenylthio)ethyl]-piperidine-4-carboxylic acid 4-[3-(3-Chloro-6-methoxyquinolin-4-yl)propyl]-1-[3-(2,3-difluorophenylthio)propyl]-piperidine-4-carboxylic acid 4-[3-(3-Chloro-6-methoxyquinolin-4-yl)propyl]-1-[2-(2,6-difluorophenylthio)ethyl]-piperidine-4-carboxylic acid 4-[3-(3-Chloro-6-methoxyquinolin-4-yl)propyl]-1-[2-(2,3,5-trifluorophenylthio)ethyl]-piperidine-4-carboxylic acid 4-[3-(3-Chloro-6-methoxyquinolin-4-yl)propyl]-1-[2-(2,4,6-trifluorophenylthio)ethyl]-piperidine-4-carboxylic acid 4-[3-(3-Chloro-6-methoxyquinolin-4-yl)propyl]-1-[2-(3,4,5-trifluorophenylthio)ethyl]-piperidine-4-carboxylic acid 4-[3-(3-Chloro-6-methoxyquinolin-4-yl)propyl]-1-[2-(2,3,5-trifluorophenoxy)ethyl]-piperidine-4-carboxylic acid 4-[3-(3-Chloro-6-methoxyquinolin-4-yl)propyl]-1-[2-(2,4,6-trifluorophenoxy)ethyl]-piperidine-4-carboxylic acid 4-[3-(3-Chloro-6-methoxyquinolin-4-yl)propyl]-1-[2-(3,4,5-trifluorophenoxy)ethyl]-piperidine-4-carboxylic acid 4-[3-(3-Chloro-6-methoxyquinolin-4-yl)propyl]-1-[2-(3,5-difluorophenylamino)ethyl]-piperidine-4-carboxylic acid 4-[3-(3-Chloro-6-methoxyquinolin-4-yl)propyl]-1-[2-(2,3,5-trifluorophenylamino)ethyl]-piperidine-4-carboxylic acid 4-[3-(3-Chloro-6-methoxyquinolin-4-yl)propyl]-1-[2-(2,4,6-trifluorophenylamino)ethyl]-piperidine-4-carboxylic acid 4-[3-(3-Chloro-6-methoxyquinolin-4-yl)propyl]-1-[2-(3,4,5-trifluorophenylamino)ethyl]-piperidine-4-carboxylic acid 4-[3-(3-Chloro-6-methoxyquinolin-4-yl)propyl]-1-[3-(2,6-difluorophenylthio)propyl]-piperidine-4-carboxylic acid 4-[3-(3-Chloro-6-methoxyquinolin-4-yl)propyl]-1-[2-(2-chlorophenylthio)ethyl]piperidine-4-carboxylic acid 4-[3-(3-Chloro-6-methoxyquinolin-4-yl)propyl]-1-[3-(2-chlorophenylthio)propyl]piperidine-4-carboxylic acid 4-[3-(3-Chloro-6-methoxyquinolin-4-yl)propyl]-1-[2-(3-chlorophenylthio)ethyl]piperidine-4-carboxylic acid 4-[3-(3-Chloro-6-methoxyquinolin-4-yl)propyl]-1-[3-(3-chlorophenylthio)propyl]piperidine-4-carboxylic acid 4-[3-(3-Chloro-6-methoxyquinolin-4-yl)propyl]-1-[2-(4-chlorophenylthio)ethyl]piperidine-4-carboxylic acid 4-[3-(3-Chloro-6-methoxyquinolin-4-yl)propyl]-1-[3-(4-chlorophenylthio)propyl]piperidine-4-carboxylic acid 4-[3-(3-Chloro-6-methoxyquinolin-4-yl)propyl]-1-[2-(2-methylphenylthio)ethyl]piperidine-4-carboxylic acid 4-[3-(3-Chloro-6-methoxyquinolin-4-yl)propyl]-1-[3-(2-methylphenylthio)propyl]-piperidine-4-carboxylic acid 4-[3-(3-Chloro-6-methoxyquinolin-4-yl)propyl]-1-[2-(3-methylphenylthio)ethyl]piperidine-4-carboxylic acid 4-[3-(3-Chloro-6-methoxyquinolin-4-yl)propyl]-1-[3-(3-methylphenylthio)propyl]-piperidine-4-carboxylic acid 4-[3-(3-Chloro-6-methoxyquinolin-4-yl)propyl]-1-[2-(4-methylphenylthio)ethyl]piperidine-4-carboxylic acid 4-[3-(3-Chloro-6-methoxyquinolin-4-yl)propyl]-1-[3-(4-methylphenylthio)propyl]-piperidine-4-carboxylic acid 4-[3-(3-Chloro-6-methoxyquinolin-4-yl)propyl]-1-[2-(2-trifluoromethylphenylthio)ethyl]-piperidine-4-carboxylic acid 4-[3-(3-Chloro-6-methoxyquinolin-4-yl)propyl]-1-[3-(2-trifluoromethylphenylthio)propyl]-piperidine-4-carboxylic acid 4-[3-(3-Chloro-6-methoxyquinolin-4-yl)propyl]-1-[2-(3-trifluoromethylphenylthio)ethyl]-piperidine-4-carboxylic acid 4-[3-(3-Chloro-6-methoxyquinolin-4-yl)propyl]-1-[3-(3-trifluoromethylphenylthio)propyl]-piperidine-4-carboxylic acid 4-[3-(3-Chloro-6-methoxyquinolin-4-yl)propyl]-1-[2-(4-trifluoromethylphenylthio)ethyl]-piperidine-4-carboxylic acid 4-[3-(3-Chloro-6-methoxyquinolin-4-yl)propyl]-1-[3-(4-trifluoromethylphenylthio)propyl]-piperidine-4-carboxylic acid 4-[3-(3-Chloro-6-methoxyquinolin-4-yl)propyl]-1-[2-(2-methoxyphenylthio)ethyl]-piperidine-4-carboxylic acid 4-[3-(3-Chloro-6-methoxyquinolin-4-yl)propyl]-1-[3-(2-methoxyphenylthio)propyl]-piperidine-4-carboxylic acid 4-[3-(3-Chloro-6-methoxyquinolin-4-yl)propyl]-1-[2-(3-methoxyphenylthio)ethyl]-piperidine-4-carboxylic acid 4-[3-(3-Chloro-6-methoxyquinolin-4-yl)propyl]-1-[3-(3-methoxyphenylthio)propyl]-piperidine-4-carboxylic acid 4-[3-(3-Chloro-6-methoxyquinolin-4-yl)propyl]-1-[2-(4-methoxyphenylthio)ethyl]piperidine-4-carboxylic acid 4-[3-(3-Chloro-6-methoxyquinolin-4-yl)propyl]-1-[3-(4-methoxyphenylthio)propyl]-piperidine-4-carboxylic acid 4-[3-(3-Chloro-6-methoxyquinolin-4-yl)propyl]-1-[cyclopentylmethyl]piperidine-4-carboxylic acid 4-[3-(3-Chloro-6-methoxyquinolin-4-yl)propyl]-1-[2-(cyclopentyl)ethyl]piperidine-4-carboxylic acid
4-[3-(3-Chloro-6-methoxyquinolin-4-yl)propyl]-1-[2-(cyclopentylthio)ethyl]piperidine-4-carboxylic acid
4-[3-(3-Chloro-6-methoxyquinolin-4-yl)propyl]-1-[3-(cyclopentylthio)propyl]piperidine-4-carboxylic acid
4-[3-(3-Chloro-6-methoxyquinolin-4-yl)propyl]-1-[3-(cyclohexylthio)propyl]piperidine-4-carboxylic acid
4-[3-(3-Chloro-6-methoxyquinolin-4-yl)propyl]-1-[4-(thien-2-yl)butyl]piperidine-4-carboxylic acid
4-[3-(3-Chloro-6-methoxyquinolin-4-yl)propyl]-1-[3-(thien-2-yl)thiopropyl]piperidine-4-carboxylic acid
4-[3-(3-Chloro-6-methoxyquinolin-4-yl)propyl]-1-[3-(thien-3-yl)propyl]piperidine-4-carboxylic acid
4-[3-(3-Chloro-6-methoxyquinolin-4-yl)propyl]-1-[4-(thien-3-yl)butyl]piperidine-4-carboxylic acid
4-[3-(3-Chloro-6-methoxyquinolin-4-yl)propyl]-1-[2-(thien-3-yl)thioethyl]piperidine-4-carboxylic acid
4-[3-(3-Chloro-6-methoxyquinolin-4-yl)propyl]-1-[3-(thien-3-yl)thiopropyl]piperidine-4-carboxylic acid
4-[3-(3-Chloro-6-methoxyquinolin-4-yl)propyl]-1-[3-(1,3-thiazol-2-yl)propyl]piperidine-4-carboxylic acid
4-[3-(3-Chloro-6-methoxyquinolin-4-yl)propyl]-1-[4-(1,3-thiazol-2-yl)butyl]piperidine-4-carboxylic acid
4-[3-(3-Chloro-6-methoxyquinolin-4-yl)propyl]-1-[3-(1,3-thiazol-2-yl)thioethyl]piperidine-4-carboxylic acid
4-[3-(3-Chloro-6-methoxyquinolin-4-yl)propyl]-1-[3-(pyrid-2-yl)propyl]piperidine-4-carboxylic acid
4-[3-(3-Chloro-6-methoxyquinolin-4-yl)propyl]-1-[4-(pyrid-2-yl)butyl]piperidine-4-carboxylic acid
4-[3-(3-Chloro-6-methoxyquinolin-4-yl)propyl]-1-[3-(pyrid-2-yl)thiopropyl]piperidine-4-carboxylic acid
4-[3-(3-Chloro-6-methoxyquinolin-4-yl)propyl]-1-[3-(pyrid-3-yl)propyl]piperidine-4-carboxylic acid
4-[3-(3-Chloro-6-methoxyquinolin-4-yl)propyl]-1-[4-(pyrid-3-yl)butyl]piperidine-4-carboxylic acid
4-[3-(3-Chloro-6-methoxyquinolin-4-yl)propyl]-1-[2-(pyrid-3-yl)thioethyl]piperidine-4-carboxylic acid
4-[3-(3-Chloro-6-methoxyquinolin-4-yl)propyl]-1-[3-(pyrid-3-yl)thiopropyl]piperidine-4-carboxylic acid
4-[3-(3-Chloro-6-methoxyquinolin-4-yl)propyl]-1-[3-(pyrid-4-yl)propyl]piperidine-4-carboxylic acid
4-[3-(3-Chloro-6-methoxyquinolin-4-yl)propyl]-1-[4-(pyrid-4-yl)butyl]piperidine-4-carboxylic acid
4-[3-(3-Chloro-6-methoxyquinolin-4-yl)propyl]-1-[2-(pyrid-4-yl)thioethyl]piperidine-4-carboxylic acid
4-[3-(3-Chloro-6-methoxyquinolin-4-yl)propyl]-1-[3-(pyrid-4-yl)thiopropyl]piperidine-4-carboxylic acid
4-[3-(3-Chloro-6-methoxyquinolin-4-yl)propyl]-1-[3-(pyrazin-2-yl)propyl]piperidine-4-carboxylic acid
4-[3-(3-Chloro-6-methoxyquinolin-4-yl)propyl]-1-[4-(pyrazin-2-yl)butyl]piperidine-4-carboxylic acid
4-[3-(3-Chloro-6-methoxyquinolin-4-yl)propyl]-1-[2-(pyrazin-2-yl)thioethyl]piperidine-4-carboxylic acid
4-[3-(3-Chloro-6-methoxyquinolin-4-yl)propyl]-1-[3-(pyrazin-2-yl)thiopropyl]piperidine-4-carboxylic acid
4-[3-(3-Chloro-6-methoxyquinolin-4-yl)propyl]-1-[3-(4-fluorophenyl)prop-2-ynyl]piperidine-4-carboxylic acid
4-[3-(3-Chloro-6-methoxyquinolin-4-yl)propyl]-1-[3-(3,4-difluorophenyl)prop-2-ynyl]piperidine-4-carboxylic acid
4-[3-(3-Chloro-6-methoxyquinolin-4-yl)propyl]-1-[3-(2,4-difluorophenyl)prop-2-ynyl]piperidine-4-carboxylic acid
4-[3-(3-Chloro-6-methoxyquinolin-4-yl)propyl]-1-[3-(2,3,5-trifluorophenyl)prop-2-ynyl]piperidine-4-carboxylic acid
4-[3-(3-Chloro-6-methoxyquinolin-4-yl)propyl]-1-[3-(2,4,6-trifluorophenyl)prop-2-ynyl]piperidine-4-carboxylic acid
4-[3-(3-Chloro-6-methoxyquinolin-4-yl)propyl]-1-[3-(3,4,5-trifluorophenyl)prop-2-ynyl]piperidine-4-carboxylic acid
4-[3-(3-Chloro-6-methoxyquinolin-4-yl)propyl]-1-[3-(4-chloro-3-fluorophenyl)prop-2-ynyl]piperidine-4-carboxylic acid
4-[3-(3-Chloro-6-methoxyquinolin-4-yl)propyl]-1-[3-(3-chloro-4-fluorophenyl)prop-2-ynyl]piperidine-4-carboxylic acid
4-[3-(3-Chloro-6-methoxyquinolin-4-yl)propyl]-1-[3-(2-chloro-4-fluorophenyl)prop-2-ynyl]piperidine-4-carboxylic acid
4-[3-(3-Chloro-6-methoxyquinolin-4-yl)propyl]-1-[3-(3-chloro-5-fluorophenyl)prop-2-ynyl]piperidine-4-carboxylic acid
4-[3-(3-Chloro-6-methoxyquinolin-4-yl)propyl]-1-[3-(4-chloro-2-fluorophenyl)prop-2-ynyl]piperidine-4-carboxylic acid
4-[3-(3-Chloro-6-methoxyquinolin-4-yl)propyl]-1-[3-(3-fluoro-4-methylphenyl)prop-2-ynyl]piperidine-4-carboxylic acid
4-[3-(3-Chloro-6-methoxyquinolin-4-yl)propyl]-1-[3-(3,5-bis(trifluoromethyl)phenyl)prop-2-ynyl]piperidine-4-carboxylic acid
4-[3-(3-Chloro-6-methoxyquinolin-4-yl)propyl]-1-[3-(thien-2-yl)prop-2-ynyl]piperidine-4-carboxylic acid
4-[3-(3-Chloro-6-methoxyquinolin-4-yl)propyl]-1-[3-(thien-3-yl)prop-2-ynyl]piperidine-4-carboxylic acid
4-[3-(3-Chloro-6-methoxyquinolin-4-yl)propyl]-1-[3-(1,3-thiazol-2-yl)prop-2-ynyl]piperidine-4-carboxylic acid
4-[3-(3-Chloro-6-methoxyquinolin-4-yl)propyl]-1-[3-(1,3-thiazol-4-yl)prop-2-ynyl]piperidine-4-carboxylic acid
4-[3-(3-Chloro-6-methoxyquinolin-4-yl)propyl]-1-[3-(1,3-thiazol-5-yl)prop-2-ynyl]piperidine-4-carboxylic acid
4-[3-(3-Chloro-6-methoxyquinolin-4-yl)propyl]-1-[3-(pyrid-2-yl)prop-2-ynyl]piperidine-4-carboxylic acid
4-[3-(3-Chloro-6-methoxyquinolin-4-yl)propyl]-1-[3-(pyrid-3-yl)prop-2-ynyl]piperidine-4-carboxylic acid
4-[3-(3-Chloro-6-methoxyquinolin-4-yl)propyl]-1-[3-(pyrid-4-yl)prop-2-ynyl]piperidine-4-carboxylic acid
4-[3-(3-Methyl-6-methoxyquinolin-4-yl)propyl]-1-[2-(cyclohexyl)ethyl]piperidine-4-carboxylic acid
4-[3-(3-Methyl-6-methoxyquinolin-4-yl)propyl]-1-[3-(phenyl)propyl]piperidine-4-carboxylic acid
4-[3-(3-Methyl-6-methoxyquinolin-4-yl)propyl]-1-[3-(2,3,5-trifluorophenyl)propyl]piperidine-4-carboxylic acid
4-[3-(3-Methyl-6-methoxyquinolin-4-yl)propyl]-1-[2-(3,5-difluorophenylamino)ethyl]-piperidine-4-carboxylic acid
4-[3-(3-Methyl-6-methoxyquinolin-4-yl)propyl]-1-[2-(2,3,5-trifluorophenylamino)ethyl]-piperidine-4-carboxylic acid
4-[3-(3-Methyl-6-methoxyquinolin-4-yl)propyl]-1-[2-(3,5-difluorophenoxy)ethyl]-piperidine-4-carboxylic acid 4-[3-(3-Methyl-6-methoxyquinolin-4-yl)propyl]-1-[2-(2,3,5-trifluorophenoxy)ethyl]-piperidine-4-carboxylic acid 4-[3-(3-Methyl-6-methoxyquinolin-4-yl)propyl]-1-[2-(cyclopentylthio)ethyl]piperidine-4-carboxylic acid 4-[3-(3-Methyl-6-methoxyquinolin-4-yl)propyl]-1-[2-(pyrid-2-yl)thioethyl]piperidine-4-carboxylic acid 4-[3-(3-Methyl-6-methoxyquinolin-4-yl)propyl]-1-[2-(thien-2-yl)thioethyl]piperidine-4-carboxylic acid 4-[3-(3-Methyl-6-methoxyquinolin-4-yl)propyl]-1-[3-(2,3,5-trifluorophenyl)prop-2-ynyl]piperidine-4-carboxylic acid 4-[3-(3-Methyl-6-methoxyquinolin-4-yl)propyl]-1-[3-(thien-2-yl)prop-2-ynyl]piperidine-4-carboxylic acid 4-[3-(3-Fluoro-6-methoxyquinolin-4-yl)propyl]-1-[3-(2,3,5-trifluorophenyl)propyl]piperidine-4-carboxylic acid 4-[3-(3-Fluoro-6-methoxyquinolin-4-yl)propyl]-1-[2-(3,5-difluorophenylamino)ethyl]piperidine-4-carboxylic acid 4-[3-(3-Fluoro-6-methoxyquinolin-4-yl)propyl]-1-[2-(2,3,5-trifluorophenylamino)ethyl]piperidine-4-carboxylic acid 4-[3-(3-Fluoro-6-methoxyquinolin-4-yl)propyl]-1-[2-(3,5-difluorophenoxy)ethyl]piperidine-4-carboxylic acid 4-[3-(3-Fluoro-6-methoxyquinolin-4-yl)propyl]-1-[2-(2,3,5-trifluorophenoxy)ethyl]piperidine-4-carboxylic acid 4-[3-(3-Fluoro-6-methoxyquinolin-4-yl)propyl]-1-[2-(2,3,5-trifluorophenylthio)ethyl]piperidine-4-carboxylic acid 4-[3-(3-Fluoro-6-methoxyquinolin-4-yl)propyl]-1-[2-(pyrid-2-yl)thioethyl]piperidine-4-carboxylic acid 4-[3-(3-Fluoro-6-methoxyquinolin-4-yl)propyl]-1-[3-(2,3,5-trifluorophenyl)prop-2-ynyl]piperidine-4-carboxylic acid 4-[3-(3-Fluoro-6-methoxyquinolin-4-yl)propyl]-1-[3-(thien-2-yl)prop-2-ynyl]piperidine-4-carboxylic acid 4-[3-(3-Dimethylamino-6-methoxyquinolin-4-yl)propyl]-1-[2-(cyclohexyl)ethyl]piperidine-4-carboxylic acid 4-[3-(3-Dimethylamino-6-methoxyquinolin-4-yl)propyl]-1-[3-(phenyl)propyl]piperidine-4-carboxylic acid 4-[3-(3-Dimethylamino-6-methoxyquinolin-4-yl)propyl]-1-[3-(2,3,5-trifluorophenyl)propyl]piperidine-4-carboxylic acid 4-[3-(3-Dimethylamino-6-methoxyquinolin-4-yl)propyl]-1-[2-(3,5-difluorophenylamino)ethyl]piperidine-4-carboxylic acid 4-[3-(3-Dimethylamino-6-methoxyquinolin-4-yl)propyl]-1-[2-(2,3,5-trifluorophenylamino)ethyl]piperidine-4-carboxylic acid 4-[3-(3-Dimethylamino-6-methoxyquinolin-4-yl)propyl]-1-[2-(3,5-difluorophenoxy)ethyl]piperidine-4-carboxylic acid 4-[3-(3-Dimethylamino-6-methoxyquinolin-4-yl)propyl]-1-[2-(2,3,5-trifluorophenoxy)ethyl]piperidine-4-carboxylic acid 4-[3-(3-Dimethylamino-6-methoxyquinolin-4-yl)propyl]-1-[2-(2,3,5-trifluorophenylthio)ethyl]piperidine-4-carboxylic acid 4-[3-(3-Dimethylamino-6-methoxyquinolin-4-yl)propyl]-1-[2-(cyclopentylthio)ethyl]piperidine-4-carboxylic acid 4-[3-(3-Dimethylamino-6-methoxyquinolin-4-yl)propyl]-1-[2-(pyrid-2-yl)thioethyl]piperidine-4-carboxylic acid 4-[3-(3-Dimethylamino-6-methoxyquinolin-4-yl)propyl]-1-[2-(thien-2-yl)thioethyl]piperidine-4-carboxylic acid 4-[3-(3-Dimethylamino-6-methoxyquinolin-4-yl)propyl]-1-[3-(2,3,5-trifluorophenyl)prop-2-ynyl]piperidine-4-carboxylic acid 4-[3-(3-Dimethylamino-6-methoxyquinolin-4-yl)propyl]-1-[3-(thien-2-yl)prop-2-ynyl]piperidine-4-carboxylic acid 4-[3-(3-Hydroxymethyl-6-methoxyquinolin-4-yl)propyl]-1-[2-(cyclohexyl)ethyl]piperidine-4-carboxylic acid 4-[3-(3-Hydroxymethyl-6-methoxyquinolin-4-yl)propyl]-1-[3-(phenyl)propyl]piperidine-4-carboxylic acid 4-[3-(3-Hydroxymethyl-6-methoxyquinolin-4-yl)propyl]-1-[3-(2,3,5-trifluorophenyl)propyl]piperidine-4-carboxylic acid 4-[3-(3-Hydroxymethyl-6-methoxyquinolin-4-yl)propyl]-1-[2-(3,5-difluorophenylamino)ethyl]piperidine-4-carboxylic acid 4-[3-(3-Hydroxymethyl-6-methoxyquinolin-4-yl)propyl]-1-[2-(2,3,5-trifluorophenylamino)ethyl]piperidine-4-carboxylic acid 4-[3-(3-Hydroxymethyl-6-methoxyquinolin-4-yl)propyl]-1-[2-(3,5-difluorophenoxy)ethyl]piperidine-4-carboxylic acid 4-[3-(3-Hydroxymethyl-6-methoxyquinolin-4-yl)propyl]-1-[2-(2,3,5-trifluorophenoxy)ethyl]piperidine-4-carboxylic acid 4-[3-(3-Hydroxymethyl-6-methoxyquinolin-4-yl)propyl]-1-[2-(2,3,5-trifluorophenylthio)ethyl]piperidine-4-carboxylic acid 4-[3-(3-Hydroxymethyl-6-methoxyquinolin-4-yl)propyl]-1-[2-(cyclopentylthio)ethyl]piperidine-4-carboxylic acid 4-[3-(3-Hydroxymethyl-6-methoxyquinolin-4-yl)propyl]-1-[2-(pyrid-2-yl)thioethyl]piperidine-4-carboxylic acid 4-[3-(3-Hydroxymethyl-6-methoxyquinolin-4-yl)propyl]-1-[2-(thien-2-yl)thioethyl]piperidine-4-carboxylic acid 4-[3-(3-Hydroxymethyl-6-methoxyquinolin-4-yl)propyl]-1-[3-(2,3,5-trifluorophenyl)prop-2-ynyl]piperidine-4-carboxylic acid 4-[3-(3-Hydroxymethyl-6-methoxyquinolin-4-yl)propyl]-1-[3-(thien-2-yl)prop-2-ynyl]piperidine-4-carboxylic acid 4-[3-(3-Fluoromethyl-6-methoxyquinolin-4-yl)propyl]-1-[2-(cyclohexyl)ethyl]piperidine-4-carboxylic acid 4-[3-(3-Fluoromethyl-6-methoxyquinolin-4-yl)propyl]-1-[3-(phenyl)propyl]piperidine-4-carboxylic acid 4-[3-(3-Fluoromethyl-6-methoxyquinolin-4-yl)propyl]-1-[3-(2,3,5-trifluorophenyl)propyl]piperidine-4-carboxylic acid 4-[3-(3-Fluoromethyl-6-methoxyquinolin-4-yl)propyl]-1-[2-(3,5-difluorophenylamino)ethyl]piperidine-4-carboxylic acid 4-[3-(3-Fluoromethyl-6-methoxyquinolin-4-yl)propyl]-1-[2-(2,3,5-trifluorophenylamino)ethyl]piperidine-4-carboxylic acid 4-[3-(3-Fluoromethyl-6-methoxyquinolin-4-yl)propyl]-1-[2-(3,5-difluorophenoxy)ethyl]piperidine-4-carboxylic acid 4-[3-(3-Fluoromethyl-6-methoxyquinolin-4-yl)propyl]-1-[2-(2,3,5-trifluorophenoxy)ethyl]piperidine-4-carboxylic acid 4-[3-(3-Fluoromethyl-6-methoxyquinolin-4-yl)propyl]-1-[2-(2,3,5-trifluorophenylthio)ethyl]piperidine-4-carboxylic acid 4-[3-(3-Fluoromethyl-6-methoxyquinolin-4-yl)propyl]-1-[2-(cyclopentylthio)ethyl]piperidine-4-carboxylic acid 4-[3-(3-Fluoromethyl-6-methoxyquinolin-4-yl)propyl]-1-[2-(pyrid-2-yl)thioethyl]piperidine-4-carboxylic acid 4-[3-(3-Fluoromethyl-6-methoxyquinolin-4-yl)propyl]-1-[2-(thien-2-yl)thioethyl]piperidine-4-carboxylic acid 4-[3-(3-Fluoromethyl-6-methoxyquinolin-4-yl)propyl]-1-[3-(2,3,5-trifluorophenyl)prop-2-ynyl]piperidine-4-carboxylic acid 4-[3-(3-Fluoromethyl-6-methoxyquinolin-4-yl)propyl]-1-[3-(thien-2-yl)prop-2-ynyl]piperidine-4-carboxylic acid 4-[3-(3-Aminomethyl-6-methoxyquinolin-4-yl)propyl]-1-[2-(cyclohexyl)ethyl]piperidine-4-carboxylic acid 4-[3-(3-Aminomethyl-6-methoxyquinolin-4-yl)propyl]-1-[3-(phenyl)propyl]piperidine-4-carboxylic acid 4-[3-(3-Aminomethyl-6-methoxyquinolin-4-yl)propyl]-1-[3-(2,3,5-trifluorophenyl)propyl]piperidine-4-carboxylic acid 4-[3-(3-Aminomethyl-6-methoxyquinolin-4-yl)propyl]-1-[2-(3,5-difluorophenylamino)ethyl]piperidine-4-carboxylic acid 4-[3-(3-Aminomethyl-6-methoxyquinolin-4-yl)propyl]-1-[2-(2,3,5-trifluorophenylamino)ethyl]piperidine-4-carboxylic acid 4-[3-(3-Aminomethyl-6-methoxyquinolin-4-yl)propyl]-1-[2-(3,5-difluorophenoxy)ethyl]piperidine-4-carboxylic acid 4-[3-(3-Aminomethyl-6-methoxyquinolin-4-yl)propyl]-1-[2-(2,3,5-trifluorophenoxy)ethyl]piperidine-4-carboxylic acid 4-[3-(3-Aminomethyl-6-methoxyquinolin-4-yl)propyl]-1-[2-(2,3,5-trifluorophenylthio)ethyl]piperidine-4-carboxylic acid 4-[3-(3-Aminomethyl-6-methoxyquinolin-4-yl)propyl]-1-[2-(cyclopentylthio)ethyl]piperidine-4-carboxylic acid 4-[3-(3-Aminomethyl-6-methoxyquinolin-4-yl)propyl]-1-[2-(pyrid-2-yl)thioethyl]piperidine-4-carboxylic acid 4-[3-(3-Aminomethyl-6-methoxyquinolin-4-yl)propyl]-1-[2-(thien-2-yl)thioethyl]piperidine-4-carboxylic acid 4-[3-(3-Aminomethyl-6-methoxyquinolin-4-yl)propyl]-1-[3-(2,3,5-trifluorophenyl)prop-2-ynyl]piperidine-4-carboxylic acid 4-[3-(3-Aminomethyl-6-methoxyquinolin-4-yl)propyl]-1-[3-(thien-2-yl)prop-2-ynyl]piperidine-4-carboxylic acid 4-[3-(3-Morpholinomethyl-6-methoxyquinolin-4-yl)propyl]-1-[2-(cyclohexyl)ethyl]piperidine-4-carboxylic acid 4-[3-(3-Morpholinomethyl-6-methoxyquinolin-4-yl)propyl]-1-[3-(phenyl)propyl]piperidine-4-carboxylic acid 4-[3-(3-Morpholinomethyl-6-methoxyquinolin-4-yl)propyl]-1-[3-(2,3,5-trifluorophenyl)propyl]piperidine-4-carboxylic acid 4-[3-(3-Morpholinomethyl-6-methoxyquinolin-4-yl)propyl]-1-[2-(3,5-difluorophenylamino)ethyl]piperidine-4-carboxylic acid 4-[3-(3-Morpholinomethyl-6-methoxyquinolin-4-yl)propyl]-1-[2-(2,3,5-trifluorophenylamino)ethyl]piperidine-4-carboxylic acid 4-[3-(3-Morpholinomethyl-6-methoxyquinolin-4-yl)propyl]-1-[2-(3,5-difluorophenoxy)ethyl]piperidine-4-carboxylic acid 4-[3-(3-Morpholinomethyl-6-methoxyquinolin-4-yl)propyl]-1-[2-(2,3,5-trifluorophenoxy)ethyl]piperidine-4-carboxylic acid 4-[3-(3-Morpholinomethyl-6-methoxyquinolin-4-yl)propyl]-1-[2-(2,3,5-trifluorophenylthio)ethyl]piperidine-4-carboxylic acid 4-[3-(3-Morpholinomethyl-6-methoxyquinolin-4-yl)propyl]-1-[2-(cyclopentylthio)ethyl]piperidine-4-carboxylic acid 4-[3-(3-Morpholinomethyl-6-methoxyquinolin-4-yl)propyl]-1-[2-(pyrid-2-yl)thioethyl]piperidine-4-carboxylic acid 4-[3-(3-Morpholinomethyl-6-methoxyquinolin-4-yl)propyl]-1-[2-(thien-2-yl)thioethyl]piperidine-4-carboxylic acid 4-[3-(3-Morpholinomethyl-6-methoxyquinolin-4-yl)propyl]-1-[3-(2,3,5-trifluorophenyl)prop-2-ynyl]piperidine-4-carboxylic acid 4-[3-(3-Morpholinomethyl-6-methoxyquinolin-4-yl)propyl]-1-[3-(thien-2-yl)prop-2-ynyl]piperidine-4-carboxylic acid 4-[3-(3-Methyl-6-methoxyquinolin-4-yl)propyl]-1-[3-(2,4,6-trifluorophenyl)propyl]piperidine-4-carboxylic acid 4-[3-(3-Methyl-6-methoxyquinolin-4-yl)propyl]-1-[3-(3,4,5-trifluorophenyl)propyl]piperidine-4-carboxylic acid 4-[3-(3-Methyl-6-methoxyquinolin-4-yl)propyl]-1-[2-(2,4,6-trifluorophenylthio)ethyl]piperidine-4-carboxylic acid 4-[3-(3-Methyl-6-methoxyquinolin-4-yl)propyl]-1-[2-(3,4,5-trifluorophenylthio)ethyl]piperidine-4-carboxylic acid 4-[3-(3-Methyl-6-methoxyquinolin-4-yl)propyl]-1-[2-(2,4,6-trifluorophenylamino)ethyl]piperidine-4-carboxylic acid 4-[3-(3-Methyl-6-methoxyquinolin-4-yl)propyl]-1-[2-(3,4,5-trifluorophenylamino)ethyl]piperidine-4-carboxylic acid 4-[3-(3-Methyl-6-methoxyquinolin-4-yl)propyl]-1-[2-(2,4,6-trifluorophenoxy)ethyl]piperidine-4-carboxylic acid 4-[3-(3-Methyl-6-methoxyquinolin-4-yl)propyl]-1-[2-(3,4,5-trifluorophenoxy)ethyl]piperidine-4-carboxylic acid 4-[3-(3-Methyl-6-methoxyquinolin-4-yl)propyl]-1-[3-(2,4,6-trifluorophenyl)prop-2-ynyl]piperidine-4-carboxylic acid 4-[3-(3-Methyl-6-methoxyquinolin-4-yl)propyl]-1-[3-(3,4,5-trifluorophenyl)prop-2-ynyl]piperidine-4-carboxylic acid 4-[3-(3-Fluoro-6-methoxyquinolin-4-yl)propyl]-1-[3-(2,4,6-trifluorophenyl)propyl]piperidine-4-carboxylic acid 4-[3-(3-Fluoro-6-methoxyquinolin-4-yl)propyl]-1-[3-(3,4,5-trifluorophenyl)propyl]piperidine-4-carboxylic acid 4-[3-(3-Fluoro-6-methoxyquinolin-4-yl)propyl]-1-[2-(2,4,6-trifluorophenylthio)ethyl]-piperidine-4-carboxylic acid 4-[3-(3-Fluoro-6-methoxyquinolin-4-yl)propyl]-1-[2-(3,4,5-trifluorophenylthio)ethyl]-piperidine-4-carboxylic acid 4-[3-(3-Fluoro-6-methoxyquinolin-4-yl)propyl]-1-[2-(2,4,6-trifluorophenylamino)ethyl]-piperidine-4-carboxylic acid 4-[3-(3-Fluoro-6-methoxyquinolin-4-yl)propyl]-1-[2-(3,4,5-trifluorophenylamino)ethyl]-piperidine-4-carboxylic acid 4-[3-(3-Fluoro-6-methoxyquinolin-4-yl)propyl]-1-[2-(2,4,6-trifluorophenoxy)ethyl]-piperidine-4-carboxylic acid 4-[3-(3-Fluoro-6-methoxyquinolin-4-yl)propyl]-1-[2-(3,4,5-trifluorophenoxy)ethyl]-piperidine-4-carboxylic acid 4-[3-(3-Fluoro-6-methoxyquinolin-4-yl)propyl]-1-[3-(2,4,6-trifluorophenyl)prop-2-ynyl]piperidine-4-carboxylic acid 4-[3-(3-Fluoro-6-methoxyquinolin-4-yl)propyl]-1-[3-(3,4,5-trifluorophenyl)prop-2-ynyl]piperidine-4-carboxylic acid 4-[3-(3-Dimethylamino-6-methoxyquinolin-4-yl)propyl]-1-[3-(2,4,6-trifluorophenyl)-propyl]piperidine-4-carboxylic acid 4-[3-(3-Dimethylamino-6-methoxyquinolin-4-yl)propyl]-1-[3-(3,4,5-trifluorophenyl)-propyl]piperidine-4-carboxylic acid 4-[3-(3-Dimethylamino-6-methoxyquinolin-4-yl)propyl]-1-[2-(2,4,6-trifluorophenylthio)-ethyl]piperidine-4-carboxylic acid 4-[3-(3-Dimethylamino-6-methoxyquinolin-4-yl)propyl]-1-[2-(3,4,5-trifluorophenylthio)-ethyl]piperidine-4-carboxylic acid 4-[3-(3-Dimethylamino-6-methoxyquinolin-4-yl)propyl]-1-[2-(2,4,6-trifluorophenylamino)-ethyl]-piperidine-4-carboxylic acid 4-[3-(3-Dimethylamino-6-methoxyquinolin-4-yl)propyl]-1-[2-(3,4,5-trifluorophenylamino)-ethyl]-piperidine-4-carboxylic acid 4-[3-(3-Dimethylamino-6-methoxyquinolin-4-yl)propyl]-1-[2-(2,4,6-trifluorophenoxy)-ethyl]piperidine-4-carboxylic acid 4-[3-(3-Dimethylamino-6-methoxyquinolin-4-yl)propyl]-1-[2-(3,4,5-trifluorophenoxy)-ethyl]piperidine-4-carboxylic acid 4-[3-(3-Dimethylamino-6-methoxyquinolin-4-yl)propyl]-1-[3-(2,4,6-trifluorophenyl)prop-2-ynyl]piperidine-4-carboxylic acid 4-[3-(3-Dimethylamino-6-methoxyquinolin-4-yl)propyl]-1-[3-(3,4,5-trifluorophenyl)prop-2-ynyl]piperidine-4-carboxylic acid 4-[3-(3-Hydroxymethyl-6-methoxyquinolin-4-yl)propyl]-1-[3-(3,4,5-trifluorophenyl)propyl]piperidine-4-carboxylic acid 4-[3-(3-Hydroxymethyl-6-methoxyquinolin-4-yl)propyl]-1-[2-(2,4,6-trifluorophenylthio)ethyl]piperidine-4-carboxylic acid 4-[3-(3-Hydroxymethyl-6-methoxyquinolin-4-yl)propyl]-1-[2-(3,4,5-trifluorophenylthio)ethyl]piperidine-4-carboxylic acid 4-[3-(3-Hydroxymethyl-6-methoxyquinolin-4-yl)propyl]-1-[2-(2,4,6-trifluorophenylamino)ethyl]piperidine-4-carboxylic acid 4-[3-(3-Hydroxymethyl-6-methoxyquinolin-4-yl)propyl]-1-[2-(3,4,5-trifluorophenylamino)ethyl]piperidine-4-carboxylic acid 4-[3-(3-Hydroxymethyl-6-methoxyquinolin-4-yl)propyl]-1-[2-(2,4,6-trifluorophenoxy)-ethyl]piperidine-4-carboxylic acid 4-[3-(3-Hydroxymethyl-6-methoxyquinolin-4-yl)propyl]-1-[2-(3,4,5-trifluorophenoxy)-ethyl]piperidine-4-carboxylic acid 4-[3-(3-Hydroxymethyl-6-methoxyquinolin-4-yl)propyl]-1-[3-(2,4,6-trifluorophenyl)prop-2-ynyl]piperidine-4-carboxylic acid 4-[3-(3-Hydroxymethyl-6-methoxyquinolin-4-yl)propyl]-1-[3-(3,4,5-trifluorophenyl)prop-2-ynyl]piperidine-4-carboxylic acid 4-[3-(3-Fluoromethyl-6-methoxyquinolin-4-yl)propyl]-1-[3-(2,4,6-trifluorophenyl)propyl]piperidine-4-carboxylic acid 4-[3-(3-Fluoromethyl-6-methoxyquinolin-4-yl)propyl]-1-[3-(3,4,5-trifluorophenyl)propyl]piperidine-4-carboxylic acid 4-[3-(3-Fluoromethyl-6-methoxyquinolin-4-yl)propyl]-1-[2-(2,4,6-trifluorophenylthio)ethyl]piperidine-4-carboxylic acid 4-[3-(3-Fluoromethyl-6-methoxyquinolin-4-yl)propyl]-1-[2-(3,4,5-trifluorophenylthio)-ethyl]-piperidine-4-carboxylic acid 4-[3-(3-Fluoromethyl-6-methoxyquinolin-4-yl)propyl]-1-[2-(2,4,6-trifluorophenylamino)-ethyl]piperidine-4-carboxylic acid 4-[3-(3-Fluoromethyl-6-methoxyquinolin-4-yl)propyl]-1-[2-(3,4,5-trifluorophenylamino)-ethyl]piperidine-4-carboxylic acid 4-[3-(3-Fluoromethyl-6-methoxyquinolin-4-yl)propyl]-1-[2-(2,4,6-trifluorophenoxy)-ethyl]piperidine-4-carboxylic acid 4-[3-(3-Fluoromethyl-6-methoxyquinolin-4-yl)propyl]-1-[2-(3,4,5-trifluorophenoxy)-ethyl]piperidine-4-carboxylic acid 4-[3-(3-Fluoromethyl-6-methoxyquinolin-4-yl)propyl]-1-[3-(2,4,6-trifluorophenyl)prop-2-ynyl]piperidine-4-carboxylic acid 4-[3-(3-Fluoromethyl-6-methoxyquinolin-4-yl)propyl]-1-[3-(3,4,5-trifluorophenyl)prop-2-ynyl]piperidine-4-carboxylic acid 4-[3-(3-Aminomethyl-6-methoxyquinolin-4-yl)propyl]-1-[3-(2,4,6-trifluorophenyl)propyl]piperidine-4-carboxylic acid 4-[3-(3-Aminomethyl-6-methoxyquinolin-4-yl)propyl]-1-[3-(3,4,5-trifluorophenyl)propyl]piperidine-4-carboxylic acid 4-[3-(3-Aminomethyl-6-methoxyquinolin-4-yl)propyl]-1-[2-(2,4,6-trifluorophenylthio)ethyl]piperidine-4-carboxylic acid 4-[3-(3-Aminomethyl-6-methoxyquinolin-4-yl)propyl]-1-[2-(3,4,5-trifluorophenylthio)ethyl]piperidine-4-carboxylic acid 4-[3-(3-Aminomethyl-6-methoxyquinolin-4-yl)propyl]-1-[2-(2,4,6-trifluorophenylamino)ethyl]piperidine-4-carboxylic acid 4-[3-(3-Aminomethyl-6-methoxyquinolin-4-yl)propyl]-1-[2-(3,4,5-trifluorophenylamino)ethyl]piperidine-4-carboxylic acid 4-[3-(3-Aminomethyl-6-methoxyquinolin-4-yl)propyl]-1-[2-(2,4,6-trifluorophenoxy)ethyl]piperidine-4-carboxylic acid 4-[3-(3-Aminomethyl-6-methoxyquinolin-4-yl)propyl]-1-[2-(3,4,5-trifluorophenoxy)ethyl]piperidine-4-carboxylic acid 4-[3-(3-Aminomethyl-6-methoxyquinolin-4-yl)propyl]-1-[3-(2,4,6-trifluorophenyl)prop-2-ynyl]piperidine-4-carboxylic acid 4-[3-(3-Aminomethyl-6-methoxyquinolin-4-yl)propyl]-1-[3-(3,4,5-trifluorophenyl)prop-2-ynyl]piperidine-4-carboxylic acid 4-[3-(3-Morpholinomethyl-6-methoxyquinolin-4-yl)propyl]-1-[3-(2,4,6-trifluorophenyl)-propyl]piperidine-4-carboxylic acid 4-[3-(3-Morpholinomethyl-6-methoxyquinolin-4-yl)propyl]-1-[3-(3,4,5-trifluorophenyl)-propyl]piperidine-4-carboxylic acid 4-[3-(3-Morpholinomethyl-6-methoxyquinolin-4-yl)propyl]-1-[2-(2,4,6-trifluorophenylthio)-ethyl]piperidine-4-carboxylic acid 4-[3-(3-Morpholinomethyl-6-methoxyquinolin-4-yl)propyl]-1-[2-(3,4,5-trifluorophenylthio)-ethyl]piperidine-4-carboxylic acid 4-[3-(3-Morpholinomethyl-6-methoxyquinolin-4-yl)propyl]-1-[2-(2,4,6-trifluorophenylamino)ethyl]piperidine-4-carboxylic acid 4-[3-(3-Morpholinomethyl-6-methoxyquinolin-4-yl)propyl]-1-[2-(3,4,5-trifluorophenylamino)ethyl]piperidine-4-carboxylic acid 4-[3-(3-Morpholinomethyl-6-methoxyquinolin-4-yl)propyl]-1-[2-(2,4,6-trifluorophenoxy)-ethyl]piperidine-4-carboxylic acid 4-[3-(3-Morpholinomethyl-6-methoxyquinolin-4-yl)propyl]-1-[2-(3,4,5-trifluorophenoxy)ethyl]piperidine-4-carboxylic acid 4-[3-(3-Morpholinomethyl-6-methoxyquinolin-4-yl)propyl]-1-[3-(2,4,6-trifluorophenyl)-prop-2-ynyl]piperidine-4-carboxylic acid 4-[3-(3-Morpholinomethyl-6-methoxyquinolin-4-yl)propyl]-1-[3-(3,4,5-trifluorophenyl)-prop-2-ynyl]piperidine-4-carboxylic acid 4-[3-(R,S)-Hydroxy-3-(3-chloro-6-methoxyquinolin-4-yl)propyl]-1-heptylpiperidine-4-carboxylic acid 4-[3-(R,S)-Hydroxy-3-(3-chloro-6-methoxyquinolin-4-yl)propyl]-1-[4-phenylbutyl]piperidine-4-carboxylic acid 4-[3-(R,S)-Hydroxy-3-(3-chloro-6-methoxyquinolin-4-yl)propyl]-1-[3-(phenyl)propyl]piperidine-4-carboxylic acid 4-[3-(R,S)-Hydroxy-3-(3-chloro-6-methoxyquinolin-4-yl)propyl]-1-[4-(2-fluorophenyl)propyl]piperidine-4-carboxylic acid 4-[3-(R,S)-Hydroxy-3-(3-chloro-6-methoxyquinolin-4-yl)propyl]-1-[4-(3-fluorophenyl)propyl]piperidine-4-carboxylic acid 4-[3-(R,S)-Hydroxy-3-(3-chloro-6-methoxyquinolin-4-yl)propyl]-1-[3-(4-fluorophenyl)propyl]piperidine-4-carboxylic acid 4-[3-(R,S)-Hydroxy-3-(3-chloro-6-methoxyquinolin-4-yl)propyl]-1-[4-(4-fluorophenyl)butyl]piperidine-4-carboxylic acid 4-[3-(R,S)-Hydroxy-3-(3-chloro-6-methoxyquinolin-4-yl)propyl]-1-[3-(2,3-difluorophenyl)propyl]piperidine-4-carboxylic acid 4-[3-(R,S)-Hydroxy-3-(3-chloro-6-methoxyquinolin-4-yl)propyl]-1-[4-(2,3-difluorophenyl)propyl]piperidine-4-carboxylic acid 4-[3-(R,S)-Hydroxy-3-(3-chloro-6-methoxyquinolin-4-yl)propyl]-1-[3-(2,6-difluorophenyl)propyl]piperidine-4-carboxylic acid 4-[3-(R,S)-Hydroxy-3-(3-chloro-6-methoxyquinolin-4-yl)propyl]-1-[4-(2,6-difluorophenyl)propyl]piperidine-4-carboxylic acid 4-[3-(R,S)-Hydroxy-3-(3-chloro-6-methoxyquinolin-4-yl)propyl]-1-[3-(3,5-difluorophenyl)propyl]piperidine-4-carboxylic acid 4-[3-(R,S)-Hydroxy-3-(3-chloro-6-methoxyquinolin-4-yl)propyl]-1-[3-(2,3,5-trifluorophenyl)propyl]piperidine-4-carboxylic acid 4-[3-(R,S)-Hydroxy-3-(3-chloro-6-methoxyquinolin-4-yl)propyl]-1-[3-phenylthio-propyl]piperidine-4-carboxylic acid 4-[3-(R,S)-Hydroxy-3-(3-chloro-6-methoxyquinolin-4-yl)propyl]-1-[3-(2-fluorophenylthio)propyl]piperidine-4-carboxylic acid 4-[3-(R,S)-Hydroxy-3-(3-chloro-6-methoxyquinolin-4-yl)propyl]-1-[3-(3-fluorophenylthio)propyl]piperidine-4-carboxylic acid 4-[3-(R,S)-Hydroxy-3-(3-chloro-6-methoxyquinolin-4-yl)propyl]-1-[2-(4-fluorophenylthio)ethyl]piperidine-4-carboxylic acid 4-[3-(R,S)-Hydroxy-3-(3-chloro-6-methoxyquinolin-4-yl)propyl]-1-[3-(4-fluorophenylthio)propyl]piperidine-4-carboxylic acid 4-[3-(R,S)-Hydroxy-3-(3-chloro-6-methoxyquinolin-4-yl)propyl]-1-[2-(2,3-difluorophenylthio)ethyl]piperidine-4-carboxylic acid 4-[3-(R,S)-Hydroxy-3-(3-chloro-6-methoxyquinolin-4-yl)propyl]-1-[3-(2,3-difluorophenylthio)propyl]piperidine-4-carboxylic acid 4-[3-(R,S)-Hydroxy-3-(3-chloro-6-methoxyquinolin-4-yl)propyl]-1-[2-(2,6-difluorophenylthio)ethyl]piperidine-4-carboxylic acid 4-[3-(R,S)-Hydroxy-3-(3-chloro-6-methoxyquinolin-4-yl)propyl]-1-[2-(2,3,5-trifluorophenylthio)ethyl]piperidine-4-carboxylic acid 4-[3-(R,S)-Hydroxy-3-(3-chloro-6-methoxyquinolin-4-yl)propyl]-1-[2-(2,4,6-trifluorophenylthio)ethyl]piperidine-4-carboxylic acid 4-[3-(R,S)-Hydroxy-3-(3-chloro-6-methoxyquinolin-4-yl)propyl]-1-[2-(3,4,5-trifluorophenylthio)ethyl]piperidine-4-carboxylic acid 4-[3-(R,S)-Hydroxy-3-(3-chloro-6-methoxyquinolin-4-yl)propyl]-1-[2-(3,5-difluorophenoxy)ethyl]piperidine-4-carboxylic acid 4-[3-(R,S)-Hydroxy-3-(3-chloro-6-methoxyquinolin-4-yl)propyl]-1-[2-(2,3,5-trifluorophenoxy)ethyl]piperidine-4-carboxylic acid 4-[3-(R,S)-Hydroxy-3-(3-chloro-6-methoxyquinolin-4-yl)propyl]-1-[2-(2,4,6-trifluorophenoxy)ethyl]piperidine-4-carboxylic acid 4-[3-(R,S)-Hydroxy-3-(3-chloro-6-methoxyquinolin-4-yl)propyl]-1-[2-(3,4,5-trifluorophenoxy)ethyl]piperidine-4-carboxylic acid 4-[3-(R,S)-Hydroxy-3-(3-chloro-6-methoxyquinolin-4-yl)propyl]-1-[2-(3,5-difluorophenylamino)ethyl]piperidine-4-carboxylic acid 4-[3-(R,S)-Hydroxy-3-(3-chloro-6-methoxyquinolin-4-yl)propyl]-1-[2-(2,3,5-trifluorophenylamino)ethyl]piperidine-4-carboxylic acid 4-[3-(R,S)-Hydroxy-3-(3-chloro-6-methoxyquinolin-4-yl)propyl]-1-[2-(2,4,6-trifluorophenylamino)ethyl]piperidine-4-carboxylic acid 4-[3-(R,S)-Hydroxy-3-(3-chloro-6-methoxyquinolin-4-yl)propyl]-1-[2-(3,4,5-trifluorophenylamino)ethyl]piperidine-4-carboxylic acid 4-[3-(R,S)-Hydroxy-3-(3-chloro-6-methoxyquinolin-4-yl)propyl]-1-[3-(2,6-difluorophenylthio)propyl]piperidine-4-carboxylic acid 4-[3-(R,S)-Hydroxy-3-(3-chloro-6-methoxyquinolin-4-yl)propyl]-1-[2-(2-chlorophenylthio)ethyl]piperidine-4-carboxylic acid 4-[3-(R,S)-Hydroxy-3-(3-chloro-6-methoxyquinolin-4-yl)propyl]-1-[3-(2-chlorophenylthio)propyl]piperidine-4-carboxylic acid 4-[3-(R,S)-Hydroxy-3-(3-chloro-6-methoxyquinolin-4-yl)propyl]-1-[2-(3-chlorophenylthio)ethyl]piperidine-4-carboxylic acid 4-[3-(R,S)-Hydroxy-3-(3-chloro-6-methoxyquinolin-4-yl)propyl]-1-[3-(3-chlorophenylthio)propyl]piperidine-4-carboxylic acid 4-[3-(R,S)-Hydroxy-3-(3-chloro-6-methoxyquinolin-4-yl)propyl]-1-[2-(4-chlorophenylthio)ethyl]piperidine-4-carboxylic acid 4-[3-(R,S)-Hydroxy-3-(3-chloro-6-methoxyquinolin-4-yl)propyl]-1-[3-(4-chlorophenylthio)propyl]piperidine-4-carboxylic acid 4-[3-(R,S)-Hydroxy-3-(3-chloro-6-methoxyquinolin-4-yl)propyl]-1-[2-(2-methylphenylthio)ethyl]piperidine-4-carboxylic acid 4-[3-(R,S)-Hydroxy-3-(3-chloro-6-methoxyquinolin-4-yl)propyl]-1-[3-(2-methylphenylthio)propyl]piperidine-4-carboxylic acid 4-[3-(R,S)-Hydroxy-3-(3-chloro-6-methoxyquinolin-4-yl)propyl]-1-[2-(3-methylphenylthio)ethyl]piperidine-4-carboxylic acid 4-[3-(R,S)-Hydroxy-3-(3-chloro-6-methoxyquinolin-4-yl)propyl]-1-[3-(3-methylphenylthio)propyl]piperidine-4-carboxylic acid 4-[3-(R,S)-Hydroxy-3-(3-chloro-6-methoxyquinolin-4-yl)propyl]-1-[2-(4-methylphenylthio)ethyl]piperidine-4-carboxylic acid 4-[3-(R,S)-Hydroxy-3-(3-chloro-6-methoxyquinolin-4-yl)propyl]-1-[3-(4-methylphenylthio)propyl]piperidine-4-carboxylic acid 4-[3-(R,S)-Hydroxy-3-(3-chloro-6-methoxyquinolin-4-yl)propyl]-1-[2-(2-trifluoromethylphenylthio)ethyl]piperidine-4-carboxylic acid 4-[3-(R,S)-Hydroxy-3-(3-chloro-6-methoxyquinolin-4-yl)propyl]-1-[3-(2-trifluoromethylphenylthio)propyl]piperidine-4-carboxylic acid 4-[3-(R,S)-Hydroxy-3-(3-chloro-6-methoxyquinolin-4-yl)propyl]-1-[2-(3-trifluoromethylphenylthio)ethyl]piperidine-4-carboxylic acid 4-[3-(R,S)-Hydroxy-3-(3-chloro-6-methoxyquinolin-4-yl)propyl]-1-[3-(3-trifluoromethylphenylthio)propyl]piperidine-4-carboxylic acid 4-[3-(R,S)-Hydroxy-3-(3-chloro-6-methoxyquinolin-4-yl)propyl]-1-[2-(4-trifluoromethylphenylthio)ethyl]piperidine-4-carboxylic acid 4-[3-(R,S)-Hydroxy-3-(3-chloro-6-methoxyquinolin-4-yl)propyl]-1-[3-(4-trifluoromethylphenylthio)propyl]piperidine-4-carboxylic acid 4-[3-(R,S)-Hydroxy-3-(3-chloro-6-methoxyquinolin-4-yl)propyl]-1-[2-(2-methoxyphenylthio)ethyl]piperidine-4-carboxylic acid 4-[3-(R,S)-Hydroxy-3-(3-chloro-6-methoxyquinolin-4-yl)propyl]-1-[3-(2-methoxyphenylthio)propyl]piperidine-4-carboxylic acid 4-[3-(R,S)-Hydroxy-3-(3-chloro-6-methoxyquinolin-4-yl)propyl]-1-[2-(3-methoxyphenylthio)ethyl]piperidine-4-carboxylic acid 4-[3-(R,S)-Hydroxy-3-(3-chloro-6-methoxyquinolin-4-yl)propyl]-1-[3-(3-methoxyphenylthio)propyl]piperidine-4-carboxylic acid 4-[3-(R,S)-Hydroxy-3-(3-chloro-6-methoxyquinolin-4-yl)propyl]-1-[2-(4-methoxyphenylthio)ethyl]piperidine-4-carboxylic acid 4-[3-(R,S)-Hydroxy-3-(3-chloro-6-methoxyquinolin-4-yl)propyl]-1-[3-(4-methoxyphenylthio)propyl]piperidine-4-carboxylic acid 4-[3-(R,S)-Hydroxy-3-(3-chloro-6-methoxyquinolin-4-yl)propyl]-1-[cyclopentylmethyl]piperidine-4-carboxylic acid 4-[3-(R,S)-Hydroxy-3-(3-chloro-6-methoxyquinolin-4-yl)propyl]-1-[2-(cyclopentyl)ethyl]piperidine-4-carboxylic acid 4-[3-(R,S)-Hydroxy-3-(3-chloro-6-methoxyquinolin-4-yl)propyl]-1-[2-(cyclohexyl)ethyl]piperidine-4-carboxylic acid 4-[3-(R,S)-Hydroxy-3-(3-chloro-6-methoxyquinolin-4-yl)propyl]-1-[2-(cyclopentylthio)ethyl]piperidine-4-carboxylic acid 4-[3-(R,S)-Hydroxy-3-(3-chloro-6-methoxyquinolin-4-yl)propyl]-1-[3-(cyclopentylthio)propyl]piperidine-4-carboxylic acid 4-[3-(R,S)-Hydroxy-3-(3-chloro-6-methoxyquinolin-4-yl)propyl]-1-[3-(cyclohexylthio)propyl]piperidine-4-carboxylic acid 4-[3-(R,S)-Hydroxy-3-(3-chloro-6-methoxyquinolin-4-yl)propyl]-1-[2-(pyrid-2-yl)thioethyl]piperidine-4-carboxylic acid 4-[3-(R,S)-Hydroxy-3-(3-chloro-6-methoxyquinolin-4-yl)propyl]-1-[4-(thien-2-yl)butyl]piperidine-4-carboxylic acid 4-[3-(R,S)-Hydroxy-3-(3-chloro-6-methoxyquinolin-4-yl)propyl]-1-[3-(thien-2-yl)thiopropyl]piperidine-4-carboxylic acid 4-[3-(R,S)-Hydroxy-3-(3-chloro-6-methoxyquinolin-4-yl)propyl]-1-[3-(thien-3-yl)propyl]piperidine-4-carboxylic acid 4-[3-(R,S)-Hydroxy-3-(3-chloro-6-methoxyquinolin-4-yl)propyl]-1-[4-(thien-3-yl)butyl]piperidine-4-carboxylic acid 4-[3-(R,S)-Hydroxy-3-(3-chloro-6-methoxyquinolin-4-yl)propyl]-1-[2-(thien-2-yl)thioethyl]piperidine-4-carboxylic acid 4-[3-(R,S)-Hydroxy-3-(3-chloro-6-methoxyquinolin-4-yl)propyl]-1-[2-(thien-3-yl)thioethyl]piperidine-4-carboxylic acid 4-[3-(R,S)-Hydroxy-3-(3-chloro-6-methoxyquinolin-4-yl)propyl]-1-[3-(thien-3-yl)thiopropyl]piperidine-4-carboxylic acid 4-[3-(R,S)-Hydroxy-3-(3-chloro-6-methoxyquinolin-4-yl)propyl]-1-[3-(1,3-thiazol-2-yl)propyl]piperidine-4-carboxylic acid 4-[3-(R,S)-Hydroxy-3-(3-chloro-6-methoxyquinolin-4-yl)propyl]-1-[4-(1,3-thiazol-2-yl)butyl]piperidine-4-carboxylic acid 4-[3-(R,S)-Hydroxy-3-(3-chloro-6-methoxyquinolin-4-yl)propyl]-1-[3-(1,3-thiazol-2-yl)thioethyl]piperidine-4-carboxylic acid 4-[3-(R,S)-Hydroxy-3-(3-chloro-6-methoxyquinolin-4-yl)propyl]-1-[3-(pyrid-2-yl)propyl]piperidine-4-carboxylic acid 4-[3-(R,S)-Hydroxy-3-(3-chloro-6-methoxyquinolin-4-yl)propyl]-1-[4-(pyrid-2-yl)butyl]piperidine-4-carboxylic acid 4-[3-(R,S)-Hydroxy-3-(3-chloro-6-methoxyquinolin-4-yl)propyl]-1-[3-(pyrid-2-yl)thiopropyl]piperidine-4-carboxylic acid 4-[3-(R,S)-Hydroxy-3-(3-chloro-6-methoxyquinolin-4-yl)propyl]-1-[3-(pyrid-3-yl)propyl]piperidine-4-carboxylic acid 4-[3-(R,S)-Hydroxy-3-(3-chloro-6-methoxyquinolin-4-yl)propyl]-1-[4-(pyrid-3-yl)butyl]piperidine-4-carboxylic acid 4-[3-(R,S)-Hydroxy-3-(3-chloro-6-methoxyquinolin-4-yl)propyl]-1-[2-(pyrid-3-yl)thioethyl]piperidine-4-carboxylic acid 4-[3-(R,S)-Hydroxy-3-(3-chloro-6-methoxyquinolin-4-yl)propyl]-1-[3-(pyrid-3-yl)thiopropyl]piperidine-4-carboxylic acid 4-[3-(R,S)-Hydroxy-3-(3-chloro-6-methoxyquinolin-4-yl)propyl]-1-[3-(pyrid-4-yl)propyl]piperidine-4-carboxylic acid 4-[3-(R,S)-Hydroxy-3-(3-chloro-6-methoxyquinolin-4-yl)propyl]-1-[4-(pyrid-4-yl)butyl]piperidine-4-carboxylic acid 4-[3-(R,S)-Hydroxy-3-(3-chloro-6-methoxyquinolin-4-yl)propyl]-1-[2-(pyrid-4-yl)thioethyl]piperidine-4-carboxylic acid 4-[3-(R,S)-Hydroxy-3-(3-chloro-6-methoxyquinolin-4-yl)propyl]-1-[3-(pyrid-4-yl)thiopropyl]piperidine-4-carboxylic acid 4-[3-(R,S)-Hydroxy-3-(3-chloro-6-methoxyquinolin-4-yl)propyl]-1-[3-(pyrazin-2-yl)propyl]piperidine-4-carboxylic acid 4-[3-(R,S)-Hydroxy-3-(3-chloro-6-methoxyquinolin-4-yl)propyl]-1-[4-(pyrazin-2-yl)butyl]piperidine-4-carboxylic acid 4-[3-(R,S)-Hydroxy-3-(3-chloro-6-methoxyquinolin-4-yl)propyl]-1-[2-(pyrazin-2-yl)thioethyl]piperidine-4-carboxylic acid 4-[3-(R,S)-Hydroxy-3-(3-chloro-6-methoxyquinolin-4-yl)propyl]-1-[3-(pyrazin-2-yl)thiopropyl]piperidine-4-carboxylic acid 4-[3-(R,S)-Hydroxy-3-(3-chloro-6-methoxyquinolin-4-yl)propyl]-1-[3-(4-fluorophenyl)prop-2-ynyl]piperidine-4-carboxylic acid 4-[3-(R,S)-Hydroxy-3-(3-chloro-6-methoxyquinolin-4-yl)propyl]-1-[3-(3,4-difluorophenyl)prop-2-ynyl]piperidine-4-carboxylic acid 4-[3-(R,S)-Hydroxy-3-(3-chloro-6-methoxyquinolin-4-yl)propyl]-1-[3-(2,4-difluorophenyl)prop-2-ynyl]piperidine-4-carboxylic acid 4-[3-(R,S)-Hydroxy-3-(3-chloro-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-chloro-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-chloro-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-chloro-6-methoxyquinolin-4-yl)propyl]-1-[3-(4-chloro-3-fluorophenyl)prop-2-ynyl]piperidine-4-carboxylic acid 4-[3-(R,S)-Hydroxy-3-(3-chloro-6-methoxyquinolin-4-yl)propyl]-1-[3-(3-chloro-4-fluorophenyl)prop-2-ynyl]piperidine-4-carboxylic acid 4-[3-(R,S)-Hydroxy-3-(3-chloro-6-methoxyquinolin-4-yl)propyl]-1-[3-(2-chloro-4-fluorophenyl)prop-2-ynyl]piperidine-4-carboxylic acid 4-[3-(R,S)-Hydroxy-3-(3-chloro-6-methoxyquinolin-4-yl)propyl]-1-[3-(3-chloro-5-fluorophenyl)prop-2-ynyl]piperidine-4-carboxylic acid 4-[3-(R,S)-Hydroxy-3-(3-chloro-6-methoxyquinolin-4-yl)propyl]-1-[3-(4-chloro-2-fluorophenyl)prop-2-ynyl]piperidine-4-carboxylic acid 4-[3-(R,S)-Hydroxy-3-(3-chloro-6-methoxyquinolin-4-yl)propyl]-1-[3-(3-fluoro-4-methylphenyl)prop-2-ynyl]piperidine-4-carboxylic acid 4-[3-(R,S)-Hydroxy-3-(3-chloro-6-methoxyquinolin-4-yl)propyl]-1-[3-(3,5-bis(trifluoromethyl)phenyl)prop-2-ynyl]piperidine-4-carboxylic acid 4-[3-(R,S)-Hydroxy-3-(3-chloro-6-methoxyquinolin-4-yl)propyl]-1-[3-(thien-2-yl)prop-2-ynyl]piperidine-4-carboxylic acid 4-[3-(R,S)-Hydroxy-3-(3-chloro-6-methoxyquinolin-4-yl)propyl]-1-[3-(thien-3-yl)prop-2-ynyl]piperidine-4-carboxylic acid 4-[3-(R,S)-Hydroxy-3-(3-chloro-6-methoxyquinolin-4-yl)propyl]-1-[3-(1,3-thiazol-2-yl)prop-2-ynyl]piperidine-4-carboxylic acid 4-[3-(R,S)-Hydroxy-3-(3-chloro-6-methoxyquinolin-4-yl)propyl]-1-[3-(1,3-thiazol-4-yl)prop-2-ynyl]piperidine-4-carboxylic acid 4-[3-(R,S)-Hydroxy-3-(3-chloro-6-methoxyquinolin-4-yl)propyl]-1-[3-(1,3-thiazol-5-yl)prop-2-ynyl]piperidine-4-carboxylic acid 4-[3-(R,S)-Hydroxy-3-(3-chloro-6-methoxyquinolin-4-yl)propyl]-1-[3-(pyrid-2-yl)prop-2-ynyl]piperidine-4-carboxylic acid 4-[3-(R,S)-Hydroxy-3-(3-chloro-6-methoxyquinolin-4-yl)propyl]-1-[3-(pyrid-3-yl)prop-2-ynyl]piperidine-4-carboxylic acid 4-[3-(R,S)-Hydroxy-3-(3-chloro-6-methoxyquinolin-4-yl)propyl]-1-[3-(pyrid-4-yl)prop-2-ynyl]piperidine-4-carboxylic acid 4-[3-(R,S)-Hydroxy-3-(3-methyl-6-methoxyquinolin-4-yl)propyl]-1-[2-(cyclohexyl)ethyl]piperidine-4-carboxylic acid 4-[3-(R,S)-Hydroxy-3-(3-methyl-6-methoxyquinolin-4-yl)propyl]-1-[3-(phenyl)propyl]piperidine-4-carboxylic acid 4-[3-(R,S)-Hydroxy-3-(3-methyl-6-methoxyquinolin-4-yl)propyl]-1-[3-(2,3,5-trifluorophenyl)propyl]piperidine-4-carboxylic acid 4-[3-(R,S)-Hydroxy-3-(3-methyl-6-methoxyquinolin-4-yl)propyl]-1-[2-(3,5-difluorophenylamino)ethyl]piperidine-4-carboxylic acid 4-[3-(R,S)-Hydroxy-3-(3-methyl-6-methoxyquinolin-4-yl)propyl]-1-[2-(2,3,5-trifluorophenylamino)ethyl]piperidine-4-carboxylic acid 4-[3-(R,S)-Hydroxy-3-(3-methyl-6-methoxyquinolin-4-yl)propyl]-1-[2-(3,5-difluorophenoxy)ethyl]piperidine-4-carboxylic acid 4-[3-(R,S)-Hydroxy-3-(3-methyl-6-methoxyquinolin-4-yl)propyl]-1-[2-(2,3,5-trifluorophenoxy)ethyl]piperidine-4-carboxylic acid 4-[3-(R,S)-Hydroxy-3-(3-methyl-6-methoxyquinolin-4-yl)propyl]-1-[2-(2,3,5-trifluorophenylthio)ethyl]piperidine-4-carboxylic acid 4-[3-(R,S)-Hydroxy-3-(3-methyl-6-methoxyquinolin-4-yl)propyl]-1-[2-(cyclopentylthio)ethyl]piperidine-4-carboxylic acid 4-[3-(R,S)-Hydroxy-3-(3-methyl-6-methoxyquinolin-4-yl)propyl]-1-[2-(pyrid-2-yl)thioethyl]piperidine-4-carboxylic acid 4-[3-(R,S)-Hydroxy-3-(3-methyl-6-methoxyquinolin-4-yl)propyl]-1-[2-(thien-2-yl)thioethyl]piperidine-4-carboxylic acid 4-[3-(R,S)-Hydroxy-3-(3-methyl-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-methyl-6-methoxyquinolin-4-yl)propyl]-1-[3-(thien-2-yl)prop-2-ynyl]piperidine-4-carboxylic acid 4-[3-(R,S)-Hydroxy-3-(3-fluoro-6-methoxyquinolin-4-yl)propyl]-1-[2-(cyclohexyl)ethyl]piperidine-4-carboxylic acid 4-[3-(R,S)-Hydroxy-3-(3-fluoro-6-methoxyquinolin-4-yl)propyl]-1-[3-(phenyl)propyl]piperidine-4-carboxylic acid 4-[3-(R,S)-Hydroxy-3-(3-fluoro-6-methoxyquinolin-4-yl)propyl]-1-[3-(2,3,5-trifluorophenyl)propyl]piperidine-4-carboxylic acid 4-[3-(R,S)-Hydroxy-3-(3-fluoro-6-methoxyquinolin-4-yl)propyl]-1-[2-(3,5-difluorophenylamino)ethyl]piperidine-4-carboxylic acid 4-[3-(R,S)-Hydroxy-3-(3-fluoro-6-methoxyquinolin-4-yl)propyl]-1-[2-(2,3,5-trifluorophenylamino)ethyl]piperidine-4-carboxylic acid 4-[3-(R,S)-Hydroxy-3-(3-fluoro-6-methoxyquinolin-4-yl)propyl]-1-[2-(2,3,5-trifluorophenoxy)ethyl]piperidine-4-carboxylic acid 4-[3-(R,S)-Hydroxy-3-(3-fluoro-6-methoxyquinolin-4-yl)propyl]-1-[2-(2,3,5-trifluorophenylthio)ethyl]piperidine-4-carboxylic acid 4-[3-(R,S)-Hydroxy-3-(3-fluoro-6-methoxyquinolin-4-yl)propyl]-1-[2-(cyclopentylthio)ethyl]piperidine-4-carboxylic acid 4-[3-(R,S)-Hydroxy-3-(3-fluoro-6-methoxyquinolin-4-yl)propyl]-1-[2-(pyrid-2-yl)thioethyl]piperidine-4-carboxylic acid 4-[3-(R,S)-Hydroxy-3-(3-fluoro-6-methoxyquinolin-4-yl)propyl]-1-[2-(thien-2-yl)thioethyl]piperidine-4-carboxylic acid 4-[3-(R,S)-Hydroxy-3-(3-fluoro-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-fluoro-6-methoxyquinolin-4-yl)propyl]-1-[3-(thien-2-yl)prop-2-ynyl]piperidine-4-carboxylic acid 4-[3-(R,S)-Hydroxy-3-(3-dimethylamino-6-methoxyquinolin-4-yl)propyl]-1-[2-(cyclohexyl)ethyl]piperidine-4-carboxylic acid 4-[3-(R,S)-Hydroxy-3-(3-dimethylamino-6-methoxyquinolin-4-yl)propyl]-1-[3-(phenyl)propyl]piperidine-4-carboxylic acid 4-[3-(R,S)-Hydroxy-3-(3-dimethylamino-6-methoxyquinolin-4-yl)propyl]-1-[3-(2,3,5-trifluorophenyl)propyl]piperidine-4-carboxylic acid 4-[3-(R,S)-Hydroxy-3-(3-dimethylamino-6-methoxyquinolin-4-yl)propyl]-1-[2-(3,5-difluorophenylamino)ethyl]piperidine-4-carboxylic acid 4-[3-(R,S)-Hydroxy-3-(3-dimethylamino-6-methoxyquinolin-4-yl)propyl]-1-[2-(2,3,5-trifluorophenylamino)ethyl]piperidine-4-carboxylic acid 4-[3-(R,S)-Hydroxy-3-(3-dimethylamino-6-methoxyquinolin-4-yl)propyl]-1-[2-(3,5-difluorophenoxy)ethyl]piperidine-4-carboxylic acid 4-[3-(R,S)-Hydroxy-3-(3-dimethylamino-6-methoxyquinolin-4-yl)propyl]-1-[2-(2,3,5-trifluorophenoxy)ethyl]piperidine-4-carboxylic acid 4-[3-(R,S)-Hydroxy-3-(3-dimethylamino-6-methoxyquinolin-4-yl)propyl]-1-[2-(2,3,5-trifluorophenylthio)ethyl]piperidine-4-carboxylic acid 4-[3-(R,S)-Hydroxy-3-(3-dimethylamino-6-methoxyquinolin-4-yl)propyl]-1-[2-(cyclopentylthio)ethyl]piperidine-4-carboxylic acid 4-[3-(R,S)-Hydroxy-3-(3-dimethylamino-6-methoxyquinolin-4-yl)propyl]-1-[2-(pyrid-2-yl)thioethyl]piperidine-4-carboxylic acid 4-[3-(R,S)-Hydroxy-3-(3-dimethylamino-6-methoxyquinolin-4-yl)propyl]-1-[2-(thien-2-yl)thioethyl]piperidine-4-carboxylic acid 4-[3-(R,S)-Hydroxy-3-(3-dimethylamino-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-dimethylamino-6-methoxyquinolin-4-yl)propyl]-1-[3-(thien-2-yl)prop-2-ynyl]piperidine-4-carboxylic acid 4-[3-(R,S)-Hydroxy-3-(3-hydroxymethyl-6-methoxyquinolin-4-yl)propyl]-1-[2-(cyclohexyl)ethyl]piperidine-4-carboxylic acid 4-[3-(R,S)-Hydroxy-3-(3-hydroxymethyl-6-methoxyquinolin-4-yl)propyl]-1-[3-(phenyl)propyl]piperidine-4-carboxylic acid 4-[3-(R,S)-Hydroxy-3-(3-hydroxymethyl-6-methoxyquinolin-4-yl)propyl]-1-[3-(2,3,5-trifluorophenyl)propylpiperidine-4-carboxylic acid 4-[3-(R,S)-Hydroxy-3-(3-hydroxymethyl-6-methoxyquinolin-4-yl)propyl]-1-[2-(3,5-difluorophenylamino)ethyl]piperidine-4-carboxylic acid 4-[3-(R,S)-Hydroxy-3-(3-hydroxymethyl-6-methoxyquinolin-4-yl)propyl]-1-[2-(2,3,5-trifluorophenylamino)ethyl]piperidine-4-carboxylic acid 4-[3-(R,S)-Hydroxy-3-(3-hydroxymethyl-6-methoxyquinolin-4-yl)propyl]-1-[2-(3,5-difluorophenoxy)ethyl]piperidine-4-carboxylic acid 4-[3-(R,S)-Hydroxy-3-(3-hydroxymethyl-6-methoxyquinolin-4-yl)propyl]-1-[2-(2,3,5-trifluorophenoxy)ethyl]piperidine-4-carboxylic acid 4-[3-(R,S)-Hydroxy-3-(3-hydroxymethyl-6-methoxyquinolin-4-yl)propyl]-1-[2-(2,3,5-trifluorophenylthio)ethyl]piperidine-4-carboxylic acid 4-[3-(R,S)-Hydroxy-3-(3-hydroxymethyl-6-methoxyquinolin-4-yl)propyl]-1-[2-(cyclopentylthio)ethyl]piperidine-4-carboxylic acid 4-[3-(R,S)-Hydroxy-3-(3-hydroxymethyl-6-methoxyquinolin-4-yl)propyl]-1-[2-(pyrid-2-yl)thioethyl]piperidine-4-carboxylic acid 4-[3-(R,S)-Hydroxy-3-(3-hydroxymethyl-6-methoxyquinolin-4-yl)propyl]-1-[2-(thien-2-yl)thioethyl]piperidine-4-carboxylic acid 4-[3-(R,S)-Hydroxy-3-(3-hydroxymethyl-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-hydroxymethyl-6-methoxyquinolin-4-yl)propyl]-1-[3-(thien-2-yl)prop-2-ynyl]piperidine-4-carboxylic acid 4-[3-(R,S)-Hydroxy-3-(3-fluoromethyl-6-methoxyquinolin-4-yl)propyl]-1-[2-(cyclohexyl)ethyl]piperidine-4-carboxylic acid 4-[3-(R,S)-Hydroxy-3-(3-fluoromethyl-6-methoxyquinolin-4-yl)propyl]-1-[3-(phenyl)propyl]piperidine-4-carboxylic acid 4-[3-(R,S)-Hydroxy-3-(3-fluoromethyl-6-methoxyquinolin-4-yl)propyl]-1-[3-(2,3,5-trifluorophenyl)propyl]piperidine-4-carboxylic acid 4-[3-(R,S)-Hydroxy-3-(3-fluoromethyl-6-methoxyquinolin-4-yl)propyl]-1-[2-(3,5-difluorophenylamino)ethyl]piperidine-4-carboxylic acid 4-[3-(R,S)-Hydroxy-3-(3-fluoromethyl-6-methoxyquinolin-4-yl)propyl]-1-[2-(2,3,5-trifluorophenylamino)ethyl]piperidine-4-carboxylic acid 4-[3-(R,S)-Hydroxy-3-(3-fluoromethyl-6-methoxyquinolin-4-yl)propyl]-1-[2-(3,5-difluorophenoxy)ethyl]piperidine-4-carboxylic acid 4-[3-(R,S)-Hydroxy-3-(3-fluoromethyl-6-methoxyquinolin-4-yl)propyl]-1-[2-(2,3,5-trifluorophenoxy)ethyl]piperidine-4-carboxylic acid 4-[3-(R,S)-Hydroxy-3-(3-fluoromethyl-6-methoxyquinolin-4-yl)propyl]-1-[2-(2,3,5-trifluorophenylthio)ethyl]piperidine-4-carboxylic acid 4-[3-(R,S)-Hydroxy-3-(3-fluoromethyl-6-methoxyquinolin-4-yl)propyl]-1-[2-(cyclopentylthio)ethyl]piperidine-4-carboxylic acid 4-[3-(R,S)-Hydroxy-3-(3-fluoromethyl-6-methoxyquinolin-4-yl)propyl]-1-[2-(pyrid-2-yl)thioethyl]piperidine-4-carboxylic acid 4-[3-(R,S)-Hydroxy-3-(3-fluoromethyl-6-methoxyquinolin-4-yl)propyl]-1-[2-(thien-2-yl)thioethyl]piperidine-4-carboxylic acid 4-[3-(R,S)-Hydroxy-3-(3-fluoromethyl-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-fluoromethyl-6-methoxyquinolin-4-yl)propyl]-1-[3-(thien-2-yl)prop-2-ynyl]piperidine-4-carboxylic acid 4-[3-(R,S)-Hydroxy-3-(3-aminomethyl-6-methoxyquinolin-4-yl)propyl]-1-[2-(cyclohexyl)ethyl]piperidine-4-carboxylic acid 4-[3-(R,S)-Hydroxy-3-(3-aminomethyl-6-methoxyquinolin-4-yl)propyl]-1-[3-(phenyl)propyl]piperidine-4-carboxylic acid 4-[3-(R,S)-Hydroxy-3-(3-aminomethyl-6-methoxyquinolin-4-yl)propyl]-1-[3-(2,3,5-trifluorophenyl)propyl]piperidine-4-carboxylic acid 4-[3-(R,S)-Hydroxy-3-(3-aminomethyl-6-methoxyquinolin-4-yl)propyl]-1-[2-(3,5-difluorophenylamino)ethyl]piperidine-4-carboxylic acid 4-[3-(R,S)-Hydroxy-3-(3-aminomethyl-6-methoxyquinolin-4-yl)propyl]-1-[2-(2,3,5-trifluorophenylamino)ethyl]piperidine-4-carboxylic acid 4-[3-(R,S)-Hydroxy-3-(3-aminomethyl-6-methoxyquinolin-4-yl)propyl]-1-[2-(3,5-difluorophenoxy)ethyl]piperidine-4-carboxylic acid 4-[3-(R,S)-Hydroxy-3-(3-aminomethyl-6-methoxyquinolin-4-yl)propyl]-1-[2-(2,3,5-trifluorophenoxy)ethyl]piperidine-4-carboxylic acid 4-[3-(R,S)-Hydroxy-3-(3-aminomethyl-6-methoxyquinolin-4-yl)propyl]-1-[2-(2,3,5-trifluorophenylthio)ethyl]piperidine-4-carboxylic acid 4-[3-(R,S)-Hydroxy-3-(3-aminomethyl-6-methoxyquinolin-4-yl)propyl]-1-[2-(cyclopentylthio)ethyl]piperidine-4-carboxylic acid 4-[3-(R,S)-Hydroxy-3-(3-aminomethyl-6-methoxyquinolin-4-yl)propyl]-1-[2-(pyrid-2-yl)thioethyl]piperidine-4-carboxylic acid 4-[3-(R,S)-Hydroxy-3-(3-aminomethyl-6-methoxyquinolin-4-yl)propyl]-1-[2-(thien-2-yl)thioethyl]piperidine-4-carboxylic acid 4-[3-(R,S)-Hydroxy-3-(3-aminomethyl-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-aminomethyl-6-methoxyquinolin-4-yl)propyl]-1-[3-(thien-2-yl)prop-2-ynyl]piperidine-4-carboxylic acid 4-[3-(R,S)-Hydroxy-3-(3-morpholinomethyl-6-methoxyquinolin-4-yl)propyl]-1-[2-(cyclohexyl)ethyl]piperidine-4-carboxylic acid 4-[3-(R,S)-Hydroxy-3-(3-morpholinomethyl-6-methoxyquinolin-4-yl)propyl]-1-[3-(phenyl)propyl]piperidine-4-carboxylic acid 4-[3-(R,S)-Hydroxy-3-(3-morpholinomethyl-6-methoxyquinolin-4-yl)propyl]-1-[3-(2,3,5-trifluorophenyl)propyl]piperidine-4-carboxylic acid 4-[3-(R,S)-Hydroxy-3-(3-morpholinomethyl-6-methoxyquinolin-4-yl)propyl]-1-[2-(3,5-difluorophenylamino)ethyl]piperidine-4-carboxylic acid 4-[3-(R,S)-Hydroxy-3-(3-morpholinomethyl-6-methoxyquinolin-4-yl)propyl]-1-[2-(2,3,5-trifluorophenylamino)ethyl]piperidine-4-carboxylic acid 4-[3-(R,S)-Hydroxy-3-(3-morpholinomethyl-6-methoxyquinolin-4-yl)propyl]-1-[2-(3,5-difluorophenoxy)ethyl]piperidine-4-carboxylic acid 4-[3-(R,S)-Hydroxy-3-(3-morpholinomethyl-6-methoxyquinolin-4-yl)propyl]-1-[2-(2,3,5-trifluorophenoxy)ethyl]piperidine-4-carboxylic acid 4-[3-(R,S)-Hydroxy-3-(3-morpholinomethyl-6-methoxyquinolin-4-yl)propyl]-1-[2-(2,3,5-trifluorophenylthio)ethyl]piperidine-4-carboxylic acid 4-[3-(R,S)-Hydroxy-3-(3-morpholinomethyl-6-methoxyquinolin-4-yl)propyl]-1-[2-(cyclopentylthio)ethyl]piperidine-4-carboxylic acid 4-[3-(R,S)-Hydroxy-3-(3-morpholinomethyl-6-methoxyquinolin-4-yl)propyl]-1-[2-(pyrid-2-yl)thioethyl]piperidine-4-carboxylic acid 4-[3-(R,S)-Hydroxy-3-(3-morpholinomethyl-6-methoxyquinolin-4-yl)propyl]-1-[2-(thien-2-yl)thioethyl]piperidine-4-carboxylic acid 4-[3-(R,S)-Hydroxy-3-(3-morpholinomethyl-6-methoxyquinolin-4-yl)propyl]-1-[3-(2,3,5-trifluorophenyl)prop-2-ynyl]piperidine-4-carboxylic acid 4-[3-(R,S)-Hydroxy-3-(3-morpholinomethyl-6-methoxyquinolin-4-yl)propyl]-1-[3-(thien-2-yl)prop-2-ynyl]piperidine-4-carboxylic acid 4-[3-(R,S)-Hydroxy-3-(3-methyl-6-methoxyquinolin-4-yl)propyl]-1-[3-(2,4,6-trifluorophenyl)propyl]piperidine-4-carboxylic acid 4-[3-(R,S)-Hydroxy-3-(3-methyl-6-methoxyquinolin-4-yl)propyl]-1-[3-(3,4,5-trifluorophenyl)propyl]piperidine-4-carboxylic acid 4-[3-(R,S)-Hydroxy-3-(3-methyl-6-methoxyquinolin-4-yl)propyl]-1-[2-(2,4,6-trifluorophenylthio)ethyl]piperidine-4-carboxylic acid 4-[3-(R,S)-Hydroxy-3-(3-methyl-6-methoxyquinolin-4-yl)propyl]-1-[2-(3,4,5-trifluorophenylthio)ethyl]piperidine-4-carboxylic acid 4-[3-(R,S)-Hydroxy-3-(3-methyl-6-methoxyquinolin-4-yl)propyl]-1-[2-(2,4,6-trifluorophenylamino)ethyl]piperidine-4-carboxylic acid 4-yl)propyl]-1-[2-(2,4,6-trifluorophenylamino)ethyl]piperidine-4-carboxylic acid 4-[3-(R,S)-Hydroxy-3-(3-methyl-6-methoxyquinolin-4-yl)propyl]-1-[2-(3,4,5-trifluorophenylamino)ethyl]piperidine-4-carboxylic acid 4-[3-(R,S)-Hydroxy-3-(3-methyl-6-methoxyquinolin-4-yl)propyl]-1-[2-(2,4,6-trifluorophenoxy)ethyl]piperidine-4-carboxylic acid 4-[3-(R,S)-Hydroxy-3-(3-methyl-6-methoxyquinolin-4-yl)propyl]-1-[2-(3,4,5-trifluorophenoxy)ethyl]piperidine-4-carboxylic acid 4-[3-(R,S)-Hydroxy-3-(3-methyl-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-methyl-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-fluoro-6-methoxyquinolin-4-yl)propyl]-1-[3-(2,4,6-trifluorophenyl)propyl]piperidine-4-carboxylic acid 4-[3-(R,S)-Hydroxy-3-(3-fluoro-6-methoxyquinolin-4-yl)propyl]-1-[3-(3,4,5-trifluorophenyl)propyl]piperidine-4-carboxylic acid 4-[3-(R,S)-Hydroxy-3-(3-fluoro-6-methoxyquinolin-4-yl)propyl]-1-[2-(2,4,6-trifluorophenylthio)ethyl]piperidine-4-carboxylic acid 4-[3-(R,S)-Hydroxy-3-(3-fluoro-6-methoxyquinolin-4-yl)propyl]-1-[2-(3,4,5-trifluorophenylthio)ethyl]piperidine-4-carboxylic acid 4-[3-(R,S)-Hydroxy-3-(3-fluoro-6-methoxyquinolin-4-yl)propyl]-1-[2-(2,4,6-trifluorophenylamino)ethyl]piperidine-4-carboxylic acid 4-[3-(R,S)-Hydroxy-3-(3-fluoro-6-methoxyquinolin-4-yl)propyl]-1-[2-(3,4,5-trifluorophenylamino)ethyl]piperidine-4-carboxylic acid 4-[3-(R,S)-Hydroxy-3-(3-fluoro-6-methoxyquinolin-4-yl)propyl]-1-[2-(2,4,6-trifluorophenoxy)ethyl]piperidine-4-carboxylic acid 4-[3-(R,S)-Hydroxy-3-(3-fluoro-6-methoxyquinolin-4-yl)propyl]-1-[2-(3,4,5-trifluorophenoxy)ethyl]piperidine-4-carboxylic acid 4-[3-(R,S)-Hydroxy-3-(3-fluoro-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-fluoro-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-dimethylamino-6-methoxyquinolin-4-yl)propyl]-1-[3-(2,4,6-trifluorophenyl)propyl]piperidine-4-carboxylic acid 4-[3-(R,S)-Hydroxy-3-(3-dimethylamino-6-methoxyquinolin-4-yl)propyl]-1-[3-(3,4,5-trifluorophenyl)propyl]piperidine-4-carboxylic acid 4-[3-(R,S)-Hydroxy-3-(3-dimethylamino-6-methoxyquinolin-4-yl)propyl]-1-[2-(2,4,6-trifluorophenylthio)ethyl]piperidine-4-carboxylic acid 4-[3-(R,S)-Hydroxy-3-(3-dimethylamino-6-methoxyquinolin-4-yl)propyl]-1-[2-(3,4,5-trifluorophenylthio)ethyl]piperidine-4-carboxylic acid 4-[3-(R,S)-Hydroxy-3-(3-dimethylamino-6-methoxyquinolin-4-yl)propyl]-1-[2-(2,4,6-trifluorophenylamino)ethyl]piperidine-4-carboxylic acid 4-[3-(R,S)-Hydroxy-3-(3-dimethylamino-6-methoxyquinolin-4-yl)propyl]-1-[2-(3,4,5-trifluorophenylamino)ethyl]piperidine-4-carboxylic acid 4-[3-(R,S)-Hydroxy-3-(3-dimethylamino-6-methoxyquinolin-4-yl)propyl]-1-[2-(2,4,6-trifluorophenoxy)ethyl]piperidine-4-carboxylic acid 4-[3-(R,S)-Hydroxy-3-(3-dimethylamino-6-methoxyquinolin-4-yl)propyl]-1-[2-(3,4,5-trifluorophenoxy)ethyl]piperidine-4-carboxylic acid 4-[3-(R,S)-Hydroxy-3-(3-dimethylamino-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-dimethylamino-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-hydroxymethyl-6-methoxyquinolin-4-yl)propyl]-1-[3-(3,4,5-trifluorophenyl)propyl]piperidine-4-carboxylic acid 4-[3-(R,S)-Hydroxy-3-(3-hydroxymethyl-6-methoxyquinolin-4-yl)propyl]-1-[2-(2,4,6-trifluorophenylthio)ethyl]piperidine-4-carboxylic acid 4-[3-(R,S)-Hydroxy-3-(3-hydroxymethyl-6-methoxyquinolin-4-yl)propyl]-1-[2-(3,4,5-trifluorophenylthio)ethyl]piperidine-4-carboxylic acid 4-[3-(R,S)-Hydroxy-3-(3-hydroxymethyl-6-methoxyquinolin-4-yl)propyl]-1-[2-(2,4,6-trifluorophenylamino)ethyl]piperidine-4-carboxylic acid 4-[3-(R,S)-Hydroxy-3-(3-hydroxymethyl-6-methoxyquinolin-4-yl)propyl]-1-[2-(3,4,5-trifluorophenylamino)ethyl]piperidine-4-carboxylic acid 4-[3-(R,S)-Hydroxy-3-(3-hydroxymethyl-6-methoxyquinolin-4-yl)propyl]-1-[2-(2,4,6-trifluorophenoxy)ethyl]piperidine-4-carboxylic acid 4-[3-(R,S)-Hydroxy-3-(3-hydroxymethyl-6-methoxyquinolin-4-yl)propyl]-1-[2-(3,4,5-trifluorophenoxy)ethyl]piperidine-4-carboxylic acid 4-[3-(R,S)-Hydroxy-3-(3-hydroxymethyl-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-hydroxymethyl-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-fluoromethyl-6-methoxyquinolin-4-yl)propyl]-1-[3-(2,4,6-trifluorophenyl)propyl]piperidine-4-carboxylic acid 4-[3-(R,S)-Hydroxy-3-(3-fluoromethyl-6-methoxyquinolin-4-yl)propyl]-1-[3-(3,4,5-trifluorophenyl)propyl]piperidine-4-carboxylic acid 4-[3-(R,S)-Hydroxy-3-(3-fluoromethyl-6-methoxyquinolin-4-yl)propyl]-1-[2-(2,4,6-trifluorophenylthio)ethyl]piperidine-4-carboxylic acid 4-[3-(R,S)-Hydroxy-3-(3-fluoromethyl-6-methoxyquinolin-4-yl)propyl]-1-[2-(3,4,5-trifluorophenylthio)ethyl]piperidine-4-carboxylic acid 4-[3-(R,S)-Hydroxy-3-(3-fluoromethyl-6-methoxyquinolin-4-yl)propyl]-1-[2-(2,4,6-trifluorophenylamino)ethyl]piperidine-4-carboxylic acid 4-[3-(R,S)-Hydroxy-3-(3-fluoromethyl-6-methoxyquinolin-4-yl)propyl]-1-[2-(3,4,5-trifluorophenylamino)ethyl]piperidine-4-carboxylic acid 4-[3-(R,S)-Hydroxy-3-(3-fluoromethyl-6-methoxyquinolin-4-yl)propyl]-1-[2-(2,4,6-trifluorophenoxy)ethyl]piperidine-4-carboxylic acid 4-[3-(R,S)-Hydroxy-3-(3-fluoromethyl-6-methoxyquinolin-4-yl)propyl]-1-[2-(3,4,5-trifluorophenoxy)ethyl]piperidine-4-carboxylic acid 4-[3-(R,S)-Hydroxy-3-(3-fluoromethyl-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-fluoromethyl-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-aminomethyl-6-methoxyquinolin-4-yl)propyl]-1-[3-(2,4,6-trifluorophenyl)propyl]piperidine-4-carboxylic acid 4-[3-(R,S)-Hydroxy-3-(3-aminomethyl-6-methoxyquinolin-4-yl)propyl]-1-[3-(3,4,5-trifluorophenyl)propyl]piperidine-4-carboxylic acid 4-[3-(R,S)-Hydroxy-3-(3-aminomethyl-6-methoxyquinolin-4-yl)propyl]-1-[2-(2,4,6-trifluorophenylthio)ethyl]piperidine-4-carboxylic acid 4-[3-(R,S)-Hydroxy-3-(3-aminomethyl-6-methoxyquinolin-4-yl)propyl]-1-[2-(3,4,5-trifluorophenylthio)ethyl]piperidine-4-carboxylic acid 4-[3-(R,S)-Hydroxy-3-(3-aminomethyl-6-methoxyquinolin-4-yl)propyl]-1-[2-(2,4,6-trifluorophenylamino)ethyl]piperidine-4-carboxylic acid 4-[3-(R,S)-Hydroxy-3-(3-aminomethyl-6-methoxyquinolin-4-yl)propyl]-1-[2-(3,4,5-trifluorophenylamino)ethyl]piperidine-4-carboxylic acid 4-[3-(R,S)-Hydroxy-3-(3-aminomethyl-6-methoxyquinolin-4-yl)propyl]-1-[2-(2,4,6-trifluorophenoxy)ethyl]piperidine-4-carboxylic acid 4-[3-(R,S)-Hydroxy-3-(3-aminomethyl-6-methoxyquinolin-4-yl)propyl]-1-[2-(3,4,5-trifluorophenoxy)ethyl]piperidine-4-carboxylic acid 4-[3-(R,S)-Hydroxy-3-(3-aminomethyl-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-aminomethyl-6-methoxyquinolin-4-yl)propyl]-1-[3-(3,4,5-trifluorophenyl)prop-2-ynyl]piperidine-4-carboxylic acid 4-[3-(R,S)-Hydroxy-3-(3-morpholinomethyl-6-methoxyquinolin-4-yl)propyl]-1-[3-(2,4,6-trifluorophenyl)propyl]piperidine-4-carboxylic acid 4-[3-(R,S)-Hydroxy-3-(3-morpholinomethyl-6-methoxyquinolin-4-yl)propyl]-1-[3-(3,4,5-trifluorophenyl)propyl]piperidine-4-carboxylic acid 4-[3-(R,S)-Hydroxy-3-(3-morpholinomethyl-6-methoxyquinolin-4-yl)propyl]-1-[2-(2,4,6-trifluorophenylthio)ethyl]piperidine-4-carboxylic acid 4-[3-(R,S)-Hydroxy-3-(3-morpholinomethyl-6-methoxyquinolin-4-yl)propyl]-1-[2-(3,4,5-trifluorophenylthio)ethyl]piperidine-4-carboxylic acid 4-[3-(R,S)-Hydroxy-3-(3-morpholinomethyl-6-methoxyquinolin-4-yl)propyl]-1-[2-(2,4,6-trifluorophenylamino)ethyl]piperidine-4-carboxylic acid 4-[3-(R,S)-Hydroxy-3-(3-morpholinomethyl-6-methoxyquinolin-4-yl)propyl]-1-[2-(3,4,5-trifluorophenylamino)ethyl]piperidine-4-carboxylic acid 4-[3-(R,S)-Hydroxy-3-(3-morpholinomethyl-6-methoxyquinolin-4-yl)propyl]-1-[2-(2,4,6-trifluorophenoxy)ethyl]piperidine-4-carboxylic acid 4-[3-(R,S)-Hydroxy-3-(3-morpholinomethyl-6-methoxyquinolin-4-yl)propyl]-1-[2-(3,4,5-trifluorophenoxy)ethyl]piperidine-4-carboxylic acid 4-[3-(R,S)-Hydroxy-3-(3-morpholinomethyl-6-methoxyquinolin-4-yl)propyl]-1-[3-(2,4,6-trifluorophenyl)prop-2-ynyl]piperidine-4-carboxylic acid 4-[3-(R,S)-Hydroxy-3-(3-morpholinomethyl-6-methoxyquinolin-4-yl)propyl]-1-[3-(3,4,5-trifluorophenyl)prop-2-ynyl]piperidine-4-carboxylic acid 4-[3-(R,S)-Fluoro-3-(3-chloro-6-methoxyquinolin-4-yl)propyl]-1-heptylpiperidine-4-carboxylic acid 4-[3-(R,S)-Fluoro-3-(3-chloro-6-methoxyquinolin-4-yl)propyl]-1-[4-phenylbutyl]piperidine-4-carboxylic acid 4-[3-(R,S)-Fluoro-3-(3-chloro-6-methoxyquinolin-4-yl)propyl]-1-[3-(phenyl)propyl]piperidine-4-carboxylic acid 4-[3-(R,S)-Fluoro-3-(3-chloro-6-methoxyquinolin-4-yl)propyl]-1-[4-(2-fluorophenyl)propyl]piperidine-4-carboxylic acid 4-[3-(R,S)-Fluoro-3-(3-chloro-6-methoxyquinolin-4-yl)propyl]-1-[4-(3-fluorophenyl)propyl]piperidine-4-carboxylic acid 4-[3-(R,S)-Fluoro-3-(3-chloro-6-methoxyquinolin-4-yl)propyl]-1-[3-(4-fluorophenyl)propyl]piperidine-4-carboxylic acid 4-[3-(R,S)-Fluoro-3-(3-chloro-6-methoxyquinolin-4-yl)propyl]-1-[4-(4-fluorophenyl)butyl]piperidine-4-carboxylic acid 4-[3-(R,S)-Fluoro-3-(3-chloro-6-methoxyquinolin-4-yl)propyl]-1-[3-(2,3-difluorophenyl)propyl]piperidine-4-carboxylic acid 4-[3-(R,S)-Fluoro-3-(3-chloro-6-methoxyquinolin-4-yl)propyl]-1-[4-(2,3-difluorophenyl)propyl]piperidine-4-carboxylic acid 4-[3-(R,S)-Fluoro-3-(3-chloro-6-methoxyquinolin-4-yl)propyl]-1-[3-(2,6-difluorophenyl)propyl]piperidine-4-carboxylic acid 4-[3-(R,S)-Fluoro-3-(3-chloro-6-methoxyquinolin-4-yl)propyl]-1-[4-(2,6-difluorophenyl)propyl]piperidine-4-carboxylic acid 4-[3-(R,S)-Fluoro-3-(3-chloro-6-methoxyquinolin-4-yl)propyl]-1-[3-(3,5-difluorophenyl)propyl]piperidine-4-carboxylic acid 4-[3-(R,S)-Fluoro-3-(3-chloro-6-methoxyquinolin-4-yl)propyl]-1-[3-(2,3,5-trifluorophenyl)propyl]piperidine-4-carboxylic acid 4-[3-(R,S)-Fluoro-3-(3-chloro-6-methoxyquinolin-4-yl)propyl]-1-[3-(2,4,6-trifluorophenyl)propyl]piperidine-4-carboxylic acid 4-[3-(R,S)-Fluoro-3-(3-chloro-6-methoxyquinolin-4-yl)propyl]-1-[3-(3,4,5-trifluorophenyl)propyl]piperidine-4-carboxylic acid 4-[3-(R,S)-Fluoro-3-(3-chloro-6-methoxyquinolin-4-yl)propyl]-1-[3-phenylthio-propyl]piperidine-4-carboxylic acid 4-[3-(R,S)-Fluoro-3-(3-chloro-6-methoxyquinolin-4-yl)propyl]-1-[3-(2-fluorophenylthio)propyl]piperidine-4-carboxylic acid 4-[3-(R,S)-Fluoro-3-(3-chloro-6-methoxyquinolin-4-yl)propyl]-1-[3-(3-fluorophenylthio)propyl]piperidine-4-carboxylic acid 4-[3-(R,S)-Fluoro-3-(3-chloro-6-methoxyquinolin-4-yl)propyl]-1-[2-(4-fluorophenylthio)ethyl]piperidine-4-carboxylic acid 4-[3-(R,S)-Fluoro-3-(3-chloro-6-methoxyquinolin-4-yl)propyl]-1-[3-(4-fluorophenylthio)propyl]piperidine-4-carboxylic acid 4-[3-(R,S)-Fluoro-3-(3-chloro-6-methoxyquinolin-4-yl)propyl]-1-[2-(2,3-difluorophenylthio)ethyl]piperidine-4-carboxylic acid 4-[3-(R,S)-Fluoro-3-(3-chloro-6-methoxyquinolin-4-yl)propyl]-1-[3-(2,3-difluorophenylthio)propyl]piperidine-4-carboxylic acid 4-[3-(R,S)-Fluoro-3-(3-chloro-6-methoxyquinolin-4-yl)propyl]-1-[2-(2,6-difluorophenylthio)ethyl]piperidine-4-carboxylic acid 4-[3-(R,S)-Fluoro-3-(3-chloro-6-methoxyquinolin-4-yl)propyl]-1-[2-(2,3,5-trifluorophenylthio)ethyl]piperidine-4-carboxylic acid 4-[3-(R,S)-Fluoro-3-(3-chloro-6-methoxyquinolin-4-yl)propyl]-1-[2-(2,4,6-trifluorophenylthio)ethyl]piperidine-4-carboxylic acid 4-[3-(R,S)-Fluoro-3-(3-chloro-6-methoxyquinolin-4-yl)propyl]-1-[2-(3,4,5-trifluorophenylthio)ethyl]piperidine-4-carboxylic acid 4-[3-(R,S)-Fluoro-3-(3-chloro-6-methoxyquinolin-4-yl)propyl]-1-[2-(2,3,5-trifluorophenoxy)ethyl]piperidine-4-carboxylic acid 4-[3-(R,S)-Fluoro-3-(3-chloro-6-methoxyquinolin-4-yl)propyl]-1-[2-(2,4,6-trifluorophenoxy)ethyl]piperidine-4-carboxylic acid 4-[3-(R,S)-Fluoro-3-(3-chloro-6-methoxyquinolin-4-yl)propyl]-1-[2-(3,4,5-trifluorophenoxy)ethyl]piperidine-4-carboxylic acid 4-[3-(R,S)-Fluoro-3-(3-chloro-6-methoxyquinolin-4-yl)propyl]-1-[2-(3,5-difluorophenylamino)ethyl]piperidine-4-carboxylic acid 4-[3-(R,S)-Fluoro-3-(3-chloro-6-methoxyquinolin-4-yl)propyl]-1-[2-(2,3,5-trifluorophenylamino)ethyl]piperidine-4-carboxylic acid 4-[3-(R,S)-Fluoro-3-(3-chloro-6-methoxyquinolin-4-yl)propyl]-1-[2-(2,4,6-trifluorophenylamino)ethyl]piperidine-4-carboxylic acid 4-[3-(R,S)-Fluoro-3-(3-chloro-6-methoxyquinolin-4-yl)propyl]-1-[2-(3,4,5-trifluorophenylamino)ethyl]piperidine-4-carboxylic acid 4-[3-(R,S)-Fluoro-3-(3-chloro-6-methoxyquinolin-4-yl)propyl]-1-[3-(2,6-difluorophenylthio)propyl]piperidine-4-carboxylic acid 4-[3-(R,S)-Fluoro-3-(3-chloro-6-methoxyquinolin-4-yl)propyl]-1-[2-(2-chlorophenylthio)ethyl]piperidine-4-carboxylic acid 4-[3-(R,S)-Fluoro-3-(3-chloro-6-methoxyquinolin-4-yl)propyl]-1-[3-(2-chlorophenylthio)propyl]piperidine-4-carboxylic acid 4-[3-(R,S)-Fluoro-3-(3-chloro-6-methoxyquinolin-4-yl)propyl]-1-[2-(3-chlorophenylthio)ethyl]piperidine-4-carboxylic acid 4-[3-(R,S)-Fluoro-3-(3-chloro-6-methoxyquinolin-4-yl)propyl]-1-[3-(3-chlorophenylthio)propyl]piperidine-4-carboxylic acid 4-[3-(R,S)-Fluoro-3-(3-chloro-6-methoxyquinolin-4-yl)propyl]-1-[2-(4-chlorophenylthio)ethyl]piperidine-4-carboxylic acid 4-[3-(R,S)-Fluoro-3-(3-chloro-6-methoxyquinolin-4-yl)propyl]-1-[3-(4-chlorophenylthio)propyl]piperidine-4-carboxylic acid 4-[3-(R,S)-Fluoro-3-(3-chloro-6-methoxyquinolin-4-yl)propyl]-1-[2-(2-methylphenylthio)ethyl]piperidine-4-carboxylic acid 4-[3-(R,S)-Fluoro-3-(3-chloro-6-methoxyquinolin-4-yl)propyl]-1-[3-(2-methylphenylthio)propyl]piperidine-4-carboxylic acid 4-[3-(R,S)-Fluoro-3-(3-chloro-6-methoxyquinolin-4-yl)propyl]-1-[2-(3-methylphenylthio)ethyl]piperidine-4-carboxylic acid 4-[3-(R,S)-Fluoro-3-(3-chloro-6-methoxyquinolin-4-yl)propyl]-1-[3-(3-methylphenylthio)propyl]piperidine-4-carboxylic acid 4-[3-(R,S)-Fluoro-3-(3-chloro-6-methoxyquinolin-4-yl)propyl]-1-[2-(4-methylphenylthio)ethyl]piperidine-4-carboxylic acid 4-[3-(R,S)-Fluoro-3-(3-chloro-6-methoxyquinolin-4-yl)propyl]-1-[3-(4-methylphenylthio)propyl]piperidine-4-carboxylic acid 4-[3-(R,S)-Fluoro-3-(3-chloro-6-methoxyquinolin-4-yl)propyl]-1-[2-(2-trifluoromethylphenylthio)ethyl]piperidine-4-carboxylic acid 4-[3-(R,S)-Fluoro-3-(3-chloro-6-methoxyquinolin-4-yl)propyl]-1-[3-(2-trifluoromethylphenylthio)propyl]piperidine-4-carboxylic acid 4-[3-(R,S)-Fluoro-3-(3-chloro-6-methoxyquinolin-4-yl)propyl]-1-[2-(3-trifluoromethylphenylthio)ethyl]piperidine-4-carboxylic acid 4-[3-(R,S)-Fluoro-3-(3-chloro-6-methoxyquinolin-4-yl)propyl]-1-[3-(3-trifluoromethylphenylthio)propyl]piperidine-4-carboxylic acid 4-[3-(R,S)-Fluoro-3-(3-chloro-6-methoxyquinolin-4-yl)propyl]-1-[2-(4-trifluoromethylphenylthio)ethyl]piperidine-4-carboxylic acid 4-[3-(R,S)-Fluoro-3-(3-chloro-6-methoxyquinolin-4-yl)propyl]-1-[3-(4-trifluoromethylphenylthio)propyl]piperidine-4-carboxylic acid 4-[3-(R,S)-Fluoro-3-(3-chloro-6-methoxyquinolin-4-yl)propyl]-1-[2-(2-methoxyphenylthio)ethyl]piperidine-4-carboxylic acid 4-[3-(R,S)-Fluoro-3-(3-chloro-6-methoxyquinolin-4-yl)propyl]-1-[3-(2-methoxyphenylthio)propyl]piperidine-4-carboxylic acid 4-[3-(R,S)-Fluoro-3-(3-chloro-6-methoxyquinolin-4-yl)propyl]-1-[2-(3-methoxyphenylthio)ethyl]piperidine-4-carboxylic acid 4-[3-(R,S)-Fluoro-3-(3-chloro-6-methoxyquinolin-4-yl)propyl]-1-[3-(3-methoxyphenylthio)propyl]piperidine-4-carboxylic acid 4-[3-(R,S)-Fluoro-3-(3-chloro-6-methoxyquinolin-4-yl)propyl]-1-[2-(4-methoxyphenylthio)ethyl]piperidine-4-carboxylic acid 4-[3-(R,S)-Fluoro-3-(3-chloro-6-methoxyquinolin-4-yl)propyl]-1-[3-(4-methoxyphenylthio)propyl]piperidine-4-carboxylic acid 4-[3-(R,S)-Fluoro-3-(3-chloro-6-methoxyquinolin-4-yl)propyl]-1-[cyclopentylmethyl]piperidine-4-carboxylic acid 4-[3-(R,S)-Fluoro-3-(3-chloro-6-methoxyquinolin-4-yl)propyl]-1-[2-(cyclopentyl)ethyl]piperidine-4-carboxylic acid 4-[3-(R,S)-Fluoro-3-(3-chloro-6-methoxyquinolin-4-yl)propyl]-1-[2-(cyclohexyl)ethyl]piperidine-4-carboxylic acid 4-[3-(R,S)-Fluoro-3-(3-chloro-6-methoxyquinolin-4-yl)propyl]-1-[2-(cyclopentylthio)ethyl]piperidine-4-carboxylic acid 4-[3-(R,S)-Fluoro-3-(3-chloro-6-methoxyquinolin-4-yl)propyl]-1-[3-(cyclopentylthio)propyl]piperidine-4-carboxylic acid 4-[3-(R,S)-Fluoro-3-(3-chloro-6-methoxyquinolin-4-yl)propyl]-1-[3-(cyclohexylthio)propyl]piperidine-4-carboxylic acid 4-[3-(R,S)-Fluoro-3-(3-chloro-6-methoxyquinolin-4-yl)propyl]-1-[2-(pyrid-2-yl)thioethyl]piperidine-4-carboxylic acid 4-[3-(R,S)-Fluoro-3-(3-chloro-6-methoxyquinolin-4-yl)propyl]-1-[4-(thien-2-yl)butyl]piperidine-4-carboxylic acid 4-[3-(R,S)-Fluoro-3-(3-chloro-6-methoxyquinolin-4-yl)propyl]-1-[3-(thien-2-yl)thiopropyl]piperidine-4-carboxylic acid 4-[3-(R,S)-Fluoro-3-(3-chloro-6-methoxyquinolin-4-yl)propyl]-1-[3-(thien-3-yl)propyl]piperidine-4-carboxylic acid 4-[3-(R,S)-Fluoro-3-(3-chloro-6-methoxyquinolin-4-yl)propyl]-1-[4-(thien-3-yl)butyl]piperidine-4-carboxylic acid 4-[3-(R,S)-Fluoro-3-(3-chloro-6-methoxyquinolin-4-yl)propyl]-1-[2-(thien-2-yl)thioethyl]piperidine-4-carboxylic acid 4-[3-(R,S)-Fluoro-3-(3-chloro-6-methoxyquinolin-4-yl)propyl]-1-[2-(thien-3-yl)thioethyl]piperidine-4-carboxylic acid 4-[3-(R,S)-Fluoro-3-(3-chloro-6-methoxyquinolin-4-yl)propyl]-1-[3-(thien-3-yl)thiopropyl]piperidine-4-carboxylic acid 4-[3-(R,S)-Fluoro-3-(3-chloro-6-methoxyquinolin-4-yl)propyl]-1-[3-(1,3-thiazol-2-yl)propyl]piperidine-4-carboxylic acid 4-[3-(R,S)-Fluoro-3-(3-chloro-6-methoxyquinolin-4-yl)propyl]-1-[4-(1,3-thiazol-2-yl)butyl]piperidine-4-carboxylic acid 4-[3-(R,S)-Fluoro-3-(3-chloro-6-methoxyquinolin-4-yl)propyl]-1-[3-(1,3-thiazol-2-yl)thioethyl]piperidine-4-carboxylic acid 4-[3-(R,S)-Fluoro-3-(3-chloro-6-methoxyquinolin-4-yl)propyl]-1-[3-(pyrid-2-yl)propyl]piperidine-4-carboxylic acid 4-[3-(R,S)-Fluoro-3-(3-chloro-6-methoxyquinolin-4-yl)propyl]-1-[4-(pyrid-2-yl)butyl]piperidine-4-carboxylic acid 4-[3-(R,S)-Fluoro-3-(3-chloro-6-methoxyquinolin-4-yl)propyl]-1-[3-(pyrid-2-yl)thiopropyl]piperidine-4-carboxylic acid 4-[3-(R,S)-Fluoro-3-(3-chloro-6-methoxyquinolin-4-yl)propyl]-1-[3-(pyrid-3-yl)propyl]piperidine-4-carboxylic acid 4-[3-(R,S)-Fluoro-3-(3-chloro-6-methoxyquinolin-4-yl)propyl]-1-[4-(pyrid-3-yl)butyl]piperidine-4-carboxylic acid 4-[3-(R,S)-Fluoro-3-(3-chloro-6-methoxyquinolin-4-yl)propyl]-1-[2-(pyrid-3-yl)thioethyl]piperidine-4-carboxylic acid 4-[3-(R,S)-Fluoro-3-(3-chloro-6-methoxyquinolin-4-yl)propyl]-1-[3-(pyrid-3-yl)thiopropyl]piperidine-4-carboxylic acid 4-[3-(R,S)-Fluoro-3-(3-chloro-6-methoxyquinolin-4-yl)propyl]-1-[3-(pyrid-4-yl)propyl]piperidine-4-carboxylic acid 4-[3-(R,S)-Fluoro-3-(3-chloro-6-methoxyquinolin-4-yl)propyl]-1-[4-(pyrid-4-yl)butyl]piperidine-4-carboxylic acid 4-[3-(R,S)-Fluoro-3-(3-chloro-6-methoxyquinolin-4-yl)propyl]-1-[2-(pyrid-4-yl)thioethyl]piperidine-4-carboxylic acid 4-[3-(R,S)-Fluoro-3-(3-chloro-6-methoxyquinolin-4-yl)propyl]-1-[3-(pyrid-4-yl)thiopropyl]piperidine-4-carboxylic acid 4-[3-(R,S)-Fluoro-3-(3-chloro-6-methoxyquinolin-4-yl)propyl]-1-[3-(pyrazin-2-yl)propyl]piperidine-4-carboxylic acid 4-[3-(R,S)-Fluoro-3-(3-chloro-6-methoxyquinolin-4-yl)propyl]-1-[4-(pyrazin-2-yl)butyl]piperidine-4-carboxylic acid 4-[3-(R,S)-Fluoro-3-(3-chloro-6-methoxyquinolin-4-yl)propyl]-1-[2-(pyrazin-2-yl)thioethyl]piperidine-4-carboxylic acid 4-[3-(R,S)-Fluoro-3-(3-chloro-6-methoxyquinolin-4-yl)propyl]-1-[3-(pyrazin-2-yl)thiopropyl]piperidine-4-carboxylic acid 4-[3-(R,S)-Fluoro-3-(3-chloro-6-methoxyquinolin-4-yl)propyl]-1-[3-(4-fluorophenyl)prop-2-ynyl]piperidine-4-carboxylic acid 4-[3-(R,S)-Fluoro-3-(3-chloro-6-methoxyquinolin-4-yl)propyl]-1-[3-(3,4-difluorophenyl)prop-2-ynyl]piperidine-4-carboxylic acid 4-[3-(R,S)-Fluoro-3-(3-chloro-6-methoxyquinolin-4-yl)propyl]-1-[3-(2,4-difluorophenyl)prop-2-ynyl]piperidine-4-carboxylic acid 4-[3-(R,S)-Fluoro-3-(3-chloro-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-chloro-6-methoxyquinolin-4-yl)propyl]-1-[3-(2,4,6-trifluorophenyl)prop-2-ynyl]piperidine-4-carboxylic acid 4-[3-(R,S)-Fluoro-3-(3-chloro-6-methoxyquinolin-4-yl)propyl]-1-[3-(3,4,5-trifluorophenyl)prop-2-ynyl]piperidine-4-carboxylic acid 4-[3-(R,S)-Fluoro-3-(3-chloro-6-methoxyquinolin-4-yl)propyl]-1-[3-(4-chloro-3-fluorophenyl)prop-2-ynyl]piperidine-4-carboxylic acid 4-[3-(R,S)-Fluoro-3-(3-chloro-6-methoxyquinolin-4-yl)propyl]-1-[3-(3-chloro-4-fluorophenyl)prop-2-ynyl]piperidine-4-carboxylic acid 4-[3-(R,S)-Fluoro-3-(3-chloro-6-methoxyquinolin-4-yl)propyl]-1-[3-(2-chloro-4-fluorophenyl)prop-2-ynyl]piperidine-4-carboxylic acid 4-[3-(R,S)-Fluoro-3-(3-chloro-6-methoxyquinolin-4-yl)propyl]-1-[3-(3-chloro-5-fluorophenyl)prop-2-ynyl]piperidine-4-carboxylic acid 4-[3-(R,S)-Fluoro-3-(3-chloro-6-methoxyquinolin-4-yl)propyl]-1-[3-(4-chloro-2-fluorophenyl)prop-2-ynyl]piperidine-4-carboxylic acid 4-[3-(R,S)-Fluoro-3-(3-chloro-6-methoxyquinolin-4-yl)propyl]-1-[3-(3-fluoro-4-methylphenyl)prop-2-ynyl]piperidine-4-carboxylic acid 4-[3-(R,S)-Fluoro-3-(3-chloro-6-methoxyquinolin-4-yl)propyl]-1-[3-(3,5-bis(trifluoromethyl)phenyl)prop-2-ynyl]piperidine-4-carboxylic acid 4-[3-(R,S)-Fluoro-3-(3-chloro-6-methoxyquinolin-4-yl)propyl]-1-[3-(thien-2-yl)prop-2-ynyl]piperidine-4-carboxylic acid 4-[3-(R,S)-Fluoro-3-(3-chloro-6-methoxyquinolin-4-yl)propyl]-1-[3-(thien-3-yl)prop-2-ynyl]piperidine-4-carboxylic acid 4-[3-(R,S)-Fluoro-3-(3-chloro-6-methoxyquinolin-4-yl)propyl]-1-[3-(1,3-thiazol-2-yl)prop-2-ynyl]piperidine-4-carboxylic acid 4-[3-(R,S)-Fluoro-3-(3-chloro-6-methoxyquinolin-4-yl)propyl]-1-[3-(1,3-thiazol-4-yl)prop-2-ynyl]piperidine-4-carboxylic acid 4-[3-(R,S)-Fluoro-3-(3-chloro-6-methoxyquinolin-4-yl)propyl]-1-[3-(1,3-thiazol-5-yl)prop-2-ynyl]piperidine-4-carboxylic acid 4-[3-(R,S)-Fluoro-3-(3-chloro-6-methoxyquinolin-4-yl)propyl]-1-[3-(pyrid-2-yl)prop-2-ynyl]piperidine-4-carboxylic acid 4-[3-(R,S)-Fluoro-3-(3-chloro-6-methoxyquinolin-4-yl)propyl]-1-[3-(pyrid-3-yl)prop-2-ynyl]piperidine-4-carboxylic acid 4-[3-(R,S)-Fluoro-3-(3-chloro-6-methoxyquinolin-4-yl)propyl]-1-[3-(pyrid-4-yl)prop-2-ynyl]piperidine-4-carboxylic acid 4-[3-(R,S)-Fluoro-3-(3-methyl-6-methoxyquinolin-4-yl)propyl]-1-[2-(cyclohexyl)ethyl]piperidine-4-carboxylic acid 4-[3-(R,S)-Fluoro-3-(3-methyl-6-methoxyquinolin-4-yl)propyl]-1-[3-(phenyl)propyl]piperidine-4-carboxylic acid 4-[3-(R,S)-Fluoro-3-(3-methyl-6-methoxyquinolin-4-yl)propyl]-1-[3-(2,3,5-trifluorophenyl)propyl]piperidine-4-carboxylic acid 4-[3-(R,S)-Fluoro-3-(3-methyl-6-methoxyquinolin-4-yl)propyl]-1-[2-(3,5-difluorophenylamino)ethyl]piperidine-4-carboxylic acid 4-[3-(R,S)-Fluoro-3-(3-methyl-6-methoxyquinolin-4-yl)propyl]-1-[2-(2,3,5-trifluorophenylamino)ethyl]piperidine-4-carboxylic acid 4-[3-(R,S)-Fluoro-3-(3-methyl-6-methoxyquinolin-4-yl)propyl]-1-[2-(3,5-difluorophenoxy)ethyl]piperidine-4-carboxylic acid 4-[3-(R,S)-Fluoro-3-(3-methyl-6-methoxyquinolin-4-yl)propyl]-1-[2-(2,3,5-trifluorophenoxy)ethyl]piperidine-4-carboxylic acid 4-[3-(R,S)-Fluoro-3-(3-methyl-6-methoxyquinolin-4-yl)propyl]-1-[2-(2,3,5-trifluorophenylthio)ethyl]piperidine-4-carboxylic acid 4-[3-(R,S)-Fluoro-3-(3-methyl-6-methoxyquinolin-4-yl)propyl]-1-[2-(cyclopentylthio)ethyl]piperidine-4-carboxylic acid 4-[3-(R,S)-Fluoro-3-(3-methyl-6-methoxyquinolin-4-yl)propyl]-1-[2-(pyrid-2-yl)thioethyl]piperidine-4-carboxylic acid 4-[3-(R,S)-Fluoro-3-(3-methyl-6-methoxyquinolin-4-yl)propyl]-1-[2-(thien-2-yl)thioethyl]piperidine-4-carboxylic acid 4-[3-(R,S)-Fluoro-3-(3-methyl-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-methyl-6-methoxyquinolin-4-yl)propyl]-1-[3-(thien-2-yl)prop-2-ynyl]piperidine-4-carboxylic acid 4-[3-(R,S)-Fluoro-3-(3-fluoro-6-methoxyquinolin-4-yl)propyl]-1-[2-(cyclohexyl)ethyl]piperidine-4-carboxylic acid 4-[3-(R,S)-Fluoro-3-(3-fluoro-6-methoxyquinolin-4-yl)propyl]-1-[3-(phenyl)propyl]piperidine-4-carboxylic acid 4-[3-(R,S)-Fluoro-3-(3-fluoro-6-methoxyquinolin-4-yl)propyl]-1-[3-(2,3,5-trifluorophenyl)propyl]piperidine-4-carboxylic acid 4-[3-(R,S)-Fluoro-3-(3-fluoro-6-methoxyquinolin-4-yl)propyl]-1-[2-(3,5-difluorophenylamino)ethyl]piperidine-4-carboxylic acid 4-[3-(R,S)-Fluoro-3-(3-fluoro-6-methoxyquinolin-4-yl)propyl]-1-[2-(2,3,5-trifluorophenylamino)ethyl]piperidine-4-carboxylic acid 4-[3-(R,S)-Fluoro-3-(3-fluoro-6-methoxyquinolin-4-yl)propyl]-1-[2-(3,5-difluorophenoxy)ethyl]piperidine-4-carboxylic acid 4-[3-(R,S)-Fluoro-3-(3-fluoro-6-methoxyquinolin-4-yl)propyl]-1-[2-(2,3,5-trifluorophenoxy)ethyl]piperidine-4-carboxylic acid 4-[3-(R,S)-Fluoro-3-(3-fluoro-6-methoxyquinolin-4-yl)propyl]-1-[2-(2,3,5-trifluorophenylthio)ethyl]piperidine-4-carboxylic acid 4-[3-(R,S)-Fluoro-3-(3-fluoro-6-methoxyquinolin-4-yl)propyl]-1-[2-(cyclopentylthio)ethyl]piperidine-4-carboxylic acid 4-[3-(R,S)-Fluoro-3-(3-fluoro-6-methoxyquinolin-4-yl)propyl]-1-[2-(pyrid-2-yl)thioethyl]piperidine-4-carboxylic acid 4-[3-(R,S)-Fluoro-3-(3-fluoro-6-methoxyquinolin-4-yl)propyl]-1-[2-(thien-2-yl)thioethyl]piperidine-4-carboxylic acid 4-[3-(R,S)-Fluoro-3-(3-fluoro-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-fluoro-6-methoxyquinolin-4-yl)propyl]-1-[3-(thien-2-yl)prop-2-ynyl]piperidine-4-carboxylic acid 4-[3-(R,S)-Fluoro-3-(3-dimethylamino-6-methoxyquinolin-4-yl)propyl]-1-[2-(cyclohexyl)ethyl]piperidine-4-carboxylic acid 4-[3-(R,S)-Fluoro-3-(3-dimethylamino-6-methoxyquinolin-4-yl)propyl]-1-[3-(phenyl)propyl]piperidine-4-carboxylic acid 4-[3-(R,S)-Fluoro-3-(3-dimethylamino-6-methoxyquinolin-4-yl)propyl]-1-[3-(2,3,5-trifluorophenyl)propyl]piperidine-4-carboxylic acid 4-[3-(R,S)-Fluoro-3-(3-dimethylamino-6-methoxyquinolin-4-yl)propyl]-1-[2-(3,5-difluorophenylamino)ethyl]piperidine-4-carboxylic acid 4-[3-(R,S)-Fluoro-3-(3-dimethylamino-6-methoxyquinolin-4-yl)propyl]-1-[2-(2,3,5-trifluorophenylamino)ethyl]piperidine-4-carboxylic acid 4-[3-(R,S)-Fluoro-3-(3-dimethylamino-6-methoxyquinolin-4-yl)propyl]-1-[2-(3,5-difluorophenoxy)ethyl]piperidine-4-carboxylic acid 4-[3-(R,S)-Fluoro-3-(3-dimethylamino-6-methoxyquinolin-4-yl)propyl]-1-[2-(2,3,5-trifluorophenoxy)ethyl]piperidine-4-carboxylic acid 4-[3-(R,S)-Fluoro-3-(3-dimethylamino-6-methoxyquinolin-4-yl)propyl]-1-[2-(2,3,5-trifluorophenylthio)ethyl]piperidine-4-carboxylic acid 4-[3-(R,S)-Fluoro-3-(3-dimethylamino-6-—methoxyquinolin-4-yl)propyl]-1-[2-(cyclopentylthio)ethyl]piperidine-4-carboxylic acid 4-[3-(R,S)-Fluoro-3-(3-dimethylamino-6-methoxyquinolin-4-yl)propyl]-1-[2-(pyrid-2-yl)thioethyl]piperidine-4-carboxylic acid 4-[3-(R,S)-Fluoro-3-(3-dimethylamino-6-methoxyquinolin-4-yl)propyl]-1-[2-(thien-2-yl)thioethyl]piperidine-4-carboxylic acid 4-[3-(R,S)-Fluoro-3-(3-dimethylamino-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-dimethylamino-6-methoxyquinolin-4-yl)propyl]-1-[3-(thien-2-yl)prop-2-ynyl]piperidine-4-carboxylic acid 4-[3-(R,S)-Fluoro-3-(3-hydroxymethyl-6-methoxyquinolin-4-yl)propyl]-1-[2-(cyclohexyl)ethyl]piperidine-4-carboxylic acid 4-[3-(R,S)-Fluoro-3-(3-hydroxymethyl-6-methoxyquinolin-4-yl)propyl]-1-[3-(phenyl)propyl]piperidine-4-carboxylic acid 4-[3-(R,S)-Fluoro-3-(3-hydroxymethyl-6-methoxyquinolin-4-yl)propyl]-1-[3-(2,3,5-trifluorophenyl)propyl]piperidine-4-carboxylic acid 4-[3-(R,S)-Fluoro-3-(3-hydroxymethyl-6-methoxyquinolin-4-yl)propyl]-1-[2-(3,5-difluorophenylamino)ethyl]piperidine-4-carboxylic acid 4-[3-(R,S)-Fluoro-3-(3-hydroxymethyl-6-methoxyquinolin-4-yl)propyl]-1-[2-(2,3,5-trifluorophenylamino)ethyl]piperidine-4-carboxylic acid 4-[3-(R,S)-Fluoro-3-(3-hydroxymethyl-6-methoxyquinolin-4-yl)propyl]-1-[2-(3,5-difluorophenoxy)ethyl]piperidine-4-carboxylic acid 4-[3-(R,S)-Fluoro-3-(3-hydroxymethyl-6-methoxyquinolin-4-yl)propyl]-1-[2-(2,3,5-trifluorophenoxy)ethyl]piperidine-4-carboxylic acid 4-[3-(R,S)-Fluoro-3-(3-hydroxymethyl-6-methoxyquinolin-4-yl)propyl]-1-[2-(2,3,5-trifluorophenylthio)ethyl]piperidine-4-carboxylic acid 4-[3-(R,S)-Fluoro-3-(3-hydroxymethyl-6-methoxyquinolin-4-yl)propyl]-1-[2-(cyclopentylthio)ethyl]piperidine-4-carboxylic acid 4-[3-(R,S)-Fluoro-3-(3-hydroxymethyl-6-methoxyquinolin-4-yl)propyl]-1-[2-(pyrid-2-yl)thioethyl]piperidine-4-carboxylic acid 4-[3-(R,S)-Fluoro-3-(3-hydroxymethyl-6-methoxyquinolin-4-yl)propyl]-1-[2-(thien-2-yl)thioethyl]piperidine-4-carboxylic acid 4-[3-(R,S)-Fluoro-3-(3-hydroxymethyl-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-hydroxymethyl-6-methoxyquinolin-4-yl)propyl]-1-[3-(thien-2-yl)prop-2-ynyl]piperidine-4-carboxylic acid 4-[3-(R,S)-Fluoro-3-(3-fluoromethyl-6-methoxyquinolin-4-yl)propyl]-1-[2-(cyclohexyl)ethyl]piperidine-4-carboxylic acid 4-[3-(R,S)-Fluoro-3-(3-fluoromethyl-6-methoxyquinolin-4-yl)propyl]-1-[3-(phenyl)propyl]piperidine-4-carboxylic acid 4-[3-(R,S)-Fluoro-3-(3-fluoromethyl-6-methoxyquinolin-4-yl)propyl]-1-[3-(2,3,5-trifluorophenyl)propyl]piperidine-4-carboxylic acid 4-[3-(R,S)-Fluoro-3-(3-fluoromethyl-6-methoxyquinolin-4-yl)propyl]-1-[2-(3,5-difluorophenylamino)ethyl]piperidine-4-carboxylic acid 4-[3-(R,S)-Fluoro-3-(3-fluoromethyl-6-methoxyquinolin-4-yl)propyl]-1-[2-(2,3,5-trifluorophenylamino)ethyl]piperidine-4-carboxylic acid 4-[3-(R,S)-Fluoro-3-(3-fluoromethyl-6-methoxyquinolin-4-yl)propyl]-1-[2-(3,5-difluorophenoxy)ethyl]piperidine-4-carboxylic acid 4-[3-(R,S)-Fluoro-3-(3-fluoromethyl-6-methoxyquinolin-4-yl)propyl]-1-[2-(2,3,5-trifluorophenoxy)ethyl]piperidine-4-carboxylic acid 4-[3-(R,S)-Fluoro-3-(3-fluoromethyl-6-methoxyquinolin-4-yl)propyl]-1-[2-(2,3,5-trifluorophenylthio)ethyl]piperidine-4-carboxylic acid 4-[3-(R,S)-Fluoro-3-(3-fluoromethyl-6-methoxyquinolin-4-yl)propyl]-1-[2-(cyclopentylthio)ethyl]piperidine-4-carboxylic acid 4-[3-(R,S)-Fluoro-3-(3-fluoromethyl-6-methoxyquinolin-4-yl)propyl]-1-[2-(pyrid-2-yl)thioethyl]piperidine-4-carboxylic acid 4-[3-(R,S)-Fluoro-3-(3-fluoromethyl-6-methoxyquinolin-4-yl)propyl]-1-[2-(thien-2-yl)thioethyl]piperidine-4-carboxylic acid 4-[3-(R,S)-Fluoro-3-(3-fluoromethyl-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-fluoromethyl-6-methoxyquinolin-4-yl)propyl]-1-[3-(thien-2-yl)prop-2-ynyl]piperidine-4-carboxylic acid 4-[3-(R,S)-Fluoro-3-(3-aminomethyl-6-methoxyquinolin-4-yl)propyl]-1-[2-(cyclohexyl)ethyl]piperidine-4-carboxylic acid 4-[3-(R,S)-Fluoro-3-(3-aminomethyl-6-methoxyquinolin-4-yl)propyl]-1-[3-(phenyl)propyl]piperidine-4-carboxylic acid 4-[3-(R,S)-Fluoro-3-(3-aminomethyl-6-methoxyquinolin-4-yl)propyl]-1-[3-(2,3,5-trifluorophenyl)propyl]piperidine-4-carboxylic acid 4-[3-(R,S)-Fluoro-3-(3-aminomethyl-6-methoxyquinolin-4-yl)propyl]-1-[2-(3,5-difluorophenylamino)ethyl]piperidine-4-carboxylic acid 4-[3-(R,S)-Fluoro-3-(3-aminomethyl-6-methoxyquinolin-4-yl)propyl]-1-[2-(2,3,5-trifluorophenylamino)ethyl]piperidine-4-carboxylic acid 4-[3-(R,S)-Fluoro-3-(3-aminomethyl-6-methoxyquinolin-4-yl)propyl]-1-[2-(3,5-difluorophenoxy)ethyl]piperidine-4-carboxylic acid 4-[3-(R,S)-Fluoro-3-(3-aminomethyl-6-methoxyquinolin-4-yl)propyl]-1-[2-(2,3,5-trifluorophenoxy)ethyl]piperidine-4-carboxylic acid 4-[3-(R,S)-Fluoro-3-(3-aminomethyl-6-methoxyquinolin-4-yl)propyl]-1-[2-(2,3,5-trifluorophenylthio)ethyl]piperidine-4-carboxylic acid 4-[3-(R,S)-Fluoro-3-(3-aminomethyl-6-methoxyquinolin-4-yl)propyl]-1-[2-(cyclopentylthio)ethyl]piperidine-4-carboxylic acid 4-[3-(R,S)-Fluoro-3-(3-aminomethyl-6-methoxyquinolin-4-yl)propyl]-1-[2-(pyrid-2-yl)thioethyl]piperidine-4-carboxylic acid 4-[3-(R,S)-Fluoro-3-(3-aminomethyl-6-methoxyquinolin-4-yl)propyl]-1-[2-(thien-2-yl)thioethyl]piperidine-4-carboxylic acid 4-[3-(R,S)-Fluoro-3-(3-aminomethyl-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-aminomethyl-6-methoxyquinolin-4-yl)propyl]-1-[3-(thien-2-yl)prop-2-ynyl]piperidine-4-carboxylic acid 4-[3-(R,S)-Fluoro-3-(3-morpholinomethyl-6-methoxyquinolin-4-yl)propyl]-1-[2-(cyclohexyl)ethyl]piperidine-4-carboxylic acid 4-[3-(R,S)-Fluoro-3-(3-morpholinomethyl-6-methoxyquinolin-4-yl)propyl]-1-[3-(phenyl)propyl]piperidine-4-carboxylic acid 4-[3-(R,S)-Fluoro-3-(3-morpholinomethyl-6-methoxyquinolin-4-yl)propyl]-1-[3-(2,3,5-trifluorophenyl)propyl]piperidine-4-carboxylic acid 4-[3-(R,S)-Fluoro-3-(3-morpholinomethyl-6-methoxyquinolin-4-yl)propyl]-1-[2-(3,5-difluorophenylamino)ethyl]piperidine-4-carboxylic acid 4-[3-(R,S)-Fluoro-3-(3-morpholinomethyl-6-methoxyquinolin-4-yl)propyl]-1-[2-(2,3,5-trifluorophenylamino)ethyl]piperidine-4-carboxylic acid 4-[3-(R,S)-Fluoro-3-(3-morpholinomethyl-6-methoxyquinolin-4-yl)propyl]-1-[2-(3,5-difluorophenoxy)ethyl]piperidine-4-carboxylic acid 4-[3-(R,S)-Fluoro-3-(3-morpholinomethyl-6-methoxyquinolin-4-yl)propyl]-1-[2-(2,3,5-trifluorophenoxy)ethyl]piperidine-4-carboxylic acid 4-[3-(R,S)-Fluoro-3-(3-morpholinomethyl-6-methoxyquinolin-4-yl)propyl]-1-[2-(2,3,5-trifluorophenylthio)ethyl]piperidine-4-carboxylic acid 4-[3-(R,S)-Fluoro-3-(3-morpholinomethyl-6-methoxyquinolin-4-yl)propyl]-1-[2-(cyclopentylthio)ethyl]piperidine-4-carboxylic acid 4-[3-(R,S)-Fluoro-3-(3-morpholinomethyl-6-methoxyquinolin-4-yl)propyl]-1-[2-(pyrid-2-yl)thioethyl]piperidine-4-carboxylic acid 4-[3-(R,S)-Fluoro-3-(3-morpholinomethyl-6-methoxyquinolin-4-yl)propyl]-1-[2-(thien-2-yl)thioethyl]piperidine-4-carboxylic acid 4-[3-(R,S)-Fluoro-3-(3-morpholinomethyl-6-methoxyquinolin-4-yl)propyl]-1-[3-(2,3,5-trifluorophenyl)prop-2-ynyl]piperidine-4-carboxylic acid 4-[3-(R,S)-Fluoro-3-(3-morpholinomethyl-6-methoxyquinolin-4-yl)propyl]-1-[3-(thien-2-yl)prop-2-ynyl]piperidine-4-carboxylic acid 4-[3-(R,S)-Fluoro-3-(3-methyl-6-methoxyquinolin-4-yl)propyl]-1-[3-(2,4,6-trifluorophenyl)propyl]piperidine-4-carboxylic acid 4-[3-(R,S)-Fluoro-3-(3-methyl-6-methoxyquinolin-4-yl)propyl]-1-[3-(3,4,5-trifluorophenyl)propyl]piperidine-4-carboxylic acid 4-[3-(R,S)-Fluoro-3-(3-methyl-6-methoxyquinolin-4-yl)propyl]-1-[2-(2,4,6-trifluorophenylthio)ethyl]piperidine-4-carboxylic acid 4-[3-(R,S)-Fluoro-3-(3-methyl-6-methoxyquinolin-4-yl)propyl]-1-[2-(3,4,5-trifluorophenylthio)ethyl]piperidine-4-carboxylic acid 4-[3-(R,S)-Fluoro-3-(3-methyl-6-methoxyquinolin-4-yl)propyl]-1-[2-(2,4,6-trifluorophenylamino)ethyl]piperidine-4-carboxylic acid 4-[3-(R,S)-Fluoro-3-(3-methyl-6-methoxyquinolin-4-yl)propyl]-1-[2-(3,4,5-trifluorophenylamino)ethyl]piperidine-4-carboxylic acid 4-[3-(R,S)-Fluoro-3-(3-methyl-6-methoxyquinolin-4-yl)propyl]-1-[2-(2,4,6-trifluorophenoxy)ethyl]piperidine-4-carboxylic acid 4-[3-(R,S)-Fluoro-3-(3-methyl-6-methoxyquinolin-4-yl)propyl]-1-[2-(3,4,5-trifluorophenoxy)ethyl]piperidine-4-carboxylic acid 4-[3-(R,S)-Fluoro-3-(3-methyl-6-methoxyquinolin-4-yl)propyl]-1-[3-(2,4,6-trifluorophenyl)prop-2-ynyl]piperidine-4-carboxylic acid 4-[3-(R,S)-Fluoro-3-(3-methyl-6-methoxyquinolin-4-yl)
  propyl]-1-[3-(3,4,5-trifluorophenyl)prop-2-ynyl]
  piperidine-4-carboxylic acid
4-[3-(R,S)-Fluoro-3-(3-fluoro-6-methoxyquinolin-4-yl)
  propyl]-1-[3-(2,4,6-trifluorophenyl)propyl]piperidine-
  4-carboxylic acid
4-[3-(R,S)-Fluoro-3-(3-fluoro-6-methoxyquinolin-4-yl)
  propyl]-1-[3-(3,4,5-trifluorophenyl)propyl]piperidine-
  4-carboxylic acid
4-[3-(R,S)-Fluoro-3-(3-fluoro-6-methoxyquinolin-4-yl)
  propyl]-1-[2-(2,4,6-trifluorophenylthio)ethyl]
  piperidine-4-carboxylic acid
4-[3-(R,S)-Fluoro-3-(3-fluoro-6-methoxyquinolin-4-yl)
  propyl]-1-[2-(3,4,5-trifluorophenylthio)ethyl]
  piperidine-4-carboxylic acid
4-[3-(R,S)-Fluoro-3-(3-fluoro-6-methoxyquinolin-4-yl)
  propyl]-1-[2-(2,4,6-trifluorophenylamino)ethyl]
  piperidine-4-carboxylic acid
4-[3-(R,S)-Fluoro-3-(3-fluoro-6-methoxyquinolin-4-yl)
  propyl]-1-[2-(3,4,5-trifluorophenylamino)ethyl]
  piperidine-4-carboxylic acid
4-[3-(R,S)-Fluoro-3-(3-fluoro-6-methoxyquinolin-4-yl)
  propyl]-1-[2-(2,4,6-trifluorophenoxy)ethyl]piperidine-
  4-carboxylic acid
4-[3-(R,S)-Fluoro-3-(3-fluoro-6-methoxyquinolin-4-yl)
  propyl]-1-[2-(3,4,5-trifluorophenoxy)ethyl]piperidine-
  4-carboxylic acid
4-[3-(R,S)-Fluoro-3-(3-fluoro-6-methoxyquinolin-4-yl)
  propyl]-1-[3-(2,4,6-trifluorophenyl)prop-2-ynyl]
  piperidine-4-carboxylic acid
4-[3-(R,S)-Fluoro-3-(3-fluoro-6-methoxyquinolin-4-yl)
  propyl]-1-[3-(3,4,5-trifluorophenyl)prop-2-ynyl]
  piperidine-4-carboxylic acid
4-[3-(R,S)-Fluoro-3-(3-dimethylamino-6-
  methoxyquinolin-4-yl)propyl]-1-[3-(2,4,6-
  trifluorophenyl)propyl]piperidine-4-carboxylic acid
4-[3-(R,S)-Fluoro-3-(3-dimethylamino-6-
  methoxyquinolin-4-yl)propyl]-1-[3-(3,4,5-
  trifluorophenyl)propyl]piperidine-4-carboxylic acid
4-[3-(R,S)-Fluoro-3-(3-dimethylamino-6-
  methoxyquinolin-4-yl)propyl]-1-[2-(2,4,6-
  trifluorophenylthio)ethyl]piperidine-4-carboxylic acid
4-[3-(R,S)-Fluoro-3-(3-dimethylamino-6-
  methoxyquinolin-4-yl)propyl]-1-[2-(3,4,5-
  trifluorophenylthio)ethyl]piperidine-4-carboxylic acid
4-[3-(R,S)-Fluoro-3-(3-dimethylamino-6-
  methoxyquinolin-4-yl)propyl]-1-[2-(2,4,6-
  trifluorophenylamino)ethyl]piperidine-4-carboxylic
  acid
4-[3-(R,S)-Fluoro-3-(3-dimethylamino-6-
  methoxyquinolin-4-yl)propyl]-1-[2-(3,4,5-
  trifluorophenylamino)ethyl]piperidine-4-carboxylic
  acid
4-[3-(R,S)-Fluoro-3-(3-dimethylamino-6-
  methoxyquinolin-4-yl)propyl]-1-[2-(2,4,6-
  trifluorophenoxy)ethyl]piperidine-4-carboxylic acid
4-[3-(R,S)-Fluoro-3-(3-dimethylamino-6-
  methoxyquinolin-4-yl)propyl]-1-[2-(3,4,5-
  trifluorophenoxy)ethyl]piperidine-4-carboxylic acid
4-[3-(R,S)-Fluoro-3-(3-dimethylamino-6-
  methoxyquinolin-4-yl)propyl]-1-[3-(2,4,6-
  trifluorophenyl)prop-2-ynyl]piperidine-4-carboxylic
  acid
4-[3-(R,S)-Fluoro-3-(3-dimethylamino-6-
  methoxyquinolin-4-yl)propyl]-1-[3-(3,4,5-
  trifluorophenyl)prop-2-ynyl]piperidine-4-carboxylic
  acid
4-[3-(R,S)-Fluoro-3-(3-fluoro-6-methoxyquinolin-4-yl)
  propyl]-1-[3-(2,4,6-trifluorophenyl)propyl]piperidine-
  4-carboxylic acid
4-[3-(R,S)-Fluoro-3-(3-hydroxymethyl-6-
  methoxyquinolin-4-yl)propyl]-1-[3-(3,4,5-
  trifluorophenyl)propyl]piperidine-4-carboxylic acid
4-[3-(R,S)-Fluoro-3-(3-hydroxymethyl-6-
  methoxyquinolin-4-yl)propyl]-1-[2-(2,4,6-
  trifluorophenylthio)ethyl]piperidine-4-carboxylic acid
4-[3-(R,S)-Fluoro-3-(3-hydroxymethyl-6-
  methoxyquinolin-4-yl)propyl]-1-[2-(3,4,5-
  trifluorophenylthio)ethyl]piperidine-4-carboxylic acid
4-[3-(R,S)-Fluoro-3-(3-hydroxymethyl-6-
  methoxyquinolin-4-yl)propyl]-1-[2-(2,4,6-
  trifluorophenylamino)ethyl]piperidine-4-carboxylic
  acid
4-[3-(R,S)-Fluoro-3-(3-hydroxymethyl-6-
  methoxyquinolin-4-yl)propyl]-1-[2-(3,4,5-
  trifluorophenylamino)ethyl]piperidine-4-carboxylic
  acid
4-[3-(R,S)-Fluoro-3-(3-hydroxymethyl-6-
  methoxyquinolin-4-yl)propyl]-1-[2-(2,4,6-
  trifluorophenoxy)ethyl]piperidine-4-carboxylic acid
4-[3-(R,S)-Fluoro-3-(3-hydroxymethyl-6-
  methoxyquinolin-4-yl)propyl]-1-[2-(3,4,5-
  trifluorophenoxy)ethyl]piperidine-4-carboxylic acid
4-[3-(R,S)-Fluoro-3-(3-hydroxymethyl-6-
  methoxyquinolin-4-yl)propyl]-1-[3-(2,4,6-
  trifluorophenyl)prop-2-ynyl]piperidine-4-carboxylic
  acid
4-[3-(R,S)-Fluoro-3-(3-hydroxymethyl-6-
  methoxyquinolin-4-yl)propyl]-1-[3-(3,4,5-
  trifluorophenyl)prop-2-ynyl]piperidine-4-carboxylic
  acid
4-[3-(R,S)-Fluoro-3-(3-fluoromethyl-6-
  methoxyquinolin-4-yl)propyl]-1-[3-(2,4,6-
  trifluorophenyl)propyl]piperidine-4-carboxylic acid
4-[3-(R,S)-Fluoro-3-(3-fluoromethyl-6-
  methoxyquinolin-4-yl)propyl]-1-[3-(3,4,5-
  trifluorophenyl)propyl]piperidine-4-carboxylic acid
4-[3-(R,S)-Fluoro-3-(3-fluoromethyl-6-
  methoxyquinolin-4-yl)propyl]-1-[2-(2,4,6-
  trifluorophenylthio)ethyl]piperidine-4-carboxylic acid
4-[3-(R,S)-Fluoro-3-(3-fluoromethyl-6-
  methoxyquinolin-4-yl)propyl]-1-[2-(3,4,5-
  trifluorophenylthio)ethyl]piperidine-4-carboxylic acid
4-[3-(R,S)-Fluoro-3-(3-fluoromethyl-6-
  methoxyquinolin-4-yl)propyl]-1-[2-(2,4,6-
  trifluorophenylamino)ethyl]piperidine-4-carboxylic
  acid
4-[3-(R,S)-Fluoro-3-(3-fluoromethyl-6-
  methoxyquinolin-4-yl)propyl]-1-[2-(3,4,5-
  trifluorophenylamino)ethyl]piperidine-4-carboxylic
  acid
4-[3-(R,S)-Fluoro-3-(3-fluoromethyl-6-
  methoxyquinolin-4-yl)propyl]-1-[2-(2,4,6-
  trifluorophenoxy)ethyl]piperidine-4-carboxylic acid
4-[3-(R,S)-Fluoro-3-(3-fluoromethyl-6-
  methoxyquinolin-4-yl)propyl]-1-[2-(3,4,5-
  trifluorophenoxy)ethyl]piperidine-4-carboxylic acid
4-[3-(R,S)-Fluoro-3-(3-fluoromethyl-6-
  methoxyquinolin-4-yl)propyl]-1-[3-(2,4,6-
  trifluorophenyl)prop-2-ynyl]piperidine-4-carboxylic
  acid 4-[3-(R,S)-Fluoro-3-(3-fluoromethyl-6-methoxyquinolin-4-yl)propyl]-1-[3-(3,4,5-trifluorophenyl)prop-2-ynyl]piperidine-4-carboxylic acid 4-[3-(R,S)-Fluoro-3-(3-aminomethyl-6-methoxyquinolin-4-yl)propyl]-1-[3-(2,4,6-trifluorophenyl)propyl]piperidine-4-carboxylic acid 4-[3-(R,S)-Fluoro-3-(3-aminomethyl-6-methoxyquinolin-4-yl)propyl]-1-[3-(3,4,5-trifluorophenyl)propyl]piperidine-4-carboxylic acid 4-[3-(R,S)-Fluoro-3-(3-aminomethyl-6-methoxyquinolin-4-yl)propyl]-1-[2-(2,4,6-trifluorophenylthio)ethyl]piperidine-4-carboxylic acid 4-[3-(R,S)-Fluoro-3-(3-aminomethyl-6-methoxyquinolin-4-yl)propyl]-1-[2-(3,4,5-trifluorophenylthio)ethyl]piperidine-4-carboxylic acid 4-[3-(R,S)-Fluoro-3-(3-aminomethyl-6-methoxyquinolin-4-yl)propyl]-1-[2-(2,4,6-trifluorophenylamino)ethyl]piperidine-4-carboxylic acid 4-[3-(R,S)-Fluoro-3-(3-aminomethyl-6-methoxyquinolin-4-yl)propyl]-1-[2-(3,4,5-trifluorophenylamino)ethyl]piperidine-4-carboxylic acid 4-[3-(R,S)-Fluoro-3-(3-aminomethyl-6-methoxyquinolin-4-yl)propyl]-1-[2-(2,4,6-trifluorophenoxy)ethyl]piperidine-4-carboxylic acid 4-[3-(R,S)-Fluoro-3-(3-aminomethyl-6-methoxyquinolin-4-yl)propyl]-1-[2-(3,4,5-trifluorophenoxy)ethyl]piperidine-4-carboxylic acid 4-[3-(R,S)-Fluoro-3-(3-aminomethyl-6-methoxyquinolin-4-yl)propyl]-1-[3-(2,4,6-trifluorophenyl)prop-2-ynyl]piperidine-4-carboxylic acid 4-[3-(R,S)-Fluoro-3-(3-aminomethyl-6-methoxyquinolin-4-yl)propyl]-1-[3-(3,4,5-trifluorophenyl)prop-2-ynyl]piperidine-4-carboxylic acid 4-[3-(R,S)-Fluoro-3-(3-morpholinomethyl-6-methoxyquinolin-4-yl)propyl]-1-[3-(2,4,6-trifluorophenyl)propyl]piperidine-4-carboxylic acid 4-[3-(R,S)-Fluoro-3-(3-morpholinomethyl-6-methoxyquinolin-4-yl)propyl]-1-[3-(3,4,5-trifluorophenyl)propyl]piperidine-4-carboxylic acid 4-[3-(R,S)-Fluoro-3-(3-morpholinomethyl-6-methoxyquinolin-4-yl)propyl]-1-[2-(2,4,6-trifluorophenylthio)ethyl]piperidine-4-carboxylic acid 4-[3-(R,S)-Fluoro-3-(3-morpholinomethyl-6-methoxyquinolin-4-yl)propyl]-1-[2-(3,4,5-trifluorophenylthio)ethyl]piperidine-4-carboxylic acid 4-[3-(R,S)-Fluoro-3-(3-morpholinomethyl-6-methoxyquinolin-4-yl)propyl]-1-[2-(2,4,6-trifluorophenylamino)ethyl]piperidine-4-carboxylic acid 4-[3-(R,S)-Fluoro-3-(3-morpholinomethyl-6-methoxyquinolin-4-yl)propyl]-1-[2-(3,4,5-trifluorophenylamino)ethyl]piperidine-4-carboxylic acid 4-[3-(R,S)-Fluoro-3-(3-morpholinomethyl-6-methoxyquinolin-4-yl)propyl]-1-[2-(2,4,6-trifluorophenoxy)ethyl]piperidine-4-carboxylic acid 4-[3-(R,S)-Fluoro-3-(3-morpholinomethyl-6-methoxyquinolin-4-yl)propyl]-1-[2-(3,4,5-trifluorophenoxy)ethyl]piperidine-4-carboxylic acid 4-[3-(R,S)-Fluoro-3-(3-morpholinomethyl-6-methoxyquinolin-4-yl)propyl]-1-[3-(2,4,6-trifluorophenyl)prop-2-ynyl]piperidine-4-carboxylic acid 4-[3-(R,S)-Fluoro-3-(3-morpholinomethyl-6-methoxyquinolin-4-yl)propyl]-1-[3-(3,4,5-trifluorophenyl)prop-2-ynyl]piperidine-4-carboxylic acid 4-[3-(3-Chloro-6-methoxyquinolin-4-yl)propyl]-1-heptylpiperidine-4-acetic acid 4-[3-(3-Chloro-6-methoxyquinolin-4-yl)propyl]-1-[4-phenylbutyl]piperidine-4-acetic acid 4-[3-(3-Chloro-6-methoxyquinolin-4-yl)propyl]-1-[3-(phenyl)propyl]piperidine-4-acetic acid 4-[3-(3-Chloro-6-methoxyquinolin-4-yl)propyl]-1-[4-(2-fluorophenyl)propyl]piperidine-4-acetic acid 4-[3-(3-Chloro-6-methoxyquinolin-4-yl)propyl]-1-[4-(3-fluorophenyl)propyl]piperidine-4-acetic acid 4-[3-(3-Chloro-6-methoxyquinolin-4-yl)propyl]-1-[3-(4-fluorophenyl)propyl]piperidine-4-acetic acid 4-[3-(3-Chloro-6-methoxyquinolin-4-yl)propyl]-1-[4-(4-fluorophenyl)butyl]piperidine-4-acetic acid 4-[3-(3-Chloro-6-methoxyquinolin-4-yl)propyl]-1-[3-(2,3-difluorophenyl)propyl]piperidine-4-acetic acid 4-[3-(3-Chloro-6-methoxyquinolin-4-yl)propyl]-1-[4-(2,3-difluorophenyl)propyl]piperidine-4-acetic acid 4-[3-(3-Chloro-6-methoxyquinolin-4-yl)propyl]-1-[3-(2,6-difluorophenyl)propyl]piperidine-4-acetic acid 4-[3-(3-Chloro-6-methoxyquinolin-4-yl)propyl]-1-[4-(2,6-difluorophenyl)propyl]piperidine-4-acetic acid 4-[3-(3-Chloro-6-methoxyquinolin-4-yl)propyl]-1-[3-(3,5-difluorophenyl)propyl]piperidine-4-acetic acid 4-[3-(3-Chloro-6-methoxyquinolin-4-yl)propyl]-1-[3-(2,3,5-trifluorophenyl)propyl]piperidine-4-acetic acid 4-[3-(3-Chloro-6-methoxyquinolin-4-yl)propyl]-1-[3-(2,4,6-trifluorophenyl)propyl]piperidine-4-acetic acid 4-[3-(3-Chloro-6-methoxyquinolin-4-yl)propyl]-1-[3-(3,4,5-trifluorophenyl)propyl]piperidine-4-acetic acid 4-[3-(3-Chloro-6-methoxyquinolin-4-yl)propyl]-1-[3-phenylthiopropyl]piperidine-4-acetic acid 4-[3-(3-Chloro-6-methoxyquinolin-4-yl)propyl]-1-[3-(2-fluorophenylthio)propyl]piperidine-4-acetic acid 4-[3-(3-Chloro-6-methoxyquinolin-4-yl)propyl]-1-[3-(3-fluorophenylthio)propyl]piperidine-4-acetic acid 4-[3-(3-Chloro-6-methoxyquinolin-4-yl)propyl]-1-[2-(4-fluorophenylthio)ethyl]piperidine-4-acetic acid 4-[3-(3-Chloro-6-methoxyquinolin-4-yl)propyl]-1-[3-(4-fluorophenylthio)propyl]piperidine-4-acetic acid 4-[3-(3-Chloro-6-methoxyquinolin-4-yl)propyl]-1-[2-(2,3-difluorophenylthio)-ethyl]piperidine-4-acetic acid 4-[3-(3-Chloro-6-methoxyquinolin-4-yl)propyl]-1-[3-(2,3-difluorophenylthio)-propyl]piperidine-4-acetic acid 4-[3-(3-Chloro-6-methoxyquinolin-4-yl)propyl]-1-[2-(2,6-difluorophenylthio)-ethyl]piperidine-4-acetic acid 4-[3-(3-Chloro-6-methoxyquinolin-4-yl)propyl]-1-[2-(2,3,5-trifluorophenylthio)-ethyl]piperidine-4-acetic acid 4-[3-(3-Chloro-6-methoxyquinolin-4-yl)propyl]-1-[2-(2,4,6-trifluorophenylthio)-ethyl]piperidine-4-acetic acid 4-[3-(3-Chloro-6-methoxyquinolin-4-yl)propyl]-1-[2-(3,4,5-trifluorophenylthio)-ethyl]piperidine-4-acetic acid 4-[3-(3-Chloro-6-methoxyquinolin-4-yl)propyl]-1-[2-(3,5-difluorophenoxy)ethyl]piperidine-4-acetic acid 4-[3-(3-Chloro-6-methoxyquinolin-4-yl)propyl]-1-[2-(2,3,5-trifluorophenoxy)-ethyl]piperidine-4-acetic acid
4-[3-(3-Chloro-6-methoxyquinolin-4-yl)propyl]-1-[2-(2,4,6-trifluorophenoxy)-ethyl]piperidine-4-acetic acid
4-[3-(3-Chloro-6-methoxyquinolin-4-yl)propyl]-1-[2-(3,4,5-trifluorophenoxy)-ethyl]piperidine-4-acetic acid
4-[3-(3-Chloro-6-methoxyquinolin-4-yl)propyl]-1-[2-(3,5-difluorophenylamino)-ethyl]piperidine-4-acetic acid
4-[3-(3-Chloro-6-methoxyquinolin-4-yl)propyl]-1-[2-(2,3,5-trifluorophenylamino)-ethyl]piperidine-4-acetic acid
4-[3-(3-Chloro-6-methoxyquinolin-4-yl)propyl]-1-[2-(2,4,6-trifluorophenylamino)-ethyl]piperidine-4-acetic acid
4-[3-(3-Chloro-6-methoxyquinolin-4-yl)propyl]-1-[2-(3,4,5-trifluorophenylamino)-ethyl]piperidine-4-acetic acid
4-[3-(3-Chloro-6-methoxyquinolin-4-yl)propyl]-1-[3-(2,6-difluorophenylthio)-propyl]piperidine-4-acetic acid
4-[3-(3-Chloro-6-methoxyquinolin-4-yl)propyl]-1-[2-(2-chlorophenylthio)ethyl]piperidine-4-acetic acid
4-[3-(3-Chloro-6-methoxyquinolin-4-yl)propyl]-1-[3-(2-chlorophenylthio)propyl]piperidine-4-acetic acid
4-[3-(3-Chloro-6-methoxyquinolin-4-yl)propyl]-1-[2-(3-chlorophenylthio)ethyl]piperidine-4-acetic acid
4-[3-(3-Chloro-6-methoxyquinolin-4-yl)propyl]-1-[3-(3-chlorophenylthio)propyl]piperidine-4-acetic acid
4-[3-(3-Chloro-6-methoxyquinolin-4-yl)propyl]-1-[2-(4-chlorophenylthio)ethyl]piperidine-4-acetic acid
4-[3-(3-Chloro-6-methoxyquinolin-4-yl)propyl]-1-[3-(4-chlorophenylthio)propyl]piperidine-4-acetic acid
4-[3-(3-Chloro-6-methoxyquinolin-4-yl)propyl]-1-[2-(2-methylphenylthio)ethyl]piperidine-4-acetic acid
4-[3-(3-Chloro-6-methoxyquinolin-4-yl)propyl]-1-[3-(2-methylphenylthio)-propyl]piperidine-4-acetic acid
4-[3-(3-Chloro-6-methoxyquinolin-4-yl)propyl]-1-[2-(3-methylphenylthio)ethyl]piperidine-4-acetic acid
4-[3-(3-Chloro-6-methoxyquinolin-4-yl)propyl]-1-[3-(3-methylphenylthio)-propyl]piperidine-4-acetic acid
4-[3-(3-Chloro-6-methoxyquinolin-4-yl)propyl]-1-[2-(4-methylphenylthio)ethyl]piperidine-4-acetic acid
4-[3-(3-Chloro-6-methoxyquinolin-4-yl)propyl]-1-[3-(4-methylphenylthio)-propyl]piperidine-4-acetic acid
4-[3-(3-Chloro-6-methoxyquinolin-4-yl)propyl]-1-[2-(2-trifluoromethylphenylthio)-ethyl]piperidine-4-acetic acid
4-[3-(3-Chloro-6-methoxyquinolin-4-yl)propyl]-1-[3-(2-trifluoromethylphenylthio)-propyl]piperidine-4-acetic acid
4-[3-(3-Chloro-6-methoxyquinolin-4-yl)propyl]-1-[2-(3-trifluoromethylphenylthio)-ethyl]piperidine-4-acetic acid
4-[3-(3-Chloro-6-methoxyquinolin-4-yl)propyl]-1-[3-(3-trifluoromethylphenylthio)-propyl]piperidine-4-acetic acid
4-[3-(3-Chloro-6-methoxyquinolin-4-yl)propyl]-1-[2-(4-trifluoromethylphenylthio)-ethyl]piperidine-4-acetic acid
4-[3-(3-Chloro-6-methoxyquinolin-4-yl)propyl]-1-[3-(4-trifluoromethylphenylthio)-propyl]piperidine-4-acetic acid
4-[3-(3-Chloro-6-methoxyquinolin-4-yl)propyl]-1-[2-(2-methoxyphenylthio)-ethyl]piperidine-4-acetic acid
4-[3-(3-Chloro-6-methoxyquinolin-4-yl)propyl]-1-[3-(2-methoxyphenylthio)-propyl]piperidine-4-acetic acid
4-[3-(3-Chloro-6-methoxyquinolin-4-yl)propyl]-1-[2-(3-methoxyphenylthio)-ethyl]piperidine-4-acetic acid
4-[3-(3-Chloro-6-methoxyquinolin-4-yl)propyl]-1-[3-(3-methoxyphenylthio)-propyl]piperidine-4-acetic acid
4-[3-(3-Chloro-6-methoxyquinolin-4-yl)propyl]-1-[2-(4-methoxyphenylthio)-ethyl]piperidine-4-acetic acid
4-[3-(3-Chloro-6-methoxyquinolin-4-yl)propyl]-1-[3-(4-methoxyphenylthio)-propyl]piperidine-4-acetic acid
4-[3-(3-Chloro-6-methoxyquinolin-4-yl)propyl]-1-[cyclopentylmethyl]piperidine-4-acetic acid
4-[3-(3-Chloro-6-methoxyquinolin-4-yl)propyl]-1-[2-(cyclopentyl)ethyl]piperidine-4-acetic acid
4-[3-(3-Chloro-6-methoxyquinolin-4-yl)propyl]-1-[2-(cyclohexyl)ethyl]piperidine-4-acetic acid
4-[3-(3-Chloro-6-methoxyquinolin-4-yl)propyl]-1-[2-(cyclopentylthio)ethyl]piperidine-4-acetic acid
4-[3-(3-Chloro-6-methoxyquinolin-4-yl)propyl]-1-[3-(cyclopentylthio)propyl]piperidine-4-acetic acid
4-[3-(3-Chloro-6-methoxyquinolin-4-yl)propyl]-1-[3-(cyclohexylthio)propyl]piperidine-4-acetic acid
4-[3-(3-Chloro-6-methoxyquinolin-4-yl)propyl]-1-[2-(pyrid-2-yl)thioethyl]piperidine-4-acetic acid
4-[3-(3-Chloro-6-methoxyquinolin-4-yl)propyl]-1-[4-(thien-2-yl)butyl]piperidine-4-acetic acid
4-[3-(3-Chloro-6-methoxyquinolin-4-yl)propyl]-1-[3-(thien-2-yl)thiopropyl]piperidine-4-acetic acid
4-[3-(3-Chloro-6-methoxyquinolin-4-yl)propyl]-1-[3-(thien-3-yl)propyl]piperidine-4-acetic acid
4-[3-(3-Chloro-6-methoxyquinolin-4-yl)propyl]-1-[4-(thien-3-yl)butyl]piperidine-4-acetic acid
4-[3-(3-Chloro-6-methoxyquinolin-4-yl)propyl]-1-[2-(thien-3-yl)thioethyl]piperidine-4-acetic acid
4-[3-(3-Chloro-6-methoxyquinolin-4-yl)propyl]-1-[3-(thien-3-yl)thiopropyl]piperidine-4-acetic acid
4-[3-(3-Chloro-6-methoxyquinolin-4-yl)propyl]-1-[3-(1,3-thiazol-2-yl)propyl]piperidine-4-acetic acid
4-[3-(3-Chloro-6-methoxyquinolin-4-yl)propyl]-1-[4-(1,3-thiazol-2-yl)butyl]piperidine-4-acetic acid
4-[3-(3-Chloro-6-methoxyquinolin-4-yl)propyl]-1-[3-(1,3-thiazol-2-yl)thioethyl]piperidine-4-acetic acid
4-[3-(3-Chloro-6-methoxyquinolin-4-yl)propyl]-1-[3-(pyrid-2-yl)propyl]piperidine-4-acetic acid
4-[3-(3-Chloro-6-methoxyquinolin-4-yl)propyl]-1-[4-(pyrid-2-yl)butyl]piperidine-4-acetic acid
4-[3-(3-Chloro-6-methoxyquinolin-4-yl)propyl]-1-[3-(pyrid-2-yl)thiopropyl]piperidine-4-acetic acid
4-[3-(3-Chloro-6-methoxyquinolin-4-yl)propyl]-1-[3-(pyrid-3-yl)propyl]piperidine-4-acetic acid
4-[3-(3-Chloro-6-methoxyquinolin-4-yl)propyl]-1-[4-(pyrid-3-yl)butyl]piperidine-4-acetic acid
4-[3-(3-Chloro-6-methoxyquinolin-4-yl)propyl]-1-[2-(pyrid-3-yl)thioethyl]piperidine-4-acetic acid
4-[3-(3-Chloro-6-methoxyquinolin-4-yl)propyl]-1-[3-(pyrid-3-yl)thiopropyl]piperidine-4-acetic acid
4-[3-(3-Chloro-6-methoxyquinolin-4-yl)propyl]-1-[3-(pyrid-4-yl)propyl]piperidine-4-acetic acid
4-[3-(3-Chloro-6-methoxyquinolin-4-yl)propyl]-1-[4-(pyrid-4-yl)butyl]piperidine-4-acetic acid
4-[3-(3-Chloro-6-methoxyquinolin-4-yl)propyl]-1-[2-(pyrid-4-yl)thioethyl]piperidine-4-acetic acid 4-[3-(3-Chloro-6-methoxyquinolin-4-yl)propyl]-1-[3-(pyrid-4-yl)thiopropyl]piperidine-4-acetic acid 4-[3-(3-Chloro-6-methoxyquinolin-4-yl)propyl]-1-[3-(pyrazin-2-yl)propyl]piperidine-4-acetic acid 4-[3-(3-Chloro-6-methoxyquinolin-4-yl)propyl]-1-[4-(pyrazin-2-yl)butyl]piperidine-4-acetic acid 4-[3-(3-Chloro-6-methoxyquinolin-4-yl)propyl]-1-[2-(pyrazin-2-yl)thioethyl]piperidine-4-acetic acid 4-[3-(3-Chloro-6-methoxyquinolin-4-yl)propyl]-1-[3-(pyrazin-2-yl)thiopropyl]piperidine-4-acetic acid 4-[3-(3-Chloro-6-methoxyquinolin-4-yl)propyl]-1-[3-(4-fluorophenyl)prop-2-ynyl]piperidine-4-acetic acid 4-[3-(3-Chloro-6-methoxyquinolin-4-yl)propyl]-1-[3-(3,4-difluorophenyl)prop-2-ynyl]piperidine-4-acetic acid 4-[3-(3-Chloro-6-methoxyquinolin-4-yl)propyl]-1-[3-(2,4-difluorophenyl)prop-2-ynyl]piperidine-4-acetic acid 4-[3-(3-Chloro-6-methoxyquinolin-4-yl)propyl]-1-[3-(2,3,5-trifluorophenyl)prop-2-ynyl]piperidine-4-acetic acid 4-[3-(3-Chloro-6-methoxyquinolin-4-yl)propyl]-1-[3-(2,4,6-trifluorophenyl)prop-2-ynyl]piperidine-4-acetic acid 4-[3-(3-Chloro-6-methoxyquinolin-4-yl)propyl]-1-[3-(3,4,5-trifluorophenyl)prop-2-ynyl]piperidine-4-acetic acid 4-[3-(3-Chloro-6-methoxyquinolin-4-yl)propyl]-1-[3-(4-chloro-3-fluorophenyl)prop-2-ynyl]piperidine-4-acetic acid 4-[3-(3-Chloro-6-methoxyquinolin-4-yl)propyl]-1-[3-(3-chloro-4-fluorophenyl)prop-2-ynyl]piperidine-4-acetic acid 4-[3-(3-Chloro-6-methoxyquinolin-4-yl)propyl]-1-[3-(2-chloro-4-fluorophenyl)prop-2-ynyl]piperidine-4-acetic acid 4-[3-(3-Chloro-6-methoxyquinolin-4-yl)propyl]-1-[3-(3-chloro-5-fluorophenyl)prop-2-ynyl]piperidine-4-acetic acid 4-[3-(3-Chloro-6-methoxyquinolin-4-yl)propyl]-1-[3-(4-chloro-2-fluorophenyl)prop-2-ynyl]piperidine-4-acetic acid 4-[3-(3-Chloro-6-methoxyquinolin-4-yl)propyl]-1-[3-(3-fluoro-4-methylphenyl)prop-2-ynyl]piperidine-4-acetic acid 4-[3-(3-Chloro-6-methoxyquinolin-4-yl)propyl]-1-[3-(3,5-bis(trifluoromethyl)phenyl)prop-2-ynyl]piperidine-4-acetic acid 4-[3-(3-Chloro-6-methoxyquinolin-4-yl)propyl]-1-[3-(thien-2-yl)prop-2-ynyl]piperidine-4-acetic acid 4-[3-(3-Chloro-6-methoxyquinolin-4-yl)propyl]-1-[3-(thien-3-yl)prop-2-ynyl]piperidine-4-acetic acid 4-[3-(3-Chloro-6-methoxyquinolin-4-yl)propyl]-1-[3-(1,3-thiazol-2-yl)prop-2-ynyl]piperidine-4-acetic acid 4-[3-(3-Chloro-6-methoxyquinolin-4-yl)propyl]-1-[3-(1,3-thiazol-4-yl)prop-2-ynyl]piperidine-4-acetic acid 4-[3-(3-Chloro-6-methoxyquinolin-4-yl)propyl]-1-[3-(1,3-thiazol-5-yl)prop-2-ynyl]piperidine-4-acetic acid 4-[3-(3-Chloro-6-methoxyquinolin-4-yl)propyl]-1-[3-(pyrid-2-yl)prop-2-ynyl]piperidine-4-acetic acid 4-[3-(3-Chloro-6-methoxyquinolin-4-yl)propyl]-1-[3-(pyrid-3-yl)prop-2-ynyl]piperidine-4-acetic acid 4-[3-(3-Chloro-6-methoxyquinolin-4-yl)propyl]-1-[3-(pyrid-4-yl)prop-2-ynyl]piperidine-4-acetic acid 4-[3-(3-Methyl-6-methoxyquinolin-4-yl)propyl]-1-[2-(cyclohexyl)ethyl]piperidine-4-acetic acid 4-[3-(3-Methyl-6-methoxyquinolin-4-yl)propyl]-1-[3-(phenyl)propyl]piperidine-4-acetic acid 4-[3-(3-Methyl-6-methoxyquinolin-4-yl)propyl]-1-[3-(2,3,5-trifluorophenyl)-propyl]piperidine-4-acetic acid 4-[3-(3-Methyl-6-methoxyquinolin-4-yl)propyl]-1-[2-(3,5-difluorophenyl-amino)ethyl]piperidine-4-acetic acid 4-[3-(3-Methyl-6-methoxyquinolin-4-yl)propyl]-1-[2-(2,3,5-trifluorophenyl-amino)ethyl]piperidine-4-acetic acid 4-[3-(3-Methyl-6-methoxyquinolin-4-yl)propyl]-1-[2-(3,5-difluorophenoxy)ethyl]piperidine-4-acetic acid 4-[3-(3-Methyl-6-methoxyquinolin-4-yl)propyl]-1-[2-(2,3,5-trifluorophenoxy)-ethyl]piperidine-4-acetic acid 4-[3-(3-Methyl-6-methoxyquinolin-4-yl)propyl]-1-[2-(2,3,5-trifluorophenylthio)-ethyl]piperidine-4-acetic acid 4-[3-(3-Methyl-6-methoxyquinolin-4-yl)propyl]-1-[2-(cyclopentylthio)ethyl]piperidine-4-acetic acid 4-[3-(3-Methyl-6-methoxyquinolin-4-yl)propyl]-1-[2-(pyrid-2-yl)thioethyl]piperidine-4-acetic acid 4-[3-(3-Methyl-6-methoxyquinolin-4-yl)propyl]-1-[2-(thien-2-yl)thioethyl]piperidine-4-acetic acid 4-[3-(3-Methyl-6-methoxyquinolin-4-yl)propyl]-1-[3-(2,3,5-trifluorophenyl)prop-2-ynyl]piperidine-4-acetic acid 4-[3-(3-Methyl-6-methoxyquinolin-4-yl)propyl]-1-[3-(thien-2-yl)prop-2-ynyl]piperidine-4-acetic acid 4-[3-(3-Fluoro-6-methoxyquinolin-4-yl)propyl]-1-[2-(cyclohexyl)ethyl]piperidine-4-acetic acid 4-[3-(3-Fluoro-6-methoxyquinolin-4-yl)propyl]-1-[3-(phenyl)propyl]piperidine-4-acetic acid 4-[3-(3-Fluoro-6-methoxyquinolin-4-yl)propyl]-1-[3-(2,3,5-trifluorophenyl)-propyl]piperidine-4-acetic acid 4-[3-(3-Fluoro-6-methoxyquinolin-4-yl)propyl]-1-[2-(3,5-difluorophenylamino)-ethyl]piperidine-4-acetic acid 4-[3-(3-Fluoro-6-methoxyquinolin-4-yl)propyl]-1-[2-(2,3,5-trifluorophenylamino)-ethyl]piperidine-4-acetic acid 4-[3-(3-Fluoro-6-methoxyquinolin-4-yl)propyl]-1-[2-(3,5-difluorophenoxy)ethyl]piperidine-4-acetic acid 4-[3-(3-Fluoro-6-methoxyquinolin-4-yl)propyl]-1-[2-(2,3,5-trifluorophenoxy)ethyl]-piperidine-4-acetic acid 4-[3-(3-Fluoro-6-methoxyquinolin-4-yl)propyl]-1-[2-(2,3,5-trifluorophenylthio)-ethyl]piperidine-4-acetic acid 4-[3-(3-Fluoro-6-methoxyquinolin-4-yl)propyl]-1-[2-(cyclopentylthio)ethyl]piperidine-4-acetic acid 4-[3-(3-Fluoro-6-methoxyquinolin-4-yl)propyl]-1-[2-(pyrid-2-yl)thioethyl]piperidine-4-acetic acid 4-[3-(3-Fluoro-6-methoxyquinolin-4-yl)propyl]-1-[2-(thien-2-yl)thioethyl]piperidine-4-acetic acid 4-[3-(3-Fluoro-6-methoxyquinolin-4-yl)propyl]-1-[3-(2,3,5-trifluorophenyl)prop-2-ynyl]piperidine-4-acetic acid 4-[3-(3-Fluoro-6-methoxyquinolin-4-yl)propyl]-1-[3-(thien-2-yl)prop-2-ynyl]piperidine-4-acetic acid 4-[3-(3-Dimethylamino-6-methoxyquinolin-4-yl)propyl]-1-[2-(cyclohexyl)ethyl]piperidine-4-acetic acid 4-[3-(3-Dimethylamino-6-methoxyquinolin-4-yl)propyl]-1-[3-(phenyl)propyl]piperidine-4-acetic acid 4-[3-(3-Dimethylamino-6-methoxyquinolin-4-yl)propyl]-1-[3-(2,3,5-trifluorophenyl)-propyl]piperidine-4-acetic acid 4-[3-(3-Dimethylamino-6-methoxyquinolin-4-yl)propyl]-1-[2-(3,5-difluorophenylamino)-ethyl]piperidine-4-acetic acid
4-[3-(3-Dimethylamino-6-methoxyquinolin-4-yl)propyl]-1-[2-(2,3,5-trifluorophenyl-amino)ethyl]piperidine-4-acetic acid
4-[3-(3-Dimethylamino-6-methoxyquinolin-4-yl)propyl]-1-[2-(3,5-difluorophenoxy)-ethyl]piperidine-4-acetic acid
4-[3-(3-Dimethylamino-6-methoxyquinolin-4-yl)propyl]-1-[2-(2,3,5-trifluorophenoxy)-ethyl]piperidine-4-acetic acid
4-[3-(3-Dimethylamino-6-methoxyquinolin-4-yl)propyl]-1-[2-(2,3,5-trifluorophenylthio)-ethyl]piperidine-4-acetic acid
4-[3-(3-Dimethylamino-6-methoxyquinolin-4-yl)propyl]-1-[2-(cyclopentylthio)ethyl]piperidine-4-acetic acid
4-[3-(3-Dimethylamino-6-methoxyquinolin-4-yl)propyl]-1-[2-(pyrid-2-yl)thio-ethyl]piperidine-4-acetic acid
4-[3-(3-Dimethylamino-6-methoxyquinolin-4-yl)propyl]-1-[2-(thien-2-yl)thio-ethyl]piperidine-4-acetic acid
4-[3-(3-Dimethylamino-6-methoxyquinolin-4-yl)propyl]-1-[3-(2,3,5-trifluorophenyl)prop-2-ynyl]piperidine-4-acetic acid
4-[3-(3-Dimethylamino-6-methoxyquinolin-4-yl)propyl]-1-[3-(thien-2-yl)prop-2-ynyl]piperidine-4-acetic acid
4-[3-(3-Hydroxymethyl-6-methoxyquinolin-4-yl)propyl]-1-[2-(cyclohexyl)ethyl]piperidine-4-acetic acid
4-[3-(3-Hydroxymethyl-6-methoxyquinolin-4-yl)propyl]-1-[3-(phenyl)propyl]piperidine-4-acetic acid
4-[3-(3-Hydroxymethyl-6-methoxyquinolin-4-yl)propyl]-1-[3-(2,3,5-trifluorophenyl)-propyl]piperidine-4-acetic acid
4-[3-(3-Hydroxymethyl-6-methoxyquinolin-4-yl)propyl]-1-[2-(3,5-difluorophenyl-amino)ethyl]piperidine-4-acetic acid
4-[3-(3-Hydroxymethyl-6-methoxyquinolin-4-yl)propyl]-1-[2-(2,3,5-trifluorophenyl-amino)ethyl]piperidine-4-acetic acid
4-[3-(3-Hydroxymethyl-6-methoxyquinolin-4-yl)propyl]-1-[2-(3,5-difluorophenoxy)-ethyl]piperidine-4-acetic acid
4-[3-(3-Hydroxymethyl-6-methoxyquinolin-4-yl)propyl]-1-[2-(2,3,5-trifluorophenoxy)-ethyl]piperidine-4-acetic acid
4-[3-(3-Hydroxymethyl-6-methoxyquinolin-4-yl)propyl]-1-[2-(2,3,5-trifluorophenylthio)-ethyl]piperidine-4-acetic acid
4-[3-(3-Hydroxymethyl-6-methoxyquinolin-4-yl)propyl]-1-[2-(cyclopentylthio)-ethyl]piperidine-4-acetic acid
4-[3-(3-Hydroxymethyl-6-methoxyquinolin-4-yl)propyl]-1-[2-(pyrid-2-yl)thioethyl]-piperidine-4-acetic acid
4-[3-(3-Hydroxymethyl-6-methoxyquinolin-4-yl)propyl]-1-[2-(thien-2-yl)thioethyl]-piperidine-4-acetic acid
4-[3-(3-Hydroxymethyl-6-methoxyquinolin-4-yl)propyl]-1-[3-(2,3,5-trifluorophenyl)prop-2-ynyl]piperidine-4-acetic acid
4-[3-(3-Hydroxymethyl-6-methoxyquinolin-4-yl)propyl]-1-[3-(thien-2-yl)prop-2-ynyl]piperidine-4-acetic acid
4-[3-(3-Fluoromethyl-6-methoxyquinolin-4-yl)propyl]-1-[2-(cyclohexyl)ethyl]piperidine-4-acetic acid
4-[3-(3-Fluoromethyl-6-methoxyquinolin-4-yl)propyl]-1-[3-(phenyl)propyl]piperidine-4-acetic acid
4-[3-(3-Fluoromethyl-6-methoxyquinolin-4-yl)propyl]-1-[3-(2,3,5-trifluorophenyl)-propyl]piperidine-4-acetic acid
4-[3-(3-Fluoromethyl-6-methoxyquinolin-4-yl)propyl]-1-[2-(3,5-difluorophenylamino)-ethyl]piperidine-4-acetic acid
4-[3-(3-Fluoromethyl-6-methoxyquinolin-4-yl)propyl]-1-[2-(2,3,5-trifluorophenylamino)-ethyl]piperidine-4-acetic acid
4-[3-(3-Fluoromethyl-6-methoxyquinolin-4-yl)propyl]-1-[2-(3,5-difluorophenoxy)-ethyl]piperidine-4-acetic acid
4-[3-(3-Fluoromethyl-6-methoxyquinolin-4-yl)propyl]-1-[2-(2,3,5-trifluorophenoxy)-ethyl]piperidine-4-acetic acid
4-[3-(3-Fluoromethyl-6-methoxyquinolin-4-yl)propyl]-1-[2-(2,3,5-trifluorophenylthio)-ethyl]piperidine-4-acetic acid
4-[3-(3-Fluoromethyl-6-methoxyquinolin-4-yl)propyl]-1-[2-(cyclopentylthio)-ethyl]piperidine-4-acetic acid
4-[3-(3-Fluoromethyl-6-methoxyquinolin-4-yl)propyl]-1-[2-(pyrid-2-yl)thioethyl]piperidine-4-acetic acid
4-[3-(3-Fluoromethyl-6-methoxyquinolin-4-yl)propyl]-1-[2-(thien-2-yl)thioethyl]piperidine-4-acetic acid
4-[3-(3-Fluoromethyl-6-methoxyquinolin-4-yl)propyl]-1-[3-(2,3,5-trifluorophenyl)prop-2-ynyl]piperidine-4-acetic acid
4-[3-(3-Fluoromethyl-6-methoxyquinolin-4-yl)propyl]-1-[3-(thien-2-yl)prop-2-ynyl]piperidine-4-acetic acid
4-[3-(3-Aminomethyl-6-methoxyquinolin-4-yl)propyl]-1-[2-(cyclohexyl)ethyl]piperidine-4-acetic acid
4-[3-(3-Aminomethyl-6-methoxyquinolin-4-yl)propyl]-1-[3-(phenyl)propyl]piperidine-4-acetic acid
4-[3-(3-Aminomethyl-6-methoxyquinolin-4-yl)propyl]-1-[3-(2,3,5-trifluorophenyl)-propyl]piperidine-4-acetic acid
4-[3-(3-Aminomethyl-6-methoxyquinolin-4-yl)propyl]-1-[2-(3,5-difluorophenylamino)-ethyl]piperidine-4-acetic acid
4-[3-(3-Aminomethyl-6-methoxyquinolin-4-yl)propyl]-1-[2-(2,3,5-trifluorophenylamino)-ethyl]piperidine-4-acetic acid
4-[3-(3-Aminomethyl-6-methoxyquinolin-4-yl)propyl]-1-[2-(3,5-difluorophenoxy)-ethyl]piperidine-4-acetic acid
4-[3-(3-Aminomethyl-6-methoxyquinolin-4-yl)propyl]-1-[2-(2,3,5-trifluorophenoxy)-ethyl]piperidine-4-acetic acid
4-[3-(3-Aminomethyl-6-methoxyquinolin-4-yl)propyl]-1-[2-(2,3,5-trifluorophenylthio)-ethyl]piperidine-4-acetic acid
4-[3-(3-Aminomethyl-6-methoxyquinolin-4-yl)propyl]-1-[2-(cyclopentylthio)-ethyl]piperidine-4-acetic acid
4-[3-(3-Aminomethyl-6-methoxyquinolin-4-yl)propyl]-1-[2-(pyrid-2-yl)thioethyl]piperidine-4-acetic acid
4-[3-(3-Aminomethyl-6-methoxyquinolin-4-yl)propyl]-1-[2-(thien-2-yl)thioethyl]piperidine-4-acetic acid
4-[3-(3-Aminomethyl-6-methoxyquinolin-4-yl)propyl]-1-[3-(2,3,5-trifluorophenyl)prop-2-ynyl]piperidine-4-acetic acid 4-[3-(3-Aminomethyl-6-methoxyquinolin-4-yl)propyl]-1-[3-(thien-2-yl)prop-2-ynyl]piperidine-4-acetic acid 4-[3-(3-Morpholinomethyl-6-methoxyquinolin-4-yl)propyl]-1-[2-(cyclohexyl)-ethyl]piperidine-4-acetic acid 4-[3-(3-Morpholinomethyl-6-methoxyquinolin-4-yl)propyl]-1-[3-(phenyl)propyl]piperidine-4-acetic acid 4-[3-(3-Morpholinomethyl-6-methoxyquinolin-4-yl)propyl]-1-[3-(2,3,5-trifluorophenyl)-propyl]piperidine-4-acetic acid 4-[3-(3-Morpholinomethyl-6-methoxyquinolin-4-yl)propyl]-1-[2-(3,5-difluorophenyl-amino)ethyl]piperidine-4-acetic acid 4-[3-(3-Morpholinomethyl-6-methoxyquinolin-4-yl)propyl]-1-[2-(2,3,5-trifluorophenyl-amino)ethyl]piperidine-4-acetic acid 4-[3-(3-Morpholinomethyl-6-methoxyquinolin-4-yl)propyl]-1-[2-(3,5-difluorophenoxy)-ethyl]piperidine-4-acetic acid 4-[3-(3-Morpholinomethyl-6-methoxyquinolin-4-yl)propyl]-1-[2-(2,3,5-trifluorophenoxy)-ethyl]piperidine-4-acetic acid 4-[3-(3-Morpholinomethyl-6-methoxyquinolin-4-yl)propyl]-1-[2-(2,3,5-trifluorophenyl-thio)ethyl]piperidine-4-acetic acid 4-[3-(3-Morpholinomethyl-6-methoxyquinolin-4-yl)propyl]-1-[2-(cyclopentyl-thio)ethyl]piperidine-4-acetic acid 4-[3-(3-Morpholinomethyl-6-methoxyquinolin-4-yl)propyl]-1-[2-(pyrid-2-yl)thioethyl]-piperidine-4-acetic acid 4-[3-(3-Morpholinomethyl-6-methoxyquinolin-4-yl)propyl]-1-[2-(thien-2-yl)thioethyl]-piperidine-4-acetic acid 4-[3-(3-Morpholinomethyl-6-methoxyquinolin-4-yl)propyl]-1-[3-(2,3,5-trifluorophenyl)-prop-2-ynyl]piperidine-4-acetic acid 4-[3-(3-Morpholinomethyl-6-methoxyquinolin-4-yl)propyl]-1-[3-(thien-2-yl)prop-2-ynyl]piperidine-4-acetic acid 4-[3-(3-Methyl-6-methoxyquinolin-4-yl)propyl]-1-[3-(3,4,5-trifluorophenyl)-propyl]piperidine-4-acetic acid 4-[3-(3-Methyl-6-methoxyquinolin-4-yl)propyl]-1-[2-(2,4,6-trifluorophenylthio)-ethyl]piperidine-4-acetic acid 4-[3-(3-Methyl-6-methoxyquinolin-4-yl)propyl]-1-[2-(3,4,5-trifluorophenylthio)-ethyl]piperidine-4-acetic acid 4-[3-(3-Methyl-6-methoxyquinolin-4-yl)propyl]-1-[2-(2,4,6-trifluorophenylamino)-ethyl]piperidine-4-acetic acid 4-[3-(3-Methyl-6-methoxyquinolin-4-yl)propyl]-1-[2-(3,4,5-trifluorophenylamino)-ethyl]piperidine-4-acetic acid 4-[3-(3-Methyl-6-methoxyquinolin-4-yl)propyl]-1-[2-(2,4,6-trifluorophenoxy)ethyl]-piperidine-4-acetic acid 4-[3-(3-Methyl-6-methoxyquinolin-4-yl)propyl]-1-[2-(3,4,5-trifluorophenoxy)ethyl]-piperidine-4-acetic acid 4-[3-(3-Methyl-6-methoxyquinolin-4-yl)propyl]-1-[3-(2,4,6-trifluorophenyl)prop-2-ynyl]piperidine-4-acetic acid 4-[3-(3-Methyl-6-methoxyquinolin-4-yl)propyl]-1-[3-(3,4,5-trifluorophenyl)prop-2-ynyl]piperidine-4-acetic acid 4-[3-(3-Fluoro-6-methoxyquinolin-4-yl)propyl]-1-[3-(2,4,6-trifluorophenyl)propyl]-piperidine-4-acetic acid 4-[3-(3-Fluoro-6-methoxyquinolin-4-yl)propyl]-1-[3-(3,4,5-trifluorophenyl)propyl]-piperidine-4-acetic acid 4-[3-(3-Fluoro-6-methoxyquinolin-4-yl)propyl]-1-[2-(2,4,6-trifluorophenylthio)ethyl]-piperidine-4-acetic acid 4-[3-(3-Fluoro-6-methoxyquinolin-4-yl)propyl]-1-[2-(3,4,5-trifluorophenylthio)ethyl]-piperidine-4-acetic acid 4-[3-(3-Fluoro-6-methoxyquinolin-4-yl)propyl]-1-[2-(2,4,6-trifluorophenylamino)-ethyl]piperidine-4-acetic acid 4-[3-(3-Fluoro-6-methoxyquinolin-4-yl)propyl]-1-[2-(3,4,5-trifluorophenylamino)-ethyl]piperidine-4-acetic acid 4-[3-(3-Fluoro-6-methoxyquinolin-4-yl)propyl]-1-[2-(2,4,6-trifluorophenoxy)ethyl]-piperidine-4-acetic acid 4-[3-(3-Fluoro-6-methoxyquinolin-4-yl)propyl]-1-[2-(3,4,5-trifluorophenoxy)ethyl]-piperidine-4-acetic acid 4-[3-(3-Fluoro-6-methoxyquinolin-4-yl)propyl]-1-[3-(2,4,6-trifluorophenyl)prop-2-ynyl]piperidine-4-acetic acid 4-[3-(3-Fluoro-6-methoxyquinolin-4-yl)propyl]-1-[3-(3,4,5-trifluorophenyl)prop-2-ynyl]piperidine-4-acetic acid 4-[3-(3-Dimethylamino-6-methoxyquinolin-4-yl)propyl]-1-[3-(2,4,6-trifluorophenyl)-propyl]piperidine-4-acetic acid 4-[3-(3-Dimethylamino-6-methoxyquinolin-4-yl)propyl]-1-[3-(3,4,5-trifluorophenyl)-propyl]piperidine-4-acetic acid 4-[3-(3-Dimethylamino-6-methoxyquinolin-4-yl)propyl]-1-[2-(2,4,6-trifluorophenylthio)-ethyl]piperidine-4-acetic acid 4-[3-(3-Dimethylamino-6-methoxyquinolin-4-yl)propyl]-1-[2-(3,4,5-trifluorophenylthio)-ethyl]piperidine-4-acetic acid 4-[3-(3-Dimethylamino-6-methoxyquinolin-4-yl)propyl]-1-[2-(2,4,6-trifluorophenyl-amino)ethyl]piperidine-4-acetic acid 4-[3-(3-Dimethylamino-6-methoxyquinolin-4-yl)propyl]-1-[2-(3,4,5-trifluorophenyl-amino)ethyl]piperidine-4-acetic acid 4-[3-(3-Dimethylamino-6-methoxyquinolin-4-yl)propyl]-1-[2-(2,4,6-trifluorophenoxy)-ethyl]piperidine-4-acetic acid 4-[3-(3-Dimethylamino-6-methoxyquinolin-4-yl)propyl]-1-[2-(3,4,5-trifluorophenoxy)-ethyl]piperidine-4-acetic acid 4-[3-(3-Dimethylamino-6-methoxyquinolin-4-yl)propyl]-1-[3-(2,4,6-trifluorophenyl)prop-2-ynyl]piperidine-4-acetic acid 4-[3-(3-Dimethylamino-6-methoxyquinolin-4-yl)propyl]-1-[3-(3,4,5-trifluorophenyl)prop-2-ynyl]piperidine-4-acetic acid 4-[3-(3-Hydroxymethyl-6-methoxyquinolin-4-yl)propyl]-1-[3-(3,4,5-trifluorophenyl)-propyl]piperidine-4-acetic acid 4-[3-(3-Hydroxymethyl-6-methoxyquinolin-4-yl)propyl]-1-[2-(2,4,6-trifluorophenylthio)-ethyl]piperidine-4-acetic acid 4-[3-(3-Hydroxymethyl-6-methoxyquinolin-4-yl)propyl]-1-[2-(3,4,5-trifluorophenylthio)-ethyl]piperidine-4-acetic acid 4-[3-(3-Hydroxymethyl-6-methoxyquinolin-4-yl)propyl]-1-[2-(2,4,6-trifluorophenylamino)-ethyl]piperidine-4-acetic acid 4-[3-(3-Hydroxymethyl-6-methoxyquinolin-4-yl)propyl]-1-[2-(3,4,5-trifluorophenylamino)-ethyl]piperidine-4-acetic acid 4-[3-(3-Hydroxymethyl-6-methoxyquinolin-4-yl)propyl]-1-[2-(2,4,6-trifluorophenoxy)-ethyl]piperidine-4-acetic acid 4-[3-(3-Hydroxymethyl-6-methoxyquinolin-4-yl)propyl]-1-[2-(3,4,5-trifluorophenoxy)-ethyl]piperidine-4-acetic acid 4-[3-(3-Hydroxymethyl-6-methoxyquinolin-4-yl)propyl]-1-[3-(2,4,6-trifluorophenyl)prop-2-ynyl]piperidine-4-acetic acid 4-[3-(3-Hydroxymethyl-6-methoxyquinolin-4-yl)propyl]-1-[3-(3,4,5-trifluorophenyl)prop-2-ynyl]piperidine-4-acetic acid 4-[3-(3-Fluoromethyl-6-methoxyquinolin-4-yl)propyl]-1-[3-(2,4,6-trifluorophenyl)-propyl]piperidine-4-acetic acid 4-[3-(3-Fluoromethyl-6-methoxyquinolin-4-yl)propyl]-1-[3-(3,4,5-trifluorophenyl)-propyl]piperidine-4-acetic acid 4-[3-(3-Fluoromethyl-6-methoxyquinolin-4-yl)propyl]-1-[2-(2,4,6-trifluorophenylthio)-ethyl]piperidine-4-acetic acid 4-[3-(3-Fluoromethyl-6-methoxyquinolin-4-yl)propyl]-1-[2-(3,4,5-trifluorophenylthio)-ethyl]piperidine-4-acetic acid 4-[3-(3-Fluoromethyl-6-methoxyquinolin-4-yl)propyl]-1-[2-(2,4,6-trifluorophenylamino)-ethyl]piperidine-4-acetic acid 4-[3-(3-Fluoromethyl-6-methoxyquinolin-4-yl)propyl]-1-[2-(3,4,5-trifluorophenylamino)-ethyl]piperidine-4-acetic acid 4-[3-(3-Fluoromethyl-6-methoxyquinolin-4-yl)propyl]-1-[2-(2,4,6-trifluorophenoxy)-ethyl]piperidine-4-acetic acid 4-[3-(3-Fluoromethyl-6-methoxyquinolin-4-yl)propyl]-1-[2-(3,4,5-trifluorophenoxy)ethyl]-piperidine-4-acetic acid 4-[3-(3-Fluoromethyl-6-methoxyquinolin-4-yl)propyl]-1-[3-(2,4,6-trifluorophenyl)prop-2-ynyl]piperidine-4-acetic acid 4-[3-(3-Fluoromethyl-6-methoxyquinolin-4-yl)propyl]-1-[3-(3,4,5-trifluorophenyl)prop-2-ynyl]piperidine-4-acetic acid 4-[3-(3-Aminomethyl-6-methoxyquinolin-4-yl)propyl]-1-[3-(2,4,6-trifluorophenyl)-propyl]piperidine-4-acetic acid 4-[3-(3-Aminomethyl-6-methoxyquinolin-4-yl)propyl]-1-[3-(3,4,5-trifluorophenyl)-propyl]piperidine-4-acetic acid 4-[3-(3-Aminomethyl-6-methoxyquinolin-4-yl)propyl]-1-[2-(2,4,6-trifluorophenylthio)-ethyl]piperidine-4-acetic acid 4-[3-(3-Aminomethyl-6-methoxyquinolin-4-yl)propyl]-1-[2-(3,4,5-trifluorophenylthio)-ethyl]piperidine-4-acetic acid 4-[3-(3-Aminomethyl-6-methoxyquinolin-4-yl)propyl]-1-[2-(2,4,6-trifluorophenylamino)-ethyl]piperidine-4-acetic acid 4-[3-(3-Aminomethyl-6-methoxyquinolin-4-yl)propyl]-1-[2-(3,4,5-trifluorophenylamino)-ethyl]piperidine-4-acetic acid 4-[3-(3-Aminomethyl-6-methoxyquinolin-4-yl)propyl]-1-[2-(2,4,6-trifluorophenoxy)-ethyl]piperidine-4-acetic acid 4-[3-(3-Aminomethyl-6-methoxyquinolin-4-yl)propyl]-1-[2-(3,4,5-trifluorophenoxy)-ethyl]piperidine-4-acetic acid 4-[3-(3-Aminomethyl-6-methoxyquinolin-4-yl)propyl]-1-[3-(2,4,6-trifluorophenyl)prop-2-ynyl]piperidine-4-acetic acid 4-[3-(3-Aminomethyl-6-methoxyquinolin-4-yl)propyl]-1-[3-(3,4,5-trifluorophenyl)prop-2-ynyl]piperidine-4-acetic acid 4-[3-(3-Morpholinomethyl-6-methoxyquinolin-4-yl)propyl]-1-[3-(2,4,6-trifluorophenyl)-propyl]piperidine-4-acetic acid 4-[3-(3-Morpholinomethyl-6-methoxyquinolin-4-yl)propyl]-1-[3-(3,4,5-trifluorophenyl)-propyl]piperidine-4-acetic acid 4-[3-(3-Morpholinomethyl-6-methoxyquinolin-4-yl)propyl]-1-[2-(2,4,6-trifluorophenylthio)-ethyl]piperidine-4-acetic acid 4-[3-(3-Morpholinomethyl-6-methoxyquinolin-4-yl)propyl]-1-[2-(3,4,5-trifluorophenylthio)-ethyl]piperidine-4-acetic acid 4-[3-(3-Morpholinomethyl-6-methoxyquinolin-4-yl)propyl]-1-[2-(2,4,6-trifluorophenyl-amino)ethyl]piperidine-4-acetic acid 4-[3-(3-Morpholinomethyl-6-methoxyquinolin-4-yl)propyl]-1-[2-(3,4,5-trifluorophenyl-amino)ethyl]piperidine-4-acetic acid 4-[3-(3-Morpholinomethyl-6-methoxyquinolin-4-yl)propyl]-1-[2-(2,4,6-trifluoro-phenoxy)ethyl]piperidine-4-acetic acid 4-[3-(3-Morpholinomethyl-6-methoxyquinolin-4-yl)propyl]-1-[2-(3,4,5-trifluoro-phenoxy)ethyl]piperidine-4-acetic acid 4-[3-(3-Morpholinomethyl-6-methoxyquinolin-4-yl)propyl]-1-[3-(2,4,6-trifluoro-phenyl)prop-2-ynyl]piperidine-4-acetic acid 4-[3-(3-Morpholinomethyl-6-methoxyquinolin-4-yl)propyl]-1-[3-(3,4,5-trifluoro-phenyl)prop-2-ynyl]piperidine-4-acetic acid 4-[3-(R,S)-Hydroxy-3-(3-chloro-6-methoxyquinolin-4-yl)propyl]-1-heptylpiperidine-4-acetic acid 4-[3-(R,S)-Hydroxy-3-(3-chloro-6-methoxyquinolin-4-yl)propyl]-1-[4-phenylbutyl]-piperidine-4-acetic acid 4-[3-(R,S)-Hydroxy-3-(3-chloro-6-methoxyquinolin-4-yl)propyl]-1-[3-(phenyl)propyl]-piperidine-4-acetic acid 4-[3-(R,S)-Hydroxy-3-(3-chloro-6-methoxyquinolin-4-yl)propyl]-1-[4-(2-fluorophenyl)-propyl]piperidine-4-acetic acid 4-[3-(R,S)-Hydroxy-3-(3-chloro-6-methoxyquinolin-4-yl)propyl]-1-[4-(3-fluorophenyl)-propyl]piperidine-4-acetic acid 4-[3-(R,S)-Hydroxy-3-(3-chloro-6-methoxyquinolin-4-yl)propyl]-1-[3-(4-fluorophenyl)-propyl]piperidine-4-acetic acid 4-[3-(R,S)-Hydroxy-3-(3-chloro-6-methoxyquinolin-4-yl)propyl]-1-[4-(4-fluorophenyl)-butyl]piperidine-4-acetic acid 4-[3-(R,S)-Hydroxy-3-(3-chloro-6-methoxyquinolin-4-yl)propyl]-1-[3-(2,3-difluoro-phenyl)propyl]piperidine-4-acetic acid 4-[3-(R,S)-Hydroxy-3-(3-chloro-6-methoxyquinolin-4-yl)propyl]-1-[4-(2,3-difluoro-phenyl)propyl]piperidine-4-acetic acid 4-[3-(R,S)-Hydroxy-3-(3-chloro-6-methoxyquinolin-4-yl)propyl]-1-[3-(2,6-difluoro-phenyl)propyl]piperidine-4-acetic acid 4-[3-(R,S)-Hydroxy-3-(3-chloro-6-methoxyquinolin-4-yl)propyl]-1-[4-(2,6-difluoro-phenyl)propyl]piperidine-4-acetic acid 4-[3-(R,S)-Hydroxy-3-(3-chloro-6-methoxyquinolin-4-yl)propyl]-1-[3-(3,5-difluoro-phenyl)propyl]piperidine-4-acetic acid 4-[3-(R,S)-Hydroxy-3-(3-chloro-6-methoxyquinolin-4-yl)propyl]-1-[3-(2,3,5-trifluorophenyl)propyl]piperidine-4-acetic acid 4-[3-(R,S)-Hydroxy-3-(3-chloro-6-methoxyquinolin-4-yl)propyl]-1-[3-(2,4,6-trifluorophenyl)propyl]piperidine-4-acetic acid 4-[3-(R,S)-Hydroxy-3-(3-chloro-6-methoxyquinolin-4-yl)propyl]-1-[3-(3,4,5-trifluorophenyl)propyl]piperidine-4-acetic acid 4-[3-(R,S)-Hydroxy-3-(3-chloro-6-methoxyquinolin-4-yl)propyl]-1-[3-phenylthio-propyl]piperidine-4-acetic acid 4-[3-(R,S)-Hydroxy-3-(3-chloro-6-methoxyquinolin-4-yl)propyl]-1-[3-(2-fluorophenylthio)propyl]piperidine-4-acetic acid 4-[3-(R,S)-Hydroxy-3-(3-chloro-6-methoxyquinolin-4-yl)propyl]-1-[3-(3-fluorophenylthio)propyl]piperidine-4-acetic acid 314-[3-(R,S)-Hydroxy-3-(3-chloro-6-methoxyquinolin-4-yl)propyl]-1-[2-(4-fluorophenylthio)ethyl]piperidine-4-acetic acid 4-[3-(R,S)-Hydroxy-3-(3-chloro-6-methoxyquinolin-4-yl)propyl]-1-[3-(4-fluorophenylthio)propyl]piperidine-4-acetic acid 4-[3-(R,S)-Hydroxy-3-(3-chloro-6-methoxyquinolin-4-yl)propyl]-1-[2-(2,3-difluorophenylthio)ethyl]piperidine-4-acetic acid 4-[3-(R,S)-Hydroxy-3-(3-chloro-6-methoxyquinolin-4-yl)propyl]-1-[3-(2,3-difluorophenylthio)propyl]piperidine-4-acetic acid 4-[3-(R,S)-Hydroxy-3-(3-chloro-6-methoxyquinolin-4-yl)propyl]-1-[2-(2,6-difluorophenylthio)ethyl]piperidine-4-acetic acid 4-[3-(R,S)-Hydroxy-3-(3-chloro-6-methoxyquinolin-4-yl)propyl]-1-[2-(2,3,5-trifluorophenylthio)ethyl]piperidine-4-acetic acid 4-[3-(R,S)-Hydroxy-3-(3-chloro-6-methoxyquinolin-4-yl)propyl]-1-[2-(2,4,6-trifluorophenylthio)ethyl]piperidine-4-acetic acid 4-[3-(R,S)-Hydroxy-3-(3-chloro-6-methoxyquinolin-4-yl)propyl]-1-[2-(3,4,5-trifluorophenylthio)ethyl]piperidine-4-acetic acid 4-[3-(R,S)-Hydroxy-3-(3-chloro-6-methoxyquinolin-4-yl)propyl]-1-[2-(3,5-difluorophenoxy)ethyl]piperidine-4-acetic acid 4-[3-(R,S)-Hydroxy-3-(3-chloro-6-methoxyquinolin-4-yl)propyl]-1-[2-(2,3,5-trifluorophenoxy)ethyl]piperidine-4-acetic acid 4-[3-(R,S)-Hydroxy-3-(3-chloro-6-methoxyquinolin-4-yl)propyl]-1-[2-(2,4,6-trifluorophenoxy)ethyl]piperidine-4-acetic acid 4-[3-(R,S)-Hydroxy-3-(3-chloro-6-methoxyquinolin-4-yl)propyl]-1-[2-(3,4,5-trifluorophenoxy)ethyl]piperidine-4-acetic acid 4-[3-(R,S)-Hydroxy-3-(3-chloro-6-methoxyquinolin-4-yl)propyl]-1-[2-(3,5-difluorophenylamino)ethyl]piperidine-4-acetic acid 4-[3-(R,S)-Hydroxy-3-(3-chloro-6-methoxyquinolin-4-yl)propyl]-1-[2-(2,3,5-trifluorophenylamino)ethyl]piperidine-4-acetic acid 4-[3-(R,S)-Hydroxy-3-(3-chloro-6-methoxyquinolin-4-yl)propyl]-1-[2-(2,4,6-trifluorophenylamino)ethyl]piperidine-4-acetic acid 4-[3-(R,S)-Hydroxy-3-(3-chloro-6-methoxyquinolin-4-yl)propyl]-1-[2-(3,4,5-trifluorophenylamino)ethyl]piperidine-4-acetic acid 4-[3-(R,S)-Hydroxy-3-(3-chloro-6-methoxyquinolin-4-yl)propyl]-1-[3-(2,6-difluorophenylthio)propyl]piperidine-4-acetic acid 4-[3-(R,S)-Hydroxy-3-(3-chloro-6-methoxyquinolin-4-yl)propyl]-1-[2-(2-chlorophenylthio)ethyl]piperidine-4-acetic acid 4-[3-(R,S)-Hydroxy-3-(3-chloro-6-methoxyquinolin-4-yl)propyl]-1-[3-(2-chlorophenylthio)propyl]piperidine-4-acetic acid 4-[3-(R,S)-Hydroxy-3-(3-chloro-6-methoxyquinolin-4-yl)propyl]-1-[2-(3-chlorophenylthio)ethyl]piperidine-4-acetic acid 4-[3-(R,S)-Hydroxy-3-(3-chloro-6-methoxyquinolin-4-yl)propyl]-1-[3-(3-chlorophenylthio)propyl]piperidine-4-acetic acid 4-[3-(R,S)-Hydroxy-3-(3-chloro-6-methoxyquinolin-4-yl)propyl]-1-[2-(4-chlorophenylthio)ethyl]piperidine-4-acetic acid 4-[3-(R,S)-Hydroxy-3-(3-chloro-6-methoxyquinolin-4-yl)propyl]-1-[3-(4-chlorophenylthio)propyl]piperidine-4-acetic acid 4-[3-(R,S)-Hydroxy-3-(3-chloro-6-methoxyquinolin-4-yl)propyl]-1-[2-(2-methylphenylthio)ethyl]piperidine-4-acetic acid 4-[3-(R,S)-Hydroxy-3-(3-chloro-6-methoxyquinolin-4-yl)propyl]-1-[3-(2-methylphenylthio)propyl]piperidine-4-acetic acid 4-[3-(R,S)-Hydroxy-3-(3-chloro-6-methoxyquinolin-4-yl)propyl]-1-[2-(3-methylphenylthio)ethyl]piperidine-4-acetic acid 4-[3-(R,S)-Hydroxy-3-(3-chloro-6-methoxyquinolin-4-yl)propyl]-1-[3-(3-methylphenylthio)propyl]piperidine-4-acetic acid 4-[3-(R,S)-Hydroxy-3-(3-chloro-6-methoxyquinolin-4-yl)propyl]-1-[2-(4-methylphenylthio)ethyl]piperidine-4-acetic acid 4-[3-(R,S)-Hydroxy-3-(3-chloro-6-methoxyquinolin-4-yl)propyl]-1-[3-(4-methylphenylthio)propyl]piperidine-4-acetic acid 4-[3-(R,S)-Hydroxy-3-(3-chloro-6-methoxyquinolin-4-yl)propyl]-1-[2-(2-trifluoromethylphenylthio)ethyl]piperidine-4-acetic acid 4-[3-(R,S)-Hydroxy-3-(3-chloro-6-methoxyquinolin-4-yl)propyl]-1-[3-(2-trifluoromethylphenylthio)propyl]piperidine-4-acetic acid 4-[3-(R,S)-Hydroxy-3-(3-chloro-6-methoxyquinolin-4-yl)propyl]-1-[2-(3-trifluoromethylphenylthio)ethyl]piperidine-4-acetic acid 4-[3-(R,S)-Hydroxy-3-(3-chloro-6-methoxyquinolin-4-yl)propyl]-1-[3-(3-trifluoromethylphenylthio)propyl]piperidine-4-acetic acid 4-[3-(R,S)-Hydroxy-3-(3-chloro-6-methoxyquinolin-4-yl)propyl]-1-[2-(4-trifluoromethylphenylthio)ethyl]piperidine-4-acetic acid 4-[3-(R,S)-Hydroxy-3-(3-chloro-6-methoxyquinolin-4-yl)propyl]-1-[3-(4-trifluoromethylphenylthio)propyl]piperidine-4-acetic acid 4-[3-(R,S)-Hydroxy-3-(3-chloro-6-methoxyquinolin-4-yl)propyl]-1-[2-(2-methoxyphenylthio)ethyl]piperidine-4-acetic acid 4-[3-(R,S)-Hydroxy-3-(3-chloro-6-methoxyquinolin-4-yl)propyl]-1-[3-(2-methoxyphenylthio)propyl]piperidine-4-acetic acid 4-[3-(R,S)-Hydroxy-3-(3-chloro-6-methoxyquinolin-4-yl)propyl]-1-[2-(3-methoxyphenylthio)ethyl]piperidine-4-acetic acid 4-[3-(R,S)-Hydroxy-3-(3-chloro-6-methoxyquinolin-4-yl)propyl]-1-[3-(3-methoxyphenylthio)propyl]piperidine-4-acetic acid 4-[3-(R,S)-Hydroxy-3-(3-chloro-6-methoxyquinolin-4-yl)propyl]-1-[2-(4-methoxyphenylthio)ethyl]piperidine-4-acetic acid 4-[3-(R,S)-Hydroxy-3-(3-chloro-6-methoxyquinolin-4-yl)propyl]-1-[3-(4-methoxyphenylthio)propyl]piperidine-4-acetic acid 4-[3-(R,S)-Hydroxy-3-(3-chloro-6-methoxyquinolin-4-yl)propyl]-1-[cyclopentylmethyl]piperidine-4-acetic acid 4-[3-(R,S)-Hydroxy-3-(3-chloro-6-methoxyquinolin-4-yl)propyl]-1-[2-(cyclopentyl)ethyl]piperidine-4-acetic acid 4-[3-(R,S)-Hydroxy-3-(3-chloro-6-methoxyquinolin-4-yl)propyl]-1-[2-(cyclohexyl)ethyl]piperidine-4-acetic acid 4-[3-(R,S)-Hydroxy-3-(3-chloro-6-methoxyquinolin-4-yl)propyl]-1-[2-(cyclopentylthio)ethyl]piperidine-4-acetic acid 4-[3-(R,S)-Hydroxy-3-(3-chloro-6-methoxyquinolin-4-yl)propyl]-1-[3-(cyclopentylthio)propyl]piperidine-4-acetic acid 4-[3-(R,S)-Hydroxy-3-(3-chloro-6-methoxyquinolin-4-yl)propyl]-1-[3-(cyclohexylthio)propyl]piperidine-4-acetic acid 4-[3-(R,S)-Hydroxy-3-(3-chloro-6-methoxyquinolin-4-yl)propyl]-1-[2-(pyrid-2-yl)thioethyl]piperidine-4-acetic acid 4-[3-(R,S)-Hydroxy-3-(3-chloro-6-methoxyquinolin-4-yl)propyl]-1-[4-(thien-2-yl)butyl]piperidine-4-acetic acid 4-[3-(R,S)-Hydroxy-3-(3-chloro-6-methoxyquinolin-4-yl)propyl]-1-[3-(thien-2-yl)thiopropyl]piperidine-4-acetic acid 4-[3-(R,S)-Hydroxy-3-(3-chloro-6-methoxyquinolin-4-yl)propyl]-1-[3-(thien-3-yl)propyl]piperidine-4-acetic acid 4-[3-(R,S)-Hydroxy-3-(3-chloro-6-methoxyquinolin-4-yl)propyl]-1-[4-(thien-3-yl)butyl]piperidine-4-acetic acid 4-[3-(R,S)-Hydroxy-3-(3-chloro-6-methoxyquinolin-4-yl)propyl]-1-[2-(thien-2-yl)thioethyl]piperidine-4-acetic acid 4-[3-(R,S)-Hydroxy-3-(3-chloro-6-methoxyquinolin-4-yl)propyl]-1-[2-(thien-3-yl)thioethyl]piperidine-4-acetic acid 4-[3-(R,S)-Hydroxy-3-(3-chloro-6-methoxyquinolin-4-yl)propyl]-1-[3-(thien-3-yl)thiopropyl]piperidine-4-acetic acid 4-[3-(R,S)-Hydroxy-3-(3-chloro-6-methoxyquinolin-4-yl)propyl]-1-[3-(1,3-thiazol-2-yl)propyl]piperidine-4-acetic acid 4-[3-(R,S)-Hydroxy-3-(3-chloro-6-methoxyquinolin-4-yl)propyl]-1-[4-(1,3-thiazol-2-yl)butyl]piperidine-4-acetic acid 4-[3-(R,S)-Hydroxy-3-(3-chloro-6-methoxyquinolin-4-yl)propyl]-1-[3-(1,3-thiazol-2-yl)thioethyl]piperidine-4-acetic acid 4-[3-(R,S)-Hydroxy-3-(3-chloro-6-methoxyquinolin-4-yl)propyl]-1-[3-(pyrid-2-yl)propyl]piperidine-4-acetic acid 4-[3-(R,S)-Hydroxy-3-(3-chloro-6-methoxyquinolin-4-yl)propyl]-1-[4-(pyrid-2-yl)butyl]piperidine-4-acetic acid 4-[3-(R,S)-Hydroxy-3-(3-chloro-6-methoxyquinolin-4-yl)propyl]-1-[3-(pyrid-2-yl)thiopropyl]piperidine-4-acetic acid 4-[3-(R,S)-Hydroxy-3-(3-chloro-6-methoxyquinolin-4-yl)propyl]-1-[3-(pyrid-3-yl)propyl]piperidine-4-acetic acid 4-[3-(R,S)-Hydroxy-3-(3-chloro-6-methoxyquinolin-4-yl)propyl]-1-[4-(pyrid-3-yl)butyl]piperidine-4-acetic acid 4-[3-(R,S)-Hydroxy-3-(3-chloro-6-methoxyquinolin-4-yl)propyl]-1-[2-(pyrid-3-yl)thioethyl]piperidine-4-acetic acid 4-[3-(R,S)-Hydroxy-3-(3-chloro-6-methoxyquinolin-4-yl)propyl]-1-[3-(pyrid-3-yl)thiopropyl]piperidine-4-acetic acid 4-[3-(R,S)-Hydroxy-3-(3-chloro-6-methoxyquinolin-4-yl)propyl]-1-[3-(pyrid-4-yl)propyl]piperidine-4-acetic acid 4-[3-(R,S)-Hydroxy-3-(3-chloro-6-methoxyquinolin-4-yl)propyl]-1-[4-(pyrid-4-yl)butyl]piperidine-4-acetic acid 4-[3-(R,S)-Hydroxy-3-(3-chloro-6-methoxyquinolin-4-yl)propyl]-1-[2-(pyrid-4-yl)thioethyl]piperidine-4-acetic acid 4-[3-(R,S)-Hydroxy-3-(3-chloro-6-methoxyquinolin-4-yl)propyl]-1-[3-(pyrid-4-yl)thiopropyl]piperidine-4-acetic acid 4-[3-(R,S)-Hydroxy-3-(3-chloro-6-methoxyquinolin-4-yl)propyl]-1-[3-(pyrazin-2-yl)propyl]piperidine-4-acetic acid 4-[3-(R,S)-Hydroxy-3-(3-chloro-6-methoxyquinolin-4-yl)propyl]-1-[4-(pyrazin-2-yl)butyl]piperidine-4-acetic acid 4-[3-(R,S)-Hydroxy-3-(3-chloro-6-methoxyquinolin-4-yl)propyl]-1-[2-(pyrazin-2-yl)thioethyl]piperidine-4-acetic acid 4-[3-(R,S)-Hydroxy-3-(3-chloro-6-methoxyquinolin-4-yl)propyl]-1-[3-(pyrazin-2-yl)thiopropyl]piperidine-4-acetic acid 4-[3-(R,S)-Hydroxy-3-(3-chloro-6-methoxyquinolin-4-yl)propyl]-1-[3-(4-fluorophenyl)prop-2-ynyl]piperidine-4-acetic acid 4-[3-(R,S)-Hydroxy-3-(3-chloro-6-methoxyquinolin-4-yl)propyl]-1-[3-(3,4-difluorophenyl)prop-2-ynyl]piperidine-4-acetic acid 4-[3-(R,S)-Hydroxy-3-(3-chloro-6-methoxyquinolin-4-yl)propyl]-1-[3-(2,4-difluorophenyl)prop-2-ynyl]piperidine-4-acetic acid 4-[3-(R,S)-Hydroxy-3-(3-chloro-6-methoxyquinolin-4-yl)propyl]-1-[3-(2,3,5-trifluorophenyl)prop-2-ynyl]piperidine-4-acetic acid 4-[3-(R,S)-Hydroxy-3-(3-chloro-6-methoxyquinolin-4-yl)propyl]-1-[3-(2,4,6-trifluorophenyl)prop-2-ynyl]piperidine-4-acetic acid 4-[3-(R,S)-Hydroxy-3-(3-chloro-6-methoxyquinolin-4-yl)propyl]-1-[3-(3,4,5-trifluorophenyl)prop-2-ynyl]piperidine-4-acetic acid 4-[3-(R,S)-Hydroxy-3-(3-chloro-6-methoxyquinolin-4-yl)propyl]-1-[3-(4-chloro-3-fluorophenyl)prop-2-ynyl]piperidine-4-acetic acid 4-[3-(R,S)-Hydroxy-3-(3-chloro-6-methoxyquinolin-4-yl)propyl]-1-[3-(3-chloro-4-fluorophenyl)prop-2-ynyl]piperidine-4-acetic acid 4-[3-(R,S)-Hydroxy-3-(3-chloro-6-methoxyquinolin-4-yl)propyl]-1-[3-(2-chloro-4-fluorophenyl)prop-2-ynyl]piperidine-4-acetic acid 4-[3-(R,S)-Hydroxy-3-(3-chloro-6-methoxyquinolin-4-yl)propyl]-1-[3-(3-chloro-5-fluorophenyl)prop-2-ynyl]piperidine-4-acetic acid 4-[3-(R,S)-Hydroxy-3-(3-chloro-6-methoxyquinolin-4-yl)propyl]-1-[3-(4-chloro-2-fluorophenyl)prop-2-ynyl]piperidine-4-acetic acid 4-[3-(R,S)-Hydroxy-3-(3-chloro-6-methoxyquinolin-4-yl)propyl]-1-[3-(3-fluoro-4-methylphenyl)prop-2-ynyl]piperidine-4-acetic acid 4-[3-(R,S)-Hydroxy-3-(3-chloro-6-methoxyquinolin-4-yl)propyl]-1-[3-(3,5-bis(trifluoromethyl)phenyl)prop-2-ynyl]piperidine-4-acetic acid 4-[3-(R,S)-Hydroxy-3-(3-chloro-6-methoxyquinolin-4-yl)propyl]-1-[-3-(thien-2-yl)prop-2-ynyl]piperidine-4-acetic acid 4-[3-(R,S)-Hydroxy-3-(3-chloro-6-methoxyquinolin-4-yl)propyl]-1-[3-(thien-3-yl)prop-2-ynyl]piperidine-4-acetic acid 4-[3-(R,S)-Hydroxy-3-(3-chloro-6-methoxyquinolin-4-yl)propyl]-1-[3-(1,3-thiazol-2-yl)prop-2-ynyl]piperidine-4-acetic acid 4-[3-(R,S)-Hydroxy-3-(3-chloro-6-methoxyquinolin-4-yl)propyl]-1-[3-(1,3-thiazol-4-yl)prop-2-ynyl]piperidine-4-acetic acid 4-[3-(R,S)-Hydroxy-3-(3-chloro-6-methoxyquinolin-4-yl)propyl]-1-[3-(1,3-thiazol-5-yl)prop-2-ynyl]piperidine-4-acetic acid 4-[3-(R,S)-Hydroxy-3-(3-chloro-6-methoxyquinolin-4-yl)propyl]-1-[3-(pyrid-2-yl)prop-2-ynyl]piperidine-4-acetic acid 4-[3-(R,S)-Hydroxy-3-(3-chloro-6-methoxyquinolin-4-yl)propyl]-1-[3-(pyrid-3-yl)prop-2-ynyl]piperidine-4-acetic acid 4-[3-(R,S)-Hydroxy-3-(3-chloro-6-methoxyquinolin-4-yl)propyl]-1-[3-(pyrid-4-yl)prop-2-ynyl]piperidine-4-acetic acid 4-[3-(R,S)-Hydroxy-3-(3-methyl-6-methoxyquinolin-4-yl)propyl]-1-[2-(cyclohexyl)ethyl]piperidine-4-acetic acid 4-[3-(R,S)-Hydroxy-3-(3-methyl-6-methoxyquinolin-4-yl)propyl]-1-[3-(phenyl)propyl]piperidine-4-acetic acid 4-[3-(R,S)-Hydroxy-3-(3-methyl-6-methoxyquinolin-4-yl)propyl]-1-[3-(2,3,5-trifluorophenyl)propyl]piperidine-4-acetic acid 4-[3-(R,S)-Hydroxy-3-(3-methyl-6-methoxyquinolin-4-yl)propyl]-1-[2-(3,5-difluorophenylamino)ethyl]piperidine-4-acetic acid 4-[3-(R,S)-Hydroxy-3-(3-methyl-6-methoxyquinolin-4-yl)propyl]-1-[2-(2,3,5-trifluorophenylamino)ethyl]piperidine-4-acetic acid 4-[3-(R,S)-Hydroxy-3-(3-methyl-6-methoxyquinolin-4-yl)propyl]-1-[2-(3,5-difluorophenoxy)ethyl]piperidine-4-acetic acid 4-[3-(R,S)-Hydroxy-3-(3-methyl-6-methoxyquinolin-4-yl)propyl]-1-[2-(2,3,5-trifluorophenoxy)ethyl]piperidine-4-acetic acid 4-[3-(R,S)-Hydroxy-3-(3-methyl-6-methoxyquinolin-4-yl)propyl]-1-[2-(2,3,5-trifluorophenylthio)ethyl]piperidine-4-acetic acid 4-[3-(R,S)-Hydroxy-3-(3-methyl-6-methoxyquinolin-4-yl)propyl]-1-[2-(cyclopentylthio)ethyl]piperidine-4-acetic acid 4-[3-(R,S)-Hydroxy-3-(3-methyl-6-methoxyquinolin-4-yl)propyl]-1-[2-(pyrid-2-yl)thioethyl]piperidine-4-acetic acid 4-[3-(R,S)-Hydroxy-3-(3-methyl-6-methoxyquinolin-4-yl)propyl]-1-[2-(thien-2-yl)thioethyl]piperidine-4-acetic acid 4-[3-(R,S)-Hydroxy-3-(3-methyl-6-methoxyquinolin-4-yl)propyl]-1-[3-(2,3,5-trifluorophenyl)prop-2-ynyl]piperidine-4-acetic acid 4-[3-(R,S)-Hydroxy-3-(3-methyl-6-methoxyquinolin-4-yl)propyl]-1-[3-(thien-2-yl)prop-2-ynyl]piperidine-4-acetic acid 4-[3-(R,S)-Hydroxy-3-(3-fluoro-6-methoxyquinolin-4-yl)propyl]-1-[2-(cyclohexyl)ethyl]piperidine-4-acetic acid 4-[3-(R,S)-Hydroxy-3-(3-fluoro-6-methoxyquinolin-4-yl)propyl]-1-[3-(phenyl)propyl]piperidine-4-acetic acid 4-[3-(R,S)-Hydroxy-3-(3-fluoro-6-methoxyquinolin-4-yl)propyl]-1-[3-(2,3,5-trifluorophenyl)propyl]piperidine-4-acetic acid 4-[3-(R,S)-Hydroxy-3-(3-fluoro-6-methoxyquinolin-4-yl)propyl]-1-[2-(3,5-difluorophenylamino)ethyl]piperidine-4-acetic acid 4-[3-(R,S)-Hydroxy-3-(3-fluoro-6-methoxyquinolin-4-yl)propyl]-1-[2-(2,3,5-trifluorophenylamino)ethyl]piperidine-4-acetic acid 4-[3-(R,S)-Hydroxy-3-(3-fluoro-6-methoxyquinolin-4-yl)propyl]-1-[2-(3,5-difluorophenoxy)ethyl]piperidine-4-acetic acid 4-[3-(R,S)-Hydroxy-3-(3-fluoro-6-methoxyquinolin-4-yl)propyl]-1-[2-(2,3,5-trifluorophenoxy)ethyl]piperidine-4-acetic acid 4-[3-(R,S)-Hydroxy-3-(3-fluoro-6-methoxyquinolin-4-yl)propyl]-1-[2-(2,3,5-trifluorophenylthio)ethyl]piperidine-4-acetic acid 4-[3-(R,S)-Hydroxy-3-(3-fluoro-6-methoxyquinolin-4-yl)propyl]-1-[2-(cyclopentylthio)ethyl]piperidine-4-acetic acid 4-[3-(R,S)-Hydroxy-3-(3-fluoro-6-methoxyquinolin-4-yl)propyl]-1-[2-(pyrid-2-yl)thioethyl]piperidine-4-acetic acid 4-[3-(R,S)-Hydroxy-3-(3-fluoro-6-methoxyquinolin-4-yl)propyl]-1-[2-(thien-2-yl)thioethyl]piperidine-4-acetic acid 4-[3-(R,S)-Hydroxy-3-(3-fluoro-6-methoxyquinolin-4-yl)propyl]-1-[3-(2,3,5-trifluorophenyl)prop-2-ynyl]piperidine-4-acetic acid 4-[3-(R,S)-Hydroxy-3-(3-fluoro-6-methoxyquinolin-4-yl)propyl]-1-[3-(thien-2-yl)prop-2-ynyl]piperidine-4-acetic acid 4-[3-(R,S)-Hydroxy-3-(3-dimethylamino-6-methoxyquinolin-4-yl)propyl]-1-[2-(cyclohexyl)ethyl]piperidine-4-acetic acid 4-[3-(R,S)-Hydroxy-3-(3-dimethylamino-6-methoxyquinolin-4-yl)propyl]-1-[3-(phenyl)propyl]piperidine-4-acetic acid 4-[3-(R,S)-Hydroxy-3-(3-dimethylamino-6-methoxyquinolin-4-yl)propyl]-1-[3-(2,3,5-trifluorophenyl)propyl]piperidine-4-acetic acid 4-[3-(R,S)-Hydroxy-3-(3-dimethylamino-6-methoxyquinolin-4-yl)propyl]-1-[2-(3,5-difluorophenylamino)ethyl]piperidine-4-acetic acid 4-[3-(R,S)-Hydroxy-3-(3-dimethylamino-6-methoxyquinolin-4-yl)propyl]-1-[2-(2,3,5-trifluorophenylamino)ethyl]piperidine-4-acetic acid 4-[3-(R,S)-Hydroxy-3-(3-dimethylamino-6-methoxyquinolin-4-yl)propyl]-1-[2-(3,5-difluorophenoxy)ethyl]piperidine-4-acetic acid 4-[3-(R,S)-Hydroxy-3-(3-dimethylamino-6-methoxyquinolin-4-yl)propyl]-1-[2-(2,3,5-trifluorophenoxy)ethyl]piperidine-4-acetic acid 4-[3-(R,S)-Hydroxy-3-(3-dimethylamino-6-methoxyquinolin-4-yl)propyl]-1-[2-(2,3,5-trifluorophenylthio)ethyl]piperidine-4-acetic acid 4-[3-(R,S)-Hydroxy-3-(3-dimethylamino-6-methoxyquinolin-4-yl)propyl]-1-[2-(cyclopentylthio)ethyl]piperidine-4-acetic acid 4-[3-(R,S)-Hydroxy-3-(3-dimethylamino-6-methoxyquinolin-4-yl)propyl]-1-[2-(pyrid-2-yl)thioethyl]piperidine-4-acetic acid 4-[3-(R,S)-Hydroxy-3-(3-dimethylamino-6-methoxyquinolin-4-yl)propyl]-1-[2-(thien-2-yl)thioethyl]piperidine-4-acetic acid 4-[3-(R,S)-Hydroxy-3-(3-dimethylamino-6-methoxyquinolin-4-yl)propyl]-1-[3-(2,3,5-trifluorophenyl)prop-2-ynyl]piperidine-4-acetic acid 4-[3-(R,S)-Hydroxy-3-(3-dimethylamino-6-methoxyquinolin-4-yl)propyl]-1-[3-(thien-2-yl)prop-2-ynyl]piperidine-4-acetic acid 4-[3-(R,S)-Hydroxy-3-(3-hydroxymethyl-6-methoxyquinolin-4-yl)propyl]-1-[2-(cyclohexyl)ethyl]piperidine-4-acetic acid 4-[3-(R,S)-Hydroxy-3-(3-hydroxymethyl-6-methoxyquinolin-4-yl)propyl]-1-[3-(phenyl)propyl]piperidine-4-acetic acid 4-[3-(R,S)-Hydroxy-3-(3-hydroxymethyl-6-methoxyquinolin-4-yl)propyl]-1-[3-(2,3,5-trifluorophenyl)propyl]piperidine-4-acetic acid 4-[3-(R,S)-Hydroxy-3-(3-hydroxymethyl-6-methoxyquinolin-4-yl)propyl]-1-[2-(3,5-difluorophenylamino)ethyl]piperidine-4-acetic acid 4-[3-(R,S)-Hydroxy-3-(3-hydroxymethyl-6-methoxyquinolin-4-yl)propyl]-1-[2-(2,3,5-trifluorophenylamino)ethyl]piperidine-4-acetic acid 4-[3-(R,S)-Hydroxy-3-(3-hydroxymethyl-6-methoxyquinolin-4-yl)propyl]-1-[2-(3,5-difluorophenoxy)ethyl]piperidine-4-acetic acid 4-[3-(R,S)-Hydroxy-3-(3-hydroxymethyl-6-methoxyquinolin-4-yl)propyl]-1-[2-(2,3,5-trifluorophenoxy)ethyl]piperidine-4-acetic acid 4-[3-(R,S)-Hydroxy-3-(3-hydroxymethyl-6-methoxyquinolin-4-yl)propyl]-1-[2-(2,3,5-trifluorophenylthio)ethyl]piperidine-4-acetic acid 4-[3-(R,S)-Hydroxy-3-(3-hydroxymethyl-6-methoxyquinolin-4-yl)propyl]-1-[2-(cyclopentylthio)ethyl]piperidine-4-acetic acid 4-[3-(R,S)-Hydroxy-3-(3-hydroxymethyl-6-methoxyquinolin-4-yl)propyl]-1-[2-(pyrid-2-yl)thioethyl]piperidine-4-acetic acid 4-[3-(R,S)-Hydroxy-3-(3-hydroxymethyl-6-methoxyquinolin-4-yl)propyl]-1-[2-(thien-2-yl)thioethyl]piperidine-4-acetic acid 4-[3-(R,S)-Hydroxy-3-(3-hydroxymethyl-6-methoxyquinolin-4-yl)propyl]-1-[3-(2,3,5-trifluorophenyl)prop-2-ynyl]piperidine-4-acetic acid 4-[3-(R,S)-Hydroxy-3-(3-hydroxymethyl-6-methoxyquinolin-4-yl)propyl]-1-[3-(thien-2-yl)prop-2-ynyl]piperidine-4-acetic acid 4-[3-(R,S)-Hydroxy-3-(3-fluoromethyl-6-methoxyquinolin-4-yl)propyl]-1-[2-(cyclohexyl)ethyl]piperidine-4-acetic acid 4-[3-(R,S)-Hydroxy-3-(3-fluoromethyl-6-methoxyquinolin-4-yl)propyl]-1-[3-(phenyl)propyl]piperidine-4-acetic acid 4-[3-(R,S)-Hydroxy-3-(3-fluoromethyl-6-methoxyquinolin-4-yl)propyl]-1-[3-(2,3,5-trifluorophenyl)propylpiperidine-4-acetic acid 4-[3-(R,S)-Hydroxy-3-(3-fluoromethyl-6-methoxyquinolin-4-yl)propyl]-1-[2-(3,5-difluorophenylamino)ethyl]piperidine-4-acetic acid 4-[3-(R,S)-Hydroxy-3-(3-fluoromethyl-6-methoxyquinolin-4-yl)propyl]-1-[2-(2,3,5-trifluorophenylamino)ethyl]piperidine-4-acetic acid 4-[3-(R,S)-Hydroxy-3-(3-fluoromethyl-6-methoxyquinolin-4-yl)propyl]-1-[2-(3,5-difluorophenoxy)ethyl]piperidine-4-acetic acid 4-[3-(R,S)-Hydroxy-3-(3-fluoromethyl-6-methoxyquinolin-4-yl)propyl]-1-[2-(2,3,5-trifluorophenoxy)ethyl]piperidine-4-acetic acid 4-[3-(R,S)-Hydroxy-3-(3-fluoromethyl-6-methoxyquinolin-4-yl)propyl]-1-[2-(2,3,5-trifluorophenylthio)ethyl]piperidine-4-acetic acid 4-[3-(R,S)-Hydroxy-3-(3-fluoromethyl-6-methoxyquinolin-4-yl)propyl]-1-[2-(cyclopentylthio)ethyl]piperidine-4-acetic acid 4-[3-(R,S)-Hydroxy-3-(3-fluoromethyl-6-methoxyquinolin-4-yl)propyl]-1-[2-(pyrid-2-yl)thioethyl]piperidine-4-acetic acid 4-[3-(R,S)-Hydroxy-3-(3-fluoromethyl-6-methoxyquinolin-4-yl)propyl]-1-[2-(thien-2-yl)thioethyl]piperidine-4-acetic acid 4-[3-(R,S)-Hydroxy-3-(3-fluoromethyl-6-methoxyquinolin-4-yl)propyl]-1-[3-(2,3,5-trifluorophenyl)prop-2-ynyl]piperidine-4-acetic acid 4-[3-(R,S)-Hydroxy-3-(3-fluoromethyl-6-methoxyquinolin-4-yl)propyl]-1-[3-(thien-2-yl)prop-2-ynyl]piperidine-4-acetic acid 4-[3-(R,S)-Hydroxy-3-(3-aminomethyl-6-methoxyquinolin-4-yl)propyl]-1-[2-(cyclohexyl)ethyl]piperidine-4-acetic acid 4-[3-(R,S)-Hydroxy-3-(3-aminomethyl-6-methoxyquinolin-4-yl)propyl]-1-[3-(phenyl)propyl]piperidine-4-acetic acid 4-[3-(R,S)-Hydroxy-3-(3-aminomethyl-6-methoxyquinolin-4-yl)propyl]-1-[3-(2,3,5-trifluorophenyl)propyl]piperidine-4-acetic acid 4-[3-(R,S)-Hydroxy-3-(3-aminomethyl-6-methoxyquinolin-4-yl)propyl]-1-[2-(3,5-difluorophenylamino)ethyl]piperidine-4-acetic acid 4-[3-(R,S)-Hydroxy-3-(3-aminomethyl-6-methoxyquinolin-4-yl)propyl]-1-[2-(2,3,5-trifluorophenylamino)ethyl]piperidine-4-acetic acid 4-[3-(R,S)-Hydroxy-3-(3-aminomethyl-6-methoxyquinolin-4-yl)propyl]-1-[2-(3,5-difluorophenoxy)ethyl]piperidine-4-acetic acid 4-[3-(R,S)-Hydroxy-3-(3-aminomethyl-6-methoxyquinolin-4-yl)propyl]-1-[2-(2,3,5-trifluorophenoxy)ethyl]piperidine-4-acetic acid 4-[3-(R,S)-Hydroxy-3-(3-aminomethyl-6-methoxyquinolin-4-yl)propyl]-1-[2-(2,3,5-trifluorophenylthio)ethyl]piperidine-4-acetic acid 4-[3-(R,S)-Hydroxy-3-(3-aminomethyl-6-methoxyquinolin-4-yl)propyl]-1-[2-(cyclopentylthio)ethyl]piperidine-4-acetic acid 4-[3-(R,S)-Hydroxy-3-(3-aminomethyl-6-methoxyquinolin-4-yl)propyl]-1-[2-(pyrid-2-yl)thioethyl]piperidine-4-acetic acid 4-[3-(R,S)-Hydroxy-3-(3-aminomethyl-6-methoxyquinolin-4-yl)propyl]-1-[2-(thien-2-yl)thioethyl]piperidine-4-acetic acid 4-[3-(R,S)-Hydroxy-3-(3-aminomethyl-6-methoxyquinolin-4-yl)propyl]-1-[3-(2,3,5-trifluorophenyl)prop-2-ynyl]piperidine-4-acetic acid 4-[3-(R,S)-Hydroxy-3-(3-aminomethyl-6-methoxyquinolin-4-yl)propyl]-1-[3-(thien-2-yl)prop-2-ynyl]piperidine-4-acetic acid 4-[3-(R,S)-Hydroxy-3-(3-morpholinomethyl-6-methoxyquinolin-4-yl)propyl]-1-[2-(cyclohexyl)ethyl]piperidine-4-acetic acid 4-[3-(R,S)-Hydroxy-3-(3-morpholinomethyl-6-methoxyquinolin-4-yl)propyl]-1-[3-(phenyl)propyl]piperidine-4-acetic acid 4-[3-(R,S)-Hydroxy-3-(3-morpholinomethyl-6-methoxyquinolin-4-yl)propyl]-1-[3-(2,3,5-trifluorophenyl)propyl]piperidine-4-acetic acid 4-[3-(R,S)-Hydroxy-3-(3-morpholinomethyl-6-methoxyquinolin-4-yl)propyl]-1-[2-(3,5-difluorophenylamino)ethyl]piperidine-4-acetic acid 4-[3-(R,S)-Hydroxy-3-(3-morpholinomethyl-6-methoxyquinolin-4-yl)propyl]-1-[2-(2,3,5-trifluorophenylamino)ethyl]piperidine-4-acetic acid 4-[3-(R,S)-Hydroxy-3-(3-morpholinomethyl-6-methoxyquinolin-4-yl)propyl]-1-[2-(3,5-difluorophenoxy)ethyl]piperidine-4-acetic acid 4-[3-(R,S)-Hydroxy-3-(3-morpholinomethyl-6-methoxyquinolin-4-yl)propyl]-1-[2-(2,3,5-trifluorophenoxy)ethyl]piperidine-4-acetic acid 4-[3-(R,S)-Hydroxy-3-(3-morpholinomethyl-6-methoxyquinolin-4-yl)propyl]-1-[2-(2,3,5-trifluorophenylthio)ethyl]piperidine-4-acetic acid 4-[3-(R,S)-Hydroxy-3-(3-morpholinomethyl-6-methoxyquinolin-4-yl)propyl]-1-[2-(cyclopentylthio)ethyl]piperidine-4-acetic acid 4-[3-(R,S)-Hydroxy-3-(3-morpholinomethyl-6-methoxyquinolin-4-yl)propyl]-1-[2-(pyrid-2-yl)thioethyl]piperidine-4-acetic acid 4-[3-(R,S)-Hydroxy-3-(3-morpholinomethyl-6-methoxyquinolin-4-yl)propyl]-1-[2-(thien-2-yl)thioethyl]piperidine-4-acetic acid 4-[3-(R,S)-Hydroxy-3-(3-morpholinomethyl-6-methoxyquinolin-4-yl)propyl]-1-[3-(2,3,5-trifluorophenyl)prop-2-ynyl]piperidine-4-acetic acid 4-[3-(R,S)-Hydroxy-3-(3-morpholinomethyl-6-methoxyquinolin-4-yl)propyl]-1-[3-(thien-2-yl)prop-2-ynyl]piperidine-4-acetic acid 4-[3-(R,S)-Hydroxy-3-(3-methyl-6-methoxyquinolin-4-yl)propyl]-1-[3-(2,4,6-trifluorophenyl)propyl]piperidine-4-acetic acid 4-[3-(R,S)-Hydroxy-3-(3-methyl-6-methoxyquinolin-4-yl)propyl]-1-[3-(3,4,5-trifluorophenyl)propyl]piperidine-4-acetic acid 4-[3-(R,S)-Hydroxy-3-(3-methyl-6-methoxyquinolin-4-yl)propyl]-1-[2-(2,4,6-trifluorophenylthio)ethyl]piperidine-4-acetic acid 4-[3-(R,S)-Hydroxy-3-(3-methyl-6-methoxyquinolin-4-yl)propyl]-1-[2-(3,4,5-trifluorophenylthio)ethyl]piperidine-4-acetic acid 4-[3-(R,S)-Hydroxy-3-(3-methyl-6-methoxyquinolin-4-yl)propyl]-1-[2-(2,4,6-trifluorophenylamino)ethyl]piperidine-4-acetic acid 4-[3-(R,S)-Hydroxy-3-(3-methyl-6-methoxyquinolin-4-yl)propyl]-1-[2-(3,4,5-trifluorophenylamino)ethyl]piperidine-4-acetic acid 4-[3-(R,S)-Hydroxy-3-(3-methyl-6-methoxyquinolin-4-yl)propyl]-1-[2-(2,4,6-trifluorophenoxy)ethyl]piperidine-4-acetic acid 4-[3-(R,S)-Hydroxy-3-(3-methyl-6-methoxyquinolin-4-yl)propyl]-1-[2-(3,4,5-trifluorophenoxy)ethyl]piperidine-4-acetic acid 4-[3-(R,S)-Hydroxy-3-(3-methyl-6-methoxyquinolin-4-yl)propyl]-1-[3-(2,4,6-trifluorophenyl)prop-2-ynyl]piperidine-4-acetic acid 4-[3-(R,S)-Hydroxy-3-(3-methyl-6-methoxyquinolin-4-yl)propyl]-1-[3-(3,4,5-trifluorophenyl)prop-2-ynyl]piperidine-4-acetic acid 4-[3-(R,S)-Hydroxy-3-(3-fluoro-6-methoxyquinolin-4-yl)propyl]-1-[3-(2,4,6-trifluorophenyl)propyl]piperidine-4-acetic acid 4-[3-(R,S)-Hydroxy-3-(3-fluoro-6-methoxyquinolin-4-yl)propyl]-1-[3-(3,4,5-trifluorophenyl)propyl]piperidine-4-acetic acid 4-[3-(R,S)-Hydroxy-3-(3-fluoro-6-methoxyquinolin-4-yl)propyl]-1-[2-(2,4,6-trifluorophenylthio)ethyl]piperidine-4-acetic acid 4-[3-(R,S)-Hydroxy-3-(3-fluoro-6-methoxyquinolin-4-yl)propyl]-1-[2-(3,4,5-trifluorophenylthio)ethyl]piperidine-4-acetic acid 4-[3-(R,S)-Hydroxy-3-(3-fluoro-6-methoxyquinolin-4-yl)propyl]-1-[2-(2,4,6-trifluorophenylamino)ethyl]piperidine-4-acetic acid 4-[3-(R,S)-Hydroxy-3-(3-fluoro-6-methoxyquinolin-4-yl)propyl]-1-[2-(3,4,5-trifluorophenylamino)ethyl]piperidine-4-acetic acid 4-[3-(R,S)-Hydroxy-3-(3-fluoro-6-methoxyquinolin-4-yl)propyl]-1-[2-(2,4,6-trifluorophenoxy)ethyl]piperidine-4-acetic acid 4-[3-(R,S)-Hydroxy-3-(3-fluoro-6-methoxyquinolin-4-yl)propyl]-1-[2-(3,4,5-trifluorophenoxy)ethyl]piperidine-4-acetic acid 4-[3-(R,S)-Hydroxy-3-(3-fluoro-6-methoxyquinolin-4-yl)propyl]-1-[3-(2,4,6-trifluorophenyl)prop-2-ynyl]piperidine-4-acetic acid 4-[3-(R,S)-Hydroxy-3-(3-fluoro-6-methoxyquinolin-4-yl)propyl]-1-[3-(3,4,5-trifluorophenyl)prop-2-ynyl]piperidine-4-acetic acid 4-[3-(R,S)-Hydroxy-3-(3-dimethylamino-6-methoxyquinolin-4-yl)propyl]-1-[3-(2,4,6-trifluorophenyl)propyl]piperidine-4-acetic acid 4-[3-(R,S)-Hydroxy-3-(3-dimethylamino-6-methoxyquinolin-4-yl)propyl]-1-[3-(3,4,5-trifluorophenyl)propyl]piperidine-4-acetic acid 4-[3-(R,S)-Hydroxy-3-(3-dimethylamino-6-methoxyquinolin-4-yl)propyl]-1-[2-(2,4,6-trifluorophenylthio)ethyl]piperidine-4-acetic acid 4-[3-(R,S)-Hydroxy-3-(3-dimethylamino-6-methoxyquinolin-4-yl)propyl]-1-[2-(3,4,5-trifluorophenylthio)ethyl]piperidine-4-acetic acid 4-[3-(R,S)-Hydroxy-3-(3-dimethylamino-6-methoxyquinolin-4-yl)propyl]-1-[2-(2,4,6-trifluorophenylamino)ethyl]piperidine-4-acetic acid 4-[3-(R,S)-Hydroxy-3-(3-dimethylamino-6-methoxyquinolin-4-yl)propyl]-1-[2-(3,4,5-trifluorophenylamino)ethyl]piperidine-4-acetic acid 4-[3-(R,S)-Hydroxy-3-(3-dimethylamino-6-methoxyquinolin-4-yl)propyl]-1-[2-(2,4,6-trifluorophenoxy)ethyl]piperidine-4-acetic acid 4-[3-(R,S)-Hydroxy-3-(3-dimethylamino-6-methoxyquinolin-4-yl)propyl]-1-[2-(3,4,5-trifluorophenoxy)ethyl]piperidine-4-acetic acid 4-[3-(R,S)-Hydroxy-3-(3-dimethylamino-6-methoxyquinolin-4-yl)propyl]-1-[3-(2,4,6-trifluorophenyl)prop-2-ynyl]piperidine-4-acetic acid 4-[3-(R,S)-Hydroxy-3-(3-dimethylamino-6-methoxyquinolin-4-yl)propyl]-1-[3-(3,4,5-trifluorophenyl)prop-2-ynyl]piperidine-4-acetic acid 4-[3-(R,S)-Hydroxy-3-(3-hydroxymethyl-6-methoxyquinolin-4-yl)propyl]-1-[3-(3,4,5-trifluorophenyl)propyl]piperidine-4-acetic acid 4-[3-(R,S)-Hydroxy-3-(3-hydroxymethyl-6-methoxyquinolin-4-yl)propyl]-1-[2-(2,4,6-trifluorophenylthio)ethyl]piperidine-4-acetic acid 4-[3-(R,S)-Hydroxy-3-(3-hydroxymethyl-6-methoxyquinolin-4-yl)propyl]-1-[2-(3,4,5-trifluorophenylthio)ethyl]piperidine-4-acetic acid 4-[3-(R,S)-Hydroxy-3-(3-hydroxymethyl-6-methoxyquinolin-4-yl)propyl]-1-[2-(2,4,6-trifluorophenylamino)ethyl]piperidine-4-acetic acid 4-[3-(R,S)-Hydroxy-3-(3-hydroxymethyl-6-methoxyquinolin-4-yl)propyl]-1-[2-(3,4,5-trifluorophenylamino)ethyl]piperidine-4-acetic acid 4-[3-(R,S)-Hydroxy-3-(3-hydroxymethyl-6-methoxyquinolin-4-yl)propyl]-1-[2-(2,4,6-trifluorophenoxy)ethyl]piperidine-4-acetic acid 4-[3-(R,S)-Hydroxy-3-(3-hydroxymethyl-6-methoxyquinolin-4-yl)propyl]-1-[2-(3,4,5-trifluorophenoxy)ethyl]piperidine-4-acetic acid 4-[3-(R,S)-Hydroxy-3-(3-hydroxymethyl-6-methoxyquinolin-4-yl)propyl]-1-[3-(2,4,6-trifluorophenyl)prop-2-ynyl]piperidine-4-acetic acid 4-[3-(R,S)-Hydroxy-3-(3-hydroxymethyl-6-methoxyquinolin-4-yl)propyl]-1-[3-(3,4,5-trifluorophenyl)prop-2-ynyl]piperidine-4-acetic acid 4-[3-(R,S)-Hydroxy-3-(3-fluoromethyl-6-methoxyquinolin-4-yl)propyl]-1-[3-(2,4,6-trifluorophenyl)propyl]piperidine-4-acetic acid 4-[3-(R,S)-Hydroxy-3-(3-fluoromethyl-6-methoxyquinolin-4-yl)propyl]-1-[3-(3,4,5-trifluorophenyl)propyl]piperidine-4-acetic acid 4-[3-(R,S)-Hydroxy-3-(3-fluoromethyl-6-methoxyquinolin-4-yl)propyl]-1-[2-(2,4,6-trifluorophenylthio)ethyl]piperidine-4-acetic acid 4-[3-(R,S)-Hydroxy-3-(3-fluoromethyl-6-methoxyquinolin-4-yl)propyl]-1-[2-(3,4,5-trifluorophenylthio)ethyl]piperidine-4-acetic acid 4-[3-(R,S)-Hydroxy-3-(3-fluoromethyl-6-methoxyquinolin-4-yl)propyl]-1-[2-(2,4,6-trifluorophenylamino)ethyl]piperidine-4-acetic acid 4-[3-(R,S)-Hydroxy-3-(3-fluoromethyl-6-methoxyquinolin-4-yl)propyl]-1-[2-(3,4,5-trifluorophenylamino)ethyl]piperidine-4-acetic acid 4-[3-(R,S)-Hydroxy-3-(3-fluoromethyl-6-methoxyquinolin-4-yl)propyl]-1-[2-(2,4,6-trifluorophenoxy)ethyl]piperidine-4-acetic acid 4-[3-(R,S)-Hydroxy-3-(3-fluoromethyl-6-methoxyquinolin-4-yl)propyl]-1-[2-(3,4,5-trifluorophenoxy)ethyl]piperidine-4-acetic acid 4-[3-(R,S)-Hydroxy-3-(3-fluoromethyl-6-methoxyquinolin-4-yl)propyl]-1-[3-(2,4,6-trifluorophenyl)prop-2-ynyl]piperidine-4-acetic acid 4-[3-(R,S)-Hydroxy-3-(3-fluoromethyl-6-methoxyquinolin-4-yl)propyl]-1-[3-(3,4,5-trifluorophenyl)prop-2-ynyl]piperidine-4-acetic acid 4-[3-(R,S)-Hydroxy-3-(3-aminomethyl-6-methoxyquinolin-4-yl)propyl]-1-[3-(2,4,6-trifluorophenyl)propyl]piperidine-4-acetic acid 4-[3-(R,S)-Hydroxy-3-(3-aminomethyl-6-methoxyquinolin-4-yl)propyl]-1-[3-(3,4,5-trifluorophenyl)propyl]piperidine-4-acetic acid 4-[3-(R,S)-Hydroxy-3-(3-aminomethyl-6-methoxyquinolin-4-yl)propyl]-1-[2-(2,4,6-trifluorophenylthio)ethyl]piperidine-4-acetic acid 4-[3-(R,S)-Hydroxy-3-(3-aminomethyl-6-methoxyquinolin-4-yl)propyl]-1-[2-(3,4,5-trifluorophenylthio)ethyl]piperidine-4-acetic acid 4-[3-(R,S)-Hydroxy-3-(3-aminomethyl-6-methoxyquinolin-4-yl)propyl]-1-[2-(2,4,6-trifluorophenylamino)ethyl]piperidine-4-acetic acid 4-[3-(R,S)-Hydroxy-3-(3-aminomethyl-6-methoxyquinolin-4-yl)propyl]-1-[2-(3,4,5-trifluorophenylamino)ethyl]piperidine-4-acetic acid 4-[3-(R,S)-Hydroxy-3-(3-aminomethyl-6-methoxyquinolin-4-yl)propyl]-1-[2-(2,4,6-trifluorophenoxy)ethyl]piperidine-4-acetic acid 4-[3-(R,S)-Hydroxy-3-(3-aminomethyl-6-methoxyquinolin-4-yl)propyl]-1-[2-(3,4,5-trifluorophenoxy)ethyl]piperidine-4-acetic acid 4-[3-(R,S)-Hydroxy-3-(3-aminomethyl-6-methoxyquinolin-4-yl)propyl]-1-[3-(2,4,6-trifluorophenyl)prop-2-ynyl]piperidine-4-acetic acid 4-[3-(R,S)-Hydroxy-3-(3-aminomethyl-6-methoxyquinolin-4-yl)propyl]-1-[3-(3,4,5-trifluorophenyl)prop-2-ynyl]piperidine-4-acetic acid 4-[3-(R,S)-Hydroxy-3-(3-morpholinomethyl-6-methoxyquinolin-4-yl)propyl]-1-[3-(2,4,6-trifluorophenyl)propyl]piperidine-4-acetic acid 4-[3-(R,S)-Hydroxy-3-(3-morpholinomethyl-6-methoxyquinolin-4-yl)propyl]-1-[3-(3,4,5-trifluorophenyl)propyl]piperidine-4-acetic acid 4-[3-(R,S)-Hydroxy-3-(3-morpholinomethyl-6-methoxyquinolin-4-yl)propyl]-1-[2-(2,4,6-trifluorophenylthio)ethyl]piperidine-4-acetic acid 4-[3-(R,S)-Hydroxy-3-(3-morpholinomethyl-6-methoxyquinolin-4-yl)propyl]-1-[2-(3,4,5-trifluorophenylthio)ethyl]piperidine-4-acetic acid 4-[3-(R,S)-Hydroxy-3-(3-morpholinomethyl-6-methoxyquinolin-4-yl)propyl]-1-[2-(2,4,6-trifluorophenylamino)ethyl]piperidine-4-acetic acid 4-[3-(R,S)-Hydroxy-3-(3-morpholinomethyl-6-methoxyquinolin-4-yl)propyl]-1-[2-(3,4,5-trifluorophenylamino)ethyl]piperidine-4-acetic acid 4-[3-(R,S)-Hydroxy-3-(3-morpholinomethyl-6-methoxyquinolin-4-yl)propyl]-1-[2-(2,4,6-trifluorophenoxy)ethyl]piperidine-4-acetic acid 4-[3-(R,S)-Hydroxy-3-(3-morpholinomethyl-6-methoxyquinolin-4-yl)propyl]-1-[2-(3,4,5-trifluorophenoxy)ethyl]piperidine-4-acetic acid 4-[3-(R,S)-Hydroxy-3-(3-morpholinomethyl-6-methoxyquinolin-4-yl)propyl]-1-[3-(2,4,6-trifluorophenyl)prop-2-ynyl]piperidine-4-acetic acid 4-[3-(R,S)-Hydroxy-3-(3-morpholinomethyl-6-methoxyquinolin-4-yl)propyl]-1-[3-(3,4,5-trifluorophenyl)prop-2-ynyl]piperidine-4-acetic acid 4-[3-(R,S)-Fluoro-3-(3-chloro-6-methoxyquinolin-4-yl)propyl]-1-heptylpiperidine-4-acetic acid 4-[3-(R,S)-Fluoro-3-(3-chloro-6-methoxyquinolin-4-yl)propyl]-1-[4-phenylbutyl]piperidine-4-acetic acid 4-[3-(R,S)-Fluoro-3-(3-chloro-6-methoxyquinolin-4-yl)propyl]-1-[3-(phenyl)propyl]piperidine-4-acetic acid 4-[3-(R,S)-Fluoro-3-(3-chloro-6-methoxyquinolin-4-yl)propyl]-1-[4-(2-fluorophenyl)propyl]piperidine-4-acetic acid 4-[3-(R,S)-Fluoro-3-(3-chloro-6-methoxyquinolin-4-yl)propyl]-1-[4-(3-fluorophenyl)propyl]piperidine-4-acetic acid 4-[3-(R,S)-Fluoro-3-(3-chloro-6-methoxyquinolin-4-yl)propyl]-1-[3-(4-fluorophenyl)propyl]piperidine-4-acetic acid 4-[3-(R,S)-Fluoro-3-(3-chloro-6-methoxyquinolin-4-yl)propyl]-1-[4-(4-fluorophenyl)butyl]piperidine-4-acetic acid 4-[3-(R,S)-Fluoro-3-(3-chloro-6-methoxyquinolin-4-yl)propyl]-1-[3-(2,3-difluorophenyl)propyl]piperidine-4-acetic acid 4-[3-(R,S)-Fluoro-3-(3-chloro-6-methoxyquinolin-4-yl)propyl]-1-[4-(2,3-difluorophenyl)propyl]piperidine-4-acetic acid 4-[3-(R,S)-Fluoro-3-(3-chloro-6-methoxyquinolin-4-yl)propyl]-1-[3-(2,6-difluorophenyl)propyl]piperidine-4-acetic acid 4-[3-(R,S)-Fluoro-3-(3-chloro-6-methoxyquinolin-4-yl)propyl]-1-[4-(2,6-difluorophenyl)propyl]piperidine-4-acetic acid 4-[3-(R,S)-Fluoro-3-(3-chloro-6-methoxyquinolin-4-yl)propyl]-1-[3-(3,5-difluorophenyl)propyl]piperidine-4-acetic acid 4-[3-(R,S)-Fluoro-3-(3-chloro-6-methoxyquinolin-4-yl)propyl]-1-[3-(2,3,5-trifluorophenyl)propyl]piperidine-4-acetic acid 4-[3-(R,S)-Fluoro-3-(3-chloro-6-methoxyquinolin-4-yl)propyl]-1-[3-(2,4,6-trifluorophenyl)propyl]piperidine-4-acetic acid 4-[3-(R,S)-Fluoro-3-(3-chloro-6-methoxyquinolin-4-yl)propyl]-1-[3-(3,4,5-trifluorophenyl)propyl]piperidine-4-acetic acid 4-[3-(R,S)-Fluoro-3-(3-chloro-6-methoxyquinolin-4-yl)propyl]-1-[3-phenylthio-propyl]piperidine-4-acetic acid 4-[3-(R,S)-Fluoro-3-(3-chloro-6-methoxyquinolin-4-yl)propyl]-1-[3-(2-fluorophenylthio)propyl]piperidine-4-acetic acid 4-[3-(R,S)-Fluoro-3-(3-chloro-6-methoxyquinolin-4-yl)propyl]-1-[3-(3-fluorophenylthio)propyl]piperidine-4-acetic acid 4-[3-(R,S)-Fluoro-3-(3-chloro-6-methoxyquinolin-4-yl)propyl]-1-[2-(4-fluorophenylthio)pethyl]piperidine-4-acetic acid 4-[3-(R,S)-Fluoro-3-(3-chloro-6-methoxyquinolin-4-yl)propyl]-1-[3-(4-fluorophenylthio)propyl]piperidine-4-acetic acid 4-[3-(R,S)-Fluoro-3-(3-chloro-6-methoxyquinolin-4-yl)propyl]-1-[2-(2,3-difluorophenylthio)ethyl]piperidine-4-acetic acid 4-[3-(R,S)-Fluoro-3-(3-chloro-6-methoxyquinolin-4-yl)propyl]-1-[3-(2,3-difluorophenylthio)propyl]piperidine-4-acetic acid 4-[3-(R,S)-Fluoro-3-(3-chloro-6-methoxyquinolin-4-yl)propyl]-1-[2-(2,6-difluorophenylthio)ethyl]piperidine-4-acetic acid 4-[3-(R,S)-Fluoro-3-(3-chloro-6-methoxyquinolin-4-yl)propyl]-1-[2-(2,3,5-trifluorophenylthio)ethyl]piperidine-4-acetic acid 4-[3-(R,S)-Fluoro-3-(3-chloro-6-methoxyquinolin-4-yl)propyl]-1-[2-(2,4,6-trifluorophenylthio)ethyl]piperidine-4-acetic acid 4-[3-(R,S)-Fluoro-3-(3-chloro-6-methoxyquinolin-4-yl)propyl]-1-[2-(3,4,5-trifluorophenylthio)ethyl]piperidine-4-acetic acid 4-[3-(R,S)-Fluoro-3-(3-chloro-6-methoxyquinolin-4-yl)propyl]-1-[2-(3,5-difluorophenoxy)ethyl]piperidine-4-acetic acid 4-[3-(R,S)-Fluoro-3-(3-chloro-6-methoxyquinolin-4-yl)propyl]-1-[2-(2,3,5-trifluorophenoxy)ethyl]piperidine-4-acetic acid 4-[3-(R,S)-Fluoro-3-(3-chloro-6-methoxyquinolin-4-yl)propyl]-1-[2-(2,4,6-trifluorophenoxy)ethyl]piperidine-4-acetic acid 4-[3-(R,S)-Fluoro-3-(3-chloro-6-methoxyquinolin-4-yl)propyl]-1-[2-(3,4,5-trifluorophenoxy)ethyl]piperidine-4-acetic acid 4-[3-(R,S)-Fluoro-3-(3-chloro-6-methoxyquinolin-4-yl)propyl]-1-[2-(3,5-difluorophenylamino)ethyl]piperidine-4-acetic acid 4-[3-(R,S)-Fluoro-3-(3-chloro-6-methoxyquinolin-4-yl)propyl]-1-[2-(2,3,5-trifluorophenylamino)ethyl]piperidine-4-acetic acid 4-[3-(R,S)-Fluoro-3-(3-chloro-6-methoxyquinolin-4-yl)propyl]-1-[2-(2,4,6-trifluorophenylamino)ethyl]piperidine-4-acetic acid 4-[3-(R,S)-Fluoro-3-(3-chloro-6-methoxyquinolin-4-yl)propyl]-1-[2-(3,4,5-trifluorophenylamino)ethyl]piperidine-4-acetic acid 4-[3-(R,S)-Fluoro-3-(3-chloro-6-methoxyquinolin-4-yl)propyl]-1-[3-(2,6-difluorophenylthio)propyl]piperidine-4-acetic acid 4-[3-(R,S)-Fluoro-3-(3-chloro-6-methoxyquinolin-4-yl)propyl]-1-[2-(2-chlorophenylthio)ethyl]piperidine-4-acetic acid 4-[3-(R,S)-Fluoro-3-(3-chloro-6-methoxyquinolin-4-yl)propyl]-1-[3-(2-chlorophenylthio)propyl]piperidine-4-acetic acid 4-[3-(R,S)-Fluoro-3-(3-chloro-6-methoxyquinolin-4-yl)propyl]-1-[2-(3-chlorophenylthio)ethyl]piperidine-4-acetic acid 4-[3-(R,S)-Fluoro-3-(3-chloro-6-methoxyquinolin-4-yl)propyl]-1-[3-(3-chlorophenylthio)propyl]piperidine-4-acetic acid 4-[3-(R,S)-Fluoro-3-(3-chloro-6-methoxyquinolin-4-yl)propyl]-1-[2-(4-chlorophenylthio)ethyl]piperidine-4-acetic acid 4-[3-(R,S)-Fluoro-3-(3-chloro-6-methoxyquinolin-4-yl)propyl]-1-[3-(4-chlorophenylthio)propyl]piperidine-4-acetic acid 4-[3-(R,S)-Fluoro-3-(3-chloro-6-methoxyquinolin-4-yl)propyl]-1-[2-(2-methylphenylthio)ethyl]piperidine-4-acetic acid 4-[3-(R,S)-Fluoro-3-(3-chloro-6-methoxyquinolin-4-yl)propyl]-1-[3-(2-methylphenylthio)propyl]piperidine-4-acetic acid 4-[3-(R,S)-Fluoro-3-(3-chloro-6-methoxyquinolin-4-yl)propyl]-1-[2-(3-methylphenylthio)ethyl]piperidine-4-acetic acid 4-[3-(R,S)-Fluoro-3-(3-chloro-6-methoxyquinolin-4-yl)propyl]-1-[3-(3-methylphenylthio)propyl]piperidine-4-acetic acid 4-[3-(R,S)-Fluoro-3-(3-chloro-6-methoxyquinolin-4-yl)propyl]-1-[2-(4-methylphenylthio)ethyl]piperidine-4-acetic acid 4-[3-(R,S)-Fluoro-3-(3-chloro-6-methoxyquinolin-4-yl)propyl]-1-[3-(4-methylphenylthio)propyl]piperidine-4-acetic acid 4-[3-(R,S)-Fluoro-3-(3-chloro-6-methoxyquinolin-4-yl)propyl]-1-[2-(2-trifluoromethylphenylthio)ethyl]piperidine-4-acetic acid 4-[3-(R,S)-Fluoro-3-(3-chloro-6-methoxyquinolin-4-yl)propyl]-1-[3-(2-trifluoromethylphenylthio)propyl]piperidine-4-acetic acid 4-[3-(R,S)-Fluoro-3-(3-chloro-6-methoxyquinolin-4-yl)propyl]-1-[2-(3-trifluoromethylphenylthio)ethyl]piperidine-4-acetic acid 4-[3-(R,S)-Fluoro-3-(3-chloro-6-methoxyquinolin-4-yl)propyl]-1-[3-(3-trifluoromethylphenylthio)propyl]piperidine-4-acetic acid 4-[3-(R,S)-Fluoro-3-(3-chloro-6-methoxyquinolin-4-yl)propyl]-1-[2-(4-trifluoromethylphenylthio)ethyl]piperidine-4-acetic acid 4-[3-(R,S)-Fluoro-3-(3-chloro-6-methoxyquinolin-4-yl)propyl]-1-[3-(4-trifluoromethylphenylthio)propyl]piperidine-4-acetic acid 4-[3-(R,S)-Fluoro-3-(3-chloro-6-methoxyquinolin-4-yl)propyl]-1-[2-(2-methoxyphenylthio)ethyl]piperidine-4-acetic acid 4-[3-(R,S)-Fluoro-3-(3-chloro-6-methoxyquinolin-4-yl)propyl]-1-[3-(2-methoxyphenylthio)propyl]piperidine-4-acetic acid 4-[3-(R,S)-Fluoro-3-(3-chloro-6-methoxyquinolin-4-yl)propyl]-1-[2-(3-methoxyphenylthio)ethyl]piperidine-4-acetic acid 4-[3-(R,S)-Fluoro-3-(3-chloro-6-methoxyquinolin-4-yl)propyl]-1-[3-(3-methoxyphenylthio)propyl]piperidine-4-acetic acid 4-[3-(R,S)-Fluoro-3-(3-chloro-6-methoxyquinolin-4-yl)propyl]-1-[2-(4-methoxyphenylthio)ethyl]piperidine-4-acetic acid 4-[3-(R,S)-Fluoro-3-(3-chloro-6-methoxyquinolin-4-yl)propyl]-1-[3-(4-methoxyphenylthio)propyl]piperidine-4-acetic acid 4-[3-(R,S)-Fluoro-3-(3-chloro-6-methoxyquinolin-4-yl)propyl]-1-[-cyclopentylmethyl]piperidine-4-acetic acid 4-[3-(R,S)-Fluoro-3-(3-chloro-6-methoxyquinolin-4-yl)propyl]-1-[2-(cyclopentyl)ethyl]piperidine-4-acetic acid 4-[3-(R,S)-Fluoro-3-(3-chloro-6-methoxyquinolin-4-yl)propyl]-1-[2-(cyclohexyl)ethyl]piperidine-4-acetic acid 4-[3-(R,S)-Fluoro-3-(3-chloro-6-methoxyquinolin-4-yl)propyl]-1-[2-(cyclopentylthio)ethyl]piperidine-4-acetic acid 4-[3-(R,S)-Fluoro-3-(3-chloro-6-methoxyquinolin-4-yl)propyl]-1-[3-(cyclopentylthio)propyl]piperidine-4-acetic acid 4-[3-(R,S)-Fluoro-3-(3-chloro-6-methoxyquinolin-4-yl)propyl]-1-[3-(cyclohexylthio)propyl]piperidine-4-acetic acid 4-[3-(R,S)-Fluoro-3-(3-chloro-6-methoxyquinolin-4-yl)propyl]-1-[2-(pyrid-2-yl)thioethyl]piperidine-4-acetic acid 4-[3-(R,S)-Fluoro-3-(3-chloro-6-methoxyquinolin-4-yl)propyl]-1-[4-(thien-2-yl)butyl]piperidine-4-acetic acid 4-[3-(R,S)-Fluoro-3-(3-chloro-6-methoxyquinolin-4-yl)propyl]-1-[3-(thien-2-yl)thiopropyl]piperidine-4-acetic acid 4-[3-(R,S)-Fluoro-3-(3-chloro-6-methoxyquinolin-4-yl)propyl]-1-[3-(thien-3-yl)propyl]piperidine-4-acetic acid 4-[3-(R,S)-Fluoro-3-(3-chloro-6-methoxyquinolin-4-yl)propyl]-1-[4-(thien-3-yl)butyl]piperidine-4-acetic acid 4-[3-(R,S)-Fluoro-3-(3-chloro-6-methoxyquinolin-4-yl)propyl]-1-[2-(thien-2-yl)thioethyl]piperidine-4-acetic acid 4-[3-(R,S)-Fluoro-3-(3-chloro-6-methoxyquinolin-4-yl)propyl]-1-[2-(thien-3-yl)thioethyl]piperidine-4-acetic acid 4-[3-(R,S)-Fluoro-3-(3-chloro-6-methoxyquinolin-4-yl)propyl]-1-[3-(thien-3-yl)thiopropyl]piperidine-4-acetic acid 4-[3-(R,S)-Fluoro-3-(3-chloro-6-methoxyquinolin-4-yl)propyl]-1-[3-(1,3-thiazol-2-yl)propyl]piperidine-4-acetic acid 4-[3-(R,S)-Fluoro-3-(3-chloro-6-methoxyquinolin-4-yl)
propyl]-1-[4-(1,3-thiazol-2-yl)butyl]piperidine-4-
acetic acid
4-[3-(R,S)-Fluoro-3-(3-chloro-6-methoxyquinolin-4-yl)
propyl]-1-[3-(1,3-thiazol-2-yl)thioethyl]piperidine-4-
acetic acid
4-[3-(R,S)-Fluoro-3-(3-chloro-6-methoxyquinolin-4-yl)
propyl]-1-[3-(pyrid-2-yl)propyl]piperidine-4-acetic
acid
4-[3-(R,S)-Fluoro-3-(3-chloro-6-methoxyquinolin-4-yl)
propyl]-1-[4-(pyrid-2-yl)butyl]piperidine-4-acetic acid
4-[3-(R,S)-Fluoro-3-(3-chloro-6-methoxyquinolin-4-yl)
propyl]-1-[3-(pyrid-2-yl)thiopropyl]piperidine-4-
acetic acid
4-[3-(R,S)-Fluoro-3-(3-chloro-6-methoxyquinolin-4-yl)
propyl]-1-[3-(pyrid-3-yl)propyl]piperidine-4-acetic
acid
4-[3-(R,S)-Fluoro-3-(3-chloro-6-methoxyquinolin-4-yl)
propyl]-1-[4-(pyrid-3-yl)butyl]piperidine-4-acetic acid
4-[3-(R,S)-Fluoro-3-(3-chloro-6-methoxyquinolin-4-yl)
propyl]-1-[2-(pyrid-3-yl)thioethyl]piperidine-4-acetic
acid
4-[3-(R,S)-Fluoro-3-(3-chloro-6-methoxyquinolin-4-yl)
propyl]-1-[3-(pyrid-3-yl)thiopropyl]piperidine-4-
acetic acid
4-[3-(R,S)-Fluoro-3-(3-chloro-6-methoxyquinolin-4-yl)
propyl]-1-[3-(pyrid-4-yl)propyl]piperidine-4-acetic
acid
4-[3-(R,S)-Fluoro-3-(3-chloro-6-methoxyquinolin-4-yl)
propyl]-1-[4-(pyrid-4-yl)butyl]piperidine-4-acetic acid
4-[3-(R,S)-Fluoro-3-(3-chloro-6-methoxyquinolin-4-yl)
propyl]-1-[2-(pyrid-4-yl)thioethyl]piperidine-4-acetic
acid
4-[3-(R,S)-Fluoro-3-(3-chloro-6-methoxyquinolin-4-yl)
propyl]-1-[3-(pyrid-4-yl)thiopropyl]piperidine-4-
acetic acid
4-[3-(R,S)-Fluoro-3-(3-chloro-6-methoxyquinolin-4-yl)
propyl]-1-[3-(pyrazin-2-yl)propyl]piperidine-4-acetic
acid
4-[3-(R,S)-Fluoro-3-(3-chloro-6-methoxyquinolin-4-yl)
propyl]-1-[4-(pyrazin-2-yl)butyl]piperidine-4-acetic
acid
4-[3-(R,S)-Fluoro-3-(3-chloro-6-methoxyquinolin-4-yl)
propyl]-1-[2-(pyrazin-2-yl)thioethyl]piperidine-4-
acetic acid
4-[3-(R,S)-Fluoro-3-(3-chloro-6-methoxyquinolin-4-yl)
propyl]-1-[3-(pyrazin-2-yl)thiopropyl]piperidine-4-
acetic acid
4-[3-(R,S)-Fluoro-3-(3-chloro-6-methoxyquinolin-4-yl)
propyl]-1-[3-(4-fluorophenyl)prop-2-ynyl]piperidine-
4-acetic acid
4-[3-(R,S)-Fluoro-3-(3-chloro-6-methoxyquinolin-4-yl)
propyl]-1-[3-(3,4-difluorophenyl)prop-2-ynyl]
piperidine-4-acetic acid
4-[3-(R,S)-Fluoro-3-(3-chloro-6-methoxyquinolin-4-yl)
propyl]-1-[3-(2,4-difluorophenyl)prop-2-ynyl]
piperidine-4-acetic acid
4-[3-(R,S)-Fluoro-3-(3-chloro-6-methoxyquinolin-4-yl)
propyl]-1-[3-(2,3,5-trifluorophenyl)prop-2-ynyl]
piperidine-4-acetic acid
4-[3-(R,S)-Fluoro-3-(3-chloro-6-methoxyquinolin-4-yl)
propyl]-1-[3-(2,4,6-trifluorophenyl)prop-2-ynyl]
piperidine-4-acetic acid
4-[3-(R,S)-Fluoro-3-(3-chloro-6-methoxyquinolin-4-yl)
propyl]-1-[3-(3,4,5-trifluorophenyl)prop-2-ynyl]
piperidine-4-acetic acid
4-[3-(R,S)-Fluoro-3-(3-chloro-6-methoxyquinolin-4-yl)
propyl]-1-[3-(4-chloro-3-fluorophenyl)prop-2-ynyl]
piperidine-4-acetic acid
4-[3-(R,S)-Fluoro-3-(3-chloro-6-methoxyquinolin-4-yl)
propyl]-1-[3-(3-chloro-4-fluorophenyl)prop-2-ynyl]
piperidine-4-acetic acid
4-[3-(R,S)-Fluoro-3-(3-chloro-6-methoxyquinolin-4-yl)
propyl]-1-[3-(2-chloro-4-fluorophenyl)prop-2-ynyl]
piperidine-4-acetic acid
4-[3-(R,S)-Fluoro-3-(3-chloro-6-methoxyquinolin-4-yl)
propyl]-1-[3-(3-chloro-5-fluorophenyl)prop-2-ynyl]
piperidine-4-acetic acid
4-[3-(R,S)-Fluoro-3-(3-chloro-6-methoxyquinolin-4-yl)
propyl]-1-[3-(4-chloro-2-fluorophenyl)prop-2-ynyl]
piperidine-4-acetic acid
4-[3-(R,S)-Fluoro-3-(3-chloro-6-methoxyquinolin-4-yl)
propyl]-1-[3-(3-fluoro-4-methylphenyl)prop-2-ynyl]
piperidine-4-acetic acid
4-[3-(R,S)-Fluoro-3-(3-chloro-6-methoxyquinolin-4-yl)
propyl]-1-[3-(3,5-bis(trifluoromethyl)phenyl)prop-2-
ynyl]piperidine-4-acetic acid
4-[3-(R,S)-Fluoro-3-(3-chloro-6-methoxyquinolin-4-yl)
propyl]-1-[3-(thien-2-yl)prop-2-ynyl]piperidine-4-
acetic acid
4-[3-(R,S)-Fluoro-3-(3-chloro-6-methoxyquinolin-4-yl)
propyl]-1-[3-(thien-3-yl)prop-2-ynyl]piperidine-4-
acetic acid
4-[3-(R,S)-Fluoro-3-(3-chloro-6-methoxyquinolin-4-yl)
propyl]-1-[3-(1,3-thiazol-2-yl)prop-2-ynyl]piperidine-
4-acetic acid
4-[3-(R,S)-Fluoro-3-(3-chloro-6-methoxyquinolin-4-yl)
propyl]-1-[3-(1,3-thiazol-4-yl)prop-2-ynyl]piperidine-
4-acetic acid
4-[3-(R,S)-Fluoro-3-(3-chloro-6-methoxyquinolin-4-yl)
propyl]-1-[3-(1,3-thiazol-5-yl)prop-2-ynyl]piperidine-
4-acetic acid
4-[3-(R,S)-Fluoro-3-(3-chloro-6-methoxyquinolin-4-yl)
propyl]-1-[3-(pyrid-2-yl)prop-2-ynyl]piperidine-4-
acetic acid
4-[3-(R,S)-Fluoro-3-(3-chloro-6-methoxyquinolin-4-yl)
propyl]-1-[3-(pyrid-3-yl)prop-2-ynyl]piperidine-4-
acetic acid
4-[3-(R,S)-Fluoro-3-(3-chloro-6-methoxyquinolin-4-yl)
propyl]-1-[3-(pyrid-4-yl)prop-2-ynyl]piperidine-4-
acetic acid
4-[3-(R,S)-Fluoro-3-(3-methyl-6-methoxyquinolin-4-yl)
propyl]-1-[2-(cyclohexyl)ethyl]piperidine-4-acetic
acid
4-[3-(R,S)-Fluoro-3-(3-methyl-6-methoxyquinolin-4-yl)
propyl]-1-[3-(phenyl)propyl]piperidine-4-acetic acid
4-[3-(R,S)-Fluoro-3-(3-methyl-6-methoxyquinolin-4-yl)
propyl]-1-[3-(2,3,5-trifluorophenyl)propyl]piperidine-
4-acetic acid
4-[3-(R,S)-Fluoro-3-(3-methyl-6-methoxyquinolin-4-yl)
propyl]-1-[2-(3,5-difluorophenylamino)ethyl]
piperidine-4-acetic acid
4-[3-(R,S)-Fluoro-3-(3-methyl-6-methoxyquinolin-4-yl)
propyl]-1-[2-(2,3,5-trifluorophenylamino)ethyl]
piperidine-4-acetic acid
4-[3-(R,S)-Fluoro-3-(3-methyl-6-methoxyquinolin-4-yl)
propyl]-1-[2-(3,5-difluorophenoxy)ethyl]piperidine-4-
acetic acid 4-[3-(R,S)-Fluoro-3-(3-methyl-6-methoxyquinolin-4-yl)propyl]-1-[2-(2,3,5-trifluorophenoxy)ethyl]piperidine-4-acetic acid 4-[3-(R,S)-Fluoro-3-(3-methyl-6-methoxyquinolin-4-yl)propyl]-1-[2-(cyclopentylthio)ethyl]piperidine-4-acetic acid 4-[3-(R,S)-Fluoro-3-(3-methyl-6-methoxyquinolin-4-yl)propyl]-1-[2-(pyrid-2-yl)thioethyl]piperidine-4-acetic acid 4-[3-(R,S)-Fluoro-3-(3-methyl-6-methoxyquinolin-4-yl)propyl]-1-[2-(thien-2-yl)thioethyl]piperidine-4-acetic acid 4-[3-(R,S)-Fluoro-3-(3-methyl-6-methoxyquinolin-4-yl)propyl]-1-[3-(2,3,5-trifluorophenyl)prop-2-ynyl]piperidine-4-acetic acid 4-[3-(R,S)-Fluoro-3-(3-methyl-6-methoxyquinolin-4-yl)propyl]-1-[3-(thien-2-yl)prop-2-ynyl]piperidine-4-acetic acid 4-[3-(R,S)-Fluoro-3-(3-fluoro-6-methoxyquinolin-4-yl)propyl]-1-[2-(cyclohexyl)ethyl]piperidine-4-acetic acid 4-[3-(R,S)-Fluoro-3-(3-fluoro-6-methoxyquinolin-4-yl)propyl]-1-[3-(phenyl)propyl]piperidine-4-acetic acid 4-[3-(R,S)-Fluoro-3-(3-fluoro-6-methoxyquinolin-4-yl)propyl]-1-[3-(2,3,5-trifluorophenyl)propyl]piperidine-4-acetic acid 4-[3-(R,S)-Fluoro-3-(3-fluoro-6-methoxyquinolin-4-yl)propyl]-1-[2-(3,5-difluorophenylamino)ethyl]piperidine-4-acetic acid 4-[3-(R,S)-Fluoro-3-(3-fluoro-6-methoxyquinolin-4-yl)propyl]-1-[2-(2,3,5-trifluorophenylamino)ethyl]piperidine-4-acetic acid 4-[3-(R,S)-Fluoro-3-(3-fluoro-6-methoxyquinolin-4-yl)propyl]-1-[2-(3,5-difluorophenoxy)ethyl]piperidine-4-acetic acid 4-[3-(R,S)-Fluoro-3-(3-fluoro-6-methoxyquinolin-4-yl)propyl]-1-[2-(2,3,5-trifluorophenoxy)ethyl]piperidine-4-acetic acid 4-[3-(R,S)-Fluoro-3-(3-fluoro-6-methoxyquinolin-4-yl)propyl]-1-[2-(2,3,5-trifluorophenylthio)ethyl]piperidine-4-acetic acid 4-[3-(R,S)-Fluoro-3-(3-fluoro-6-methoxyquinolin-4-yl)propyl]-1-[2-(cyclopentylthio)ethyl]piperidine-4-acetic acid 4-[3-(R,S)-Fluoro-3-(3-fluoro-6-methoxyquinolin-4-yl)propyl]-1-[2-(pyrid-2-yl)thioethyl]piperidine-4-acetic acid 4-[3-(R,S)-Fluoro-3-(3-fluoro-6-methoxyquinolin-4-yl)propyl]-1-[2-(thien-2-yl)thioethyl]piperidine-4-acetic acid 4-[3-(R,S)-Fluoro-3-(3-fluoro-6-methoxyquinolin-4-yl)propyl]-1-[3-(2,3,5-trifluorophenyl)prop-2-ynyl]piperidine-4-acetic acid 4-[3-(R,S)-Fluoro-3-(3-fluoro-6-methoxyquinolin-4-yl)propyl]-1-[3-(thien-2-yl)prop-2-ynyl]piperidine-4-acetic acid 4-[3-(R,S)-Fluoro-3-(3-dimethylamino-6-methoxyquinolin-4-yl)propyl]-1-[2-(cyclohexyl)ethyl]piperidine-4-acetic acid 4-[3-(R,S)-Fluoro-3-(3-dimethylamino-6-methoxyquinolin-4-yl)propyl]-1-[3-(phenyl)propyl]piperidine-4-acetic acid 4-[3-(R,S)-Fluoro-3-(3-dimethylamino-6-methoxyquinolin-4-yl)propyl]-1-[3-(2,3,5-trifluorophenyl)propyl]piperidine-4-acetic acid 4-[3-(R,S)-Fluoro-3-(3-dimethylamino-6-methoxyquinolin-4-yl)propyl]-1-[2-(3,5-difluorophenylamino)ethyl]piperidine-4-acetic acid 4-[3-(R,S)-Fluoro-3-(3-dimethylamino-6-methoxyquinolin-4-yl)propyl]-1-[2-(2,3,5-trifluorophenylamino)ethyl]piperidine-4-acetic acid 4-[3-(R,S)-Fluoro-3-(3-dimethylamino-6-methoxyquinolin-4-yl)propyl]-1-[2-(3,5-difluorophenoxy)ethyl]piperidine-4-acetic acid 4-[3-(R,S)-Fluoro-3-(3-dimethylamino-6-methoxyquinolin-4-yl)propyl]-1-[2-(2,3,5-trifluorophenoxy)ethyl]piperidine-4-acetic acid 4-[3-(R,S)-Fluoro-3-(3-dimethylamino-6-methoxyquinolin-4-yl)propyl]-1-[2-(cyclopentylthio)ethyl]piperidine-4-acetic acid 4-[3-(R,S)-Fluoro-3-(3-dimethylamino-6-methoxyquinolin-4-yl)propyl]-1-[2-(pyrid-2-yl)thioethyl]piperidine-4-acetic acid 4-[3-(R,S)-Fluoro-3-(3-dimethylamino-6-methoxyquinolin-4-yl)propyl]-1-[2-(thien-2-yl)thioethyl]piperidine-4-acetic acid 4-[3-(R,S)-Fluoro-3-(3-dimethylamino-6-methoxyquinolin-4-yl)propyl]-1-[3-(2,3,5-trifluorophenyl)prop-2-ynyl]piperidine-4-acetic acid 4-[3-(R,S)-Fluoro-3-(3-dimethylamino-6-methoxyquinolin-4-yl)propyl]-1-[3-(thien-2-yl)prop-2-ynyl]piperidine-4-acetic acid 4-[3-(R,S)-Fluoro-3-(3-hydroxymethyl-6-methoxyquinolin-4-yl)propyl]-1-[2-(cyclohexyl)ethyl]piperidine-4-acetic acid 4-[3-(R,S)-Fluoro-3-(3-hydroxymethyl-6-methoxyquinolin-4-yl)propyl]-1-[3-(phenyl)propyl]piperidine-4-acetic acid 4-[3-(R,S)-Fluoro-3-(3-hydroxymethyl-6-methoxyquinolin-4-yl)propyl]-1-[3-(2,3,5-trifluorophenyl)propyl]piperidine-4-acetic acid 4-[3-(R,S)-Fluoro-3-(3-hydroxymethyl-6-methoxyquinolin-4-yl)propyl]-1-[2-(3,5-difluorophenylamino)ethyl]piperidine-4-acetic acid 4-[3-(R,S)-Fluoro-3-(3-hydroxymethyl-6-methoxyquinolin-4-yl)propyl]-1-[2-(2,3,5-trifluorophenylamino)ethyl]piperidine-4-acetic acid 4-[3-(R,S)-Fluoro-3-(3-hydroxymethyl-6-methoxyquinolin-4-yl)propyl]-1-[2-(3,5-difluorophenoxy)ethyl]piperidine-4-acetic acid 4-[3-(R,S)-Fluoro-3-(3-hydroxymethyl-6-methoxyquinolin-4-yl)propyl]-1-[2-(2,3,5-trifluorophenoxy)ethyl]piperidine-4-acetic acid 4-[3-(R,S)-Fluoro-3-(3-hydroxymethyl-6-methoxyquinolin-4-yl)propyl]-1-[2-(2,3,5-trifluorophenylthio)ethyl]piperidine-4-acetic acid 4-[3-(R,S)-Fluoro-3-(3-hydroxymethyl-6-methoxyquinolin-4-yl)propyl]-1-[2-(cyclopentylthio)ethyl]piperidine-4-acetic acid 4-[3-(R,S)-Fluoro-3-(3-hydroxymethyl-6-methoxyquinolin-4-yl)propyl]-1-[2-(pyrid-2-yl)thioethyl]piperidine-4-acetic acid 4-[3-(R,S)-Fluoro-3-(3-hydroxymethyl-6-methoxyquinolin-4-yl)propyl]-1-[2-(thien-2-yl)thioethyl]piperidine-4-acetic acid 4-[3-(R,S)-Fluoro-3-(3-hydroxymethyl-6-methoxyquinolin-4-yl)propyl]-1-[3-(2,3,5-trifluorophenyl)prop-2-ynyl]piperidine-4-acetic acid 4-[3-(R,S)-Fluoro-3-(3-hydroxymethyl-6-methoxyquinolin-4-yl)propyl]-1-[3-(thien-2-yl)prop-2-ynyl]piperidine-4-acetic acid 4-[3-(R,S)-Fluoro-3-(3-fluoromethyl-6-methoxyquinolin-4-yl)propyl]-1-[2-(cyclohexyl)ethyl]piperidine-4-acetic acid 4-[3-(R,S)-Fluoro-3-(3-fluoromethyl-6-methoxyquinolin-4-yl)propyl]-1-[3-(phenyl)propyl]piperidine-4-acetic acid 4-[3-(R,S)-Fluoro-3-(3-fluoromethyl-6-methoxyquinolin-4-yl)propyl]-1-[3-(2,3,5-trifluorophenyl)propyl]piperidine-4-acetic acid 4-[3-(R,S)-Fluoro-3-(3-fluoromethyl-6-methoxyquinolin-4-yl)propyl]-1-[2-(3,5-difluorophenylamino)ethyl]piperidine-4-acetic acid 4-[3-(R,S)-Fluoro-3-(3-fluoromethyl-6-methoxyquinolin-4-yl)propyl]-1-[2-(2,3,5-trifluorophenylamino)ethyl]piperidine-4-acetic acid 4-[3-(R,S)-Fluoro-3-(3-fluoromethyl-6-methoxyquinolin-4-yl)propyl]-1-[2-(3,5-difluorophenoxy)ethyl]piperidine-4-acetic acid 4-[3-(R,S)-Fluoro-3-(3-fluoromethyl-6-methoxyquinolin-4-yl)propyl]-1-[2-(2,3,5-trifluorophenylthio)ethyl]piperidine-4-acetic acid 4-[3-(R,S)-Fluoro-3-(3-fluoromethyl-6-methoxyquinolin-4-yl)propyl]-1-[2-(cyclopentylthio)ethyl]piperidine-4-acetic acid 4-[3-(R,S)-Fluoro-3-(3-fluoromethyl-6-methoxyquinolin-4-yl)propyl]-1-[2-(pyrid-2-yl)thioethyl]piperidine-4-acetic acid 4-[3-(R,S)-Fluoro-3-(3-fluoromethyl-6-methoxyquinolin-4-yl)propyl]-1-[2-(thien-2-yl)thioethyl]piperidine-4-acetic acid 4-[3-(R,S)-Fluoro-3-(3-fluoromethyl-6-methoxyquinolin-4-yl)propyl]-1-[3-(2,3,5-trifluorophenyl)prop-2-ynyl]piperidine-4-acetic acid 4-[3-(R,S)-Fluoro-3-(3-fluoromethyl-6-methoxyquinolin-4-yl)propyl]-1-[3-(thien-2-yl)prop-2-ynyl]piperidine-4-acetic acid 4-[3-(R,S)-Fluoro-3-(3-aminomethyl-6-methoxyquinolin-4-yl)propyl]-1-[2-(cyclohexyl)ethyl]piperidine-4-acetic acid 4-[3-(R,S)-Fluoro-3-(3-aminomethyl-6-methoxyquinolin-4-yl)propyl]-1-[3-(phenyl)propyl]piperidine-4-acetic acid 4-[3-(R,S)-Fluoro-3-(3-aminomethyl-6-methoxyquinolin-4-yl)propyl]-1-[3-(2,3,5-trifluorophenyl)propyl]piperidine-4-acetic acid 4-[3-(R,S)-Fluoro-3-(3-aminomethyl-6-methoxyquinolin-4-yl)propyl]-1-[2-(3,5-difluorophenylamino)ethyl]piperidine-4-acetic acid 4-[3-(R,S)-Fluoro-3-(3-aminomethyl-6-methoxyquinolin-4-yl)propyl]-1-[2-(2,3,5-trifluorophenylamino)ethyl]piperidine-4-acetic acid 4-[3-(R,S)-Fluoro-3-(3-aminomethyl-6-methoxyquinolin-4-yl)propyl]-1-[2-(3,5-difluorophenoxy)ethyl]piperidine-4-acetic acid 4-[3-(R,S)-Fluoro-3-(3-aminomethyl-6-methoxyquinolin-4-yl)propyl]-1-[2-(2,3,5-trifluorophenoxy)ethyl]piperidine-4-acetic acid 4-[3-(R,S)-Fluoro-3-(3-aminomethyl-6-methoxyquinolin-4-yl)propyl]-1-[2-(2,3,5-trifluorophenylthio)ethyl]piperidine-4-acetic acid 4-[3-(R,S)-Fluoro-3-(3-aminomethyl-6-methoxyquinolin-4-yl)propyl]-1-[2-(cyclopentylthio)ethyl]piperidine-4-acetic acid 4-[3-(R,S)-Fluoro-3-(3-aminomethyl-6-methoxyquinolin-4-yl)propyl]-1-[2-(pyrid-2-yl)thioethyl]piperidine-4-acetic acid 4-[3-(R,S)-Fluoro-3-(3-aminomethyl-6-methoxyquinolin-4-yl)propyl]-1-[2-(thien-2-yl)thioethyl]piperidine-4-acetic acid 4-[3-(R,S)-Fluoro-3-(3-aminomethyl-6-methoxyquinolin-4-yl)propyl]-1-[3-(2,3,5-trifluorophenyl)prop-2-ynyl]piperidine-4-acetic acid 4-[3-(R,S)-Fluoro-3-(3-aminomethyl-6-methoxyquinolin-4-yl)propyl]-1-[3-(thien-2-yl)prop-2-ynyl]piperidine-4-acetic acid 4-[3-(R,S)-Fluoro-3-(3-morpholinomethyl-6-methoxyquinolin-4-yl)propyl]-1-[2-(cyclohexyl)ethyl]piperidine-4-acetic acid 4-[3-(R,S)-Fluoro-3-(3-morpholinomethyl-6-methoxyquinolin-4-yl)propyl]-1-[3-(phenyl)propyl]piperidine-4-acetic acid 4-[3-(R,S)-Fluoro-3-(3-morpholinomethyl-6-methoxyquinolin-4-yl)propyl]-1-[3-(2,3,5-trifluorophenyl)propyl]piperidine-4-acetic acid 4-[3-(R,S)-Fluoro-3-(3-morpholinomethyl-6-methoxyquinolin-4-yl)propyl]-1-[2-(3,5-difluorophenylamino)ethyl]piperidine-4-acetic acid 4-[3-(R,S)-Fluoro-3-(3-morpholinomethyl-6-methoxyquinolin-4-yl)propyl]-1-[2-(2,3,5-trifluorophenylamino)ethyl]piperidine-4-acetic acid 4-[3-(R,S)-Fluoro-3-(3-morpholinomethyl-6-methoxyquinolin-4-yl)propyl]-1-[2-(3,5-difluorophenoxy)ethyl]piperidine-4-acetic acid 4-[3-(R,S)-Fluoro-3-(3-morpholinomethyl-6-methoxyquinolin-4-yl)propyl]-1-[2-(2,3,5-trifluorophenoxy)ethyl]piperidine-4-acetic acid 4-[3-(R,S)-Fluoro-3-(3-morpholinomethyl-6-methoxyquinolin-4-yl)propyl]-1-[2-(2,3,5-trifluorophenylthio)ethyl]piperidine-4-acetic acid 4-[3-(R,S)-Fluoro-3-(3-morpholinomethyl-6-methoxyquinolin-4-yl)propyl]-1-[2-(cyclopentylthio)ethyl]piperidine-4-acetic acid 4-[3-(R,S)-Fluoro-3-(3-morpholinomethyl-6-methoxyquinolin-4-yl)propyl]-1-[2-(pyrid-2-yl)thioethyl]piperidine-4-acetic acid 4-[3-(R,S)-Fluoro-3-(3-morpholinomethyl-6-methoxyquinolin-4-yl)propyl]-1-[2-(thien-2-yl)thioethyl]piperidine-4-acetic acid 4-[3-(R,S)-Fluoro-3-(3-morpholinomethyl-6-methoxyquinolin-4-yl)propyl]-1-[3-(2,3,5-trifluorophenyl)prop-2-ynyl]piperidine-4-acetic acid 4-[3-(R,S)-Fluoro-3-(3-morpholinomethyl-6-methoxyquinolin-4-yl)propyl]-1-[3-(thien-2-yl)prop-2-ynyl]piperidine-4-acetic acid 4-[3-(R,S)-Fluoro-3-(3-methyl-6-methoxyquinolin-4-yl)propyl]-1-[3-(2,4,6-trifluorophenyl)propyl]piperidine-4-acetic acid 4-[3-(R,S)-Fluoro-3-(3-methyl-6-methoxyquinolin-4-yl)propyl]-1-[3-(3,4,5-trifluorophenyl)propyl]piperidine-4-acetic acid 4-[3-(R,S)-Fluoro-3-(3-methyl-6-methoxyquinolin-4-yl)propyl]-1-[2-(2,4,6-trifluorophenylthio)ethyl]piperidine-4-acetic acid 4-[3-(R,S)-Fluoro-3-(3-methyl-6-methoxyquinolin-4-yl)propyl]-1-[2-(3,4,5-trifluorophenylthio)ethyl]piperidine-4-acetic acid 4-[3-(R,S)-Fluoro-3-(3-methyl-6-methoxyquinolin-4-yl)propyl]-1-[2-(2,4,6-trifluorophenylamino)ethyl]piperidine-4-acetic acid 4-[3-(R,S)-Fluoro-3-(3-methyl-6-methoxyquinolin-4-yl)propyl]-1-[2-(3,4,5-trifluorophenylamino)ethyl]piperidine-4-acetic acid 4-[3-(R,S)-Fluoro-3-(3-methyl-6-methoxyquinolin-4-yl)propyl]-1-[2-(2,4,6-trifluorophenoxy)ethyl]piperidine-4-acetic acid 4-[3-(R,S)-Fluoro-3-(3-methyl-6-methoxyquinolin-4-yl)propyl]-1-[2-(3,4,5-trifluorophenoxy)ethyl]piperidine-4-acetic acid 4-[3-(R,S)-Fluoro-3-(3-methyl-6-methoxyquinolin-4-yl)propyl]-1-[3-(2,4,6-trifluorophenyl)prop-2-ynyl]piperidine-4-acetic acid 4-[3-(R,S)-Fluoro-3-(3-methyl-6-methoxyquinolin-4-yl)propyl]-1-[3-(3,4,5-trifluorophenyl)prop-2-ynyl]piperidine-4-acetic acid 4-[3-(R,S)-Fluoro-3-(3-fluoro-6-methoxyquinolin-4-yl)propyl]-1-[3-(2,4,6-trifluorophenyl)propyl]piperidine-4-acetic acid 4-[3-(R,S)-Fluoro-3-(3-fluoro-6-methoxyquinolin-4-yl)propyl]-1-[3-(3,4,5-trifluorophenyl)propyl]piperidine-4-acetic acid 4-[3-(R,S)-Fluoro-3-(3-fluoro-6-methoxyquinolin-4-yl)propyl]-1-[2-(2,4,6-trifluorophenylthio)ethyl]piperidine-4-acetic acid 4-[3-(R,S)-Fluoro-3-(3-fluoro-6-methoxyquinolin-4-yl)propyl]-1-[2-(3,4,5-trifluorophenylthio)ethyl]piperidine-4-acetic acid 4-[3-(R,S)-Fluoro-3-(3-fluoro-6-methoxyquinolin-4-yl)propyl]-1-[2-(2,4,6-trifluorophenylamino)ethyl]piperidine-4-acetic acid 4-[3-(R,S)-Fluoro-3-(3-fluoro-6-methoxyquinolin-4-yl)propyl]-1-[2-(3,4,5-trifluorophenylamino)ethyl]piperidine-4-acetic acid 4-[3-(R,S)-Fluoro-3-(3-fluoro-6-methoxyquinolin-4-yl)propyl]-1-[2-(2,4,6-trifluorophenoxy)ethyl]piperidine-4-acetic acid 4-[3-(R,S)-Fluoro-3-(3-fluoro-6-methoxyquinolin-4-yl)propyl]-1-[2-(3,4,5-trifluorophenoxy)ethyl]piperidine-4-acetic acid 4-[3-(R,S)-Fluoro-3-(3-fluoro-6-methoxyquinolin-4-yl)propyl]-1-[3-(2,4,6-trifluorophenyl)prop-2-ynyl]piperidine-4-acetic acid 4-[3-(R,S)-Fluoro-3-(3-fluoro-6-methoxyquinolin-4-yl)propyl]-1-[3-(3,4,5-trifluorophenyl)prop-2-ynyl]piperidine-4-acetic acid 4-[3-(R,S)-Fluoro-3-(3-dimethylamino-6-methoxyquinolin-4-yl)propyl]-1-[3-(2,4,6-trifluorophenyl)propyl]piperidine-4-acetic acid 4-[3-(R,S)-Fluoro-3-(3-dimethylamino-6-methoxyquinolin-4-yl)propyl]-1-[3-(3,4,5-trifluorophenyl)propyl]piperidine-4-acetic acid 4-[3-(R,S)-Fluoro-3-(3-dimethylamino-6-methoxyquinolin-4-yl)propyl]-1-[2-(2,4,6-trifluorophenylthio)ethyl]piperidine-4-acetic acid 4-[3-(R,S)-Fluoro-3-(3-dimethylamino-6-methoxyquinolin-4-yl)propyl]-1-[2-(3,4,5-trifluorophenylthio)ethyl]piperidine-4-acetic acid 4-[3-(R,S)-Fluoro-3-(3-dimethylamino-6-methoxyquinolin-4-yl)propyl]-1-[2-(2,4,6-trifluorophenylamino)ethyl]piperidine-4-acetic acid 4-[3-(R,S)-Fluoro-3-(3-dimethylamino-6-methoxyquinolin-4-yl)propyl]-1-[2-(3,4,5-trifluorophenylamino)ethyl]piperidine-4-acetic acid 4-[3-(R,S)-Fluoro-3-(3-dimethylamino-6-methoxyquinolin-4-yl)propyl]-1-[2-(2,4,6-trifluorophenoxy)ethyl]piperidine-4-acetic acid 4-[3-(R,S)-Fluoro-3-(3-dimethylamino-6-methoxyquinolin-4-yl)propyl]-1-[2-(3,4,5-trifluorophenoxy)ethyl]piperidine-4-acetic acid 4-[3-(R,S)-Fluoro-3-(3-dimethylamino-6-methoxyquinolin-4-yl)propyl]-1-[3-(2,4,6-trifluorophenyl)prop-2-ynyl]piperidine-4-acetic acid 4-[3-(R,S)-Fluoro-3-(3-dimethylamino-6-methoxyquinolin-4-yl)propyl]-1-[3-(3,4,5-trifluorophenyl)prop-2-ynyl]piperidine-4-acetic acid 4-[3-(R,S)-Fluoro-3-(3-fluoro-6-methoxyquinolin-4-yl)propyl]-1-[3-(2,4,6-trifluorophenyl)propyl]piperidine-4-acetic acid 4-[3-(R,S)-Fluoro-3-(3-hydroxymethyl-6-methoxyquinolin-4-yl)propyl]-1-[3-(3,4,5-trifluorophenyl)propyl]piperidine-4-acetic acid 4-[3-(R,S)-Fluoro-3-(3-hydroxymethyl-6-methoxyquinolin-4-yl)propyl]-1-[2-(2,4,6-trifluorophenylthio)ethyl]piperidine-4-acetic acid 4-[3-(R,S)-Fluoro-3-(3-hydroxymethyl-6-methoxyquinolin-4-yl)propyl]-1-[2-(3,4,5-trifluorophenylthio)ethyl]piperidine-4-acetic acid 4-[3-(R,S)-Fluoro-3-(3-hydroxymethyl-6-methoxyquinolin-4-yl)propyl]-1-[2-(2,4,6-trifluorophenylamino)ethyl]piperidine-4-acetic acid 4-[3-(R,S)-Fluoro-3-(3-hydroxymethyl-6-methoxyquinolin-4-yl)propyl]-1-[2-(3,4,5-trifluorophenylamino)ethyl]piperidine-4-acetic acid 4-[3-(R,S)-Fluoro-3-(3-hydroxymethyl-6-methoxyquinolin-4-yl)propyl]-1-[2-(2,4,6-trifluorophenoxy)ethyl]piperidine-4-acetic acid 4-[3-(R,S)-Fluoro-3-(3-hydroxymethyl-6-methoxyquinolin-4-yl)propyl]-1-[2-(3,4,5-trifluorophenoxy)ethyl]piperidine-4-acetic acid 4-[3-(R,S)-Fluoro-3-(3-hydroxymethyl-6-methoxyquinolin-4-yl)propyl]-1-[3-(2,4,6-trifluorophenyl)prop-2-ynyl]piperidine-4-acetic acid 4-[3-(R,S)-Fluoro-3-(3-hydroxymethyl-6-methoxyquinolin-4-yl)propyl]-1-[3-(3,4,5-trifluorophenyl)prop-2-ynyl]piperidine-4-acetic acid 4-[3-(R,S)-Fluoro-3-(3-fluoromethyl-6-methoxyquinolin-4-yl)propyl]-1-[3-(2,4,6-trifluorophenyl)propyl]piperidine-4-acetic acid 4-[3-(R,S)-Fluoro-3-(3-fluoromethyl-6-methoxyquinolin-4-yl)propyl]-1-[3-(3,4,5-trifluorophenyl)propyl]piperidine-4-acetic acid 4-[3-(R,S)-Fluoro-3-(3-fluoromethyl-6-methoxyquinolin-4-yl)propyl]-1-[2-(2,4,6-trifluorophenylthio)ethyl]piperidine-4-acetic acid 4-[3-(R,S)-Fluoro-3-(3-fluoromethyl-6-methoxyquinolin-4-yl)propyl]-1-[2-(3,4,5-trifluorophenylthio)ethyl]piperidine-4-acetic acid 4-[3-(R,S)-Fluoro-3-(3-fluoromethyl-6-methoxyquinolin-4-yl)propyl]-1-[2-(2,4,6-trifluorophenylamino)ethyl]piperidine-4-acetic acid 4-[3-(R,S)-Fluoro-3-(3-fluoromethyl-6-methoxyquinolin-4-yl)propyl]-1-[2-(3,4,5-trifluorophenylamino)ethyl]piperidine-4-acetic acid 4-[3-(R,S)-Fluoro-3-(3-fluoromethyl-6-methoxyquinolin-4-yl)propyl]-1-[2-(2,4,6-trifluorophenoxy)ethyl]piperidine-4-acetic acid 4-[3-(R,S)-Fluoro-3-(3-fluoromethyl-6-methoxyquinolin-4-yl)propyl]-1-[2-(3,4,5-trifluorophenoxy)ethyl]piperidine-4-acetic acid 4-[3-(R,S)-Fluoro-3-(3-fluoromethyl-6-methoxyquinolin-4-yl)propyl]-1-[3-(2,4,6-trifluorophenyl)prop-2-ynyl]piperidine-4-acetic acid 4-[3-(R,S)-Fluoro-3-(3-fluoromethyl-6-methoxyquinolin-4-yl)propyl]-1-[3-(3,4,5-trifluorophenyl)prop-2-ynyl]piperidine-4-acetic acid 4-[3-(R,S)-Fluoro-3-(3-aminomethyl-6-methoxyquinolin-4-yl)propyl]-1-[3-(2,4,6-trifluorophenyl)propyl]piperidine-4-acetic acid 4-[3-(R,S)-Fluoro-3-(3-aminomethyl-6-methoxyquinolin-4-yl)propyl]-1-[3-(3,4,5-trifluorophenyl)propyl]piperidine-4-acetic acid 4-[3-(R,S)-Fluoro-3-(3-aminomethyl-6-methoxyquinolin-4-yl)propyl]-1-[2-(2,4,6-trifluorophenylthio)ethyl]piperidine-4-acetic acid 4-[3-(R,S)-Fluoro-3-(3-aminomethyl-6-methoxyquinolin-4-yl)propyl]-1-[2-(3,4,5-trifluorophenylthio)ethyl]piperidine-4-acetic acid 4-[3-(R,S)-Fluoro-3-(3-aminomethyl-6-methoxyquinolin-4-yl)propyl]-1-[2-(2,4,6-trifluorophenylamino)ethyl]piperidine-4-acetic acid 4-[3-(R,S)-Fluoro-3-(3-aminomethyl-6-methoxyquinolin-4-yl)propyl]-1-[2-(3,4,5-trifluorophenylamino)ethyl]piperidine-4-acetic acid 4-[3-(R,S)-Fluoro-3-(3-aminomethyl-6-methoxyquinolin-4-yl)propyl]-1-[2-(2,4,6-trifluorophenoxy)ethyl]piperidine-4-acetic acid 4-[3-(R,S)-Fluoro-3-(3-aminomethyl-6-methoxyquinolin-4-yl)propyl]-1-[2-(3,4,5-trifluorophenoxy)ethyl]piperidine-4-acetic acid 4-[3-(R,S)-Fluoro-3-(3-aminomethyl-6-methoxyquinolin-4-yl)propyl]-1-[3-(2,4,6-trifluorophenyl)prop-2-ynyl]piperidine-4-acetic acid 4-[3-(R,S)-Fluoro-3-(3-aminomethyl-6-methoxyquinolin-4-yl)propyl]-1-[3-(3,4,5-trifluorophenyl)prop-2-ynyl]piperidine-4-acetic acid 4-[3-(R,S)-Fluoro-3-(3-morpholinomethyl-6-methoxyquinolin-4-yl)propyl]-1-[3-(2,4,6-trifluorophenyl)propyl]piperidine-4-acetic acid 4-[3-(R,S)-Fluoro-3-(3-morpholinomethyl-6-methoxyquinolin-4-yl)propyl]-1-[3-(3,4,5-trifluorophenyl)propyl]piperidine-4-acetic acid 4-[3-(R,S)-Fluoro-3-(3-morpholinomethyl-6-methoxyquinolin-4-yl)propyl]-1-[2-(2,4,6-trifluorophenylthio)ethyl]piperidine-4-acetic acid 4-[3-(R,S)-Fluoro-3-(3-morpholinomethyl-6-methoxyquinolin-4-yl)propyl]-1-[2-(3,4,5-trifluorophenylthio)ethyl]piperidine-4-acetic acid 4-[3-(R,S)-Fluoro-3-(3-morpholinomethyl-6-methoxyquinolin-4-yl)propyl]-1-[2-(2,4,6-trifluorophenylamino)ethyl]piperidine-4-acetic acid 4-[3-(R,S)-Fluoro-3-(3-morpholinomethyl-6-methoxyquinolin-4-yl)propyl]-1-[2-(3,4,5-trifluorophenylamino)ethyl]piperidine-4-acetic acid 4-[3-(R,S)-Fluoro-3-(3-morpholinomethyl-6-methoxyquinolin-4-yl)propyl]-1-[2-(2,4,6-trifluorophenoxy)ethyl]piperidine-4-acetic acid 4-[3-(R,S)-Fluoro-3-(3-morpholinomethyl-6-methoxyquinolin-4-yl)propyl]-1-[2-(3,4,5-trifluorophenoxy)ethyl]piperidine-4-acetic acid 4-[3-(R,S)-Fluoro-3-(3-morpholinomethyl-6-methoxyquinolin-4-yl)propyl]-1-[3-(2,4,6-trifluorophenyl)prop-2-ynyl]piperidine-4-acetic acid 4-[3-(R,S)-Fluoro-3-(3-morpholinomethyl-6-methoxyquinolin-4-yl)propyl]-1-[3-(3,4,5-trifluorophenyl)prop-2-ynyl]piperidine-4-acetic acid 4-[3-(3-Chloro-6-methoxyquinolin-4-yl)propyl]-1-heptylpiperid-4-ylmethanol 4-[3-(3-Chloro-6-methoxyquinolin-4-yl)propyl]-1-[4-phenylbutyl]piperid-4-ylmethanol 4-[3-(3-Chloro-6-methoxyquinolin-4-yl)propyl]-1-[4-(2-fluorophenyl)propyl]piperid-4-ylmethanol 4-[3-(3-Chloro-6-methoxyquinolin-4-yl)propyl]-1-[4-(3-fluorophenyl)propyl]piperid-4-ylmethanol 4-[3-(3-Chloro-6-methoxyquinolin-4-yl)propyl]-1-[3-(4-fluorophenyl)propyl]piperid-4-ylmethanol 4-[3-(3-Chloro-6-methoxyquinolin-4-yl)propyl]-1-[4-(4-fluorophenyl)butyl]piperid-4-ylmethanol 4-[3-(3-Chloro-6-methoxyquinolin-4-yl)propyl]-1-[3-(2,3-difluorophenyl)propyl]piperid-4-ylmethanol 4-[3-(3-Chloro-6-methoxyquinolin-4-yl)propyl]-1-[4-(2,3-difluorophenyl)propyl]piperid-4-ylmethanol 4-[3-(3-Chloro-6-methoxyquinolin-4-yl)propyl]-1-[3-(2,6-difluorophenyl)propyl]piperid-4-ylmethanol 4-[3-(3-Chloro-6-methoxyquinolin-4-yl)propyl]-1-[4-(2,6-difluorophenyl)propyl]piperid-4-ylmethanol 4-[3-(3-Chloro-6-methoxyquinolin-4-yl)propyl]-1-[3-(3,5-difluorophenyl)propyl]piperid-4-ylmethanol 4-[3-(3-Chloro-6-methoxyquinolin-4-yl)propyl]-1-[3-(2,3,5-trifluorophenyl)-propyl]piperid-4-ylmethanol 4-[3-(3-Chloro-6-methoxyquinolin-4-yl)propyl]-1-[3-(2,4,6-trifluorophenyl)-propyl]piperid-4-ylmethanol 4-[3-(3-Chloro-6-methoxyquinolin-4-yl)propyl]-1-[3-(3,4,5-trifluorophenyl)-propyl]piperid-4-ylmethanol 4-[3-(3-Chloro-6-methoxyquinolin-4-yl)propyl]-1-[3-phenylthiopropyl]piperid-4-ylmethanol 4-[3-(3-Chloro-6-methoxyquinolin-4-yl)propyl]-1-[3-(2-fluorophenylthio)propyl]piperid-4-ylmethanol 4-[3-(3-Chloro-6-methoxyquinolin-4-yl)propyl]-1-[3-(3-fluorophenylthio)propyl]piperid-4-ylmethanol 4-[3-(3-Chloro-6-methoxyquinolin-4-yl)propyl]-1-[2-(4-fluorophenylthio)ethyl]piperid-4-ylmethanol 4-[3-(3-Chloro-6-methoxyquinolin-4-yl)propyl]-1-[3-(4-fluorophenylthio)propyl]piperid-4-ylmethanol 4-[3-(3-Chloro-6-methoxyquinolin-4-yl)propyl]-1-[2-(2,3-difluorophenyl-thio)ethyl]piperid-4-ylmethanol 4-[3-(3-Chloro-6-methoxyquinolin-4-yl)propyl]-1-[3-(2,3-difluorophenyl-thio)propyl]piperid-4-ylmethanol 4-[3-(3-Chloro-6-methoxyquinolin-4-yl)propyl]-1-[2-(2,6-difluorophenyl-thio)ethyl]piperid-4-ylmethanol 4-[3-(3-Chloro-6-methoxyquinolin-4-yl)propyl]-1-[2-(2,3,5-trifluorophenyl-thio)ethyl]piperid-4-ylmethanol 4-[3-(3-Chloro-6-methoxyquinolin-4-yl)propyl]-1-[2-(2,4,6-trifluorophenyl-thio)ethyl]piperid-4-ylmethanol 4-[3-(3-Chloro-6-methoxyquinolin-4-yl)propyl]-1-[2-(3,4,5-trifluorophenyl-thio)ethyl]piperid-4-ylmethanol 4-[3-(3-Chloro-6-methoxyquinolin-4-yl)propyl]-1-[2-(2,3,5-trifluorophenoxy)-ethyl]piperid-4-ylmethanol
4-[3-(3-Chloro-6-methoxyquinolin-4-yl)propyl]-1-[2-(2,4,6-trifluorophenoxy)-ethyl]piperid-4-ylmethanol
4-[3-(3-Chloro-6-methoxyquinolin-4-yl)propyl]-1-[2-(3,4,5-trifluorophenoxy)-ethyl]piperid-4-ylmethanol
4-[3-(3-Chloro-6-methoxyquinolin-4-yl)propyl]-1-[2-(3,5-difluorophenylamino)-ethyl]piperid-4-ylmethanol
4-[3-(3-Chloro-6-methoxyquinolin-4-yl)propyl]-1-[2-(2,3,5-trifluorophenylamino)-ethyl]piperid-4-ylmethanol
4-[3-(3-Chloro-6-methoxyquinolin-4-yl)propyl]-1-[2-(2,4,6-trifluorophenylamino)-ethyl]piperid-4-ylmethanol
4-[3-(3-Chloro-6-methoxyquinolin-4-yl)propyl]-1-[2-(3,4,5-trifluorophenylamino)-ethyl]piperid-4-ylmethanol
4-[3-(3-Chloro-6-methoxyquinolin-4-yl)propyl]-1-[3-(2,6-difluorophenylthio)-propyl]piperid-4-ylmethanol
4-[3-(3-Chloro-6-methoxyquinolin-4-yl)propyl]-1-[2-(2-chlorophenylthio)ethyl]piperid-4-ylmethanol
4-[3-(3-Chloro-6-methoxyquinolin-4-yl)propyl]-1-[3-(2-chlorophenylthio)propyl]piperid-4-ylmethanol
4-[3-(3-Chloro-6-methoxyquinolin-4-yl)propyl]-1-[2-(3-chlorophenylthio)ethyl]piperid-4-ylmethanol
4-[3-(3-Chloro-6-methoxyquinolin-4-yl)propyl]-1-[3-(3-chlorophenylthio)propyl]piperid-4-ylmethanol
4-[3-(3-Chloro-6-methoxyquinolin-4-yl)propyl]-1-[2-(4-chlorophenylthio)ethyl]piperid-4-ylmethanol
4-[3-(3-Chloro-6-methoxyquinolin-4-yl)propyl]-1-[3-(4-chlorophenylthio)propyl]piperid-4-ylmethanol
4-[3-(3-Chloro-6-methoxyquinolin-4-yl)propyl]-1-[2-(2-methylphenylthio)ethyl]piperid-4-ylmethanol
4-[3-(3-Chloro-6-methoxyquinolin-4-yl)propyl]-1-[3-(2-methylphenylthio)propyl]piperid-4-ylmethanol
4-[3-(3-Chloro-6-methoxyquinolin-4-yl)propyl]-1-[2-(3-methylphenylthio)ethyl]piperid-4-ylmethanol
4-[3-(3-Chloro-6-methoxyquinolin-4-yl)propyl]-1-[3-(3-methylphenylthio)propyl]piperid-4-ylmethanol
4-[3-(3-Chloro-6-methoxyquinolin-4-yl)propyl]-1-[2-(4-methylphenylthio)ethyl]piperid-4-ylmethanol
4-[3-(3-Chloro-6-methoxyquinolin-4-yl)propyl]-1-[3-(4-methylphenylthio)propyl]piperid-4-ylmethanol
4-[3-(3-Chloro-6-methoxyquinolin-4-yl)propyl]-1-[2-(2-trifluoromethylphenylthio)-ethyl]piperid-4-ylmethanol
4-[3-(3-Chloro-6-methoxyquinolin-4-yl)propyl]-1-[3-(2-trifluoromethylphenylthio)-propyl]piperid-4-ylmethanol
4-[3-(3-Chloro-6-methoxyquinolin-4-yl)propyl]-1-[2-(3-trifluoromethylphenylthio)-ethyl]piperid-4-ylmethanol
4-[3-(3-Chloro-6-methoxyquinolin-4-yl)propyl]-1-[3-(3-trifluoromethylphenylthio)-propyl]piperid-4-ylmethanol
4-[3-(3-Chloro-6-methoxyquinolin-4-yl)propyl]-1-[2-(4-trifluoromethylphenylthio)-ethyl]piperid-4-ylmethanol
4-[3-(3-Chloro-6-methoxyquinolin-4-yl)propyl]-1-[3-(4-trifluoromethylphenylthio)-propyl]piperid-4-ylmethanol
4-[3-(3-Chloro-6-methoxyquinolin-4-yl)propyl]-1-[2-(2-methoxyphenylthio)ethyl]piperid-4-ylmethanol
4-[3-(3-Chloro-6-methoxyquinolin-4-yl)propyl]-1-[3-(2-methoxyphenylthio)-propyl]piperid-4-ylmethanol
4-[3-(3-Chloro-6-methoxyquinolin-4-yl)propyl]-1-[2-(3-methoxyphenylthio)ethyl]piperid-4-ylmethanol
4-[3-(3-Chloro-6-methoxyquinolin-4-yl)propyl]-1-[3-(3-methoxyphenylthio)-propyl]piperid-4-ylmethanol
4-[3-(3-Chloro-6-methoxyquinolin-4-yl)propyl]-1-[2-(4-methoxyphenylthio)ethyl]piperid-4-ylmethanol
4-[3-(3-Chloro-6-methoxyquinolin-4-yl)propyl]-1-[3-(4-methoxyphenylthio)-propyl]piperid-4-ylmethanol
4-[3-(3-Chloro-6-methoxyquinolin-4-yl)propyl]-1-[cyclopentylmethyl]piperid-4-ylmethanol
4-[3-(3-Chloro-6-methoxyquinolin-4-yl)propyl]-1-[2-(cyclopentyl)ethyl]piperid-4-ylmethanol
4-[3-(3-Chloro-6-methoxyquinolin-4-yl)propyl]-1-[2-(cyclopentylthio)ethyl]piperid-4-ylmethanol
4-[3-(3-Chloro-6-methoxyquinolin-4-yl)propyl]-1-[3-(cyclopentylthio)propyl]piperid-4-ylmethanol
4-[3-(3-Chloro-6-methoxyquinolin-4-yl)propyl]-1-[3-(cyclohexylthio)propyl]piperid-4-ylmethanol
4-[3-(3-Chloro-6-methoxyquinolin-4-yl)propyl]-1-[4-(thien-2-yl)butyl]piperid-4-ylmethanol
4-[3-(3-Chloro-6-methoxyquinolin-4-yl)propyl]-1-[3-(thien-2-yl)thiopropyl]piperid-4-ylmethanol
4-[3-(3-Chloro-6-methoxyquinolin-4-yl)propyl]-1-[3-(thien-3-yl)propyl]piperid-4-ylmethanol
4-[3-(3-Chloro-6-methoxyquinolin-4-yl)propyl]-1-[4-(thien-3-yl)butyl]piperid-4-ylmethanol
4-[3-(3-Chloro-6-methoxyquinolin-4-yl)propyl]-1-[2-(thien-3-yl)thioethyl]piperid-4-ylmethanol
4-[3-(3-Chloro-6-methoxyquinolin-4-yl)propyl]-1-[3-(thien-3-yl)thiopropyl]piperid-4-ylmethanol
4-[3-(3-Chloro-6-methoxyquinolin-4-yl)propyl]-1-[3-(1,3-thiazol-2-yl)propyl]piperid-4-ylmethanol
4-[3-(3-Chloro-6-methoxyquinolin-4-yl)propyl]-1-[4-(1,3-thiazol-2-yl)butyl]piperid-4-ylmethanol
4-[3-(3-Chloro-6-methoxyquinolin-4-yl)propyl]-1-[3-(1,3-thiazol-2-yl)thioethyl]piperid-4-ylmethanol
4-[3-(3-Chloro-6-methoxyquinolin-4-yl)propyl]-1-[3-(pyrid-2-yl)propyl]piperid-4-ylmethanol
4-[3-(3-Chloro-6-methoxyquinolin-4-yl)propyl]-1-[4-(pyrid-2-yl)butyl]piperid-4-ylmethanol
4-[3-(3-Chloro-6-methoxyquinolin-4-yl)propyl]-1-[3-(pyrid-2-yl)thiopropyl]piperid-4-ylmethanol
4-[3-(3-Chloro-6-methoxyquinolin-4-yl)propyl]-1-[3-(pyrid-3-yl)propyl]piperid-4-ylmethanol
4-[3-(3-Chloro-6-methoxyquinolin-4-yl)propyl]-1-[4-(pyrid-3-yl)butyl]piperid-4-ylmethanol
4-[3-(3-Chloro-6-methoxyquinolin-4-yl)propyl]-1-[2-(pyrid-3-yl)thioethyl]piperid-4-ylmethanol
4-[3-(3-Chloro-6-methoxyquinolin-4-yl)propyl]-1-[3-(pyrid-3-yl)thiopropyl]piperid-4-ylmethanol
4-[3-(3-Chloro-6-methoxyquinolin-4-yl)propyl]-1-[3-(pyrid-4-yl)propyl]piperid-4-ylmethanol
4-[3-(3-Chloro-6-methoxyquinolin-4-yl)propyl]-1-[4-(pyrid-4-yl)butyl]piperid-4-ylmethanol
4-[3-(3-Chloro-6-methoxyquinolin-4-yl)propyl]-1-[2-(pyrid-4-yl)thioethyl]piperid-4-ylmethanol
4-[3-(3-Chloro-6-methoxyquinolin-4-yl)propyl]-1-[3-(pyrid-4-yl)thiopropyl]piperid-4-ylmethanol
4-[3-(3-Chloro-6-methoxyquinolin-4-yl)propyl]-1-[3-(pyrazin-2-yl)propyl]piperid-4-ylmethanol
4-[3-(3-Chloro-6-methoxyquinolin-4-yl)propyl]-1-[4-(pyrazin-2-yl)butyl]piperid-4-ylmethanol
4-[3-(3-Chloro-6-methoxyquinolin-4-yl)propyl]-1-[2-(pyrazin-2-yl)thioethyl]piperid-4-ylmethanol
4-[3-(3-Chloro-6-methoxyquinolin-4-yl)propyl]-1-[3-(pyrazin-2-yl)thiopropyl]piperid-4-ylmethanol 4-[3-(3-Chloro-6-methoxyquinolin-4-yl)propyl]-1-[3-(4-fluorophenyl)prop-2-ynyl]piperid-4-ylmethanol
4-[3-(3-Chloro-6-methoxyquinolin-4-yl)propyl]-1-[3-(3,4-difluorophenyl)prop-2-ynyl]piperid-4-ylmethanol
4-[3-(3-Chloro-6-methoxyquinolin-4-yl)propyl]-1-[3-(2,4-difluorophenyl)prop-2-ynyl]piperid-4-ylmethanol
4-[3-(3-Chloro-6-methoxyquinolin-4-yl)propyl]-1-[3-(2,3,5-trifluorophenyl)prop-2-ynyl]piperid-4-ylmethanol
4-[3-(3-Chloro-6-methoxyquinolin-4-yl)propyl]-1-[3-(2,4,6-trifluorophenyl)prop-2-ynyl]piperid-4-ylmethanol
4-[3-(3-Chloro-6-methoxyquinolin-4-yl)propyl]-1-[3-(3,4,5-trifluorophenyl)prop-2-ynyl]piperid-4-ylmethanol
4-[3-(3-Chloro-6-methoxyquinolin-4-yl)propyl]-1-[3-(4-chloro-3-fluorophenyl)prop-2-ynyl]piperid-4-ylmethanol
4-[3-(3-Chloro-6-methoxyquinolin-4-yl)propyl]-1-[3-(3-chloro-4-fluorophenyl)prop-2-ynyl]piperid-4-ylmethanol
4-[3-(3-Chloro-6-methoxyquinolin-4-yl)propyl]-1-[3-(2-chloro-4-fluorophenyl)prop-2-ynyl]piperid-4-ylmethanol
4-[3-(3-Chloro-6-methoxyquinolin-4-yl)propyl]-1-[3-(3-chloro-5-fluorophenyl)prop-2-ynyl]piperid-4-ylmethanol
4-[3-(3-Chloro-6-methoxyquinolin-4-yl)propyl]-1-[3-(4-chloro-2-fluorophenyl)prop-2-ynyl]piperid-4-ylmethanol
4-[3-(3-Chloro-6-methoxyquinolin-4-yl)propyl]-1-[3-(3-fluoro-4-methylphenyl)prop-2-ynyl]piperid-4-ylmethanol
4-[3-(3-Chloro-6-methoxyquinolin-4-yl)propyl]-1-[3-(3,5-bis(trifluoromethyl)phenyl)prop-2-ynyl]piperid-4-ylmethanol
4-[3-(3-Chloro-6-methoxyquinolin-4-yl)propyl]-1-[3-(thien-2-yl)prop-2-ynyl]piperid-4-ylmethanol
4-[3-(3-Chloro-6-methoxyquinolin-4-yl)propyl]-1-[3-(thien-3-yl)prop-2-ynyl]piperid-4-ylmethanol
4-[3-(3-Chloro-6-methoxyquinolin-4-yl)propyl]-1-[3-(1,3-thiazol-2-yl)prop-2-ynyl]piperid-4-ylmethanol
4-[3-(3-Chloro-6-methoxyquinolin-4-yl)propyl]-1-[3-(1,3-thiazol-4-yl)prop-2-ynyl]piperid-4-ylmethanol
4-[3-(3-Chloro-6-methoxyquinolin-4-yl)propyl]-1-[3-(1,3-thiazol-5-yl)prop-2-ynyl]piperid-4-ylmethanol
4-[3-(3-Chloro-6-methoxyquinolin-4-yl)propyl]-1-[3-(pyrid-2-yl)prop-2-ynyl]piperid-4-ylmethanol
4-[3-(3-Chloro-6-methoxyquinolin-4-yl)propyl]-1-[3-(pyrid-3-yl)prop-2-ynyl]piperid-4-ylmethanol
4-[3-(3-Chloro-6-methoxyquinolin-4-yl)propyl]-1-[3-(pyrid-4-yl)prop-2-ynyl]piperid-4-ylmethanol
4-[3-(3-Methyl-6-methoxyquinolin-4-yl)propyl]-1-[2-(cyclohexyl)ethyl]piperid-4-ylmethanol
4-[3-(3-Methyl-6-methoxyquinolin-4-yl)propyl]-1-[3-(phenyl)propyl]piperid-4-ylmethanol
4-[3-(3-Methyl-6-methoxyquinolin-4-yl)propyl]-1-[3-(2,3,5-trifluorophenyl)propyl]piperid-4-ylmethanol
4-[3-(3-Methyl-6-methoxyquinolin-4-yl)propyl]-1-[2-(3,5-difluorophenylamino)ethyl]piperid-4-ylmethanol
4-[3-(3-Methyl-6-methoxyquinolin-4-yl)propyl]-1-[2-(2,3,5-trifluorophenylamino)ethyl]piperid-4-ylmethanol
4-[3-(3-Methyl-6-methoxyquinolin-4-yl)propyl]-1-[2-(3,5-difluorophenoxy)ethyl]piperid-4-ylmethanol
4-[3-(3-Methyl-6-methoxyquinolin-4-yl)propyl]-1-[2-(2,3,5-trifluorophenoxy)-ethyl]piperid-4-ylmethanol
4-[3-(3-Methyl-6-methoxyquinolin-4-yl)propyl]-1-[2-(cyclopentylthio)ethyl]piperid-4-ylmethanol
4-[3-(3-Methyl-6-methoxyquinolin-4-yl)propyl]-1-[2-(pyrid-2-yl)thioethyl]piperid-4-ylmethanol
4-[3-(3-Methyl-6-methoxyquinolin-4-yl)propyl]-1-[2-(thien-2-yl)thioethyl]piperid-4-ylmethanol
4-[3-(3-Methyl-6-methoxyquinolin-4-yl)propyl]-1-[3-(2,3,5-trifluorophenyl)prop-2-ynyl]piperid-4-ylmethanol
4-[3-(3-Methyl-6-methoxyquinolin-4-yl)propyl]-1-[3-(thien-2-yl)prop-2-ynyl]piperid-4-ylmethanol
4-[3-(3-Fluoro-6-methoxyquinolin-4-yl)propyl]-1-[2-(cyclohexyl)ethyl]piperid-4-ylmethanol
4-[3-(3-Fluoro-6-methoxyquinolin-4-yl)propyl]-1-[3-(phenyl)propyl]piperid-4-ylmethanol
4-[3-(3-Fluoro-6-methoxyquinolin-4-yl)propyl]-1-[3-(2,3,5-trifluorophenyl)-propyl]piperid-4-ylmethanol
4-[3-(3-Fluoro-6-methoxyquinolin-4-yl)propyl]-1-[2-(3,5-difluorophenyl-amino)ethyl]piperid-4-ylmethanol
4-[3-(3-Fluoro-6-methoxyquinolin-4-yl)propyl]-1-[2-(2,3,5-trifluorophenyl-amino)ethyl]piperid-4-ylmethanol
4-[3-(3-Fluoro-6-methoxyquinolin-4-yl)propyl]-1-[2-(3,5-difluorophenoxy)ethyl]piperid-4-ylmethanol
4-[3-(3-Fluoro-6-methoxyquinolin-4-yl)propyl]-1-[2-(2,3,5-trifluorophenoxy)-ethyl]piperid-4-ylmethanol
4-[3-(3-Fluoro-6-methoxyquinolin-4-yl)propyl]-1-[2-(2,3,5-trifluorophenylthio)-ethyl]piperid-4-ylmethanol
4-[3-(3-Fluoro-6-methoxyquinolin-4-yl)propyl]-1-[2-(cyclopentylthio)ethyl]piperid-4-ylmethanol
4-[3-(3-Fluoro-6-methoxyquinolin-4-yl)propyl]-1-[2-(pyrid-2-yl)thioethyl]piperid-4-ylmethanol
4-[3-(3-Fluoro-6-methoxyquinolin-4-yl)propyl]-1-[2-(thien-2-yl)thioethyl]piperid-4-ylmethanol
4-[3-(3-Fluoro-6-methoxyquinolin-4-yl)propyl]-1-[3-(2,3,5-trifluorophenyl)prop-2-ynyl]piperid-4-ylmethanol
4-[3-(3-Fluoro-6-methoxyquinolin-4-yl)propyl]-1-[3-(thien-2-yl)prop-2-ynyl]piperid-4-ylmethanol
4-[3-(3-Dimethylamino-6-methoxyquinolin-4-yl)propyl]-1-[2-(cyclohexyl)ethyl]piperid-4-ylmethanol
4-[3-(3-Dimethylamino-6-methoxyquinolin-4-yl)propyl]-1-[3-(phenyl)propyl]piperid-4-ylmethanol
4-[3-(3-Dimethylamino-6-methoxyquinolin-4-yl)propyl]-1-[3-(2,3,5-trifluorophenyl)propyl]piperid-4-ylmethanol
4-[3-(3-Dimethylamino-6-methoxyquinolin-4-yl)propyl]-1-[2-(3,5-difluoro-phenylamino)ethyl]piperid-4-ylmethanol
4-[3-(3-Dimethylamino-6-methoxyquinolin-4-yl)propyl]-1-[2-(2,3,5-trifluoro-phenylamino)ethyl]piperid-4-ylmethanol
4-[3-(3-Dimethylamino-6-methoxyquinolin-4-yl)propyl]-1-[2-(3,5-difluorophenoxy)-ethyl]piperid-4-ylmethanol
4-[3-(3-Dimethylamino-6-methoxyquinolin-4-yl)propyl]-1-[2-(2,3,5-trifluorophenoxy)-ethyl]piperid-4-ylmethanol
4-[3-(3-Dimethylamino-6-methoxyquinolin-4-yl)propyl]-1-[2-(2,3,5-trifluorophenylthio)-ethyl]piperid-4-ylmethanol
4-[3-(3-Dimethylamino-6-methoxyquinolin-4-yl)propyl]-1-[2-(cyclopentylthio)-ethyl]piperid-4-ylmethanol
4-[3-(3-Dimethylamino-6-methoxyquinolin-4-yl)propyl]-1-[2-(pyrid-2-yl)thioethyl]-piperid-4-ylmethanol 4-[3-(3-Dimethylamino-6-methoxyquinolin-4-yl)propyl]-1-[2-(thien-2-yl)thioethyl]-piperid-4-ylmethanol 4-[3-(3-Dimethylamino-6-methoxyquinolin-4-yl)propyl]-1-[3-(2,3,5-trifluorophenyl)prop-2-ynyl]piperid-4-ylmethanol 4-[3-(3-Dimethylamino-6-methoxyquinolin-4-yl)propyl]-1-[3-(thien-2-yl)prop-2-ynyl]piperid-4-ylmethanol 4-[3-(3-Hydroxymethyl-6-methoxyquinolin-4-yl)propyl]-1-[2-(cyclohexyl)ethyl]piperid-4-ylmethanol 4-[3-(3-Hydroxymethyl-6-methoxyquinolin-4-yl)propyl]-1-[3-(phenyl)propyl]piperid-4-ylmethanol 4-[3-(3-Hydroxymethyl-6-methoxyquinolin-4-yl)propyl]-1-[3-(2,3,5-trifluorophenyl)-propyl]piperid-4-ylmethanol 4-[3-(3-Hydroxymethyl-6-methoxyquinolin-4-yl)propyl]-1-[2-(3,5-difluorophenylamino)-ethyl]piperid-4-ylmethanol 4-[3-(3-Hydroxymethyl-6-methoxyquinolin-4-yl)propyl]-1-[2-(2,3,5-trifluorophenylamino)-ethyl]piperid-4-ylmethanol 4-[3-(3-Hydroxymethyl-6-methoxyquinolin-4-yl)propyl]-1-[2-(3,5-difluorophenoxy)-ethyl]piperid-4-ylmethanol 4-[3-(3-Hydroxymethyl-6-methoxyquinolin-4-yl)propyl]-1-[2-(2,3,5-trifluorophenoxy)-ethyl]piperid-4-ylmethanol 4-[3-(3-Hydroxymethyl-6-methoxyquinolin-4-yl)propyl]-1-[2-(2,3,5-trifluorophenylthio)-ethyl]piperid-4-ylmethanol 4-[3-(3-Hydroxymethyl-6-methoxyquinolin-4-yl)propyl]-1-[2-(cyclopentylthio)-ethyl]piperid-4-ylmethanol 4-[3-(3-Hydroxymethyl-6-methoxyquinolin-4-yl)propyl]-1-[2-(pyrid-2-yl)thio-ethyl]piperid-4-ylmethanol 4-[3-(3-Hydroxymethyl-6-methoxyquinolin-4-yl)propyl]-1-[2-(thien-2-yl)thio-ethyl]piperid-4-ylmethanol 4-[3-(3-Hydroxymethyl-6-methoxyquinolin-4-yl)propyl]-1-[3-(2,3,5-trifluorophenyl)prop-2-ynyl]piperid-4-ylmethanol 4-[3-(3-Hydroxymethyl-6-methoxyquinolin-4-yl)propyl]-1-[3-(thien-2-yl)prop-2-ynyl]-piperid-4-ylmethanol 4-[3-(3-Fluoromethyl-6-methoxyquinolin-4-yl)propyl]-1-[2-(cyclohexyl)ethyl]piperid-4-ylmethanol 4-[3-(3-Fluoromethyl-6-methoxyquinolin-4-yl)propyl]-1-[3-(phenyl)propyl]piperid-4-ylmethanol 4-[3-(3-Fluoromethyl-6-methoxyquinolin-4-yl)propyl]-1-[3-(2,3,5-trifluorophenyl)propyl]piperid-4-ylmethanol 4-[3-(3-Fluoromethyl-6-methoxyquinolin-4-yl)propyl]-1-[2-(3,5-difluorophenyl-amino)ethyl]piperid-4-ylmethanol 4-[3-(3-Fluoromethyl-6-methoxyquinolin-4-yl)propyl]-1-[2-(2,3,5-trifluorophenyl-amino)ethyl]piperid-4-ylmethanol 4-[3-(3-Fluoromethyl-6-methoxyquinolin-4-yl)propyl]-1-[2-(3,5-difluorophenoxy)-ethyl]piperid-4-ylmethanol 4-[3-(3-Fluoromethyl-6-methoxyquinolin-4-yl)propyl]-1-[2-(2,3,5-trifluorophenoxy)-ethyl]piperid-4-ylmethanol 4-[3-(3-Fluoromethyl-6-methoxyquinolin-4-yl)propyl]-1-[2-(2,3,5-trifluorophenylthio)-ethyl]piperid-4-ylmethanol 4-[3-(3-Fluoromethyl-6-methoxyquinolin-4-yl)propyl]-1-[2-(cyclopentylthio)ethyl]-piperid-4-ylmethanol 4-[3-(3-Fluoromethyl-6-methoxyquinolin-4-yl)propyl]-1-[2-(pyrid-2-yl)thioethyl]piperid-4-ylmethanol 4-[3-(3-Fluoromethyl-6-methoxyquinolin-4-yl)propyl]-1-[2-(thien-2-yl)thioethyl]-piperid-4-ylmethanol 4-[3-(3-Fluoromethyl-6-methoxyquinolin-4-yl)propyl]-1-[3-(2,3,5-trifluorophenyl)prop-2-ynyl]piperid-4-ylmethanol 4-[3-(3-Fluoromethyl-6-methoxyquinolin-4-yl)propyl]-1-[3-(thien-2-yl)prop-2-ynyl]piperid-4-ylmethanol 4-[3-(3-Aminomethyl-6-methoxyquinolin-4-yl)propyl]-1-[2-(cyclohexyl)ethyl]piperid-4-ylmethanol 4-[3-(3-Aminomethyl-6-methoxyquinolin-4-yl)propyl]-1-[3-(phenyl)propyl]piperid-4-ylmethanol 4-[3-(3-Aminomethyl-6-methoxyquinolin-4-yl)propyl]-1-[3-(2,3,5-trifluorophenyl)-propyl]piperid-4-ylmethanol 4-[3-(3-Aminomethyl-6-methoxyquinolin-4-yl)propyl]-1-[2-(3,5-difluorophenylamino)-ethyl]piperid-4-ylmethanol 4-[3-(3-Aminomethyl-6-methoxyquinolin-4-yl)propyl]-1-[2-(2,3,5-trifluorophenylamino)-ethyl]piperid-4-ylmethanol 4-[3-(3-Aminomethyl-6-methoxyquinolin-4-yl)propyl]-1-[2-(3,5-difluorophenoxy)-ethyl]piperid-4-ylmethanol 4-[3-(3-Aminomethyl-6-methoxyquinolin-4-yl)propyl]-1-[2-(2,3,5-trifluorophenoxy)-ethyl]piperid-4-ylmethanol 4-[3-(3-Aminomethyl-6-methoxyquinolin-4-yl)propyl]-1-[2-(2,3,5-trifluorophenylthio)-ethyl]piperid-4-ylmethanol 4-[3-(3-Aminomethyl-6-methoxyquinolin-4-yl)propyl]-1-[2-(cyclopentylthio)-ethyl]piperid-4-ylmethanol 4-[3-(3-Aminomethyl-6-methoxyquinolin-4-yl)propyl]-1-[2-(pyrid-2-yl)thioethyl]piperid-4-ylmethanol 4-[3-(3-Aminomethyl-6-methoxyquinolin-4-yl)propyl]-1-[2-(thien-2-yl)thioethyl]piperid-4-ylmethanol 4-[3-(3-Aminomethyl-6-methoxyquinolin-4-yl)propyl]-1-[3-(2,3,5-trifluorophenyl)prop-2-ynyl]piperid-4-ylmethanol 4-[3-(3-Aminomethyl-6-methoxyquinolin-4-yl)propyl]-1-[3-(thien-2-yl)prop-2-ynyl]piperid-4-ylmethanol 4-[3-(3-Morpholinomethyl-6-methoxyquinolin-4-yl)propyl]-1-[2-(cyclohexyl)-ethyl]piperid-4-ylmethanol 4-[3-(3-Morpholinomethyl-6-methoxyquinolin-4-yl)propyl]-1-[3-(phenyl)propyl]piperid-4-ylmethanol 4-[3-(3-Morpholinomethyl-6-methoxyquinolin-4-yl)propyl]-1-[3-(2,3,5-trifluorophenyl)-propyl]piperid-4-ylmethanol 4-[3-(3-Morpholinomethyl-6-methoxyquinolin-4-yl)propyl]-1-[2-(3,5-difluorophenylamino)ethyl]piperid-4-ylmethanol 4-[3-(3-Morpholinomethyl-6-methoxyquinolin-4-yl)propyl]-1-[2-(2,3,5-trifluorophenyl-amino)ethyl]piperid-4-ylmethanol 4-[3-(3-Morpholinomethyl-6-methoxyquinolin-4-yl)propyl]-1-[2-(3,5-difluorophenoxy)-ethyl]piperid-4-ylmethanol 4-[3-(3-Morpholinomethyl-6-methoxyquinolin-4-yl)propyl]-1-[2-(2,3,5-trifluorophenoxy)-ethyl]piperid-4-ylmethanol 4-[3-(3-Morpholinomethyl-6-methoxyquinolin-4-yl)
propyl]-1-[2-(2,3,5-trifluorophenyl-thio)ethyl]piperid-4-ylmethanol 4-[3-(3-Morpholinomethyl-6-methoxyquinolin-4-yl)
propyl]-1-[2-(cyclopentylthio)-ethyl]piperid-4-ylmethanol 4-[3-(3-Morpholinomethyl-6-methoxyquinolin-4-yl)
propyl]-1-[2-(pyrid-2-yl)thioethyl]-piperid-4-ylmethanol 4-[3-(3-Morpholinomethyl-6-methoxyquinolin-4-yl)
propyl]-1-[2-(thien-2-yl)thioethyl]-piperid-4-ylmethanol 4-[3-(3-Morpholinomethyl-6-methoxyquinolin-4-yl)
propyl]-1-[3-(2,3,5-trifluoro-phenyl)prop-2-ynyl]piperid-4-ylmethanol 4-[3-(3-Morpholinomethyl-6-methoxyquinolin-4-yl)
propyl]-1-[3-(thien-2-yl)prop-2-ynyl]piperid-4-ylmethanol 4-[3-(3-Methyl-6-methoxyquinolin-4-yl)propyl]-1-[3-(2,4,6-trifluoro-phenyl)propyl]piperid-4-ylmethanol 4-[3-(3-Methyl-6-methoxyquinolin-4-yl)propyl]-1-[3-(3,4,5-trifluoro-phenyl)propyl]piperid-4-ylmethanol 4-[3-(3-Methyl-6-methoxyquinolin-4-yl)propyl]-1-[2-(2,4,6-trifluorophenyl-thio)ethyl]piperid-4-ylmethanol 4-[3-(3-Methyl-6-methoxyquinolin-4-yl)propyl]-1-[2-(3,4,5-trifluorophenylthio)-ethyl]piperid-4-ylmethanol 4-[3-(3-Methyl-6-methoxyquinolin-4-yl)propyl]-1-[2-(2,4,6-trifluorophenylamino)-ethyl]piperid-4-ylmethanol 4-[3-(3-Methyl-6-methoxyquinolin-4-yl)propyl]-1-[2-(3,4,5-trifluorophenylamino)-ethyl]piperid-4-ylmethanol 4-[3-(3-Methyl-6-methoxyquinolin-4-yl)propyl]-1-[2-(2,4,6-trifluorophenoxy)-ethyl]piperid-4-ylmethanol 4-[3-(3-Methyl-6-methoxyquinolin-4-yl)propyl]-1-[2-(3,4,5-trifluorophenoxy)-ethyl]piperid-4-ylmethanol 4-[3-(3-Methyl-6-methoxyquinolin-4-yl)propyl]-1-[3-(2,4,6-trifluorophenyl)prop-2-ynyl]piperid-4-ylmethanol 4-[3-(3-Methyl-6-methoxyquinolin-4-yl)propyl]-1-[3-(3,4,5-trifluorophenyl)prop-2-ynyl]piperid-4-ylmethanol 4-[3-(3-Fluoro-6-methoxyquinolin-4-yl)propyl]-1-[3-(2,4,6-trifluorophenyl)-propyl]piperid-4-ylmethanol 4-[3-(3-Fluoro-6-methoxyquinolin-4-yl)propyl]-1-[3-(3,4,5-trifluorophenyl)-propyl]piperid-4-ylmethanol 4-[3-(3-Fluoro-6-methoxyquinolin-4-yl)propyl]-1-[2-(2,4,6-trifluorophenylthio)-ethyl]piperid-4-ylmethanol 4-[3-(3-Fluoro-6-methoxyquinolin-4-yl)propyl]-1-[2-(3,4,5-trifluorophenylthio)-ethyl]piperid-4-ylmethanol 4-[3-(3-Fluoro-6-methoxyquinolin-4-yl)propyl]-1-[2-(2,4,6-trifluorophenyl-amino)ethyl]piperid-4-ylmethanol 4-[3-(3-Fluoro-6-methoxyquinolin-4-yl)propyl]-1-[2-(3,4,5-trifluorophenyl-amino)ethyl]piperid-4-ylmethanol 4-[3-(3-Fluoro-6-methoxyquinolin-4-yl)propyl]-1-[2-(2,4,6-trifluorophenoxy)-ethyl]piperid-4-ylmethanol 4-[3-(3-Fluoro-6-methoxyquinolin-4-yl)propyl]-1-[2-(3,4,5-trifluorophenoxy)-ethyl]piperid-4-ylmethanol 4-[3-(3-Fluoro-6-methoxyquinolin-4-yl)propyl]-1-[3-(2,4,6-trifluorophenyl)prop-2-ynyl]piperid-4-ylmethanol 4-[3-(3-Fluoro-6-methoxyquinolin-4-yl)propyl]-1-[3-(3,4,5-trifluorophenyl)prop-2-ynyl]piperid-4-ylmethanol 4-[3-(3-Dimethylamino-6-methoxyquinolin-4-yl)propyl]-1-[3-(2,4,6-trifluorophenyl)-propyl]piperid-4-ylmethanol 4-[3-(3-Dimethylamino-6-methoxyquinolin-4-yl)propyl]-1-[3-(3,4,5-trifluorophenyl)-propyl]piperid-4-ylmethanol 4-[3-(3-Dimethylamino-6-methoxyquinolin-4-yl)propyl]-1-[2-(2,4,6-trifluorophenyl-thio)ethyl]piperid-4-ylmethanol 4-[3-(3-Dimethylamino-6-methoxyquinolin-4-yl)propyl]-1-[2-(3,4,5-trifluorophenyl-thio)ethyl]piperid-4-ylmethanol 4-[3-(3-Dimethylamino-6-methoxyquinolin-4-yl)propyl]-1-[2-(2,4,6-trifluorophenyl-amino)ethyl]piperid-4-ylmethanol 4-[3-(3-Dimethylamino-6-methoxyquinolin-4-yl)propyl]-1-[2-(3,4,5-trifluorophenyl-amino)ethyl]piperid-4-ylmethanol 4-[3-(3-Dimethylamino-6-methoxyquinolin-4-yl)propyl]-1-[2-(2,4,6-trifluorophenoxy)-ethyl]piperid-4-ylmethanol 4-[3-(3-Dimethylamino-6-methoxyquinolin-4-yl)propyl]-1-[2-(3,4,5-trifluoro-phenoxy)ethyl]piperid-4-ylmethanol 4-[3-(3-Dimethylamino-6-methoxyquinolin-4-yl)propyl]-1-[3-(2,4,6-trifluorophenyl)prop-2-ynyl]piperid-4-ylmethanol 4-[3-(3-Dimethylamino-6-methoxyquinolin-4-yl)propyl]-1-[3-(3,4,5-trifluorophenyl)prop-2-ynyl]piperid-4-ylmethanol 4-[3-(3-Hydroxymethyl-6-methoxyquinolin-4-yl)
propyl]-1-[3-(3,4,5-trifluoro-phenyl)propyl]piperid-4-ylmethanol 4-[3-(3-Hydroxymethyl-6-methoxyquinolin-4-yl)
propyl]-1-[2-(2,4,6-trifluorophenyl-thio)ethyl]piperid-4-ylmethanol 4-[3-(3-Hydroxymethyl-6-methoxyquinolin-4-yl)
propyl]-1-[2-(3,4,5-trifluorophenyl-thio)ethyl]piperid-4-ylmethanol 4-[3-(3-Hydroxymethyl-6-methoxyquinolin-4-yl)
propyl]-1-[2-(2,4,6-trifluorophenyl-amino)ethyl]piperid-4-ylmethanol 4-[3-(3-Hydroxymethyl-6-methoxyquinolin-4-yl)
propyl]-1-[2-(3,4,5-trifluorophenyl-amino)ethyl]piperid-4-ylmethanol 4-[3-(3-Hydroxymethyl-6-methoxyquinolin-4-yl)
propyl]-1-[2-(2,4,6-trifluorophenoxy)-ethyl]piperid-4-ylmethanol 4-[3-(3-Hydroxymethyl-6-methoxyquinolin-4-yl)
propyl]-1-[2-(3,4,5-trifluorophenoxy)-ethyl]piperid-4-ylmethanol 4-[3-(3-Hydroxymethyl-6-methoxyquinolin-4-yl)
propyl]-1-[3-(2,4,6-trifluorophenyl)prop-2-ynyl]piperid-4-ylmethanol 4-[3-(3-Hydroxymethyl-6-methoxyquinolin-4-yl)
propyl]-1-[3-(3,4,5-trifluorophenyl)prop-2-ynyl]piperid-4-ylmethanol 4-[3-(3-Fluoromethyl-6-methoxyquinolin-4-yl)propyl]-1-[3-(2,4,6-trifluorophenyl)propyl]piperid-4-ylmethanol 4-[3-(3-Fluoromethyl-6-methoxyquinolin-4-yl)propyl]-1-[3-(3,4,5-trifluorophenyl)propyl]piperid-4-ylmethanol 4-[3-(3-Fluoromethyl-6-methoxyquinolin-4-yl)propyl]-1-[2-(2,4,6-trifluorophenyl-thio)ethyl]piperid-4-ylmethanol 4-[3-(3-Fluoromethyl-6-methoxyquinolin-4-yl)propyl]-1-[2-(3,4,5-trifluorophenyl-thio)ethyl]piperid-4-ylmethanol 4-[3-(3-Fluoromethyl-6-methoxyquinolin-4-yl)propyl]-1-[2-(2,4,6-trifluorophenyl-amino)ethyl]piperid-4-ylmethanol 4-[3-(3-Fluoromethyl-6-methoxyquinolin-4-yl)propyl]-1-[2-(3,4,5-trifluorophenyl-amino)ethyl]piperid-4-ylmethanol 4-[3-(3-Fluoromethyl-6-methoxyquinolin-4-yl)propyl]-1-[2-(2,4,6-trifluorophenoxy)-ethyl]piperid-4-ylmethanol 4-[3-(3-Fluoromethyl-6-methoxyquinolin-4-yl)propyl]-1-[2-(3,4,5-trifluorophenoxy)-ethyl]piperid-4-ylmethanol 4-[3-(3-Fluoromethyl-6-methoxyquinolin-4-yl)propyl]-1-[3-(2,4,6-trifluorophenyl)prop-2-ynyl]piperid-4-ylmethanol 4-[3-(3-Fluoromethyl-6-methoxyquinolin-4-yl)propyl]-1-[3-(3,4,5-trifluorophenyl)prop-2-ynyl]piperid-4-ylmethanol 4-[3-(3-Aminomethyl-6-methoxyquinolin-4-yl)propyl]-1-[3-(2,4,6-trifluorophenyl)-propyl]piperid-4-ylmethanol 4-[3-(3-Aminomethyl-6-methoxyquinolin-4-yl)propyl]-1-[3-(3,4,5-trifluorophenyl)-propyl]piperid-4-ylmethanol 4-[3-(3-Aminomethyl-6-methoxyquinolin-4-yl)propyl]-1-[2-(2,4,6-trifluorophenylthio)-ethyl]piperid-4-ylmethanol 4-[3-(3-Aminomethyl-6-methoxyquinolin-4-yl)propyl]-1-[2-(3,4,5-trifluorophenylthio)-ethyl]piperid-4-ylmethanol 4-[3-(3-Aminomethyl-6-methoxyquinolin-4-yl)propyl]-1-[2-(2,4,6-trifluorophenyl-amino)ethyl]piperid-4-ylmethanol 4-[3-(3-Aminomethyl-6-methoxyquinolin-4-yl)propyl]-1-[2-(3,4,5-trifluorophenylamino)-ethyl]piperid-4-ylmethanol 4-[3-(3-Aminomethyl-6-methoxyquinolin-4-yl)propyl]-1-[2-(2,4,6-trifluorophenoxy)-ethyl]piperid-4-ylmethanol 4-[3-(3-Aminomethyl-6-methoxyquinolin-4-yl)propyl]-1-[2-(3,4,5-trifluorophenoxy)-ethyl]piperid-4-ylmethanol 4-[3-(3-Aminomethyl-6-methoxyquinolin-4-yl)propyl]-1-[3-(2,4,6-trifluorophenyl)prop-2-ynyl]piperid-4-ylmethanol 4-[3-(3-Aminomethyl-6-methoxyquinolin-4-yl)propyl]-1-[3-(3,4,5-trifluorophenyl)prop-2-ynyl]piperid-4-ylmethanol 4-[3-(3-Morpholinomethyl-6-methoxyquinolin-4-yl)propyl]-1-[3-(2,4,6-trifluorophenyl)-propyl]piperid-4-ylmethanol 4-[3-(3-Morpholinomethyl-6-methoxyquinolin-4-yl)propyl]-1-[3-(3,4,5-trifluorophenyl)-propyl]piperid-4-ylmethanol 4-[3-(3-Morpholinomethyl-6-methoxyquinolin-4-yl)propyl]-1-[2-(2,4,6-trifluorophenylthio)-ethyl]piperid-4-ylmethanol 4-[3-(3-Morpholinomethyl-6-methoxyquinolin-4-yl)propyl]-1-[2-(3,4,5-trifluorophenylthio)-ethyl]piperid-4-ylmethanol 4-[3-(3-Morpholinomethyl-6-methoxyquinolin-4-yl)propyl]-1-[2-(2,4,6-trifluorophenyl-amino)ethyl]piperid-4-ylmethanol 4-[3-(3-Morpholinomethyl-6-methoxyquinolin-4-yl)propyl]-1-[2-(3,4,5-trifluorophenyl-amino)ethyl]piperid-4-ylmethanol 4-[3-(3-Morpholinomethyl-6-methoxyquinolin-4-yl)propyl]-1-[2-(2,4,6-trifluorophenoxy)-ethyl]piperid-4-ylmethanol 4-[3-(3-Morpholinomethyl-6-methoxyquinolin-4-yl)propyl]-1-[2-(3,4,5-trifluorophenoxy)-ethyl]piperid-4-ylmethanol 4-[3-(3-Morpholinomethyl-6-methoxyquinolin-4-yl)propyl]-1-[3-(2,4,6-trifluorophenyl)-prop-2-ynyl]piperid-4-ylmethanol 4-[3-(3-Morpholinomethyl-6-methoxyquinolin-4-yl)propyl]-1-[3-(3,4,5-trifluorophenyl)-prop-2-ynyl]piperid-4-ylmethanol 4-[3-(R,S)-Hydroxy-3-(3-chloro-6-methoxyquinolin-4-yl)propyl]-1-heptylpiperid-4-ylmethanol 4-[3-(R,S)-Hydroxy-3-(3-chloro-6-methoxyquinolin-4-yl)propyl]-1-[4-phenylbutyl]piperid-4-ylmethanol 4-[3-(R,S)-Hydroxy-3-(3-chloro-6-methoxyquinolin-4-yl)propyl]-1-[3-(phenyl)propyl]-piperid-4-ylmethanol 4-[3-(R,S)-Hydroxy-3-(3-chloro-6-methoxyquinolin-4-yl)propyl]-1-[4-(2-fluorophenyl)propyl]piperid-4-ylmethanol 4-[3-(R,S)-Hydroxy-3-(3-chloro-6-methoxyquinolin-4-yl)propyl]-1-[4-(3-fluorophenyl)propyl]piperid-4-ylmethanol 4-[3-(R,S)-Hydroxy-3-(3-chloro-6-methoxyquinolin-4-yl)propyl]-1-[3-(4-fluorophenyl)-propyl]piperid-4-ylmethanol 4-[3-(R,S)-Hydroxy-3-(3-chloro-6-methoxyquinolin-4-yl)propyl]-1-[4-(4-fluorophenyl)-butyl]piperid-4-ylmethanol 4-[3-(R,S)-Hydroxy-3-(3-chloro-6-methoxyquinolin-4-yl)propyl]-1-[3-(2,3-difluorophenyl)-propyl]piperid-4-ylmethanol 4-[3-(R,S)-Hydroxy-3-(3-chloro-6-methoxyquinolin-4-yl)propyl]-1-[4-(2,3-difluorophenyl)-propyl]piperid-4-ylmethanol 4-[3-(R,S)-Hydroxy-3-(3-chloro-6-methoxyquinolin-4-yl)propyl]-1-[3-(2,6-difluorophenyl)-propyl]piperid-4-ylmethanol 4-[3-(R,S)-Hydroxy-3-(3-chloro-6-methoxyquinolin-4-yl)propyl]-1-[4-(2,6-difluorophenyl)-propyl]piperid-4-ylmethanol 4-[3-(R,S)-Hydroxy-3-(3-chloro-6-methoxyquinolin-4-yl)propyl]-1-[3-(3,5-difluorophenyl)-propyl]piperid-4-ylmethanol 4-[3-(R,S)-Hydroxy-3-(3-chloro-6-methoxyquinolin-4-yl)propyl]-1-[3-(2,3,5-trifluorophenyl)propyl]piperid-4-ylmethanol 4-[3-(R,S)-Hydroxy-3-(3-chloro-6-methoxyquinolin-4-yl)propyl]-1-[3-phenylthio-propyl]piperid-4-ylmethanol 4-[3-(R,S)-Hydroxy-3-(3-chloro-6-methoxyquinolin-4-yl)propyl]-1-[3-(2-fluorophenyl-thio)propyl]piperid-4-ylmethanol 4-[3-(R,S)-Hydroxy-3-(3-chloro-6-methoxyquinolin-4-yl)propyl]-1-[3-(3-fluorophenyl-thio)propyl]piperid-4-ylmethanol 4-[3-(R,S)-Hydroxy-3-(3-chloro-6-methoxyquinolin-4-yl)propyl]-1-[2-(4-fluorophenyl-thio)ethyl]piperid-4-ylmethanol 4-[3-(R,S)-Hydroxy-3-(3-chloro-6-methoxyquinolin-4-yl)propyl]-1-[3-(4-fluorophenyl-thio)propyl]piperid-4-ylmethanol 4-[3-(R,S)-Hydroxy-3-(3-chloro-6-methoxyquinolin-4-yl)propyl]-1-[2-(2,3-difluorophenyl-thio)ethyl]piperid-4-ylmethanol 4-[3-(R,S)-Hydroxy-3-(3-chloro-6-methoxyquinolin-4-yl)propyl]-1-[3-(2,3-difluorophenyl-thio)propyl]piperid-4-ylmethanol 4-[3-(R,S)-Hydroxy-3-(3-chloro-6-methoxyquinolin-4-yl)propyl]-1-[2-(2,6-difluorophenyl-thio)ethyl]piperid-4-ylmethanol 4-[3-(R,S)-Hydroxy-3-(3-chloro-6-methoxyquinolin-4-yl)propyl]-1-[2-(2,3,5-trifluorophenylthio)ethyl]piperid-4-ylmethanol 4-[3-(R,S)-Hydroxy-3-(3-chloro-6-methoxyquinolin-4-yl)propyl]-1-[2-(2,4,6-trifluorophenylthio)ethyl]piperid-4-ylmethanol 4-[3-(R,S)-Hydroxy-3-(3-chloro-6-methoxyquinolin-4-yl)propyl]-1-[2-(3,4,5-trifluorophenylthio)ethyl]piperid-4-ylmethanol 4-[3-(R,S)-Hydroxy-3-(3-chloro-6-methoxyquinolin-4-yl)propyl]-1-[2-(3,5-difluoro-phenoxy)ethyl]piperid-4-ylmethanol 4-[3-(R,S)-Hydroxy-3-(3-chloro-6-methoxyquinolin-4-yl)propyl]-1-[2-(2,3,5-trifluoro-phenoxy)ethyl]piperid-4-ylmethanol 4-[3-(R,S)-Hydroxy-3-(3-chloro-6-methoxyquinolin-4-yl)propyl]-1-[2-(2,4,6-trifluoro-phenoxy)ethyl]piperid-4-ylmethanol 4-[3-(R,S)-Hydroxy-3-(3-chloro-6-methoxyquinolin-4-yl)propyl]-1-[2-(3,4,5-trifluoro-phenoxy)ethyl]piperid-4-ylmethanol 4-[3-(R,S)-Hydroxy-3-(3-chloro-6-methoxyquinolin-4-yl)propyl]-1-[2-(3,5-difluoro-phenylamino)ethyl]piperid-4-ylmethanol 4-[3-(R,S)-Hydroxy-3-(3-chloro-6-methoxyquinolin-4-yl)propyl]-1-[2-(2,3,5-trifluoro-phenylamino)ethyl]piperid-4-ylmethanol 4-[3-(R,S)-Hydroxy-3-(3-chloro-6-methoxyquinolin-4-yl)propyl]-1-[2-(2,4,6-trifluoro-phenylamino)ethyl]piperid-4-ylmethanol 4-[3-(R,S)-Hydroxy-3-(3-chloro-6-methoxyquinolin-4-yl)propyl]-1-[2-(3,4,5-trifluoro-phenylamino)ethyl]piperid-4-ylmethanol 4-[3-(R,S)-Hydroxy-3-(3-chloro-6-methoxyquinolin-4-yl)propyl]-1-[3-(2,6-difluoro-phenylthio)propyl]piperid-4-ylmethanol 4-[3-(R,S)-Hydroxy-3-(3-chloro-6-methoxyquinolin-4-yl)propyl]-1-[2-(2-chloro-phenylthio)ethyl]piperid-4-ylmethanol 4-[3-(R,S)-Hydroxy-3-(3-chloro-6-methoxyquinolin-4-yl)propyl]-1-[3-(2-chloro-phenylthio)propyl]piperid-4-ylmethanol 4-[3-(R,S)-Hydroxy-3-(3-chloro-6-methoxyquinolin-4-yl)propyl]-1-[2-(3-chloro-phenylthio)ethyl]piperid-4-ylmethanol 4-[3-(R,S)-Hydroxy-3-(3-chloro-6-methoxyquinolin-4-yl)propyl]-1-[3-(3-chloro-phenylthio)propyl]piperid-4-ylmethanol 4-[3-(R,S)-Hydroxy-3-(3-chloro-6-methoxyquinolin-4-yl)propyl]-1-[2-(4-chloro-phenylthio)ethyl]piperid-4-ylmethanol 4-[3-(R,S)-Hydroxy-3-(3-chloro-6-methoxyquinolin-4-yl)propyl]-1-[3-(4-chloro-phenylthio)propyl]piperid-4-ylmethanol 4-[3-(R,S)-Hydroxy-3-(3-chloro-6-methoxyquinolin-4-yl)propyl]-1-[2-(2-methylphenyl-thio)ethyl]piperid-4-ylmethanol 4-[3-(R,S)-Hydroxy-3-(3-chloro-6-methoxyquinolin-4-yl)propyl]-1-[3-(2-methylphenyl-thio)propyl]piperid-4-ylmethanol 4-[3-(R,S)-Hydroxy-3-(3-chloro-6-methoxyquinolin-4-yl)propyl]-1-[2-(3-methylphenyl-thio)ethyl]piperid-4-ylmethanol 4-[3-(R,S)-Hydroxy-3-(3-chloro-6-methoxyquinolin-4-yl)propyl]-1-[3-(3-methylphenyl-thio)propyl]piperid-4-ylmethanol 4-[3-(R,S)-Hydroxy-3-(3-chloro-6-methoxyquinolin-4-yl)propyl]-1-[2-(4-methylphenyl-thio)ethyl]piperid-4-ylmethanol 4-[3-(R,S)-Hydroxy-3-(3-chloro-6-methoxyquinolin-4-yl)propyl]-1-[3-(4-methylphenyl-thio)propyl]piperid-4-ylmethanol 4-[3-(R,S)-Hydroxy-3-(3-chloro-6-methoxyquinolin-4-yl)propyl]-1-[2-(2-trifluoromethyl-phenylthio)ethyl]piperid-4-ylmethanol 4-[3-(R,S)-Hydroxy-3-(3-chloro-6-methoxyquinolin-4-yl)propyl]-1-[3-(2-trifluoromethyl-phenylthio)propyl]piperid-4-ylmethanol 4-[3-(R,S)-Hydroxy-3-(3-chloro-6-methoxyquinolin-4-yl)propyl]-1-[2-(3-trifluoromethyl-phenylthio)ethyl]piperid-4-ylmethanol 4-[3-(R,S)-Hydroxy-3-(3-chloro-6-methoxyquinolin-4-yl)propyl]-1-[3-(3-trifluoromethyl-phenylthio)propyl]piperid-4-ylmethanol 4-[3-(R,S)-Hydroxy-3-(3-chloro-6-methoxyquinolin-4-yl)propyl]-1-[2-(4-trifluoromethyl-phenylthio)ethyl]piperid-4-ylmethanol 4-[3-(R,S)-Hydroxy-3-(3-chloro-6-methoxyquinolin-4-yl)propyl]-1-[3-(4-trifluoromethyl-phenylthio)propyl]piperid-4-ylmethanol 4-[3-(R,S)-Hydroxy-3-(3-chloro-6-methoxyquinolin-4-yl)propyl]-1-[2-(2-methoxyphenyl-thio)ethyl]piperid-4-ylmethanol 4-[3-(R,S)-Hydroxy-3-(3-chloro-6-methoxyquinolin-4-yl)propyl]-1-[3-(2-methoxyphenyl-thio)propyl]piperid-4-ylmethanol 4-[3-(R,S)-Hydroxy-3-(3-chloro-6-methoxyquinolin-4-yl)propyl]-1-[2-(3-methoxyphenyl-thio)ethyl]piperid-4-ylmethanol 4-[3-(R,S)-Hydroxy-3-(3-chloro-6-methoxyquinolin-4-yl)propyl]-1-[3-(3-methoxyphenyl-thio)propyl]piperid-4-ylmethanol 4-[3-(R,S)-Hydroxy-3-(3-chloro-6-methoxyquinolin-4-yl)propyl]-1-[2-(4-methoxyphenyl-thio)ethyl]piperid-4-ylmethanol 4-[3-(R,S)-Hydroxy-3-(3-chloro-6-methoxyquinolin-4-yl)propyl]-1-[3-(4-methoxyphenyl-thio)propyl]piperid-4-ylmethanol 4-[3-(R,S)-Hydroxy-3-(3-chloro-6-methoxyquinolin-4-yl)propyl]-1-[cyclopentylmethyl]-piperid-4-ylmethanol 4-[3-(R,S)-Hydroxy-3-(3-chloro-6-methoxyquinolin-4-yl)propyl]-1-[2-(cyclopentyl)ethyl]-piperid-4-ylmethanol 4-[3-(R,S)-Hydroxy-3-(3-chloro-6-methoxyquinolin-4-yl)propyl]-1-[2-(cyclohexyl)ethyl]-piperid-4-ylmethanol 4-[3-(R,S)-Hydroxy-3-(3-chloro-6-methoxyquinolin-4-yl)propyl]-1-[2-(cyclopentylthio)ethyl]piperid-4-ylmethanol
4-[3-(R,S)-Hydroxy-3-(3-chloro-6-methoxyquinolin-4-yl)propyl]-1-[3-(cyclopentylthio)-propyl]piperid-4-ylmethanol
4-[3-(R,S)-Hydroxy-3-(3-chloro-6-methoxyquinolin-4-yl)propyl]-1-[3-(cyclohexylthio)propyl]piperid-4-ylmethanol
4-[3-(R,S)-Hydroxy-3-(3-chloro-6-methoxyquinolin-4-yl)propyl]-1-[2-(pyrid-2-yl)thioethyl]piperid-4-ylmethanol
4-[3-(R,S)-Hydroxy-3-(3-chloro-6-methoxyquinolin-4-yl)propyl]-1-[4-(thien-2-yl)butyl]piperid-4-ylmethanol
4-[3-(R,S)-Hydroxy-3-(3-chloro-6-methoxyquinolin-4-yl)propyl]-1-[3-(thien-2-yl)thiopropyl]piperid-4-ylmethanol
4-[3-(R,S)-Hydroxy-3-(3-chloro-6-methoxyquinolin-4-yl)propyl]-1-[3-(thien-3-yl)propyl]piperid-4-ylmethanol
4-[3-(R,S)-Hydroxy-3-(3-chloro-6-methoxyquinolin-4-yl)propyl]-1-[4-(thien-3-yl)butyl]piperid-4-ylmethanol
4-[3-(R,S)-Hydroxy-3-(3-chloro-6-methoxyquinolin-4-yl)propyl]-1-[2-(thien-2-yl)thioethyl]piperid-4-ylmethanol
4-[3-(R,S)-Hydroxy-3-(3-chloro-6-methoxyquinolin-4-yl)propyl]-1-[3-(thien-3-yl)thiopropyl]piperid-4-ylmethanol
4-[3-(R,S)-Hydroxy-3-(3-chloro-6-methoxyquinolin-4-yl)propyl]-1-[3-(1,3-thiazol-2-yl)propyl]piperid-4-ylmethanol
4-[3-(R,S)-Hydroxy-3-(3-chloro-6-methoxyquinolin-4-yl)propyl]-1-[4-(1,3-thiazol-2-yl)butyl]piperid-4-ylmethanol
4-[3-(R,S)-Hydroxy-3-(3-chloro-6-methoxyquinolin-4-yl)propyl]-1-[3-(1,3-thiazol-2-yl)thioethyl]piperid-4-ylmethanol
4-[3-(R,S)-Hydroxy-3-(3-chloro-6-methoxyquinolin-4-yl)propyl]-1-[3-(pyrid-2-yl)propyl]piperid-4-ylmethanol
4-[3-(R,S)-Hydroxy-3-(3-chloro-6-methoxyquinolin-4-yl)propyl]-1-[4-(pyrid-2-yl)butyl]piperid-4-ylmethanol
4-[3-(R,S)-Hydroxy-3-(3-chloro-6-methoxyquinolin-4-yl)propyl]-1-[3-(pyrid-2-yl)thiopropyl]piperid-4-ylmethanol
4-[3-(R,S)-Hydroxy-3-(3-chloro-6-methoxyquinolin-4-yl)propyl]-1-[3-(pyrid-3-yl)propyl]piperid-4-ylmethanol
4-[3-(R,S)-Hydroxy-3-(3-chloro-6-methoxyquinolin-4-yl)propyl]-1-[4-(pyrid-3-yl)butyl]piperid-4-ylmethanol
4-[3-(R,S)-Hydroxy-3-(3-chloro-6-methoxyquinolin-4-yl)propyl]-1-[2-(pyrid-3-yl)thioethyl]piperid-4-ylmethanol
4-[3-(R,S)-Hydroxy-3-(3-chloro-6-methoxyquinolin-4-yl)propyl]-1-[3-(pyrid-3-yl)thiopropyl]piperid-4-ylmethanol
4-[3-(R,S)-Hydroxy-3-(3-chloro-6-methoxyquinolin-4-yl)propyl]-1-[3-(pyrid-4-yl)propyl]piperid-4-ylmethanol
4-[3-(R,S)-Hydroxy-3-(3-chloro-6-methoxyquinolin-4-yl)propyl]-1-[4-(pyrid-4-yl)butyl]piperid-4-ylmethanol
4-[3-(R,S)-Hydroxy-3-(3-chloro-6-methoxyquinolin-4-yl)propyl]-1-[2-(pyrid-4-yl)thioethyl]piperid-4-ylmethanol
4-[3-(R,S)-Hydroxy-3-(3-chloro-6-methoxyquinolin-4-yl)propyl]-1-[3-(pyrid-4-yl)thiopropyl]piperid-4-ylmethanol
4-[3-(R,S)-Hydroxy-3-(3-chloro-6-methoxyquinolin-4-yl)propyl]-1-[3-(pyrazin-2-yl)propyl]piperid-4-ylmethanol
4-[3-(R,S)-Hydroxy-3-(3-chloro-6-methoxyquinolin-4-yl)propyl]-1-[4-(pyrazin-2-yl)butyl]piperid-4-ylmethanol
4-[3-(R,S)-Hydroxy-3-(3-chloro-6-methoxyquinolin-4-yl)propyl]-1-[2-(pyrazin-2-yl)thioethyl]piperid-4-ylmethanol
4-[3-(R,S)-Hydroxy-3-(3-chloro-6-methoxyquinolin-4-yl)propyl]-1-[3-(pyrazin-2-yl)thiopropyl]piperid-4-ylmethanol
4-[3-(R,S)-Hydroxy-3-(3-chloro-6-methoxyquinolin-4-yl)propyl]-1-[3-(4-fluorophenyl)prop-2-ynyl]piperid-4-ylmethanol
4-[3-(R,S)-Hydroxy-3-(3-chloro-6-methoxyquinolin-4-yl)propyl]-1-[3-(3,4-difluorophenyl)prop-2-ynyl]piperid-4-ylmethanol
4-[3-(R,S)-Hydroxy-3-(3-chloro-6-methoxyquinolin-4-yl)propyl]-1-[3-(2,4-difluorophenyl)prop-2-ynyl]piperid-4-ylmethanol
4-[3-(R,S)-Hydroxy-3-(3-chloro-6-methoxyquinolin-4-yl)propyl]-1-[3-(2,3,5-trifluorophenyl)prop-2-ynyl]piperid-4-ylmethanol
4-[3-(R,S)-Hydroxy-3-(3-chloro-6-methoxyquinolin-4-yl)propyl]-1-[3-(2,4,6-trifluorophenyl)prop-2-ynyl]piperid-4-ylmethanol
4-[3-(R,S)-Hydroxy-3-(3-chloro-6-methoxyquinolin-4-yl)propyl]-1-[3-(3,4,5-trifluorophenyl)prop-2-ynyl]piperid-4-ylmethanol
4-[3-(R,S)-Hydroxy-3-(3-chloro-6-methoxyquinolin-4-yl)propyl]-1-[3-(4-chloro-3-fluorophenyl)prop-2-ynyl]piperid-4-ylmethanol
4-[3-(R,S)-Hydroxy-3-(3-chloro-6-methoxyquinolin-4-yl)propyl]-1-[3-(3-chloro-4-fluorophenyl)prop-2-ynyl]piperid-4-ylmethanol
4-[3-(R,S)-Hydroxy-3-(3-chloro-6-methoxyquinolin-4-yl)propyl]-1-[3-(2-chloro-4-fluorophenyl)prop-2-ynyl]piperid-4-ylmethanol
4-[3-(R,S)-Hydroxy-3-(3-chloro-6-methoxyquinolin-4-yl)propyl]-1-[3-(3-chloro-5-fluorophenyl)prop-2-ynyl]piperid-4-ylmethanol
4-[3-(R,S)-Hydroxy-3-(3-chloro-6-methoxyquinolin-4-yl)propyl]-1-[3-(4-chloro-2-fluorophenyl)prop-2-ynyl]piperid-4-ylmethanol
4-[3-(R,S)-Hydroxy-3-(3-chloro-6-methoxyquinolin-4-yl)propyl]-1-[3-(3-fluoro-4-methylphenyl)prop-2-ynyl]piperid-4-ylmethanol
4-[3-(R,S)-Hydroxy-3-(3-chloro-6-methoxyquinolin-4-yl)propyl]-1-[3-(3,5-bis(trifluoromethyl)phenyl)prop-2-ynyl]piperid-4-ylmethanol
4-[3-(R,S)-Hydroxy-3-(3-chloro-6-methoxyquinolin-4-yl)propyl]-1-[3-(thien-2-yl)prop-2-ynyl]piperid-4-ylmethanol
4-[3-(R,S)-Hydroxy-3-(3-chloro-6-methoxyquinolin-4-yl)propyl]-1-[3-(thien-3-yl)prop-2-ynyl]piperid-4-ylmethanol
4-[3-(R,S)-Hydroxy-3-(3-chloro-6-methoxyquinolin-4-yl)propyl]-1-[3-(1,3-thiazol-2-yl)prop-2-ynyl]piperid-4-ylmethanol 4-[3-(R,S)-Hydroxy-3-(3-chloro-6-methoxyquinolin-4-yl)propyl]-1-[3-(1,3-thiazol-4-yl)prop-2-ynyl]piperid-4-ylmethanol 4-[3-(R,S)-Hydroxy-3-(3-chloro-6-methoxyquinolin-4-yl)propyl]-1-[3-(1,3-thiazol-5-yl)prop-2-ynyl]piperid-4-ylmethanol 4-[3-(R,S)-Hydroxy-3-(3-chloro-6-methoxyquinolin-4-yl)propyl]-1-[3-(pyrid-2-yl)prop-2-ynyl]piperid-4-ylmethanol 4-[3-(R,S)-Hydroxy-3-(3-chloro-6-methoxyquinolin-4-yl)propyl]-1-[3-(pyrid-3-yl)prop-2-ynyl]piperid-4-ylmethanol 4-[3-(R,S)-Hydroxy-3-(3-chloro-6-methoxyquinolin-4-yl)propyl]-1-[3-(pyrid-4-yl)prop-2-ynyl]piperid-4-ylmethanol 4-[3-(R,S)-Hydroxy-3-(3-methyl-6-methoxyquinolin-4-yl)propyl]-1-[2-(cyclohexyl)ethyl]piperid-4-ylmethanol 4-[3-(R,S)-Hydroxy-3-(3-methyl-6-methoxyquinolin-4-yl)propyl]-1-[3-(phenyl)propyl]piperid-4-ylmethanol 4-[3-(R,S)-Hydroxy-3-(3-methyl-6-methoxyquinolin-4-yl)propyl]-1-[3-(2,3,5-trifluorophenyl)propyl]piperid-4-ylmethanol 4-[3-(R,S)-Hydroxy-3-(3-methyl-6-methoxyquinolin-4-yl)propyl]-1-[2-(3,5-difluorophenylamino)ethyl]piperid-4-ylmethanol 4-[3-(R,S)-Hydroxy-3-(3-methyl-6-methoxyquinolin-4-yl)propyl]-1-[2-(2,3,5-trifluorophenylamino)ethyl]piperid-4-ylmethanol 4-[3-(R,S)-Hydroxy-3-(3-methyl-6-methoxyquinolin-4-yl)propyl]-1-[2-(3,5-difluorophenoxy)ethyl]piperid-4-ylmethanol 4-[3-(R,S)-Hydroxy-3-(3-methyl-6-methoxyquinolin-4-yl)propyl]-1-[2-(2,3,5-trifluorophenoxy)ethyl]piperid-4-ylmethanol 4-[3-(R,S)-Hydroxy-3-(3-methyl-6-methoxyquinolin-4-yl)propyl]-1-[2-(2,3,5-trifluorophenylthio)ethyl]piperid-4-ylmethanol 4-[3-(R,S)-Hydroxy-3-(3-methyl-6-methoxyquinolin-4-yl)propyl]-1-[2-(cyclopentylthio)ethyl]piperid-4-ylmethanol 4-[3-(R,S)-Hydroxy-3-(3-methyl-6-methoxyquinolin-4-yl)propyl]-1-[2-(pyrid-2-yl)thioethyl]piperid-4-ylmethanol 4-[3-(R,S)-Hydroxy-3-(3-methyl-6-methoxyquinolin-4-yl)propyl]-1-[2-(thien-2-yl)thioethyl]piperid-4-ylmethanol 4-[3-(R,S)-Hydroxy-3-(3-methyl-6-methoxyquinolin-4-yl)propyl]-1-[3-(2,3,5-trifluorophenyl)prop-2-ynyl]piperid-4-ylmethanol 4-[3-(R,S)-Hydroxy-3-(3-methyl-6-methoxyquinolin-4-yl)propyl]-1-[3-(thien-2-yl)prop-2-ynyl]piperid-4-ylmethanol 4-[3-(R,S)-Hydroxy-3-(3-fluoro-6-methoxyquinolin-4-yl)propyl]-1-[2-(cyclohexyl)ethyl]piperid-4-ylmethanol 4-[3-(R,S)-Hydroxy-3-(3-fluoro-6-methoxyquinolin-4-yl)propyl]-1-[3-(phenyl)propyl]piperid-4-ylmethanol 4-[3-(R,S)-Hydroxy-3-(3-fluoro-6-methoxyquinolin-4-yl)propyl]-1-[3-(2,3,5-trifluorophenyl)propyl]piperid-4-ylmethanol 4-[3-(R,S)-Hydroxy-3-(3-fluoro-6-methoxyquinolin-4-yl)propyl]-1-[2-(3,5-difluorophenylamino)ethyl]piperid-4-ylmethanol 4-[3-(R,S)-Hydroxy-3-(3-fluoro-6-methoxyquinolin-4-yl)propyl]-1-[2-(2,3,5-trifluorophenylamino)ethyl]piperid-4-ylmethanol 4-[3-(R,S)-Hydroxy-3-(3-fluoro-6-methoxyquinolin-4-yl)propyl]-1-[2-(3,5-difluorophenoxy)ethyl]piperid-4-ylmethanol 4-[3-(R,S)-Hydroxy-3-(3-fluoro-6-methoxyquinolin-4-yl)propyl]-1-[2-(2,3,5-trifluorophenoxy)ethyl]piperid-4-ylmethanol 4-[3-(R,S)-Hydroxy-3-(3-fluoro-6-methoxyquinolin-4-yl)propyl]-1-[2-(2,3,5-trifluorophenylthio)ethyl]piperid-4-ylmethanol 4-[3-(R,S)-Hydroxy-3-(3-fluoro-6-methoxyquinolin-4-yl)propyl]-1-[2-(cyclopentylthio)ethyl]piperid-4-ylmethanol 4-[3-(R,S)-Hydroxy-3-(3-fluoro-6-methoxyquinolin-4-yl)propyl]-1-[2-(pyrid-2-yl)thioethyl]piperid-4-ylmethanol 4-[3-(R,S)-Hydroxy-3-(3-fluoro-6-methoxyquinolin-4-yl)propyl]-1-[2-(thien-2-yl)thioethyl]piperid-4-ylmethanol 4-[3-(R,S)-Hydroxy-3-(3-fluoro-6-methoxyquinolin-4-yl)propyl]-1-[3-(2,3,5-trifluorophenyl)prop-2-ynyl]piperid-4-ylmethanol 4-[3-(R,S)-Hydroxy-3-(3-fluoro-6-methoxyquinolin-4-yl)propyl]-1-[3-(thien-2-yl)prop-2-ynyl]piperid-4-ylmethanol 4-[3-(R,S)-Hydroxy-3-(3-dimethylamino-6-methoxyquinolin-4-yl)propyl]-1-[2-(cyclohexyl)ethyl]piperid-4-ylmethanol 4-[3-(R,S)-Hydroxy-3-(3-dimethylamino-6-methoxyquinolin-4-yl)propyl]-1-[3-(phenyl)propyl]piperid-4-ylmethanol 4-[3-(R,S)-Hydroxy-3-(3-dimethylamino-6-methoxyquinolin-4-yl)propyl]-1-[3-(2,3,5-trifluorophenyl)propyl]piperid-4-ylmethanol 4-[3-(R,S)-Hydroxy-3-(3-dimethylamino-6-methoxyquinolin-4-yl)propyl]-1-[2-(3,5-difluorophenylamino)ethyl]piperid-4-ylmethanol 4-[3-(R,S)-Hydroxy-3-(3-dimethylamino-6-methoxyquinolin-4-yl)propyl]-1-[2-(2,3,5-trifluorophenylamino)ethyl]piperid-4-ylmethanol 4-[3-(R,S)-Hydroxy-3-(3-dimethylamino-6-methoxyquinolin-4-yl)propyl]-1-[2-(3,5-difluorophenoxy)ethyl]piperid-4-ylmethanol 4-[3-(R,S)-Hydroxy-3-(3-dimethylamino-6-methoxyquinolin-4-yl)propyl]-1-[2-(2,3,5-trifluorophenoxy)ethyl]piperid-4-ylmethanol 4-[3-(R,S)-Hydroxy-3-(3-dimethylamino-6-methoxyquinolin-4-yl)propyl]-1-[2-(2,3,5-trifluorophenylthio)ethyl]piperid-4-ylmethanol 4-[3-(R,S)-Hydroxy-3-(3-dimethylamino-6-methoxyquinolin-4-yl)propyl]-1-[2-(cyclopentylthio)ethyl]piperid-4-ylmethanol 4-[3-(R,S)-Hydroxy-3-(3-dimethylamino-6-methoxyquinolin-4-yl)propyl]-1-[2-(pyrid-2-yl)thioethyl]piperid-4-ylmethanol 4-[3-(R,S)-Hydroxy-3-(3-dimethylamino-6-methoxyquinolin-4-yl)propyl]-1-[2-(thien-2-yl)thioethyl]piperid-4-ylmethanol 4-[3-(R,S)-Hydroxy-3-(3-dimethylamino-6-methoxyquinolin-4-yl)propyl]-1-[3-(2,3,5-trifluorophenyl)prop-2-ynyl]piperid-4-ylmethanol 4-[3-(R,S)-Hydroxy-3-(3-dimethylamino-6-methoxyquinolin-4-yl)propyl]-1-[3-(thien-2-yl)prop-2-ynyl]piperid-4-ylmethanol 4-[3-(R,S)-Hydroxy-3-(3-hydroxymethyl-6-methoxyquinolin-4-yl)propyl]-1-[2-(cyclohexyl)ethyl]piperid-4-ylmethanol 4-[3-(R,S)-Hydroxy-3-(3-hydroxymethyl-6-methoxyquinolin-4-yl)propyl]-1-[3-(phenyl)propyl]piperid-4-ylmethanol 4-[3-(R,S)-Hydroxy-3-(3-hydroxymethyl-6-methoxyquinolin-4-yl)propyl]-1-[3-(2,3,5-trifluorophenyl)propyl]piperid-4-ylmethanol 4-[3-(R,S)-Hydroxy-3-(3-hydroxymethyl-6-methoxyquinolin-4-yl)propyl]-1-[2-(3,5-difluorophenylamino)ethyl]piperid-4-ylmethanol 4-[3-(R,S)-Hydroxy-3-(3-hydroxymethyl-6-methoxyquinolin-4-yl)propyl]-1-[2-(2,3,5-trifluorophenylamino)ethyl]piperid-4-ylmethanol 4-[3-(R,S)-Hydroxy-3-(3-hydroxymethyl-6-methoxyquinolin-4-yl)propyl]-1-[2-(3,5-difluorophenoxy)ethyl]piperid-4-ylmethanol 4-[3-(R,S)-Hydroxy-3-(3-hydroxymethyl-6-methoxyquinolin-4-yl)propyl]-1-[2-(2,3,5-trifluorophenoxy)ethyl]piperid-4-ylmethanol 4-[3-(R,S)-Hydroxy-3-(3-hydroxymethyl-6-methoxyquinolin-4-yl)propyl]-1-[2-(2,3,5-trifluorophenylthio)ethyl]piperid-4-ylmethanol 4-[3-(R,S)-Hydroxy-3-(3-hydroxymethyl-6-methoxyquinolin-4-yl)propyl]-1-[2-(cyclopentylthio)ethyl]piperid-4-ylmethanol 4-[3-(R,S)-Hydroxy-3-(3-hydroxymethyl-6-methoxyquinolin-4-yl)propyl]-1-[2-(pyrid-2-yl)thioethyl]piperid-4-ylmethanol 4-[3-(R,S)-Hydroxy-3-(3-hydroxymethyl-6-methoxyquinolin-4-yl)propyl]-1-[2-(thien-2-yl)thioethyl]piperid-4-ylmethanol 4-[3-(R,S)-Hydroxy-3-(3-hydroxymethyl-6-methoxyquinolin-4-yl)propyl]-1-[3-(2,3,5-trifluorophenyl)prop-2-ynyl]piperid-4-ylmethanol 4-[3-(R,S)-Hydroxy-3-(3-hydroxymethyl-6-methoxyquinolin-4-yl)propyl]-1-[3-(thien-2-yl)prop-2-ynyl]piperid-4-ylmethanol 4-[3-(R,S)-Hydroxy-3-(3-fluoromethyl-6-methoxyquinolin-4-yl)propyl]-1-[2-(cyclohexyl)ethyl]piperid-4-ylmethanol 4-[3-(R,S)-Hydroxy-3-(3-fluoromethyl-6-methoxyquinolin-4-yl)propyl]-1-[3-(phenyl)propyl]piperid-4-ylmethanol 4-[3-(R,S)-Hydroxy-3-(3-fluoromethyl-6-methoxyquinolin-4-yl)propyl]-1-[3-(2,3,5-trifluorophenyl)propyl]piperid-4-ylmethanol 4-[3-(R,S)-Hydroxy-3-(3-fluoromethyl-6-methoxyquinolin-4-yl)propyl]-1-[2-(3,5-difluorophenylamino)ethyl]piperid-4-ylmethanol 4-[3-(R,S)-Hydroxy-3-(3-fluoromethyl-6-methoxyquinolin-4-yl)propyl]-1-[2-(2,3,5-trifluorophenylamino)ethyl]piperid-4-ylmethanol 4-[3-(R,S)-Hydroxy-3-(3-fluoromethyl-6-methoxyquinolin-4-yl)propyl]-1-[2-(3,5-difluorophenoxy)ethyl]piperid-4-ylmethanol 4-[3-(R,S)-Hydroxy-3-(3-fluoromethyl-6-methoxyquinolin-4-yl)propyl]-1-[2-(2,3,5-trifluorophenoxy)ethyl]piperid-4-ylmethanol 4-[3-(R,S)-Hydroxy-3-(3-fluoromethyl-6-methoxyquinolin-4-yl)propyl]-1-[2-(2,3,5-trifluorophenylthio)ethyl]piperid-4-ylmethanol 4-[3-(R,S)-Hydroxy-3-(3-fluoromethyl-6-methoxyquinolin-4-yl)propyl]-1-[2-(cyclopentylthio)ethyl]piperid-4-ylmethanol 4-[3-(R,S)-Hydroxy-3-(3-fluoromethyl-6-methoxyquinolin-4-yl)propyl]-1-[2-(pyrid-2-yl)thioethyl]piperid-4-ylmethanol 4-[3-(R,S)-Hydroxy-3-(3-fluoromethyl-6-methoxyquinolin-4-yl)propyl]-1-[2-(thien-2-yl)thioethyl]piperid-4-ylmethanol 4-[3-(R,S)-Hydroxy-3-(3-fluoromethyl-6-methoxyquinolin-4-yl)propyl]-1-[3-(2,3,5-trifluorophenyl)prop-2-ynyl]piperid-4-ylmethanol 4-[3-(R,S)-Hydroxy-3-(3-fluoromethyl-6-methoxyquinolin-4-yl)propyl]-1-[3-(thien-2-yl)prop-2-ynyl]piperid-4-ylmethanol 4-[3-(R,S)-Hydroxy-3-(3-aminomethyl-6-methoxyquinolin-4-yl)propyl]-1-[2-(cyclohexyl)ethyl]piperid-4-ylmethanol 4-[3-(R,S)-Hydroxy-3-(3-aminomethyl-6-methoxyquinolin-4-yl)propyl]-1-[3-(phenyl)propyl]piperid-4-ylmethanol 4-[3-(R,S)-Hydroxy-3-(3-aminomethyl-6-methoxyquinolin-4-yl)propyl]-1-[3-(2,3,5-trifluorophenyl)propyl]piperid-4-ylmethanol 4-[3-(R,S)-Hydroxy-3-(3-aminomethyl-6-methoxyquinolin-4-yl)propyl]-1-[2-(3,5-difluorophenylamino)ethyl]piperid-4-ylmethanol 4-[3-(R,S)-Hydroxy-3-(3-aminomethyl-6-methoxyquinolin-4-yl)propyl]-1-[2-(2,3,5-trifluorophenylamino)ethyl]piperid-4-ylmethanol 4-[3-(R,S)-Hydroxy-3-(3-aminomethyl-6-methoxyquinolin-4-yl)propyl]-1-[2-(3,5-difluorophenoxy)ethyl]piperid-4-ylmethanol 4-[3-(R,S)-Hydroxy-3-(3-aminomethyl-6-methoxyquinolin-4-yl)propyl]-1-[2-(2,3,5-trifluorophenoxy)ethyl]piperid-4-ylmethanol 4-[3-(R,S)-Hydroxy-3-(3-aminomethyl-6-methoxyquinolin-4-yl)propyl]-1-[2-(2,3,5-trifluorophenylthio)ethyl]piperid-4-ylmethanol 4-[3-(R,S)-Hydroxy-3-(3-aminomethyl-6-methoxyquinolin-4-yl)propyl]-1-[2-(cyclopentylthio)ethyl]piperid-4-ylmethanol 4-[3-(R,S)-Hydroxy-3-(3-aminomethyl-6-methoxyquinolin-4-yl)propyl]-1-[2-(pyrid-2-yl)thioethyl]piperid-4-ylmethanol 4-[3-(R,S)-Hydroxy-3-(3-aminomethyl-6-methoxyquinolin-4-yl)propyl]-1-[2-(thien-2-yl)thioethyl]piperid-4-ylmethanol 4-[3-(R,S)-Hydroxy-3-(3-aminomethyl-6-methoxyquinolin-4-yl)propyl]-1-[3-(2,3,5-trifluorophenyl)prop-2-ynyl]piperid-4-ylmethanol 4-[3-(R,S)-Hydroxy-3-(3-aminomethyl-6-methoxyquinolin-4-yl)propyl]-1-[3-(thien-2-yl)prop-2-ynyl]piperid-4-ylmethanol 4-[3-(R,S)-Hydroxy-3-(3-morpholinomethyl-6-methoxyquinolin-4-yl)propyl]-1-[2-(cyclohexyl)ethyl]piperid-4-ylmethanol 4-[3-(R,S)-Hydroxy-3-(3-morpholinomethyl-6-methoxyquinolin-4-yl)propyl]-1-[3-(phenyl)propyl]piperid-4-ylmethanol 4-[3-(R,S)-Hydroxy-3-(3-morpholinomethyl-6-methoxyquinolin-4-yl)propyl]-1-[3-(2,3,5-trifluorophenyl)propyl]piperid-4-ylmethanol 4-[3-(R,S)-Hydroxy-3-(3-morpholinomethyl-6-methoxyquinolin-4-yl)propyl]-1-[2-(3,5-difluorophenylamino)ethyl]piperid-4-ylmethanol 4-[3-(R,S)-Hydroxy-3-(3-morpholinomethyl-6-methoxyquinolin-4-yl)propyl]-1-[2-(2,3,5-trifluorophenylamino)ethyl]piperid-4-ylmethanol 4-[3-(R,S)-Hydroxy-3-(3-morpholinomethyl-6-methoxyquinolin-4-yl)propyl]-1-[2-(3,5-difluorophenoxy)ethyl]piperid-4-ylmethanol 4-[3-(R,S)-Hydroxy-3-(3-morpholinomethyl-6-methoxyquinolin-4-yl)propyl]-1-[2-(2,3,5-trifluorophenoxy)ethyl]piperid-4-ylmethanol 4-[3-(R,S)-Hydroxy-3-(3-morpholinomethyl-6-methoxyquinolin-4-yl)propyl]-1-[2-(2,3,5-trifluorophenylthio)ethyl]piperid-4-ylmethanol 4-[3-(R,S)-Hydroxy-3-(3-morpholinomethyl-6-methoxyquinolin-4-yl)propyl]-1-[2-(cyclopentylthio)ethyl]piperid-4-ylmethanol 4-[3-(R,S)-Hydroxy-3-(3-morpholinomethyl-6-methoxyquinolin-4-yl)propyl]-1-[2-(pyrid-2-yl)thioethyl]piperid-4-ylmethanol 4-[3-(R,S)-Hydroxy-3-(3-morpholinomethyl-6-methoxyquinolin-4-yl)propyl]-1-[2-(thien-2-yl)thioethyl]piperid-4-ylmethanol 4-[3-(R,S)-Hydroxy-3-(3-morpholinomethyl-6-methoxyquinolin-4-yl)propyl]-1-[3-(2,3,5-trifluorophenyl)prop-2-ynyl]piperid-4-ylmethanol 4-[3-(R,S)-Hydroxy-3-(3-morpholinomethyl-6-methoxyquinolin-4-yl)propyl]-1-[3-(thien-2-yl)prop-2-ynyl]piperid-4-ylmethanol 4-[3-(R,S)-Hydroxy-3-(3-methyl-6-methoxyquinolin-4-yl)propyl]-1-[3-(2,4,6-trifluorophenyl)propyl]piperid-4-ylmethanol 4-[3-(R,S)-Hydroxy-3-(3-methyl-6-methoxyquinolin-4-yl)propyl]-1-[3-(3,4,5-trifluorophenyl)propyl]piperid-4-ylmethanol 4-[3-(R,S)-Hydroxy-3-(3-methyl-6-methoxyquinolin-4-yl)propyl]-1-[2-(2,4,6-trifluorophenylthio)ethyl]piperid-4-ylmethanol 4-[3-(R,S)-Hydroxy-3-(3-methyl-6-methoxyquinolin-4-yl)propyl]-1-[2-(3,4,5-trifluorophenylthio)ethyl]piperid-4-ylmethanol 4-[3-(R,S)-Hydroxy-3-(3-methyl-6-methoxyquinolin-4-yl)propyl]-1-[2-(2,4,6-trifluorophenylamino)ethyl]piperid-4-ylmethanol 4-[3-(R,S)-Hydroxy-3-(3-methyl-6-methoxyquinolin-4-yl)propyl]-1-[2-(3,4,5-trifluorophenylamino)ethyl]piperid-4-ylmethanol 4-[3-(R,S)-Hydroxy-3-(3-methyl-6-methoxyquinolin-4-yl)propyl]-1-[2-(2,4,6-trifluorophenylamino)ethyl]piperid-4-ylmethanol 4-[3-(R,S)-Hydroxy-3-(3-methyl-6-methoxyquinolin-4-yl)propyl]-1-[2-(3,4,5-trifluorophenoxy)ethyl]piperid-4-ylmethanol 4-[3-(R,S)-Hydroxy-3-(3-methyl-6-methoxyquinolin-4-yl)propyl]-1-[3-(2,4,6-trifluorophenyl)prop-2-ynyl]piperid-4-ylmethanol 4-[3-(R,S)-Hydroxy-3-(3-methyl-6-methoxyquinolin-4-yl)propyl]-1-[3-(3,4,5-trifluorophenyl)prop-2-ynyl]piperid-4-ylmethanol 4-[3-(R,S)-Hydroxy-3-(3-fluoro-6-methoxyquinolin-4-yl)propyl]-1-[3-(2,4,6-trifluorophenyl)propyl]piperid-4-ylmethanol 4-[3-(R,S)-Hydroxy-3-(3-fluoro-6-methoxyquinolin-4-yl)propyl]-1-[3-(3,4,5-trifluorophenyl)propyl]piperid-4-ylmethanol 4-[3-(R,S)-Hydroxy-3-(3-fluoro-6-methoxyquinolin-4-yl)propyl]-1-[2-(2,4,6-trifluorophenylthio)ethyl]piperid-4-ylmethanol 4-[3-(R,S)-Hydroxy-3-(3-fluoro-6-methoxyquinolin-4-yl)propyl]-1-[2-(3,4,5-trifluorophenylthio)ethyl]piperid-4-ylmethanol 4-[3-(R,S)-Hydroxy-3-(3-fluoro-6-methoxyquinolin-4-yl)propyl]-1-[2-(2,4,6-trifluorophenylamino)ethyl]piperid-4-ylmethanol 4-[3-(R,S)-Hydroxy-3-(3-fluoro-6-methoxyquinolin-4-yl)propyl]-1-[2-(3,4,5-trifluorophenylamino)ethyl]piperid-4-ylmethanol 4-[3-(R,S)-Hydroxy-3-(3-fluoro-6-methoxyquinolin-4-yl)propyl]-1-[2-(2,4,6-trifluorophenoxy)ethyl]piperid-4-ylmethanol 4-[3-(R,S)-Hydroxy-3-(3-fluoro-6-methoxyquinolin-4-yl)propyl]-1-[2-(3,4,5-trifluorophenoxy)ethyl]piperid-4-ylmethanol 4-[3-(R,S)-Hydroxy-3-(3-fluoro-6-methoxyquinolin-4-yl)propyl]-1-[3-(2,4,6-trifluorophenyl)prop-2-ynyl]piperid-4-ylmethanol 4-[3-(R,S)-Hydroxy-3-(3-fluoro-6-methoxyquinolin-4-yl)propyl]-1-[3-(3,4,5-trifluorophenyl)prop-2-ynyl]piperid-4-ylmethanol 4-[3-(R,S)-Hydroxy-3-(3-dimethylamino-6-methoxyquinolin-4-yl)propyl]-1-[3-(2,4,6-trifluorophenyl)propyl]piperid-4-ylmethanol 4-[3-(R,S)-Hydroxy-3-(3-dimethylamino-6-methoxyquinolin-4-yl)propyl]-1-[3-(3,4,5-trifluorophenyl)propyl]piperid-4-ylmethanol 4-[3-(R,S)-Hydroxy-3-(3-dimethylamino-6-methoxyquinolin-4-yl)propyl]-1-[2-(2,4,6-trifluorophenylthio)ethyl]piperid-4-ylmethanol 4-[3-(R,S)-Hydroxy-3-(3-dimethylamino-6-methoxyquinolin-4-yl)propyl]-1-[2-(3,4,5-trifluorophenylthio)ethyl]piperid-4-ylmethanol 4-[3-(R,S)-Hydroxy-3-(3-dimethylamino-6-methoxyquinolin-4-yl)propyl]-1-[2-(2,4,6-trifluorophenylamino)ethyl]piperid-4-ylmethanol 4-[3-(R,S)-Hydroxy-3-(3-dimethylamino-6-methoxyquinolin-4-yl)propyl]-1-[2-(3,4,5-trifluorophenylamino)ethyl]piperid-4-ylmethanol 4-[3-(R,S)-Hydroxy-3-(3-dimethylamino-6-methoxyquinolin-4-yl)propyl]-1-[2-(2,4,6-trifluorophenoxy)ethyl]piperid-4-ylmethanol 4-[3-(R,S)-Hydroxy-3-(3-dimethylamino-6-methoxyquinolin-4-yl)propyl]-1-[2-(3,4,5-trifluorophenoxy)ethyl]piperid-4-ylmethanol 4-[3-(R,S)-Hydroxy-3-(3-dimethylamino-6-methoxyquinolin-4-yl)propyl]-1-[3-(2,4,6-trifluorophenyl)prop-2-ynyl]piperid-4-ylmethanol 4-[3-(R,S)-Hydroxy-3-(3-dimethylamino-6-methoxyquinolin-4-yl)propyl]-1-[3-(3,4,5-trifluorophenyl)prop-2-ynyl]piperid-4-ylmethanol 4-[3-(R,S)-Hydroxy-3-(3-hydroxymethyl-6-methoxyquinolin-4-yl)propyl]-1-[3-(3,4,5-trifluorophenyl)propyl]piperid-4-ylmethanol 4-[3-(R,S)-Hydroxy-3-(3-hydroxymethyl-6-methoxyquinolin-4-yl)propyl]-1-[2-(2,4,6-trifluorophenylthio)ethyl]piperid-4-ylmethanol 4-[3-(R,S)-Hydroxy-3-(3-hydroxymethyl-6-methoxyquinolin-4-yl)propyl]-1-[2-(3,4,5-trifluorophenylthio)ethyl]piperid-4-ylmethanol 4-[3-(R,S)-Hydroxy-3-(3-hydroxymethyl-6-methoxyquinolin-4-yl)propyl]-1-[2-(2,4,6-trifluorophenylamino)ethyl]piperid-4-ylmethanol 4-[3-(R,S)-Hydroxy-3-(3-hydroxymethyl-6-methoxyquinolin-4-yl)propyl]-1-[2-(3,4,5-trifluorophenylamino)ethyl]piperid-4-ylmethanol 4-[3-(R,S)-Hydroxy-3-(3-hydroxymethyl-6-methoxyquinolin-4-yl)propyl]-1-[2-(2,4,6-trifluorophenoxy)ethyl]piperid-4-ylmethanol 4-[3-(R,S)-Hydroxy-3-(3-hydroxymethyl-6-methoxyquinolin-4-yl)propyl]-1-[2-(3,4,5-trifluorophenoxy)ethyl]piperid-4-ylmethanol 4-[3-(R,S)-Hydroxy-3-(3-hydroxymethyl-6-methoxyquinolin-4-yl)propyl]-1-[3-(2,4,6-trifluorophenyl)prop-2-ynyl]piperid-4-ylmethanol 4-[3-(R,S)-Hydroxy-3-(3-hydroxymethyl-6-methoxyquinolin-4-yl)propyl]-1-[3-(3,4,5-trifluorophenyl)prop-2-ynyl]piperid-4-ylmethanol 4-[3-(R,S)-Hydroxy-3-(3-fluoromethyl-6-methoxyquinolin-4-yl)propyl]-1-[3-(2,4,6-trifluorophenyl)propyl]piperid-4-ylmethanol 4-[3-(R,S)-Hydroxy-3-(3-fluoromethyl-6-methoxyquinolin-4-yl)propyl]-1-[3-(3,4,5-trifluorophenyl)propyl]piperid-4-ylmethanol 4-[3-(R,S)-Hydroxy-3-(3-fluoromethyl-6-methoxyquinolin-4-yl)propyl]-1-[2-(2,4,6-trifluorophenylthio)ethyl]piperid-4-ylmethanol 4-[3-(R,S)-Hydroxy-3-(3-fluoromethyl-6-methoxyquinolin-4-yl)propyl]-1-[2-(3,4,5-trifluorophenylthio)ethyl]piperid-4-ylmethanol 4-[3-(R,S)-Hydroxy-3-(3-fluoromethyl-6-methoxyquinolin-4-yl)propyl]-1-[2-(2,4,6-trifluorophenylamino)ethyl]piperid-4-ylmethanol 4-[3-(R,S)-Hydroxy-3-(3-fluoromethyl-6-methoxyquinolin-4-yl)propyl]-1-[2-(3,4,5-trifluorophenylamino)ethyl]piperid-4-ylmethanol 4-[3-(R,S)-Hydroxy-3-(3-fluoromethyl-6-methoxyquinolin-4-yl)propyl]-1-[2-(2,4,6-trifluorophenoxy)ethyl]piperid-4-ylmethanol 4-[3-(R,S)-Hydroxy-3-(3-fluoromethyl-6-methoxyquinolin-4-yl)propyl]-1-[2-(3,4,5-trifluorophenoxy)ethyl]piperid-4-ylmethanol 4-[3-(R,S)-Hydroxy-3-(3-fluoromethyl-6-methoxyquinolin-4-yl)propyl]-1-[3-(2,4,6-trifluorophenyl)prop-2-ynyl]piperid-4-ylmethanol 4-[3-(R,S)-Hydroxy-3-(3-fluoromethyl-6-methoxyquinolin-4-yl)propyl]-1-[3-(3,4,5-trifluorophenyl)prop-2-ynyl]piperid-4-ylmethanol 4-[3-(R,S)-Hydroxy-3-(3-aminomethyl-6-methoxyquinolin-4-yl)propyl]-1-[3-(2,4,6-trifluorophenyl)propyl]piperid-4-ylmethanol 4-[3-(R,S)-Hydroxy-3-(3-aminomethyl-6-methoxyquinolin-4-yl)propyl]-1-[3-(3,4,5-trifluorophenyl)propyl]piperid-4-ylmethanol 4-[3-(R,S)-Hydroxy-3-(3-aminomethyl-6-methoxyquinolin-4-yl)propyl]-1-[2-(2,4,6-trifluorophenylthio)ethyl]piperid-4-ylmethanol 4-[3-(R,S)-Hydroxy-3-(3-aminomethyl-6-methoxyquinolin-4-yl)propyl]-1-[2-(3,4,5-trifluorophenylthio)ethyl]piperid-4-ylmethanol 4-[3-(R,S)-Hydroxy-3-(3-aminomethyl-6-methoxyquinolin-4-yl)propyl]-1-[2-(2,4,6-trifluorophenylamino)ethyl]piperid-4-ylmethanol 4-[3-(R,S)-Hydroxy-3-(3-aminomethyl-6-methoxyquinolin-4-yl)propyl]-1-[2-(3,4,5-trifluorophenylamino)ethyl]piperid-4-ylmethanol 4-[3-(R,S)-Hydroxy-3-(3-aminomethyl-6-methoxyquinolin-4-yl)propyl]-1-[2-(2,4,6-trifluorophenoxy)ethyl]piperid-4-ylmethanol 4-[3-(R,S)-Hydroxy-3-(3-aminomethyl-6-methoxyquinolin-4-yl)propyl]-1-[2-(3,4,5-trifluorophenoxy)ethyl]piperid-4-ylmethanol 4-[3-(R,S)-Hydroxy-3-(3-aminomethyl-6-methoxyquinolin-4-yl)propyl]-1-[3-(2,4,6-trifluorophenyl)prop-2-ynyl]piperid-4-ylmethanol 4-[3-(R,S)-Hydroxy-3-(3-aminomethyl-6-methoxyquinolin-4-yl)propyl]-1-[3-(3,4,5-trifluorophenyl)prop-2-ynyl]piperid-4-ylmethanol 4-[3-(R,S)-Hydroxy-3-(3-morpholinomethyl-6-methoxyquinolin-4-yl)propyl]-1-[3-(2,4,6-trifluorophenyl)propyl]piperid-4-ylmethanol 4-[3-(R,S)-Hydroxy-3-(3-morpholinomethyl-6-methoxyquinolin-4-yl)propyl]-1-[3-(3,4,5-trifluorophenyl)propyl]piperid-4-ylmethanol 4-[3-(R,S)-Hydroxy-3-(3-morpholinomethyl-6-methoxyquinolin-4-yl)propyl]-1-[2-(2,4,6-trifluorophenylthio)ethyl]piperid-4-ylmethanol 4-[3-(R,S)-Hydroxy-3-(3-morpholinomethyl-6-methoxyquinolin-4-yl)propyl]-1-[2-(3,4,5-trifluorophenylthio)ethyl]piperid-4-ylmethanol 4-[3-(R,S)-Hydroxy-3-(3-morpholinomethyl-6-methoxyquinolin-4-yl)propyl]-1-[2-(2,4,6-trifluorophenylamino)ethyl]piperid-4-ylmethanol 4-[3-(R,S)-Hydroxy-3-(3-morpholinomethyl-6-methoxyquinolin-4-yl)propyl]-1-[2-(3,4,5-trifluorophenylamino)ethyl]piperid-4-ylmethanol 4-[3-(R,S)-Hydroxy-3-(3-morpholinomethyl-6-methoxyquinolin-4-yl)propyl]-1-[2-(2,4,6-trifluorophenoxy)ethyl]piperid-4-ylmethanol 4-[3-(R,S)-Hydroxy-3-(3-morpholinomethyl-6-methoxyquinolin-4-yl)propyl]-1-[2-(3,4,5-trifluorophenoxy)ethyl]piperid-4-ylmethanol 4-[3-(R,S)-Hydroxy-3-(3-morpholinomethyl-6-methoxyquinolin-4-yl)propyl]-1-[3-(2,4,6-trifluorophenyl)prop-2-ynyl]piperid-4-ylmethanol 4-[3-(R,S)-Hydroxy-3-(3-morpholinomethyl-6-methoxyquinolin-4-yl)propyl]-1-[3-(3,4,5-trifluorophenyl)prop-2-ynyl]piperid-4-ylmethanol 4-[3-(R,S)-Fluoro-3-(3-chloro-6-methoxyquinolin-4-yl)propyl]-1-heptylpiperid-4-ylmethanol 4-[3-(R,S)-Fluoro-3-(3-chloro-6-methoxyquinolin-4-yl)propyl]-1-[4-phenylbutyl]piperid-4-ylmethanol 4-[3-(R,S)-Fluoro-3-(3-chloro-6-methoxyquinolin-4-yl)propyl]-1-[3-(phenyl)propyl]piperid-4-ylmethanol 4-[3-(R,S)-Fluoro-3-(3-chloro-6-methoxyquinolin-4-yl)propyl]-1-[4-(2-fluorophenyl)propyl]piperid-4-ylmethanol 4-[3-(R,S)-Fluoro-3-(3-chloro-6-methoxyquinolin-4-yl)propyl]-1-[4-(3-fluorophenyl)propyl]piperid-4-ylmethanol 4-[3-(R,S)-Fluoro-3-(3-chloro-6-methoxyquinolin-4-yl)propyl]-1-[3-(4-fluorophenyl)propyl]piperid-4-ylmethanol 4-[3-(R,S)-Fluoro-3-(3-chloro-6-methoxyquinolin-4-yl)propyl]-1-[4-(4-fluorophenyl)butyl]piperid-4-ylmethanol 4-[3-(R,S)-Fluoro-3-(3-chloro-6-methoxyquinolin-4-yl)propyl]-1-[3-(2,3-difluorophenyl)propyl]piperid-4-ylmethanol 4-[3-(R,S)-Fluoro-3-(3-chloro-6-methoxyquinolin-4-yl)propyl]-1-[4-(2,3-difluorophenyl)propyl]piperid-4-ylmethanol 4-[3-(R,S)-Fluoro-3-(3-chloro-6-methoxyquinolin-4-yl)propyl]-1-[3-(2,6-difluorophenyl)propyl]piperid-4-ylmethanol 4-[3-(R,S)-Fluoro-3-(3-chloro-6-methoxyquinolin-4-yl)propyl]-1-[4-(2,6-difluorophenyl)propyl]piperid-4-ylmethanol 4-[3-(R,S)-Fluoro-3-(3-chloro-6-methoxyquinolin-4-yl)propyl]-1-[3-(3,5-difluorophenyl)propyl]piperid-4-ylmethanol 4-[3-(R,S)-Fluoro-3-(3-chloro-6-methoxyquinolin-4-yl)propyl]-1-[3-(2,3,5-trifluorophenyl)propyl]piperid-4-ylmethanol 4-[3-(R,S)-Fluoro-3-(3-chloro-6-methoxyquinolin-4-yl)propyl]-1-[3-(2,4,6-trifluorophenyl)propyl]piperid-4-ylmethanol 4-[3-(R,S)-Fluoro-3-(3-chloro-6-methoxyquinolin-4-yl)propyl]-1-[3-(3,4,5-trifluorophenyl)propyl]piperid-4-ylmethanol 4-[3-(R,S)-Fluoro-3-(3-chloro-6-methoxyquinolin-4-yl)propyl]-1-[3-phenylthio-propyl]piperid-4-ylmethanol 4-[3-(R,S)-Fluoro-3-(3-chloro-6-methoxyquinolin-4-yl)propyl]-1-[3-(2-fluorophenylthio)propyl]piperid-4-ylmethanol 4-[3-(R,S)-Fluoro-3-(3-chloro-6-methoxyquinolin-4-yl)propyl]-1-[3-(3-fluorophenylthio)propyl]piperid-4-ylmethanol 4-[3-(R,S)-Fluoro-3-(3-chloro-6-methoxyquinolin-4-yl)propyl]-1-[2-(4-fluorophenylthio)ethyl]piperid-4-ylmethanol 4-[3-(R,S)-Fluoro-3-(3-chloro-6-methoxyquinolin-4-yl)propyl]-1-[3-(4-fluorophenylthio)propyl]piperid-4-ylmethanol 4-[3-(R,S)-Fluoro-3-(3-chloro-6-methoxyquinolin-4-yl)propyl]-1-[2-(2,3-difluorophenylthio)ethyl]piperid-4-ylmethanol 4-[3-(R,S)-Fluoro-3-(3-chloro-6-methoxyquinolin-4-yl)propyl]-1-[3-(2,3-difluorophenylthio)propyl]piperid-4-ylmethanol 4-[3-(R,S)-Fluoro-3-(3-chloro-6-methoxyquinolin-4-yl)propyl]-1-[2-(2,6-difluorophenylthio)ethyl]piperid-4-ylmethanol 4-[3-(R,S)-Fluoro-3-(3-chloro-6-methoxyquinolin-4-yl)propyl]-1-[2-(2,3,5-trifluorophenylthio)ethyl]piperid-4-ylmethanol 4-[3-(R,S)-Fluoro-3-(3-chloro-6-methoxyquinolin-4-yl)propyl]-1-[2-(2,4,6-trifluorophenylthio)ethyl]piperid-4-ylmethanol 4-[3-(R,S)-Fluoro-3-(3-chloro-6-methoxyquinolin-4-yl)propyl]-1-[2-(3,4,5-trifluorophenylthio)ethyl]piperid-4-ylmethanol 4-[3-(R,S)-Fluoro-3-(3-chloro-6-methoxyquinolin-4-yl)propyl]-1-[2-(3,5-difluorophenoxy)ethyl]piperid-4-ylmethanol 4-[3-(R,S)-Fluoro-3-(3-chloro-6-methoxyquinolin-4-yl)propyl]-1-[2-(2,3,5-trifluorophenoxy)ethyl]piperid-4-ylmethanol 4-[3-(R,S)-Fluoro-3-(3-chloro-6-methoxyquinolin-4-yl)propyl]-1-[2-(2,4,6-trifluorophenoxy)ethyl]piperid-4-ylmethanol 4-[3-(R,S)-Fluoro-3-(3-chloro-6-methoxyquinolin-4-yl)propyl]-1-[2-(3,4,5-trifluorophenoxy)ethyl]piperid-4-ylmethanol 4-[3-(R,S)-Fluoro-3-(3-chloro-6-methoxyquinolin-4-yl)propyl]-1-[2-(3,5-difluorophenylamino)ethyl]piperid-4-ylmethanol 4-[3-(R,S)-Fluoro-3-(3-chloro-6-methoxyquinolin-4-yl)propyl]-1-[2-(2,3,5-trifluorophenylamino)ethyl]piperid-4-ylmethanol 4-[3-(R,S)-Fluoro-3-(3-chloro-6-methoxyquinolin-4-yl)propyl]-1-[2-(2,4,6-trifluorophenylamino)ethyl]piperid-4-ylmethanol 4-[3-(R,S)-Fluoro-3-(3-chloro-6-methoxyquinolin-4-yl)propyl]-1-[2-(3,4,5-trifluorophenylamino)ethyl]piperid-4-ylmethanol 4-[3-(R,S)-Fluoro-3-(3-chloro-6-methoxyquinolin-4-yl)propyl]-1-[3-(2,6-difluorophenylthio)propyl]piperid-4-ylmethanol 4-[3-(R,S)-Fluoro-3-(3-chloro-6-methoxyquinolin-4-yl)propyl]-1-[2-(2-chlorophenylthio)ethyl]piperid-4-ylmethanol 4-[3-(R,S)-Fluoro-3-(3-chloro-6-methoxyquinolin-4-yl)propyl]-1-[3-(2-chlorophenylthio)propyl]piperid-4-ylmethanol 4-[3-(R,S)-Fluoro-3-(3-chloro-6-methoxyquinolin-4-yl)propyl]-1-[2-(3-chlorophenylthio)ethyl]piperid-4-ylmethanol 4-[3-(R,S)-Fluoro-3-(3-chloro-6-methoxyquinolin-4-yl)propyl]-1-[3-(3-chlorophenylthio)propyl]piperid-4-ylmethanol 4-[3-(R,S)-Fluoro-3-(3-chloro-6-methoxyquinolin-4-yl)propyl]-1-[2-(4-chlorophenylthio)ethyl]piperid-4-ylmethanol 4-[3-(R,S)-Fluoro-3-(3-chloro-6-methoxyquinolin-4-yl)propyl]-1-[3-(4-chlorophenylthio)propyl]piperid-4-ylmethanol 4-[3-(R,S)-Fluoro-3-(3-chloro-6-methoxyquinolin-4-yl)propyl]-1-[2-(2-methylphenylthio)ethyl]piperid-4-ylmethanol 4-[3-(R,S)-Fluoro-3-(3-chloro-6-methoxyquinolin-4-yl)propyl]-1-[3-(2-methylphenylthio)propyl]piperid-4-ylmethanol 4-[3-(R,S)-Fluoro-3-(3-chloro-6-methoxyquinolin-4-yl)propyl]-1-[2-(3-methylphenylthio)ethyl]piperid-4-ylmethanol 4-[3-(R,S)-Fluoro-3-(3-chloro-6-methoxyquinolin-4-yl)propyl]-1-[3-(3-methylphenylthio)propyl]piperid-4-ylmethanol 4-[3-(R,S)-Fluoro-3-(3-chloro-6-methoxyquinolin-4-yl)propyl]-1-[2-(4-methylphenylthio)ethyl]piperid-4-ylmethanol 4-[3-(R,S)-Fluoro-3-(3-chloro-6-methoxyquinolin-4-yl)propyl]-1-[3-(4-methylphenylthio)propyl]piperid-4-ylmethanol 4-[3-(R,S)-Fluoro-3-(3-chloro-6-methoxyquinolin-4-yl)propyl]-1-[2-(2-trifluoromethylphenylthio)ethyl]piperid-4-ylmethanol 4-[3-(R,S)-Fluoro-3-(3-chloro-6-methoxyquinolin-4-yl)propyl]-1-[3-(2-trifluoromethylphenylthio)propyl]piperid-4-ylmethanol 4-[3-(R,S)-Fluoro-3-(3-chloro-6-methoxyquinolin-4-yl)propyl]-1-[2-(3-trifluoromethylphenylthio)ethyl]piperid-4-ylmethanol 4-[3-(R,S)-Fluoro-3-(3-chloro-6-methoxyquinolin-4-yl)propyl]-1-[3-(3-trifluoromethylphenylthio)propyl]piperid-4-ylmethanol 4-[3-(R,S)-Fluoro-3-(3-chloro-6-methoxyquinolin-4-yl)propyl]-1-[2-(4-trifluoromethylphenylthio)ethyl]piperid-4-ylmethanol 4-[3-(R,S)-Fluoro-3-(3-chloro-6-methoxyquinolin-4-yl)propyl]-1-[3-(4-trifluoromethylphenylthio)propyl]piperid-4-ylmethanol 4-[3-(R,S)-Fluoro-3-(3-chloro-6-methoxyquinolin-4-yl)propyl]-1-[2-(2-methoxyphenylthio)ethyl]piperid-4-ylmethanol 4-[3-(R,S)-Fluoro-3-(3-chloro-6-methoxyquinolin-4-yl)propyl]-1-[3-(2-methoxyphenylthio)propyl]piperid-4-ylmethanol 4-[3-(R,S)-Fluoro-3-(3-chloro-6-methoxyquinolin-4-yl)propyl]-1-[2-(3-methoxyphenylthio)ethyl]piperid-4-ylmethanol 4-[3-(R,S)-Fluoro-3-(3-chloro-6-methoxyquinolin-4-yl)propyl]-1-[3-(3-methoxyphenylthio)propyl]piperid-4-ylmethanol 4-[3-(R,S)-Fluoro-3-(3-chloro-6-methoxyquinolin-4-yl)propyl]-1-[2-(4-methoxyphenylthio)ethyl]piperid-4-ylmethanol 4-[3-(R,S)-Fluoro-3-(3-chloro-6-methoxyquinolin-4-yl)propyl]-1-[3-(4-methoxyphenylthio)propyl]piperid-4-ylmethanol 4-[3-(R,S)-Fluoro-3-(3-chloro-6-methoxyquinolin-4-yl)propyl]-1-[cyclopentylmethyl]piperid-4-ylmethanol 4-[3-(R,S)-Fluoro-3-(3-chloro-6-methoxyquinolin-4-yl)propyl]-1-[2-(cyclopentyl)ethyl]piperid-4-ylmethanol 4-[3-(R,S)-Fluoro-3-(3-chloro-6-methoxyquinolin-4-yl)propyl]-1-[2-(cyclohexyl)-ethyl]piperid-4-ylmethanol 4-[3-(R,S)-Fluoro-3-(3-chloro-6-methoxyquinolin-4-yl)propyl]-1-[2-(cyclopentylthio)-ethyl]piperid-4-ylmethanol 4-[3-(R,S)-Fluoro-3-(3-chloro-6-methoxyquinolin-4-yl)propyl]-1-[3-(cyclopentylthio)-propyl]piperid-4-ylmethanol 4-[3-(R,S)-Fluoro-3-(3-chloro-6-methoxyquinolin-4-yl)propyl]-1-[3-(cyclohexylthio)-propyl]piperid-4-ylmethanol 4-[3-(R,S)-Fluoro-3-(3-chloro-6-methoxyquinolin-4-yl)propyl]-1-[2-(pyrid-2-yl)thioethyl]-piperid-4-ylmethanol 4-[3-(R,S)-Fluoro-3-(3-chloro-6-methoxyquinolin-4-yl)propyl]-1-[4-(thien-2-yl)butyl]-piperid-4-ylmethanol 4-[3-(R,S)-Fluoro-3-(3-chloro-6-methoxyquinolin-4-yl)propyl]-1-[3-(thien-2-yl)thiopropyl]-piperid-4-ylmethanol 4-[3-(R,S)-Fluoro-3-(3-chloro-6-methoxyquinolin-4-yl)propyl]-1-[3-(thien-3-yl)propyl]-piperid-4-ylmethanol 4-[3-(R,S)-Fluoro-3-(3-chloro-6-methoxyquinolin-4-yl)propyl]-1-[4-(thien-3-yl)butyl]-piperid-4-ylmethanol 4-[3-(R,S)-Fluoro-3-(3-chloro-6-methoxyquinolin-4-yl)propyl]-1-[2-(thien-2-yl)thioethyl]-piperid-4-ylmethanol 4-[3-(R,S)-Fluoro-3-(3-chloro-6-methoxyquinolin-4-yl)propyl]-1-[2-(thien-3-yl)thioethyl]-piperid-4-ylmethanol 4-[3-(R,S)-Fluoro-3-(3-chloro-6-methoxyquinolin-4-yl)propyl]-1-[3-(thien-3-yl)thiopropyl]-piperid-4-ylmethanol 4-[3-(R,S)-Fluoro-3-(3-chloro-6-methoxyquinolin-4-yl)propyl]-1-[3-(1,3-thiazol-2-yl)propyl]piperid-4-ylmethanol 4-[3-(R,S)-Fluoro-3-(3-chloro-6-methoxyquinolin-4-yl)propyl]-1-[4-(1,3-thiazol-2-yl)butyl]piperid-4-ylmethanol 4-[3-(R,S)-Fluoro-3-(3-chloro-6-methoxyquinolin-4-yl)propyl]-1-[3-(1,3-thiazol-2-yl)thioethyl]piperid-4-ylmethanol 4-[3-(R,S)-Fluoro-3-(3-chloro-6-methoxyquinolin-4-yl)propyl]-1-[3-(pyrid-2-yl)propyl]piperid-4-ylmethanol 4-[3-(R,S)-Fluoro-3-(3-chloro-6-methoxyquinolin-4-yl)propyl]-1-[4-(pyrid-2-yl)butyl]piperid-4-ylmethanol 4-[3-(R,S)-Fluoro-3-(3-chloro-6-methoxyquinolin-4-yl)propyl]-1-[3-(pyrid-2-yl)thiopropyl]piperid-4-ylmethanol 4-[3-(R,S)-Fluoro-3-(3-chloro-6-methoxyquinolin-4-yl)propyl]-1-[3-(pyrid-3-yl)propyl]piperid-4-ylmethanol 4-[3-(R,S)-Fluoro-3-(3-chloro-6-methoxyquinolin-4-yl)propyl]-1-[4-(pyrid-3-yl)butyl]piperid-4-ylmethanol 4-[3-(R,S)-Fluoro-3-(3-chloro-6-methoxyquinolin-4-yl)propyl]-1-[2-(pyrid-3-yl)thioethyl]piperid-4-ylmethanol 4-[3-(R,S)-Fluoro-3-(3-chloro-6-methoxyquinolin-4-yl)propyl]-1-[3-(pyrid-3-yl)thiopropyl]piperid-4-ylmethanol 4-[3-(R,S)-Fluoro-3-(3-chloro-6-methoxyquinolin-4-yl)propyl]-1-[3-(pyrid-4-yl)propyl]piperid-4-ylmethanol 4-[3-(R,S)-Fluoro-3-(3-chloro-6-methoxyquinolin-4-yl)propyl]-1-[4-(pyrid-4-yl)butyl]piperid-4-ylmethanol 4-[3-(R,S)-Fluoro-3-(3-chloro-6-methoxyquinolin-4-yl)propyl]-1-[2-(pyrid-4-yl)thioethyl]piperid-4-ylmethanol 4-[3-(R,S)-Fluoro-3-(3-chloro-6-methoxyquinolin-4-yl)propyl]-1-[3-(pyrid-4-yl)thiopropyl]piperid-4-ylmethanol 4-[3-(R,S)-Fluoro-3-(3-chloro-6-methoxyquinolin-4-yl)propyl]-1-[3-(pyrazin-2-yl)propyl]piperid-4-ylmethanol 4-[3-(R,S)-Fluoro-3-(3-chloro-6-methoxyquinolin-4-yl)propyl]-1-[4-(pyrazin-2-yl)butyl]piperid-4-ylmethanol 4-[3-(R,S)-Fluoro-3-(3-chloro-6-methoxyquinolin-4-yl)propyl]-1-[2-(pyrazin-2-yl)thioethyl]piperid-4-ylmethanol 4-[3-(R,S)-Fluoro-3-(3-chloro-6-methoxyquinolin-4-yl)propyl]-1-[3-(pyrazin-2-yl)thiopropyl]piperid-4-ylmethanol 4-[3-(R,S)-Fluoro-3-(3-chloro-6-methoxyquinolin-4-yl)propyl]-1-[3-(4-fluorophenyl)prop-2-ynyl]piperid-4-ylmethanol 4-[3-(R,S)-Fluoro-3-(3-chloro-6-methoxyquinolin-4-yl)propyl]-1-[3-(3,4-difluorophenyl)prop-2-ynyl]piperid-4-ylmethanol 4-[3-(R,S)-Fluoro-3-(3-chloro-6-methoxyquinolin-4-yl)propyl]-1-[3-(2,4-difluorophenyl)prop-2-ynyl]piperid-4-ylmethanol 4-[3-(R,S)-Fluoro-3-(3-chloro-6-methoxyquinolin-4-yl)propyl]-1-[3-(2,3,5-trifluorophenyl)prop-2-ynyl]piperid-4-ylmethanol 4-[3-(R,S)-Fluoro-3-(3-chloro-6-methoxyquinolin-4-yl)
propyl]-1-[3-(2,4,6-trifluorophenyl)prop-2-ynyl]
piperid-4-ylmethanol 4-[3-(R,S)-Fluoro-3-(3-chloro-6-methoxyquinolin-4-yl)
propyl]-1-[3-(3,4,5-trifluorophenyl)prop-2-ynyl]
piperid-4-ylmethanol 4-[3-(R,S)-Fluoro-3-(3-chloro-6-methoxyquinolin-4-yl)
propyl]-1-[3-(4-chloro-3-fluorophenyl)prop-2-ynyl]
piperid-4-ylmethanol 4-[3-(R,S)-Fluoro-3-(3-chloro-6-methoxyquinolin-4-yl)
propyl]-1-[3-(3-chloro-4-fluorophenyl)prop-2-ynyl]
piperid-4-ylmethanol 4-[3-(R,S)-Fluoro-3-(3-chloro-6-methoxyquinolin-4-yl)
propyl]-1-[3-(2-chloro-4-fluorophenyl)prop-2-ynyl]
piperid-4-ylmethanol 4-[3-(R,S)-Fluoro-3-(3-chloro-6-methoxyquinolin-4-yl)
propyl]-1-[3-(3-chloro-5-fluorophenyl)prop-2-ynyl]
piperid-4-ylmethanol 4-[3-(R,S)-Fluoro-3-(3-chloro-6-methoxyquinolin-4-yl)
propyl]-1-[3-(4-chloro-2-fluorophenyl)prop-2-ynyl]
piperid-4-ylmethanol 4-[3-(R,S)-Fluoro-3-(3-chloro-6-methoxyquinolin-4-yl)
propyl]-1-[3-(3-fluoro-4-methylphenyl)prop-2-ynyl]
piperid-4-ylmethanol 4-[3-(R,S)-Fluoro-3-(3-chloro-6-methoxyquinolin-4-yl)
propyl]-1-[3-(3,5-bis(trifluoromethyl)phenyl)prop-2-
ynyl]piperid-4-ylmethanol 4-[3-(R,S)-Fluoro-3-(3-chloro-6-methoxyquinolin-4-yl)
propyl]-1-[3-(thien-2-yl)prop-2-ynyl]piperid-4-
ylmethanol 4-[3-(R,S)-Fluoro-3-(3-chloro-6-methoxyquinolin-4-yl)
propyl]-1-[3-(thien-3-yl)prop-2-ynyl]piperid-4-
ylmethanol 4-[3-(R,S)-Fluoro-3-(3-chloro-6-methoxyquinolin-4-yl)
propyl]-1-[3-(1,3-thiazol-2-yl)prop-2-ynyl]piperid-4-
ylmethanol 4-[3-(R,S)-Fluoro-3-(3-chloro-6-methoxyquinolin-4-yl)
propyl]-1-[3-(1,3-thiazol-4-yl)prop-2-ynyl]piperid-4-
ylmethanol 4-[3-(R,S)-Fluoro-3-(3-chloro-6-methoxyquinolin-4-yl)
propyl]-1-[3-(1,3-thiazol-5-yl)prop-2-ynyl]piperid-4-
ylmethanol 4-[3-(R,S)-Fluoro-3-(3-chloro-6-methoxyquinolin-4-yl)
propyl]-1-[3-(pyrid-2-yl)prop-2-ynyl]piperid-4-
ylmethanol 4-[3-(R,S)-Fluoro-3-(3-chloro-6-methoxyquinolin-4-yl)
propyl]-1-[3-(pyrid-3-yl)prop-2-ynyl]piperid-4-
ylmethanol 4-[3-(R,S)-Fluoro-3-(3-chloro-6-methoxyquinolin-4-yl)
propyl]-1-[3-(pyrid-4-yl)prop-2-ynyl]piperid-4-
ylmethanol 4-[3-(R,S)-Fluoro-3-(3-methyl-6-methoxyquinolin-4-yl)
propyl]-1-[2-(cyclohexyl)ethyl]piperid-4-ylmethanol 4-[3-(R,S)-Fluoro-3-(3-methyl-6-methoxyquinolin-4-yl)
propyl]-1-[3-(phenyl)propyl]piperid-4-ylmethanol 4-[3-(R,S)-Fluoro-3-(3-methyl-6-methoxyquinolin-4-yl)
propyl]-1-[3-(2,3,5-trifluorophenyl)propyl]piperid-4-
ylmethanol 4-[3-(R,S)-Fluoro-3-(3-methyl-6-methoxyquinolin-4-yl)
propyl]-1-[2-(3,5-difluorophenylamino)ethyl]piperid-
4-ylmethanol 4-[3-(R,S)-Fluoro-3-(3-methyl-6-methoxyquinolin-4-yl)
propyl]-1-[2-(2,3,5-trifluorophenylamino)ethyl]
piperid-4-ylmethanol 4-[3-(R,S)-Fluoro-3-(3-methyl-6-methoxyquinolin-4-yl)
propyl]-1-[2-(3,5-difluorophenoxy)ethyl]piperid-4-
ylmethanol 4-[3-(R,S)-Fluoro-3-(3-methyl-6-methoxyquinolin-4-yl)
propyl]-1-[2-(2,3,5-trifluorophenoxy)ethyl]piperid-4-
ylmethanol 4-[3-(R,S)-Fluoro-3-(3-methyl-6-methoxyquinolin-4-yl)
propyl]-1-[2-(2,3,5-trifluorophenylthio)ethyl]piperid-
4-ylmethanol 4-[3-(R,S)-Fluoro-3-(3-methyl-6-methoxyquinolin-4-yl)
propyl]-1-[2-(cyclopentylthio)ethyl]piperid-4-
ylmethanol 4-[3-(R,S)-Fluoro-3-(3-methyl-6-methoxyquinolin-4-yl)
propyl]-1-[2-(pyrid-2-yl)thioethyl]piperid-4-
ylmethanol 4-[3-(R,S)-Fluoro-3-(3-methyl-6-methoxyquinolin-4-yl)
propyl]-1-[2-(thien-2-yl)thioethyl]piperid-4-
ylmethanol 4-[3-(R,S)-Fluoro-3-(3-methyl-6-methoxyquinolin-4-yl)
propyl]-1-[3-(2,3,5-trifluorophenyl)prop-2-ynyl]
piperid-4-ylmethanol 4-[3-(R,S)-Fluoro-3-(3-methyl-6-methoxyquinolin-4-yl)
propyl]-1-[3-(thien-2-yl)prop-2-ynyl]piperid-4-
ylmethanol 4-[3-(R,S)-Fluoro-3-(3-fluoro-6-methoxyquinolin-4-yl)
propyl]-1-[2-(cyclohexyl)ethyl]piperid-4-ylmethanol 4-[3-(R,S)-Fluoro-3-(3-fluoro-6-methoxyquinolin-4-yl)
propyl]-1-[3-(phenyl)propyl]piperid-4-ylmethanol 4-[3-(R,S)-Fluoro-3-(3-fluoro-6-methoxyquinolin-4-yl)
propyl]-1-[3-(2,3,5-trifluorophenyl)propyl]piperid-4-
ylmethanol 4-[3-(R,S)-Fluoro-3-(3-fluoro-6-methoxyquinolin-4-yl)
propyl]-1-[2-(3,5-difluorophenylamino)ethyl]piperid-
4-ylmethanol 4-[3-(R,S)-Fluoro-3-(3-fluoro-6-methoxyquinolin-4-yl)
propyl]-1-[2-(2,3,5-trifluorophenylamino)ethyl]
piperid-4-ylmethanol 4-[3-(R,S)-Fluoro-3-(3-fluoro-6-methoxyquinolin-4-yl)
propyl]-1-[2-(3,5-difluorophenoxy)ethyl]piperid-4-
ylmethanol 4-[3-(R,S)-Fluoro-3-(3-fluoro-6-methoxyquinolin-4-yl)
propyl]-1-[2-(2,3,5-trifluorophenoxy)ethyl]piperid-4-
ylmethanol 4-[3-(R,S)-Fluoro-3-(3-fluoro-6-methoxyquinolin-4-yl)
propyl]-1-[2-(2,3,5-trifluorophenylthio)ethyl]piperid-
4-ylmethanol 4-[3-(R,S)-Fluoro-3-(3-fluoro-6-methoxyquinolin-4-yl)
propyl]-1-[2-(cyclopentylthio)ethyl]piperid-4-
ylmethanol 4-[3-(R,S)-Fluoro-3-(3-fluoro-6-methoxyquinolin-4-yl)
propyl]-1-[2-(pyrid-2-yl)thioethyl]piperid-4-
ylmethanol 4-[3-(R,S)-Fluoro-3-(3-fluoro-6-methoxyquinolin-4-yl)
propyl]-1-[2-(thien-2-yl)thioethyl]piperid-4-
ylmethanol 4-[3-(R,S)-Fluoro-3-(3-fluoro-6-methoxyquinolin-4-yl)
propyl]-1-[3-(2,3,5-trifluorophenyl)prop-2-ynyl]
piperid-4-ylmethanol 4-[3-(R,S)-Fluoro-3-(3-fluoro-6-methoxyquinolin-4-yl)
propyl]-1-[3-(thien-2-yl)prop-2-ynyl]piperid-4-
ylmethanol 4-[3-(R,S)-Fluoro-3-(3-dimethylamino-6-
methoxyquinolin-4-yl)propyl]-1-[2-(cyclohexyl)ethyl]
piperid-4-ylmethanol 4-[3-(R,S)-Fluoro-3-(3-dimethylamino-6-methoxyquinolin-4-yl)propyl]-1-[3-(phenyl)propyl]piperid-4-ylmethanol 4-[3-(R,S)-Fluoro-3-(3-dimethylamino-6-methoxyquinolin-4-yl)propyl]-1-[3-(2,3,5-trifluorophenyl)propyl]piperid-4-ylmethanol 4-[3-(R,S)-Fluoro-3-(3-dimethylamino-6-methoxyquinolin-4-yl)propyl]-1-[2-(3,5-difluorophenylamino)ethyl]piperid-4-ylmethanol 4-[3-(R,S)-Fluoro-3-(3-dimethylamino-6-methoxyquinolin-4-yl)propyl]-1-[2-(2,3,5-trifluorophenylamino)ethyl]piperid-4-ylmethanol 4-[3-(R,S)-Fluoro-3-(3-dimethylamino-6-methoxyquinolin-4-yl)propyl]-1-[2-(3,5-difluorophenoxy)ethyl]piperid-4-ylmethanol 4-[3-(R,S)-Fluoro-3-(3-dimethylamino-6-methoxyquinolin-4-yl)propyl]-1-[2-(2,3,5-trifluorophenoxy)ethyl]piperid-4-ylmethanol 4-[3-(R,S)-Fluoro-3-(3-dimethylamino-6-methoxyquinolin-4-yl)propyl]-1-[2-(2,3,5-trifluorophenylthio)ethyl]piperid-4-ylmethanol 4-[3-(R,S)-Fluoro-3-(3-dimethylamino-6-methoxyquinolin-4-yl)propyl]-1-[2-(cyclopentylthio)ethyl]piperid-4-ylmethanol 4-[3-(R,S)-Fluoro-3-(3-dimethylamino-6-methoxyquinolin-4-yl)propyl]-1-[2-(pyrid-2-yl)thioethyl]piperid-4-ylmethanol 4-[3-(R,S)-Fluoro-3-(3-dimethylamino-6-methoxyquinolin-4-yl)propyl]-1-[2-(thien-2-yl)thioethyl]piperid-4-ylmethanol 4-[3-(R,S)-Fluoro-3-(3-dimethylamino-6-methoxyquinolin-4-yl)propyl]-1-[3-(2,3,5-trifluorophenyl)prop-2-ynyl]piperid-4-ylmethanol 4-[3-(R,S)-Fluoro-3-(3-dimethylamino-6-methoxyquinolin-4-yl)propyl]-1-[3-(thien-2-yl)prop-2-ynyl]piperid-4-ylmethanol 4-[3-(R,S)-Fluoro-3-(3-hydroxymethyl-6-methoxyquinolin-4-yl)propyl]-1-[2-(cyclohexyl)ethyl]piperid-4-ylmethanol 4-[3-(R,S)-Fluoro-3-(3-hydroxymethyl-6-methoxyquinolin-4-yl)propyl]-1-[3-(phenyl)propyl]piperid-4-ylmethanol 4-[3-(R,S)-Fluoro-3-(3-hydroxymethyl-6-methoxyquinolin-4-yl)propyl]-1-[3-(2,3,5-trifluorophenyl)propyl]piperid-4-ylmethanol 4-[3-(R,S)-Fluoro-3-(3-hydroxymethyl-6-methoxyquinolin-4-yl)propyl]-1-[2-(3,5-difluorophenylamino)ethyl]piperid-4-ylmethanol 4-[3-(R,S)-Fluoro-3-(3-hydroxymethyl-6-methoxyquinolin-4-yl)propyl]-1-[2-(2,3,5-trifluorophenylamino)ethyl]piperid-4-ylmethanol 4-[3-(R,S)-Fluoro-3-(3-hydroxymethyl-6-methoxyquinolin-4-yl)propyl]-1-[2-(3,5-difluorophenoxy)ethyl]piperid-4-ylmethanol 4-[3-(R,S)-Fluoro-3-(3-hydroxymethyl-6-methoxyquinolin-4-yl)propyl]-1-[2-(2,3,5-trifluorophenoxy)ethyl]piperid-4-ylmethanol 4-[3-(R,S)-Fluoro-3-(3-hydroxymethyl-6-methoxyquinolin-4-yl)propyl]-1-[2-(2,3,5-trifluorophenylthio)ethyl]piperid-4-ylmethanol 4-[3-(R,S)-Fluoro-3-(3-hydroxymethyl-6-methoxyquinolin-4-yl)propyl]-1-[2-(cyclopentylthio)ethyl]piperid-4-ylmethanol 4-[3-(R,S)-Fluoro-3-(3-hydroxymethyl-6-methoxyquinolin-4-yl)propyl]-1-[2-(pyrid-2-yl)thioethyl]piperid-4-ylmethanol 4-[3-(R,S)-Fluoro-3-(3-hydroxymethyl-6-methoxyquinolin-4-yl)propyl]-1-[2-(thien-2-yl)thioethyl]piperid-4-ylmethanol 4-[3-(R,S)-Fluoro-3-(3-hydroxymethyl-6-methoxyquinolin-4-yl)propyl]-1-[3-(2,3,5-trifluorophenyl)prop-2-ynyl]piperid-4-ylmethanol 4-[3-(R,S)-Fluoro-3-(3-hydroxymethyl-6-methoxyquinolin-4-yl)propyl]-1-[3-(thien-2-yl)prop-2-ynyl]piperid-4-ylmethanol 4-[3-(R,S)-Fluoro-3-(3-fluoromethyl-6-methoxyquinolin-4-yl)propyl]-1-[2-(cyclohexyl)ethyl]piperid-4-ylmethanol 4-[3-(R,S)-Fluoro-3-(3-fluoromethyl-6-methoxyquinolin-4-yl)propyl]-1-[3-(phenyl)propyl]piperid-4-ylmethanol 4-[3-(R,S)-Fluoro-3-(3-fluoromethyl-6-methoxyquinolin-4-yl)propyl]-1-[3-(2,3,5-trifluorophenyl)propyl]piperid-4-ylmethanol 4-[3-(R,S)-Fluoro-3-(3-fluoromethyl-6-methoxyquinolin-4-yl)propyl]-1-[2-(3,5-difluorophenylamino)ethyl]piperid-4-ylmethanol 4-[3-(R,S)-Fluoro-3-(3-fluoromethyl-6-methoxyquinolin-4-yl)propyl]-1-[2-(2,3,5-trifluorophenylamino)ethyl]piperid-4-ylmethanol 4-[3-(R,S)-Fluoro-3-(3-fluoromethyl-6-methoxyquinolin-4-yl)propyl]-1-[2-(3,5-difluorophenoxy)ethyl]piperid-4-ylmethanol 4-[3-(R,S)-Fluoro-3-(3-fluoromethyl-6-methoxyquinolin-4-yl)propyl]-1-[2-(2,3,5-trifluorophenoxy)ethyl]piperid-4-ylmethanol 4-[3-(R,S)-Fluoro-3-(3-fluoromethyl-6-methoxyquinolin-4-yl)propyl]-1-[2-(2,3,5-trifluorophenylthio)ethyl]piperid-4-ylmethanol 4-[3-(R,S)-Fluoro-3-(3-fluoromethyl-6-methoxyquinolin-4-yl)propyl]-1-[2-(cyclopentylthio)ethyl]piperid-4-ylmethanol 4-[3-(R,S)-Fluoro-3-(3-fluoromethyl-6-methoxyquinolin-4-yl)propyl]-1-[2-(pyrid-2-yl)thioethyl]piperid-4-ylmethanol 4-[3-(R,S)-Fluoro-3-(3-fluoromethyl-6-methoxyquinolin-4-yl)propyl]-1-[2-(thien-2-yl)thioethyl]piperid-4-ylmethanol 4-[3-(R,S)-Fluoro-3-(3-fluoromethyl-6-methoxyquinolin-4-yl)propyl]-1-[3-(2,3,5-trifluorophenyl)prop-2-ynyl]piperid-4-ylmethanol 4-[3-(R,S)-Fluoro-3-(3-fluoromethyl-6-methoxyquinolin-4-yl)propyl]-1-[3-(thien-2-yl)prop-2-ynyl]piperid-4-ylmethanol 4-[3-(R,S)-Fluoro-3-(3-aminomethyl-6-methoxyquinolin-4-yl)propyl]-1-[2-(cyclohexyl)ethyl]piperid-4-ylmethanol 4-[3-(R,S)-Fluoro-3-(3-aminomethyl-6-methoxyquinolin-4-yl)propyl]-1-[3-(phenyl)propyl]piperid-4-ylmethanol 4-[3-(R,S)-Fluoro-3-(3-aminomethyl-6-methoxyquinolin-4-yl)propyl]-1-[3-(2,3,5-trifluorophenyl)propyl]piperid-4-ylmethanol 4-[3-(R,S)-Fluoro-3-(3-aminomethyl-6-methoxyquinolin-4-yl)propyl]-1-[2-(3,5-difluorophenylamino)ethyl]piperid-4-ylmethanol 4-[3-(R,S)-Fluoro-3-(3-aminomethyl-6-methoxyquinolin-4-yl)propyl]-1-[2-(2,3,5-trifluorophenylamino)ethyl]piperid-4-ylmethanol 4-[3-(R,S)-Fluoro-3-(3-aminomethyl-6-methoxyquinolin-4-yl)propyl]-1-[2-(3,5-difluorophenoxy)ethyl]piperid-4-ylmethanol 4-[3-(R,S)-Fluoro-3-(3-aminomethyl-6-methoxyquinolin-4-yl)propyl]-1-[2-(2,3,5-trifluorophenoxy)ethyl]piperid-4-ylmethanol 4-[3-(R,S)-Fluoro-3-(3-aminomethyl-6-methoxyquinolin-4-yl)propyl]-1-[2-(2,3,5-trifluorophenylthio)ethyl]piperid-4-ylmethanol 4-[3-(R,S)-Fluoro-3-(3-aminomethyl-6-methoxyquinolin-4-yl)propyl]-1-[2-(cyclopentylthio)ethyl]piperid-4-ylmethanol 4-[3-(R,S)-Fluoro-3-(3-aminomethyl-6-methoxyquinolin-4-yl)propyl]-1-[2-(pyrid-2-yl)thioethyl]piperid-4-ylmethanol 4-[3-(R,S)-Fluoro-3-(3-aminomethyl-6-methoxyquinolin-4-yl)propyl]-1-[2-(thien-2-yl)thioethyl]piperid-4-ylmethanol 4-[3-(R,S)-Fluoro-3-(3-aminomethyl-6-methoxyquinolin-4-yl)propyl]-1-[3-(2,3,5-trifluorophenyl)prop-2-ynyl]piperid-4-ylmethanol 4-[3-(R,S)-Fluoro-3-(3-aminomethyl-6-methoxyquinolin-4-yl)propyl]-1-[3-(thien-2-yl)prop-2-ynyl]piperid-4-ylmethanol 4-[3-(R,S)-Fluoro-3-(3-morpholinomethyl-6-methoxyquinolin-4-yl)propyl]-1-[2-(cyclohexyl)ethyl]piperid-4-ylmethanol 4-[3-(R,S)-Fluoro-3-(3-morpholinomethyl-6-methoxyquinolin-4-yl)propyl]-1-[3-(phenyl)propyl]piperid-4-ylmethanol 4-[3-(R,S)-Fluoro-3-(3-morpholinomethyl-6-methoxyquinolin-4-yl)propyl]-1-[3-(2,3,5-trifluorophenyl)propyl]piperid-4-ylmethanol 4-[3-(R,S)-Fluoro-3-(3-morpholinomethyl-6-methoxyquinolin-4-yl)propyl]-1-[2-(3,5-difluorophenylamino)ethyl]piperid-4-ylmethanol 4-[3-(R,S)-Fluoro-3-(3-morpholinomethyl-6-methoxyquinolin-4-yl)propyl]-1-[2-(2,3,5-trifluorophenylamino)ethyl]piperid-4-ylmethanol 4-[3-(R,S)-Fluoro-3-(3-morpholinomethyl-6-methoxyquinolin-4-yl)propyl]-1-[2-(3,5-difluorophenoxy)ethyl]piperid-4-ylmethanol 4-[3-(R,S)-Fluoro-3-(3-morpholinomethyl-6-methoxyquinolin-4-yl)propyl]-1-[2-(2,3,5-trifluorophenoxy)ethyl]piperid-4-ylmethanol 4-[3-(R,S)-Fluoro-3-(3-morpholinomethyl-6-methoxyquinolin-4-yl)propyl]-1-[2-(2,3,5-trifluorophenylthio)ethyl]piperid-4-ylmethanol 4-[3-(R,S)-Fluoro-3-(3-morpholinomethyl-6-methoxyquinolin-4-yl)propyl]-1-[2-(cyclopentylthio)ethyl]piperid-4-ylmethanol 4-[3-(R,S)-Fluoro-3-(3-morpholinomethyl-6-methoxyquinolin-4-yl)propyl]-1-[2-(pyrid-2-yl)thioethyl]piperid-4-ylmethanol 4-[3-(R,S)-Fluoro-3-(3-morpholinomethyl-6-methoxyquinolin-4-yl)propyl]-1-[2-(thien-2-yl)thioethyl]piperid-4-ylmethanol 4-[3-(R,S)-Fluoro-3-(3-morpholinomethyl-6-methoxyquinolin-4-yl)propyl]-1-[3-(2,3,5-trifluorophenyl)prop-2-ynyl]piperid-4-ylmethanol 4-[3-(R,S)-Fluoro-3-(3-morpholinomethyl-6-methoxyquinolin-4-yl)propyl]-1-[3-(thien-2-yl)prop-2-ynyl]piperid-4-ylmethanol 4-[3-(R,S)-Fluoro-3-(3-methyl-6-methoxyquinolin-4-yl)propyl]-1-[3-(2,4,6-trifluorophenyl)propyl]piperid-4-ylmethanol 4-[3-(R,S)-Fluoro-3-(3-methyl-6-methoxyquinolin-4-yl)propyl]-1-[3-(3,4,5-trifluorophenyl)propyl]piperid-4-ylmethanol 4-[3-(R,S)-Fluoro-3-(3-methyl-6-methoxyquinolin-4-yl)propyl]-1-[2-(2,4,6-trifluorophenylthio)ethyl]piperid-4-ylmethanol 4-[3-(R,S)-Fluoro-3-(3-methyl-6-methoxyquinolin-4-yl)propyl]-1-[2-(3,4,5-trifluorophenylthio)ethyl]piperid-4-ylmethanol 4-[3-(R,S)-Fluoro-3-(3-methyl-6-methoxyquinolin-4-yl)propyl]-1-[2-(2,4,6-trifluorophenylamino)ethyl]piperid-4-ylmethanol 4-[3-(R,S)-Fluoro-3-(3-methyl-6-methoxyquinolin-4-yl)propyl]-1-[2-(3,4,5-trifluorophenylamino)ethyl]piperid-4-ylmethanol 4-[3-(R,S)-Fluoro-3-(3-methyl-6-methoxyquinolin-4-yl)propyl]-1-[2-(2,4,6-trifluorophenoxy)ethyl]piperid-4-ylmethanol 4-[3-(R,S)-Fluoro-3-(3-methyl-6-methoxyquinolin-4-yl)propyl]-1-[2-(3,4,5-trifluorophenoxy)ethyl]piperid-4-ylmethanol 4-[3-(R,S)-Fluoro-3-(3-methyl-6-methoxyquinolin-4-yl)propyl]-1-[3-(2,4,6-trifluorophenyl)prop-2-ynyl]piperid-4-ylmethanol 4-[3-(R,S)-Fluoro-3-(3-methyl-6-methoxyquinolin-4-yl)propyl]-1-[3-(3,4,5-trifluorophenyl)prop-2-ynyl]piperid-4-ylmethanol 4-[3-(R,S)-Fluoro-3-(3-fluoro-6-methoxyquinolin-4-yl)propyl]-1-[3-(2,4,6-trifluorophenyl)propyl]piperid-4-ylmethanol 4-[3-(R,S)-Fluoro-3-(3-fluoro-6-methoxyquinolin-4-yl)propyl]-1-[3-(3,4,5-trifluorophenyl)propyl]piperid-4-ylmethanol 4-[3-(R,S)-Fluoro-3-(3-fluoro-6-methoxyquinolin-4-yl)propyl]-1-[2-(2,4,6-trifluorophenylthio)ethyl]piperid-4-ylmethanol 4-[3-(R,S)-Fluoro-3-(3-fluoro-6-methoxyquinolin-4-yl)propyl]-1-[2-(3,4,5-trifluorophenylthio)ethyl]piperid-4-ylmethanol 4-[3-(R,S)-Fluoro-3-(3-fluoro-6-methoxyquinolin-4-yl)propyl]-1-[2-(2,4,6-trifluorophenylamino)ethyl]piperid-4-ylmethanol 4-[3-(R,S)-Fluoro-3-(3-fluoro-6-methoxyquinolin-4-yl)propyl]-1-[2-(3,4,5-trifluorophenylamino)ethyl]piperid-4-ylmethanol 4-[3-(R,S)-Fluoro-3-(3-fluoro-6-methoxyquinolin-4-yl)propyl]-1-[2-(2,4,6-trifluorophenoxy)ethyl]piperid-4-ylmethanol 4-[3-(R,S)-Fluoro-3-(3-fluoro-6-methoxyquinolin-4-yl)propyl]-1-[2-(3,4,5-trifluorophenoxy)ethyl]piperid-4-ylmethanol 4-[3-(R,S)-Fluoro-3-(3-fluoro-6-methoxyquinolin-4-yl)propyl]-1-[3-(2,4,6-trifluorophenyl)prop-2-ynyl]piperid-4-ylmethanol 4-[3-(R,S)-Fluoro-3-(3-fluoro-6-methoxyquinolin-4-yl)propyl]-1-[3-(3,4,5-trifluorophenyl)prop-2-ynyl]piperid-4-ylmethanol 4-[3-(R,S)-Fluoro-3-(3-dimethylamino-6-methoxyquinolin-4-yl)propyl]-1-[3-(2,4,6-trifluorophenyl)propyl]piperid-4-ylmethanol 4-[3-(R,S)-Fluoro-3-(3-dimethylamino-6-methoxyquinolin-4-yl)propyl]-1-[3-(3,4,5-trifluorophenyl)propyl]piperid-4-ylmethanol 4-[3-(R,S)-Fluoro-3-(3-dimethylamino-6-methoxyquinolin-4-yl)propyl]-1-[2-(2,4,6-trifluorophenylthio)ethyl]piperid-4-ylmethanol 4-[3-(R,S)-Fluoro-3-(3-dimethylamino-6-methoxyquinolin-4-yl)propyl]-1-[2-(3,4,5-trifluorophenylthio)ethyl]piperid-4-ylmethanol 4-[3-(R,S)-Fluoro-3-(3-dimethylamino-6-methoxyquinolin-4-yl)propyl]-1-[2-(2,4,6-trifluorophenylamino)ethyl]piperid-4-ylmethanol 4-[3-(R,S)-Fluoro-3-(3-dimethylamino-6-methoxyquinolin-4-yl)propyl]-1-[2-(3,4,5-trifluorophenylamino)ethyl]piperid-4-ylmethanol 4-[3-(R,S)-Fluoro-3-(3-dimethylamino-6-methoxyquinolin-4-yl)propyl]-1-[2-(2,4,6-trifluorophenoxy)ethyl]piperid-4-ylmethanol 4-[3-(R,S)-Fluoro-3-(3-dimethylamino-6-methoxyquinolin-4-yl)propyl]-1-[2-(3,4,5-trifluorophenoxy)ethyl]piperid-4-ylmethanol 4-[3-(R,S)-Fluoro-3-(3-dimethylamino-6-methoxyquinolin-4-yl)propyl]-1-[3-(2,4,6-trifluorophenyl)prop-2-ynyl]piperid-4-ylmethanol 4-[3-(R,S)-Fluoro-3-(3-dimethylamino-6-methoxyquinolin-4-yl)propyl]-1-[3-(3,4,5-trifluorophenyl)prop-2-ynyl]piperid-4-ylmethanol 4-[3-(R,S)-Fluoro-3-(3-fluoro-6-methoxyquinolin-4-yl)propyl]-1-[3-(2,4,6-trifluorophenyl)propyl]piperid-4-ylmethanol 4-[3-(R,S)-Fluoro-3-(3-hydroxymethyl-6-methoxyquinolin-4-yl)propyl]-1-[3-(3,4,5-trifluorophenyl)propyl]piperid-4-ylmethanol 4-[3-(R,S)-Fluoro-3-(3-hydroxymethyl-6-methoxyquinolin-4-yl)propyl]-1-[2-(2,4,6-trifluorophenylthio)ethyl]piperid-4-ylmethanol 4-[3-(R,S)-Fluoro-3-(3-hydroxymethyl-6-methoxyquinolin-4-yl)propyl]-1-[2-(3,4,5-trifluorophenylthio)ethyl]piperid-4-ylmethanol 4-[3-(R,S)-Fluoro-3-(3-hydroxymethyl-6-methoxyquinolin-4-yl)propyl]-1-[2-(2,4,6-trifluorophenylamino)ethyl]piperid-4-ylmethanol 4-[3-(R,S)-Fluoro-3-(3-hydroxymethyl-6-methoxyquinolin-4-yl)propyl]-1-[2-(3,4,5-trifluorophenylamino)ethyl]piperid-4-ylmethanol 4-[3-(R,S)-Fluoro-3-(3-hydroxymethyl-6-methoxyquinolin-4-yl)propyl]-1-[2-(2,4,6-trifluorophenoxy)ethyl]piperid-4-ylmethanol 4-[3-(R,S)-Fluoro-3-(3-hydroxymethyl-6-methoxyquinolin-4-yl)propyl]-1-[2-(3,4,5-trifluorophenoxy)ethyl]piperid-4-ylmethanol 4-[3-(R,S)-Fluoro-3-(3-hydroxymethyl-6-methoxyquinolin-4-yl)propyl]-1-[3-(2,4,6-trifluorophenyl)prop-2-ynyl]piperid-4-ylmethanol 4-[3-(R,S)-Fluoro-3-(3-hydroxymethyl-6-methoxyquinolin-4-yl)propyl]-1-[3-(3,4,5-trifluorophenyl)prop-2-ynyl]piperid-4-ylmethanol 4-[3-(R,S)-Fluoro-3-(3-fluoromethyl-6-methoxyquinolin-4-yl)propyl]-1-[3-(2,4,6-trifluorophenyl)propyl]piperid-4-ylmethanol 4-[3-(R,S)-Fluoro-3-(3-fluoromethyl-6-methoxyquinolin-4-yl)propyl]-1-[3-(3,4,5-trifluorophenyl)propyl]piperid-4-ylmethanol 4-[3-(R,S)-Fluoro-3-(3-fluoromethyl-6-methoxyquinolin-4-yl)propyl]-1-[2-(2,4,6-trifluorophenylthio)ethyl]piperid-4-ylmethanol 4-[3-(R,S)-Fluoro-3-(3-fluoromethyl-6-methoxyquinolin-4-yl)propyl]-1-[2-(3,4,5-trifluorophenylthio)ethyl]piperid-4-ylmethanol 4-[3-(R,S)-Fluoro-3-(3-fluoromethyl-6-methoxyquinolin-4-yl)propyl]-1-[2-(2,4,6-trifluorophenylamino)ethyl]piperid-4-ylmethanol 4-[3-(R,S)-Fluoro-3-(3-fluoromethyl-6-methoxyquinolin-4-yl)propyl]-1-[2-(3,4,5-trifluorophenylamino)ethyl]piperid-4-ylmethanol 4-[3-(R,S)-Fluoro-3-(3-fluoromethyl-6-methoxyquinolin-4-yl)propyl]-1-[2-(2,4,6-trifluorophenoxy)ethyl]piperid-4-ylmethanol 4-[3-(R,S)-Fluoro-3-(3-fluoromethyl-6-methoxyquinolin-4-yl)propyl]-1-[2-(3,4,5-trifluorophenoxy)ethyl]piperid-4-ylmethanol 4-[3-(R,S)-Fluoro-3-(3-fluoromethyl-6-methoxyquinolin-4-yl)propyl]-1-[3-(2,4,6-trifluorophenyl)prop-2-ynyl]piperid-4-ylmethanol 4-[3-(R,S)-Fluoro-3-(3-fluoromethyl-6-methoxyquinolin-4-yl)propyl]-1-[3-(3,4,5-trifluorophenyl)prop-2-ynyl]piperid-4-ylmethanol 4-[3-(R,S)-Fluoro-3-(3-aminomethyl-6-methoxyquinolin-4-yl)propyl]-1-[3-(2,4,6-trifluorophenyl)propyl]piperid-4-ylmethanol 4-[3-(R,S)-Fluoro-3-(3-aminomethyl-6-methoxyquinolin-4-yl)propyl]-1-[3-(3,4,5-trifluorophenyl)propyl]piperid-4-ylmethanol 4-[3-(R,S)-Fluoro-3-(3-aminomethyl-6-methoxyquinolin-4-yl)propyl]-1-[2-(2,4,6-trifluorophenylthio)ethyl]piperid-4-ylmethanol 4-[3-(R,S)-Fluoro-3-(3-aminomethyl-6-methoxyquinolin-4-yl)propyl]-1-[2-(3,4,5-trifluorophenylthio)ethyl]piperid-4-ylmethanol 4-[3-(R,S)-Fluoro-3-(3-aminomethyl-6-methoxyquinolin-4-yl)propyl]-1-[2-(2,4,6-trifluorophenylamino)ethyl]piperid-4-ylmethanol 4-[3-(R,S)-Fluoro-3-(3-aminomethyl-6-methoxyquinolin-4-yl)propyl]-1-[2-(3,4,5-trifluorophenylamino)ethyl]piperid-4-ylmethanol 4-[3-(R,S)-Fluoro-3-(3-aminomethyl-6-methoxyquinolin-4-yl)propyl]-1-[2-(2,4,6-trifluorophenoxy)ethyl]piperid-4-ylmethanol 4-[3-(R,S)-Fluoro-3-(3-aminomethyl-6-methoxyquinolin-4-yl)propyl]-1-[2-(3,4,5-trifluorophenoxy)ethyl]piperid-4-ylmethanol 4-[3-(R,S)-Fluoro-3-(3-aminomethyl-6-methoxyquinolin-4-yl)propyl]-1-[3-(2,4,6-trifluorophenyl)prop-2-ynyl]piperid-4-ylmethanol 4-[3-(R,S)-Fluoro-3-(3-aminomethyl-6-methoxyquinolin-4-yl)propyl]-1-[3-(3,4,5-trifluorophenyl)prop-2-ynyl]piperid-4-ylmethanol 4-[3-(R,S)-Fluoro-3-(3-morpholinomethyl-6-methoxyquinolin-4-yl)propyl]-1-[3-(2,4,6-trifluorophenyl)propyl]piperid-4-ylmethanol 4-[3-(R,S)-Fluoro-3-(3-morpholinomethyl-6-methoxyquinolin-4-yl)propyl]-1-[3-(3,4,5-trifluorophenyl)propyl]piperid-4-ylmethanol 4-[3-(R,S)-Fluoro-3-(3-morpholinomethyl-6-methoxyquinolin-4-yl)propyl]-1-[2-(2,4,6-trifluorophenylthio)ethyl]piperid-4-ylmethanol 4-[3-(R,S)-Fluoro-3-(3-morpholinomethyl-6-methoxyquinolin-4-yl)propyl]-1-[2-(3,4,5-trifluorophenylthio)ethyl]piperid-4-ylmethanol 4-[3-(R,S)-Fluoro-3-(3-morpholinomethyl-6-methoxyquinolin-4-yl)propyl]-1-[2-(2,4,6-trifluorophenylamino)ethyl]piperid-4-ylmethanol 4-[3-(R,S)-Fluoro-3-(3-morpholinomethyl-6-methoxyquinolin-4-yl)propyl]-1-[2-(3,4,5-trifluorophenylamino)ethyl]piperid-4-ylmethanol 4-[3-(R,S)-Fluoro-3-(3-morpholinomethyl-6-methoxyquinolin-4-yl)propyl]-1-[2-(2,4,6-trifluorophenoxy)ethyl]piperid-4-ylmethanol 4-[3-(R,S)-Fluoro-3-(3-morpholinomethyl-6-methoxyquinolin-4-yl)propyl]-1-[2-(3,4,5-trifluorophenoxy)ethyl]piperid-4-ylmethanol 4-[3-(R,S)-Fluoro-3-(3-morpholinomethyl-6-methoxyquinolin-4-yl)propyl]-1-[3-(2,4,6-trifluorophenyl)prop-2-ynyl]piperid-4-ylmethanol 4-[3-(R,S)-Fluoro-3-(3-morpholinomethyl-6-methoxyquinolin-4-yl)propyl]-1-[3-(3,4,5-trifluorophenyl)prop-2-ynyl]piperid-4-ylmethanol 4-[3-(3-Chloro-6-methoxyquinolin-4-yl)propyl]-1-heptyl piperidine-4-hydroxamic acid 4-[3-(3-Chloro-6-methoxyquinolin-4-yl)propyl]-1-[4-phenylbutyl]piperidine-4-hydroxamic acid 4-[3-(3-Chloro-6-methoxyquinolin-4-yl)propyl]-1-[4-(2-fluorophenyl)propyl]piperidine-4-hydroxamic acid 4-[3-(3-Chloro-6-methoxyquinolin-4-yl)propyl]-1-[4-(3-fluorophenyl)propyl]piperidine-4-hydroxamic acid 4-[3-(3-Chloro-6-methoxyquinolin-4-yl)propyl]-1-[3-(4-fluorophenyl)propyl]piperidine-4-hydroxamic acid 4-[3-(3-Chloro-6-methoxyquinolin-4-yl)propyl]-1-[4-(4-fluorophenyl)butyl]piperidine-4-hydroxamic acid 4-[3-(3-Chloro-6-methoxyquinolin-4-yl)propyl]-1-[3-(2,3-difluorophenyl)propyl]piperidine-4-hydroxamic acid 4-[3-(3-Chloro-6-methoxyquinolin-4-yl)propyl]-1-[4-(2,3-difluorophenyl)propyl]piperidine-4-hydroxamic acid 4-[3-(3-Chloro-6-methoxyquinolin-4-yl)propyl]-1-[3-(2,6-difluorophenyl)propyl]piperidine-4-hydroxamic acid 4-[3-(3-Chloro-6-methoxyquinolin-4-yl)propyl]-1-[4-(2,6-difluorophenyl)propyl]piperidine-4-hydroxamic acid 4-[3-(3-Chloro-6-methoxyquinolin-4-yl)propyl]-1-[3-(3,5-difluorophenyl)propyl]piperidine-4-hydroxamic acid 4-[3-(3-Chloro-6-methoxyquinolin-4-yl)propyl]-1-[3-(2,3,5-trifluorophenyl)propyl]piperidine-4-hydroxamic acid 4-[3-(3-Chloro-6-methoxyquinolin-4-yl)propyl]-1-[3-(2,4,6-trifluorophenyl)propyl]piperidine-4-hydroxamic acid 4-[3-(3-Chloro-6-methoxyquinolin-4-yl)propyl]-1-[3-(3,4,5-trifluorophenyl)propyl]piperidine-4-hydroxamic acid 4-[3-(3-Chloro-6-methoxyquinolin-4-yl)propyl]-1-[3-phenylthiopropyl]piperidine-4-hydroxamic acid 4-[3-(3-Chloro-6-methoxyquinolin-4-yl)propyl]-1-[3-(2-fluorophenylthio)propyl]piperidine-4-hydroxamic acid 4-[3-(3-Chloro-6-methoxyquinolin-4-yl)propyl]-1-[3-(3-fluorophenylthio)propyl]piperidine-4-hydroxamic acid 4-[3-(3-Chloro-6-methoxyquinolin-4-yl)propyl]-1-[2-(4-fluorophenylthio)ethyl]piperidine-4-hydroxamic acid 4-[3-(3-Chloro-6-methoxyquinolin-4-yl)propyl]-1-[3-(4-fluorophenylthio)propyl]piperidine-4-hydroxamic acid 4-[3-(3-Chloro-6-methoxyquinolin-4-yl)propyl]-1-[2-(2,3-difluorophenylthio)ethyl]piperidine-4-hydroxamic acid 4-[3-(3-Chloro-6-methoxyquinolin-4-yl)propyl]-1-[3-(2,3-difluorophenylthio)propyl]piperidine-4-hydroxamic acid 4-[3-(3-Chloro-6-methoxyquinolin-4-yl)propyl]-1-[2-(2,6-difluorophenylthio)ethyl]piperidine-4-hydroxamic acid 4-[3-(3-Chloro-6-methoxyquinolin-4-yl)propyl]-1-[2-(2,3,5-trifluorophenylthio)ethyl]piperidine-4-hydroxamic acid 4-[3-(3-Chloro-6-methoxyquinolin-4-yl)propyl]-1-[2-(2,4,6-trifluorophenylthio)ethyl]piperidine-4-hydroxamic acid 4-[3-(3-Chloro-6-methoxyquinolin-4-yl)propyl]-1-[2-(3,4,5-trifluorophenylthio)ethyl]piperidine-4-hydroxamic acid 4-[3-(3-Chloro-6-methoxyquinolin-4-yl)propyl]-1-[2-(2,3,5-trifluorophenoxy)ethyl]piperidine-4-hydroxamic acid 4-[3-(3-Chloro-6-methoxyquinolin-4-yl)propyl]-1-[2-(2,4,6-trifluorophenoxy)ethyl]piperidine-4-hydroxamic acid 4-[3-(3-Chloro-6-methoxyquinolin-4-yl)propyl]-1-[2-(3,4,5-trifluorophenoxy)ethyl]piperidine-4-hydroxamic acid 4-[3-(3-Chloro-6-methoxyquinolin-4-yl)propyl]-1-[2-(3,5-difluorophenylamino)ethyl]piperidine-4-hydroxamic acid 4-[3-(3-Chloro-6-methoxyquinolin-4-yl)propyl]-1-[2-(2,3,5-trifluorophenylamino)ethyl]piperidine-4-hydroxamic acid 4-[3-(3-Chloro-6-methoxyquinolin-4-yl)propyl]-1-[2-(2,4,6-trifluorophenylamino)ethyl]piperidine-4-hydroxamic acid 4-[3-(3-Chloro-6-methoxyquinolin-4-yl)propyl]-1-[2-(3,4,5-trifluorophenylamino)ethyl]piperidine-4-hydroxamic acid 4-[3-(3-Chloro-6-methoxyquinolin-4-yl)propyl]-1-[3-(2,6-difluorophenylthio)propyl]piperidine-4-hydroxamic acid 4-[3-(3-Chloro-6-methoxyquinolin-4-yl)propyl]-1-[2-(2-chlorophenylthio)ethyl]piperidine-4-hydroxamic acid 4-[3-(3-Chloro-6-methoxyquinolin-4-yl)propyl]-1-[3-(2-chlorophenylthio)propyl]piperidine-4-hydroxamic acid 4-[3-(3-Chloro-6-methoxyquinolin-4-yl)propyl]-1-[2-(3-chlorophenylthio)ethyl]piperidine-4-hydroxamic acid 4-[3-(3-Chloro-6-methoxyquinolin-4-yl)propyl]-1-[3-(3-chlorophenylthio)propyl]piperidine-4-hydroxamic acid 4-[3-(3-Chloro-6-methoxyquinolin-4-yl)propyl]-1-[2-(4-chlorophenylthio)ethyl]piperidine-4-hydroxamic acid 4-[3-(3-Chloro-6-methoxyquinolin-4-yl)propyl]-1-[3-(4-chlorophenylthio)propyl]piperidine-4-hydroxamic acid 4-[3-(3-Chloro-6-methoxyquinolin-4-yl)propyl]-1-[2-(2-methylphenylthio)ethyl]piperidine-4-hydroxamic acid 4-[3-(3-Chloro-6-methoxyquinolin-4-yl)propyl]-1-[3-(2-methylphenylthio)propyl]piperidine-4-hydroxamic acid 4-[3-(3-Chloro-6-methoxyquinolin-4-yl)propyl]-1-[2-(3-methylphenylthio)ethyl]piperidine-4-hydroxamic acid 4-[3-(3-Chloro-6-methoxyquinolin-4-yl)propyl]-1-[3-(3-methylphenylthio)propyl]piperidine-4-hydroxamic acid
4-[3-(3-Chloro-6-methoxyquinolin-4-yl)propyl]-1-[2-(4-methylphenylthio)ethyl]piperidine-4-hydroxamic acid
4-[3-(3-Chloro-6-methoxyquinolin-4-yl)propyl]-1-[3-(4-methylphenylthio)propyl]piperidine-4-hydroxamic acid
4-[3-(3-Chloro-6-methoxyquinolin-4-yl)propyl]-1-[2-(2-trifluoromethylphenylthio)ethyl]piperidine-4-hydroxamic acid
4-[3-(3-Chloro-6-methoxyquinolin-4-yl)propyl]-1-[3-(2-trifluoromethylphenylthio)propyl]piperidine-4-hydroxamic acid
4-[3-(3-Chloro-6-methoxyquinolin-4-yl)propyl]-1-[2-(3-trifluoromethylphenylthio)ethyl]piperidine-4-hydroxamic acid
4-[3-(3-Chloro-6-methoxyquinolin-4-yl)propyl]-1-[3-(3-trifluoromethylphenylthio)propyl]piperidine-4-hydroxamic acid
4-[3-(3-Chloro-6-methoxyquinolin-4-yl)propyl]-1-[2-(4-trifluoromethylphenylthio)ethyl]piperidine-4-hydroxamic acid
4-[3-(3-Chloro-6-methoxyquinolin-4-yl)propyl]-1-[3-(4-trifluoromethylphenylthio)propyl]piperidine-4-hydroxamic acid
4-[3-(3-Chloro-6-methoxyquinolin-4-yl)propyl]-1-[2-(2-methoxyphenylthio)ethyl]piperidine-4-hydroxamic acid
4-[3-(3-Chloro-6-methoxyquinolin-4-yl)propyl]-1-[3-(2-methoxyphenylthio)propyl]piperidine-4-hydroxamic acid
4-[3-(3-Chloro-6-methoxyquinolin-4-yl)propyl]-1-[2-(3-methoxyphenylthio)ethyl]piperidine-4-hydroxamic acid
4-[3-(3-Chloro-6-methoxyquinolin-4-yl)propyl]-1-[3-(3-methoxyphenylthio)propyl]piperidine-4-hydroxamic acid
4-[3-(3-Chloro-6-methoxyquinolin-4-yl)propyl]-1-[2-(4-methoxyphenylthio)ethyl]piperidine-4-hydroxamic acid
4-[3-(3-Chloro-6-methoxyquinolin-4-yl)propyl]-1-[3-(4-methoxyphenylthio)propyl]piperidine-4-hydroxamic acid
4-[3-(3-Chloro-6-methoxyquinolin-4-yl)propyl]-1-[cyclopentylmethyl]piperidine-4-hydroxamic acid
4-[3-(3-Chloro-6-methoxyquinolin-4-yl)propyl]-1-[2-(cyclopentyl)ethyl]piperidine-4-hydroxamic acid
4-[3-(3-Chloro-6-methoxyquinolin-4-yl)propyl]-1-[2-(cyclopentylthio)ethyl]piperidine-4-hydroxamic acid
4-[3-(3-Chloro-6-methoxyquinolin-4-yl)propyl]-1-[3-(cyclopentylthio)propyl]piperidine-4-hydroxamic acid
4-[3-(3-Chloro-6-methoxyquinolin-4-yl)propyl]-1-[3-(cyclohexylthio)propyl]piperidine-4-hydroxamic acid
4-[3-(3-Chloro-6-methoxyquinolin-4-yl)propyl]-1-[4-(thien-2-yl)butyl]piperidine-4-hydroxamic acid
4-[3-(3-Chloro-6-methoxyquinolin-4-yl)propyl]-1-[3-(thien-2-yl)thiopropyl]piperidine-4-hydroxamic acid
4-[3-(3-Chloro-6-methoxyquinolin-4-yl)propyl]-1-[3-(thien-3-yl)propyl]piperidine-4-hydroxamic acid
4-[3-(3-Chloro-6-methoxyquinolin-4-yl)propyl]-1-[4-(thien-3-yl)butyl]piperidine-4-hydroxamic acid
4-[3-(3-Chloro-6-methoxyquinolin-4-yl)propyl]-1-[2-(thien-3-yl)thioethyl]piperidine-4-hydroxamic acid
4-[3-(3-Chloro-6-methoxyquinolin-4-yl)propyl]-1-[3-(thien-3-yl)thiopropyl]piperidine-4-hydroxamic acid
4-[3-(3-Chloro-6-methoxyquinolin-4-yl)propyl]-1-[3-(1,3-thiazol-2-yl)propyl]piperidine-4-hydroxamic acid
4-[3-(3-Chloro-6-methoxyquinolin-4-yl)propyl]-1-[4-(1,3-thiazol-2-yl)butyl]piperidine-4-hydroxamic acid
4-[3-(3-Chloro-6-methoxyquinolin-4-yl)propyl]-1-[3-(1,3-thiazol-2-yl)thioethyl]piperidine-4-hydroxamic acid
4-[3-(3-Chloro-6-methoxyquinolin-4-yl)propyl]-1-[3-(pyrid-2-yl)propyl]piperidine-4-hydroxamic acid
4-[3-(3-Chloro-6-methoxyquinolin-4-yl)propyl]-1-[4-(pyrid-2-yl)butyl]piperidine-4-hydroxamic acid
4-[3-(3-Chloro-6-methoxyquinolin-4-yl)propyl]-1-[3-(pyrid-2-yl)thiopropyl]piperidine-4-hydroxamic acid
4-[3-(3-Chloro-6-methoxyquinolin-4-yl)propyl]-1-[3-(pyrid-3-yl)propyl]piperidine-4-hydroxamic acid
4-[3-(3-Chloro-6-methoxyquinolin-4-yl)propyl]-1-[4-(pyrid-3-yl)butyl]piperidine-4-hydroxamic acid
4-[3-(3-Chloro-6-methoxyquinolin-4-yl)propyl]-1-[2-(pyrid-3-yl)thioethyl]piperidine-4-hydroxamic acid
4-[3-(3-Chloro-6-methoxyquinolin-4-yl)propyl]-1-[3-(pyrid-3-yl)thiopropyl]piperidine-4-hydroxamic acid
4-[3-(3-Chloro-6-methoxyquinolin-4-yl)propyl]-1-[3-(pyrid-4-yl)propyl]piperidine-4-hydroxamic acid
4-[3-(3-Chloro-6-methoxyquinolin-4-yl)propyl]-1-[4-(pyrid-4-yl)butyl]piperidine-4-hydroxamic acid
4-[3-(3-Chloro-6-methoxyquinolin-4-yl)propyl]-1-[2-(pyrid-4-yl)thioethyl]piperidine-4-hydroxamic acid
4-[3-(3-Chloro-6-methoxyquinolin-4-yl)propyl]-1-[3-(pyrid-4-yl)thiopropyl]piperidine-4-hydroxamic acid
4-[3-(3-Chloro-6-methoxyquinolin-4-yl)propyl]-1-[3-(pyrazin-2-yl)propyl]piperidine-4-hydroxamic acid
4-[3-(3-Chloro-6-methoxyquinolin-4-yl)propyl]-1-[4-(pyrazin-2-yl)butyl]piperidine-4-hydroxamic acid
4-[3-(3-Chloro-6-methoxyquinolin-4-yl)propyl]-1-[2-(pyrazin-2-yl)thioethyl]piperidine-4-hydroxamic acid
4-[3-(3-Chloro-6-methoxyquinolin-4-yl)propyl]-1-[3-(pyrazin-2-yl)thiopropyl]piperidine-4-hydroxamic acid
4-[3-(3-Chloro-6-methoxyquinolin-4-yl)propyl]-1-[3-(4-fluorophenyl)prop-2-ynyl]piperidine-4-hydroxamic acid
4-[3-(3-Chloro-6-methoxyquinolin-4-yl)propyl]-1-[3-(3,4-difluorophenyl)prop-2-ynyl]piperidine-4-hydroxamic acid
4-[3-(3-Chloro-6-methoxyquinolin-4-yl)propyl]-1-[3-(2,4-difluorophenyl)prop-2-ynyl]piperidine-4-hydroxamic acid
4-[3-(3-Chloro-6-methoxyquinolin-4-yl)propyl]-1-[3-(2,3,5-trifluorophenyl)prop-2-ynyl]piperidine-4-hydroxamic acid
4-[3-(3-Chloro-6-methoxyquinolin-4-yl)propyl]-1-[3-(2,4,6-trifluorophenyl)prop-2-ynyl]piperidine-4-hydroxamic acid
4-[3-(3-Chloro-6-methoxyquinolin-4-yl)propyl]-1-[3-(3,4,5-trifluorophenyl)prop-2-ynyl]piperidine-4-hydroxamic acid
4-[3-(3-Chloro-6-methoxyquinolin-4-yl)propyl]-1-[3-(4-chloro-3-fluorophenyl)prop-2-ynyl]piperidine-4-hydroxamic acid
4-[3-(3-Chloro-6-methoxyquinolin-4-yl)propyl]-1-[3-(3-chloro-4-fluorophenyl)prop-2-ynyl]piperidine-4-hydroxamic acid 4-[3-(3-Chloro-6-methoxyquinolin-4-yl)propyl]-1-[3-(2-chloro-4-fluorophenyl)prop-2-ynyl]piperidine-4-hydroxamic acid 4-[3-(3-Chloro-6-methoxyquinolin-4-yl)propyl]-1-[3-(3-chloro-5-fluorophenyl)prop-2-ynyl]piperidine-4-hydroxamic acid 4-[3-(3-Chloro-6-methoxyquinolin-4-yl)propyl]-1-[3-(4-chloro-2-fluorophenyl)prop-2-ynyl]piperidine-4-hydroxamic acid 4-[3-(3-Chloro-6-methoxyquinolin-4-yl)propyl]-1-[3-(3-fluoro-4-methylphenyl)prop-2-ynyl]piperidine-4-hydroxamic acid 4-[3-(3-Chloro-6-methoxyquinolin-4-yl)propyl]-1-[3-(3,5-bistrifluoromethylphenyl)prop-2-ynyl]piperidine-4-hydroxamic acid 4-[3-(3-Chloro-6-methoxyquinolin-4-yl)propyl]-1-[3-(thien-2-yl)prop-2-ynyl]piperidine-4-hydroxamic acid 4-[3-(3-Chloro-6-methoxyquinolin-4-yl)propyl]-1-[3-(thien-3-yl)-2-ynyl]piperidine-4-hydroxamic acid 4-[3-(3-Chloro-6-methoxyquinolin-4-yl)propyl]-1-[3-(1,3-thiazol-2-yl)prop-2-ynyl]piperidine-4-hydroxamic acid 4-[3-(3-Chloro-6-methoxyquinolin-4-yl)propyl]-1-[3-(1,3-thiazol-4-yl)prop-2-ynyl]piperidine-4-hydroxamic acid 4-[3-(3-Chloro-6-methoxyquinolin-4-yl)propyl]-1-[3-(1,3-thiazol-5-yl)prop-2-ynyl]piperidine-4-hydroxamic acid 4-[3-(3-Chloro-6-methoxyquinolin-4-yl)propyl]-1-[3-(pyrid-2-yl)prop-2-ynyl]piperidine-4-hydroxamic acid 4-[3-(3-Chloro-6-methoxyquinolin-4-yl)propyl]-1-[3-(pyrid-3-yl)prop-2-ynyl]piperidine-4-hydroxamic acid 4-[3-(3-Chloro-6-methoxyquinolin-4-yl)propyl]-1-[3-(pyrid-4-yl)prop-2-ynyl]piperidine-4-hydroxamic acid 4-[3-(3-Methyl-6-methoxyquinolin-4-yl)propyl]-1-[2-(cyclohexyl)ethyl]piperidine-4-hydroxamic acid 4-[3-(3-Methyl-6-methoxyquinolin-4-yl)propyl]-1-[3-(phenyl)propyl]piperidine-4-hydroxamic acid 4-[3-(3-Methyl-6-methoxyquinolin-4-yl)propyl]-1-[3-(2,3,5-trifluorophenyl)propyl]piperidine-4-hydroxamic acid 4-[3-(3-Methyl-6-methoxyquinolin-4-yl)propyl]-1-[2-(3,5-difluorophenylamino)ethyl]piperidine-4-hydroxamic acid 4-[3-(3-Methyl-6-methoxyquinolin-4-yl)propyl]-1-[2-(2,3,5-trifluorophenylamino)ethyl]piperidine-4-hydroxamic acid 4-[3-(3-Methyl-6-methoxyquinolin-4-yl)propyl]-1-[2-(3,5-difluorophenoxy)ethyl]piperidine-4-hydroxamic acid 4-[3-(3-Methyl-6-methoxyquinolin-4-yl)propyl]-1-[2-(2,3,5-trifluorophenoxy)ethyl]piperidine-4-hydroxamic acid 4-[3-(3-Methyl-6-methoxyquinolin-4-yl)propyl]-1-[2-(cyclopentylthio)ethyl]piperidine-4-hydroxamic acid 4-[3-(3-Methyl-6-methoxyquinolin-4-yl)propyl]-1-[2-(pyrid-2-yl)thioethyl]piperidine-4-hydroxamic acid 4-[3-(3-Methyl-6-methoxyquinolin-4-yl)propyl]-1-[2-(thien-2-yl)thioethyl]piperidine-4-hydroxamic acid 4-[3-(3-Methyl-6-methoxyquinolin-4-yl)propyl]-1-[3-(2,3,5-trifluorophenyl)prop-2-ynyl]piperidine-4-hydroxamic acid 4-[3-(3-Methyl-6-methoxyquinolin-4-yl)propyl]-1-[3-(thien-2-yl)prop-2-ynyl]piperidine-4-hydroxamic acid 4-[3-(3-Fluoro-6-methoxyquinolin-4-yl)propyl]-1-[2-(cyclohexyl)ethyl]piperidine-4-hydroxamic acid 4-[3-(3-Fluoro-6-methoxyquinolin-4-yl)propyl]-1-[3-(phenyl)propyl]piperidine-4-hydroxamic acid 4-[3-(3-Fluoro-6-methoxyquinolin-4-yl)propyl]-1-[3-(2,3,5-trifluorophenyl)propyl]piperidine-4-hydroxamic acid 4-[3-(3-Fluoro-6-methoxyquinolin-4-yl)propyl]-1-[2-(3,5-difluorophenylamino)ethyl]piperidine-4-hydroxamic acid 4-[3-(3-Fluoro-6-methoxyquinolin-4-yl)propyl]-1-[2-(2,3,5-trifluorophenylamino)ethyl]piperidine-4-hydroxamic acid 4-[3-(3-Fluoro-6-methoxyquinolin-4-yl)propyl]-1-[2-(3,5-difluorophenoxy)ethyl]piperidine-4-hydroxamic acid 4-[3-(3-Fluoro-6-methoxyquinolin-4-yl)propyl]-1-[2-(2,3,5-trifluorophenoxy)ethyl]piperidine-4-hydroxamic acid 4-[3-(3-Fluoro-6-methoxyquinolin-4-yl)propyl]-1-[2-(2,3,5-trifluorophenylthio)ethyl]piperidine-4-hydroxamic acid 4-[3-(3-Fluoro-6-methoxyquinolin-4-yl)propyl]-1-[2-(cyclopentylthio)ethyl]piperidine-4-hydroxamic acid 4-[3-(3-Fluoro-6-methoxyquinolin-4-yl)propyl]-1-[2-(pyrid-2-yl)thioethyl]piperidine-4-hydroxamic acid 4-[3-(3-Fluoro-6-methoxyquinolin-4-yl)propyl]-1-[2-(thien-2-yl)thioethyl]piperidine-4-hydroxamic acid 4-[3-(3-Fluoro-6-methoxyquinolin-4-yl)propyl]-1-[3-(2,3,5-trifluorophenyl)prop-2-ynyl]piperidine-4-hydroxamic acid 4-[3-(3-Fluoro-6-methoxyquinolin-4-yl)propyl]-1-[3-(thien-2-yl)prop-2-ynyl]piperidine-4-hydroxamic acid 4-[3-(3-Dimethylamino-6-methoxyquinolin-4-yl)propyl]-1-[2-(cyclohexyl)ethyl]piperidine-4-hydroxamic acid 4-[3-(3-Dimethylamino-6-methoxyquinolin-4-yl)propyl]-1-[3-(phenyl)propyl]piperidine-4-hydroxamic acid 4-[3-(3-Dimethylamino-6-methoxyquinolin-4-yl)propyl]-1-[3-(2,3,5-trifluorophenyl)propyl]piperidine-4-hydroxamic acid 4-[3-(3-Dimethylamino-6-methoxyquinolin-4-yl)propyl]-1-[2-(3,5-difluorophenylamino)ethyl]piperidine-4-hydroxamic acid 4-[3-(3-Dimethylamino-6-methoxyquinolin-4-yl)propyl]-1-[2-(2,3,5-trifluorophenylamino)ethyl]piperidine-4-hydroxamic acid 4-[3-(3-Dimethylamino-6-methoxyquinolin-4-yl)propyl]-1-[2-(3,5-difluorophenoxy)ethyl]piperidine-4-hydroxamic acid 4-[3-(3-Dimethylamino-6-methoxyquinolin-4-yl)propyl]-1-[2-(2,3,5-trifluorophenoxy)ethyl]piperidine-4-hydroxamic acid 4-[3-(3-Dimethylamino-6-methoxyquinolin-4-yl)propyl]-1-[2-(2,3,5-trifluorophenylthio)ethyl]piperidine-4-hydroxamic acid 4-[3-(3-Dimethylamino-6-methoxyquinolin-4-yl)propyl]-1-[2-(cyclopentylthio)ethyl]piperidine-4-hydroxamic acid 4-[3-(3-Dimethylamino-6-methoxyquinolin-4-yl)propyl]-1-[2-(pyrid-2-yl)thioethyl]piperidine-4-hydroxamic acid 4-[3-(3-Dimethylamino-6-methoxyquinolin-4-yl)propyl]-1-[2-(thien-2-yl)thioethyl]piperidine-4-hydroxamic acid 4-[3-(3-Dimethylamino-6-methoxyquinolin-4-yl)propyl]-1-[3-(2,3,5-trifluorophenyl)prop-2-ynyl]piperidine-4-hydroxamic acid 4-[3-(3-Dimethylamino-6-methoxyquinolin-4-yl)propyl]-1-[3-(thien-2-yl)prop-2-ynyl]piperidine-4-hydroxamic acid 4-[3-(3-Hydroxymethyl-6-methoxyquinolin-4-yl)propyl]-1-[2-(cyclohexyl)ethyl]piperidine-4-hydroxamic acid 4-[3-(3-Hydroxymethyl-6-methoxyquinolin-4-yl)propyl]-1-[3-(phenyl)propyl]piperidine-4-hydroxamic acid 4-[3-(3-Hydroxymethyl-6-methoxyquinolin-4-yl)propyl]-1-[3-(2,3,5-trifluorophenyl)propyl]piperidine-4-hydroxamic acid 4-[3-(3-Hydroxymethyl-6-methoxyquinolin-4-yl)propyl]-1-[2-(3,5-difluorophenylamino)ethyl]piperidine-4-hydroxamic acid 4-[3-(3-Hydroxymethyl-6-methoxyquinolin-4-yl)propyl]-1-[2-(2,3,5-trifluorophenylamino)ethyl]piperidine-4-hydroxamic acid 4-[3-(3-Hydroxymethyl-6-methoxyquinolin-4-yl)propyl]-1-[2-(3,5-difluorophenoxy)ethyl]piperidine-4-hydroxamic acid 4-[3-(3-Hydroxymethyl-6-methoxyquinolin-4-yl)propyl]-1-[2-(2,3,5-trifluorophenoxy)ethyl]piperidine-4-hydroxamic acid 4-[3-(3-Hydroxymethyl-6-methoxyquinolin-4-yl)propyl]-1-[2-(2,3,5-trifluorophenylthio)ethyl]piperidine-4-hydroxamic acid 4-[3-(3-Hydroxymethyl-6-methoxyquinolin-4-yl)propyl]-1-[2-(cyclopentylthio)ethyl]piperidine-4-hydroxamic acid 4-[3-(3-Hydroxymethyl-6-methoxyquinolin-4-yl)propyl]-1-[2-(pyrid-2-yl)thioethyl]piperidine-4-hydroxamic acid 4-[3-(3-Hydroxymethyl-6-methoxyquinolin-4-yl)propyl]-1-[2-(thien-2-yl)thioethyl]piperidine-4-hydroxamic acid 4-[3-(3-Hydroxymethyl-6-methoxyquinolin-4-yl)propyl]-1-[3-(2,3,5-trifluorophenyl)prop-2-ynyl]piperidine-4-hydroxamic acid 4-[3-(3-Hydroxymethyl-6-methoxyquinolin-4-yl)propyl]-1-[3-(thien-2-yl)prop-2-ynyl]piperidine-4-hydroxamic acid 4-[3-(3-Fluoromethyl-6-methoxyquinolin-4-yl)propyl]-1-[2-(cyclohexyl)ethyl]piperidine-4-hydroxamic acid 4-[3-(3-Fluoromethyl-6-methoxyquinolin-4-yl)propyl]-1-[3-(phenyl)propyl]piperidine-4-hydroxamic acid 4-[3-(3-Fluoromethyl-6-methoxyquinolin-4-yl)propyl]-1-[3-(2,3,5-trifluorophenyl)propyl]piperidine-4-hydroxamic acid 4-[3-(3-Fluoromethyl-6-methoxyquinolin-4-yl)propyl]-1-[2-(3,5-difluorophenylamino)ethyl]piperidine-4-hydroxamic acid 4-[3-(3-Fluoromethyl-6-methoxyquinolin-4-yl)propyl]-1-[2-(2,3,5-trifluorophenylamino)ethyl]piperidine-4-hydroxamic acid 4-[3-(3-Fluoromethyl-6-methoxyquinolin-4-yl)propyl]-1-[2-(3,5-difluorophenoxy)ethyl]piperidine-4-hydroxamic acid 4-[3-(3-Fluoromethyl-6-methoxyquinolin-4-yl)propyl]-1-[2-(2,3,5-trifluorophenoxy)ethyl]piperidine-4-hydroxamic acid 4-[3-(3-Fluoromethyl-6-methoxyquinolin-4-yl)propyl]-1-[2-(2,3,5-trifluorophenylthio)ethyl]piperidine-4-hydroxamic acid 4-[3-(3-Fluoromethyl-6-methoxyquinolin-4-yl)propyl]-1-[2-(cyclopentylthio)ethyl]piperidine-4-hydroxamic acid 4-[3-(3-Fluoromethyl-6-methoxyquinolin-4-yl)propyl]-1-[2-(pyrid-2-yl)thioethyl]piperidine-4-hydroxamic acid 4-[3-(3-Fluoromethyl-6-methoxyquinolin-4-yl)propyl]-1-[2-(thien-2-yl)thioethyl]piperidine-4-hydroxamic acid 4-[3-(3-Fluoromethyl-6-methoxyquinolin-4-yl)propyl]-1-[3-(2,3,5-trifluorophenyl)prop-2-ynyl]piperidine-4-hydroxamic acid 4-[3-(3-Fluoromethyl-6-methoxyquinolin-4-yl)propyl]-1-[3-(thien-2-yl)prop-2-ynyl]piperidine-4-hydroxamic acid 4-[3-(3-Aminomethyl-6-methoxyquinolin-4-yl)propyl]-1-[2-(cyclohexyl)ethyl]piperidine-4-hydroxamic acid 4-[3-(3-Aminomethyl-6-methoxyquinolin-4-yl)propyl]-1-[3-(phenyl)propyl]piperidine-4-hydroxamic acid 4-[3-(3-Aminomethyl-6-methoxyquinolin-4-yl)propyl]-1-[3-(2,3,5-trifluorophenyl)propyl]piperidine-4-hydroxamic acid 4-[3-(3-Aminomethyl-6-methoxyquinolin-4-yl)propyl]-1-[2-(3,5-difluorophenylamino)ethyl]piperidine-4-hydroxamic acid 4-[3-(3-Aminomethyl-6-methoxyquinolin-4-yl)propyl]-1-[2-(2,3,5-trifluorophenylamino)ethyl]piperidine-4-hydroxamic acid 4-[3-(3-Aminomethyl-6-methoxyquinolin-4-yl)propyl]-1-[2-(3,5-difluorophenoxy)ethyl]piperidine-4-hydroxamic acid 4-[3-(3-Aminomethyl-6-methoxyquinolin-4-yl)propyl]-1-[2-(2,3,5-trifluorophenoxy)ethyl]piperidine-4-hydroxamic acid 4-[3-(3-Aminomethyl-6-methoxyquinolin-4-yl)propyl]-1-[2-(2,3,5-trifluorophenylthio)ethyl]piperidine-4-hydroxamic acid 4-[3-(3-Aminomethyl-6-methoxyquinolin-4-yl)propyl]-1-[2-(cyclopentylthio)ethyl]piperidine-4-hydroxamic acid 4-[3-(3-Aminomethyl-6-methoxyquinolin-4-yl)propyl]-1-[2-(pyrid-2-yl)thioethyl]piperidine-4-hydroxamic acid 4-[3-(3-Aminomethyl-6-methoxyquinolin-4-yl)propyl]-1-[2-(thien-2-yl)thioethyl]piperidine-4-hydroxamic acid 4-[3-(3-Aminomethyl-6-methoxyquinolin-4-yl)propyl]-1-[3-(2,3,5-trifluorophenyl)prop-2-ynyl]piperidine-4-hydroxamic acid 4-[3-(3-Aminomethyl-6-methoxyquinolin-4-yl)propyl]-1-[3-(thien-2-yl)prop-2-ynyl]piperidine-4-hydroxamic acid 4-[3-(3-Morpholinomethyl-6-methoxyquinolin-4-yl)propyl]-1-[2-(cyclohexyl)ethyl]piperidine-4-hydroxamic acid 4-[3-(3-Morpholinomethyl-6-methoxyquinolin-4-yl)propyl]-1-[3-(phenyl)propyl]piperidine-4-hydroxamic acid 4-[3-(3-Morpholinomethyl-6-methoxyquinolin-4-yl)propyl]-1-[3-(2,3,5-trifluorophenyl)propyl]piperidine-4-hydroxamic acid 4-[3-(3-Morpholinomethyl-6-methoxyquinolin-4-yl)propyl]-1-[2-(3,5-difluorophenylamino)ethyl]piperidine-4-hydroxamic acid 4-[3-(3-Morpholinomethyl-6-methoxyquinolin-4-yl)propyl]-1-[2-(2,3,5-trifluorophenylamino)ethyl]piperidine-4-hydroxamic acid 4-[3-(3-Morpholinomethyl-6-methoxyquinolin-4-yl)propyl]-1-[2-(3,5-difluorophenoxy)ethyl]piperidine-4-hydroxamic acid 4-[3-(3-Morpholinomethyl-6-methoxyquinolin-4-yl)propyl]-1-[2-(2,3,5-trifluorophenoxy)ethyl]piperidine-4-hydroxamic acid 4-[3-(3-Morpholinomethyl-6-methoxyquinolin-4-yl)propyl]-1-[2-(2,3,5-trifluorophenylthio)ethyl]piperidine-4-hydroxamic acid 4-[3-(3-Morpholinomethyl-6-methoxyquinolin-4-yl)propyl]-1-[2-(cyclopentylthiol)ethyl]piperidine-4-hydroxamic acid 4-[3-(3-Morpholinomethyl-6-methoxyquinolin-4-yl)propyl]-1-[2-(pyrid-2-yl)thioethyl]piperidine-4-hydroxamic acid 4-[3-(3-Morpholinomethyl-6-methoxyquinolin-4-yl)propyl]-1-[2-(thien-2-yl)thioethyl]piperidine-4-hydroxamic acid 4-[3-(3-Morpholinomethyl-6-methoxyquinolin-4-yl)propyl]-1-[3-(2,3,5-trifluorophenyl)prop-2-ynyl]piperidine-4-hydroxamic acid 4-[3-(3-Morpholinomethyl-6-methoxyquinolin-4-yl)propyl]-1-[3-(thien-2-yl)prop-2-ynyl]piperidine-4-hydroxamic acid 4-[3-(3-Methyl-6-methoxyquinolin-4-yl)propyl]-1-[3-(2,4,6-trifluorophenyl)propyl]piperidine-4-hydroxamic acid 4-[3-(3-Methyl-6-methoxyquinolin-4-propyl]-1-[3-(3,4,5-trifluorophenyl)propyl]piperidine-4-hydroxamic acid 4-[3-(3-Methyl-6-methoxyquinolin-4-yl)propyl]-1-[2-(2,4,6-trifluorophenylthio)ethyl]piperidine-4-hydroxamic acid 4-[3-(3-Methyl-6-methoxyquinolin-4-yl)propyl]-1-[2-(3,4,5-trifluorophenylthio)ethyl]piperidine-4-hydroxamic acid 4-[3-(3-Methyl-6-methoxyquinolin-4-yl)propyl]-1-[2-(2,4,6-trifluorophenylamino)ethyl]piperidine-4-hydroxamic acid 4-[3-(3-Methyl-6-methoxyquinolin-4-yl)propyl]-1-[2-(3,4,5-trifluorophenylamino)ethyl]piperidine-4-hydroxamic acid 4-[3-(3-Methyl-6-methoxyquinolin-4-yl)propyl]-1-[2-(2,4,6-trifluorophenoxy)ethyl]piperidine-4-hydroxamic acid 4-[3-(3-Methyl-6-methoxyquinolin-4-yl)propyl]-1-[2-(3,4,5-trifluorophenoxy)ethyl]piperidine-4-hydroxamic acid 4-[3-(3-Methyl-6-methoxyquinolin-4-yl)propyl]-1-[3-(2,4,6-trifluorophenyl)prop-2-ynyl]piperidine-4-hydroxamic acid 4-[3-(3-Methyl-6-methoxyquinolin-4-yl)propyl]-1-[3-(3,4,5-trifluorophenyl)prop-2-ynyl]piperidine-4-hydroxamic acid 4-[3-(3-Fluoro-6-methoxyquinolin-4-yl)propyl]-1-[3-(2,4,6-trifluorophenyl)propyl]piperidine-4-hydroxamic acid 4-[3-(3-Fluoro-6-methoxyquinolin-4-yl)propyl]-1-[3-(3,4,5-trifluorophenyl)propyl]piperidine-4-hydroxamic acid 4-[3-(3-Fluoro-6-methoxyquinolin-4-yl)propyl]-1-[2-(2,4,6-trifluorophenylthio)ethyl]piperidine-4-hydroxamic acid 4-[3-(3-Fluoro-6-methoxyquinolin-4-yl)propyl]-1-[2-(3,4,5-trifluorophenylthio)ethyl]piperidine-4-hydroxamic acid 4-[3-(3-Fluoro-6-methoxyquinolin-4-yl)propyl]-1-[2-(2,4,6-trifluorophenylamino)ethyl]piperidine-4-hydroxamic acid 4-[3-(3-Fluoro-6-methoxyquinolin-4-yl)propyl]-1-[2-(3,4,5-trifluorophenylamino)ethyl]piperidine-4-hydroxamic acid 4-[3-(3-Fluoro-6-methoxyquinolin-4-yl)propyl]-1-[2-(2,4,6-trifluorophenoxy)ethyl]piperidine-4-hydroxamic acid 4-[3-(3-Fluoro-6-methoxyquinolin-4-yl)propyl]-1-[2-(3,4,5-trifluorophenoxy)ethyl]piperidine-4-hydroxamic acid 4-[3-(3-Fluoro-6-methoxyquinolin-4-yl)propyl]-1-[3-(2,4,6-trifluorophenyl)prop-2-ynyl]piperidine-4-hydroxamic acid 4-[3-(3-Fluoro-6-methoxyquinolin-4-yl)propyl]-1-[3-(3,4,5-trifluorophenyl)prop-2-ynyl]piperidine-4-hydroxamic acid 4-[3-(3-Dimethylamino-6-methoxyquinolin-4-yl)propyl]-1-[3-(2,4,6-trifluorophenyl)propyl]piperidine-4-hydroxamic acid 4-[3-(3-Dimethylamino-6-methoxyquinolin-4-yl)propyl]-1-[3-(3,4,5-trifluorophenyl)propyl]piperidine-4-hydroxamic acid 4-[3-(3-Dimethylamino-6-methoxyquinolin-4-yl)propyl]-1-[2-(2,4,6-trifluorophenylthio)ethyl]piperidine-4-hydroxamic acid 4-[3-(3-Dimethylamino-6-methoxyquinolin-4-yl)propyl]-1-[2-(3,4,5-trifluorophenylthio)ethyl]piperidine-4-hydroxamic acid 4-[3-(3-Dimethylamino-6-methoxyquinolin-4-yl)propyl]-1-[2-(2,4,6-trifluorophenylamino)ethyl]piperidine-4-hydroxamic acid 4-[3-(3-Dimethylamino-6-methoxyquinolin-4-yl)propyl]-1-[2-(3,4,5-trifluorophenylamino)ethyl]piperidine-4-hydroxamic acid 4-[3-(3-Dimethylamino-6-methoxyquinolin-4-yl)propyl]-1-[2-(2,4,6-trifluorophenoxy)ethyl]piperidine-4-hydroxamic acid 4-[3-(3-Dimethylamino-6-methoxyquinolin-4-yl)propyl]-1-[2-(3,4,5-trifluorophenoxy)ethyl]piperidine-4-hydroxamic acid 4-[3-(3-Dimethylamino-6-methoxyquinolin-4-yl)propyl]-1-[3-(2,4,6-trifluorophenyl)prop-2-ynyl]piperidine-4-hydroxamic acid 4-[3-(3-Dimethylamino-6-methoxyquinolin-4-yl)propyl]-1-[3-(3,4,5-trifluorophenyl)prop-2-ynyl]piperidine-4-hydroxamic acid 4-[3-(3-Hydroxymethyl-6-methoxyquinolin-4-yl)propyl]-1-[3-(3,4,5-trifluorophenyl)propyl]piperidine-4-hydroxamic acid 4-[3-(3-Hydroxymethyl-6-methoxyquinolin-4-yl)propyl]-1-[2-(2,4,6-trifluorophenylthio)ethyl]piperidine-4-hydroxamic acid 4-[3-(3-Hydroxymethyl-6-methoxyquinolin-4-yl)propyl]-1-[2-(3,4,5-trifluorophenylthio)ethyl]piperidine-4-hydroxamic acid 4-[3-(3-Hydroxymethyl-6-methoxyquinolin-4-yl)propyl]-1-[2-(2,4,6-trifluorophenylamino)ethyl]piperidine-4-hydroxamic acid 4-[3-(3-Hydroxymethyl-6-methoxyquinolin-4-yl)propyl]-1-[2-(3,4,5-trifluorophenylamino)ethyl]piperidine-4-hydroxamic acid 4-[3-(3-Hydroxymethyl-6-methoxyquinolin-4-yl)propyl]-1-[2-(2,4,6-trifluorophenoxy)ethyl]piperidine-4-hydroxamic acid 4-[3-(3-Hydroxymethyl-6-methoxyquinolin-4-yl)propyl]-1-[2-(3,4,5-trifluorophenoxy)ethyl]piperidine-4-hydroxamic acid 4-[3-(3-Hydroxymethyl-6-methoxyquinolin-4-yl)propyl]-1-[3-(2,4,6-trifluorophenyl)prop-2-ynyl]piperidine-4-hydroxamic acid 4-[3-(3-Hydroxymethyl-6-methoxyquinolin-4-yl)propyl]-1-[3-(3,4,5-trifluorophenyl)prop-2-ynyl]piperidine-4-hydroxamic acid 4-[3-(3-Fluoromethyl-6-methoxyquinolin-4-yl)propyl]-1-[3-(2,4,6-trifluorophenyl)propyl]piperidine-4-hydroxamic acid 4-[3-(3-Fluoromethyl-6-methoxyquinolin-4-yl)propyl]-1-[3-(3,4,5-trifluorophenyl)propyl]piperidine-4-hydroxamic acid 4-[3-(3-Fluoromethyl-6-methoxyquinolin-4-yl)propyl]-1-[2-(2,4,6-trifluorophenylthio)pethyl]piperidine-4-hydroxamic acid 4-[3-(3-Fluoromethyl-6-methoxyquinolin-4-yl)propyl]-1-[2-(3,4,5-trifluorophenylthio)ethyl]piperidine-4-hydroxamic acid 4-[3-(3-Fluoromethyl-6-methoxyquinolin-4-yl)propyl]-1-[2-(2,4,6-trifluorophenylamino)ethyl]piperidine-4-hydroxamic acid 4-[3-(3-Fluoromethyl-6-methoxyquinolin-4-yl)propyl]-1-[2-(3,4,5-trifluorophenylamino)ethyl]piperidine-4-hydroxamic acid 4-[3-(3-Fluoromethyl-6-methoxyquinolin-4-yl)propyl]-1-[2-(2,4,6-trifluorophenoxy)ethyl]piperidine-4-hydroxamic acid 4-[3-(3-Fluoromethyl-6-methoxyquinolin-4-yl)propyl]-1-[2-(3,4,5-trifluorophenoxy)ethyl]piperidine-4-hydroxamic acid 4-[3-(3-Fluoromethyl-6-methoxyquinolin-4-yl)propyl]-1-[3-(2,4,6-trifluorophenyl)prop-2-ynyl]piperidine-4-hydroxamic acid 4-[3-(3-Fluoromethyl-6-methoxyquinolin-4-yl)propyl]-1-[3-(3,4,5-trifluorophenyl)prop-2-ynyl]piperidine-4-hydroxamic acid 4-[3-(3-Aminomethyl-6-methoxyquinolin-4-yl)propyl]-1-[3-(2,4,6-trifluorophenyl)propyyl]piperidine-4-hydroxamic acid 4-[3-(3-Aminomethyl-6-methoxyquinolin-4-yl)propyl]-1-[3-(3,4,5-trifluorophenyl)propyl]piperidine-4-hydroxamic acid 4-[3-(3-Aminomethyl-6-methoxyquinolin-4-yl)propyl]-1-[2-(2,4,6-trifluorophenylthio)ethyl]piperidine-4-hydroxamic acid 4-[3-(3-Aminomethyl-6-methoxyquinolin-4-yl)propyl]-1-[2-(3,4,5-trifluorophenylthio)ethyl]piperidine-4-hydroxamic acid 4-[3-(3-Aminomethyl-6-methoxyquinolin-4-yl)propyl]-1-[2-(2,4,6-trifluorophenylamino)ethyl]piperidine-4-hydroxamic acid 4-[3-(3-Aminomethyl-6-methoxyquinolin-4-yl)propyl]-1-[2-(3,4,5-trifluorophenylamino)ethyl]piperidine-4-hydroxamic acid 4-[3-(3-Aminomethyl-6-methoxyquinolin-4-yl)propyl]-1-[2-(2,4,6-trifluorophenoxy)ethyl]piperidine-4-hydroxamic acid 4-[3-(3-Aminomethyl-6-methoxyquinolin-4-yl)propyl]-1-[2-(3,4,5-trifluorophenoxy)ethyl]piperidine-4-hydroxamic acid 4-[3-(3-Aminomethyl-6-methoxyquinolin-4-yl)propyl]-1-[3-(2,4,6-trifluorophenyl)prop-2-ynyl]piperidine-4-hydroxamic acid 4-[3-(3-Aminomethyl-6-methoxyquinolin-4-yl)propyl]-1-[3-(3,4,5-trifluorophenyl)prop-2-ynyl]piperidine-4-hydroxamic acid 4-[3-(3-Morpholinomethyl-6-methoxyquinolin-4-yl)propyl]-1-[3-(2,4,6-trifluorophenyl)propyl]piperidine-4-hydroxamic acid 4-[3-(3-Morpholinomethyl-6-methoxyquinolin-4-yl)propyl]-1-[3-(3,4,5-trifluorophenyl)propyl]piperidine-4-hydroxamic acid 4-[3-(3-Morpholinomethyl-6-methoxyquinolin-4-yl)propyl]-1-[2-(2,4,6-trifluorophenylthio)ethyl]piperidine-4-hydroxamic acid 4-[3-(3-Morpholinomethyl-6-methoxyquinolin-4-yl)propyl]-1-[2-(3,4,5-trifluorophenylthio)ethyl]piperidine-4-hydroxamic acid 4-[3-(3-Morpholinomethyl-6-methoxyquinolin-4-yl)propyl]-1-[2-(2,4,6-trifluorophenylamino)ethyl]piperidine-4-hydroxamic acid 4-[3-(3-Morpholinomethyl-6-methoxyquinolin-4-yl)propyl]-1-[2-(3,4,5-trifluorophenylamino)ethyl]piperidine-4-hydroxamic acid 4-[3-(3-Morpholinomethyl-6-methoxyquinolin-4-yl)propyl]-1-[2-(2,4,6-trifluorophenoxy)ethyl]piperidine-4-hydroxamic acid 4-[3-(3-Morpholinomethyl-6-methoxyquinolin-4-yl)propyl]-1-[2-(3,4,5-trifluorophenoxy)ethyl]piperidine-4-hydroxamic acid 4-[3-(3-Morpholinomethyl-6-methoxyquinolin-4-yl)propyl]-1-[3-(2,4,6-trifluorophenyl)prop-2-ynyl]piperidine-4-hydroxamic acid 4-[3-(3-Morpholinomethyl-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-chloro-6-methoxyquinolin-4-yl)propyl]-1-heptyl piperidine-4-hydroxamic acid 4-[3-(R,S)-Hydroxy-3-(3-chloro-6-methoxyquinolin-4-yl)propyl]-1-[4-phenylbutyl]piperidine-4-hydroxamic acid 4-[3-(R,S)-Hydroxy-3-(3-chloro-6-methoxyquinolin-4-yl)propyl]-1-[3-(phenyl)propyl]piperidine-4-hydroxamic acid 4-[3-(R,S)-Hydroxy-3-(3-chloro-6-methoxyquinolin-4-yl)propyl]-1-[4-(2-fluorophenyl)propyl]piperidine-4-hydroxamic acid 4-[3-(R,S)-Hydroxy-3-(3-chloro-6-methoxyquinolin-4-yl)propyl]-1-[4-(3-fluorophenyl)propyl]piperidine-4-hydroxamic acid 4-[3-(R,S)-Hydroxy-3-(3-chloro-6-methoxyquinolin-4-yl)propyl]-1-[3-(4-fluorophenyl)propyl]piperidine-4-hydroxamic acid 4-[3-(R,S)-Hydroxy-3-(3-chloro-6-methoxyquinolin-4-yl)propyl]-1-[4-(4-fluorophenyl)butyl]piperidine-4-hydroxamic acid 4-[3-(R,S)-Hydroxy-3-(3-chloro-6-methoxyquinolin-4-yl)propyl]-1-[3-(2,3-difluorophenyl)propyl]piperidine-4-hydroxamic acid 4-[3-(R,S)-Hydroxy-3-(3-chloro-6-methoxyquinolin-4-yl)propyl]-1-[4-(2,3-difluorophenyl)propyl]piperidine-4-hydroxamic acid 4-[3-(R,S)-Hydroxy-3-(3-chloro-6-methoxyquinolin-4-yl)propyl]-1-[3-(2,6-difluorophenyl)propyl]piperidine-4-hydroxamic acid 4-[3-(R,S)-Hydroxy-3-(3-chloro-6-methoxyquinolin-4-yl)propyl]-1-[4-(2,6-difluorophenyl)propyl]piperidine-4-hydroxamic acid 4-[3-(R,S)-Hydroxy-3-(3-chloro-6-methoxyquinolin-4-yl)propyl]-1-[3-(3,5-difluorophenyl)propyl]piperidine-4-hydroxamic acid 4-[3-(R,S)-Hydroxy-3-(3-chloro-6-methoxyquinolin-4-yl)propyl]-1-[3-(2,3,5-trifluorophenyl)propyl]piperidine-4-hydroxamic acid 4-[3-(R,S)-Hydroxy-3-(3-chloro-6-methoxyquinolin-4-yl)propyl]-1-[3-phenylthiopropyl]piperidine-4-hydroxamic acid 4-[3-(R,S)-Hydroxy-3-(3-chloro-6-methoxyquinolin-4-yl)propyl]-1-[3-(2-fluorophenylthio)propyl]piperidine-4-hydroxamic acid 4-[3-(R,S)-Hydroxy-3-(3-chloro-6-methoxyquinolin-4-yl)propyl]-1-[3-(3-fluorophenylthio)propyl]piperidine-4-hydroxamic acid 4-[3-(R,S)-Hydroxy-3-(3-chloro-6-methoxyquinolin-4-yl)propyl]-1-[2-(4-fluorophenylthio)ethyl]piperidine-4-hydroxamic acid 4-[3-(R,S)-Hydroxy-3-(3-chloro-6-methoxyquinolin-4-yl)propyl]-1-[3-(4-fluorophenylthio)propyl]piperidine-4-hydroxamic acid 4-[3-(R,S)-Hydroxy-3-(3-chloro-6-methoxyquinolin-4-yl)propyl]-1-[2-(2,3-difluorophenylthio)ethyl]piperidine-4-hydroxamic acid 4-[3-(R,S)-Hydroxy-3-(3-chloro-6-methoxyquinolin-4-yl)propyl]-1-[3-(2,3-difluorophenylthio)propyl]piperidine-4-hydroxamic acid 4-[3-(R,S)-Hydroxy-3-(3-chloro-6-methoxyquinolin-4-yl)propyl]-1-[2-(2,6-difluorophenylthio)ethyl]piperidine-4-hydroxamic acid 4-[3-(R,S)-Hydroxy-3-(3-chloro-6-methoxyquinolin-4-yl)propyl]-1-[2-(2,3,5-trifluorophenylthio)ethyl]piperidine-4-hydroxamic acid 4-[3-(R,S)-Hydroxy-3-(3-chloro-6-methoxyquinolin-4-yl)propyl]-1-[2-(2,4,6-trifluorophenylthio)ethyl]piperidine-4-hydroxamic acid 4-[3-(R,S)-Hydroxy-3-(3-chloro-6-methoxyquinolin-4-yl)propyl]-1-[2-(3,4,5-trifluorophenylthio)ethyl]piperidine-4-hydroxamic acid 4-[3-(R,S)-Hydroxy-3-(3-chloro-6-methoxyquinolin-4-yl)propyl]-1-[2-(3,5-difluorophenoxy)ethyl]piperidine-4-hydroxamic acid 4-[3-(R,S)-Hydroxy-3-(3-chloro-6-methoxyquinolin-4-yl)propyl]-1-[2-(2,3,5-trifluorophenoxy)ethyl]piperidine-4-hydroxamic acid 4-[3-(R,S)-Hydroxy-3-(3-chloro-6-methoxyquinolin-4-yl)propyl]-1-[2-(2,4,6-trifluorophenoxy)ethyl]piperidine-4-hydroxamic acid 4-[3-(R,S)-Hydroxy-3-(3-chloro-6-methoxyquinolin-4-yl)propyl]-1-[2-(3,4,5-trifluorophenoxy)ethyl]piperidine-4-hydroxamic acid 4-[3-(R,S)-Hydroxy-3-(3-chloro-6-methoxyquinolin-4-yl)propyl]-1-[2-(3,5-difluorophenylamino)ethyl]piperidine-4-hydroxamic acid 4-[3-(R,S)-Hydroxy-3-(3-chloro-6-methoxyquinolin-4-yl)propyl]-1-[2-(2,3,5-trifluorophenylamino)ethyl]piperidine-4-hydroxamic acid 4-[3-(R,S)-Hydroxy-3-(3-chloro-6-methoxyquinolin-4-yl)propyl]-1-[2-(2,4,6-trifluorophenylamino)ethyl]piperidine-4-hydroxamic acid 4-[3-(R,S)-Hydroxy-3-(3-chloro-6-methoxyquinolin-4-yl)propyl]-1-[2-(3,4,5-trifluorophenylamino)ethyl]piperidine-4-hydroxamic acid 4-[3-(R,S)-Hydroxy-3-(3-chloro-6-methoxyquinolin-4-yl)propyl]-1-[3-(2,6-difluorophenylthio)propyl]piperidine-4-hydroxamic acid 4-[3-(R,S)-Hydroxy-3-(3-chloro-6-methoxyquinolin-4-yl)propyl]-1-[2-(2-chlorophenylthio)ethyl]piperidine-4-hydroxamic acid 4-[3-(R,S)-Hydroxy-3-(3-chloro-6-methoxyquinolin-4-yl)propyl]-1-[3-(2-chlorophenylthio)propyl]piperidine-4-hydroxamic acid 4-[3-(R,S)-Hydroxy-3-(3-chloro-6-methoxyquinolin-4-yl)propyl]-1-[2-(3-chlorophenylthio)ethyl]piperidine-4-hydroxamic acid 4-[3-(R,S)-Hydroxy-3-(3-chloro-6-methoxyquinolin-4-yl)propyl]-1-[3-(3-chlorophenylthio)propyl]piperidine-4-hydroxamic acid 4-[3-(R,S)-Hydroxy-3-(3-chloro-6-methoxyquinolin-4-yl)propyl]-1-[2-(4-chlorophenylthio)ethyl]piperidine-4-hydroxamic acid 4-[3-(R,S)-Hydroxy-3-(3-chloro-6-methoxyquinolin-4-yl)propyl]-1-[3-(4-chlorophenylthio)propyl]piperidine-4-hydroxamic acid 4-[3-(R,S)-Hydroxy-3-(3-chloro-6-methoxyquinolin-4-yl)propyl]-1-[2-(2-methylphenylthio)ethyl]piperidine-4-hydroxamic acid 4-[3-(R,S)-Hydroxy-3-(3-chloro-6-methoxyquinolin-4-yl)propyl]-1-[3-(2-methylphenylthio)propyl]piperidine-4-hydroxamic acid 4-[3-(R,S)-Hydroxy-3-(3-chloro-6-methoxyquinolin-4-yl)propyl]-1-[2-(3-methylphenylthio)ethyl]piperidine-4-hydroxamic acid 4-[3-(R,S)-Hydroxy-3-(3-chloro-6-methoxyquinolin-4-yl)propyl]-1-[3-(3-methylphenylthio)propyl]piperidine-4-hydroxamic acid 4-[3-(R,S)-Hydroxy-3-(3-chloro-6-methoxyquinolin-4-yl)propyl]-1-[2-(4-methylphenylthio)ethyl]piperidine-4-hydroxamic acid 4-[3-(R,S)-Hydroxy-3-(3-chloro-6-methoxyquinolin-4-yl)propyl]-1-[3-(4-methylphenylthio)propyl]piperidine-4-hydroxamic acid 4-[3-(R,S)-Hydroxy-3-(3-chloro-6-methoxyquinolin-4-yl)propyl]-1-[2-(2-trifluoromethylphenylthio)ethyl]piperidine-4-hydroxamic acid 4-[3-(R,S)-Hydroxy-3-(3-chloro-6-methoxyquinolin-4-yl)propyl]-1-[3-(2-trifluoromethylphenylthio)propyl]piperidine-4-hydroxamic acid 4-[3-(R,S)-Hydroxy-3-(3-chloro-6-methoxyquinolin-4-yl)propyl]-1-[2-(3-trifluoromethylphenylthio)ethyl]piperidine-4-hydroxamic acid 4-[3-(R,S)-Hydroxy-3-(3-chloro-6-methoxyquinolin-4-yl)propyl]-1-[3-(3-trifluoromethylphenylthio)propyl]piperidine-4-hydroxamic acid 4-[3-(R,S)-Hydroxy-3-(3-chloro-6-methoxyquinolin-4-yl)propyl]-1-[2-(4-trifluoromethylphenylthio)ethyl]piperidine-4-hydroxamic acid 4-[3-(R,S)-Hydroxy-3-(3-chloro-6-methoxyquinolin-4-yl)propyl]-1-[3-(4-trifluoromethylphenylthio)propyl]piperidine-4-hydroxamic acid 4-[3-(R,S)-Hydroxy-3-(3-chloro-6-methoxyquinolin-4-yl)propyl]-1-[2-(2-methoxyphenylthio)ethyl]piperidine-4-hydroxamic acid 4-[3-(R,S)-Hydroxy-3-(3-chloro-6-methoxyquinolin-4-yl)propyl]-1-[3-(2-methoxyphenylthio)propyl]piperidine-4-hydroxamic acid 4-[3-(R,S)-Hydroxy-3-(3-chloro-6-methoxyquinolin-4-yl)propyl]-1-[2-(3-methoxyphenylthio)ethyl]piperidine-4-hydroxamic acid 4-[3-(R,S)-Hydroxy-3-(3-chloro-6-methoxyquinolin-4-yl)propyl]-1-[3-(3-methoxyphenylthio)propyl]piperidine-4-hydroxamic acid 4-[3-(R,S)-Hydroxy-3-(3-chloro-6-methoxyquinolin-4-yl)propyl]-1-[2-(4-methoxyphenylthio)ethyl]piperidine-4-hydroxamic acid 4-[3-(R,S)-Hydroxy-3-(3-chloro-6-methoxyquinolin-4-yl)propyl]-1-[3-(4-methoxyphenylthio)propyl]piperidine-4-hydroxamic acid 4-[3-(R,S)-Hydroxy-3-(3-chloro-6-methoxyquinolin-4-yl)propyl]-1-[cyclopentylmethyl]piperidine-4-hydroxamic acid 4-[3-(R,S)-Hydroxy-3-(3-chloro-6-methoxyquinolin-4-yl)propyl]-1-[2-(cyclopentyl)ethyl]piperidine-4-hydroxamic acid 4-[3-(R,S)-Hydroxy-3-(3-chloro-6-methoxyquinolin-4-yl)propyl]-1-[2-(cyclohexyl)ethyl]piperidine-4-hydroxamic acid 4-[3-(R,S)-Hydroxy-3-(3-chloro-6-methoxyquinolin-4-yl)propyl]-1-[2-(cyclopentylthio)ethyl]piperidine-4-hydroxamic acid 4-[3-(R,S)-Hydroxy-3-(3-chloro-6-methoxyquinolin-4-yl)propyl]-1-[3-(cyclopentylthio)propyl]piperidine-4-hydroxamic acid 4-[3-(R,S)-Hydroxy-3-(3-chloro-6-methoxyquinolin-4-yl)propyl]-1-[3-(cyclohexylthio)propyl]piperidine-4-hydroxamic acid 4-[3-(R,S)-Hydroxy-3-(3-chloro-6-methoxyquinolin-4-yl)propyl]-1-[2-(pyrid-2-yl)thioethyl]piperidine-4-hydroxamic acid 4-[3-(R,S)-Hydroxy-3-(3-chloro-6-methoxyquinolin-4-yl)propyl]-1-[4-(thien-2-yl)butyl]piperidine-4-hydroxamic acid 4-[3-(R,S)-Hydroxy-3-(3-chloro-6-methoxyquinolin-4-yl)propyl]-1-[3-(thien-2-yl)thiopropyl]piperidine-4-hydroxamic acid 4-[3-(R,S)-Hydroxy-3-(3-chloro-6-methoxyquinolin-4-yl)propyl]-1-[3-(thien-3-yl)propyl]piperidine-4-hydroxamic acid 4-[3-(R,S)-Hydroxy-3-(3-chloro-6-methoxyquinolin-4-yl)propyl]-1-[4-(thien-3-yl)butyl]piperidine-4-hydroxamic acid 4-[3-(R,S)-Hydroxy-3-(3-chloro-6-methoxyquinolin-4-yl)propyl]-1-[2-(thien-2-yl)thioethyl]piperidine-4-hydroxamic acid 4-[3-(R,S)-Hydroxy-3-(3-chloro-6-methoxyquinolin-4-yl)propyl]-1-[2-(thien-3-yl)thioethyl]piperidine-4-hydroxamic acid 4-[3-(R,S)-Hydroxy-3-(3-chloro-6-methoxyquinolin-4-yl)propyl]-1-[3-(thien-3-yl)thiopropyl]piperidine-4-hydroxamic acid 4-[3-(R,S)-Hydroxy-3-(3-chloro-6-methoxyquinolin-4-yl)propyl]-1-[3-(1,3-thiazol-2-yl)propyl]piperidine-4-hydroxamic acid 4-[3-(R,S)-Hydroxy-3-(3-chloro-6-methoxyquinolin-4-yl)propyl]-1-[4-(1,3-thiazol-2-yl)butyl]piperidine-4-hydroxamic acid 4-[3-(R,S)-Hydroxy-3-(3-chloro-6-methoxyquinolin-4-yl)propyl]-1-[3-(1,3-thiazol-2-yl)thioethyl]piperidine-4-hydroxamic acid 4-[3-(R,S)-Hydroxy-3-(3-chloro-6-methoxyquinolin-4-yl)propyl]-1-[3-(pyrid-2-yl)propyl]piperidine-4-hydroxamic acid 4-[3-(R,S)-Hydroxy-3-(3-chloro-6-methoxyquinolin-4-yl)propyl]-1-[4-(pyrid-2-yl)butyl]piperidine-4-hydroxamic acid 4-[3-(R,S)-Hydroxy-3-(3-chloro-6-methoxyquinolin-4-yl)propyl]-1-[3-(pyrid-2-yl)thiopropyl]piperidine-4-hydroxamic acid 4-[3-(R,S)-Hydroxy-3-(3-chloro-6-methoxyquinolin-4-yl)propyl]-1-[3-(pyrid-3-yl)propyl]piperidine-4-hydroxamic acid 4-[3-(R,S)-Hydroxy-3-(3-chloro-6-methoxyquinolin-4-yl)propyl]-1-[4-(pyrid-3-yl)butyl]piperidine-4-hydroxamic acid 4-[3-(R,S)-Hydroxy-3-(3-chloro-6-methoxyquinolin-4-yl)propyl]-1-[2-(pyrid-3-yl)thioethyl]piperidine-4-hydroxamic acid 4-[3-(R,S)-Hydroxy-3-(3-chloro-6-methoxyquinolin-4-yl)propyl]-1-[3-(pyrid-3-yl)thiopropyl]piperidine-4-hydroxamic acid 4-[3-(R,S)-Hydroxy-3-(3-chloro-6-methoxyquinolin-4-yl)propyl]-1-[3-(pyrid-4-yl)propyl]piperidine-4-hydroxamic acid 4-[3-(R,S)-Hydroxy-3-(3-chloro-6-methoxyquinolin-4-yl)propyl]-1-[4-(pyrid-4-yl)butyl]piperidine-4-hydroxamic acid 4-[3-(R,S)-Hydroxy-3-(3-chloro-6-methoxyquinolin-4-yl)propyl]-1-[2-(pyrid-4-yl)thioethyl]piperidine-4-hydroxamic acid 4-[3-(R,S)-Hydroxy-3-(3-chloro-6-methoxyquinolin-4-yl)propyl]-1-[3-(pyrid-4-yl)thiopropyl]piperidine-4-hydroxamic acid 4-[3-(R,S)-Hydroxy-3-(3-chloro-6-methoxyquinolin-4-yl)propyl]-1-[3-(pyrazin-2-yl)propyl]piperidine-4-hydroxamic acid 4-[3-(R,S)-Hydroxy-3-(3-chloro-6-methoxyquinolin-4-yl)propyl]-1-[4-(pyrazin-2-yl)butyl]piperidine-4-hydroxamic acid 4-[3-(R,S)-Hydroxy-3-(3-chloro-6-methoxyquinolin-4-yl)propyl]-1-[2-(pyrazin-2-yl)thioethyl]piperidine-4-hydroxamic acid 4-[3-(R,S)-Hydroxy-3-(3-chloro-6-methoxyquinolin-4-yl)propyl ]-1-[3-(pyrazin-2-yl)thiopropyl]piperidine-4-hydroxamic acid 4-[3-(R,S)-Hydroxy-3-(3-chloro-6-methoxyquinolin-4-yl)propyl]-1-[3-(4-fluorophenyl)prop-2-ynyl]piperidine-4-hydroxamic acid 4-[3-(R,S)-Hydroxy-3-(3-chloro-6-methoxyquinolin-4-yl)propyl]-1-[3-(3,4-difluorophenyl)prop-2-ynyl]piperidine-4-hydroxamic acid 4-[3-(R,S)-Hydroxy-3-(3-chloro-6-methoxyquinolin-4-yl)propyl]-1-[3-(2,4-difluorophenyl)prop-2-ynyl]piperidine-4-hydroxamic acid 4-[3-(R,S)-Hydroxy-3-(3-chloro-6-methoxyquinolin-4-yl)propyl]-1-[3-(2,3,5-trifluorophenyl)prop-2-ynyl] piperidine-4-hydroxamic acid 4-[3-(R,S)-Hydroxy-3-(3-chloro-6-methoxyquinolin-4-yl)propyl]-1-[3-(2,4,6-trifluorophenyl)prop-2-ynyl] piperidine-4-hydroxamic acid 4-[3-(R,S)-Hydroxy-3-(3-chloro-6-methoxyquinolin-4-yl)propyl]-1-[3-(3,4,5-trifluorophenyl)prop-2-ynyl] piperidine-4-hydroxamic acid 4-[3-(R,S)-Hydroxy-3-(3-chloro-6-methoxyquinolin-4-yl)propyl]-1-[3-(4-chloro-3-fluorophenyl)prop-2-ynyl] piperidine-4-hydroxamic acid 4-[3-(R,S)-Hydroxy-3-(3-chloro-6-methoxyquinolin-4-yl)propyl]-1-[3-(3-chloro-4-fluorophenyl)prop-2-ynyl] piperidine-4-hydroxamic acid 4-[3-(R,S)-Hydroxy-3-(3-chloro-6-methoxyquinolin-4-yl)propyl]-1-[3-(2-chloro-4-fluorophenyl)prop-2-ynyl] piperidine-4-hydroxamic acid 4-[3-(R,S)-Hydroxy-3-(3-chloro-6-methoxyquinolin-4-yl)propyl]-1-[3-(3-chloro-5-fluorophenyl)prop-2-ynyl] piperidine-4-hydroxamic acid 4-[3-(R,S)-Hydroxy-3-(3-chloro-6-methoxyquinolin-4-yl)propyl]-1-[3-(4-chloro-2-fluorophenyl)prop-2-ynyl] piperidine-4-hydroxamic acid 4-[3-(R,S)-Hydroxy-3-(3-chloro-6-methoxyquinolin-4-yl)propyl]-1-[3-(3-fluoro-4-methylphenyl)prop-2-ynyl]piperidine-4-hydroxamic acid 4-[3-(R,S)-Hydroxy-3-(3-chloro-6-methoxyquinolin-4-yl)propyl]-1-[3-(3,5-bistrifluoromethylphenyl)prop-2-ynyl]piperidine-4-hydroxamic acid 4-[3-(R,S)-Hydroxy-3-(3-chloro-6-methoxyquinolin-4-yl)propyl]-1-[3-(thien-2-yl)prop-2-ynyl]piperidine-4-hydroxamic acid 4-[3-(R,S)-Hydroxy-3-(3-chloro-6-methoxyquinolin-4-yl)propyl]-1-[3-(thien-3-yl)prop-2-ynyl]piperidine-4-hydroxamic acid 4-[3-(R,S)-Hydroxy-3-(3-chloro-6-methoxyquinolin-4-yl)propyl]-1-[3-(1,3-thiazol-2-yl)prop-2-ynyl] piperidine-4-hydroxamic acid 4-[3-(R,S)-Hydroxy-3-(3-chloro-6-methoxyquinolin-4-yl)propyl]-1-[3-(1,3-thiazol-4-yl)prop-2-ynyl] piperidine-4-hydroxamic acid 4-[3-(R,S)-Hydroxy-3-(3-chloro-6-methoxyquinolin-4-yl)propyl]-1-[3-(1,3-thiazol-5-yl)prop-2-ynyl] piperidine-4-hydroxamic acid 4-[3-(R,S)-Hydroxy-3-(3-chloro-6-methoxyquinolin-4-yl)propyl]-1-[3-(pyrid-2-yl)prop-2-ynyl]piperidine-4-hydroxamic acid 4-[3-(R,S)-Hydroxy-3-(3-chloro-6-methoxyquinolin-4-yl)propyl]-1-[3-(pyrid-3-yl)prop-2-ynyl]piperidine-4-hydroxamic acid 4-[3-(R,S)-Hydroxy-3-(3-chloro-6-methoxyquinolin-4-yl)propyl]-1-[3-(pyrid-4-yl)prop-2-ynyl]piperidine-4-hydroxamic acid 4-[3-(R,S)-Hydroxy-3-(3-methyl-6-methoxyquinolin-4-yl)propyl]-1-[2-(cyclohexyl)ethyl]piperidine-4-hydroxamic acid 4-[3-(R,S)-Hydroxy-3-(3-methyl-6-methoxyquinolin-4-yl)propyl]-1-[3-(phenyl)propyl]piperidine-4-hydroxamic acid 4-[3-(R,S)-Hydroxy-3-(3-methyl-6-methoxyquinolin-4-yl)propyl]-1-[3-(2,3,5-trifluorophenyl)propyl] piperidine-4-hydroxamic acid 4-[3-(R,S)-Hydroxy-3-(3-methyl-6-methoxyquinolin-4-yl)propyl]-1-[2-(3,5-difluorophenylamino)ethyl] piperidine-4-hydroxamic acid 4-[3-(R,S)-Hydroxy-3-(3-methyl-6-methoxyquinolin-4-yl)propyl]-1-[2-(2,3,5-trifluorophenylamino)ethyl] piperidine-4-hydroxamic acid 4-[3-(R,S)-Hydroxy-3-(3-methyl-6-methoxyquinolin-4-yl)-propyl]-1-[2-(3,5-difluorophenoxy)ethyl] piperidine-4-hydroxamic acid 4-[3-(R,S)-Hydroxy-3-(3-methyl-6-methoxyquinolin-4-yl)-propyl]-1-[2-(2,3,5-trifluorophenoxy)ethyl] piperidine-4-hydroxamic acid 4-[3-(R,S)-Hydroxy-3-(3-methyl-6-methoxyquinolin-4-yl)propyl]-1-[2-(2,3,5-trifluorophenylthio)ethyl] piperidine-4-hydroxamic acid 4-[3-(R,S)-Hydroxy-3-(3-methyl-6-methoxyquinolin-4-yl)propyl]-1-[2-(cyclopentylthio)ethyl]piperidine-4-hydroxamic acid 4-[3-(R,S)-Hydroxy-3-(3-methyl-6-methoxyquinolin-4-yl)propyl]-1-[2-(pyrid-2-yl)thioethyl]piperidine-4-hydroxamic acid 4-[3-(R,S)-Hydroxy-3-(3-methyl-6-methoxyquinolin-4-yl)propyl]-1-[2-(thien-2-yl)thioethyl]piperidine-4-hydroxamic acid 4-[3-(R,S)-Hydroxy-3-(3-methyl-6-methoxyquinolin-4-yl)propyl]-1-[3-(2,3,5-trifluorophenyl)prop-2-ynyl] piperidine-4-hydroxamic acid 4-[3-(R,S)-Hydroxy-3-(3-methyl-6-methoxyquinolin-4-yl)propyl]-1-[3-(thien-2-yl)prop-2-ynyl]piperidine-4-hydroxamic acid 4-[3-(R,S)-Hydroxy-3-(3-fluoro-6-methoxyquinolin-4-yl)propyl]-1-[2-(cyclohexyl)ethyl]piperidine-4-hydroxamic acid 4-[3-(R,S)-Hydroxy-3-(3-fluoro-6-methoxyquinolin-4-yl)propyl]-1-[3-(phenyl)propyl]piperidine-4-hydroxamic acid 4-[3-(R,S)-Hydroxy-3-(3-fluoro-6-methoxyquinolin-4-yl)propyl]-1-[3-(2,3,5-trifluorophenyl)propyl] piperidine-4-hydroxamic acid 4-[3-(R,S)-Hydroxy-3-(3-fluoro-6-methoxyquinolin-4-yl)propyl]-1-[2-(3,5-difluorophenylamino)ethyl] piperidine-4-hydroxamic acid 4-[3-(R,S)-Hydroxy-3-(3-fluoro-6-methoxyquinolin-4-yl)propyl]-1-[2-(2,3,5-trifluorophenylamino)ethyl] piperidine-4-hydroxamic acid 4-[3-(R,S)-Hydroxy-3-(3-fluoro-6-methoxyquinolin-4-yl)propyl]-1-[2-(3,5-difluorophenoxy)ethyl] piperidine-4-hydroxamic acid 4-[3-(R,S)-Hydroxy-3-(3-fluoro-6-methoxyquinolin-4-yl)propyl]-1-[2-(2,3,5-trifluorophenoxy)ethyl] piperidine-4-hydroxamic acid 4-[3-(R,S)-Hydroxy-3-(3-fluoro-6-methoxyquinolin-4-yl)propyl]-1-[2-(2,3,5-trifluorophenylthio)ethyl] piperidine-4-hydroxamic acid 4-[3-(R,S)-Hydroxy-3-(3-fluoro-6-methoxyquinolin-4-yl)propyl]-1-[2-(cyclopentylthio)ethyl]piperidine-4-hydroxamic acid 4-[3-(R,S)-Hydroxy-3-(3-fluoro-6-methoxyquinolin-4-yl)propyl]-1-[2-(pyrid-2-yl)thioethyl]piperidine-4-hydroxamic acid 4-[3-(R,S)-Hydroxy-3-(3-fluoro-6-methoxyquinolin-4-yl)propyl]-1-[2-(thien-2-yl)thioethyl]piperidine-4-hydroxamic acid 4-[3-(R,S)-Hydroxy-3-(3-fluoro-6-methoxyquinolin-4-yl)propyl]-1-[3-(2,3,5-trifluorophenyl)prop-2-ynyl]piperidine-4-hydroxamic acid 4-[3-(R,S)-Hydroxy-3-(3-fluoro-6-methoxyquinolin-4-yl)propyl]-1-[3-(thien-2-yl)prop-2-ynyl]piperidine-4-hydroxamic acid 4-[3-(R,S)-Hydroxy-3-(3-dimethylamino-6-methoxyquinolin-4-yl)propyl]-1-[2-(cyclohexyl)ethyl]-piperidine-4-hydroxamic acid 4-[3-(R,S)-Hydroxy-3-(3-dimethylamino-6-methoxyquinolin-4-yl)propyl]-1-[3-(phenyl)propyl]piperidine-4-hydroxamic acid 4-[3-(R,S)-Hydroxy-3-(3-dimethylamino-6-methoxyquinolin-4-yl)propyl]-1-[3-(2,3,5-trifluorophenyl)-propyl]piperidine-4-hydroxamic acid 4-[3-(R,S)-Hydroxy-3-(3-dimethylamino-6-methoxyquinolin-4-yl)propyl]-1-[2-(3,5-difluorophenylamino)-ethyl]piperidine-4-hydroxamic acid 4-[3-(R,S)-Hydroxy-3-(3-dimethylamino-6-methoxyquinolin-4-yl)propyl]-1-[2-(2,3,5-trifluorophenylamino)ethyl]piperidine-4-hydroxamic acid 4-[3-(R,S)-Hydroxy-3-(3-dimethylamino-6-methoxyquinolin-4-yl)propyl]-1-[2-(3,5-difluorophenoxy)ethyl]-piperidine-4-hydroxamic acid 4-[3-(R,S)-Hydroxy-3-(3-dimethylamino-6-methoxyquinolin-4-yl)propyl]-1-[2-(2,3,5-trifluorophenoxy)-ethyl]piperidine-4-hydroxamic acid 4-[3-(R,S)-Hydroxy-3-(3-dimethylamino-6-methoxyquinolin-4-yl)propyl]-1-[2-(2,3,5-trifluorophenylthio)-ethyl]piperidine-4-hydroxamic acid 4-[3-(R,S)-Hydroxy-3-(3-dimethylamino-6-methoxyquinolin-4-yl)propyl]-1-[2-(cyclopentylthio)ethyl]-piperidine-4-hydroxamic acid 4-[3-(R,S)-Hydroxy-3-(3-dimethylamino-6-methoxyquinolin-4-yl)propyl]-1-[2-(pyrid-2-yl)thioethyl]-piperidine-4-hydroxamic acid 4-[3-(R,S)-Hydroxy-3-(3-dimethylamino-6-methoxyquinolin-4-yl)propyl]-1-[2-(thien-2-yl)thioethyl]-piperidine-4-hydroxamic acid 4-[3-(R,S)-Hydroxy-3-(3-dimethylamino-6-methoxyquinolin-4-yl)propyl]-1-[3-(2,3,5-trifluorophenyl)prop-2-ynyl]piperidine-4-hydroxamic acid 4-[3-(R,S)-Hydroxy-3-(3-dimethylamino-6-methoxyquinolin-4-yl)propyl]-1-[3-(thien-2-yl)prop-2-ynyl]piperidine-4-hydroxamic acid 4-[3-(R,S)-Hydroxy-3-(3-hydroxymethyl-6-methoxyquinolin-4-yl)propyl]-1-[2-(cyclohexyl)ethyl]-piperidine-4-hydroxamic acid 4-[3-(R,S)-Hydroxy-3-(3-hydroxymethyl-6-methoxyquinolin-4-yl)propyl]-1-[3-(phenyl)propyl]piperidine-4-hydroxamic acid 4-[3-(R,S)-Hydroxy-3-(3-hydroxymethyl-6-methoxyquinolin-4-yl)propyl]-1-[3-(2,3,5-trifluorophenyl)-propyl]piperidine-4-hydroxamic acid 4-[3-(R,S)-Hydroxy-3-(3-hydroxymethyl-6-methoxyquinolin-4-yl)propyl]-1-[2-(3,5-difluorophenylamino)-ethyl]piperidine-4-hydroxamic acid 4-[3-(R,S)-Hydroxy-3-(3-hydroxymethyl-6-methoxyquinolin-4-yl)propyl]-1-[2-(2,3,5-trifluorophenylamino)ethyl]piperidine-4-hydroxamic acid 4-[3-(R,S)-Hydroxy-3-(3-hydroxymethyl-6-methoxyquinolin-4-yl)propyl]-1-[2-(3,5-difluorophenoxy)ethyl]-piperidine-4-hydroxamic acid 4-[3-(R,S)-Hydroxy-3-(3-hydroxymethyl-6-methoxyquinolin-4-yl)propyl]-1-[2-(2,3,5-trifluorophenoxy)-ethyl]piperidine-4-hydroxamic acid 4-[3-(R,S)-Hydroxy-3-(3-hydroxymethyl-6-methoxyquinolin-4-yl)propyl]-1-[2-(2,3,5-trifluorophenylthio)-ethyl]piperidine-4-hydroxamic acid 4-[3-(R,S)-Hydroxy-3-(3-hydroxymethyl-6-methoxyquinolin-4-yl)propyl]-1-[2-(cyclopentylthio)ethyl]-piperidine-4-hydroxamic acid 4-[3-(R,S)-Hydroxy-3-(3-hydroxymethyl-6-methoxyquinolin-4-yl)propyl]-1-[2-(pyrid-2-yl)thioethyl]-piperidine-4-hydroxamic acid 4-[3-(R,S)-Hydroxy-3-(3-hydroxymethyl-6-methoxyquinolin-4-yl)propyl]-1-[2-(thien-2-yl)thioethyl]-piperidine-4-hydroxamic acid 4-[3-(R,S)-Hydroxy-3-(3-hydroxymethyl-6-prop-2-ynyl]piperidine-4-hydroxamic acid 4-[3-(R,S)-Hydroxy-3-(3-hydroxymethyl-6-methoxyquinolin-4-yl)propyl]-1-[3-(thien-2-yl)prop-2-ynyl]-piperidine-4-hydroxamic acid 4-[3-(R,S)-Hydroxy-3-(3-fluoromethyl-6-methoxyquinolin-4-yl)propyl]-1-[2-(cyclohexyl)ethyl]piperidine-4-hydroxamic acid 4-[3-(R,S)-Hydroxy-3-(3-fluoromethyl-6-methoxyquinolin-4-yl)propyl]-1-[3-(phenyl)propyl]piperidine-4-hydroxamic acid 4-[3-(R,S)-Hydroxy-3-(3-fluoromethyl-6-methoxyquinolin-4-yl)propyl]-1-[3-(2,3,5-trifluorophenyl)propyl]piperidine-4-hydroxamic acid 4-[3-(R,S)-Hydroxy-3-(3-fluoromethyl-6-methoxyquinolin-4-yl)propyl]-1-[2-(3,5-difluorophenylamino)ethyl]piperidine-4-hydroxamic acid 4-[3-(R,S)-Hydroxy-3-(3-fluoromethyl-6-methoxyquinolin-4-yl)propyl]-1-[2-(2,3,5-trifluorophenylamino)ethyl]piperidine-4-hydroxamic acid 4-[3-(R,S)-Hydroxy-3-(3-fluoromethyl-6-methoxyquinolin-4-yl)propyl]-1-[2-(3,5-difluorophenoxy)ethyl]-piperidine-4-hydroxamic acid 4-[3-(R,S)-Hydroxy-3-(3-fluoromethyl-6-methoxyquinolin-4-yl)propyl]-1-[2-(2,3,5-trifluorophenoxy)ethyl]piperidine-4-hydroxamic acid 4-[3-(R,S)-Hydroxy-3-(3-fluoromethyl-6-methoxyquinolin-4-yl)propyl]-1-[2-(2,3,5-trifluorophenylthio)ethyl]piperidine-4-hydroxamic acid 4-[3-(R,S)-Hydroxy-3-(3-fluoromethyl-6-methoxyquinolin-4-yl)propyl]-1-[2-(cyclopentylthio)ethyl]piperidine-4-hydroxamic acid 4-[3-(R,S)-Hydroxy-3-(3-fluoromethyl-6-methoxyquinolin-4-yl)propyl]-1-[2-(pyrid-2-yl)thioethyl]piperidine-4-hydroxamic acid 4-[3-(R,S)-Hydroxy-3-(3-fluoromethyl-6-methoxyquinolin-4-yl)propyl]-1-[2-(thien-2-yl)thioethyl]piperidine-4-hydroxamic acid 4-[3-(R,S)-Hydroxy-3-(3-fluoromethyl-6-methoxyquinolin-4-yl)propyl]-1-[3-(2,3,5-trifluorophenyl)prop-2-ynyl]piperidine-4-hydroxamic acid 4-[3-(R,S)-Hydroxy-3-(3-fluoromethyl-6-methoxyquinolin-4-yl)propyl]-1-[3-(thien-2-yl)prop-2-ynyl]piperidine-4-hydroxamic acid 4-[3-(R,S)-Hydroxy-3-(3-aminomethyl-6-methoxyquinolin-4-yl)propyl]-1-[2-(cyclohexyl)ethyl]piperidine-4-hydroxamic acid 4-[3-(R,S)-Hydroxy-3-(3-aminomethyl-6-methoxyquinolin-4-yl)propyl]-1-[3-(phenyl)propyl]piperidine-4-hydroxamic acid 4-[3-(R,S)-Hydroxy-3-(3-aminomethyl-6-methoxyquinolin-4-yl)propyl]-1-[3-(2,3,5-trifluorophenyl)propyl]piperidine-4-hydroxamic acid 4-[3-(R,S)-Hydroxy-3-(3-aminomethyl-6-methoxyquinolin-4-yl)propyl]-1-[2-(3,5-difluorophenylamino)ethyl]piperidine-4-hydroxamic acid 4-[3-(R,S)-Hydroxy-3-(3-aminomethyl-6-methoxyquinolin-4-yl)propyl]-1-[2-(2,3,5-trifluorophenylamino)ethyl]piperidine-4-hydroxamic acid 4-[3-(R,S)-Hydroxy-3-(3-aminomethyl-6-methoxyquinolin-4-yl)propyl]-1-[2-(3,5-difluorophenoxy)ethyl]-piperidine-4-hydroxamic acid 4-[3-(R,S)-Hydroxy-3-(3-aminomethyl-6-methoxyquinolin-4-yl)propyl]-1-[2-(2,3,5-trifluorophenoxy)ethyl]piperidine-4-hydroxamic acid 4-[3-(R,S)-Hydroxy-3-(3-aminomethyl-6-methoxyquinolin-4-yl)propyl]-1-[2-(2,3,5-trifluorophenylthio)ethyl]piperidine-4-hydroxamic acid 4-[3-(R,S)-Hydroxy-3-(3-aminomethyl-6-methoxyquinolin-4-yl)propyl]-1-[2-(cyclopentylthio)ethyl]piperidine-4-hydroxamic acid 4-[3-(R,S)-Hydroxy-3-(3-aminomethyl-6-methoxyquinolin-4-yl)propyl]-1-[2-(pyrid-2-yl)thioethyl]piperidine-4-hydroxamic acid 4-[3-(R,S)-Hydroxy-3-(3-aminomethyl-6-methoxyquinolin-4-yl)propyl]-1-[2-(thien-2-yl)thioethyl]piperidine-4-hydroxamic acid 4-[3-(R,S)-Hydroxy-3-(3-aminomethyl-6-methoxyquinolin-4-yl)propyl]-1-[3-(2,3,5-trifluorophenyl)prop-2-ynyl]piperidine-4-hydroxamic acid 4-[3-(R,S)-Hydroxy-3-(3-aminomethyl-6-methoxyquinolin-4-yl)propyl]-1-[3-(thien-2-yl)prop-2-ynyl]piperidine-4-hydroxamic acid 4-[3-(R,S)-Hydroxy-3-(3-morpholinomethyl-6-methoxyquinolin-4-yl)propyl]-1-[2-(cyclohexyl)ethyl]-piperidine-4-hydroxamic acid 4-[3-(R,S)-Hydroxy-3-(3-morpholinomethyl-6-methoxyquinolin-4-yl)propyl]-1-[3-(phenyl)propyl]piperidine-4-hydroxamic acid 4-[3-(R,S)-Hydroxy-3-(3-morpholinomethyl-6-methoxyquinolin-4-yl)propyl]-1-[3-(2,3,5-trifluorophenyl)-propyl]piperidine-4-hydroxamic acid 4-[3-(R,S)-Hydroxy-3-(3-morpholinomethyl-6-methoxyquinolin-4-yl)propyl]-1-[2-(3,5-difluorophenylamino)-ethyl]piperidine-4-hydroxamic acid 4-[3-(R,S)-Hydroxy-3-(3-morpholinomethyl-6-methoxyquinolin-4-yl)propyl]-1-[2-(2,3,5-trifluorophenyl-amino)ethyl]piperidine-4-hydroxamic acid 4-[3-(R,S)-Hydroxy-3-(3-morpholinomethyl-6-methoxyquinolin-4-yl)propyl]-1-[2-(3,5-difluorophenoxy)-ethyl]piperidine-4-hydroxamic acid 4-[3-(R,S)-Hydroxy-3-(3-morpholinomethyl-6-methoxyquinolin-4-yl)propyl]-1-[2-(2,3,5-trifluorophenoxy)-ethyl]piperidine-4-hydroxamic acid 4-[3-(R,S)-Hydroxy-3-(3-morpholinomethyl-6-methoxyquinolin-4-yl)propyl]-1-[2-(2,3,5-trifluorophenylthio)-ethyl]piperidine-4-hydroxamic acid 4-[3-(R,S)-Hydroxy-3-(3-morpholinomethyl-6-methoxyquinolin-4-yl)propyl]-1-[2-(cyclopentylthio)ethyl]-piperidine-4-hydroxamic acid 4-[3-(R,S)-Hydroxy-3-(3-morpholinomethyl-6-methoxyquinolin-4-yl)propyl]-1-[2-(pyrid-2-yl)thioethyl]-piperidine-4-hydroxamic acid 4-[3-(R,S)-Hydroxy-3-(3-morpholinomethyl-6-methoxyquinolin-4-yl)propyl]-1-[2-(thien-2-yl)thioethyl]-piperidine-4-hydroxamic acid 4-[3-(R,S)-Hydroxy-3-(3-morpholinomethyl-6-methoxyquinolin-4-yl)propyl]-1-[3-(2,3,5-trifluorophenyl)-prop-2-ynyl]piperidine-4-hydroxamic acid 4-[3-(R,S)-Hydroxy-3-(3-morpholinomethyl-6-methoxyquinolin-4-yl)propyl]-1-[3-(thien-2-yl)prop-2-ynyl]-piperidine-4-hydroxamic acid 4-[3-(R,S)-Hydroxy-3-(3-methyl-6-methoxyquinolin-4-yl)propyl]-1-[3-(2,4,6-trifluorophenyl)propyl]piperidine-4-hydroxamic acid 4-[3-(R,S)-Hydroxy-3-(3-methyl-6-methoxyquinolin-4-yl)propyl]-1-[3-(3,4,5-trifluorophenyl)propyl]piperidine-4-hydroxamic acid 4-[3-(R,S)-Hydroxy-3-(3-methyl-6-methoxyquinolin-4-yl)propyl]-1-[2-(2,4,6-trifluorophenylthio)ethyl]piperidine-4-hydroxamic acid 4-[3-(R,S)-Hydroxy-3-(3-methyl-6-methoxyquinolin-4-yl)propyl]-1-[2-(3,4,5-trifluorophenylthio)ethyl]piperidine-4-hydroxamic acid 4-[3-(R,S)-Hydroxy-3-(3-methyl-6-methoxyquinolin-4-yl)propyl]-1-[2-(2,4,6-trifluorophenylamino)ethyl]piperidine-4-hydroxamic acid 4-[3-(R,S)-Hydroxy-3-(3-methyl-6-methoxyquinolin-4-yl)propyl]-1-[2-(3,4,5-trifluorophenylamino)ethyl]piperidine-4-hydroxamic acid 4-[3-(R,S)-Hydroxy-3-(3-methyl-6-methoxyquinolin-4-yl)propyl]-1-[2-(2,4,6-trifluorophenoxy)ethyl]piperidine-4-hydroxamic acid 4-[3-(R,S)-Hydroxy-3-(3-methyl-6-methoxyquinolin-4-yl)propyl]-1-[2-(3,4,5-trifluorophenoxy)ethyl]piperidine-4-hydroxamic acid 4-[3-(R,S)-Hydroxy-3-(3-methyl-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-methyl-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-fluoro-6-methoxyquinolin-4-yl)propyl]-1-[3-(2,4,6-trifluorophenyl)propyl]piperidine-4-hydroxamic acid 4-[3-(R,S)-Hydroxy-3-(3-fluoro-6-methoxyquinolin-4-yl)propyl]-1-[3-(3,4,5-trifluorophenyl)propyl]piperidine-4-hydroxamic acid 4-[3-(R,S)-Hydroxy-3-(3-fluoro-6-methoxyquinolin-4-yl)propyl]-1-[2-(2,4,6-trifluorophenylthio)ethyl]piperidine-4-hydroxamic acid 4-[3-(R,S)-Hydroxy-3-(3-fluoro-6-methoxyquinolin-4-yl)propyl]-1-[2-(3,4,5-trifluorophenylthio)ethyl]piperidine-4-hydroxamic acid 4-[3-(R,S)-Hydroxy-3-(3-fluoro-6-methoxyquinolin-4-yl)propyl]-1-[2-(2,4,6-trifluorophenylamino)ethyl]piperidine-4-hydroxamic acid 4-[3-(R,S)-Hydroxy-3-(3-fluoro-6-methoxyquinolin-4-yl)propyl]-1-[2-(3,4,5-trifluorophenylamino)ethyl]piperidine-4-hydroxamic acid 4-[3-(R,S)-Hydroxy-3-(3-fluoro-6-methoxyquinolin-4-yl)propyl]-1-[2-(2,4,6-trifluorophenoxy)ethyl]piperidine-4-hydroxamic acid 4-[3-(R,S)-Hydroxy-3-(3-fluoro-6-methoxyquinolin-4-yl)propyl]-1-[2-(3,4,5-trifluorophenoxy)ethyl]piperidine-4-hydroxamic acid 4-[3-(R,S)-Hydroxy-3-(3-fluoro-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-fluoro-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-dimethylamino-6-methoxyquinolin-4-yl)propyl]-1-[3-(2,4,6-trifluorophenyl)-propyl]piperidine-4-hydroxamic acid 4-[3-(R,S)-Hydroxy-3-(3-dimethylamino-6-methoxyquinolin-4-yl)propyl]-1-[3-(3,4,5-trifluorophenyl)propyl]-piperidine-4-hydroxamic acid 4-[3-(R,S)-Hydroxy-3-(3-dimethylamino-6-methoxyquinolin-4-yl)propyl]-1-[2-(2,4,6-trifluorophenylthio)-ethyl]piperidine-4-hydroxamic acid 4-[3-(R,S)-Hydroxy-3-(3-dimethylamino-6-methoxyquinolin-4-yl)propyl]-1-[2-(3,4,5-trifluorophenylthio)ethyl]-piperidine-4-hydroxamic acid 4-[3-(R,S)-Hydroxy-3-(3-dimethylamino-6-methoxyquinolin-4-yl)propyl]-1-[2-(2,4,6-trifluorophenylamino)ethyl]-piperidine-4-hydroxamic acid 4-[3-(R,S)-Hydroxy-3-(3-dimethylamino-6-methoxyquinolin-4-yl)propyl]-1-[2-(3,4,5-trifluorophenyl-amino)ethyl]piperidine-4-hydroxamic acid 4-[3-(R,S)-Hydroxy-3-(3-dimethylamino-6-methoxyquinolin-4-yl)propyl]-1-[2-(2,4,6-trifluorophenoxy)-ethyl]piperidine-4-hydroxamic acid 4-[3-(R,S)-Hydroxy-3-(3-dimethylamino-6-methoxyquinolin-4-yl)propyl]-1-[2-(3,4,5-trifluorophenoxy)-ethyl]piperidine-4-hydroxamic acid 4-[3-(R,S)-Hydroxy-3-(3-dimethylamino-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-dimethylamino-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-hydroxymethyl-6-methoxyquinolin-4-yl)propyl]-1-[3-(3,4,5-trifluorophenyl)-propyl]piperidine-4-hydroxamic acid 4-[3-(R,S)-Hydroxy-3-(3-hydroxymethyl-6-methoxyquinolin-4-yl)propyl]-1-[2-(2,4,6-trifluorophenylthio)-ethyl]piperidine-4-hydroxamic acid 4-[3-(R,S)-Hydroxy-3-(3-hydroxymethyl-6-methoxyquinolin-4-yl)propyl]-1-[2-(3,4,5-trifluorophenylthio)-ethyl]piperidine-4-hydroxamic acid 4-[3-(R,S)-Hydroxy-3-(3-hydroxymethyl-6-methoxyquinolin-4-yl)propyl]-1-[2-(2,4,6-trifluorophenyl-amino)ethyl]piperidine-4-hydroxamic acid 4-[3-(R,S)-Hydroxy-3-(3-hydroxymethyl-6-methoxyquinolin-4-yl)propyl]-1-[2-(3,4,5-trifluorophenyl-amino)ethyl]piperidine-4-hydroxamic acid 4-[3-(R,S)-Hydroxy-3-(3-hydroxymethyl-6-methoxyquinolin-4-yl)propyl]-1-[2-(2,4,6-trifluorophenoxy)-ethyl]piperidine-4-hydroxamic acid 4-[3-(R,S)-Hydroxy-3-(3-hydroxymethyl-6-methoxyquinolin-4-yl)propyl]-1-[2-(3,4,5-trifluorophenoxy)-ethyl]piperidine-4-hydroxamic acid 4-[3-(R,S)-Hydroxy-3-(3-hydroxymethyl-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-hydroxymethyl-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-fluoromethyl-6-methoxyquinolin-4-yl)propyl]-1-[3-(2,4,6-trifluorophenyl)propyl]piperidine-4-hydroxamic acid 4-[3-(R,S)-Hydroxy-3-(3-fluoromethyl-6-methoxyquinolin-4-yl)propyl]-1-[3-(3,4,5-trifluorophenyl)propyl]piperidine-4-hydroxamic acid 4-[3-(R,S)-Hydroxy-3-(3-fluoromethyl-6-methoxyquinolin-4-yl)propyl]-1-[2-(2,4,6-trifluorophenylthio)ethyl]piperidine-4-hydroxamic acid 4-[3-(R,S)-Hydroxy-3-(3-fluoromethyl-6-methoxyquinolin-4-yl)propyl]-1-[2-(3,4,5-trifluorophenylthio)ethyl]piperidine-4-hydroxamic acid 4-[3-(R,S)-Hydroxy-3-(3-fluoromethyl-6-methoxyquinolin-4-yl)propyl]-1-[2-(2,4,6-trifluorophenylamino)ethyl]piperidine-4-hydroxamic acid 4-[3-(R,S)-Hydroxy-3-(3-fluoromethyl-6-methoxyquinolin-4-yl)propyl]-1-[2-(3,4,5-trifluorophenylamino)ethyl]piperidine-4-hydroxamic acid 4-[3-(R,S)-Hydroxy-3-(3-fluoromethyl-6-methoxyquinolin-4-yl)propyl]-1-[2-(2,4,6-trifluorophenoxy)ethyl]piperidine-4-hydroxamic acid 4-[3-(R,S)-Hydroxy-3-(3-fluoromethyl-6-methoxyquinolin-4-yl)propyl]-1-[2-(3,4,5-trifluorophenoxy)ethyl]piperidine-4-hydroxamic acid 4-[3-(R,S)-Hydroxy-3-(3-fluoromethyl-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-fluoromethyl-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-aminomethyl-6-methoxyquinolin-4-yl)propyl]-1-[3-(2,4,6-trifluorophenyl)propyl]piperidine-4-hydroxamic acid 4-[3-(R,S)-Hydroxy-3-(3-aminomethyl-6-methoxyquinolin-4-yl)propyl]-1-[3-(3,4,5-trifluorophenyl)propyl]piperidine-4-hydroxamic acid 4-[3-(R,S)-Hydroxy-3-(3-aminomethyl-6-methoxyquinolin-4-yl)propyl]-1-[2-(2,4,6-trifluorophenylthio)ethyl]piperidine-4-hydroxamic acid 4-[3-(R,S)-Hydroxy-3-(3-aminomethyl-6-methoxyquinolin-4-yl)propyl]-1-[2-(3,4,5-trifluorophenylthio)ethyl]piperidine-4-hydroxamic acid 4-[3-(R,S)-Hydroxy-3-(3-aminomethyl-6-methoxyquinolin-4-yl)propyl]-1-[2-(2,4,6-trifluorophenylamino)ethyl]piperidine-4-hydroxamic acid 4-[3-(R,S)-Hydroxy-3-(3-aminomethyl-6-methoxyquinolin-4-yl)propyl]-1-[2-(3,4,5-trifluorophenylamino)ethyl]piperidine-4-hydroxamic acid 4-[3-(R,S)-Hydroxy-3-(3-aminomethyl-6-methoxyquinolin-4-yl)propyl]-1-[2-(2,4,6-trifluorophenoxy)ethyl]piperidine-4-hydroxamic acid 4-[3-(R,S)-Hydroxy-3-(3-aminomethyl-6-methoxyquinolin-4-yl)propyl]-1-[2-(3,4,5-trifluorophenoxy)ethyl]piperidine-4-hydroxamic acid 4-[3-(R,S)-Hydroxy-3-(3-aminomethyl-6-methoxyquinolin-4-yl)propyl]-1-[3-(2,4,6-trifluorophenyl)prop-2-ynyl]piperidine-4-hydroxamic acid 4-[3-(R,S)-Hydroxy-3-(3-aminomethyl-6-methoxyquinolin-4-yl)propyl]-1-[3-(3,4,5-trifluorophenyl)prop-2-ynyl]piperidine-4-hydroxamic acid 4-[3-(R,S)-Hydroxy-3-(3-morpholinomethyl-6-methoxyquinolin-4-yl)propyl]-1-[3-(2,4,6-trifluorophenyl)-propyl]piperidine-4-hydroxamic acid 4-[3-(R,S)-Hydroxy-3-(3-morpholinomethyl-6-methoxyquinolin-4-yl)propyl]-1-[3-(3,4,5-trifluorophenyl)-propyl]piperidine-4-hydroxamic acid 4-[3-(R,S)-Hydroxy-3-(3-morpholinomethyl-6-methoxyquinolin-4-yl)propyl]-1-[2-(2,4,6-trifluorophenylthio)-ethyl]piperidine-4-hydroxamic acid 4-[3-(R,S)-Hydroxy-3-(3-morpholinomethyl-6-methoxyquinolin-4-yl)propyl]-1-[2-(3,4,5-trifluorophenylthio)-ethyl]piperidine-4-hydroxamic acid 4-[3-(R,S)-Hydroxy-3-(3-morpholinomethyl-6-methoxyquinolin-4-yl)propyl]-1-[2-(2,4,6-trifluorophenyl-amino)ethyl]piperidine-4-hydroxamic acid 4-[3-(R,S)-Hydroxy-3-(3-morpholinomethyl-6-methoxyquinolin-4-yl)propyl]-1-[2-(3,4,5-trifluorophenyl-amino)ethyl]piperidine-4-hydroxamic acid 4-[3-(R,S)-Hydroxy-3-(3-morpholinomethyl-6-methoxyquinolin-4-yl)propyl]-1-[2-(2,4,6-trifluorophenoxy)-ethyl]piperidine-4-hydroxamic acid 4-[3-(R,S)-Hydroxy-3-(3-morpholinomethyl-6-methoxyquinolin-4-yl)propyl]-1-[2-(3,4,5-trifluorophenoxy)-ethyl]piperidine-4-hydroxamic acid 4-[3-(R,S)-Hydroxy-3-(3-morpholinomethyl-6-methoxyquinolin-4-yl)propyl]-1-[3-(2,4,6-trifluorophenyl)-prop-2-ynyl]piperidine-4-hydroxamic acid 4-[3-(R,S)-Hydroxy-3-(3-morpholinomethyl-6-methoxyquinolin-4-yl)propyl]-1-[3-(3,4,5-trifluorophenyl)-prop-2-ynyl]piperidine-4-hydroxamic acid 4-[3-(R,S)-Fluoro-3-(3-chloro-6-methoxyquinolin-4-yl)propyl]-1-heptylpiperidine-4-hydroxamic acid 4-[3-(R,S)-Fluoro-3-(3-chloro-6-methoxyquinolin-4-yl)propyl]-1-[4-phenylbutyl]piperidine-4-hydroxamic acid 4-[3-(R,S)-Fluoro-3-(3-chloro-6-methoxyquinolin-4-yl)propyl]-1-[3-(phenyl)propyl]piperidine-4-hydroxamic acid 4-[3-(R,S)-Fluoro-3-(3-chloro-6-methoxyquinolin-4-yl)propyl]-1-[4-(2-fluorophenyl)propyl]piperidine-4-hydroxamic acid 4-[3-(R,S)-Fluoro-3-(3-chloro-6-methoxyquinolin-4-yl)propyl]-1-[4-(3-fluorophenyl)propyl]piperidine-4-hydroxamic acid 4-[3-(R,S)-Fluoro-3-(3-chloro-6-methoxyquinolin-4-yl)propyl]-1-(3-(4-fluorophenyl)propyl]piperidine-4-hydroxamic acid 4-[3-(R,S)-Fluoro-3-(3-chloro-6-methoxyquinolin-4-yl)propyl]-1-[4-(4-fluorophenyl)butyl]piperidine-4-hydroxamic acid 4-[3-(R,S)-Fluoro-3-(3-chloro-6-methoxyquinolin-4-yl)propyl]-1-[3-(2,3-difluorophenyl)propyl]piperidine-4-hydroxamic acid 4-[3-(R,S)-Fluoro-3-(3-chloro-6-methoxyquinolin-4-yl)propyl]-1-[4-(2,3-difluorophenyl)propyl]piperidine-4-hydroxamic acid 4-[3-(R,S)-Fluoro-3-(3-chloro-6-methoxyquinolin-4-yl)propyl]-1-[3-(2,6-difluorophenyl)propyl]piperidine-4-hydroxamic acid 4-[3-(R,S)-Fluoro-3-(3-chloro-6-methoxyquinolin-4-yl)propyl]-1-[4-(2,6-difluorophenyl)propyl]piperidine-4-hydroxamic acid 4-[3-(R,S)-Fluoro-3-(3-chloro-6-methoxyquinolin-4-yl)propyl]-1-[3-(3,5-difluorophenyl)propyl]piperidine-4-hydroxamic acid 4-[3-(R,S)-Fluoro-3-(3-chloro-6-methoxyquinolin-4-yl)propyl]-1-[3-(2,3,5-trifluorophenyl)propyl]piperidine-4-hydroxamic acid 4-[3-(R,S)-Fluoro-3-(3-chloro-6-methoxyquinolin-4-yl)propyl]-1-[3-(2,4,6-trifluorophenyl)propyl]piperidine-4-hydroxamic acid 4-[3-(R,S)-Fluoro-3-(3-chloro-6-methoxyquinolin-4-yl)propyl]-1-[3-(3,4,5-trifluorophenyl)propyl]piperidine-4-hydroxamic acid 4-[3-(R,S)-Fluoro-3-(3-chloro-6-methoxyquinolin-4-yl)propyl]-1-[3-phenylthiopropyl]piperidine-4-hydroxamic acid 4-[3-(R,S)-Fluoro-3-(3-chloro-6-methoxyquinolin-4-yl)propyl]-1-[3-(2-fluorophenylthio)propyl]piperidine-4-hydroxamic acid 4-[3-(R,S)-Fluoro-3-(3-chloro-6-methoxyquinolin-4-yl)propyl]-1-[3-(3-fluorophenylthio)propyl]piperidine-4-hydroxamic acid 4-[3-(R,S)-Fluoro-3-(3-chloro-6-methoxyquinolin-4-yl)propyl]-1-[2-(4-fluorophenylthio)ethyl]piperidine-4-hydroxamic acid 4-[3-(R,S)-Fluoro-3-(3-chloro-6-methoxyquinolin-4-yl)propyl]-1-[3-(4-fluorophenylthio)propyl]piperidine-4-hydroxamic acid 4-[3-(R,S)-Fluoro-3-(3-chloro-6-methoxyquinolin-4-yl)propyl]-1-[2-(2,3-difluorophenylthio)ethyl]piperidine-4-hydroxamic acid 4-[3-(R,S)-Fluoro-3-(3-chloro-6-methoxyquinolin-4-yl)propyl]-1-[3-(2,3-difluorophenylthio)propyl]piperidine-4-hydroxamic acid 4-[3-(R,S)-Fluoro-3-(3-chloro-6-methoxyquinolin-4-yl)propyl]-1-[2-(2,6-difluorophenylthio)ethyl]piperidine-4-hydroxamic acid 4-[3-(R,S)-Fluoro-3-(3-chloro-6-methoxyquinolin-4-yl)propyl]-1-[2-(2,3,5-trifluorophenylthio)ethyl]piperidine-4-hydroxamic acid 4-[3-(R,S)-Fluoro-3-(3-chloro-6-methoxyquinolin-4-yl)propyl]-1-[2-(2,4,6-trifluorophenylthio)ethyl]piperidine-4-hydroxamic acid 4-[3-(R,S)-Fluoro-3-(3-chloro-6-methoxyquinolin-4-yl)propyl]-1-[2-(3,4,5-trifluorophenylthio)ethyl]piperidine-4-hydroxamic acid 4-[3-(R,S)-Fluoro-3-(3-chloro-6-methoxyquinolin-4-yl)propyl]-1-[2-(3,5-difluorophenoxy)ethyl]piperidine-4-hydroxamic acid 4-[3-(R,S)-Fluoro-3-(3-chloro-6-methoxyquinolin-4-yl)propyl]-1-[2-(2,3,5-trifluorophenoxy)ethyl]piperidine-4-hydroxamic acid 4-[3-(R,S)-Fluoro-3-(3-chloro-6-methoxyquinolin-4-yl)propyl]-1-[2-(2,4,6-trifluorophenoxy)ethyl]piperidine-4-hydroxamic acid 4-[3-(R,S)-Fluoro-3-(3-chloro-6-methoxyquinolin-4-yl)propyl]-1-[2-(3,4,5-trifluorophenoxy)ethyl]piperidine-4-hydroxamic acid 4-[3-(R,S)-Fluoro-3-(3-chloro-6-methoxyquinolin-4-yl)propyl]-1-[2-(3,5-difluorophenylamino)ethyl]piperidine-4-hydroxamic acid 4-[3-(R,S)-Fluoro-3-(3-chloro-6-methoxyquinolin-4-yl)propyl]-1-[2-(2,3,5-trifluorophenylamino)ethyl]piperidine-4-hydroxamic acid 4-[3-(R,S)-Fluoro-3-(3-chloro-6-methoxyquinolin-4-yl)propyl]-1-[2-(2,4,6-trifluorophenylamino)ethyl]piperidine-4-hydroxamic acid 4-[3-(R,S)-Fluoro-3-(3-chloro-6-methoxyquinolin-4-yl)propyl]-1-[2-(3,4,5-trifluorophenylamino)ethyl]piperidine-4-hydroxamic acid 4-[3-(R,S)-Fluoro-3-(3-chloro-6-methoxyquinolin-4-yl)propyl]-1-[3-(2,6-difluorophenylthio)propyl]piperidine-4-hydroxamic acid 4-[3-(R,S)-Fluoro-3-(3-chloro-6-methoxyquinolin-4-yl)propyl]-1-[2-(2-chlorophenylthio)ethyl]piperidine-4-hydroxamic acid 4-[3-(R,S)-Fluoro-3-(3-chloro-6-methoxyquinolin-4-yl)propyl]-1-[3-(2-chlorophenylthio)propyl]piperidine-4-hydroxamic acid 4-[3-(R,S)-Fluoro-3-(3-chloro-6-methoxyquinolin-4-yl)propyl]-1-[2-(3-chlorophenylthio)ethyl]piperidine-4-hydroxamic acid 4-[3-(R,S)-Fluoro-3-(3-chloro-6-methoxyquinolin-4-yl)propyl]-1-[3-(3-chlorophenylthio)propyl]piperidine-4-hydroxamic acid 4-[3-(R,S)-Fluoro-3-(3-chloro-6-methoxyquinolin-4-yl)propyl]-1-[2-(4-chlorophenylthio)ethyl]piperidine-4-hydroxamic acid 4-[3-(R,S)-Fluoro-3-(3-chloro-6-methoxyquinolin-4-yl)propyl]-1-[3-(4-chlorophenylthio)propyl]piperidine-4-hydroxamic acid 4-[3-(R,S)-Fluoro-3-(3-chloro-6-methoxyquinolin-4-yl)propyl]-1-[2-(2-methylphenylthio)ethyl]piperidine-4-hydroxamic acid 4-[3-(R,S)-Fluoro-3-(3-chloro-6-methoxyquinolin-4-yl)propyl]-1-[3-(2-methylphenylthio)propyl]piperidine-4-hydroxamic acid 4-[3-(R,S)-Fluoro-3-(3-chloro-6-methoxyquinolin-4-yl)propyl]-1-[2-(3-methylphenylthio)ethyl]piperidine-4-hydroxamic acid 4-[3-(R,S)-Fluoro-3-(3-chloro-6-methoxyquinolin-4-yl)propyl]-1-[3-(3-methylphenylthio)propyl]piperidine-4-hydroxamic acid 4-[3-(R,S)-Fluoro-3-(3-chloro-6-methoxyquinolin-4-yl)propyl]-1-[2-(4-methylphenylthio)ethyl]piperidine-4-hydroxamic acid 4-[3-(R,S)-Fluoro-3-(3-chloro-6-methoxyquinolin-4-yl)propyl]-1-[3-(4-methylphenylthio)propyl]piperidine-4-hydroxamic acid 4-[3-(R,S)-Fluoro-3-(3-chloro-6-methoxyquinolin-4-yl)propyl]-1-[2-(2-trifluoromethylphenylthio)ethyl]-piperidine-4-hydroxamic acid 4-[3-(R,S)-Fluoro-3-(3-chloro-6-methoxyquinolin-4-yl)propyl]-1-[3-(2-trifluoromethylphenylthio)propyl]-piperidine-4-hydroxamic acid 4-[3-(R,S)-Fluoro-3-(3-chloro-6-methoxyquinolin-4-yl)propyl]-1-[2-(3-trifluoromethylphenylthio)ethyl]-piperidine-4-hydroxamic acid 4-[3-(R,S)-Fluoro-3-(3-chloro-6-methoxyquinolin-4-yl)propyl]-1-[3-(3-trifluoromethylphenylthio)propyl]-piperidine-4-hydroxamic acid 4-[3-(R,S)-Fluoro-3-(3-chloro-6-methoxyquinolin-4-yl)propyl]-1-[2-(4-trifluoromethylphenylthio)ethyl]-piperidine-4-hydroxamic acid 4-[3-(R,S)-Fluoro-3-(3-chloro-6-methoxyquinolin-4-yl)propyl]-1-[3-(4-trifluoromethylphenylthio)propyl]-piperidine-4-hydroxamic acid 4-[3-(R,S)-Fluoro-3-(3-chloro-6-methoxyquinolin-4-yl)propyl]-1-[2-(2-methoxyphenylthio)ethyl]piperidine-4-hydroxamic acid 4-[3-(R,S)-Fluoro-3-(3-chloro-6-methoxyquinolin-4-yl)propyl]-1-[3-(2-methoxyphenylthio)propyl]piperidine-4-hydroxamic acid 4-[3-(R,S)-Fluoro-3-(3-chloro-6-methoxyquinolin-4-yl)propyl]-1-[2-(3-methoxyphenylthio)ethyl]piperidine-4-hydroxamic acid 4-[3-(R,S)-Fluoro-3-(3-chloro-6-methoxyquinolin-4-yl)propyl]-1-[3-(3-methoxyphenylthio)propyl]piperidine-4-hydroxamic acid 4-[3-(R,S)-Fluoro-3-(3-chloro-6-methoxyquinolin-4-yl)propyl]-1-[2-(4-methoxyphenylthio)ethyl]piperidine-4-hydroxamic acid 4-[3-(R,S)-Fluoro-3-(3-chloro-6-methoxyquinolin-4-yl)propyl]-1-[3-(4-methoxyphenylthio)propyl]piperidine-4-hydroxamic acid 4-[3-(R,S)-Fluoro-3-(3-chloro-6-methoxyquinolin-4-yl)propyl]-1-[cyclopentylmethyl]piperidine-4-hydroxamic acid 4-[3-(R,S)-Fluoro-3-(3-chloro-6-methoxyquinolin-4-yl)propyl]-1-[2-(cyclopentyl)ethyl]piperidine-4-hydroxamic acid 4-[3-(R,S)-Fluoro-3-(3-chloro-6-methoxyquinolin-4-yl)propyl]-1-[2-(cyclohexyl)ethyl]piperidine-4-hydroxamic acid 4-[3-(R,S)-Fluoro-3-(3-chloro-6-methoxyquinolin-4-yl)propyl]-1-[2-(cyclopentylthio)ethyl]piperidine-4-hydroxamic acid 4-[3-(R,S)-Fluoro-3-(3-chloro-6-methoxyquinolin-4-yl)propyl]-1-[3-(cyclopentylthio)propyl]piperidine-4-hydroxamic acid 4-[3-(R,S)-Fluoro-3-(3-chloro-6-methoxyquinolin-4-yl)
propyl]-1-[3-(cyclohexylthio)propyl]piperidine-4-
hydroxamic acid 4-[3-(R,S)-Fluoro-3-(3-chloro-6-methoxyquinolin-4-yl)
propyl]-1-[2-(pyrid-2-yl)thioethyl]piperidine-4-
hydroxamic acid 4-[3-(R,S)-Fluoro-3-(3-chloro-6-methoxyquinolin-4-yl)
propyl]-1-[4-(thien-2-yl)butyl]piperidine-4-
hydroxamic acid 4-[3-(R,S)-Fluoro-3-(3-chloro-6-methoxyquinolin-4-yl)
propyl]-1-[3-(thien-2-yl)thiopropyl]piperidine-4-
hydroxamic acid 4-[3-(R,S)-Fluoro-3-(3-chloro-6-methoxyquinolin-4-yl)
propyl]-1-[3-(thien-2-yl)thiopehyl]piperidine-4-
hydroxamic acid 4-[3-(R,S)-Fluoro-3-(3-chloro-6-methoxyquinolin-4-yl)
propyl]-1-[4-(thien-3-yl)propyl]piperidine-4-
hydroxamic acid 4-[3-(R,S)-Fluoro-3-(3-chloro-6-methoxyquinolin-4-yl)
propyl]-1-[2-(thien-2-yl)thioethyl]piperidine-4-
hydroxamic acid 4-[3-(R,S)-Fluoro-3-(3-chloro-6-methoxyquinolin-4-yl)
propyl]-1-[2-(thien-3-yl)thioethyl]piperidine-4-
hydroxamic acid 4-[3-(R,S)-Fluoro-3-(3-chloro-6-methoxyquinolin-4-yl)
propyl]-1-[3-(thien-3-yl)thiopropyl]piperidine-4-
hydroxamic acid 4-[3-(R,S)-Fluoro-3-(3-chloro-6-methoxyquinolin-4-yl)
propyl]-1-[3-(1,3-thiazol-2-yl)propyl]piperidine-4-
hydroxamic acid 4-[3-(R,S)-Fluoro-3-(3-chloro-6-methoxyquinolin-4-yl)
propyl]-1-[4-(1,3-thiazol-2-yl)butyl]piperidine-4-
hydroxamic acid 4-[3-(R,S)-Fluoro-3-(3-chloro-6-methoxyquinolin-4-yl)
propyl]-1-[3-(1,3-thiazol-2-yl)thioethyl]piperidine-4-
hydroxamic acid 4-[3-(R,S)-Fluoro-3-(3-chloro-6-methoxyquinolin-4-yl)
propyl]-1-[3-(pyrid-2-yl)propyl]piperidine-4-
hydroxamic acid 4-[3-(R,S)-Fluoro-3-(3-chloro-6-methoxyquinolin-4-yl)
propyl]-1-[4-(pyrid-2-yl)butyl]piperidine-4-
hydroxamic acid 4-[3-(R,S)-Fluoro-3-(3-chloro-6-methoxyquinolin-4-yl)
propyl]-[3-(pyrid-2-yl)thiopropyl]piperidine-4-
hydroxamic acid 4-[3-(R,S)-Fluoro-3-(3-chloro-6-methoxyquinolin-4-yl)
propyl]-1-[3-(pyrid-3-yl)propyl]piperidine-4-
hydroxamic acid 4-[3-(R,S)-Fluoro-3-(3-chloro-6-methoxyquinolin-4-yl)
propyl]-1-[4-(pyrid-3-yl)butyl]piperidine-4-
hydroxamic acid 4-[3-(R,S)-Fluoro-3-(3-chloro-6-methoxyquinolin-4-yl)
propyl]-1-[2-(pyrid-3-yl)thioethyl]piperidine-4-
hydroxamic acid 4-[3-(R,S)-Fluoro-3-(3-chloro-6-methoxyquinolin-4-yl)
propyl]-1-[3-(pyrid-3-yl)thiopropyl]piperidine-4-
hydroxamic acid 4-[3-(R,S)-Fluoro-3-(3-chloro-6-methoxyquinolin-4-yl)
propyl]-1-[3-(pyrid-4-yl)propyl]piperidine-4-
hydroxamic acid 4-[3-(R,S)-Fluoro-3-(3-chloro-6-methoxyquinolin-4-yl)
propyl]-1-[4-(pyrid-4-yl)butyl]piperidine-4-
hydroxamic acid 4-[3-(R,S)-Fluoro-3-(3-chloro-6-methoxyquinolin-4-yl)
propyl]-1-[2-(pyrid-4-yl)thioethyl]piperidine-4-
hydroxamic acid 4-[3-(R,S)-Fluoro-3-(3-chloro-6-methoxyquinolin-4-yl)
propyl]-1-[3-(pyrid-4-yl)thiopropyl]piperidine-4-
hydroxamic acid 4-[3-(R,S)-Fluoro-3-(3-chloro-6-methoxyquinolin-4-yl)
propyl]-1-[3-(pyrazin-2-yl)propyl]piperidine-4-
hydroxamic acid 4-[3-(R,S)-Fluoro-3-(3-chloro-6-methoxyquinolin-4-yl)
propyl]-1-[4-(pyrazin-2-yl)butyl]piperidine-4-
hydroxamic acid 4-[3-(R,S)-Fluoro-3-(3-chloro-6-methoxyquinolin-4-yl)
propyl]-1-[2-(pyrazin-2-yl)thioethyl]piperidine-4-
hydroxamic acid 4-[3-(R,S)-Fluoro-3-(3-chloro-6-methoxyquinolin-4-yl)
propyl]-1-[3-(pyrazin-2-yl)thiopropyl]piperidine-4-
hydroxamic acid 4-[3-(R,S)-Fluoro-3-(3-chloro-6-methoxyquinolin-4-yl)
propyl]-1-[3-(4-fluorophenyl)prop-2-ynyl]piperidine-
4-hydroxamic acid 4-[3-(R,S)-Fluoro-3-(3-chloro-6-methoxyquinolin-4-yl)
propyl]-1-[3-(3,4-difluorophenyl)prop-2-ynyl]
piperidine-4-hydroxamic acid 4-[3-(R,S)-Fluoro-3-(3-chloro-6-methoxyquinolin-4-yl)
propyl]-1-[3-(2,4-difluorophenyl)prop-2-ynyl]
piperidine-4-hydroxamic acid 4-[3-(R,S)-Fluoro-3-(3-chloro-6-methoxyquinolin-4-yl)
propyl]-1-[3-(2,3,5-trifluorophenyl)prop-2-ynyl]-
piperidine-4-hydroxamic acid 4-[3-(R,S)-Fluoro-3-(3-chloro-6-methoxyquinolin-4-yl)
propyl]-1-[3-(2,4,6-trifluorophenyl)prop-2-ynyl]-
piperidine-4-hydroxamic acid 4-[3-(R,S)-Fluoro-3-(3-chloro-6-methoxyquinolin-4-yl)
propyl]-1-[3-(3,4,5-trifluorophenyl)prop-2-ynyl]-
piperidine-4-hydroxamic acid 4-[3-(R,S)-Fluoro-3-(3-chloro-6-methoxyquinolin-4-yl)
propyl]-1-[3-(4-chloro-3-fluorophenyl)prop-2-ynyl]-
piperidine-4-hydroxamic acid 4-[3-(R,S)-Fluoro-3-(3-chloro-6-methoxyquinolin-4-yl)
propyl]-1-[3-(3-chloro-4-fluorophenyl)prop-2-ynyl]
piperidine-4-hydroxamic acid 4-[3-(R,S)-Fluoro-3-(3-chloro-6-methoxyquinolin-4-yl)
propyl]-1-[3-(2-chloro-4-fluorophenyl)prop-2-ynyl]-
piperidine-4-hydroxamic acid 4-[3-(R,S)-Fluoro-3-(3-chloro-6-methoxyquinolin-4-yl)
propyl]-1-[3-(3-chloro-5-fluorophenyl)prop-2-ynyl]-
piperidine-4-hydroxamic acid 4-[3-(R,S)-Fluoro-3-(3-chloro-6-methoxyquinolin-4-yl)
propyl]-1-[3-(4-chloro-2-fluorophenyl)prop-2-ynyl]-
piperidine-4-hydroxamic acid 4-[3-(R,S)-Fluoro-3-(3-chloro-6-methoxyquinolin-4-yl)
propyl]-1-[3-(3-fluoro-4-methylphenyl)prop-2-ynyl]-
piperidine-4-hydroxamic acid 4-[3-(R,S)-Fluoro-3-(3-chloro-6-methoxyquinolin-4-yl)
propyl]-1-[3-(3,5-bistrifluoromethylphenyl)prop-2-
ynyl]piperidine-4-hydroxamic acid 4-[3-(R,S)-Fluoro-3-(3-chloro-6-methoxyquinolin-4-yl)
propyl]-1-[3-(thien-2-yl)prop-2-ynyl]piperidine-4-
hydroxamic acid 4-[3-(R,S)-Fluoro-3-(3-chloro-6-methoxyquinolin-4-yl)
propyl]-1-[3-(thien-3-yl)prop-2-ynyl]piperidine-4-
hydroxamic acid 4-[3-(R,S)-Fluoro-3-(3-chloro-6-methoxyquinolin-4-yl)propyl]-1-[3-(1,3-thiazol-2-yl)prop-2-ynyl]piperidine-4-hydroxamic acid 4-[3-(R,S)-Fluoro-3-(3-chloro-6-methoxyquinolin-4-yl)propyl]-1-[3-(1,3-thiazol-4-yl)prop-2-ynyl]piperidine-4-hydroxamic acid 4-[3-(R,S)-Fluoro-3-(3-chloro-6-methoxyquinolin-4-yl)propyl]-1-[3-(1,3-thiazol-5-yl)prop-2-ynyl]piperidine-4-hydroxamic acid 4-[3-(R,S)-Fluoro-3-(3-chloro-6-methoxyquinolin-4-yl)propyl]-1-[3-(pyrid-2-yl)prop-2-ynyl]piperidine-4-hydroxamic acid 4-[3-(R,S)-Fluoro-3-(3-chloro-6-methoxyquinolin-4-yl)propyl]-1-[3-(pyrid-3-yl)prop-2-ynyl]piperidine-4-hydroxamic acid 4-[3-(R,S)-Fluoro-3-(3-chloro-6-methoxyquinolin-4-yl)propyl]-1-[3-(pyrid-4-yl)prop-2-ynyl]piperidine-4-hydroxamic acid 4-[3-(R,S)-Fluoro-3-(3-methyl-6-methoxyquinolin-4-yl)propyl]-1-[2-(cyclohexyl)ethyl]piperidine-4-hydroxamic acid 4-[3-(R,S)-Fluoro-3-(3-methyl-6-methoxyquinolin-4-yl)propyl]-1-[3-(phenyl)propyl]piperidine-4-hydroxamic acid 4-[3-(R,S)-Fluoro-3-(3-methyl-6-methoxyquinolin-4-yl)propyl]-1-[3-(2,3,5-trifluorophenyl)propyl]piperidine-4-hydroxamic acid 4-[3-(R,S)-Fluoro-3-(3-methyl-6-methoxyquinolin-4-yl)propyl]-1-[2-(3,5-difluorophenylamino)ethyl]piperidine-4-hydroxamic acid 4-[3-(R,S)-Fluoro-3-(3-methyl-6-methoxyquinolin-4-yl)propyl]-1-[2-(2,3,5-trifluorophenylamino)ethyl]piperidine-4-hydroxamic acid 4-[3-(R,S)-Fluoro-3-(3-methyl-6-methoxyquinolin-4-yl)propyl]-1-[2-(3,5-difluorophenoxy)ethyl]piperidine-4-hydroxamic acid 4-[3-(R,S)-Fluoro-3-(3-methyl-6-methoxyquinolin-4-yl)propyl]-1-[2-(2,3,5-trifluorophenoxy)ethyl]piperidine-4-hydroxamic acid 4-[3-(R,S)-Fluoro-3-(3-methyl-6-methoxyquinolin-4-yl)propyl]-1-[2-(2,3,5-trifluorophenylthio)ethyl]piperidine-4-hydroxamic acid 4-[3-(R,S)-Fluoro-3-(3-methyl-6-methoxyquinolin-4-yl)propyl]-1-[2-(cyclopentylthio)ethyl]piperidine-4-hydroxamic acid 4-[3-(R,S)-Fluoro-3-(3-methyl-6-methoxyquinolin-4-yl)propyl]-1-[2-(pyrid-2-yl)thioethyl]piperidine-4-hydroxamic acid 4-[3-(R,S)-Fluoro-3-(3-methyl-6-methoxyquinolin-4-yl)propyl]-1-[2-(thien-2-yl)thioethyl]piperidine-4-hydroxamic acid 4-[3-(R,S)-Fluoro-3-(3-methyl-6-methoxyquinolin-4-yl)propyl]-1-[3-(2,3,5-trifluorophenyl)prop-2-ynyl]-piperidine-4-hydroxamic acid 4-[3-(R,S)-Fluoro-3-(3-methyl-6-methoxyquinolin-4-yl)propyl]-1-[3-(thien-2-yl)prop-2-ynyl]-piperidine-4-hydroxamic acid 4-[3-(R,S)-Fluoro-3-(3-fluoro-6-methoxyquinolin-4-yl)propyl]-1-[2-(cyclohexyl)ethyl]piperidine-4-hydroxamic acid 4-[3-(R,S)-Fluoro-3-(3-fluoro-6-methoxyquinolin-4-yl)propyl]-1-[3-(phenyl)propyl]piperidine-4-hydroxamic acid 4-[3-(R,S)-Fluoro-3-(3-fluoro-6-methoxyquinolin-4-yl)propyl]-1-[3-(2,3,5-trifluorophenyl)propyl]piperidine-4-hydroxamic acid 4-[3-(R,S)-Fluoro-3-(3-fluoro-6-methoxyquinolin-4-yl)propyl]-1-[2-(3,5-difluorophenylamino)ethyl]piperidine-4-hydroxamic acid 4-[3-(R,S)-Fluoro-3-(3-fluoro-6-methoxyquinolin-4-yl)propyl]-1-[2-(2,3,5-trifluorophenylamino)ethyl]-piperidine-4-hydroxamic acid 4-[3-(R,S)-Fluoro-3-(3-fluoro-6-methoxyquinolin-4-yl)propyl]-1-[2-(3,5-difluorophenoxy)ethyl]piperidine-4-hydroxamic acid 4-[3-(R,S)-Fluoro-3-(3-fluoro-6-methoxyquinolin-4-yl)propyl]-1-[2-(2,3,5-trifluorophenoxy)ethyl]piperidine-4-hydroxamic acid 4-[3-(R,S)-Fluoro-3-(3-fluoro-6-methoxyquinolin-4-yl)propyl]-1-[2-(2,3,5-trifluorophenylthio)ethyl]piperidine-4-hydroxamic acid 4-[3-(R,S)-Fluoro-3-(3-fluoro-6-methoxyquinolin-4-yl)propyl]-1-[2-(cyclopentylthio)ethyl]piperidine-4-hydroxamic acid 4-[3-(R,S)-Fluoro-3-(3-fluoro-6-methoxyquinolin-4-yl)propyl]-1-[2-(pyrid-2-yl)thioethyl]piperidine-4-hydroxamic acid 4-[3-(R,S)-Fluoro-3-(3-fluoro-6-methoxyquinolin-4-yl)propyl]-1-[2-(thien-2-yl)thioethyl]piperidine-4-hydroxamic acid 4-[3-(R,S)-Fluoro-3-(3-fluoro-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-fluoro-6-methoxyquinolin-4-yl)propyl]-1-[3-(thien-2-yl)prop-2-ynyl]piperidine-4-hydroxamic acid 4-[3-(R,S)-Fluoro-3-(3-dimethylamino-6-methoxyquinolin-4-yl)propyl]-1-[2-(cyclohexyl)ethyl]piperidine-4-hydroxamic acid 4-[3-(R,S)-Fluoro-3-(3-dimethylamino-6-methoxyquinolin-4-yl)propyl]-1-[3-(phenyl)propyl]piperidine-4-hydroxamic acid 4-[3-(R,S)-Fluoro-3-(3-dimethylamino-6-methoxyquinolin-4-yl)propyl]-1-[3-(2,3,5-trifluorophenyl)propyl]piperidine-4-hydroxamic acid 4-[3-(R,S)-Fluoro-3-(3-dimethylamino-6-methoxyquinolin-4-yl)propyl]-1-[2-(3,5-difluorophenylamino)ethyl]piperidine-4-hydroxamic acid 4-[3-(R,S)-Fluoro-3-(3-dimethylamino-6-methoxyquinolin-4-yl)propyl]-1-[2-(2,3,5-trifluorophenylamino)ethyl]piperidine-4-hydroxamic acid 4-[3-(R,S)-Fluoro-3-(3-dimethylamino-6-methoxyquinolin-4-yl)propyl]-1-[2-(3,5-difluorophenoxy)ethyl]-piperidine-4-hydroxamic acid 4-[3-(R,S)-Fluoro-3-(3-dimethylamino-6-methoxyquinolin-4-yl)propyl]-1-[2-(2,3,5-trifluorophenoxy)ethyl]piperidine-4-hydroxamic acid 4-[3-(R,S)-Fluoro-3-(3-dimethylamino-6-methoxyquinolin-4-yl)propyl]-1-[2-(2,3,5-trifluorophenylthio)ethyl]piperidine-4-hydroxamic acid 4-[3-(R,S)-Fluoro-3-(3-dimethylamino-6-methoxyquinolin-4-yl)propyl]-1-[2-(cyclopentylthio)ethyl]-piperidine-4-hydroxamic acid 4-[3-(R,S)-Fluoro-3-(3-dimethylamino-6-methoxyquinolin-4-yl)propyl]-1-[2-(pyrid-2-yl)thioethyl]piperidine-4-hydroxamic acid 4-[3-(R,S)-Fluoro-3-(3-dimethylamino-6-methoxyquinolin-4-yl)propyl]-1-[2-(thien-2-yl)thioethyl]piperidine-4-hydroxamic acid 4-[3-(R,S)-Fluoro-3-(3-dimethylamino-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-dimethylamino-6-methoxyquinolin-4-yl)propyl]-1-[3-(thien-2-yl)prop-2-ynyl]piperidine-4-hydroxamic acid 4-[3-(R,S)-Fluoro-3-(3-hydroxymethyl-6-methoxyquinolin-4-yl)propyl]-1-[2-(cyclohexyl)ethyl]piperidine-4-hydroxamic acid 4-[3-(R,S)-Fluoro-3-(3-hydroxymethyl-6-methoxyquinolin-4-yl)propyl]-1-[3-(phenyl)propyl]piperidine-4-hydroxamic acid 4-[3-(R,S)-Fluoro-3-(3-hydroxymethyl-6-methoxyquinolin-4-yl)propyl]-1-[3-(2,3,5-trifluorophenyl)propyl]piperidine-4-hydroxamic acid 4-[3-(R,S)-Fluoro-3-(3-hydroxymethyl-6-methoxyquinolin-4-yl)propyl]-1-[2-(3,5-difluorophenylamino)ethyl]piperidine-4-hydroxamic acid 4-[3-(R,S)-Fluoro-3-(3-hydroxymethyl-6-methoxyquinolin-4-yl)propyl]-1-[2-(2,3,5-trifluorophenylamino)ethyl]piperidine-4-hydroxamic acid 4-[3-(R,S)-Fluoro-3-(3-hydroxymethyl-6-methoxyquinolin-4-yl)propyl]-1-[2-(3,5-difluorophenoxy)ethyl]-piperidine-4-hydroxamic acid 4-[3-(R,S)-Fluoro-3-(3-hydroxymethyl-6-methoxyquinolin-4-yl)propyl]-1-[2-(2,3,5-trifluorophenoxy)ethyl]piperidine-4-hydroxamic acid 4-[3-(R,S)-Fluoro-3-(3-hydroxymethyl-6-methoxyquinolin-4-yl)propyl]-1-[2-(2,3,5-trifluorophenylthio)ethyl]piperidine-4-hydroxamic acid 4-[3-(R,S)-Fluoro-3-(3-hydroxymethyl-6-methoxyquinolin-4-yl)propyl]-1-[2-(cyclopentylthio)ethyl]piperidine-4-hydroxamic acid 4-[3-(R,S)-Fluoro-3-(3-hydroxymethyl-6-methoxyquinolin-4-yl)propyl]-1-[2-(pyrid-2-yl)thioethyl]piperidine-4-hydroxamic acid 4-[3-(R,S)-Fluoro-3-(3-hydroxymethyl-6-methoxyquinolin-4-yl)propyl]-1-[2-(thien-2-yl)thioethyl]piperidine-4-hydroxamic acid 4-[3-(R,S)-Fluoro-3-(3-hydroxymethyl-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-hydroxymethyl-6-methoxyquinolin-4-yl)propyl]-1-[3-(thien-2-yl)prop-2-ynyl]piperidine-4-hydroxamic acid 4-[3-(R,S)-Fluoro-3-(3-fluoromethyl-6-methoxyquinolin-4-yl)propyl]-1-[2-(cyclohexyl)ethyl]piperidine-4-hydroxamic acid 4-[3-(R,S)-Fluoro-3-(3-fluoromethyl-6-methoxyquinolin-4-yl)propyl]-1-[3-(phenyl)propyl]piperidine-4-hydroxamic acid 4-[3-(R,S)-Fluoro-3-(3-fluoromethyl-6-methoxyquinolin-4-yl)propyl]-1-[3-(2,3,5-trifluorophenyl)propyl]piperidine-4-hydroxamic acid 4-[3-(R,S)-Fluoro-3-(3-fluoromethyl-6-methoxyquinolin-4-yl)propyl]-1-[2-(3,5-difluorophenylamino)ethyl]piperidine-4-hydroxamic acid 4-[3-(R,S)-Fluoro-3-(3-fluoromethyl-6-methoxyquinolin-4-yl)propyl]-1-[2-(2,3,5-trifluorophenylamino)ethyl]piperidine-4-hydroxamic acid 4-[3-(R,S)-Fluoro-3-(3-fluoromethyl-6-methoxyquinolin-4-yl)propyl]-1-[2-(3,5-difluorophenoxyl)ethyl]-piperidine-4-hydroxamic acid 4-[3-(R,S)-Fluoro-3-(3-fluoromethyl-6-methoxyquinolin-4-yl)propyl]-1-[2-(2,3,5-trifluorophenoxy)ethyl]piperidine-4-hydroxamic acid 4-[3-(R,S)-Fluoro-3-(3-fluoromethyl-6-methoxyquinolin-4-yl)propyl]-1-[2-(2,3,5-trifluorophenylthio)ethyl]piperidine-4-hydroxamic acid 4-[3-(R,S)-Fluoro-3-(3-fluoromethyl-6-methoxyquinolin-4-yl)propyl]-1-[2-(cyclopentylthio)ethyl]piperidine-4-hydroxamic acid 4-[3-(R,S)-Fluoro-3-(3-fluoromethyl-6-methoxyquinolin-4-yl)propyl]-1-[2-(pyrid-2-yl)thioethyl]piperidine-4-hydroxamic acid 4-[3-(R,S)-Fluoro-3-(3-fluoromethyl-6-methoxyquinolin-4-yl)propyl]-1-[2-(thien-2-yl)thioethyl]piperidine-4-hydroxamic acid 4-[3-(R,S)-Fluoro-3-(3-fluoromethyl-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-fluoromethyl-6-methoxyquinolin-4-yl)propyl]-1-[3-(thien-2-yl)prop-2-ynyl]piperidine-4-hydroxamic acid 4-[3-(R,S)-Fluoro-3-(3-aminomethyl-6-methoxyquinolin-4-yl)propyl]-1-[2-(cyclohexyl)ethyl]piperidine-4-hydroxamic acid 4-[3-(R,S)-Fluoro-3-(3-aminomethyl-6-methoxyquinolin-4-yl)propyl]-1-[3-(phenyl)propyl]piperidine-4-hydroxamic acid 4-[3-(R,S)-Fluoro-3-(3-aminomethyl-6-methoxyquinolin-4-yl)propyl]-1-[3-(2,3,5-trifluorophenyl)propyl]piperidine-4-hydroxamic acid 4-[3-(R,S)-Fluoro-3-(3-aminomethyl-6-methoxyquinolin-4-yl)propyl]-1-[2-(3,5-difluorophenylamino)ethyl]piperidine-4-hydroxamic acid 4-[3-(R,S)-Fluoro-3-(3-aminomethyl-6-methoxyquinolin-4-yl)propyl]-1-[2-(2,3,5-trifluorophenylamino)ethyl]piperidine-4-hydroxamic acid 4-[3-(R,S)-Fluoro-3-(3-aminomethyl-6-methoxyquinolin-4-yl)propyl]-1-[2-(3,5-difluorophenoxy)ethyl]piperidine-4-hydroxamic acid 4-[3-(R,S)-Fluoro-3-(3-aminomethyl-6-methoxyquinolin-4-yl)propyl]-1-[2-(2,3,5-trifluorophenoxy)ethyl]piperidine-4-hydroxamic acid 4-[3-(R,S)-Fluoro-3-(3-aminomethyl-6-methoxyquinolin-4-yl)propyl]-1-[2-(2,3,5-trifluorophenylthio)ethyl]piperidine-4-hydroxamic acid 4-[3-(R,S)-Fluoro-3-(3-aminomethyl-6-methoxyquinolin-4-yl)propyl]-1-[2-(cyclopentylthio)ethyl]-piperidine-4-hydroxamic acid 4-[3-(R,S)-Fluoro-3-(3-aminomethyl-6-methoxyquinolin-4-yl)propyl]-1-[2-(pyrid-2-yl)thioethyl]piperidine-4-hydroxamic acid 4-[3-(R,S)-Fluoro-3-(3-aminomethyl-6-methoxyquinolin-4-yl)propyl]-1-[2-(thien-2-yl)thioethyl]piperidine-4-hydroxamic acid 4-[3-(R,S)-Fluoro-3-(3-aminomethyl-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-aminomethyl-6-methoxyquinolin-4-yl)propyl]-1-[3-(thien-2-yl)prop-2-ynyl]piperidine-4-hydroxamic acid 4-[3-(R,S)-Fluoro-3-(3-morpholinomethyl-6-methoxyquinolin-4-yl)propyl]-1-[2-(cyclohexyl)ethyl]piperidine-4-hydroxamic acid 4-[3-(R,S)-Fluoro-3-(3-morpholinomethyl-6-methoxyquinolin-4-yl)propyl]-1-[3-(phenyl)propyl]piperidine-4-hydroxamic acid 4-[3-(R,S)-Fluoro-3-(3-morpholinomethyl-6-methoxyquinolin-4-yl)propyl]-1-[3-(2,3,5-trifluorophenyl)-propyl]piperidine-4-hydroxamic acid 4-[3-(R,S)-Fluoro-3-(3-morpholinomethyl-6-methoxyquinolin-4-yl)propyl]-1-[2-(3,5-difluorophenylamino)-ethyl]piperidine-4-hydroxamic acid 4-[3-(R,S)-Fluoro-3-(3-morpholinomethyl-6-methoxyquinolin-4-yl)propyl]-1-[2-(2,3,5-trifluorophenyl-amino)ethyl]piperidine-4-hydroxamic acid 4-[3-(R,S)-Fluoro-3-(3-morpholinomethyl-6-methoxyquinolin-4-yl)propyl]-1-[2-(3,5-difluorophenoxy)-ethyl]piperidine-4-hydroxamic acid 4-[3-(R,S)-Fluoro-3-(3-morpholinomethyl-6-methoxyquinolin-4-yl)propyl]-1-[2-(2,3,5-trifluorophenoxy)-ethyl]piperidine-4-hydroxamic acid 4-[3-(R,S)-Fluoro-3-(3-morpholinomethyl-6-methoxyquinolin-4-yl)propyl]-1-[2-(2,3,5-trifluorophenyl-thio)ethyl]piperidine-4-hydroxamic acid 4-[3-(R,S)-Fluoro-3-(3-morpholinomethyl-6-methoxyquinolin-4-yl)propyl]-1-[2-(cyclopentylthio)ethyl]-piperidine-4-hydroxamic acid 4-[3-(R,S)-Fluoro-3-(3-morpholinomethyl-6-methoxyquinolin-4-yl)propyl]-1-[2-(pyrid-2-yl)thioethyl]-piperidine-4-hydroxamic acid 4-[3-(R,S)-Fluoro-3-(3-morpholinomethyl-6-methoxyquinolin-4-yl)propyl]-1-[2-(thien-2-yl)thioethyl]-piperidine-4-hydroxamic acid 4-[3-(R,S)-Fluoro-3-(3-morpholinomethyl-6-methoxyquinolin-4-yl)propyl]-1-[3-(2,3,5-trifluorophenyl)prop-2-ynyl]piperidine-4-hydroxamic acid 4-[3-(R,S)-Fluoro-3-(3-morpholinomethyl-6-methoxyquinolin-4-yl)propyl]-1-[3-(thien-2-yl)prop-2-ynyl]-piperidine-4-hydroxamic acid 4-[3-(R,S)-Fluoro-3-(3-methyl-6-methoxyquinolin-4-yl)propyl]-1-[3-(2,4,6-trifluorophenyl)propyl]piperidine-4-hydroxamic acid 4-[3-(R,S)-Fluoro-3-(3-methyl-6-methoxyquinolin-4-yl)propyl]-1-[3-(3,4,5-trifluorophenyl)propyl]piperidine-4-hydroxamic acid 4-[3-(R,S)-Fluoro-3-(3-methyl-6-methoxyquinolin-4-yl)propyl]-1-[2-(2,4,6-trifluorophenylthio)ethyl]piperidine-4-hydroxamic acid 4-[3-(R,S)-Fluoro-3-(3-methyl-6-methoxyquinolin-4-yl)propyl]-1-[2-(3,4,5-trifluorophenylthio)ethyl]piperidine-4-hydroxamic acid 4-[3-(R,S)-Fluoro-3-(3-methyl-6-methoxyquinolin-4-yl)propyl]-1-[2-(2,4,6-trifluorophenylamino)ethyl]-piperidine-4-hydroxamic acid 4-[3-(R,S)-Fluoro-3-(3-methyl-6-methoxyquinolin-4-yl)propyl]-1-[2-(3,4,5-trifluorophenylamino)ethyl]-piperidine-4-hydroxamic acid 4-[3-(R,S)-Fluoro-3-(3-methyl-6-methoxyquinolin-4-yl)propyl]-1-[2-(2,4,6-trifluorophenoxy)ethyl]piperidine-4-hydroxamic acid 4-[3-(R,S)-Fluoro-3-(3-methyl-6-methoxyquinolin-4-yl)propyl]-1-[2-(3,4,5-trifluorophenoxy)ethyl]piperidine-4-hydroxamic acid 4-[3-(R,S)-Fluoro-3-(3-methyl-6-methoxyquinolin-4-yl)propyl]-1-[3-(2,4,6-trifluorophenyl)prop-2-ynyl]-piperidine-4-hydroxamic acid 4-[3-(R,S)-Fluoro-3-(3-methyl-6-methoxyquinolin-4-yl)propyl]-1-[3-(3,4,5-trifluorophenyl)prop-2-ynyl]-piperidine-4-hydroxamic acid 4-[3-(R,S)-Fluoro-3-(3-fluoro-6-methoxyquinolin-4-yl)propyl]-1-[3-(2,4,6-trifluorophenyl)propyl]piperidine-4-hydroxamic acid 4-[3-(R,S)-Fluoro-3-(3-fluoro-6-methoxyquinolin-4-yl)propyl]-1-[3-(3,4,5-trifluorophenyl)propyl]piperidine-4-hydroxamic acid 4-[3-(R,S)-Fluoro-3-(3-fluoro-6-methoxyquinolin-4-yl)propyl]-1-[2-(2,4,6-trifluorophenylthio)ethyl]piperidine-4-hydroxamic acid 4-[3-(R,S)-Fluoro-3-(3-fluoro-6-methoxyquinolin-4-yl)propyl]-1-[2-(3,4,5-trifluorophenylthio)ethyl]piperidine-4-hydroxamic acid 4-[3-(R,S)-Fluoro-3-(3-fluoro-6-methoxyquinolin-4-yl)propyl]-1-[2-(2,4,6-trifluorophenylamino)ethyl]-piperidine-4-hydroxamic acid 4-[3-(R,S)-Fluoro-3-(3-fluoro-6-methoxyquinolin-4-yl)propyl]-1-[2-(3,4,5-trifluorophenylamino)ethyl]-piperidine-4-hydroxamic acid 4-[3-(R,S)-Fluoro-3-(3-fluoro-6-methoxyquinolin-4-yl)propyl]-1-[2-(2,4,6-trifluorophenoxy)ethyl]piperidine-4-hydroxamic acid 4-[3-(R,S)-Fluoro-3-(3-fluoro-6-methoxyquinolin-4-yl)propyl]-1-[2-(3,4,5-trifluorophenoxy)ethyl]piperidine-4-hydroxamic acid 4-[3-(R,S)-Fluoro-3-(3-fluoro-6-methoxyquinolin-4-yl)propyl]-1-[3-(2,4,6-trifluorophenyl)prop-2-ynyl]-piperidine-4-hydroxamic acid 4-[3-(R,S)-Fluoro-3-(3-fluoro-6-methoxyquinolin-4-yl)propyl]-1-[3-(3,4,5-trifluorophenyl)prop-2-ynyl]-piperidine-4-hydroxamic acid 4-[3-(R,S)-Fluoro-3-(3-dimethylamino-6-methoxyquinolin-4-yl)propyl]-1-[3-(2,4,6-trifluorophenyl)propyl]piperidine-4-hydroxamic acid 4-[3-(R,S)-Fluoro-3-(3-dimethylamino-6-methoxyquinolin-4-yl)propyl]-1-[3-(3,4,5-trifluorophenyl)propyl]piperidine-4-hydroxamic acid 4-[3-(R,S)-Fluoro-3-(3-dimethylamino-6-methoxyquinolin-4-yl)propyl]-1-[2-(2,4,6-trifluorophenylthio)ethyl]piperidine-4-hydroxamic acid 4-[3-(R,S)-Fluoro-3-(3-dimethylamino-6-methoxyquinolin-4-yl)propyl]-1-[2-(3,4,5-trifluorophenylthio)ethyl]piperidine-4-hydroxamic acid 4-[3-(R,S)-Fluoro-3-(3-dimethylamino-6-methoxyquinolin-4-yl)propyl]1-[2-(2,4,6-trifluorophenylamino)ethyl]piperidine-4-hydroxamic acid 4-[3-(R,S)-Fluoro-3-(3-dimethylamino-6-methoxyquinolin-4-yl)propyl]-1-[2-(3,4,5-trifluorophenylamino)ethyl]piperidine-4-hydroxamic acid 4-[3-(R,S)-Fluoro-3-(3-dimethylamino-6-methoxyquinolin-4-yl)propyl]-1-[2-(2,4,6-trifluorophenoxy)ethyl]piperidine-4-hydroxamic acid 4-[3-(R,S)-Fluoro-3-(3-dimethylamino-6-methoxyquinolin-4-yl)propyl]-1-[2-(3,4,5-trifluorophenoxy)ethyl]piperidine-4-hydroxamic acid 4-[3-(R,S)-Fluoro-3-(3-dimethylamino-6-methoxyquinolin-4-yl)propyl]-1-[3-(2,4,6-trifluorophenyl)prop-2-ynyl]piperidine-4-hydroxamic acid 4-[3-(R,S)-Fluoro-3-(3-dimethylamino-6-methoxyquinolin-4-yl)propyl]-1-[3-(3,4,5-trifluorophenyl)prop-2-ynyl]piperidine-4-hydroxamic acid 4-[3-(R,S)-Fluoro-3-(3-fluoro-6-methoxyquinolin-4-yl)propyl]-1-[3-(2,4,6-trifluorophenyl)propyl]piperidine-4-hydroxamic acid 4-[3-(R,S)-Fluoro-3-(3-hydroxymethyl-6-methoxyquinolin-4-yl)propyl]-1-[3-(3,4,5-trifluorophenyl)propyl]piperidine-4-hydroxamic acid 4-[3-(R,S)-Fluoro-3-(3-hydroxymethyl-6-methoxyquinolin-4-yl)propyl]-1-[2-(2,4,6-trifluorophenylthio)ethyl]piperidine-4-hydroxamic acid 4-[3-(R,S)-Fluoro-3-(3-hydroxymethyl-6-methoxyquinolin-4-yl)propyl]-1-[2-(3,4,5-trifluorophenylthio)ethyl]piperidine-4-hydroxamic acid 4-[3-(R,S)-Fluoro-3-(3-hydroxymethyl-6-methoxyquinolin-4-yl)propyl]-1-[2-(2,4,6-trifluorophenylamino)ethyl]piperidine-4-hydroxamic acid 4-[3-(R,S)-Fluoro-3-(3-hydroxymethyl-6-methoxyquinolin-4-yl)propyl]-1-[2-(3,4,5-trifluorophenylamino)ethyl]piperidine-4-hydroxamic acid 4-[3-(R,S)-Fluoro-3-(3-hydroxymethyl-6-methoxyquinolin-4-yl)propyl]-1-[2-(2,4,6-trifluorophenoxy)ethyl]piperidine-4-hydroxamic acid 4-[3-(R,S)-Fluoro-3-(3-hydroxymethyl-6-methoxyquinolin-4-yl)propyl]-1-[2-(3,4,5-trifluorophenoxy)ethyl]piperidine-4-hydroxamic acid 4-[3-(R,S)-Fluoro-3-(3-hydroxymethyl-6-methoxyquinolin-4-yl)propyl]-1-[3-(2,4,6-trifluorophenyl)prop-2-ynyl]piperidine-4-hydroxamic acid 4-[3-(R,S)-Fluoro-3-(3-hydroxymethyl-6-methoxyquinolin-4-yl)propyl]-1-[3-(3,4,5-trifluorophenyl)prop-2-ynyl]piperidine-4-hydroxamic acid 4-[3-(R,S)-Fluoro-3-(3-fluoromethyl-6-methoxyquinolin-4-yl)propyl]-1-[3-(2,4,6-trifluorophenyl)propyl]piperidine-4-hydroxamic acid 4-[3-(R,S)-Fluoro-3-(3-fluoromethyl-6-methoxyquinolin-4-yl)propyl]-1-[3-(3,4,5-trifluorophenyl)propyl]piperidine-4-hydroxamic acid 4-[3-(R,S)-Fluoro-3-(3-fluoromethyl-6-methoxyquinolin-4-yl)propyl]-1-[2-(2,4,6-trifluorophenylthio)ethyl]piperidine-4-hydroxamic acid 4-[3-(R,S)-Fluoro-3-(3-fluoromethyl-6-methoxyquinolin-4-yl)propyl]-1-[2-(3,4,5-trifluorophenylthio)ethyl]piperidine-4-hydroxamic acid 4-[3-(R,S)-Fluoro-3-(3-fluoromethyl-6-methoxyquinolin-4-yl)propyl]-1-[2-(2,4,6-trifluorophenylamino)ethyl]piperidine-4-hydroxamic acid 4-[3-(R,S)-Fluoro-3-(3-fluoromethyl-6-methoxyquinolin-4-yl)propyl]-1-[2-(3,4,5-trifluorophenylamino)ethyl]piperidine-4-hydroxamic acid 4-[3-(R,S)-Fluoro-3-(3-fluoromethyl-6-methoxyquinolin-4-yl)propyl]-1-[2-(2,4,6-trifluorophenoxy)ethyl]piperidine-4-hydroxamic acid 4-[3-(R,S)-Fluoro-3-(3-fluoromethyl-6-methoxyquinolin-4-yl)propyl]-1-[2-(3,4,5-trifluorophenoxy)ethyl]piperidine-4-hydroxamic acid 4-[3-(R,S)-Fluoro-3-(3-fluoromethyl-6-methoxyquinolin-4-yl)propyl]-1-[3-(2,4,6-trifluorophenyl)prop-2-ynyl]piperidine-4-hydroxamic acid 4-[3-(R,S)-Fluoro-3-(3-fluoromethyl-6-methoxyquinolin-4-yl)propyl]-1-[3-(3,4,5-trifluorophenyl)prop-2-ynyl]piperidine-4-hydroxamic acid 4-[3-(R,S)-Fluoro-3-(3-aminomethyl-6-methoxyquinolin-4-yl)propyl]-1-[3-(2,4,6-trifluorophenyl)propyl]piperidine-4-hydroxamic acid 4-[3-(R,S)-Fluoro-3-(3-aminomethyl-6-methoxyquinolin-4-yl)propyl]-1-[3-(3,4,5-trifluorophenyl)propyl]piperidine-4-hydroxamic acid 4-[3-(R,S)-Fluoro-3-(3-aminomethyl-6-methoxyquinolin-4-yl)propyl]-1-[2-(2,4,6-trifluorophenylthio)ethyl]piperidine-4-hydroxamic acid 4-[3-(R,S)-Fluoro-3-(3-aminomethyl-6-methoxyquinolin-4-yl)propyl]-1-[2-(3,4,5-trifluorophenylthio)ethyl]piperidine-4-hydroxamic acid 4-[3-(R,S)-Fluoro-3-(3-aminomethyl-6-methoxyquinolin-4-yl)propyl]-1-[2-(2,4,6-trifluorophenylamino)ethyl]piperidine-4-hydroxamic acid 4-[3-(R,S)-Fluoro-3-(3-aminomethyl-6-methoxyquinolin-4-yl)propyl]-1-[2-(3,4,5-trifluorophenylamino)ethyl]piperidine-4-hydroxamic acid 4-[3-(R,S)-Fluoro-3-(3-aminomethyl-6-methoxyquinolin-4-yl)propyl]-1-[2-(2,4,6-trifluorophenoxy)ethyl]piperidine-4-hydroxamic acid 4-[3-(R,S)-Fluoro-3-(3-aminomethyl-6-methoxyquinolin-4-yl)propyl]-1-[2-(3,4,5-trifluorophenoxy)ethyl]piperidine-4-hydroxamic acid 4-[3-(R,S)-Fluoro-3-(3-aminomethyl-6-methoxyquinolin-4-yl)propyl]-1-[3-(2,4,6-trifluorophenyl)prop-2-ynyl]piperidine-4-hydroxamic acid 4-[3-(R,S)-Fluoro-3-(3-aminomethyl-6-methoxyquinolin-4-yl)propyl]-1-[3-(3,4,5-trifluorophenyl)prop-2-ynyl]piperidine-4-hydroxamic acid 4-[3-(R,S)-Fluoro-3-(3-morpholinomethyl-6-methoxyquinolin-4-yl)propyl]-1-[3-(2,4,6-trifluorophenyl)-propyl]piperidine-4-hydroxamic acid 4-[3-(R,S)-Fluoro-3-(3-morpholinomethyl-6-methoxyquinolin-4-yl)propyl]-1-[3-(3,4,5-trifluorophenyl)-propyl]piperidine-4-hydroxamic acid 4-[3-(R,S)-Fluoro-3-(3-morpholinomethyl-6-methoxyquinolin-4-yl)propyl]-1-[2-(2,4,6-trifluorophenylthio)-ethyl]piperidine-4-hydroxamic acid 4-[3-(R,S)-Fluoro-3-(3-morpholinomethyl-6-methoxyquinolin-4-yl)propyl]-1-[2-(3,4,5-trifluorophenylthio)-ethyl]piperidine-4-hydroxamic acid 4-[3-(R,S)-Fluoro-3-(3-morpholinomethyl-6-methoxyquinolin-4-yl)propyl]-1-[2-(2,4,6-trifluorophenyl-amino)ethyl]piperidine-4-hydroxamic acid 4-[3-(R,S)-Fluoro-3-(3-morpholinomethyl-6-methoxyquinolin-4-yl)propyl]-1-[2-(3,4,5-trifluorophenyl-amino)ethyl]piperidine-4-hydroxamic acid 4-[3-(R,S)-Fluoro-3-(3-morpholinomethyl-6-methoxyquinolin-4-yl)propyl]-1-[2-(2,4,6-trifluorophenoxy)-ethyl]piperidine-4-hydroxamic acid 4-[3-(R,S)-Fluoro-3-(3-morpholinomethyl-6-methoxyquinolin-4-yl)propyl]-1-[2-(3,4,5-trifluorophenoxy)-ethyl]piperidine-4-hydroxamic acid 4-[3-(R,S)-Fluoro-3-(3-morpholinomethyl-6-methoxyquinolin-4-yl)propyl]-1-[3-(2,4,6-trifluorophenyl)-prop-2-ynyl]piperidine-4-hydroxamic acid 4-[3-(R,S)-Fluoro-3-(3-morpholinomethyl-6-methoxyquinolin-4-yl)propyl]-1-[3-(3,4,5-trifluorophenyl)-prop-2-ynyl]piperidine-4-hydroxamic acid 4-[3-(3-fluoro-6-methoxy-quinolin-4-yl)-propyl]-1-[3-(2-fluorophenyl)-allyl]-piperidin-4-carboxylic acid 4-[3-(3-fluoro-6-methoxy-quinolin-4-yl)-propyl]-1-[3-(3-fluorophenyl)-allyl]-piperidin-4-carboxylic acid 4-[3-(3-fluoro-6-methoxy-quinolin-4-yl)-propyl]-1-[3-(4-fluorophenyl)-allyl]-piperidin-4-carboxylic acid 4-[3-(3-fluoro-6-methoxy-quinolin-4-yl)-propyl]-1-[3-(2,3-difluorophenyl)-allyl]-piperidin-4-carboxylic acid 4-[3-(3-fluoro-6-methoxy-quinolin-4-yl)-propyl]-1-[3-(2,4-difluorophenyl)-allyl]-piperidin-4-carboxylic acid 4-[3-(3-fluoro-6-methoxy-quinolin-4-yl)-propyl]-1-[3-(2,6-difluorophenyl)-allyl]-piperidin-4-carboxylic acid 4-[3-(3-fluoro-6-methoxy-quinolin-4-yl)-propyl]-1-[3-(3,5-difluorophenyl)-allyl]-piperidin-4-carboxylic acid 4-[3-(3-fluoro-6-methoxy-quinolin-4-yl)-propyl]-1-[3-(3,4-difluorophenyl)-allyl]-piperidin-4-carboxylic acid 4-[3-(3-fluoro-6-methoxy-quinolin-4-yl)-propyl]-1-[3-(2,3,5-trifluorophenyl)-allyl]-piperidin-4-carboxylic acid 4-[3-(3-fluoro-6-methoxy-quinolin-4-yl)-propyl]-1-[3-(2,3,4-trifluorophenyl)-allyl]-piperidin-4-carboxylic acid 4-[3-(3-fluoro-6-methoxy-quinolin-4-yl)-propyl]-1-[3-(2,3,6-trifluorophenyl)-allyl]-piperidin-4-carboxylic acid 4-[3-(3-fluoro-6-methoxy-quinolin-4-yl)-propyl]-1-[3-(2,4,5-trifluorophenyl)-allyl]-piperidin-4-carboxylic acid 4-[3-(3-fluoro-6-methoxy-quinolin-4-yl)-propyl]-1-[3-(2,4,6-trifluorophenyl)-allyl]-piperidin-4-carboxylic acid 4-[3-(3-fluoro-6-methoxy-quinolin-4-yl)-propyl]-1-[3-(3,4,5-trifluorophenyl)-allyl]-piperidin-4-carboxylic acid 4-[3-(3-fluoro-6-methoxy-quinolin-4-yl)-propyl]-1-[3-(3,5,6-trifluorophenyl)-allyl]-piperidin-4-carboxylic acid.

The examples which follow, given in a non-limiting manner, illustrate the present invention.

EXAMPLE 1

4-[3-(3-Chloro-6-methoxyquinolin-4-yl)propyl]-1-[2-(thien-2-yl)thioethyl]-piperidine-4-carboxylic Acid Dihydrochloride.

A mixture of 0.6 g of benzyl 4-[3-(3-chloro-6-methoxyquinolin-4-yl)propyl]-1-[2-(thien-2-yl)thioethyl]-piperidine-4-carboxylate in 7.72 cm³ of aqueous 6N hydrochloric acid was maintained at a temperature in the region of 100° C. with stirring and under an inert atmosphere for 2 hours. After cooling to about 20° C., the reaction mixture was concentrated to dryness under reduced pressure (5 kPa) at a temperature in the region of 40° C.

The residue obtained was taken up in 10 cm³ of a dichloromethane/methanol mixture (90/10 by volume). The mixture was concentrated to dryness under the above conditions. 0.58 g of 4-[3-(3-chloro-6-methoxyquinolin-4-yl)propyl]-1-[2-(thien-2-yl)thioethyl]piperidine-4-carboxylic acid dihydrochloride, was obtained in the form of a beige-colored foam melting at 130° C. with decomposition.

$^1$H NMR spectrum (250 MHz, (CD$_3$)$_2$SO-d$_6$ at a temperature of 373 K, δ in ppm): from 1.50 to 2.30 (mts: 8H in total); from 2.70 to 3.80 (mts: 10H in total); 3.99 (s: 3H); 7.09 (dd, J=5 and 3.5 Hz: 1H); 7.29 (broad d, J=3.5 Hz: 1H); 7.40 (d, J=2.5 Hz: 1H); 7.46 (dd, J=9 and 2.5 Hz: 1H); 7.64 (broad d, J=5 Hz: 1H); 7.99 (d, J=9 Hz: 1H); 8.67 (s: 1H).

Benzyl 4-[3-(3-chloro-6-methoxyquinolin-4-yl)propyl]-1-[2-(thien-2-yl)thioethyl]-piperidine-4-carboxylate A mixture of 0.6 g of benzyl 4-[3-(3-chloro-6-methoxyquinolin-4-yl)propyl]piperidine-4-carboxylate, 0.36 g of 2-(2-bromoethylthio)thiophene and 0.22 g of potassium carbonate in 20 cm³ of acetonitrile was heated for 16 hours at a temperature in the region of 80° C., with stirring and under an inert atmosphere. After cooling to a temperature in the region of 20° C., the reaction mixture was concentrated under reduced pressure (5 kPa) at a temperature in the region of 40° C.

A residue was obtained, which was purified by chromatography, under a nitrogen pressure of 100 kPa, on a column of silica gel (particle size 40–63μ; diameter 3.5 cm; height 28 cm), eluting with a mixture of dichloromethane/methanol (97.5/2.5 by volume) and collecting 35-cm³ fractions. Fractions 15 to 20 were combined and then concentrated to dryness under the above conditions. 0.67 g of benzyl 4-[3-(3-chloro-6-methoxyquinolin-4-yl)propyl]-1-[2-(thien-2-yl)thioethyl]piperidine-4-carboxylate was obtained in the form of an orange-colored viscous oil.

Infra-red spectrum (CCl$_4$) 2955; 1727; 1622; 1503; 1229; 1117; 833 and 698 cm$^{-1}$.

Benzyl 4-[3-(3-chloro-6-methoxyquinolin-4-yl)propyl] piperidine-4-carboxylate 1.27 cm³ of trifluoroacetic acid were added, with stirring and under an inert atmosphere, at a temperature in the region of 20° C., to a solution of 2.05 g of benzyl 4-[3-(3-chloro-6-methoxyquinolin-4-yl)propyl]-1-(tert-butyloxycarbonyl) piperidine-4-carboxylate in 50 cm³ of dichloromethane. After 30 minutes, a further 1.27 cm³ of trifluoroacetic acid were added and, after a further 30 minutes, a further 1.27 cm³ were added. The reaction was completed by a final addition of 1.27 cm³ of trifluoroacetic acid. After one hour, the reaction mixture was concentrated under reduced pressure (5 kPa) at a temperature in the region of 40° C.

The evaporation residue was taken up in 50 cm³ of ethyl acetate and 20 cm³ of water. After addition of 5 g of potassium carbonate and stirring for 5 minutes, phases were allowed to separate by settling and the organic phase separated out was washed with twice 10 cm³ of distilled water and then with 20 cm³ of aqueous 10% (by weight) sodium chloride solution. After drying over magnesium sulfate and then filtration, the organic solution was concentrated under reduced pressure (5 kPa) at a temperature in the region of 40° C.

The residue obtained was purified by chromatography, under a nitrogen pressure of 100 kPa, on a column of silica gel (particle size 40–63µ; diameter 3.5 cm; height 30 cm), eluting with a mixture of dichloromethane/methanol/32% aqueous ammonia (89/10/1 by volume), and collecting 40-cm³ fractions. Fractions 14 to 23 were combined and then concentrated to dryness under the above conditions. 1.36 g of benzyl 4-[3-(3-chloro-6-methoxyquinolin-4-yl)propyl]piperidine-4-carboxylate were obtained in the form of a beige-colored solid melting at 95° C.

Infra-red spectrum (KBr) 2960; 1721; 1621; 1503; 1232; 1115; 829 and 744 cm$^{-1}$.

Benzyl 4-[3-(3-chloro-6-methoxyquinolin-4-yl)propyl]-1-(tert-butyloxycarbonyl)-piperidine-4-carboxylate.

1.98 g of benzyl 4-allyl-1-(tert-butyloxycarbonyl)-piperidine-4-carboxylate were cooled to a temperature in the region of −30° C. and 11.32 cm³ of a 0.5M solution of 9-borabicyclo[3.3.1]nonane in tetrahydrofuran were added with stirring and under an inert atmosphere. After the addition, the temperature of the mixture was brought to about 20° C. The solution obtained was stirred for a further 4 hours, followed by addition of 40 cm³ of dioxane, 0.183 g of diphenylphosphinoferrocenepalladium chloride, 2 g of 4-bromo-3-chloro-6-methoxyquinoline and 3.0 g of tribasic potassium phosphate. After stirring for 16 hours at a temperature in the region of 60° C., the reaction mixture was cooled to about 20° C. and then filtered. The insoluble material was washed with 3 times 20 cm³ of ethyl acetate and the filtrate and washing waters were then combined and stirred with 40 cm³ of water and 100 cm³ of ethyl acetate. The organic phase was separated out by settling, washed with twice 20 cm³ of water and then with 40 cm³ of aqueous 10% (by weight) sodium chloride solution, dried over magnesium sulfate, filtered and concentrated under reduced pressure (5 kPa) at a temperature in the region of 40° C.

The residue obtained was purified by chromatography, under a nitrogen pressure of 100 kPa, on a column of silica gel (particle size 40–63µ; diameter 3.5 cm; height 30 cm), eluting with a mixture of dichloromethane/methanol (98.5/1.5 by volume) and collecting 35-cm³ fractions. Fractions 22 to 29 were combined and then concentrated under the above conditions. 2.09 g of benzyl 4-[3-(3-chloro-6-methoxyquinolin-4-yl)propyl]-1-(tert-butyloxycarbonyl)piperidine-4-carboxylate were obtained in the form of a thick yellow oil.

Infra-red spectrum (CCl$_4$) 2930; 1728; 1695; 1622; 1503; 1230; 1172; 833 and 697 cm$^{-1}$.

Benzyl 4-allyl-1-(tert-butyloxycarbonyl)piperidine-4-carboxylate.

15.4 g of potassium carbonate and then 10.6 cm³ of benzyl bromide were added, at a temperature in the region of 20° C., with stirring and under an inert atmosphere, to a solution of 20 g of 4-allyl-1-(tert-butyloxycarbonyl)-piperidine-4-carboxylic acid in 200 cm³ of dimethylformamide. The mixture was stirred for 16 hours at about 20° C. and then filtered. The insoluble material was washed with twice 100 cm³ of ethyl acetate. The filtrate and the washing waters were combined, 250 cm³ of water were added and the mixture was then extracted once with 500 cm³ and once with 150 cm³ of ethyl acetate. The organic extracts were combined, washed with twice 125 cm³ of aqueous 10% (by weight) sodium chloride solution, dried over magnesium sulfate, filtered and concentrated under reduced pressure (5 kPa) at a temperature in the region of 40° C.

An oil was obtained, which was purified by chromatography, under a pressure of 100 kPa of nitrogen, on a column of silica gel (particle size 40–63µ; diameter 7 cm; height 30 cm), eluting with a mixture of dichloromethane/methanol (99/1 by volume) and collecting 200-cm³ fractions. Fractions 6 to 16 were combined and concentrated to dryness under reduced pressure (5 kPa) at a temperature in the region of 40° C. 25 g of benzyl 4-allyl-1-(tert-butyloxycarbonyl)piperidine-4-carboxylate were obtained in the form of a pale yellow liquid.

Infra-red spectrum (CH$_2$Cl$_2$): 2980; 1725; 1683; 1426; 1171; 1142; 974 and 924 cm$^{-1}$.

4-Allyl-1-(tert-butyloxycarbonyl)piperidine-4-carboxylic Acid.

4.44 cm³ of water and then 30.62 g of ethyl 4-allyl-1-(tert-butyloxycarbonyl)-piperidine-4-carboxylate predissolved in 150 cm³ of tetrahydrofuran were added, with stirring and under an inert atmosphere, to a mixture of 48.52 g of potassium tert-butoxide in 350 cm³ of tetrahydrofuran, cooled to a temperature in the region of 0° C. After allowing the temperature to return to the region of 20° C., the mixture was stirred for 24 hours at this temperature. 300 cm³ of ice-cold water were added to the reaction mixture and the mixture was then concentrated to dryness under reduced pressure (5 kPa) at a temperature in the region of 40° C. The aqueous residue was extracted with 300 cm³ of diethyl ether. After leaving to stand for 16 hours, the aqueous phase was acidified at a pH in the region of 3–4 by addition of about 215 cm³ of aqueous hydrochloric acid, and was then extracted with three times 300 cm³ of diethyl ether.

The ether extracts were combined, dried over magnesium sulfate, filtered and concentrated to dryness under reduced pressure (5 kPa) at a temperature in the region of 40° C. 26.1 g of 4-allyl-1-(tert-butyloxycarbonyl)piperidine-4-carboxylic acid were obtained in the form of an off-white solid.

Mass spectrum: EI m/z=269 M$^{+\cdot}$ m/z=168 (M-C$_5$H$_9$O$_2$)$^+$ m/z=124(m/z=168-CO$_2$)$^+$ m/z=57 C$_4$H$_9^+$ base peak Ethyl allyl-1-(tert-butyloxycarbonyl)piperidine-4-carboxylate.

70 cm³ of a solution of butyllithium in hexane (2.5M concentration) were added, with stirring and under an inert atmosphere, to 150 cm³ of tetrahydrofuran cooled to a temperature in the region of −70° C., followed by addition of 50 cm³ of tetrahydrofuran and 23 cm³ of diisopropylamine predissolved in 300 cm³ of tetrahydrofuran. After a further addition of 50 cm³ of tetrahydrofuran, the mixture was stirred for 15 minutes at about −70° C., followed by addition of 45.15 g of ethyl de 1-(tert-butyloxycarbonyl) isonipecotate predissolved in 400 cm³ of tetrahydrofuran, and finally 50 cm³ of this same solvent. After stirring the mixture for 1 hour at a temperature in the region of −70° C., 16.7 cm³ of allyl bromide predissolved in 150 cm³ of tetrahydrofuran were added and the mixture was then warmed to about 20° C. and stirred for 17 hours. The mixture was poured into 200 cm³ of saturated aqueous ammonium chloride solution and then extracted with about 2 liters of ethyl acetate.

The combined extracts were dried over sodium sulfate, filtered and concentrated under reduced pressure (5 kPa) at a temperature in the region of 40° C. An oil was obtained, which was purified by chromatography, under a nitrogen pressure of 100 kPa, on a column of silica gel (diameter 12 cm; height 50 cm), eluting with a mixture of dichloromethane/methanol (99.5/0.5 by volume) and collecting 200-cm³ fractions. Fractions 20 to 84 were combined and concentrated under reduced pressure (5 kPa) at a temperature in the region of 40° C. 27.85 g of ethyl 4-allyl-1-

(tert-butyloxycarbonyl)-piperidine-4-carboxylate were obtained in the form of a yellow oil.

Mass spectrum: EI m/z=297 M$^{+\cdot}$ m/z=240 (M-C$_4$H$_9$)$^+$ m/z=196(m/z=240-CO$_2$)$^+$ m/z=168 (m/z=240-CO$_2$Et)$^+$ m/z=124 (m/z=168-CO$_2$)$^+$ m/z=57 C$_4$H$_9$$^+$ base peak Ethyl 1-(tert-butyloxycarbonyl)isonipecotate.

88.3 cm$^3$ of triethylamine were added over 1 hour, with stirring and under an inert atmosphere, to a solution of 100 g of ethyl isonipecotate in 1500 cm$^3$ of dichloromethane cooled to a temperature in the region of 5° C., followed, over the same time, by addition of 166.6 g of di-tert-butyl dicarbonate predissolved in 300 cm$^3$ of dichloromethane. The reaction mixture was stirred for 16 hours while allowing the temperature to return to the region of 20° C. After a further addition of 41.6 g of di-tert-butyl dicarbonate dissolved in 70 cm$^3$ of dichloromethane, the reaction mixture was stirred for 3 hours at about 20° C. and then washed with twice 600 cm$^3$ of saturated aqueous sodium chloride solution, dried over sodium sulfate, filtered and concentrated under reduced pressure (5 kPa) at a temperature in the region of 40° C. 171 g of ethyl 1-(tert-butyloxycarbonyl) isonipecotate were obtained in the form of a brown oil.

Mass spectrum: DCI m/z=275 MNH$_4$$^+$ base peak m/z= 258 MH$^+$ 2-(2-Bromoethylsulfanyl)thiophene may be prepared according to Sadykhov, K. I., Aliev, S. M. and Seidov, M. M. *Khim. Geterotsikl. Soedin,* 3, 344–5 (1975).

4-Bromo-3-chloro-6-methoxyquinoline.

A mixture of 20 g of 3-chloro-4-hydroxy-6-methoxyquinoline in 1000 cm$^3$ of acetonitrile, to which was added 80.8 g of triphenylphosphine bromide, was stirred for 2 hours 30 minutes at a temperature in the region of 85° C. The solution obtained was cooled to the region of 20° C. and then stirred for 16 hours at this same temperature. The reaction mixture was concentrated under reduced pressure (5 kPa) at a temperature in the region of 40° C. and the evaporation residue was then taken up in 200 cm$^3$ of saturated aqueous sodium hydrogen carbonate solution and 200 cm$^3$ of ethyl acetate.

The organic phase was separated out after settling has taken place and was washed with twice 200 cm$^3$ of distilled water. The aqueous phase was extracted once more with ethyl acetate and the organic extracts were then combined, dried over magnesium sulfate, filtered and concentrated under reduced pressure (5 kPa) at a temperature in the region of 40° C. A product was obtained, which was purified by chromatography under a nitrogen pressure of 100 kPa, on a column of silica gel (diameter 7.5 cm; mass of silica 700 g), eluting with a mixture of cyclohexane/ethyl acetate (70/30 by volume). The fractions corresponding to the expected product were collected.

These fractions were combined and then concentrated under the same conditions as above. 20.7 g of 4-bromo-3-chloro-6-methoxyquinoline were obtained in the form of a white solid melting at 108° C.

Mass spectrum: EI m/z=271 M$^{+\cdot}$ base peak m/z=256 (M-CH$_3$)$^+$ m/z=228 (m/z=256-CO)$^+$ m/z=149 (m/z=228-Br)$^{+\cdot}$ m/z=114(m/z=149-Cl)$^{+\cdot}$ 3-Chloro-4-hydroxy-6-methoxyquinoline.

14.26 g of N-chlorosuccinimide were added, at a temperature in the region of 20° C. and with stirring, to a mixture of 17 g of 4-hydroxy-6-methoxyquinoline in 700 cm$^3$ of acetic acid and the mixture was then heated at a temperature of between 50 and 70° C. for 4 hours. The solution obtained was subsequently cooled to about 20° C. and then concentrated to dryness under reduced pressure (5 kPa) at a temperature in the region of 40° C.

The solid residue was taken up in 250 cm$^3$ of saturated aqueous sodium hydrogen carbonate solution. The mixture was stirred for 1 hour. The insoluble material was filtered off and washed with 3 times 250 cm$^3$ of water. The crystals obtained were dried under reduced pressure (10 Pa) for 3 hours at a temperature in the region of 20° C. 20 g of 3-chloro-4-hydroxy-6-methoxyquinoline were obtained in the form of a yellow solid.

Mass spectrum: EI m/z=209 M$^{+\cdot}$ base peak m/z=194 (M-CH$_3$)$^+$ m/z=166 (m/z=194-CO)$^+$.

4-Hydroxy-6-methoxyquinoline.

A suspension of 53.5 g of 4-hydroxy-6-methoxyquinoline-3-carboxylic acid in 1000 cm$^3$ of diphenyl ether was heated with stirring, at a temperature of between 250° C. and 260° C., for 2 hours 45 minutes. The reaction mixture was cooled to about 20° C. After stirring for 16 hours at this temperature, the mixture was poured with stirring into 1 liter of pentane and then filtered. The cake obtained was washed with 3 times 100 cm$^3$ of pentane and then with 3 times 100 cm$^3$ of diisopropyl ether. After drying in air, 37 g of 4-hydroxy-6-methoxyquinoline were obtained in the form of a beige-colored solid.

Mass spectrum: DCI m/z=176 MH$^+$ base peak 4-Hydroxy-6-methoxyquinoline-3-carboxylic acid can be prepared according to B. R. Baker and Ray R. Bramhall, *J. Med. Chem.* 15, 230 (1972).

EXAMPLE 2

4-[3-(3-Chloro-6-methoxyquinolin-4-yl)propyl]-1-[2-(3, 5-difluorophenoxy)ethyl]piperidine-4-carboxylic Acid.

A mixture of 0.7 g of benzyl 4-[3-(3-chloro-6-methoxyquinolin-4-yl)propyl]-1-[2-(3,5-difluorophenoxy)-ethyl]piperidine-4-carboxylate in 10 cm$^3$ of aqueous 5M hydrochloric acid was stirred for 5 hours at a temperature in the region of 100° C. After cooling to about 20° C., the reaction mixture was concentrated to dryness under reduced pressure (5 kPa) at a temperature in the region of 40° C. The residue obtained was purified by chromatography under a nitrogen pressure of 100 kPa, on a column of silica gel (particle size 40–63µ; diameter 2.5 cm; height 35 cm), eluting with a mixture of dichloromethane/methanol/28% aqueous ammonia (89/10/1 by volume) and collecting 25-cm$^3$ fractions. Fractions 16 to 25 were collected.

These fractions were combined and then concentrated under the above conditions. The evaporation residue obtained was slurried in 10 cm$^3$ of diisopropyl ether. The resulting crystalline product was filtered off, washed with twice 5 cm$^3$ of the same solvent and air-dried. 0.37 g of 4-[3-(3-chloro-6-methoxyquinolin-4-yl)propyl]-1-[2-(3,5-difluorophenoxy)ethyl]piperidine-4-carboxylic acid was obtained in the form of a white solid melting at 204° C.

$^1$H NMR spectrum (300 MHz, (CD$_3$)$_2$SO-d$_6$, δ in ppm) from 1.20 to 2.15 (mt: 10H); 2,62 (t, J=5.5 Hz; 2H); from 2.65 to 2.80 (mt: 2H); 3.18 (mt: 2H); 3.96 (s: 3H); 4.08 (t, J=5.5 Hz: 2H); from 6.60 to 6.85 (mt: 3H); 7.38 (d, J=2.5 Hz: 1H); 7.46 (dd, J=9 and 2.5 Hz: 1H); 7.97 (d, J=9 Hz: 1H); 8.68 (s: 1H)

Benzyl 4-[3-(3-chloro-6-methoxyquinolin-4-yl)propyl]-1-[2-(3,5-difluorophenoxy)ethyl]piperidine-4-carboxylate.

A suspension composed of 1.36 g of benzyl 4-[3-(3-chloro-6-methoxyquinolin-4-yl)propyl]piperidine-4-carboxylate, 0.95 g of 1-(2-bromoethoxy)-3,5-difluorobenzene (90% pure) and 0.5 g of potassium carbonate in 45 cm³ of acetonitrile was heated at a temperature in the region of 80° C. for 16 hours, with stirring and under an inert atmosphere. After cooling to a temperature in the region of 20° C., the reaction mixture was filtered and the insoluble material was washed with acetonitrile. The filtrate and the washing waters were combined and concentrated under reduced pressure (5 kPa) at a temperature in the region of 40° C.

The evaporation residue was purified by chromatography under a nitrogen pressure of 100 kPa, on a column of silica gel (particle size 40–63μ; diameter 3.5 cm; height 45 cm), eluting with a mixture of dichloromethane/methanol (97/3 by volume) and collecting 40-cm³ fractions. Fractions 18 to 23 were collected. These fractions were combined and then concentrated to dryness under reduced pressure (5 kPa) at a temperature in the region of 40° C. 1.56 g of benzyl 4-[3-(3-chloro-6-methoxyquinolin-4-yl)propyl]-1-[2-(3,5-difluorophenoxy)ethyl]piperidine-4-carboxylate were obtained in the form of an orange-colored oil.

Infra-red spectrum (CH₂Cl₂): 2955; 1723; 1622; 1599; 1229; 1153; 1116 and 843 cm⁻¹.

Benzyl 4-[3-(3-chloro-6-methoxyquinolin-4-yl)propyl]piperidine-4-carboxylate were prepared as described in Example 1.

EXAMPLE 3

4-[3-(3-Chloro-6-methoxyquinolin-4-yl)propyl]-1-(2-cyclohexylethyl)piperidine-4-carboxylic Acid.

A mixture of 0.6 g of benzyl 4-[3-(3-chloro-6-methoxyquinolin-4-yl)propyl]-1-(2-cyclohexylethyl)piperidine-4-carboxylate in 9.6 cm³ of aqueous 5M hydrochloric acid was heated at a temperature in the region of 100° C. with stirring for 5 hours.

The solution obtained was concentrated under reduced pressure (5 kPa) at a temperature in the region of 40° C. The evaporation residue obtained was slurried in diisopropyl ether. The resulting crystalline product was filtered off, washed with the same solvent and oven-dried at a temperature in the region of 60° C., under reduced pressure (10 Pa). A solid was obtained, which was purified by chromatography under a nitrogen pressure of 100 kPa, on a column of silica gel (particle size 40–63μ; diameter 2.5 cm; height 40 cm), eluting with a mixture of dichloromethane/methanol/32% aqueous ammonia (89/10/1 by volume), and collecting 25-cm³ fractions. Fractions 16 to 25 were combined and then concentrated under reduced pressure (5 kPa) at a temperature in the region of 40° C. A crystalline product was obtained, which was stirred in 5 cm³ of diisopropyl ether. The product obtained was filtered off, washed with the same solvent and air-dried. 0.33 g of 4-[3-(3-chloro-6-methoxyquinolin-4-yl)propyl]-1-(2-cyclohexylethyl)piperidine-4-carboxylic acid was obtained in the form of a white solid melting at 234° C.

¹H NMR spectrum (300 MHz, CD₃OD-d₄, δ in ppm) from 0.95 to 2.20–2.42-from 2.90 to 3.15 and from 3.30 to 3.50 (respectively, mt, broad d, J=13.5 Hz, mt and mt: 29H in total); 4.11 (s: 3H); 7.52 (mt: 2H); 8.02 (broad d, J=9 Hz: 1H); 8.68 (s: 1H).

Benzyl 4-[3-(3-chloro-6-methoxyquinolin-4-yl)propyl]-1-(2-cyclohexylethyl)piperidine-4-carboxylate.

0.56 cm³ of 2-cyclohexylethyl bromide and 0.5 g of potassium carbonate were added, with stirring and under an inert atmosphere, at a temperature in the region of 20° C., to a solution of 1.36 g of benzyl 4-[3-(3-chloro-6-methoxyquinolin-4-yl)propyl]piperidine-4-carboxylate in 50 cm³ of acetonitrile. The suspension obtained was heated at about 80° C. for 16 hours and, after cooling to a temperature in the region of 20° C., the reaction mixture was filtered and concentrated to dryness under reduced pressure (5 kPa) at a temperature in the region of 40° C.

The residue obtained was purified by chromatography under a nitrogen pressure of 100 kPa, on a column of silica gel (particle size 40–63μ; diameter 3.5 cm; height 45 cm), eluting with a mixture of dichloromethane/methanol (97/3 by volume) and collecting 40-cm³ fractions. Fractions 22 to 30 were combined and concentrated to dryness under reduced pressure (5 kPa) at a temperature in the region of 40° C. 1.33 g of benzyl 4-[3-(3-chloro-6-methoxyquinolin-4-yl)propyl]-1-(2-cyclohexylethyl)piperidine-4-carboxylate were obtained in the form of an orange-colored oil.

Infra-red spectrum (CCl₄): 2925; 1727; 1622; 1503; 1230; 1116; 833 and 697 cm⁻¹.

Benzyl 4-[3-(3-chloro-6-methoxyquinolin-4-yl)-propyl]piperidine-4-carboxylate was prepared as described in Example 1.

EXAMPLE 4

4-[3-(3-Chloro-6-methoxyquinolin-4-yl)propyl]-1-(3-phenylpropyl)piperidine-4-carboxylic Acid Dihydrochloride.

0.5 g of benzyl 4-[3-(3-chloro-6-methoxyquinolin-4-yl)propyl]-1-(3-phenylpropyl)-piperidine-4-carboxylate in 8 cm³ of 5M hydrochloric acid was heated at a temperature in the region of 100° C., with stirring, for 5 hours. After cooling to about 20° C., the reaction mass was concentrated under reduced pressure (5 kPa) at a temperature in the region of 40° C.

The evaporation residue obtained was taken up in 6 cm³ of a mixture of dichloromethane/methanol (90/10 by volume) and the mixture was again concentrated to dryness under the above conditions. A foam was obtained, which was slurried in 5 cm³ of diisopropyl ether. The crystalline product formed was filtered off, washed with three times 5 cm³ of the same solvent and dried in an oven under reduced pressure (10 Pa) at a temperature in the region of 50° C. 0.46 g of 4-[3-(3-chloro-6-methoxyquinolin-4-yl)propyl]-1-(3-phenylpropyl)piperidine-4-carboxylic acid dihydrochloride was obtained in the form of a beige-colored solid.

1H NMR spectrum (300 MHz, (CD₃)₂SO-d₆, δ in ppm) from 1.40 to 2.25 and from 2.50 to 3.60 (mts: 20H in total); 3.96 (s: 3H); from 7.10 to 7.45 (mt: 5H); 7.39 (d, J=2.5 Hz: 1H); 7.47 (dd, J=9 and 2.5 Hz: 1H); 7.98 (d, J=9 Hz: 1H); 8.70 (s: 1H); 10.25 (broad multiplet: 1H).

Benzyl 4-[3-(3-chloro-6-methoxyquinolin-4-yl)propyl]-1-(3-phenylpropyl)piperidine-4-carboxylate.

A mixture composed of 1.36 g of benzyl 4-[3-(3-chloro-6-methoxyquinolin-4-yl)propyl]piperidine-4-carboxylate, 0.55 cm³ of 1-bromo-3-phenylpropane and 0.5 g of potassium carbonate in 45 cm³ of acetonitrile was heated with stirring and under an inert atmosphere for 16 hours at a temperature in the region of 80° C. After cooling, the reaction mixture was filtered and the insoluble material was then washed with acetonitrile. The filtrate was concentrated to dryness under reduced pressure (5 kPa) at a temperature in the region of 40° C.

An oil was obtained, which was purified by chromatography under a nitrogen pressure of 100 kPa, on a column of silica gel (particle size 40–63μ; diameter 3.5 cm; height 30 cm), eluting with a mixture of dichloromethane/methanol (97/3 by volume) and collecting 40-cm³ fractions. Fractions 21 to 25 were combined and then concentrated as above. 21 g of benzyl 4-[3-(3-chloro-6-methoxyquinolin-4-yl)propyl]-1-(3-phenylpropyl)piperidine-4-carboxylate were obtained in the form of an orange-colored viscous oil.

Infra-red spectrum (CH$_2$Cl$_2$): 2948; 2812; 1722; 1622; 1504; 1229; 1118; 1029 and 834 cm$^{-1}$.

Benzyl 4-[3-(3-chloro-6-methoxyquinolin-4-yl)propyl]piperidine-4-carboxylate was prepared as described in Example 1.

EXAMPLE 5

4-[3-(3-Chloro-6-methoxyquinolin-4-yl)propyl]-1-[2-(pyrid-2-yl)thioethyl]piperidine-4-carboxylic Acid Trihydrochloride.

A mixture of 0.4 g of ethyl 4-[3-(3-chloro-6-methoxyquinolin-4-yl)propyl]-1-[2-(pyrid-2-yl)thio-ethyl]piperidine-4-carboxylate in 7 cm$^3$ of aqueous 5M hydrochloric acid was maintained at a temperature in the region of 100° C., with stirring and under an inert atmosphere, for 4 hours. After cooling to about 20° C., the reaction mixture was concentrated to dryness under reduced pressure (5 kPa) at a temperature in the region of 40° C.

The residue obtained was taken up in 10 cm$^3$ of a mixture of dichloromethane/methanol (90/10 by volume). The mixture was concentrated to dryness under the above conditions. 0.45 g of 4-[3-(3-chloro-6-methoxyquinolin-4-yl)propyl]-1-[2-(pyrid-2-yl)thioethyl]piperidine-4-carboxylic acid trihydrochloride was obtained in the form of a foam melting with decomposition at 132° C.

$^1$H NMR spectrum (300 MHz, (CD$_3$)$_2$SO-d$_6$, δ in ppm) 1.59 (mt: 2H); from 1.65 to 1.95 (mt: 4H); 2.20 (broad d, J=13.5 Hz: 2H); 2.86 (mt: 2H); from 3.10 to 3.65 (mt: 8H); 3.99 (s: 3H); 7.19 (broad dd, J=7,5 and 4.5 Hz: 1H); from 7.35 to 7.50 (mt: 2H); 7.50 (dd, J=9 and 3 Hz: 1H); 7.71 (resolved t, J=7,5 and 1.5 Hz: 1H); 8.01 (d, J=9 Hz: 1H); 8.48 (broad d, J=4.5 Hz: 1H); 8.74 (s: 1H); 10.70 (multiplet: 1H).

Ethyl 4-[3-(3-chloro-6-methoxyquinolin-4-yl)propyl]-1-[2-(2-pyrid-2-yl)thioethyl]piperidine-4-carboxylate.

Ethyl 4-[3-(3-chloro-6-methoxyquinolin-4-yl)-propyl]-1-[2-(2-pyrid-2-yl)thioethyl]piperidine-4-carboxylate was prepared by analogy with the method described in Example 1, starting with ethyl 4-[3-(3-chloro-6-methoxyquinolin-4-yl)propyl]piperidine-4-carboxylate hydrochloride.

Infra-red spectrum (CCl$_4$): 2955; 1726; 1622; 1580; 1503; 1414; 1229; 1125; 1030 and 833 cm$^{-1}$.

Ethyl 4-[3-(3-chloro-6-methoxyquinolin-4-yl)propyl]piperidine-4-carboxylate Hydrochloride.

A mixture of 2.6 g of ethyl 4-[3-(3-chloro-6-methoxyquinolin-4-yl)propyl]-1-(tert-butyloxycarbonyl)-piperidine-4-carboxylate in 40 cm$^3$ of dioxane, to which was added 14 cm$^3$ of 4 N hydrochloric dioxane, was stirred for 16 hours at a temperature in the region of 20° C. The suspension obtained was diluted by addition of 100 cm$^3$ of diethyl ether, stirred at about 20° C. for 1 hour and then filtered. The cake was washed with twice 40 cm$^3$ of diethyl ether and then dried in a desiccator under reduced pressure (5 kPa). 1.9 g of ethyl 4-[3-(3-chloro-6-methoxyquinolin-4-yl)propyl]piperidine-4-carboxylate were obtained in the form of a white solid.

Infra-red spectrum (KBr): 2965; 2474; 1720; 1620; 1584; 1416; 1241; 1119; 1019; 872 and 743 cm$^{-1}$.

Ethyl 4-[3-(3-chloro-6-methoxyquinolin-4-yl)propyl]-1-(tert-butyloxycarbonyl)piperidine-4-carboxylate.

30 cm$^3$ of a 0.5M solution of 9-borabicyclo-[3.3.1]nonane in tetrahydrofuran were added to a solution of 2.96 g of ethyl 4-allyl-1-(tert-butyloxycarbonyl)piperidine-4-carboxylate in 30 cm$^3$ of tetrahydrofuran, stirred at a temperature in the region of −10° C. under an inert atmosphere, while keeping the temperature below 0° C. After the addition, the temperature of the mixture was brought to about 20° C. and the mixture was then stirred for a further 4 hours. 3.1 g of 4-bromo-3-chloro-6-methoxyquinoline were added, followed by 50 cm$^3$ of dioxane, 6.4 g of tribasic potassium phosphate and 0.22 g of diphenylphosphinoferrocene palladium chloride. The reaction mixture was heated at a temperature in the region of 50° C. for 16 hours. After cooling to a temperature in the region of 20° C., the mixture was filtered and the cake was then washed with 3 times 50 cm$^3$ of ethyl acetate. The filtrate was washed with 100 cm$^3$ of water and then with twice 50 cm$^3$ of saturated aqueous sodium chloride solution. The organic phase was dried over magnesium sulfate, filtered and concentrated under reduced pressure (5 kPa), at a temperature in the region of 40° C.

A brown oil was obtained, which was purified by chromatography, under a pressure of 50 kPa of nitrogen, on a column of silica gel (particle size 20–45μ; diameter 4.5 cm; height 42 cm), eluting with a mixture of cyclohexane/ethyl acetate (80/20 by volume). The fractions containing the expected product were collected. These fractions were combined and then concentrated under reduced pressure (5 kPa) at a temperature in the region of 40° C. 2.62 g of ethyl 4-[3-(3-chloro-6-methoxyquinolin-4-yl)propyl]-1-(tert-butyloxycarbonyl)piperidine-4-carboxylate were obtained in the form of a yellow oil.

Infra-red spectrum: (CH$_2$Cl$_2$): 1720; 1682; 1622; 1504; 1423; 1367; 1229; 1174; 1027 and 834 cm$^{-1}$.

Ethyl 4-allyl-1-(tert-butyloxycarbonyl)-piperidine-4-carboxylate was prepared as described in Example 1.

EXAMPLE 6

Sodium Salt of 4-[3-(3-chloro-6-methoxyquinolin-4-yl)propyl]-1-heptylpiperidine-4-carboxylic Acid.

A mixture of 0.48 g of benzyl 4-[3-(3-chloro-6-methoxyquinolin-4-yl)propyl]-1-heptylpiperidine-4-carboxylate in 7 cm$^3$ of aqueous 5 M hydrochloric acid was maintained at a temperature in the region of 100° C., with stirring and under an inert atmosphere, for 6 hours. After cooling to about 20° C., the reaction mixture was stirred for 24 hours and then evaporated under reduced pressure (5 kPa) at a temperature in the region of 40° C. The residue obtained was purified by chromatography under a nitrogen pressure of 100 kPa, on a column of silica gel (particle size 40–60μ; diameter 2.5 cm, height 35 cm), eluting with a mixture of dichloromethane/methanol/aqueous ammonia (84/15/1 by volume) and collecting 40-cm$^3$ fractions. Fractions 19 to 24 were combined and then concentrated as above. The solid obtained was stirred in 10 cm$^3$ of diisopropyl ether, filtered and washed with 3 times 5 cm$^3$ of diisopropyl ether. 0.35 g of the sodium salt of 4-[3-(3-chloro-6-methoxyquinolin-4-yl)propyl]-1-heptylpiperidine-4-carboxylic acid was obtained in the form of a solid melting at 223° C.

$^1$H NMR spectrum (300 MHz, (CD$_3$)$_2$SO-d$_6$, δ in ppm): 0.87 (t, J=7 Hz: 3H); from 1.10 to 1.45 (mt: 12H); from 1.45 to 1.70 (mt: 4H); from 1.85 to 2.05 (mt: 2H); 1.97 (broad d, J=10.5 Hz: 2H); 2.17 (broad t, J=7.5 Hz: 2H); from 2.45 to 2.60 (mt: 2H); 3.15 (mt: 2H); 3.97 (s: 3H); 7.40 (mt: 1H); 7.44 (dd, J=9 and 3 Hz: 1H); 7.95 (d, J=9 Hz: 1H); 8.66 (s: 1H).

Benzyl 4-[3-(3-chloro-6-methoxyquinolin-4-yl)propyl]-1-heptylpiperidine-4-carboxylate.

1.36 g of benzyl 4-[3-(3-chloro-6-methoxyquinolin-4-yl)propyl]piperidine-4-carboxylate and 0.5 g of potassium carbonate were added, at a temperature in the region of 20° C., with stirring and under an inert atmosphere, to a solution of 0.61 cm³ of 1-iodoheptane in 45 cm³ of acetonitrile. After heating for 18 hours at a temperature in the region of 80° C., a further 1.17 cm³ of 1-iodoheptane were added. After heating for 40 hours at a temperature in the region of 80° C., the reaction mixture was cooled to about 20° C., filtered and concentrated under reduced pressure (1 kPa) at a temperature in the region of 50° C.

The residue obtained was purified by chromatography under a nitrogen pressure of 100 kPa, on a column of silica gel (particle size 40–60μ; diameter 3.5 cm; height 35 cm), eluting with a mixture of dichloromethane/methanol (95/05 by volume) and collecting 35-cm³ fractions. Fractions 18 to 26 were combined and then concentrated as above. 0.36 g of benzyl 4-[3-(3-chloro-6-methoxyquinolin-4-yl)propyl]-1-heptylpiperidine-4-carboxylate was obtained.

Infra-red spectrum (CH$_2$Cl$_2$): 2957; 2931; 1722; 1622; 1504; 1229; 1159; 1118; 1028 and 834 cm¹.

Benzyl 4-[3-(3-chloro-6-methoxyquinolin-4-yl)propyl]piperidine-4-carboxylate was prepared as described in Example 1.

EXAMPLE 7

4-[3-(3-Chloro-6-methoxyquinolin-4-yl)propyl]-1-[2-(cyclopentylthio)ethyl]piperidine-4-carboxylic Acid Dihydrochloride.

A mixture of 0.55 g of ethyl 4-[3-(3-chloro-6-methoxyquinolin-4-yl)propyl]-1-[2-(cyclopentylthio)ethyl]-piperidine-4-carboxylate in 8 cm³ of aqueous 6 N hydrochloric acid was heated at a temperature in the region of 100° C., with stirring and under an inert atmosphere, for 5 hours. After stirring for 18 hours at a temperature in the region of 20° C., the solution obtained was concentrated under reduced pressure (5 kPa) at a temperature in the region of 40° C. The evaporation residue obtained was taken up in 10 cm³ of a mixture of dichloromethane/methanol (90/10 by volume) and then concentrated under the same conditions as above. 0.59 g of 4-[3-(3-chloro-6-methoxyquinolin-4-yl)propyl]-1-[2-(cyclopentylthio)ethyl]piperidine-4-carboxylic acid dihydrochloride was obtained in the form of a foam melting at 129° C. with softening.

¹H NMR spectrum: (300 MHz, (CD$_3$)$_2$SO-d$_6$, δ in ppm): from 1.30 to 2.10 (mt: 14H); 2.15 (broad d, J=13.5 Hz: 2H); from 2.65 to 3.00 (mt: 4H); from 3.05 to 3.40 (mt: 5H); 3.46 (broad d, J=12 Hz: 2H); 3.97 (s: 3H); 7.42 (d, J=2.5 Hz: 1H); 7.48 (dd, J=9 and 2.5 Hz: 1H); 7.99 (d, J=9 Hz: 1H); 8.72 (s: 1H); from 10.55 to 10.90 (multiplet: 1H).

Ethyl 4-[3-(3-chloro-6-methoxyquinolin-4-yl)propyl]-1-[2-(cyclopentylthio)ethyl]piperidine-4-carboxylate.

1.2 g of ethyl 4-[3-(3-chloro-6-methoxyquinolin-4-yl)propyl]piperidine-4-carboxylate, 0.51 g of potassium carbonate and 0.61 g of potassium iodide were added, at a temperature in the region of 20° C., with stirring and under an inert atmosphere, to a solution of 0.607 g of (2-chloroethylthio)cyclopentane in 50 cm³ of acetonitrile. After heating for 20 hours at a temperature in the region of 80° C., the reaction mixture was cooled to about 20° C., filtered and concentrated under reduced pressure (1 kPa) at a temperature in the region of 50° C. The residue obtained was purified by chromatography under a nitrogen pressure of 100 kPa, on a column of silica gel (particle size 40–60μ; diameter 3.5 cm), eluting with a mixture of dichloromethane/methanol (98/2 by volume) and collecting 35-cm³ fractions. Fractions 25 to 31 were combined and then concentrated as above. 0.9 g of ethyl 4-[3-(3-chloro-6-methoxyquinolin-4-yl)propyl]-1-[2-(cyclopentylthio)ethyl]piperidine-4-carboxylate was obtained.

Infra-red spectrum (CCl$_4$): 958; 1726; 1622; 1503; 1229; 1117; 1030 and 833 cm⁻¹.

Ethyl 4-[3-(3-chloro-6-methoxyquinolin-4-yl)propyl]piperidine-4-carboxylate was prepared as described in Example 5.

EXAMPLE 8

4-[3-(3-Chloro-6-methoxyquinolin-4-yl)propyl]-1-[2-(2-thien-2-yl)thioethyl]piperidine-4-acetic Acid.

Working in a manner analogous to that of the preceding examples, 4-[3-(3-chloro-6-methoxyquinolin-4-yl)propyl]-1-[2-(2-thien-2-yl)thioethyl]piperidine-4-acetic acid was prepared.

¹H NMR spectrum (300 MHz, (CD$_3$)$_2$SO-d$_6$, δ in ppm) from 1.30 to 1.70 (mt: 8H); 2.14 (s: 2H); 2.33 (mt: 4H); from 2.45 to 2.60 (mt: 2H); 2.92 (broad t, J=7 Hz: 2H); 3.13 (mt: 2H); 3.96 (s: 3H); 7.05 (dd, J=5.5 and 3.5 Hz: 1H); 7.18 (dd, J=3.5 and 1 Hz: 1H); 7.39 (d, J=3 Hz: 1H); 7.44 (dd, J=9 and 3 Hz: 1H); 7.60 (dd, J=5.5 and 1 Hz: 1H); 7.95 (d, J=9 Hz: 1H); 8.66 (s: 1H).

EXAMPLE 9

{4-[3-(3-Chloro-6-methoxyquinolin-4-yl)propyl]-1-[2-(cyclopentylthio)ethyl]piperidine-4-yl}methanol.

Working in a manner analogous to that of the preceding examples, {4-[3-(3-chloro-6-methoxyquinolin-4-yl)propyl]-1-[2-(cyclopentylthio)ethyl]piperidine-4-yl}methanol was prepared.

¹H NMR spectrum (300 MHz, (CD$_3$)$_2$SO-d$_6$, δ in ppm) from 1.15 to 1.75 (mt: 14H); 1.95 (mt: 2H); from 2.20 to 2.40 (mt: 4H); 2.44 (mt: 2H); 2.57 (mt: 2H); from 3.05 to 3.25 (mt: 5H); 3.97 (s: 3H); 4.38 (t, J=5.5 Hz: 1H); 7.38 (d, J=3 Hz: 1H); 7.45 (dd, J=9 and 3 Hz: 1H); 7.96 (d, J=9 Hz: 1H); 8.68 (s: 1H)

EXAMPLE 10

4-[3-(3-Chloro-6-methoxyquinolin-4-yl)propyl]-1-[(3-phenylpropyl)piperidine-4-yl]methanol.

Working in a manner analogous to that of the preceding examples, 4-[3-(3-chloro-6-methoxyquinolin-4-yl)propyl]-1-[(3-phenylpropyl)piperidine-4-yl]methanol was prepared.

¹H NMR spectrum (300 MHz, (CD$_3$)$_2$SO-d$_6$, δ in ppm) 1.59 (mt: 2H); from 1.65 to 1.95 (mt: 4H); 2.20 (broad d, J=13.5 Hz: 2H); 2.86 (mt: 2H); from 3.10 to 3.65 (mt: 8H); 3.99 (s: 3H); 7.19 (broad dd, J=7.5 and 4.5 Hz: 1H); from 7.35 to 7.50 (mt: 2H); 7.50 (dd, J=9 and 3 Hz: 1H); 7.71 (resolved t, J=7.5 and 1.5 Hz: 1H); 8.01 (d, J=9 Hz: 1H); 8.48 (broad d, J=4.5 Hz: 1H); 8.74 (s: 1H); 10.70 (multiplet: 1H).

EXAMPLE 11

4-[3-(3-Fluoro-6-methoxyquinolin-4-yl)propyl]-1-[2-(thien-2-yl)thioethyl]piperidine-4-carboxylic Acid A mixture of 0.4 g of ethyl 4-[3-(3-fluoro-6-methoxyquinolin-4-yl)propyl]-1-[2-(thien-2-yl)thioethyl]-piperidine-4-carboxylate in 5 cm³ of aqueous 5N hydrochloric acid and 3 cm³ of dioxane was maintained at a temperature in t h e region of 100° C. with stirring and under an inert atmosphere for 20 hours. After cooling to about 20° C., the reaction mixture was concentrated to dryness under reduced pressure (2 kPa) at a temperature in the region of 40° C. The mixture was filtered and then chromatographed, under atmospheric pressure, on a column of silica gel (particle size 40–63μ; diameter 1.5 cm; mass 55 g), eluting with a mixture of chloroform/methanol/aqueous ammonia (12/3/0.5 by volume) and collecting 15-cm³ fractions. Fractions 5 to 12 were combined and then concentrated to dryness under the above conditions. 0.26 g of 4-[3-(3-fluoro-6-methoxyquinolin-4-yl)propyl]-1-[2-(thien-2-yl)thioethyl] piperidine-4-carboxylic acid was obtained in the form of a white crystalline solid melting at 180° C.

$^1$H NMR Spectrum (300 MHz, $(CD_3)_2SO-d_6$, δ in ppm): 1.31 (very broad t), J=13 Hz: 2H); from 1.50 to 1.70 (mt: 4H); from 1.85 to 2.05 (mt: 4H); 2.45 (broad t, J=7 Hz: 2H); 2.60 (broad d, J=11 Hz: 2H); 2.91 (broad t, J=7 Hz: 2H); 3.04 (very broad t, J=6 Hz: 2H); 3.96 (s: 3H); 7.04 (dd, J=5 and 3.5 Hz: 1H); 7.17 (dd, J=3.5 and 1 Hz: 1H); 7.35 (d, J=2.5 Hz: 1H); 7.40 (dd, J=9 and 2.5 Hz: 1H); 7.60 (dd, J=5 and 1 Hz: 1H); 7.97 (d, J=9 Hz: 1H); 8.70 (broad s: 1H).

Ethyl 4-[3-(3-fluoro-6-methoxyquinolin-4-yl)propyl]-1-[2-(thien-2-yl)thioethyl]piperidine-4-carboxylate A mixture of 0.8 g of ethyl 4-[3-(3-fluoro-6-methoxyquinolin-4-yl)propyl]piperidine-4-carboxylate, 0.6 g of 2-(2-bromoethylthio)thiophene and 1.5 g of potassium carbonate in 10 cm³ of acetonitrile was heated for 18 hours at a temperature in the region of 80° C., with stirring and under an inert atmosphere. After cooling to a temperature in the region of 20° C., the reaction mixture was concentrated to dryness under reduced pressure (2 kPa) at a temperature in the region of 40° C.

The residue obtained was taken up in dichloromethane and water. The organic phase was washed with water and a saturated sodium chloride solution, dried over magnesium sulfate, filtered and concentrated to dryness under the above conditions. The residue was purified by chromatography under atmospheric pressure, on a column of silica gel (particle size 70–200μ; diameter 3 cm; mass 50 g), eluting with a mixture of ethyl acetate/petroleum ether (40–65° C.) (75/25 by volume) and collecting 30-cm³ fractions. Fractions 3 to 5 were combined and then concentrated to dryness under the above conditions. 0.7 g of ethyl 4-[3-(3-fluoro-6-methoxyquinolin-4-yl)propyl]-1-[2-(thien-2-yl)thioethyl] piperidine-4-carboxylate was obtained in the form of a thick colorless oil.

$^1$H NMR Spectrum (300 MHz, $(CD_3)_2SO-d_6$, δ in ppm) 0.99 (t, J=7 Hz: 3H); 1.34 (very broad t, J=12 Hz: 2H); from 1.45 to 1.65 (mt: 4H); from 1.85 to 2.00 (mt: 4H); 2.44 (broad t, J=7 Hz: 2H); 2.59 (broad d, J=11.5 Hz: 2H); 2.89 (broad t, J=7 Hz: 2H); 3.03 (very broad t, J=6.5 Hz: 2H); 3.94 (s: 3H); 3.96 (q, J=7 Hz: 2H); 7.02 (dd, J=5 and 3.5 Hz: 1H); 7.16 (dd, J=3.5 and 1 Hz: 1H); 7.32 (d, J=2.5 Hz: 1H); 7.39 (dd, J=9 and 2.5 Hz: 1H); 7.58 (dd, J=5 and 1 Hz: 1H); 7.96 (d, J=9 Hz: 1H); 8.69 (broad s: 1H).

Ethyl 4-[3-(3-fluoro-6-methoxyquinolin-4-yl)propyl] piperidine-4-carboxylate 2 cm³ of trifluoroacetic acid were added, with stirring and under an inert atmosphere, at a temperature in the region of 5° C., to a solution of 0.5 g of ethyl 4-[3-(3-fluoro-6-methoxyquinolin-4-yl)propyl]-1-(tert-butyloxycarbonyl) piperidine-4-carboxylate in 10 cm³ of dichloromethane. After 45 minutes, the reaction mixture was concentrated to dryness under reduced pressure (2 kPa) at a temperature in the region of 40° C.

The residue was taken up in diethyl ether and washed with a saturated potassium bicarbonate solution and then with a saturated potassium carbonate solution. The organic phase was washed with twice 5 cm³ of water and then with a saturated sodium chloride solution, dried over magnesium sulfate, filtered and then concentrated to dryness under reduced pressure (2 kPa) at a temperature in the region of 40° C. 0.26 g of ethyl 4-[3-(3-fluoro-6-methoxyquinolin-4-yl)propyl]piperidine-4-carboxylate was obtained in the form of a thick oil.

$^1$H NMR Spectrum (300 MHz, $(CD_3)_2SO-d_6$, δ in ppm): 1.02 (t, J=7 Hz: 3H); 1.28 (mt: 2H); from 1.45 to 1.70 (mt: 4H); 1.90 (broad d, J=13.5 Hz: 2H); 2.46 (broad t, J=12 Hz: 2H); 2.79 (d mt, J=12 Hz: 2H); 3.06 (broad t, J=6 Hz: 2H); 3.95 (s: 3H); 3.98 (q, J=7 Hz: 2H); 7.35 (d, J=2.5 Hz: 1H); 7.40 (dd, J=9 and 2.5 Hz: 1H); 7.97 (d, J=9 Hz: 1H); 8.70 (d, J=1 Hz: 1H).

Ethyl 4-[3-(3-fluoro-6-methoxyquinolin-4-yl)propyl]-1-(tert-butyloxycarbonyl)piperidine-4-carboxylate 1.4 g of ethyl 4-allyl-1-(tert-butyloxy-carbonyl) piperidine-4-carboxylate were cooled to a temperature in the region of −30° C. and 11 cm³ of a 0.5 M solution of 9-borabicyclo[3.3.1]nonane in tetrahydrofuran were added, with stirring and under an inert atmosphere. After the addition, the temperature of the mixture was returned to about 20° C.

The solution obtained was stirred for a further 4 hours, followed by addition of 0.09 g of palladium diphenylphosphinoferrocene chloride, 1.4 g of 4-iodo-3-fluoro-6-methoxyquinoline and 2.5 g of tribasic potassium phosphate. After stirring for 16 hours at a temperature in the region of 60° C., the reaction mixture was cooled to about 20° C. and then concentrated to dryness under reduced pressure (2 kPa) at a temperature in the region of 40° C. The residue obtained was taken up in ethyl acetate and water, the phases were separated by settling and the organic phase was dried over magnesium sulfate, filtered and concentrated to dryness under reduced pressure (2 kPa) at a temperature in the region of 40° C.

The residue obtained was purified by chromatography, under atmospheric pressure, on a column of silica gel (particle size 70–200μ; diameter 4.5 cm; mass 125 g), eluting with a mixture of dichloromethane/ethyl acetate (98/2 by volume), and collecting 20-cm³ fractions. Fractions 98 to 170 were combined and then concentrated to dryness under the above conditions. 1.5 g of ethyl 4-[3-(3-fluoro-6-methoxyquinolin-4-yl)propyl]-1-(tert-butyloxycarbonyl) piperidine-4-carboxylate were obtained in the form of a thick brown oil.

$^1$H NMR Spectrum (300 MHz, $(CD_3)_2SO-d_6$, δ in ppm): 1.02 (t, J=7 Hz: 3H); 1.30 (mt: 2H); 1.39 (s: 9H); from 1.45 to 1.70 (mt: 4H); 1.92 (broad d, J=13.5 Hz: 2H); 2.81 (mt: 2H); 3.05 (broad t, J=6.5 Hz: 2H); 3.69 (broad d, J=13.5 Hz: 2H); 3.95 (s: 3H); 4.00 (q, J=7 Hz: 2H); 7.34 (d, J=2.5 Hz: 1H); 7.40 (dd, J=9 and 2.5 Hz: 1H); 7.97 (d, J=9 Hz: 1H); 8.70 (d, J=1 Hz: 1H).

4-Iodo-3-fluoro-6-methoxyquinoline 1.8 cm³ of diisopropylamine in 80 cm³ of tetrahydrofuran were cooled to a temperature in the region of −75° C. and 7.7 cm³ of a 1.6 M solution of butyl lithium in hexane were added, with stirring and under an inert atmosphere. After stirring for 20 minutes at a temperature in the region of −75° C., a solution of 2.2 g of 3-fluoro-6-methoxyquinoline in 20 cm³ of tetrahydrofuran was added. The solution obtained was stirred for a further 4 hours, followed by addition of a solution of 3.3 g of double-sublimated iodine in 10 cm³ of tetrahydrofuran. After stirring for 2 hours at a temperature in the region of 20° C., the reaction mixture was hydrolyzed with 200 cm³ of a 90/10 tetrahydrofuran/water mixture and then 100 cm³ of a saturated sodium chloride solution and 150 cm³ of ethyl acetate. The mixture was washed with 3 times 80 cm³ of a saturated sodium chloride solution, dried over magnesium sulfate, filtered and concentrated to dryness under reduced pressure (2 kPa) at a temperature in the region of 40° C.

The residue obtained was purified by chromatography, under atmospheric pressure, on a column of silica gel (particle size 70–200µ; diameter 5 cm; height 35 cm), eluting with a mixture of 90/10 petroleum ether/ethyl acetate. Fractions 66 to 95 were combined and then concentrated to dryness under reduced pressure (5 kPa) at a temperature in the region of 40° C. 0.9 g of 4-iodo-3-fluoro-6-methoxyquinoline was obtained in the form of a cream-colored solid.

$^1$H NMR Spectrum (300 MHz, $(CD_3)_2SO$-$d_6$, δ in ppm) 4.00 (s: 3H); 7.31 (d, J=2.5 Hz: 1H); 7.47 (dd, J=9 and 2.5 Hz: 1H); 8.01 (d, J=9 Hz: 1H); 8.64 (s: 1H).

3-Fluoro-6-methoxyquinoline

A mixture of 1.35 g of 4-chloro-3-fluoro-6-methoxyquinoline, 1.1 cm³ of triethylamine and 100 mg of palladium-on-charcoal in 23 cm³ of methanol was stirred at a temperature in the region of 20° C. under a pressure of 2 bar of hydrogen for 18 hours. The reaction mixture was filtered and then concentrated to dryness under reduced pressure (2 kPa) at a temperature in the region of 40° C.

The residue obtained was purified by chromatography under atmospheric pressure, on a column of silica gel (particle size 70–200µ; diameter 3 cm; mass 40 g), eluting with dichloromethane/ethyl acetate (95/5 by volume). The fractions containing the product were combined and then concentrated to dryness according to the above conditions. 1 g of 3-fluoro-6-methoxyquinoline was obtained.

$^1$H NMR Spectrum (300 MHz, $(CD_3)_2SO$-$d_6$, δ in ppm) 3.92 (s: 3H); 7.40 (mt: 2H); 8.07 (d, J=9 Hz: 1H); 8.04 (dd, J=10 and 3 Hz: 1H); 8.77 (d, J=3 Hz: 1H).

4-Chloro-3-fluoro-6-methoxyquinoline 1.3 cm³ of diisopropylamine in 50 cm³ of tetrahydrofuran were cooled to a temperature in the region of −75° C. and 5.8 cm³ of a 1.6 M solution of butyl lithium in hexane were added, with stirring and under an inert atmosphere. After stirring for 20 minutes at a temperature in the region of −75° C., a solution of 1.2 g of 4-chloro-6-methoxyquinoline in 20 cm³ of tetrahydrofuran was added. The solution obtained was stirred for a further 4 hours, followed by addition of a solution of 2.9 g of N-fluorobenzene sulfonimide in 10 cm³ of tetrahydrofuran. After stirring for 2 hours at a temperature in the region of 20° C., the reaction mixture was hydrolyzed with 200 cm³ of a 90/10 tetrahydrofuran/water mixture and then 100 cm³ of a saturated sodium chloride solution and 150 cm³ of ethyl acetate. The mixture was washed with 3 times 80 cm³ of a saturated sodium chloride solution, dried over magnesium sulfate, filtered and concentrated to dryness under reduced pressure (2 kPa) at a temperature in the region of 40° C.

The residue obtained was purified by chromatography, under atmospheric pressure, on a column of silica gel (particle size 70–200µ; diameter 4 cm; mass 100 g), eluting with dichloromethane. The fractions containing the product were combined and then concentrated to dryness under reduced pressure (5 kPa) at a temperature in the region of 40° C. 0.4 g of 4-chloro-3-fluoro-6-methoxyquinoline was obtained.

$^1$H NMR Spectrum (300 MHz, $(CD_3)_2SO$-$d_6$, δ in ppm) 4.01 (s: 3H); 7.43 (d, J=2.5 Hz: 1H); 7.52 (dd, J=9 and 2.5 Hz: 1H); 8.07 (d, J=9 Hz: 1H); 8.91 (d, J=1 Hz: 1H).

4-Chloro-6-methoxyquinoline

A mixture of 12 g of 4-hydroxy-6-methoxyquinoline in 50 cm³ of phosphorus oxychloride was maintained at a temperature in the region of 100° C., with stirring and under an inert atmosphere, for 2 hours. After cooling to about 20° C., the reaction mixture was concentrated to dryness under reduced pressure (2 kPa) at a temperature in the region of 40° C. and then hydrolyzed with ice and brought to pH=10 using a 5 N sodium hydroxide solution. The mixture was extracted with ethyl acetate, dried over magnesium sulfate, filtered and concentrated to dryness under reduced pressure (2 kPa) at a temperature in the region of 40° C.

The residue obtained was chromatographed, under atmospheric pressure, on a column of silica gel (particle size 70–200µ), eluting with a mixture of dichloromethane/methanol (85/15 by volume). The fractions containing the product were combined and then concentrated to dryness according to the above conditions. 12 g of 4-chloro-6-methoxyquinoline were obtained in the form of a white solid melting at 82° C.

$^1$H NMR Spectrum (300 MHz, $(CD_3)_2SO$-$d_6$, δ in ppm) 3.958 (s: 3H); 7.45 (d, J=2.5 Hz: 1H); 7.53 (dd, J=9 and 2.5 Hz: 1H); 7.76 (d, J=4.5 Hz: 1H); 8.04 (d, J=9 Hz: 1H); 8.70 (d, J=4.5 Hz: 1H).

The ethyl 4-allyl-1-(tert-butyloxycarbonyl)-piperidine-4-carboxylate was prepared as described in Example 1.

The 4-hydroxy-6-methoxyquinoline was prepared as described in Example 1.

EXAMPLE 12

4-[3-(3-Fluoro-6-methoxyquinolin-4-yl)propyl]-1-[2-(3,5-difluoro-6-phenoxy)ethyl]piperidine-4-carboxylic Acid A mixture of 0.4 g of ethyl 4-[3-(3-fluoro-6-methoxyquinolin-4-yl)propyl]-1-[2-(3,5-difluoro-6-phenoxy)ethyl]piperidine-4-carboxylate in 6 cm³ of aqueous 5N hydrochloric acid and 10 cm³ of dioxane was maintained at a temperature in the region of 100° C., with stirring and under an inert atmosphere, for 20 hours. After cooling to about 20° C., the reaction mixture was concentrated to dryness under reduced pressure (2 kPa) at a temperature in the region of 40° C.

The residue obtained was chromatographed, at atmospheric pressure, on a column of silica gel (particle size 70–200µ; diameter 1.5 cm; mass 50 g), eluting with a mixture of chloroform/methanol/aqueous ammonia (12/3/0.5 by volume) and collecting 15-cm³ fractions. Fractions 10 to 15 were combined and then concentrated to dryness according to the above conditions. 0.2 g of 4-[3-(3-Fluoro-6-methoxyquinolin-4-yl)propyl]-1-[2-(3,5-difluoro-6-phenoxy)ethyl]piperidine-4-carboxylic acid was obtained in the form of a white solid melting at 175° C.

$^1$H NMR Spectrum (300 MHz, $(CD_3)_2SO$-$d_6$, δ in ppm): 1.33 (very broad t, J=13 Hz: 2H); from 1.50 to 1.70 (mt: 4H); 1.95 (broad d, J=13 Hz: 2H); 2.05 (broad t, J=11.5 Hz: 2H); 2.60 (t, J=6 Hz: 2H); 2.69 (broad d, J=11.5 Hz: 2H); 3.04 (mt: 2H); 3.96 (s: 3H); 4.06 (t, J=6 Hz: 2H); from 6.65 to 6.85 (mt: 3H); 7.34 (d, J=2.5 Hz: 1H); 7.39 (dd, J=9 and 2.5 Hz: 1H); 7.96 (d, J=9 Hz: 1H); 8.69 (broad s: 1H).

Ethyl 4-[3-(3-fluoro-6-methoxyquinolin-4-yl)propyl]-1-[2-(3,5-difluoro-6-phenoxy)ethyl]piperidine-4-carboxylate A mixture of 0.4 g of ethyl 4-[3-(3-fluoro-6-methoxyquinolin-4-yl)propyl]piperidine-4-carboxylate, 0.3 g of 1-(2-bromoethoxy)-3,5-difluorobenzene, 0.18 g of potassium iodide and 0.74 g of potassium carbonate in 10 cm³ of acetonitrile was heated for 18 hours at a temperature in the region of 75° C., with stirring and under an inert atmosphere. After cooling to a temperature in the region of 20° C., the reaction mixture was concentrated to dryness under reduced pressure (5 kPa) at a temperature in the region of 40° C.

The residue obtained was taken up in ethyl acetate and water. The organic phase was washed with water and a saturated sodium chloride solution, dried over magnesium sulfate, filtered and concentrated to dryness under the above conditions. The residue was purified by chromatography, under atmospheric pressure, on a column of silica gel (particle size 70–200μ; diameter 1.5 cm; mass 35 g), eluting with dichloromethane. Fractions 7 to 11 were combined and then concentrated to dryness according to the above conditions. 0.4 g of ethyl 4-[3-(3-fluoro-6-methoxyquinolin-4-yl) propyl]-1-[2-(3,5-difluoro-6-phenoxy)ethyl]piperidine-4-carboxylate was obtained in the form of a thick colorless oil.

$^1$H NMR Spectrum (300 MHz, $(CD_3)_2SO$-$d_6$, δ in ppm): 1.00 (t, J=7 Hz: 3H); 1.38 (very broad t, J=12 Hz: 2H); from 1.45 to 1.70 (mt: 4H); from 1.90 to 2.10 (mt: 4H); 2.60 (t, J=6 Hz: 2H); 2.69 (very broad d, J=12 Hz: 2H); 3.05 (very broad t, J=6.5 Hz: 2H); 3.95 (s: 3H); 3.98 (q, J=7 Hz: 2H); 4.06 (t, J=6 Hz: 2H); from 6.65 to 6.85 (mt: 3H); 7.34 (d, J=2.5 Hz: 1H); 7.40 (dd, J=9 and 2.5 Hz: 1H); 7.97 (d, J=9 Hz: 1H); 8.70 (broad s: 1H).

The ethyl 4-allyl-1-(tert-butyloxycarbonyl)-piperidine-4-carboxylate was prepared as described in Example 1.

The 1-(2-bromoethoxy)-3,5-difluorobenzene may be obtained by applying the method described in Example 16.

EXAMPLE 13

4-[3-(3-Chloro-6-methoxyquinolin-4-yl)propyl]-1-[2-(2,3,5-trifluoro-6-phenoxy)ethyl]piperidine-4-carboxylic Acid Dihydrochloride A mixture of 1 g of benzyl 4-[3-(3-chloro-6-methoxyquinolin-4-yl)propyl]-1-[2-(2,3,5-trifluoro-6-phenoxy)ethyl]piperidine-4-carboxylate in 50 cm$^3$ of aqueous 5N hydrochloric acid was maintained at a temperature in the region of 100° C. with stirring for 20 hours. After cooling to about 20° C., the reaction mixture was concentrated to dryness under reduced pressure (2 kPa) at a temperature in the region of 40° C.

The residue obtained was taken up in 50 cm$^3$ of acetone, filtered, washed with 3 times 15 cm$^3$ of [lacuna]and then dried in a desiccator under reduced pressure (0.1 kPa) at a temperature in the region of 40° C. 0.88 g of 4-[3-(3-chloro-6-methoxyquinolin-4-yl)propyl]-1-[2-(2,3,5-trifluoro-6-phenoxy)ethyl]piperidine-4-carboxylic acid dihydrochloride was obtained in the form of a white solid melting at 170° C.

$^1$H NMR Spectrum (300 MHz, $(CD_3)_2SO$-$d_6$, δ in ppm) from 1.45 to 2.30 (mt: 8H); from 2.85 to 3.70 (mt: 8H); 3.97 (s: 3H); 4.50 (mt: 2H); 7.15 (mt: 2H); 7.40 (d, J=3 Hz: 1H); 7.46 (dd, J=9 and 3 Hz: 1H); 7.97 (d, J=9 Hz: 1H); 8.69 (s: 1H); 10.07 (unresolved peak: 1H); from 12.50 to 13.10 (broad unresolved peak: 1H).

Benzyl 4-[3-(3-chloro-6-methoxyquinolin-4-yl)propyl]-1-[2-(2,3,5-trifluoro-6-phenoxy)ethyl]piperidine-4-carboxylate A mixture of 1.4 g of benzyl 4-[3-(3-chloro-6-methoxyquinolin-4-yl)propyl]piperidine-4-carboxylate hydrochloride, 0.9 g of 1-(2-bromoethoxy)-2,3,5-trifluorobenzene, 0.6 g of potassium iodide and 2 g of potassium carbonate in 100 cm$^3$ of acetonitrile was heated for 18 hours at a temperature in the region of 75° C. with stirring and under an inert atmosphere. After cooling to a temperature in the region of 20° C., the reaction mixture was filtered and washed with 3 times 30 cm$^3$ of acetonitrile. The filtrate was concentrated to dryness under reduced pressure (2 kPa) at a temperature in the region of 40° C. The residue obtained was purified by chromatography under atmospheric pressure, on a column of silica gel (particle size 20–45μ; diameter 3 cm; height: 27 cm), eluting with ethyl acetate and collecting 50-cm$^3$ fractions. Fractions 9 to 23 were combined and then concentrated to dryness according to the above conditions. 1.27 g of benzyl 4-[3-(3-chloro-6-methoxyquinolin-4-yl)propyl]-1-[2-(2,3,5-trifluoro-6-phenoxy)ethyl]piperidine-4-carboxylate were obtained in the form of a thick yellow oil.

$^1$H NMR Spectrum (300 MHz, $(CD_3)_2SO$-$d_6$, δ in ppm) from 1.30 to 1.60 (mt: 4H); 1.72 (mt: 2H); from 1.95 to 2.15 (mt: 4H); 2.64 (t, J=5.5 Hz: 2H); 2.71 (DMF, J=12 Hz: 2H); 3.13 (broad t, J=7.5 Hz: 2H); 3.93 (s: 3H); 4.16 (t, J=5.5 Hz: 2H); 5.04 (s: 2H); from 6.95 to 7.15 (mt: 2H); from 7.20 to 7.30 (mt: 5H); 7.34 (d, J=3 Hz: 1H); 7.45 (dd, J=9 and 3 Hz: 1H); 7.97 (d, J=9 Hz: 1H); 8.67 (s: 1H).

Benzyl 4-[3-(3-chloro-6-methoxyquinolin-4-yl)propyl] piperidine-4-carboxylate Hydrochloride A mixture of 17.4 g of benzyl 1-tert-butyloxycarbonyl-4-[3-(3-chloro-6-methoxyquinolin-4-yl)propyl]piperidine-4-carboxylate in 75 cm$^3$ of 5N hydrochloric acid dissolved in dioxane and 200 cm$^3$ of dioxane was stirred at a temperature in the region of 20° C. for 20 hours. 200 cm$^3$ of diethyl ether were added to the reaction mixture. The precipitate formed was filtered off to give 14.26 g of benzyl 4-[3-(3-fluoro-6-methoxyquinolin-4-yl)propyl]piperidine-4-carboxylate hydrochloride.

$^1$H NMR Spectrum (300 MHz, $(CD_3)_2SO$-$d_6$, δ in ppm) 1.49 (mt: 2H); from 1.65 to 1.85 (mt: 4H); 2.11 (DMF, J=14 Hz: 2H); 2.78 (mt: 2H); from 3.10 to 3.25 (mt: 2H); 3.20 (broad t, J=7.5 Hz: 2H); 3.96 (s: 3H); 5.09 (s: 2H); 7.28 (mt: 5H); 7.43 (d, J=3 Hz: 1H); 7.53 (dd, J=9 and 3 Hz: 1H); 8.06 (d, J=9 Hz: 1H); 8.80 (s: 1H); from 9.05 to 9.30 (unresolved peak: 2H).

1-(2-Bromoethoxy)-2,3,5-trifluorobenzene

A mixture of 11.4 g of 2,3,5-trifluorophenol, 40.5 cm$^3$ of 1,2-dibromoethane and 15.3 g of potassium carbonate in 200 cm$^3$ of acetonitrile was heated for 18 hours at a temperature in the region of 75° C., with stirring and under an inert atmosphere. After cooling to a temperature in the region of 20° C., the reaction mixture was filtered and washed with 4 times 50 cm$^3$ of acetonitrile. The filtrate was concentrated to dryness under reduced pressure (2 kPa) at a temperature in the region of 40° C. The residue obtained was taken up in 150 cm$^3$ of petroleum ether (40–65° C.), filtered and washed with 3 times 30 cm$^3$ of petroleum ether (40–65° C.). The filtrate was concentrated to dryness under reduced pressure (2 kPa) at a temperature in the region of 40° C.

The residue obtained was purified by chromatography under atmospheric pressure, on a column of silica gel (particle size 20–45μ; diameter 5 cm; height: 33 cm), eluting with petroleum ether (40–65° C.) and collecting 100-cm$^3$ fractions. Fractions 28 to 63 were combined and then concentrated to dryness according to the above conditions. 16.15 g of 1-(2-bromoethoxy)-2,3,5-trifluorobenzene were obtained in the form of a thick colorless oil.

$^1$H NMR Spectrum (300 MHz, $(CD_3)_2SO$-$d_6$, δ in ppm) 3.83 (broad t, J=5.5 Hz: 2H); 4.45 (broad t, J=5.5 Hz: 2H); from 7.00 to 7.15 (mt: 2H).

The benzyl 4-allyl-1-(tert-butyloxycarbonyl)-piperidine-4-carboxylate was prepared as described in Example 1.

EXAMPLE 14

4-[3-(3-Chloro-6-methoxyquinolin-4-yl)propyl]-1-[2-(2,5-difluoro-6-phenylthio)ethyl]piperidine-4-carboxylic Acid A mixture of 1.3 g of benzyl 4-[3-(3-chloro-6-methoxyquinolin-4-yl)propyl]-1-[2-(2,5-difluoro-6-piperidine-4-carboxylate in 15 cm³ of aqueous 5N hydrochloric acid and 15 cm³ of dioxane was maintained at a temperature in the region of 100° C. with stirring and under an inert atmosphere for 20 hours. After cooling to about 20° C., the reaction mixture was evaporated under reduced pressure (2 kPa) at a temperature in the region of 40° C.

The residue obtained was taken up 4 times in toluene, evaporating between each washing. The oil obtained was taken up in a chloroform/methanol/aqueous ammonia mixture (12/3/0.5 by volume), the phases were separated by settling and the organic phase was washed with water and then left to crystallize for 20 hours. The solid obtained was filtered off and then dried in a desiccator under reduced pressure (0.1 kPa) at a temperature in the region of 40° C. 0.6 g of 4-[3-(3-chloro-6-methoxyquinolin-4-yl)propyl]-1-[2-(2,5-difluoro-6-phenylthio)ethyl]piperidine-4-carboxylic acid was obtained in the form of a white crystalline solid melting at 205° C.

$^1$H NMR Spectrum (400 MHz, $(CD_3)_2SO-d_6$, δ in ppm): 1.39 (unresolved peak: 2H); 1.55 (mt: 2H); 1.70 (mt: 2H); from 1.90 to 2.20 (mt: 4H); from 2.40 to 2.85 (broad unresolved peak: 4H); from 3.05 to 3.25 (mt: 2H); 3.17 (broad t, J=7.5 Hz: 2H); 3.96 (s: 3H); 7.07 (mt: 1H); 7.26 (mt: 1H); 7.33 (mt: 1H); 7.38 (d, J=2.5 Hz: 1H); 7.46 (dd, J=9 and 2.5 Hz: 1H); 7.97 (d, J=9 Hz: 1H); 8.68 (s: 1H); from 12.00 to 12.50 (unresolved peak: 1H).

Benzyl 4-[3-(3-chloro-6-methoxyquinolin-4-yl)-propyl]-1-[2-(2,5-difluoro-6-phenylthio)ethyl]piperidine-4-carboxylate A mixture of 1.4 g of benzyl 4-[3-(3-chloro-6-methoxyquinolin-4-yl)propyl]piperidine-4-carboxylate, 0.9 g of 1-(2-bromoethylthio)-2,5-difluorobenzene, 0.6 g of potassium iodide and 2 g of potassium carbonate in 100 cm³ of acetonitrile was heated for 18 hours at a temperature in the region of 75° C., with stirring and under an inert atmosphere. After cooling to a temperature in the region of 20° C., the reaction mixture was concentrated to dryness under reduced pressure (2 kPa) at a temperature in the region of 40° C. The residue obtained was taken up in water and extracted with ethyl acetate. The organic phase was washed with saturated sodium chloride solution, dried over magnesium sulfate and then concentrated to dryness as above.

The residue obtained was purified by chromatography, under atmospheric pressure, on a column of silica gel (particle size 70–200μ; diameter 2.5 cm; mass: 50 g), eluting with a mixture of ethyl acetate and dichloromethane (05/95 by volume) and collecting 15-cm³ fractions. Fractions 21 to 100 were combined and then concentrated to dryness according to the above conditions. 1.35 g of benzyl 4-[3-(3-chloro-6-methoxyquinolin-4-yl)-propyl]-1-[2-(2,5-difluoro-6-phenylthio)-ethyl]-piperidine-4-carboxylate were obtained in the form of a white solid melting at 95° C.

$^1$H NMR Spectrum (300 MHz, $(CD_3)_2SO-d_6$, δ in ppm) from 1.30 to 1.60 (mt: 4H); 1.71 (mt: 2H); from 1.85 to 2.05 (mt: 4H); from 2.40 to 2.60 (mt: 2H); 2.66 (DMF, J=12 Hz: 2H); from 3.05 to 3.20 (mt: 2H); 3.11 (broad t, J=7.5 Hz: 2H); 3.92 (s: 3H); 5.03 (s: 2H); 7.04 (mt: 1H); from 7.15 to 7.35 (mt: 7H); 7.35 (d, J=3 Hz: 1H); 7.44 (dd, J=9 and 3 Hz: 1H); 7.95 (d, J=9 Hz: 1H); 8.66 (s: 1H).

1-(2-Bromoethylthio)-2,5-difluorobenzene

A mixture of 5.8 g of S-(2,5)-difluorophenyl-dimethyl thiocarbamate in 80 cm³ of a 10% solution of potassium hydroxide in methanol was heated for 1 hour at a temperature in the region of 100° C. with stirring and under an inert atmosphere. After cooling to a temperature in the region of 20° C., the reaction mixture was concentrated to dryness under reduced pressure (2 kPa) at a temperature in the region of 40° C.

The residue obtained was taken up in water, extracted with diethyl ether and then acidified with 40 cm³ of 5N hydrochloric acid. The aqueous phase was extracted with twice 30 cm³ of diethyl ether. The organic phases were combined, washed with saturated sodium chloride solution, dried over sodium sulfate, filtered and then concentrated to dryness as above. The residue obtained was taken up in 30 cm³ of 1,2-dibromoethane and 0.5 g of aliquat 336, followed by addition of 20 cm³ of cold sodium hydroxide solution. The solution obtained was stirred for a further 18 hours at a temperature in the region of 20° C. and then washed with twice 15 cm³ of water. The organic phases were combined, washed with saturated sodium chloride solution, dried over sodium sulfate, filtered and then concentrated to dryness as above.

The residue obtained was purified by chromatography under atmospheric pressure, on a column of silica gel (particle size 70–200μ; diameter 2.5 cm; mass: 75 g), eluting with petroleum ether and collecting 50-cm³ fractions. Fractions 4 to 13 were combined and then concentrated to dryness according to the above conditions. 4.4 g of 1-(2-bromoethylthio)-2,5-difluorobenzene were obtained in the form of a colorless fluid oil.

$^1$H NMR Spectrum (300 MHz, $(CD_3)_2SO-d_6$, δ in ppm) 3.50 (mt: 2H); 3.66 (mt: 2H); 7.15 (mt: 1H); 7.32 (doubled triplet, J=9 and 4.5 Hz: 1H); 7.42 (ddd, J=9–6.5 and 3 Hz: 1H).

Dimethyl S-(2,5)-difluorophenylthiocarbamate 2 g of dimethyl O-(2,5)-difluorophenylthiocarbamate were heated at a temperature in the region of 235° C. for 40 minutes. The residue obtained was purified by chromatography under atmospheric pressure, on a column of silica gel (particle size 70–200μ; diameter 3 cm; mass: 25 g), eluting with a mixture of petroleum ether and dichloromethane (50/50 by volume) and collecting 15-cm³ fractions. Fractions 6 to 11 were combined and then concentrated to dryness under reduced pressure (2 kPa) at a temperature in the region of 40° C. 1.25 g of dimethyl S-(2,5)-difluorophenylthiocarbamate were obtained in the form of a white solid melting at 96° C.

$^1$H NMR Spectrum (300 MHz, $(CD_3)_2SO-d_6$, δ in ppm): 2.96 (unresolved peak: 3H); 3.08 (unresolved peak: 3H); from 7.35 to 7.50 (mt: 3H).

Dimethyl O-(2,5)-difluorophenylthiocarbamate 14.1 g of dimethylthiocarbamate chloride and 13 g of 1,4-diaza[2.2.2]tricyclooctane were added with stirring to a solution of 7.5 g of 2,5-difluorophenol in 120 cm³ of dimethylformamide. After stirring for 1 hour at a temperature in the region of 20° C., the reaction mixture was taken up in 1 dm³ of water and 100 cm³ of dry concentrated hydrochloric acid, and extracted with 400 cm³ of diethyl ether. The organic phase was dried over sodium sulfate, filtered and then concentrated to dryness under reduced pressure (2 kPa) at a temperature in the region of 40° C. The residue obtained was purified by chromatography under atmospheric pressure, on a column of silica gel (particle size 70–200μ; diameter 10 cm; mass: 400 g), eluting with a mixture of petroleum ether and dichloromethane (50/50 by volume). The fractions containing the expected product were combined and then concentrated to dryness under reduced pressure (5 kPa) at a temperature in the region of 40° C. 12.4 g of dimethyl O-(2,5)-difluorophenylthiocarbamate were obtained in the form of a solid melting at 62° C.

$^1$H NMR Spectrum (300 MHz, $(CD_3)_2SO-d_6$, δ in ppm): 3.35 (s: 3H); 3.40 (s: 3H); from 7.15 to 7.30 (mt: 2H); 7.42 (doubled triplet, J=9.5 and 5.5 Hz: 1H).

The benzyl 4-[3-(3-chloro-6-methoxyquinolin-4-yl) propyl]piperidine-4-carboxylate hydrochloride was prepared as described in Example 13.

EXAMPLE 15

4-[3-(3-Chloro-6-methoxyquinolin-4-yl)propyl]-1-[2-(2,6-difluorophenoxy)ethyl]piperidine-4-carboxylic Acid Dihydrochloride A mixture of 1 g of benzyl 4-[3-(3-chloro-6-methoxyquinolin-4-yl)propyl]-1-[2-(2,6-difluorophenoxy)-ethyl]piperidine-4-carboxylate in 50 cm$^3$ of aqueous 5N hydrochloric acid was maintained at a temperature in the region of 100° C., with stirring and under an inert atmosphere for 20 hours. After cooling to about 20° C., the reaction mixture was concentrated to dryness under reduced pressure (2 kPa) at a temperature in the region of 40° C.

The residue obtained was taken up in 50 cm$^3$ of acetone and then stirred for 1 hour at a temperature in the region of 20° C. The mixture was filtered, washed with 3 times 15 cm$^3$ of acetone and then dried in a desiccator under reduced pressure (0.1 kPa) at a temperature in the region of 40° C. 0.86 g of 4-[3-(3-chloro-6-methoxyquinolin-4-yl)propyl]-1-[2-(2,6-difluorophenoxy)ethyl]piperidine-4-carboxylic acid dihydrochloride was obtained in the form of a white solid melting at 218° C.

$^1$H NMR Spectrum (300 MHz, $(CD_3)_2SO-d_6$, δ in ppm) 1.59 (mt: 2H); 1.75 (mt: 2H); 1.82 (very broad t, J=14 Hz: 2H); 2.22 (broad d, J=14 Hz: 2H); 2.98 (mt: 2H); 3.22 (broad t, J=7.5 Hz: 2H); from 3.45 to 3.70 (mt: 4H); 3.98 (s: 3H); 4.51 (t, J=5 Hz: 2H); from 7.15 to 7.25 (mt: 3H); 7.42 (d, J=3 Hz: 1H); 7.48 (dd, J=9 and 3 Hz: 1H); 7.99 (d, J=9 Hz: 1H); 8.72 (s: 1H); 10.66 (unresolved peak: 1H).

Benzyl 4-[3-(3-chloro-6-methoxyquinolin-4-yl)propyl]-1-[2-(2,6-difluorophenoxy)ethyl]piperidine-4-carboxylate A mixture of 1.4 g of benzyl 4-[3-(3-chloro-6-methoxyquinolin-4-yl)propyl]piperidine-4-carboxylate, 0.82 g of 1-(2-bromoethoxy)-2,6-difluorobenzene, 0.6 g of potassium iodide and 2 g of potassium carbonate in 100 cm$^3$ of acetonitrile was heated for 18 hours at a temperature in the region of 75° C., with stirring and under an inert atmosphere. After cooling to a temperature in the region of 20° C., the reaction mixture was filtered and washed with three times 30 cm$^3$ of acetonitrile. The filtrate was concentrated to dryness under reduced pressure (2 kPa) at a temperature in the region of 40° C. The residue obtained was purified by chromatography under atmospheric pressure, on a column of silica gel (particle size 20–45μ; diameter 3 cm; height: 27 cm), eluting with ethyl acetate and collecting 50-cm$^3$ fractions. Fractions 7 to 17 were combined and then concentrated to dryness under the above conditions. 1.65 g of benzyl 4-[3-(3-chloro-6-methoxyquinolin-4-yl)propyl]-1-[2-(2,6-difluorophenoxy)ethyl]piperidine-4-carboxylate were obtained in the form of a thick yellow oil.

$^1$H NMR Spectrum (300 MHz, $(CD_3)_2SO-d_6$, δ in ppm) from 1.25 to 1.55 (mt: 4H); 1.70 (mt: 2H); from 1.90 to 2.10 (mt: 4H); 2.59 (t, J=6 Hz: 2H); 2.66 (DMF, J=12 Hz: 2H); 3.13 (broad t, J=7.5 Hz: 2H); 3.93 (s: 3H); 4.14 (t, J=6 Hz: 2H); 5.03 (s: 2H); from 7.05 to 7.20 (mt: 3H); 7.35 (mt: 5H); 7.35 (d, J=3 Hz: 1H); 7.46 (dd, J=9 and 3 Hz: 1H); 7.97 (d, J=9 Hz: 1H); 8.67 (s: 1H).

1-(2-Bromoethoxy)-2,6-difluorobenzene

A mixture of 10 g of 2,6-difluorophenol, 40.5 cm$^3$ of 1,2-dibromoethane and 15.3 g of potassium carbonate in 300 cm$^3$ of acetonitrile was heated for 18 hours at a temperature in the region of 75° C., with stirring and under an inert atmosphere. After cooling to a temperature in the region of 20° C., the reaction mixture was filtered and washed with 3 times 30 cm$^3$ of acetonitrile. The filtrate was concentrated to dryness under reduced pressure (2 kPa) at a temperature in the region of 40° C. The residue obtained was taken up in 200 cm$^3$ of petroleum ether (40–65° C.), filtered and washed with 3 times 30 cm$^3$ of petroleum ether (40–65° C.). The filtrate was concentrated to dryness under reduced pressure (2 kPa) at a temperature in the region of 40° C. The residue obtained was purified by chromatography under atmospheric pressure, on a column of silica gel (particle size 20–45μ; diameter 7 cm; height: 28 cm), eluting with petroleum ether (40–65° C.) and collecting 100-cm$^3$ fractions. Fractions 22 to 58 were combined and then concentrated to dryness under the above conditions. 14.5 g of 1-(2-bromoethoxy)-2,6-difluorobenzene were obtained in the form of a thick colorless oil.

$^1$H NMR Spectrum (300 MHz, $(CD_3)_2SO-d_6$, δ in ppm) 3.76 (broad t, J=6 Hz: 2H); 4.42 (broad t, J=6 Hz: 2H); from 7.10 to 7.25 (mt: 3H).

The benzyl 4-[3-(3-chloro-6-methoxyquinolin-4-yl) propyl]piperidine-4-carboxylate hydrochloride was prepared as described in Example 13.

EXAMPLE 16

4-[3-(3-Chloro-6-methoxyquinolin-4-yl)propyl]-1-[2-(2,5-difluorophenoxy)ethyl]piperidine-4-carboxylic Acid Dihydrochloride A mixture of 1 g of benzyl 4-[3-(3-chloro-6-methoxyquinolin-4-yl)propyl]-1-[2-(2,5-difluorophenoxy) ethyl]piperidine-4-carboxylate in 50 cm$^3$ of 5N hydrochloric acid was maintained at a temperature in the region of 100° C., with stirring and under an inert atmosphere for 20 hours. After cooling to about 20° C., the reaction mixture was concentrated to dryness under reduced pressure (2 kPa) at a temperature in the region of 40° C.

The residue obtained was taken up in 50 cm$^3$ of acetone and then stirred for 1 hour at a temperature in the region of 20° C. The mixture was filtered, washed with 3 times 15 cm$^3$ of acetone and then dried in a desiccator under reduced pressure (0.1 kPa) at a temperature in the region of 40° C. 0.8 g of 4-[3-(3-chloro-6-methoxyquinolin-4-yl)propyl]-1-[2-(2,5-difluorophenoxy)-ethyl]piperidine-4-carboxylic acid dihydrochloride was obtained in the form of a white solid melting at 180° C.

$^1$H NMR Spectrum (400 MHz, $(CD_3)_2SO-d_6$, δ in ppm): 1.58 (mt: 2H); 1.72 (mt: 2H); 1.84 (very broad t, J=14 Hz: 2H); 2.19 (broad d, J=14 Hz: 2H); 2.95 (mt: 2H); 3.22 (broad t, J=7.5 Hz: 2H); 3.53 (mt: 4H); 3.98 (s: 3H); 4.52 (t, J=5 Hz: 2H); 6.84 (mt: 1H); 7.22 (ddd, J=9–7 and 3 Hz: 1H); 7.30 (ddd, J=10.5–9 and 4.5 Hz: 1H); 7.42 (d, J=2.5 Hz: 1H); 7.49 (dd, J=9 and 2.5 Hz: 1H); 8.00 (d, J=9 Hz: 1H); 8.74 (s: 1H); 10.97 (unresolved peak: 1H).

Benzyl 4-[3-(3-chloro-6-methoxyquinolin-4-yl)propyl]-1-[2-(2,5-difluorophenoxy)ethyl]piperidine-4-carboxylate A mixture of 1.4 g of benzyl 4-[3-(3-chloro-6-methoxyquinolin-4-yl)propyl]piperidine-4-carboxylate hydrochloride, 0.82 g of 1-(2-bromoethoxy)-2,5-difluorobenzene, 0.6 g of potassium iodide and 2 g of potassium carbonate in 100 cm³ of acetonitrile was heated for 18 hours at a temperature in the region of 75° C. with stirring and under an inert atmosphere. After cooling to a temperature in the region of 20° C., the reaction mixture was filtered and washed with 3 times 30 cm³ of acetonitrile. The filtrate was concentrated to dryness under reduced pressure (2 kPa) at a temperature in the region of 40° C.

The residue obtained was purified by chromatography under atmospheric pressure, on a column of silica gel (particle size 20–45µ; diameter 2.4 cm; height: 26 cm), eluting with ethyl acetate and collecting 30-cm³ fractions. Fractions 7 to 14 were combined and then concentrated to dryness under the above conditions. 1.6 g of benzyl 4-[3-(3-chloro-6-methoxyquinolin-4-yl)propyl]-1-[2-(2,5-difluorophenoxy)ethyl]piperidine-4-carboxylate were obtained in the form of a thick yellow oil.

$^1$H NMR Spectrum (300 MHz, $(CD_3)_2SO$-$d_6$, δ in ppm) from 1.35 to 1.60 (mt: 4H); 1.73 (mt: 2H); from 1.95 to 2.15 (mt: 4H); 2.63 (t, J=5.5 Hz: 2H); 2.72 (DMF, J=12 Hz: 2H); 3.14 (broad t, J=7.5 Hz: 2H); 3.92 (s: 3H); 4.12 (t, J=5.5 Hz: 2H); 5.04 (s: 2H); 6.75 (tripled triplet, J=9 and 3 Hz: 1H); 7.13 (ddd, J=10.5–7.5 and 3 Hz: 1H); from 7.20 to 7.30 (mt: 6H); 7.34 (d, J=3 Hz: 1H); 7.45 (dd, J=9 and 3 Hz: 1H); 7.97 (d, J=9 Hz: 1H); 8.67 (s: 1H).

1-(2-Bromoethoxy)-2,5-difluorobenzene

A mixture of 10 g of 2,5-difluorophenol, 40.5 cm³ of 1,2-dibromoethane and 15.3 g of potassium carbonate in 200 cm³ of acetonitrile was heated for 18 hours at a temperature in the region of 75° C., with stirring and under an inert atmosphere. After cooling to a temperature in the region of 20° C., the reaction mixture was filtered and washed with 4 times 50 cm³ of acetonitrile. The filtrate was concentrated to dryness under reduced pressure (2 kPa) at a temperature in the region of 40° C. The residue obtained was taken up in 150 cm³ of petroleum ether (40–65° C.), filtered and washed with 3 times 30 cm³ of petroleum ether (40–65°). The filtrate was concentrated to dryness under reduced pressure (2 kPa) at a temperature in the region of 40° C.

The residue obtained was purified by chromatography under atmospheric pressure, on a column of silica gel (particle size 20–45µ; diameter 7 cm; height: 49 cm), eluting with petroleum ether (40–65° C.) and collecting 100-cm³ fractions. Fractions 29 to 88 were combined and then concentrated to dryness under the above conditions. 13.5 g of 1-(2-bromoethoxy)-2,5-difluorobenzene were obtained in the form of a colorless fluid oil.

$^1$H NMR Spectrum (300 MHz, $(CD_3)_2SO$-$d_6$, δ in ppm): 3.85 (broad t, J=6 Hz: 2H); 4.44 (broad t, J=6 Hz: 2H); 6.82 (mt: 1H); 7.18 (ddd, J=9–7 and 3 Hz: 1H); 7.29 (ddd, J=11–9 and 5 Hz: 1H).

The benzyl 4-[3-(3-chloro-6-methoxyquinolin-4-yl) propyl]piperidine-4-carboxylate hydrochloride was prepared as described in Example 13.

EXAMPLE 17

4-[3-(3-Chloro-6-methoxyquinolin-4-yl)propyl]-1-[2-(2,3-difluorophenoxy)ethyl]piperidine-4-carboxylic Acid Dihydrochloride A mixture of 1 g of benzyl 4-[3-(3-chloro-6-methoxyquinolin-4-yl)propyl]-1-[2-(2,3-difluorophenoxy)-ethyl]piperidine-4-carboxylate in 50 cm³ of aqueous 5N hydrochloric acid was maintained at a temperature in the region of 100° C., with stirring and under an inert atmosphere for 20 hours. After cooling to about 20° C., the reaction mixture was concentrated to dryness under reduced pressure (2 kPa) at a temperature in the region of 40° C.

The residue obtained was taken up in 50 cm³ of acetone and then stirred for 1 hour at a temperature in the region of 20° C. The mixture was filtered, washed with 3 times 15 cm³ of acetone and then dried in a desiccator under reduced pressure (0.1 kPa) at a temperature in the region of 40° C. 0.9 g of 4-[3-(3-chloro-6-methoxy-quinolin-4-yl)propyl]-1-[2-(2,3-difluorophenoxy)-ethyl]piperidine-4-carboxylic acid dihydrochloride was obtained in the form of a white solid melting at 259° C.

$^1$H NMR Spectrum (400 MHz $(CD_3)_2SO$-$d_6$, δ in ppm): from 1.45 to 1.65 (mt: 2H); 1.73 (mt: 2H); 1.81 (very broad t, J=14 Hz: 2H); 2.20 (broad d, J=14 Hz: 2H); 2.97 (mt: 2H); 3.22 (broad t, J=7.5 Hz: 2H); from 3.45 to 3.60 (mt: 4H); 3.98 (s: 3H); 4.54 (t, J=5 Hz: 2H); 7.09 (mt: 2H); 7.20 (mt: 1H); 7.42 (d, J=2.5 Hz: 1H); 7.48 (dd, J=9 and 2.5 Hz: 1H); 7.99 (d, J=9 Hz: 1H); 8.72 (s: 1H); 10.70 (unresolved peak: 1H); from 12.40 to 13.30 (broad unresolved peak: 1H).

Benzyl 4-[3-(3-chloro-6-methoxyquinolin-4-yl)propyl]-1-[2-(2,3-difluorophenoxy)ethyl]piperidine-4-carboxylate A mixture of 1.4 g of benzyl 4-[3-(3-chloro-6-methoxyquinolin-4-yl)propyl]piperidine-4-carboxylate hydrochloride, 0.82 g of 1-(2-bromoethoxy)-2,3-difluorobenzene, 0.6 g of potassium iodide and 2 g of potassium carbonate in 100 cm³ of acetonitrile was heated for 18 hours at a temperature in the region of 75° C., with stirring and under an inert atmosphere. After cooling to a temperature in the region of 20° C., the reaction mixture was filtered and washed with 3 times 30 cm³ of acetonitrile. The filtrate was concentrated to dryness under reduced pressure (2 kPa) at a temperature in the region of 40° C.

The residue obtained was purified by chromatography under atmospheric pressure, on a column of silica gel (particle size 20–45µ; diameter 2.7 cm; height: 32 cm), eluting with ethyl acetate and collecting 30-cm³ fractions. Fractions 7 to 21 were combined and then concentrated to dryness under the above conditions. 1.6 g of benzyl 4-[3-(3-chloro-6-methoxyquinolin-4-yl)propyl]-1-[2-(2,3-difluorophenoxy)ethyl]piperidine-4-carboxylate were obtained in the form of a thick yellow oil.

$^1$H NMR Spectrum (300 MHz, $(CD_3)_2SO$-$d_6$, δ in ppm) from 1.35 to 1.55 (mt: 4H); 1.72 (mt: 2H); from 1.95 to 2.15 (mt: 4H); 2.64 (t, J=6 Hz: 2H); 2.72 (DMF, J=12 Hz: 2H); 3.13 (broad t, J=7.5 Hz: 2H); 3.93 (s: 3H); 4.15 (t, J=6 Hz: 2H); 5.04 (s: 2H); from 6.90 to 7.20 (mts: 3H); 7.25 (mt: 5H); 7.35 (d, J=3 Hz: 1H); 7.46 (dd, J=9 and 3 Hz: 1H); 7.97 (d, J=9 Hz: 1H); 8.67 (s: 1H).

1-(2-Bromoethoxy)-2,3-difluorobenzene

A mixture of 10 g of 2,3-difluorophenol, 40.5 cm³ of 1,2-dibromoethane and 15.3 g of potassium carbonate in 200 cm³ of acetonitrile was heated for 48 hours at a temperature in the region of 75° C., with stirring and under an inert atmosphere. After cooling to a temperature in the region of 20° C., the reaction mixture was filtered and washed with 6 times 30 cm³ of acetonitrile. The filtrate was concentrated to dryness under reduced pressure (2 kPa) at a temperature in the region of 40° C.

The residue obtained was purified by chromatography under atmospheric pressure, on a column of silica gel (particle size 20–45µ; diameter 7 cm; height: 42 cm), eluting with a mixture of dichloromethane and ethyl acetate (90/10 by volume) and collecting 100-cm³ fractions. Fractions 4 to 10 were combined and then concentrated to dryness under the above conditions. The residue obtained was purified by chromatography under atmospheric pressure, on a column of silica gel (particle size 20–45µ; diameter 5 cm; height: 30 cm), eluting with petroleum ether (40–65° C.) and collecting 100-cm³ fractions. Fractions 34 to 82 were combined and then concentrated to dryness under the above conditions. 13.6 g of 1-(2-bromoethoxy)-2,3-difluorobenzene were obtained in the form of a colorless fluid oil.

$^1$H NMR Spectrum (300 MHz, (CD$_3$)$_2$SO-d$_6$, δ in ppm): 3.85 (broad t, J=6 Hz: 2H); 4.44 (broad t, J=6 Hz: 2H); 6.82 (mt: 1H); 7.18 (ddd, J=9–7 and 3 Hz: 1H); 7.29 (ddd, J=11–9 and 5 Hz: 1H).

The benzyl 4-[3-(3-chloro-6-methoxyquinolin-4-yl) propyl]piperidine-4-carboxylate hydrochloride was prepared as described in Example 13.

EXAMPLE 18

4-[3-(3-Chloro-6-methoxyquinolin-4-yl)propyl]-1-(2-thiazole-2-thioethyl)piperidine-4-carboxylic Acid A mixture of 0.3 g of ethyl 4-[3-(3-chloro-6-methoxyquinolin-4-yl)propyl]-1-(2-thiazole-2-thioethyl) piperidine-4-carboxylate in 6 cm³ of aqueous 5N hydrochloric acid was maintained at a temperature in the region of 100° C., with stirring and under an inert atmosphere for 6 hours. After cooling and stirring for 16 hours at a temperature in the region of 20° C., the reaction mixture was concentrated to dryness under reduced pressure (2 kPa) at a temperature in the region of 40° C.

The residue obtained was taken up in 10 cm³ of dichloroethane containing 10% methanol, and then concentrated to dryness under reduced pressure (2 kPa) at a temperature in the region of 40° C. The residue obtained was purified by chromatography under atmospheric pressure, on a column of silica gel (particle size 40–60µ; diameter 2.5 cm; height: 30 cm), eluting with a dichloroethane/methanol/aqueous ammonia mixture (89/10/1 by volume). Fractions 18 to 41 were combined and then concentrated to dryness under the above conditions.

The residue obtained was taken up in 5 cm³ of isopropyl ether, filtered and dried in a desiccator under reduced pressure (0.1 kPa) at a temperature in the region of 40° C. 0.24 g of 4-[3-(3-chloro-6-methoxyquinolin-4-yl)propyl]-1-(2-thiazole-2-thioethyl)piperidine-4-carboxylic acid was obtained in the form of a white solid melting at 200° C.

$^1$H NMR Spectrum (300 MHz, (CD$_3$)$_2$SO-d$_6$, δ in ppm) 1.34 (mt: 2H); 1.55 (mt: 2H); 1.69 (mt: 2H); from 1.85 to 2.15 (mt: 4H); 2.59 (broad t, J=7 Hz: 2H); 2.67 (DMF, J=12 Hz: 2H); 3.17 (broad t, J=6 Hz: 2H); from 3.20 to 3.50 (mt: 2H); 3.96 (s: 3H); 7.38 (broad s: 1H); 7.45 (broad dd, J=9 and 2.5 Hz: 1H); 7.63 (d, J=3 Hz: 1H); 7.71 (d, J=3 Hz: 1H); 7.96 (d, J=9 Hz: 1H); 8.68 (s: 1H); from 11.90 to 12.55 (very broad unresolved peak: 1H).

Ethyl 4-[3-(3-chloro-6-methoxyquinolin-4-yl)propyl]-1-(2-thiazole-2-thioethyl)piperidine-4-carboxylate 0.28 g of 2-mercaptothiazole, 0.33 g of potassium carbonate and 0.39 g of potassium iodide were added to a solution of 0.9 g of ethyl 4-[3-(3-chloro-6-methoxyquinolin-4-yl)propyl]-1-(2-chloroethyl)piperidine-4-carboxylate in 50 cm³ of acetonitrile at a temperature in the region of 20° C., with stirring and under an inert atmosphere. After heating for 20 hours at a temperature in the region of 80° C., the reaction mixture was cooled to about 20° C., filtered and concentrated to dryness under reduced pressure (2 kPa) at a temperature in the region of 50° C.

The residue obtained was purified by chromatography under a pressure of 100 kPa of nitrogen, on a column of silica gel (particle size 40–60µ; diameter 3.5 cm; height 35 cm), eluting with a dichloromethane/methanol mixture (95/ 0.5 by volume) and collecting 40-cm³ fractions. The fractions containing the product were combined and then purified by chromatography under a pressure of 100 kPa of nitrogen, on a column of silica gel (particle size 40–60µ; diameter 3.5 cm; height 30 cm), eluting with an ethyl acetate/cyclohexane mixture (75/25 by volume) and collecting 30-cm³ fractions. Fractions 23 to 40 were combined and then concentrated to dryness as previously. 0.75 g of ethyl 4-[3-(3-chloro-6-methoxyquinolin-4-yl)propyl]-1-(2-thiazole-2-thioethyl)piperidine-4-carboxylate was obtained.

$^1$H NMR Spectrum (300 MHz, (CD$_3$)$_2$SO-d$_6$, δ in ppm) 1.05 (t, J=7 Hz: 3H); 1.38 (mt: 2H); 1.52 (mt: 2H); 1.68 (mt: 2H); from 1.90 to 2.05 (mt: 4H); 2.59 (t, J=7 Hz: 2H); 2.68 (broad d, J=12 Hz: 2H); 3.17 (broad t, J=7.5 Hz: 2H); from 3.25 to 3.40 (mt: 2H); 3.97 (s: 3H); 4.00 (q, J=7 Hz: 2H); 7.38 (d, J=2.5 Hz: 1H); 7.46 (dd, J=9 and 2.5 Hz: 1H); 7.63 (d, J=3.5 Hz: 1H); 7.71 (d, J=3.5 Hz: 1H); 7.96 (d, J=9 Hz: 1H); 8.68 (s: 1H).

Ethyl 4-[3-(3-chloro-6-methoxyquinolin-4-yl)propyl]-1-(2-chloroethyl)piperidine-4-carboxylate 1.21 cm³ of thionyl chloride were added to a solution of 1.8 g of ethyl 4-[3-(3-chloro-6-methoxyquinolin-4-yl) propyl]-1-(2-hydroxyethyl)piperidine-4-carboxylate in 40 cm³ of dichloromethane with stirring, at a temperature in the region of 20° C. After stirring for 48 hours at a temperature in the region of 20° C., the reaction mixture was concentrated under reduced pressure (1 kPa) at a temperature in the region of 50° C.

The residue was taken up in 50 cm³ of water and 50 cm³ of ethyl acetate with vigorous stirring at a temperature in the region of 20° C., followed by addition of 10 g of potassium carbonate. The organic phase was washed with 25 cm³ of water and then with 25 cm³ of saturated sodium chloride solution, dried over magnesium sulfate, filtered and concentrated under reduced pressure (1 kPa) at a temperature in the region of 50° C. 1.8 g of ethyl 4-[3-(3-chloro-6-methoxyquinolin-4-yl)propyl]-1-(2-chloroethyl)piperidine-4-carboxylate were obtained.

Infra-red Spectrum (CCl$_4$): 2957; 1726; 1622; 1503; 1230; 1116; 1029 and 833 cm$^{-1}$ Ethyl 4-[3-(3-chloro-6-methoxyquinolin-4-yl)propyl]-1-(2-hydroxyethyl)piperidine-4-carboxylate 3.9 g of ethyl 4-[3-(3-chloro-6-methoxyquinolin-4-yl) propyl]piperidine-4-carboxylate and 2.07 g of potassium carbonate were added to a solution of 1.17 cm³ of 2-iodoethanol in 80 cm³ of acetonitrile, at a temperature in the region of 20° C. with stirring and under an inert atmosphere. After heating for 23 hours at a temperature in the region of 80° C., a further 1.17 cm³ of 2-iodoethanol were added. After heating for 40 hours at a temperature in the region of 80° C., the reaction mixture was cooled to about 20° C., filtered and concentrated under reduced pressure (1 kPa) at a temperature in the region of 50° C. The residue obtained was purified by chromatography under a pressure of 100 kPa of nitrogen, on a column of silica gel (particle size 40–60µ; diameter 4 cm; height 60 cm), eluting with a dichloromethane/methanol/aqueous ammonia mixture (89/10/1 by volume) and collecting 50-cm³ fractions. Fractions 14 to 17 were combined and then concentrated as previously. 1.9 g of ethyl 4-[3-(3-chloro-6-methoxyquinolin-4-yl)propyl]-1-(2-hydroxyethyl) piperidine-4-carboxylate were obtained.

Infra-red Spectrum (CCl$_4$): 2439; 2952; 1726; 1622; 1503; 1230; 1116; 1029 and 833 cm$^{-1}$.

EXAMPLE 19

4-[3-(R,S)-Hydroxy-3-(3-chloro-6-methoxyquinolin-4-yl)propyl]-1-[2-(cyclopentylthioethyl)piperidin-4-yl]methanol Dihydrochloride A mixture of 0.6 g of {4-[3-(3-chloro-6-methoxyquinolin-4-yl)-3-(R,S)-hydroxypropyl]piperidin-4-yl}methanol dihydrochloride, 0.24 g of 1-bromo-2-(cyclopentylthio)ethyl, 0.22 g of potassium iodide and 0.9 g of potassium carbonate in 25 cm³ of acetonitrile was heated with stirring for 20 hours at a temperature in the region of 75° C. After cooling to a temperature in the region of 20° C., the reaction mixture was concentrated to dryness under reduced pressure (2 kPa) at a temperature in the region of 40° C.

The residue obtained was taken up in 20 cm³ of water and then extracted with 3 times 20 cm³ of ethyl acetate. The organic phases were combined, dried over magnesium sulfate, filtered and then concentrated to dryness as above. The residue obtained was purified by chromatography under a pressure of 50 kPa of nitrogen, on a column of silica gel (particle size 20–45μ; diameter 3 cm; height: 18 cm), eluting with a dichloromethane/methanol mixture (90/10 by volume). The fractions containing the expected product were combined and then concentrated to dryness under the above conditions. The residue obtained was taken up in 5 cm³ of acetone and then acidified with 3 cm³ of a 1N solution of hydrogen chloride in diethyl ether. The suspension obtained was diluted with 20 cm³ of diethyl ether, stirred at a temperature in the region of 20° C. for 3 hours, filtered, washed with diethyl ether and then dried in a desiccator under reduced pressure (0.1 kPa) at a temperature in the region of 40° C. 0.4 g of 4-[3-(R,S)-hydroxy-3-(3-chloro-6-methoxyquinolin-4-yl)propyl]-1-[2-(cyclopentylthioethyl)piperidin-4-yl]methanol dihydrochloride was obtained in the form of a pale yellow solid melting at 120° C.

$^1$H NMR Spectrum (400 MHz, $(CD_3)_2SO-d_6$ with addition of a few drops of $CD_3COOD-d_4$ at a temperature of 373K, δ in ppm): from 1.20 to 2.15 (mt: 16H); 2.93 (broad t, J=7.5 Hz: 2H); from 3.10 to 3.30 (mt: 7H); 3.33 (broad s: 2H); 3.91 (s: 3H); 5.49 (mt: 1H); 7.41 (dd, J=9 and 3 Hz: 1H); 7.93 (d, J=9 Hz: 1H); 8.22 (d, J=3 Hz: 1H); 8.60 (s: 1H).

{4-[3-(3-Chloro-6-methoxyquinolin-4-yl)-3-(R,S)-hydroxypropyl]piperidin-4-yl}methanol Dihydrochloride A mixture of 1.5 g of tert-butyl 4-(tert-butyldimethylsilanyloxymethyl)-4-[3-(3-chloro-6-methoxyquinolin-4-yl)-3-(R,S)-hydroxypropyl]piperidine-1-carboxylate in 6.5 cm³ of 5N hydrochloric acid dissolved in dioxane and 30 cm³ of dioxane was stirred at a temperature in the region of 20° C. for 17 hours. 100 cm³ of diethyl ether were added to the reaction mixture. The precipitate formed was filtered off to give 1.24 g of {4-[3-(3-chloro-6-methoxyquinolin-4-yl)-3-(R,S)-hydroxypropyl]piperidin-4-yl}methanol dihydrochloride in the form of a pale yellow solid.

$^1$H NMR Spectrum (300 MHz, $(CD_3)_2SO-d_6$, δ in ppm) 1.20 to 2.10 (mt: 8H); from 2.85 to 3.10 (mt: 4H); 3.26 (broad s: 2H); 3.91 (s: 3H); 5.45 (mt: 1H); 7.47 (dd, J=9 and 3 Hz: 1H); 7.98 (d, J=9 Hz: 1H); 8.23 (d, J=3 Hz: 1H); from 8.60 to 8.80 (unresolved peak: 2H); 8.69 (s: 1H).

tert-Butyl 4-(tert-butyldimethylsilanyloxymethyl)-4-[3-(3-chloro-6-methoxyquinolin-4-yl)-3-(R,S)-hydroxypropyl]piperidine-1-carboxylate A solution of 5.26 g of tert-butyl 4-(tert-butyldimethylsilanyloxymethyl)-4-[3-(3-chloro-6-methoxyquinolin-4-yl)propyl]piperidine-1-carboxylate in 300 cm³ of dimethyl sulfoxide and 75 cm³ of tert-butanol was stirred under an oxygen-saturated atmosphere at a temperature in the region of 20° C. After 5 minutes, a solution of 2.1 g of potassium tert-butoxide in 30 cm³ of tert-butanol was added to the reaction mixture. After sparging with oxygen for 1 and a half hours, the reaction mixture was poured carefully onto a mixture of 300 g of ice, 300 cm³ of water and 1.1 cm³ of acetic acid. The aqueous phase was extracted with 3 times 300 cm³ of dichloromethane. The organic phases were combined, washed with twice 300 cm³ of water, dried over magnesium sulfate and then concentrated to dryness under reduced pressure (2 kPa) at a temperature in the region of 40° C.

The residue obtained was purified by chromatography under a pressure of 50 kPa of nitrogen, on a column of silica gel (particle size 20–45μ; diameter 4 cm; height: 27 cm), eluting with a cyclohexane/ethyl acetate mixture (50/50 by volume). The fractions containing the expected product were combined and then concentrated to dryness under the above conditions. 3.4 g of tert-butyl 4-(tert-butyldimethylsilanyloxymethyl)-4-[3-(3-chloro-6-methoxyquinolin-4-yl)-3-hydroxypropyl]piperidine-1-carboxylate were obtained in the form of a white foam.

Mass spectrum: EI m/z=578 M$^+$
m/z=521 $C_{26}H_{38}ClN_2O_5Si^+$
m/z=465 $C_{22}H_{30}ClN_2O_5Si^+$
m/z=421 $C_{21}H_{30}ClN_2O_3Si^+$ base peak
m/z=57 $C_4H_9^+$
DCI m/z=579 MH$^+$
m/z=523 $C_{26}H_{40}ClN_2O_5Si^+$ tert-Butyl 4-(tert-butyldimethylsilanyloxymethyl)-4-[3-(3-chloro-6-methoxyquinolin-4-yl)propyl]piperidine-1-carboxylate A mixture of 0.45 g of tert-butyl 4-[3-(3-chloro-6-methoxyquinolin-4-yl)propyl]-4-hydroxymethylpiperidine-1-carboxylate, 0.3 g of tert-butyldimethylsilyl chloride, 0.17 cm³ of triethylamine and 0.04 g of dimethylaminopyridine in 20 cm³ of dichloromethane was stirred under an inert atmosphere at a temperature in the region of 20° C. After stirring for 18 hours, 0.3 g of tert-butyldimethylsilyl chloride, 0.04 g of dimethylaminopyridine and 0.2 cm³ of triethylamine were added. The reaction mixture was taken up in 20 cm³ of water. The aqueous phase was extracted with twice 20 cm³ of dichloromethane. The organic phases were combined, washed with twice 300 cm³ of saturated sodium chloride solution, dried over magnesium sulfate and then concentrated to dryness under reduced pressure (2 kPa) at a temperature in the region of 40° C.

The residue obtained was purified by chromatography under a pressure of 50 kPa of nitrogen, on a column of silica gel (particle size 20–45μ; diameter 2.5 cm; height: 15 cm), eluting with a cyclohexane/ethyl acetate mixture (70/30 by volume). The fractions containing the expected product were combined and then concentrated to dryness under the above conditions. 0.48 g of tert-butyl 4-(tert-butyldimethylsilanyloxymethyl)-4-[3-(3-chloro-6-methoxyquinolin-4-yl)propyl]piperidine-1-carboxylate was obtained in the form of a colorless lacquer.

$^1$H NMR Spectrum (300 MHz, $(CD_3)_2SO-d_6$, δ in ppm): −0.04 (s: 6H); 0.76 (s: 9H); 1.29 (mt: 4H); 1.39 (s: 9H); 1.58 (mt: 4H); 3.19 (mt: 2H); from 3.20 to 3.45 (mt: 6H); 3.95 (s: 3H); 7.41 (d, J=3 Hz: 1H); 7.45 (dd, J=9 and 3 Hz: 1H); 7.95 (d, J=9 Hz: 1H); 8.67 (s: 1H).

tert-Butyl 4-[3-(3-chloro-6-methoxyquinolin-4-yl)propyl]-4-hydroxymethylpiperidine-1-carboxylate 1.05 g of lithium aluminum hydride was added portionwise, with stirring and under an inert atmosphere, to a solution of 12.3 g of ethyl 4-[3-(3-chloro-6-methoxyquinolin-4-yl)propyl]-1-(tert-butyloxycarbonyl)piperidine-4-carboxylate in 250 cm³ of tetrahydrofuran, at a temperature in the region of −20° C. After stirring for 2 hours at a temperature in the region of 20° C., 0.5 g of lithium aluminum hydride was added to the reaction mixture at a temperature in the region of −20° C. After 1 and a half hours, the reaction mixture was cooled to 0° C. and was then hydrolyzed by successive addition of 1.8 cm³ of water, 1.3 cm³ of 5N sodium hydroxide and 5.7 cm³ of water. After stirring for 30 minutes at a temperature in the region of 20° C., the reaction mixture was filtered and then washed with 400 cm³ of ethyl acetate. The filtrate was washed with 200 cm³ of saturated sodium chloride solution, dried over magnesium sulfate and then concentrated to dryness under reduced pressure (2 kPa) at a temperature in the region of 40° C. 10.9 g of tert-butyl 4-[3-(3-chloro-6-methoxyquinolin-4-yl)propyl]-4-hydroxymethylpiperidine-1-carboxylate were obtained.

¹H NMR Spectrum (300 MHz, (CD₃)₂SO-d₆, δ in ppm) 1.23 (mt: 2H); 1.32 (mt: 2H); 1.39 (s: 9H); 1.58 (mt: 4H); from 3.10 to 3.40 (mt: 6H); 3.22 (d, J=5 Hz: 2H); 3.96 (s: 3H); 4.50 (t, J=5 Hz: 1H); 7.40 (d, J=3 Hz: 1H); 7.45 (dd, J=9 and 3 Hz: 1H); 7.96 (d, J=9 Hz: 1H); 8.68 (s: 1H).

The ethyl 4-[3-(3-chloro-6-methoxyquinolin-4-yl)propyl]-1-(tert-butyloxycarbonyl)piperidine-4-carboxylate was prepared as described in Example 5.

EXAMPLE 20

4-[3-(3-Chloro-6-methoxyquinolin-4-yl)-3-(R,S)-fluoropropyl]-1-(3-phenylpropyl)piperidin-4-carboxylic Acid A mixture of 0.5 g of methyl 4-[3-(3-chloro-6-methoxyquinolin-4-yl)-3-(R,S)-fluoropropyl]-1-(3-phenylpropyl)piperidine-4-carboxylate in 8 cm³ of aqueous 5N hydrochloric acid was maintained at a temperature in the region of 100° C., with stirring for 6 hours. After stirring for 18 hours at a temperature in the region of 20° C., the reaction mixture was concentrated to dryness under reduced pressure (2 kPa) at a temperature in the region of 40° C. The residue obtained was taken up in 10 cm³ of dichloromethane and filtered. The filtrate was concentrated to dryness as above, taken up in diisopropyl ether and then dried in a desiccator under reduced pressure (0.1 kPa) at a temperature in the region of 40° C.

The residue obtained was purified by chromatography under a pressure of 60 kPa of nitrogen, on a column of silica gel (particle size 20–45μ; diameter 2.5 cm; height: 40 cm); eluting with a mixture of dichloromethane/methanol/aqueous ammonia (83/15/2). Fractions 13 to 20 were combined and then concentrated to dryness under the above conditions. 0.24 g of 4-[3-(3-chloro-6-methoxyquinolin-4-yl)-3-(R,S)-fluoropropyl]-1-(3-phenylpropyl)piperidin-4-carboxylic acid was obtained in the form of a white solid melting at 240° C.

¹H NMR Spectrum (300 MHz, (CD₃)₂SO-d₆, δ in ppm): from 1.20 to 2.35 and from 2.40 to 2.70 (mts: 18H in total); 3.94 (broad s: 3H); 6.36 (2 mts, $J_{HF}$=48 Hz: 1H); from 7.10 to 7.35 (mt: 5H); 7.52 (broad d, J=9 Hz: 1H); 7.57 (broad s: 1H); 8.02 (broad d, J=9 Hz: 1H); 8.75 (broad s: 1H).

Methyl 4-[3-(3-chloro-6-methoxyquinolin-4-yl)-3-(R,S)-fluoropropyl]-1-(3-phenylpropyl)piperidine-4-carboxylate 0.31 cm³ of diethylaminosulfur trifluoride was added to a solution of 0.66 g of methyl 4-[3-(3-chloro-6-methoxyquinolin-4-yl)-3-(R,S)-hydroxypropyl]-1-(3-phenyl-propyl)piperidine-4-carboxylate in 40 cm³ of dichloromethane, with stirring and under an inert atmosphere, at a temperature in the region of −15° C. After stirring for 3 hours at a temperature in the region of 20° C., 0.31 cm³ of diethylaminosulfur trifluoride was added to the reaction mixture, followed by 20 cm³ of saturated sodium hydrogen carbonate solution. The aqueous phase was extracted with 20 cm³ of dichloromethane. The organic phases were combined, washed with saturated sodium chloride solution, dried over magnesium sulfate and then concentrated to dryness under reduced pressure (2 kPa) at a temperature in the region of 40° C.

The residue obtained was purified by chromatography under a pressure of 100 kPa of nitrogen, on a column of silica gel (particle size 20–45μ; diameter 3.5 cm; height: 35 cm), eluting with a dichloromethane/methanol mixture (97/3). Fractions 15 to 21 were combined and then concentrated to dryness according to the above conditions. 0.5 g of methyl 4-[3-(3-chloro-6-methoxyquinolin-4-yl)-3-(R,S)-fluoropropyl]-1-(3-phenylpropyl)piperidine-4-carboxylate was obtained in the form of a brown oil.

¹H NMR Spectrum (300 MHz, (CD₃)₂SO-d₆, δ in ppm): from 1.30 to 2.35 and from 2.50 to 2.80 (mts: 18H in total); 3.54 (s: 3H); 3.93 (s: 3H); 6.36 (ddd, $J_{HF}$=48–8.5 and 4.5 Hz: 1H); 7.19 (mt: 3H); 7.29 (broad t, J=7.5 Hz: 2H); 7.52 (mt: 2H); 8.04 (d, J=9 Hz: 1H); 8.75 (broad s: 1H).

Methyl 4-[3-(3-chloro-6-methoxyquinolin-4-yl)-3-(R,S)-hydroxypropyl]-1-(3-phenylpropyl)piperidine-4-carboxylate A mixture of 1 g of methyl 4-[3-(3-chloro-6-methoxyquinolin-4-yl)-3-(R,S)-hydroxypropyl]piperidine-4-carboxylate, 0.58 g of 1-bromo-3-phenylpropane and 0.53 g of potassium carbonate in 50 cm³ of acetonitrile was heated for 22 hours at a temperature in the region of 75° C., with stirring and under an inert atmosphere. After cooling to a temperature in the region of 20° C., the reaction mixture was filtered and washed with acetonitrile. The filtrate was concentrated to dryness under reduced pressure (2 kPa) at a temperature in the region of 40° C.

The residue obtained was purified by chromatography under a pressure of 100 kPa of nitrogen, on a column of silica gel (particle size 70–200μ; diameter 3.5 cm; height: 40 cm), eluting with dichloromethane/methanol (95/05). Fractions 21 to 48 were combined and then concentrated to dryness under the above conditions. 0.7 g of methyl 4-[3-(3-chloro-6-methoxyquinolin-4-yl)-3-(R,S)-hydroxypropyl]-1-(3-phenylpropyl)piperidine-4-carboxylate was obtained.

¹H NMR Spectrum (300 MHz, (CD₃)₂SO-d₆, δ in ppm): from 1.20 to 2.35 and from 2.45 to 2.75 (mts: 18H in total); 3.48 (s: 3H); 3.88 (s: 3H); 5.40 (mt: 1H); 6.07 (d, J=4 Hz: 1H); from 7.20 to 7.25 (mt: 3H); 7.27 (broad t, J=7.5 Hz: 2H); 7.44 (dd, J=9 and 3 Hz: 1H); 9.96 (d, J=9 Hz: 1H); 8.14 (d, J=3 Hz: 1H); 8.66 (s: 1H).

The methyl 4-[3-(3-chloro-6-methoxyquinolin-4-yl)-3-(R,S)-hydroxypropyl]piperidine-4-carboxylate was prepared as described in Example 49.

EXAMPLE 21

Benzyl 4-[3-(3-chloro-6-methoxyquinolin-4-yl)propyl]-1-[2-(3,5-difluorophenylamino)ethyl]piperidine-4-carboxylate was prepared in the form of a yellow oil.

¹H NMR Spectrum (300 MHz, (CD₃)₂SO-d₆, δ in ppm): from 1.35 to 1.60 (mt: 4H); 1.74 (mt: 2H); from 1.95 to 2.10

(mt: 4H); 2.40 (t, J=7 Hz: 2H); from 2.60 to 2.75 (mt: 2H); 3.07 (mt: 2H); 3.15 (broad t, J=7.5 Hz: 2H); 3.94 (s: 3H); 5.05 (s: 2H); 6.05 (broad t, J=5 Hz: 1H); from 6.15 to 6.30 (mt: 3H); 7.27 (mt: 5H); 7.36 (d, J=2.5 Hz: 1H); 7.47 (dd, J=9 and 2.5 Hz: 1H); 7.98 (d, J=9 Hz: 1H); 8.68 (s: 1H).

4-[3-(3-Chloro-6-methoxyquinolin-4-yl)propyl]-1-[2-(3,5-difluorophenylamino)ethyl]piperidin-4-carboxylic Acid A mixture of 0.73 g of benzyl 4-[3-(3-chloro-6-methoxyquinolin-4-yl)propyl]-1-[2-(3,5-difluorophenylamino)ethyl]piperidine-4-carboxylate in 12 cm$^3$ of aqueous 5N hydrochloric acid was maintained at a temperature in the region of 100° C. with stirring for 3.5 hours. After cooling to about 20° C., the reaction mixture was evaporated under reduced pressure (2 kPa) at a temperature in the region of 50° C. The evaporation residue obtained was taken up in 50 cm$^3$ of acetone and was then concentrated to dryness under the same conditions as above.

The foam obtained was purified by chromatography under a pressure of 50 kPa of argon, on a column of silica gel (particle size 20–45μ; diameter 2.5 cm; height 38 cm), eluting with a mixture of chloroform/methanol/aqueous ammonia (12/3/0.5 by volume). Fractions 31 to 46 were combined and then concentrated to dryness under the same conditions as above. The powder obtained was dried in an oven under reduced pressure (0.1 kPa) at a temperature in the region of 40° C. 0.28 g of 4-[3-(3-chloro-6-methoxyquinolin-4-yl)propyl]-1-[2-(3,5-difluorophenylamino)ethyl]piperidin-4-carboxylic acid was obtained in the form of a pink-white solid melting at 210° C.

$^1$H NMR Spectrum (300 MHz, (CD$_3$)$_2$SO-d$_6$, δ in ppm) 1.45 (broad t, J=12.5 Hz: 2H); 1.56 (mt: 2H); 1.68 (mt: 2H); from 1.90 to 2.10 (mt: 4H); 2.41 (t, J=6.5 Hz: 2H); 2.66 (broad d, J=12 Hz: 2H); 3.08 (mt: 2H); 3.18 (broad t, J=7.5 Hz: 2H); 3.97 (s: 3H); 6.08 (broad t, J=4.5 Hz: 1H); from 6.15 to 6.30 (mt: 3H); 7.38 (d, J=2.5 Hz: 1H); 7.45 (dd, J=9 and 2.5 Hz: 1H); 7.96 (d, J=9 Hz: 1H: 1H); 8.68 (s: 1H).

EXAMPLE 22

4-[3-(R,S)-Hydroxy-3-(3-chloro-6-methoxyquinolin-4-yl)propyl]-1-[2-(thien-3-yl)thioethyl]piperidin-4-yl Methanol A mixture of 0.6 g of {4-[3-(3-chloro-6-methoxyquinolin-4-yl)-3-(R,S)-hydroxypropyl]piperidin-4-yl} methanol dihydrochloride, 0.34 g of 2-(2-bromo-ethylthio)thiophene, 0.95 g of potassium carbonate and 0.23 g of potassium iodide in 25 cm$^3$ of acetonitrile was heated for 17 hours at a temperature in the region of 80° C., with stirring and under an inert atmosphere. After cooling to a temperature in the region of 20° C., the reaction mixture was diluted with 30 cm$^3$ of water and was then extracted with twice 30 cm$^3$ of ethyl acetate. The organic extracts were combined, dried over magnesium sulfate, filtered and then concentrated to dryness under reduced pressure (2 kPa) at a temperature in the region of 40° C.

The oil obtained was purified by chromatography under a pressure of 50 kPa of argon, on a column of silica gel (particle size 20–45μ; diameter 3 cm; height 27 cm), eluting with a mixture of dichloromethane/methanol (93/7 by volume). The fractions containing the product were combined and then concentrated to dryness under the above conditions. The oil obtained was acidified with 2 cm$^3$ of 1N hydrochloric ether, diluted with 20 cm$^3$ of diethyl ether and stirred for 1 hour at a temperature in the region of 20° C. The solid was filtered off, washed with diethyl ether and then dried in an oven under reduced pressure (10 kPa) at a temperature in the region of 40° C. 0.28 g of 4-[3-(R,S)-hydroxy-3-(3-chloro-6-methoxyquinolin-4-yl)propyl]-1-[2-thien-3-yl)thioethyl]piperidin-4-yl} methanol hydrochloride was obtained in the form of a yellow solid melting at 118° C. and becoming pasty.

$^1$H NMR Spectrum (400 MHz, (CD$_3$)$_2$SO-d$_6$, δ in ppm) A mixture of two diastereoisomers in 50/50 approximate proportions was observed.

* from 1.35 to 2.10 (mt: 8H); from 2.85 to 3.60 (mt: 10H); 3.86 and 3.87 (2s: 3H in total); 5.41 (mt: 1H); from 5.80 to 6.30 (broad unresolved peak: 1H); 7.10 (mt: 1H); 7.29 (mt: 1H); 7.43 (dd, J=9 and 3 Hz: 1H); 7.70 (mt: 1H); 7.94 (d, J=9 Hz: 1H); 8.19 (broad s: 1H); 8.64 (s: 1H); 9.48 (unresolved peak: 1H).

{4-[3-(3-Chloro-6-methoxyquinolin-4-yl)-3-(R,S)-hydroxypropyl]piperidin-4-yl} methanol dihydrochloride was prepared as described in Example 19.

EXAMPLE 23

4-[3-(3-Chloro-6-methoxyquinolin-4-yl)propyl]-1-(3-phenylpropyl)piperidine-4-carboxamide 15.6 cm$^3$ of a 0.5N solution of aqueous ammonia in dioxane, 0.26 g of 1-hydroxybenzotriazole hydrate, 0.75 g of 1-[3-(dimethylamino)propyl]-3-ethylcarbodiimide hydrochloride and 0.55 cm$^3$ of triethylamine were added to a mixture of 0.75 g of 4-[3-(3-chloro-6-methoxyquinolin-4-yl)propyl]-1-(3-phenylpropyl)piperidine-4-carboxylic acid in the form of the sodium salt, in 20 cm$^3$ of dichloromethane. The suspension obtained was stirred for 17 hours at a temperature in the region of 20° C. The reaction mixture was diluted with 25 cm$^3$ of water and stirred, and the phases were then separated by settling. The aqueous phase was extracted with twice 25 cm$^3$ of dichloromethane and the organic extracts were combined, washed with 25 cm$^3$ of brine, dried over magnesium sulfate and then concentrated to dryness under reduced pressure (2 kPa) at a temperature in the region of 40° C. The evaporation residue obtained was purified by chromatography under a pressure of 50 kPa of argon, on a column of silica gel (particle size 20–45μ; diameter 3 cm; height 21 cm), eluting with a mixture of dichloromethane/methanol (90/10 by volume). The fractions containing the product were combined and then concentrated to dryness under the above conditions. 0.22 g of 4-[3-(3-chloro-6-methoxyquinolin-4-yl)propyl]-1-(3-phenylpropyl)piperidine-4-carboxamide was obtained in the form of a white solid melting at 160° C.

$^1$H NMR Spectrum (400 MHz, (CD$_3$)$_2$SO-d$_6$, δ in ppm) 1.33 (broad t, J=12 Hz: 2H); 1.53 (mt: 2H); 1.67 (mt: 4H); 1.98 (mt: 4H); 2.20 (t, J=7.5 Hz: 2H); from 2.40 to 2.60 (mt: 4H); 3.15 (t, J=7.5 Hz: 2H); 3.97 (s: 3H); 6.87 (s: 1H); 7.10 (s: 1H); 7.17 (mt: 1H); 7.20 (broad d, J=7.5 Hz: 2H); 7.27 (broad t, J=7.5 Hz: 2H); 7.37 (d, J=2.5 Hz: 1H); 7.45 (dd, J=9 and 2.5 Hz: 1H); 7.96 (d, J=9 Hz: 1H); 8.68 (s: 1H).

The 4-[3-(3-chloro-6-methoxyquinolin-4-yl)-propyl]-1-(3-phenylpropyl)piperidine-4-carboxylic acid dihydrochloride was prepared as described in Example 4.

EXAMPLE 24

4-[3-(3-Chloro-6,7-dimethoxyquinolin-4-yl)propyl]-1-[2-(thiophen-2-ylthio)ethyl]piperidine-4-carboxylic Acid 26 cm$^3$ of aqueous 5N sodium hydroxide and 20 cm$^3$ of methanol were added to a solution of 1.47 g of ethyl 4-[3-(3-chloro-6,7-dimethoxyquinolin-4-yl)propyl]-1-[2-(thiophen-2-ylthio)ethyl]piperidine-4-carboxylate in 20 cm$^3$ of dioxane, with stirring and at a temperature in the region of 20° C., and the mixture was then maintained at a temperature of about 70° C. for 21 hours. The reaction mixture was concentrated to dryness under reduced pressure (2 kPa) at a temperature in the region of 40° C. The residue obtained was purified by chromatography under a pressure of 50 kPa of argon, on a column of silica gel (particle size 40–63μ; mass 60 g), eluting with a mixture of dichloromethane/methanol/aqueous ammonia (12/3/0.5 by volume). Fractions 11 to 25 were combined and then concentrated to dryness under the above conditions. 1.03 g of 4-[3-(3-chloro-6,7-dimethoxy-quinolin-4-yl)propyl]-1-[2-(thiophen-2-ylthio)ethyl]-piperidine-4-carboxylic acid was obtained in the form of a white solid melting at 214° C.

$^1$H NMR Spectrum (300 MHz, $(CD_3)_2SO$-$d_6$, δ in ppm): 1.27 (very broad t, J=12 Hz: 2H); from 1.45 to 1.75 (mt: 4H); from 1.85 to 2.10 (mt: 4H); 2.44 (mt: 2H); from 2.50 to 2.65 (mt: 2H); 2.89 (broad t, J=7.5 Hz: 2H); 3.13 (mt: 2H); 3.93 (s: 3H); 3.96 (s: 3H); 7.02 (dd, J=5.5 and 3.5 Hz: 1H); 7.15 (dd, J=3.5 and 1 Hz: 1H); 7.30 (broad s: 1H); 7.38 (broad s: 1H); 7.58 (dd, J=5.5 and 1 Hz: 1H); 8.58 (s: 1H).

Ethyl 4-[3-(3-chloro-6,7-dimethoxyquinolin-4-yl)propyl]-1-[2-(thiophen-2-ylthio)ethyl]piperidine-4-carboxylate A mixture of 1.65 g of ethyl 4-[3-(3-chloro-6,7-dimethoxyquinolin-4-yl)piperidine-4-carboxylate, 1.16 g of 2-(2-bromoethylthio)thiophene, 1.63 g of potassium carbonate and 0.685 g of potassium iodide in 50 cm$^3$ of acetonitrile was stirred for 23 hours at a temperature in the region of 20° C. The suspension was filtered and the filtrate was then concentrated to dryness under reduced pressure (2 kPa) at a temperature in the region of 40° C.

The evaporation residue was taken up in 50 cm$^3$ of ethyl acetate, washed with twice 50 cm$^3$ of water and with 40 cm$^3$ of saturated aqueous sodium chloride solution, dried over magnesium sulfate, filtered and concentrated to dryness under the above conditions. The oil obtained was purified by chromatography under a pressure of 50 kPa of argon, on a column of silica gel (particle size 40–63μ; diameter 4 cm), eluting with a mixture of dichloromethane/methanol/acetonitrile (95/2.5/2.5 by volume). The fractions containing the product were combined and then concentrated to dryness under reduced pressure (2 kPa) at a temperature in the region of 40° C. 1.47 g of 4-[3-(3-chloro-6,7-dimethoxyquinolin-4-yl)propyl]-1-[2-(thiophen-2-ylthio)ethyl]piperidine-4-carboxylic acid were obtained in the form of an oil.

$^1$H NMR spectrum (300 MHz, $(CD_3)_2SO$-$d_6$, δ in ppm): 1.05 (t, J=7 Hz: 3H); 1.37 (broad t, J=12 Hz: 2H); 1.52 (mt: 2H); from 1.60 to 1.75 (mt: 2H); from 1.85 to 2.05 (mt: 4H); 2.46 (mt: 2H); 2.61 (broad d, J=12 Hz: 2H); 2.91 (mt: 2H); 3.15 (broad t, J=7.5 Hz: 2H); 3.95 (s: 3H); 3.97 (s: 3H); 4.00 (q, J=7 Hz: 2H); 7.04 (dd, J=5.5 and 3.5 Hz: 1H); 7.17 (dd, J=3.5 and 1 Hz: 1H); 7.31 (broad s: 1H); 7.40 (broad s: 1H); 7.60 (dd, J=5.5 and 1 Hz: 1H); 8.61 (s: 1H).

Ethyl 4-[3-(3-chloro-6,7-dimethoxyquinolin-4-yl)piperidine-4-carboxylate 3 cm$^3$ of trifluoroacetic acid were added dropwise to a mixture of 2.05 g of ethyl 4-[3-(3-chloro-6,7-dimethoxyquinolin-4-yl)propyl]-1-(tert-butyloxycarbonyl)piperidine-4-carboxylate in 20 cm$^3$ of dichloromethane, with stirring and at a temperature in the region of 20° C. After 2 hours, the reaction mixture was concentrated to dryness under reduced pressure (2 kPa) at a temperature in the region of 40° C. The residue was taken up in 20 cm$^3$ of water and 10 cm$^3$ of ethyl acetate, and then extracted with twice 10 cm$^3$ of aqueous 1N hydrochloric acid solution. The aqueous phase was basified with an aqueous 30% sodium hydroxide solution until the pH was about 10, and then extracted with 3 times 30 cm$^3$ of ethyl acetate. The organic extracts were combined, dried over magnesium sulfate, filtered and then concentrated to dryness as above. 1.65 g of ethyl 4-[3-(3-chloro-6,7-dimethoxyquinolin-4-yl)piperidine-4-carboxylate were obtained in the form of a yellow oil.

Mass Spectrum: EI m/z=420 M$^+$ m/z=364 $C_{19}H_{23}ClNO_4^+$ m/z=264 $C_{14}H_{15}ClNO_2^+$ m/z=237 $C_{12}H_{12}ClNO_2^+$ base peak m/z=184 $C_{10}H_{18}NO_2^+$ Ethyl 4-[3-(3-chloro-6,7-dimethoxyquinolin-4-yl)propyl]-1-(tert-butyloxycarbonyl)piperidine-4-carboxylate 21 cm$^3$ of 0.5M 9-borabicyclo[3.3.1]nonane solution were cooled to a temperature in the region of 0° C. and 2.61 g of ethyl 4-allyl-1-(tert-butyloxycarbonyl)piperidine-4-carboxylate in 26 cm$^3$ of tetrahydrofuran were added dropwise, with stirring and under an inert atmosphere, while maintaining the temperature at about 0° C. After the addition, the temperature of the mixture was returned to about 20° C. The solution obtained was stirred for a further 4 hours at this temperature, followed by addition of 37 cm$^3$ of dioxane, 0.19 g of palladiumdiphenylphosphinoferrocene chloride, 3.05 g of 4-bromo-3-fluoro-6-methoxyquinoline and 5.58 g of tribasic potassium phosphate. After stirring for 24.75 hours at a temperature in the region of 60° C., the reaction mixture was cooled to about 20° C. and filtered, and the filtrate was then concentrated to dryness under reduced pressure (2 kPa) at a temperature in the region of 40° C.

The residue obtained was taken up in 100 cm$^3$ of ethyl acetate and 100 cm$^3$ of water, the phases were separated by settling and the organic phase was then washed with 100 cm$^3$ of saturated sodium chloride solution. The organic phase was dried over magnesium sulfate, filtered and concentrated to dryness under reduced pressure (2 kPa) at a temperature in the region of 40° C. The oil obtained was purified by chromatography, under a pressure of 50 kPa of argon, on a column of silica gel (particle size 40–63μ; volume 690 cm$^3$), eluting with a dichloromethane/methanol/acetonitrile mixture (98/1/1 by volume). The fractions containing the product were combined and then concentrated to dryness according to the same conditions as above. 2.16 g of ethyl 4-[3-(3-chloro-6,7-dimethoxyquinolin-4-yl)propyl]-1-(tert-butyloxycarbonyl)piperidine-4-carboxylate were obtained in the form of a yellow gel.

$^1$H NMR Spectrum (300 MHz, $(CD_3)_2SO$-$d_6$, δ in ppm) 1.06 (t, J=7 Hz: 3H); from 1.25 to 1.45 (mt: 2H); 1.39 (s: 9H); 1.53 (mt: 2H); 1.69 (mt: 2H); 1.93 (broad d, J=13.5 Hz: 2H), 2.82 (unresolved peak: 2H); 3.14 (broad t, J=7.5 Hz: 2H); 3.69 (broad d, J=13.5 Hz: 2H); 3.94 (s: 3H); 3.97 (s: 3H); 4.03 (q, J=7 Hz: 2H); 7.31 (broad s: 1H); 7.40 (broad s: 1H); 8.61 (s: 1H).

4-Bromo-3-chloro-6,7-dimethoxyquinoline 19 g of triphenylphosphine dibromide were added to a solution of 5.39 g of 3-chloro-4-hydroxy-6,7-dimethoxyquinoline in 270 cm$^3$ of acetonitrile, with stirring and at a temperature in the region of 20° C. The reaction mixture was heated at about 80° C. for 8.25 hours. After cooling to a temperature in the region of 20° C., the insoluble material was filtered off. 5.67 g of 4-bromo-3-chloro-6,7-dimethoxyquinoline were obtained in the form of a gray solid.

Mass spectrum: DCI m/z=302 MH$^+$

3-Chloro-4-hydroxy-6,7-dimethoxyquinoline 5.45 g of N-chlorosuccinimide were added to a solution of 6,7-dimethoxyquinolin-4-ol in 300 cm$^3$ of acetic acid, with stirring and at a temperature in the region of 20° C. The reaction mixture was heated at a temperature in the region of 50° C. for 6 hours. After cooling to about 20° C. and stirring for 18 hours at this same temperature, the reaction mixture was concentrated to dryness under reduced pressure (2 kPa) at a temperature in the region of 40° C. One hundred cm³ of sodium hydrogen carbonate solution were added dropwise to the evaporation residue and the suspension was then stirred for 24 hours in the region of 20° C. The insoluble material was filtered off and then dried in an oven under reduced pressure (20 Pa). 5.39 g of 3-chloro-4-hydroxy-6,7-dimethoxyquinoline were obtained in the form of a dark green solid.

Mass spectrum: DCI m/z=240 MH⁺

6,7-Dimethoxy-4-hydroxyquinoline

A mixture of 9.24 g of 4-hydroxy-6,7-dimethoxyquinoline-3-carboxylic acid in 185 cm³ of diphenyl ether was maintained, with mechanical stirring, at a temperature in the region of 250° C. for 1.3 hours. After cooling the reaction mixture to about 20° C., 100 cm³ of diisopropyl ether were added. The suspension was stirred for 8 hours and filtered, and the filter cake was washed with 3 times 100 cm³ of diisopropyl ether. 7.96 g of 6,7-dimethoxyquinolin-4-ol were obtained in the form of a brown solid.

Infra-red spectrum (KBr): 3242; 1605; 1548; 1500; 1273; 1239; 1220; 1075 and 822 cm⁻¹

4-Hydroxy-6,7-dimethoxyquinoline-3-carboxylic Acid 10.2 g of phosphorus pentoxide were added cautiously, with mechanical stirring, to a mixture of 21.1 g of diethyl 2-[(3,4-dimethoxyphenylamino)methylene]malonate in 42 cm³ of nitrobenzene. The reaction mixture was maintained at a temperature in the region of 150° C. for 4 hours. After cooling to about 20° C. and stirring for 18 hours at this same temperature, 14 cm³ of water were added dropwise and the reaction mixture was then heated to about 110° C. for 7 hours. After cooling to a temperature in the region of 20° C., 42 cm³ of ethyl acetate were added. The suspension was stirred under these conditions for 18 hours, the phases were then separated by settling, the organic phase was filtered and the filter cake was washed with 3 times 40 cm³ of ethyl acetate, 40 cm³ of ethanol and 40 cm³ of water. 9.25 g of 4-hydroxy-6,7-dimethoxyquinoline-3-carboxylic acid were obtained in the form of a cream-colored solid.

Infra-red spectrum (KBr): 2842; 1673; 1631; 1590; 1503; 1437; 1279; 1220; 1006; 807; 586 and 357 cm⁻.

Diethyl 2-[(3,4-dimethoxyphenylamino)methylene] malonate

A mixture of 10 g of 3,4-dimethoxyaniline in 13.2 cm³ of diethyl ethoxymethylenemalonate was stirred for 1.5 hours at a temperature in the region of 110° C. After cooling to about 20° C., the reaction mixture was concentrated to dryness under reduced pressure (2 kPa) at a temperature in the region of 50° C. 21.1 g of diethyl 2-[(3,4-dimethoxyphenylamino)methylene]malonate were obtained in the form of a brown solid.

Mass spectrum: DCI m/z=324 MH⁺

The ethyl 4-allyl-1-(tert-butyloxycarbonyl)-piperidine-4-carboxylate was prepared as described in Example 1.

EXAMPLE 25

4-[3-(3-Chloro-6-methoxyquinolin-4-yl)-3-(R,S)-hydroxypropyl]-1-[2-(2,5-difluorophenylthio)ethyl] piperidine-4-carboxylic Acid Monohydrochloride 5 cm³ of aqueous 5N sodium hydroxide were added to a solution of 0.6 g of (R,S)-3-(3-chloro-6-methoxyquinolin-4-yl)-9-[2-(2,5-difluorophenylthio)ethyl]-2-oxa-9-azaspiro [5.5]undecan-1-one in 50 cm³ of acetone, with stirring and at a temperature in the region of 20° C. After 2 hours, the reaction mixture was concentrated to dryness under reduced pressure (2 kPa) at a temperature in the region of 40° C. The evaporation residue was slurried in 10 cm³ of diethyl ether and filtered, and the filter cake was washed with diethyl ether and then dried in an oven under reduced pressure (10 Pa) at a temperature in the region of 50° C.

The solid was taken up in water and acidified with aqueous 1N hydrochloric acid solution until the pH was equal to 3. Dichloromethane was added at a temperature in the region of 20° C. with moderate stirring and the solid was then filtered off. 0.32 g of 4-[3-(3-chloro-6-methoxyquinolin-4-yl)-3-(R,S)-hydroxypropyl]-1-[2-(2,5-difluorophenylthio)ethyl]piperidine-4-carboxylic acid monohydrochloride was obtained in the form of a white solid.

¹H NMR Spectrum (300 MHz, (CD₃)₂SO-d₆, δ in ppm): from 1.30 to 2.35 (mt: 8H); 2.84 (unresolved peak: 2H); from 3.05 to 3.70 (mt: 6H); 3.90 (broad s: 3H); 5.43 (unresolved peak: 1H); 6.16 (unresolved peak: 1H); 7.14 (unresolved peak: 1H); 7.33 (unresolved peak: 1H); 7.46 (mt: 2H); 7.96 (broad d, J=9 Hz: 1H); 8.16 (broad s: 1H); 8.67 (broad s: 1H); from 10.20 to 10.60 (broad unresolved peak: 1H).

3-(3-Chloro-6-methoxyquinolin-4-yl)-9-[2-(2,5-difluorophenylthio)ethyl]-2-oxa-9-azaspiro[5.5]undecan-1-one A mixture of 1.75 g of ethyl 4-[3-(3-chloro-6-methoxyquinolin-4-yl)-(R,S)-propyl]piperidine-4-carboxylate dihydrochloride, 0.95 g of 2-(2-bromoethylthio)-1,4-difluorobenzene, 0.62 g of potassium iodide and 3.11 g of potassium carbonate in 30 cm³ of acetonitrile and 20 cm³ of dimethylformamide was heated with stirring for 18 hours at a temperature in the region of 85° C. After cooling to about 20° C., the reaction mixture was filtered through Celite and the filtrate was then concentrated to dryness under reduced pressure (2 kPa) at a temperature in the region of 40° C.

The residue obtained was taken up in water and diethyl ether. The organic phase was dried over magnesium sulfate, filtered and then concentrated to dryness as above. The residue obtained was purified by chromatography under atmospheric pressure, on a column of silica gel (particle size 70–200μ; diameter 4 cm), eluting with a dichloromethane/methanol mixture (97.5/2.5 by volume). The fractions containing the product were combined and then concentrated to dryness under the above conditions. 0.6 g of 3-(3-chloro-6-methoxyquinolin-4-yl)-9-[2-(2,5-difluorophenylthio)ethyl]-2-oxa-9-azaspiro[5.5]undecan-1-one was obtained.

Mass spectrum: EI m/z=532 M⁺ m/z=373 $C_{20}H_{22}ClN_2O_3^+$ base peak

The 2-(2-bromoethylthio)-1,4-difluorobenzene was prepared as described in Example 14.

The methyl 4-[3-(3-chloro-6-methoxyquinolin-4-yl)-3-(R,S)-hydroxypropyl]piperidine-4-carboxylate was prepared as described in Example 49.

EXAMPLE 26

4-[3-(3-chloro-6-methoxyquinolin-4-yl)-3-(R,S)-fluoropropyl]-1-[2-(3,5-difluorophenoxy)ethyl]piperidine-4-carboxylate A mixture of 0.4 g of methyl 4-[3-(3-chloro-6-methoxyquinolin-4-yl)-3-(R,S)-fluoropropyl]-1-[2-(3,5-difluorophenoxy)ethyl]piperidine-4-carboxylate in 6.6 cm³ of aqueous 5N hydrochloric acid was maintained at a temperature in the region of 100° C. with stirring for 6 hours.

After cooling to about 20° C., the reaction mixture was stirred for 20 hours at this same temperature and then concentrated to dryness under reduced pressure (2 kPa) at a temperature in the region of 40° C. The residue was taken up in a dichloromethane/methanol mixture (90/10 by volume) and was then concentrated to dryness again under the above conditions.

The evaporation residue was purified by chromatography under a pressure of 60 kPa of argon, on a column of silica gel (particle size 40–60μ; diameter 2.5 cm; height 41 cm), eluting with a dichloromethane/methanol/28% aqueous ammonia mixture (83/15/2 by volume) and collecting 30-cm³ fractions. Fractions 16 to 22 were combined and then concentrated to dryness under the above conditions. The residue was slurried in 10 cm³ of diisopropyl ether, filtered and dried. 0.21 g of 4-[3-(3-chloro-6-methoxyquinolin-4-yl)-3-(R,S)-fluoropropyl]-1-[2-(3,5-difluorophenoxy)ethyl]-piperidine-4-carboxylic acid was obtained in the form of an off-white solid melting at 205° C.

$^1$H NMR Spectrum (300 MHz, (CD$_3$)$_2$SO-d$_6$, δ in ppm) from 1.20 to 1.70 (mt: 3H); from 1.80 to 2.40 (mt: 7H); from 2.30 to 2.80 (mt: 2H); 2.61 (t, J=6 Hz: 2H); 3.92 (s: 3H); 4.17 (t, J=6 Hz: 2H); 6.36 (d mt, J$_{HF}$=48 Hz: 1H); from 6.65 to 6.85 (mt: 3H); 7.51 (dd, J=9 and 2.5 Hz: 1H); 7.55 (broad s: 1H); 8.02 (d, J=9 Hz: 1H); 8.74 (s: 1H).

Methyl 4-[3-(3-chloro-6-methoxyquinolin-4-yl)-3-(R,S)-fluoropropyl]-1-[2-(3,5-difluorophenoxy)ethyl]-piperidine-4-carboxylate 0.4 cm³ of diethylaminosulfur trifluoride was added to a solution of 1.1 g of methyl 4-[3-(3-chloro-6-methoxyquinolin-4-yl)-3-(R,S)-hydroxypropyl]-1-[2-(3,5-difluorophenoxy)ethyl]piperidine-4-carboxylate in 50 cm³ of dichloromethane, with stirring and under an inert atmosphere, at a temperature in the region of −10° C. After stirring for 4 hours at a temperature in the region of 20° C., 0.4 cm³ of diethylaminosulfur trifluoride was added to the reaction mixture and the mixture was then stirred for 20 hours at this same temperature. 20 cm³ of saturated aqueous sodium hydrogen carbonate solution were added. The aqueous phase was extracted with 25 cm³ of dichloromethane. The organic phase was washed with twice 25 cm³ of aqueous 10% (by weight) sodium chloride solution, dried over magnesium sulfate and then concentrated to dryness under reduced pressure (2 kPa) at a temperature in the region of 40° C.

The oil obtained was purified by chromatography under a pressure of 100 kPa of argon, on a column of silica gel (particle size 40–60μ; diameter 3.5 cm; height: 35 cm), eluting with a dichloromethane/methanol mixture (97/3) and collecting 35-cm³ fractions. Fractions 20 to 21 were combined and then concentrated to dryness under the above conditions. 0.62 g of methyl 4-[3-(3-chloro-6-methoxyquinolin-4-yl)-3-(R,S)-fluoropropyl]-1-[2-(3,5-difluorophenoxy)ethyl]-piperidine-4-carboxylate was obtained in the form of an orange-colored oil.

Infra-red spectrum: (CH$_2$Cl$_2$): 2953; 1725; 1622; 1599; 1504; 1466; 1234; 1152; 1117 and 837 cm$^{-1}$.

Methyl 4-[3-(3-chloro-6-methoxyquinolin-4-yl)-3-(R,S)-hydroxypropyl]-1-[2-(3,5-difluorophenoxy)ethyl]-piperidine-4-carboxylate 0.47 cm³ of thionyl chloride was added dropwise, with stirring and under an inert atmosphere, to a mixture of 1.1 g of 3-(3-chloro-6-methoxyquinolin-4-yl)-9-[2-(3,5-difluorophenoxy)ethyl]-2-oxa-9-azaspiro[5.5]undecan-1-one in 20 cm³ of methanol cooled to −20° C., and the mixture was then stirred for 24 hours at a temperature in the region of 20° C. The reaction mixture was concentrated to dryness under reduced pressure (2 kPa) at a temperature in the region of 40° C. The residue was taken up in 30 cm³ of ethyl acetate and 15 cm³ of water. After addition of 5 g of potassium carbonate and vigorous stirring for 5 minutes, the mixture was allowed to settle and the organic phase was separated out and washed with 3 times 15 cm³ of aqueous 10% (by weight) sodium chloride solution. After drying over magnesium sulfate and then filtration, the organic solution was concentrated to dryness under reduced pressure (2 kPa) at a temperature in the region of 40° C. 1.12 g of methyl 4-[3-(3-chloro-6-methoxyquinolin-4-yl)-3-(R,S)-hydroxypropyl]-1-[2-(3,5-difluorophenoxy)ethyl]-piperidine-4-carboxylate were obtained in the form of a brown lacquer.

Infra-red spectrum (CCl$_4$): 3615; 2952; 1732; 1622; 1600; 1466; 1233; 1154; 1117; 841 and 671 cm$^{-1}$.

3-(3-Chloro-6-methoxyquinolin-4-yl)-9-[2-(3,5-difluorophenoxy)ethyl]-2-oxa-9-azaspiro[5.5]undecan-1-one A mixture of 1 g of methyl 4-[3-(3-chloro-6-methoxyquinolin-4-yl)-3-(R,S)-hydroxypropyl]piperidine-4-carboxylate, 0.8 g of 1-(2-bromoethoxy)-3,5-difluorobenzene and 0.42 g of potassium carbonate in 45 cm³ of acetonitrile was maintained at a temperature of 80° C. with stirring and under an argon atmosphere for 20 hours. The suspension was filtered, the insoluble material was washed with ethyl acetate and the filtrate was then concentrated to dryness under reduced pressure (2 kPa) at a temperature in the region of 40° C. The residue was purified by chromatography under a pressure of 100 kPa of argon, on a column of silica gel (particle size 40–60μ; diameter 3.5 cm; height: 38 cm), eluting with a dichloromethane/methanol mixture (97/4 by volume) and collecting 35-cm³ fractions. Fractions 9 to 20 were combined and then concentrated to dryness under the above conditions. 1.1 g of 3-(3-chloro-6-methoxyquinolin-4-yl)-9-[2-(3,5-difluorophenoxy)ethyl]-2-oxa-9-azaspiro[5.5]undecan-1-one were obtained.

Infra-red spectrum (CCl$_4$): 2940; 1735; 1622; 1600; 1503; 1467; 1233; 1153; 1117; 841 and 671 cm$^{-1}$.

The methyl 4-[3-(3-chloro-6-methoxyquinolin-4-yl)-3-hydroxypropyl]piperidine-4-carboxylate was prepared as described in Example 49.

The 1-(2-bromoethoxy)-3,5-difluorobenzene may be obtained by applying the method described in Example 16.

EXAMPLE 27

4-[3-(3-Chloro-6-methoxyquinolin-4-yl)propyl]-1-[2-(3,5-difluorophenoxy)ethyl]piperidine-4-carboxamide 13.4 cm³ of a 0.5N solution of aqueous ammonia in dioxane, 0.229 g of 1-hydroxybenzotriazole hydrate, 0.64 g of 1-[3-(dimethylamino)propyl]-3-ethylcarbodiimide hydrochloride and 0.46 cm³ of triethylamine were added, with stirring and under an inert atmosphere, to a mixture of 0.69 g of 4-[3-(3-chloro-6-methoxyquinolin-4-yl)propyl]-1-[2-(3,5-difluorophenoxy)ethyl]piperidine-4-carboxylic acid in 30 cm³ of dichloromethane. The suspension obtained was stirred for 17 hours at a temperature in the region of 20° C. The reaction mixture was diluted with 50 cm³ of water, stirred and the phases were separated by settling. The aqueous phase was extracted with twice 25 cm³ of dichloromethane and the organic extracts were combined, washed with 25 cm³ of saturated aqueous sodium chloride solution, dried over magnesium sulfate and then concentrated to dryness under reduced pressure (2 kPa) at a temperature in the region of 40° C. The solid was taken up in 20 cm³ of diisopropyl ether, stirred and then filtered. 0.52 g of 4-[3-(3-chloro-6-methoxyquinolin-4-yl)propyl]-1-[2-(3,5-difluorophenoxy)ethyl]piperidine-4-carboxamide was obtained.

$^1$H NMR Spectrum (300 MHz, (CD$_3$)$_2$SO-d$_6$, δ in ppm) 1.34 (broad t, J=12.5 Hz: 2H); 1.54 (mt: 2H); 1.66 (mt: 2H); 2.02 (broad d, J=12.5 Hz: 2H); 2.12 (broad t, J=11 Hz: 2H); from 2.55 to 2.75 (mt: 4H); 3.16 (broad t, J=7.5 Hz: 2H); 3.97 (s: 3H); 4.08 (t, J=6 Hz: 2H); from 6.65 to 6.85 (mt: 3H); 6.91 (broad s: 1H); 7.15 (broad s: 1H); 7.37 (d, J=3 Hz: 1H); 7.45 (dd, J=9 and 3 Hz: 1H); 7.97 (d, J=9 Hz: 1H); 8.68 (s: 1H).

The 4-[3-(3-chloro-6-methoxyquinolin-4-yl)-propyl]-1-[2-(3,5-difluorophenoxy)ethyl]piperidine-4-carboxylic acid was prepared as described in Example 2.

EXAMPLE 28

Sodium Salt of 4-[3-(3-chloro-6-methoxyquinolin-4-yl) propyl]-1-(cinnamyl)piperidine-4-carboxylic Acid A mixture of 0.72 g of ethyl 4-[3-(3-chloro-6-methoxyquinolin-4-yl)propyl]-1-(cinnamyl)piperidine-4-carboxylate in 14 cm³ dioxane, 14 cm³ of methanol and 14 cm³ of aqueous 5N sodium hydroxide solution was stirred at a temperature in the region of 20° C. After 2 hours, a further 14 cm³ of aqueous 5N sodium hydroxide solution were added, followed by a further 14 cm³ after a further 18 hours. The reaction mixture was maintained at a temperature in the region of 70° C. for 21 hours. After cooling to about 20° C., the reaction mass was concentrated to dryness under reduced pressure (2 kPa) at a temperature in the region of 40° C. The residue obtained was taken up in 15 cm³ of distilled water, filtered and then dried in the open air for 18 hours. 0.49 g of the sodium salt of sodium salt of 4-[3-(3-chloro-6-methoxyquinolin-4-yl)propyl]-1-(cinnamyl)piperidine-4-carboxylic acid was obtained in the form of a white solid melting at about 230° C.

$^1$H NMR Spectrum (300 MHz, (CD$_3$)$_2$SO-d$_6$, δ in ppm): 1.16 (very broad t, J=12 Hz: 2H); from 1.45 to 1.70 (mt: 4H); from 1.95 to 2.20 (mt: 4H); from 2.45 to 2.60 (mt: 2H); 2.99 (d, J=6.5 Hz: 2H); 3.14 (broad t, J=7 Hz: 2H); 3.99 (s: 3H); 6.28 (dt, J=15.5 and 6.5 Hz: 1H); 6.48 (d, J=15.5 Hz: 1H); 7.24 (broad t, J=7.5 Hz: 1H); 7.33 (broad t, J=7.5 Hz: 2H); from 7.40 to 7.50 (mt: 4H); 7.95 (d, J=9 Hz: 1H); 8.66 (s: 1H).

Ethyl 4-[3-(3-chloro-6-methoxyquinolin-4-yl)propyl]-1-(cinnamyl)piperidine-4-carboxylate A mixture of 1 g of ethyl 4-[3-(3-chloro-6-methoxyquinolin-4-yl)propyl]piperidine-4-carboxylate, 0.551 g of cinnamyl bromide, 0.42 g of potassium iodide and 1.05 g of potassium carbonate in 20 cm³ of acetonitrile was stirred for 18.5 hours at a temperature in the region of 20° C. The reaction mixture was filtered and the insoluble material was rinsed with 20 cm³ of acetonitrile and with twice 30 cm³ of dichloromethane. The filtrate was dried over magnesium sulfate, filtered and then concentrated to dryness under reduced pressure (2 kPa) at a temperature in the region of 40° C.

The residue obtained was purified by chromatography under a pressure of 50 kPa of argon, on a column of silica gel (particle size 40–63μ; diameter 2.5 cm; mass 35 g), eluting with a cyclohexane/ethyl acetate mixture (90/10 by volume) and then with a cyclohexane/ethyl acetate mixture (60/40 by volume) and collecting 20-cm³ fractions. The fractions containing the product were combined and then concentrated to dryness under the conditions described above. 0.72 g of ethyl 4-[3-(3-chloro-6-methoxyquinolin-4-yl)propyl]-1-(3-phenylallyl)piperidine-4-carboxylate was obtained in the form of a viscous orange oil.

Mass spectrum: EI m/z=506 M$^+$
m/z=415 C$_{23}$H$_{28}$ClN$_2$O$_3$$^+$
m/z=300 C$_{19}$H$_{26}$NO$_2$$^+$
m/z=117 C$_9$H$_9$$^+$ base peak The ethyl 4-[3-(3-chloro-6-methoxyquinolin-4-yl)propyl] piperidine-4-carboxylate was prepared in the form of the monohydrochloride in Example 5.

EXAMPLE 29

4-[3-(3-Chloro-6-methoxyquinolin-4-yl)propyl]-1-[2-(3, 5-difluorophenoxy)ethyl]piperidine-4-acetic Acid A mixture of 0.18 g of methyl 4-[3-(3-chloro-6-methoxyquinolin-4-yl)propyl]-1-[2-(3,5-difluorophenoxy) ethyl]piperidin-4-yl}carboxylate in 10 cm³ of dioxane, 10 cm³ of methanol and 0.99 cm³ of aqueous 5N sodium hydroxide solution was stirred at a temperature in the region of 75° C. for 17 hours. After cooling to about 45° C., the reaction mixture was concentrated to dryness under a pressure gradually reduced to 9 kPa at a temperature in the region of 40° C. The pasty residue was taken up in 3 cm³ of chloroform/methanol/aqueous ammonia (12/3/0.5 by volume) and the organic phase was then purified by chromatography under atmospheric pressure, on a column of silica gel (Bond Elut; particle size 70–200μ; diameter 2 cm; mass 5 g), eluting with a chloroform/methanol/aqueous ammonia mixture (12/3/0.5 by volume).

The fractions containing the product were combined and then concentrated to dryness under reduced pressure (5 kPa) at a temperature in the region of 40° C. and the product was dried in an oven under reduced pressure (50 kPa) at a temperature in the region of 50° C. 0.15 g of 4-[3-(3-chloro-6-methoxyquinolin-4-yl)propyl]-1-[2-(3,5-difluorophenoxy)ethyl]piperidine-4-acetic acid was obtained.

$^1$H NMR Spectrum (500 MHz, (CD$_3$)$_2$SO-d$_6$, δ in ppm): 1.39 (mt: 2H); 1.50 (mt: 2H); 1.61 (mt: 4H); 2.15 (broad s: 2H); from 2.30 to 2.60 (mt: 4H); 2.63 (broad t, J=5.5 Hz: 2H); 3.12 (unresolved peak: 2H); 3.94 (s: 3H); 4.06 (broad t, J=5.5 Hz: 2H); from 6.65 to 6.75 (mt: 3H); 7.36 (broad s: 1H); 7.41 (broad d, J=9 Hz: 1H); 7.93 (d, J=9 Hz: 1H); 8.64 (s: 1H).

Methyl {4-[3-(3-chloro-6-methoxyquinolin-4-yl)propyl]-1-[2-(3,5-difluorophenoxy)ethyl]piperidin-4-yl}acetate A mixture of 0.35 g of methyl {4-[3-(3-chloro-6-methoxyquinolin-4-yl)propyl]piperidin-4-yl}acetate, 0.318 g of 1-(2-bromoethoxy)-3,5-difluorobenzene, 0.15 g of potassium iodide and 0.62 g of potassium carbonate in 20 cm³ of acetonitrile was stirred for 18 hours at a temperature in the region of 70° C. After cooling to about 20° C., the reaction mixture was filtered through a silica cartridge (Bond Elut) and then rinsed with twice 2 cm³ of acetonitrile. The organic phase was concentrated to dryness under reduced pressure (2.4 kPa) at a temperature in the region of 45° C.

The evaporation residue obtained was dissolved in 12 cm³ of dimethylformamide and then purified by injection of 4 times 3 cm³ per chromatography onto an SCX silica gel cartridge (mass 1 g), eluting with a gradient of from pure methanol to a mixture of 4N ammoniacal methanol. The fractions containing the product were combined and then concentrated to dryness under compressed air at a temperature in the region of 45° C. The evaporation residue obtained was taken up in dichloromethane and dried in the open air for 48 hours and then oven-dried under reduced pressure (10 kPa) at a temperature in the region of 50° C. 0.195 g of methyl {4-[3-(3-chloro-6-methoxyquinolin-4-yl)propyl]-1-[2-(3,5-difluorophenoxy)ethyl]piperidin-4-yl}acetate was obtained.

$^1$H NMR Spectrum (500 MHz, $(CD_3)_2SO-d_6$, at a temperature of 353 K, δ in ppm): from 1.45 to 2.70 (mt: 16H); 3.17 (mt: 2H); 3.51 (s: 3H); 3.96 (s: 3H); 4.24 (unresolved peak: 2H); from 6.60 to 6.70 (mt: 3H); 7.38 (broad s: 1H); 7.42 (broad d, J=9 Hz: 1H); 7.94 (d, J=9 Hz: 1H); 8.62 (broad s: 1H).

Methyl {4-[3-(3-chloro-6-methoxyquinolin-4-yl)propyl]piperidin-4-yl}acetate

A mixture of 17 g of tert-butyl 4-[3-(3-chloro-6-methoxyquinolin-4-yl)propyl]-4-cyanomethylpiperidine-1-carboxylate in 100 cm$^3$ of aqueous 12N hydrochloric acid (concentrated to dryness) was gradually brought to a temperature in the region of 100° C. with stirring over 18 hours. The reaction mixture was concentrated to dryness under reduced pressure (2 kPa) at a temperature in the region of 60° C.

The oil obtained was taken up in acetone and the precipitate was filtered off and washed with acetone. 20.4 g of {4-[3-(3-chloro-6-methoxyquinolin-4-yl)propyl]piperidin-4-yl}acetic acid dihydrochloride were obtained in the form of a grayish solid melting at 181° C. and becoming sticky. The above product was dissolved in 400 cm$^3$ of methanol and 10 cm$^3$ of dry concentrated sulfuric acid, stirred and heated in the region of 100° C. for 1.5 hours. The reaction mixture was concentrated to dryness under reduced pressure (2 kPa) at a temperature in the region of 50° C.

The oil obtained was taken up in 300 cm$^3$ of water with stirring, neutralized with sodium hydrogen carbonate, basified with potassium carbonate and extracted with ethyl acetate. The organic phase was separated out after settling has taken place, washed with water, dried over magnesium sulfate, filtered and then concentrated to dryness under reduced pressure (2 kPa) at a temperature in the region of 40° C. The aqueous phase was basified to pH 8 with aqueous 5N sodium hydroxide solution and extracted with ethyl acetate, the phases were separated by settling and the organic extracts were washed, dried with magnesium sulfate and concentrated to dryness according to the conditions described above.

All the organic evaporation residues were combined and purified by chromatography under a pressure of 50 kPa of argon, on a column of silica gel (particle size 20–43μ; mass 200 g), eluting with a dichloromethane/methanol/aqueous ammonia mixture (40/5/0.5 by volume). The fractions containing the product were combined and concentrated to dryness as under the above conditions. 7.6 g of methyl {4-[3-(3-chloro-6-methoxyquinolin-4-yl)propyl]piperidin-4-yl}acetate were obtained in the form of orange-colored oil.

Mass spectrum: EI m/z=390 M$^+$ m/z=207 $C_{11}H_{10}ClNO^+$
m/z=184 $C_{10}H_{18}NO_2^+$ tert-Butyl 4-[3-(3-chloro-6-methoxyquinolin-4-yl)propyl]-4-cyanomethylpiperidine-1-carboxylate A mixture of 30.58 g of tert-butyl 4-[3-(3-chloro-6-methoxyquinolin-4-yl)propyl]-4-methanesulfonyloxymethylpiperidine-1-carboxylate and 15.1 g of potassium cyanide in 436 cm$^3$ of dimethyl sulfoxide was heated with stirring at a temperature in the region of 100° C. for 48 hours and was then stirred in the region of 20° C. for 24 hours. 2 000 cm$^3$ of ice-water were added to the reaction mixture, the suspension was stirred for 1 hour at a temperature in the region of 20° C. and then filtered, and the filter cake was washed with 3 times 200 cm$^3$ of water and then dried in the open air.

The residue was purified by chromatography under a pressure of 50 kPa of argon, on a column of silica gel (particle size 20–45μ; diameter 9 cm; height 45 cm), eluting with a cyclohexane/ethyl acetate mixture (90/10 by volume). Fractions 40 to 100 were combined and concentrated to dryness under reduced pressure (2 kPa) at a temperature in the region of 45° C. 19.25 g of tert-butyl 4-[3-(3-chloro-6-methoxyquinolin-4-yl)propyl]-4-cyanomethylpiperidine-1-carboxylate were obtained in the form of a yellow solid melting at 160° C.

Infra-red spectrum (KBr): 2968; 2924; 2235; 1684; 1622; 1505; 1414; 1230; 1166; 1151; 826 and 738 cm$^{-1}$.

tert-Butyl 4-[3-(3-chloro-6-methoxyquinolin-4-yl)propyl]-4-methanesulfonyloxymethylpiperidine-1-carboxylate A mixture of 24.8 g of tert-butyl 4-[3-(3-chloro-6-methoxyquinolin-4-yl)propyl]-4-hydroxymethylpiperidine-1-carboxylate in 400 cm$^3$ of dichloromethane and 12.9 cm$^3$ of triethylamine was cooled to about 0° C. with stirring and under an inert atmosphere. Methanesulfonyl chloride, dissolved beforehand in 125 cm$^3$ of dichloromethane, was added dropwise and the reaction mixture was then stirred for 18 hours at a temperature in the region of 20° C. 200 cm$^3$ of water were added to the reaction mass, followed by a further addition of 3 000 cm$^3$ of water. The phases were separated by settling and the aqueous phase was extracted with 200 cm$^3$ of dichloromethane. The organic extracts were washed with 300 cm$^3$ of aqueous sodium chloride solution, dried over sodium sulfate, filtered and then concentrated to dryness under reduced pressure (2 kPa) at a temperature in the region of 45° C. 30.6 g of tert-butyl 4-[3-(3-chloro-6-methoxyquinolin-4-yl)propyl]-4-methanesulfonyloxymethylpiperidine-1-carboxylate were obtained in the form of an orange-colored oil.

Mass spectrum: DCI m/z 507 MH$^+$
m/z=431 M-$CH_3SO_3$
m/z=397 431-Cl
m/z=375 431-tBu
m/z=331 431-BOC The 1-(2-bromoethoxy)-3,5-difluorobenzene was prepared as described in Example 16.

The tert-butyl 4-[3-(3-chloro-6-methoxyquinolin-4-yl)propyl]-4-hydroxymethylpiperidine-1-carboxylate was prepared as described in Example 19.

EXAMPLE 30

{4-[3-(3-chloro-6-methoxyquinolin-4-yl)propyl]-1-[2-(2,5-difluorophenoxy)ethyl]piperidin-4-yl}acetic Acid A mixture of 0.35 g of methyl {4-[3-(3-chloro-6-methoxyquinolin-4-yl)propyl]-1-[2-(2,5-difluorophenoxy)ethyl]piperidin-4-yl}acetate in 10 cm$^3$ of dioxane, 10 cm$^3$ of methanol and 1.91 cm$^3$ of aqueous 5N sodium hydroxide solution was stirred at a temperature in the region of 75° C. for 17 hours. After cooling to about 45° C., the reaction mixture was concentrated to dryness under a pressure gradually reduced to 9 kPa at a temperature in the region of 40° C.

The pasty residue was taken up in 3 cm$^3$ of chloroform/methanol/aqueous ammonia (12/3/0.5 by volume) and the organic phase was then purified by chromatography under atmospheric pressure, on a column of silica gel (particle size 70–200μ; diameter 2 cm; mass 5 g), eluting with a chloroform/methanol/aqueous ammonia mixture (12/3/0.5 by volume). The fractions containing the product were combined and then concentrated to dryness under reduced pressure (5 kPa) at a temperature in the region of 40° C. and the product was dried in an over under reduced pressure (50 Pa) at a temperature in the region of 50° C. 0.27 g of {4-[3-(3-chloro-6-methoxyquinolin-4-yl)propyl]-1-[2-(2,5-difluorophenoxy)ethyl]piperidin-4-yl}acetic acid was obtained.

$^1$H NMR Spectrum (500 MHz, $(CD_3)_2SO$-$d_6$, δ in ppm): 1.39 (mt: 2H); 1.50 (mt: 2H); 1.60 (mt: 4H); 2.15 (broad s: 2H); from 2.30 to 2.60 (mt: 4H); 2.67 (t, J=6 Hz: 2H); 3.12 (unresolved peak: 2H); 3.93 (s: 3H); 4.12 (t, J=6 Hz: 2H); 6.72 (mt: 1H); 7.11 (mt: 1H); 7.21 (mt: 1H); 7.37 (broad s: 1H); 7.41 (broad d, J=9 Hz: 1H); 7.93 (d, J=9 Hz: 1H); 8.64 (s: 1H).

Methyl {4-[3-(3-chloro-6-methoxyquinolin-4-yl)propyl]-1-[2-(2,5-difluorophenoxy)ethyl]piperidin-4-yl}acetate A mixture of 0.35 g of methyl {4-[3-(3-chloro-6-methoxyquinolin-4-yl)propyl]piperidin-4-yl}acetate, 0.32 g of 2-(2-bromoethoxy)-1,4-difluorobenzene, 0.15 g of potassium iodide and 0.62 g of potassium carbonate in 20 cm$^3$ of acetonitrile was stirred for 18 hours at a temperature in the region of 70° C. After cooling to about 20° C., the reaction mixture was filtered through a silica cartridge (Bond Elut) and then rinsed with twice 2 cm$^3$ of acetonitrile. The organic phase was concentrated to dryness under reduced pressure (2.4 kPa) at a temperature in the region of 45° C.

The evaporation residue obtained in dissolved in 12 cm$^3$ of dimethylformamide and then purified by injection of 4 times 3 cm$^3$ per chromatography onto an SCX silica gel cartridge (mass 1 g), eluting with a gradient of from pure methanol to a mixture of 4N ammoniacal methanol. The fractions containing the product were combined and then concentrated to dryness under compressed air at a temperature in the region of 45° C. The evaporation residue obtained was taken up in dichloromethane and dried in the open air for 48 hours and then oven-dried under reduced pressure (10 Pa) at a temperature in the region of 50° C. 0.38 g of methyl {4-[3-(3-chloro-6-methoxyquinolin-4-yl)propyl]-1-[2-(2,5-difluorophenoxy)ethyl]piperidin-4-yl}acetate was obtained.

$^1$H NMR Spectrum (500 MHz, $(CD_3)_2SO$-$d_6$, δ in ppm) from 1.30 to 1.65 (mt: 8H); 2.25 (broad s: 2H); from 2.30 to 2.60 (mt: 4H); 2.69 (mt: 2H); 3.14 (mt: 2H); 3.47 (broad s: 3H); 3.95 (broad s: 3H); 4.12 (mt: 2H); 6.72 (mt: 1H); 7.11 (mt: 1H); 7.21 (mt: 1H); 7.38 (broad s: 1H); 7.43 (broad d, J=9 Hz: 1H); 7.94 (broad d, J=9 Hz: 1H); 8.66 (broad s: 1H).

The 2-(2-bromoethoxy)-1,4-difluorobenzene was prepared as described in Example 16.

The methyl {4-[3-(3-chloro-6-methoxyquinolin-4-yl)propyl]piperidin-4-yl}acetate was prepared as described in Example 29.

EXAMPLE 31

1-(2-Cyclopentylthioethyl)-4-[3-(3-fluoro-6-methoxyquinolin-4-yl)propyl]piperidine-4-carboxylic Acid A mixture of 0.4 g of ethyl 1-(2-cyclopentylthioethyl)-4-[3-(3-fluoro-6-methoxyquinolin-4-yl)propyl]piperidine-4-carboxylate in 3 cm$^3$ of dioxane, 3 cm$^3$ of methanol and 2.4 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (40/5/0.5 by volume) and then with a chloroform/methanol/aqueous ammonia mixture (13/3/0.5). The fractions containing a precipitate were combined, filtered and then washed with methanol. The solid obtained was recrystallized from 15 cm$^3$ of boiling methanol, cooled, filtered, washed with methanol and oven-dried under reduced pressure (10 Pa) in the region of 20° C. The filtration liquors were combined and concentrated to dryness under reduced pressure (2 kPa) at a temperature in the region of 40° C. The liquors, once concentrated to dryness, and the solid obtained above were combined to give 0.179 g of 1-(2-cyclopentylthioethyl)-4-[3-(3-fluoro-6-methoxyquinolin-4-yl)propyl]piperidine-4-carboxylic acid in the form of a white solid.

$^1$H NMR Spectrum (400 MHz, $(CD_3)_2SO$-$d_6$ with addition of a few drops of $CF_3COOD$, δ in ppm): 1.41 (mt: 2H); from 1.50 to 1.75 (mt: 8H); from 1.90 to 2.05 (mt: 4H); 2.20 (broad d, J=14 Hz: 2H); from 2.75 to 2.90 (mt: 4H); from 3.10 to 3.25 (mt: 1H); 3.16 (t, J=7 Hz: 2H); 3.29 (mt: 2H); 3.50 (broad d, J=14 Hz: 2H); 3.99 (s: 3H); 7.47 (d, J=2.5 Hz: 1H); 7.55 (dd, J=9 and 2.5 Hz: 1H); 8.06 (d, J=9 Hz: 1H); 8.98 (broad s: 1H).

Ethyl 4-[3-(3-fluoro-6-methoxyquinolin-4-yl)propyl]piperidine-4-carboxylate

A mixture of 0.5 g of ethyl 4-[3-(3-fluoro-6-methoxyquinolin-4-yl)propyl]piperidine-4-carboxylate, 0.253 g of (2-chloroethylthio)cyclopentane, 0.25 g of potassium iodide and 0.92 g of potassium carbonate in 15 cm$^3$ of acetonitrile was stirred for 18 hours at a temperature in the region of 70° C. After cooling to about 20° C., the reaction mixture was filtered and then rinsed with twice 3 cm$^3$ of acetonitrile. The organic phase was concentrated to dryness under reduced pressure (2.4 kPa) at a temperature in the region of 45° C.

The evaporation residue obtained was dissolved in a mixture of ethyl acetate/40–60° C. petroleum ether (8/2 by volume) and was then purified by chromatography under atmospheric pressure, on a cartridge of silica gel (Bond Elut; particle size 70–200μ; mass 10 g), eluting with a mixture of ethyl acetate/40–60° C. petroleum ether (8/2 by volume). Fractions 5 to 14 were combined and then concentrated to dryness under reduced pressure (2 kPa) at a temperature in the region of 40° C. 0.43 g of ethyl 4-[3-(3-fluoro-6-methoxyquinolin-4-yl)propyl]piperidine-4-carboxylate was obtained.

$^1$H NMR Spectrum (500 MHz, $(CD_3)_2SO$-$d_6$, δ in ppm) 0.98 (t, J=7 Hz: 3H); 1.36 (mt: 4H); from 1.40 to 1.70 (mt: 8H); from 1.80 to 2.00 (mt: 6H); from 2.30 to 2.65 (mt: 6H); 3.02 (mt: 2H); 3.09 (mt: 1H); 3.92 (s: 3H); 3.94 (q, J=7 Hz: 2H); 7.31 (broad s: 1H); 7.37 (broad d, J=9 Hz: 1H); 7.94 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

EXAMPLE 32

1-(2-Cyclohexylethyl)-4-[3-(3-fluoro-6-methoxyquinolin-4-yl)propyl]piperidine-4-carboxylic Acid A mixture of 0.2 g of ethyl 1-(2-cyclohexylethyl)-4-[3-(3-fluoro-6-methoxyquinolin-4-yl)propyl]-piperidine-4-carboxylate in 3 cm$^3$ of dioxane, 3 cm$^3$ of methanol and 1.2 cm$^3$ of aqueous 5N sodium hydroxide solution was stirred at a temperature in the region of 70° C. for 22 hours. After cooling to about 20° C., the reaction mixture was evaporated under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (40/5/0.5 by volume) and then with a chloroform/methanol/aqueous ammonia mixture (13/3/0.5). The fractions containing the product were combined, concentrated to dryness under reduced pressure (2 kPa) at a temperature in the region of 40° C. and dried in a desiccator (10 kPa). 0.14 g of 1-(2-cyclohexylethyl)-4-[3-(3-fluoro-6-methoxyquinolin-4-yl)propyl]piperidine-4-carboxylic acid was obtained in the form of a white solid.

$^1$H NMR Spectrum (400 MHz, (CD$_3$)$_2$SO-d$_6$ with addition of a few drops of CF$_3$COOD, δ in ppm): from 0.80 to 1.00 (mt: 2H); from 1.05 to 1.35 (mt: 5H); from 1.40 to 1.75 (mt: 12H); 2.19 (broad d, J=14 Hz: 2H); 2.78 (broad t, J=12.5 Hz: 2H); 3.07 (mt: 2H); 3.20 (broad t, J=6.5 Hz: 2H); 3.45 (broad d, J=12.5 Hz: 2H); 4.00 (s: 3H); 7.52 (d, J=2.5 Hz: 1H); 7.60 (dd, J=9 and 2.5 Hz: 1H); 8.10 (d, J=9 Hz: 1H); 9.10 (d, J=2 Hz: 1H).

Ethyl 1-(2-cyclohexylethyl)-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.245 g of 1-bromo-2-cyclohexylethane, 0.18 g of potassium iodide and 0.737 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.23 g of ethyl 1-(2-cyclohexylethyl)-4-[3-(3-fluoro-6-methoxyquinolin-4-yl)propyl]piperidine-4-carboxylate was obtained.

$^1$H NMR Spectrum (500 MHz, (CD$_3$)$_2$SO-d$_6$, δ in ppm) 0.84 (mt: 2H); 0.98 (t, J=7 Hz: 3H); from 1.00 to 2.65 (mt: 25H); 3.02 (mt: 2H); 3.93 (s: 3H); 3.95 (q, J=7 Hz: 2H); 7.31 (broad s: 1H); 7.35 (broad d, J=9 Hz: 1H); 7.94 (d, J=9 Hz: 1H); 8.67 (broad s: 1H).

The ethyl 4-[3-(3-fluoro-6-methoxyquinolin-4-yl)propyl]piperidine-4-carboxylate was prepared as described in Example 11.

EXAMPLE 33

1-(2-Cyclohexylthioethyl)-4-[3-(3-fluoro-6-methoxyquinolin-4-yl)propyl]piperidine-4-carboxylic Acid A mixture of 0.3 g of ethyl 1-(2-cyclohexylthioethyl)-4-[3-(3-fluoro-6-methoxyquinolin-4-yl)propyl]-piperidine-4-carboxylate in 3 cm$^3$ of dioxane, 3 cm$^3$ of methanol and 1.7 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (40/5/0.5 by volume) and then with a chloroform/methanol/aqueous ammonia mixture (13/3/0.5). The fractions containing the product were combined, concentrated to dryness under reduced pressure (2 kPa) at a temperature in the region of 40° C. and dried in a desiccator (10 kPa). 0.25 g of 1-(2-cyclohexylthioethyl)-4-[3-(3-fluoro-6-methoxyquinolin-4-yl)propyl]piperidine-4-carboxylic acid was obtained in the form of a white solid.

$^1$H NMR Spectrum (400 MHz, (CD$_3$)$_2$SO-d$_6$ with addition of a few drops of CF$_3$COOD, δ in ppm): from 1.15 to 1.35 (mt: 5H); from 1.50 to 1.75 (mt: 8H); from 1.80 to 2.05 (mt: 3H); 2.20 (broad d, J=14 Hz: 2H); from 2.65 to 2.90 (mt: 5H); 3.20 (broad t, J=7 Hz: 2H); 3.25 (mt: 2H); 3.50 (broad d, J=12 Hz: 2H); 4.00 (s: 3H); 7.50 (d, J=2.5 Hz: 1H); 7.59 (dd, J=9 and 2.5 Hz: 1H); 8.09 (d, J=9 Hz: 1H); 9.07 (d, J=2.5 Hz: 1H)

Ethyl 1-(2-cyclohexylthioethyl)-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.23 g of 2-chloroethylthiocyclohexane, 0.18 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C. The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.32 g of ethyl 1-(2-cyclohexylethyl)-4-[3-(3-fluoro-6-methoxyquinolin-4-yl)propyl]piperidine-4-carboxylate was obtained.

$^1$H NMR Spectrum (500 MHz, (CD$_3$)$_2$SO-d$_6$, δ in ppm) 0.97 (t, J=7 Hz: 3H); from 1.05 to 1.70 (mt: 14H); from 1.75 to 2.00 (mt: 6H); from 2.25 to 2.60 (mt: 6H); 2.62 (mt: 1H); 3.01 (mt: 2H); 3.91 (s: 3H); 3.94 (q, J=7 Hz: 2H); 7.30 (broad s: 1H); 7.37 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

EXAMPLE 34

4-[3-(3-Fluoro-6-methoxyquinolin-4-yl)propyl]-1-(3-phenylpropyl)piperidine-4-carboxylic Acid A mixture of 0.1 g of ethyl 4-[3-(3-fluoro-6-methoxyquinolin-4-yl)propyl]-1-(3-phenylpropyl)piperidine-4-carboxylate in 3 cm$^3$ of dioxane, 3 cm$^3$ of methanol and 0.6 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a mixture of dichloromethane/methanol/aqueous ammonia (40/5/0.5 by volume) and then with a chloroform/methanol/aqueous ammonia mixture (13/3/0.5). The fractions containing the product were combined, concentrated to dryness under reduced pressure (2 kPa) at a temperature in the region of 40° C. and dried in a desiccator (10 Pa). 0.25 g of 4-[3-(3-fluoro-6-methoxyquinolin-4-yl)propyl]-1-(3-phenylpropyl) piperidine-4-carboxylic acid was obtained in the form of a white solid.

$^1$H NMR Spectrum (400 MHz, $(CD_3)_2SO$-$d_6$ with addition of a few drops of $CF_3COOD$, δ in ppm): from 1.50 to 1.75 (mt: 6H); from 1.85 to 2.05 (mt: 2H); 2.19 (broad d, J=14 Hz: 2H); 2.60 (t, J=7.5 Hz: 2H); 2.81 (broad t, J=12.5 Hz: 2H); 3.07 (mt: 2H); 3.20 (broad t, J=7.5 Hz: 2H); 3.47 (broad d, J=12.5 Hz: 2H); 3.99 (s: 3H); from 7.15 to 7.35 (mt: 5H); 7.51 (d, J=2.5 Hz: 1H); 7.59 (dd, J=9 and 2.5 Hz: 1H); 8.10 (d, J=9 Hz: 1H); 9.08 (d, J=2 Hz: 1H).

Ethyl 4-[3-(3-fluoro-6-methoxyquinolin-4-yl)propyl]-1-(3-phenylpropyl)piperidine-4-carboxylate A mixture of 0.4 g of ethyl 4-[3-(3-fluoro-6-methoxyquinolin-4-yl)propyl]piperidine-4-carboxylate, 0.25 g of 1-bromo-3-phenylpropane, 0.181 g of potassium iodide and 0.74 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.1 g of ethyl 4-[3-(3-fluoro-6-methoxyquinolin-4-yl)propyl]-1-(3-phenylpropyl)piperidine-4-carboxylate was obtained.

$^1$H NMR Spectrum (500 MHz, $(CD_3)_2SO$-$d_6$, δ in ppm): 0.97 (t, J=7 Hz: 3H); from 1.25 to 2.00 (mt: 12H); from 2.25 to 2.70 (mt: 6H); 3.01 (mt: 2H); 3.91 (s: 3H); 3.94 (broad q, J=7 Hz: 2H); 7.15 (mt: 3H); 7.24 (broad t, J=7.5 Hz: 2H); 7.30 (broad s: 1H); 7.36 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl] piperidine-4-carboxylate was prepared as described in Example 11.

EXAMPLE 35

1-[2-(2,5-Difluorophenylthio)ethyl]-4-[3-(3-fluoro-6-methoxyquinolin-4-yl)propyl]piperidine-4-carboxylic Acid A mixture of 0.26 g of ethyl 1-[2-(2,5-difluorophenylthio) ethyl]-4-[3-(3-fluoro-6-methoxyquinolin-4-yl)propyl] piperidine-4-carboxylate in 3 cm³ of dioxane, 3 cm³ of methanol and 1.4 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C. The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a mixture of dichloromethane/methanol/aqueous ammonia (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.3 g of 1-[2-(2,5-difluorophenylthio)ethyl]-4-[3-(3-fluoro-6-methoxyquinolin-4-yl)propyl]piperidine-4-carboxylic acid was obtained in the form of a white solid.

$^1$H NMR Spectrum (400 MHz, $(CD_3)_2SO$-$d_6$ with addition of a few drops of $CF_3COOD$, δ in ppm): from 1.50 to 1.75 (mt: 6H); 2.21 (broad d, J=14 Hz: 2H); 2.89 (broad t, J=12.5 Hz: 2H); 3.16 (mt: 2H); from 3.25 to 3.50 (mt: 4H); 3.54 (broad d, J=12.5 Hz: 2H); 3.99 (s: 3H); 7.14 (mt: 1H); 7.30 (doubled triplet, J=9 and 5 Hz: 1H); 7.39 (mt: 1H); 7.47 (d, J=2.5 Hz: 1H); 7.54 (dd, J=9 and 2.5 Hz: 1H); 8.07 (d, J=9 Hz: 1H); 8.97 (d, J=2 Hz: 1H).

Ethyl 1-[2-(2,5-difluorophenylthio)ethyl]-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.324 g of 2-(2-bromoethylthio)-1,4-difluorobenzene, 0.181 g of potassium iodide and 0.74 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C. The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume).

The fractions containing the product were combined and then concentrated to dryness under reduced pressure (2 kPa) at a temperature in the region of 40° C. 0.27 g of ethyl 1-[2-(2,5-difluorophenylthio)ethyl]-4-[3-(3-fluoro-6-methoxyquinolin-4-yl)propyl]piperidine-4-carboxylate was obtained.

$^1$H NMR Spectrum (500 MHz, $(CD_3)_2SO$-$d_6$, δ in ppm): 0.97 (t, J=7 Hz: 3H); 1.31 (broad t, J=11 Hz: 2H); from 1.40 to 1.60 (mt: 4H); from 1.80 to 2.00 (mt: 4H); from 2.35 to 2.70 (mt: 4H); 3.01 (mt: 2H); 3.07 (broad t, J=7 Hz: 2H); 3.91 (s: 3H); 3.94 (q, J=7 Hz: 2H); 7.00 (mt: 1H); 7.21 (mt: 1H); 7.26 (mt: 1H); 7.30 (broad s: 1H); 7.37 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl] piperidine-4-carboxylate was prepared as described in Example 11.

The 1-(2-bromoethylthio)-2,5-difluorobenzene was prepared as described in Example 14.

EXAMPLE 36

1-[2-(2,5-Difluorophenoxy)ethyl]-4-[3-(3-fluoro-6-methoxyquinolin-4-yl)propyl]piperidine-4-carboxylic Acid A mixture of 0.38 g of ethyl 1-[2-(2,5-difluorophenoxy) ethyl]-4-[3-(3-fluoro-6-methoxyquinolin-4-yl)propyl] piperidine-4-carboxylate in 3 cm³ of dioxane, 3 cm³ of methanol and 2.1 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/ methanol/aqueous ammonia mixture (90/9/0.9 by volume) and then with a chloroform/methanol/aqueous ammonia mixture (77.5/19.5/3).

The fractions containing the product were combined, concentrated to dryness under reduced pressure (2 kPa) at a temperature in the region of 40° C. and dried in a desiccator (10 kPa). 0.36 g of 1-[2-(2,5-difluorophenoxy)ethyl]-4-[3-(3-fluoro-6-methoxyquinolin-4-yl)propyl]piperidine-4-carboxylic acid was obtained in the form of a white solid.

$^1$H NMR Spectrum (300 MHz, $(CD_3)_2SO-d_6$, δ in ppm) 1.32 (broad t, J=13 Hz: 2H); from 1.50 to 1.70 (mt: 4H); 1.96 (broad d, J=13 Hz: 2H); 2.09 (broad t, J=11.5 Hz: 2H); 2.64 (t, J=6 Hz: 2H); 2.70 (broad d, J=11.5 Hz: 2H); 3.05 (very broad t, J=6.5 Hz: 2H); 3.96 (s: 3H); 4.13 (t, J=6 Hz: 2H); 6.75 (mt: 1H); 7.14 (mt: 1H); 7.24 (mt: 1H); 7.34 (d, J=2.5 Hz: 1H); 7.41 (dd, J=9 and 2.5 Hz: 1H); 7.97 (d, J=9 Hz: 1H); 8.69 (broad s: 1H).

Ethyl 1-[2-(2,5-difluorophenoxy)ethyl]-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.30 g of 2-(2-bromoethoxy)-1,4-difluorobenzene, 0.181 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.4 g of ethyl 1-[2-(2,5-difluorophenoxy)ethyl]-4-[3-(3-fluoro-6-methoxyquinolin-4-yl)propyl]piperidine-4-carboxylate was obtained.

$^1$H NMR Spectrum (500 MHz, $(CD_3)_2SO-d_6$, δ in ppm) 0.97 (t, J=7 Hz: 3H); 1.36 (broad t, J=11.5 Hz: 2H); from 1.40 to 1.60 (mt: 4H); from 1.80 to 2.10 (mt: 4H); 2.61 (broad t, J=5.5 Hz: 2H); 2.69 (broad d, J=11 Hz: 2H); 3.02 (mt: 2H); 3.92 (s: 3H); 3.94 (q, J=7 Hz: 2H); 4.09 (mt: 2H); 6.71 (mt: 1H); 7.10 (mt: 1H); 7.19 (mt: 1H); 7.29 (broad s: 1H); 7.37 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

The 2-(2-bromoethoxy)-1,4-difluorobenzene was prepared as described in Example 16.

EXAMPLE 37

4-[3-(3-Fluoro-6-methoxyquinolin-4-yl)propyl]-1-[2-(2,3,5-trifluorophenoxy)ethyl]piperidine-4-carboxylic Acid A mixture of 0.42 g of ethyl 4-[3-(3-fluoro-6-methoxyquinolin-4-yl)propyl]-1-[2-(2,3,5-trifluorophenoxy)ethyl]piperidine-4-carboxylate in 3 cm$^3$ of dioxane, 3 cm$^3$ of methanol and 2.3 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.39 g of 4-[3-(3-fluoro-6-methoxyquinolin-4-yl)propyl]-1-[2-(2,3,5-trifluorophenoxy)ethyl]piperidine-4-carboxylic acid was obtained in the form of a white solid.

$^1$H NMR Spectrum (300 MHz, $(CD_3)_2SO-d_6$, δ in ppm) 1.32 (very broad t, J=12.5 Hz: 2H); 1.60 (mt: 4H); 1.95 (broad d, J=12.5 Hz: 2H); 2.09 (broad t, J=11 Hz: 2H); 2.64 (t, J=5.5 Hz: 2H); 2.70 (broad d, J=11 Hz: 2H); 3.04 (very broad t, J=6 Hz: 2H); 3.96 (s: 3H); 4.16 (t, J=5.5 Hz: 2H); from 6.95 to 7.15 (mt: 2H); 7.34 (d, J=2.5 Hz: 1H); 7.40 (dd, J=9 and 2.5 Hz: 1H); 7.96 (d, J=9 Hz: 1H); 8.69 (broad s: 1H).

Ethyl 4-[3-(3-fluoro-6-methoxyquinolin-4-yl)propyl]-1-[2-(2,3,5-trifluorophenoxy)ethyl]piperidine-4-carboxylate A mixture of 0.4 g of ethyl 4-[3-(3-fluoro-6-methoxyquinolin-4-yl)propyl]piperidine-4-carboxylate, 0.33 g of 1-(2-bromoethoxy)-2,3,5-trifluorobenzene, 0.181 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g; volume 25 cm$^3$), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.43 g of ethyl 4-[3-(3-fluoro-6-methoxyquinolin-4-yl)propyl]-1-[2-(2,3,5-trifluorophenoxy)ethyl]piperidine-4-carboxylate was obtained.

$^1$H NMR Spectrum (500 MHz, $(CD_3)_2SO-d_6$, δ in ppm) 0.98 (t, J=7 Hz: 3H); 1.34 (broad t, J=11.5 Hz: 2H); from 1.45 to 1.60 (mt: 4H); from 1.85 to 2.10 (mt: 4H); from 2.50 to 2.70 (mt: 4H); 3.02 (mt: 2H); 3.92 (s: 3H); 3.94 (q, J=7 Hz: 2H); 4.14 (mt: 2H); 7.02 (mt: 2H); 7.30 (broad s: 1H); 7.37 (broad d, J=9 Hz: 1H); 7.94 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

The 1-(2-bromoethoxy)-2,3,5-trifluorobenzene was prepared as described in Example 13.

EXAMPLE 38

4-[3-(3-Fluoro-6-methoxyquinolin-4-yl)propyl]-1-heptylpiperidine-4-carboxylic Acid A mixture of 0.16 g of ethyl 4-[3-(3-fluoro-6-methoxyquinolin-4-yl)propyl]-1-heptylpiperidine-4-carboxylate in 3 cm$^3$ of dioxane, 3 cm$^3$ of methanol and 1 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume)

and was then purified by chromatography under atmospheric pressure, on a cartridge of silica gel (Bond Elut; particle size 70–200μ; mass 10 g), eluting with a dichloromethane/methanol/aqueous ammonia mixture (40/5/0.5 by volume) and then with a chloroform/methanol/aqueous ammonia mixture (13/3/0.5). The fractions containing the product were combined, concentrated to dryness under reduced pressure (2 kPa) at a temperature in the region of 40° C. and dried in a desiccator (10 kPa). 0.07 g of 4-[3-(3-fluoro-6-methoxyquinolin-4-yl)propyl]-1-heptylpiperidine-4-carboxylic acid was obtained in the form of a white solid.

$^1$H NMR Spectrum (400 MHz, $(CD_3)_2SO$-$d_6$ with addition of a few drops of $CF_3COOD$, δ in ppm): 0.85 (t, J=7 Hz: 3H); from 1.15 to 1.35 (mt: 8H); from 1.50 to 1.75 (mt: 8H); 2.19 (broad d, J=14 Hz: 2H); 2.78 (broad t, J=12.5 Hz: 2H); 3.02 (mt: 2H); 3.19 (broad t, J=7 Hz: 2H); 3.45 (broad d, J=12.5 Hz: 2H); 4.00 (s: 3H); 7.50 (d, J=2.5 Hz: 1H); 7.58 (dd, J=9 and 2.5 Hz: 1H); 8.09 (d, J=9 Hz: 1H); 9.04 (d, J=2 Hz: 1H).

Ethyl 4-[3-(3-fluoro-6-methoxyquinolin-4-yl)propyl]-1-heptylpiperidine-4-carboxylate A mixture of 0.4 g of ethyl 4-[3-(3-fluoro-6-methoxyquinolin-4-yl)propyl]piperidine-4-carboxylate, 0.23 g of 1-bromoheptane, 0.18 g of potassium iodide and 0.737 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.2 g of ethyl 4-[3-(3-fluoro-6-methoxyquinolin-4-yl)propyl]-1-heptylpiperidine-4-carboxylate was obtained.

$^1$H NMR Spectrum (500 MHz, $(CD_3)_2SO$-$d_6$, δ in ppm) 0.84 (t, J=7 Hz: 3H); 0.98 (t, J=7 Hz: 3H); from 1.10 to 1.30 (mt: 8H); 1.33 (mt: 4H); from 1.40 to 1.60 (mt: 4H); 1.83 (broad t, J=11 Hz: 2H); 1.93 (broad d, J=13 Hz: 2H); 2.13 (mt: 2H); from 2.35 to 2.55 (mt: 2H); 3.01 (mt: 2H); 3.89 (s: 3H); 3.94 (mt: 2H); 7.31 (broad s: 1H); 7.37 (broad d, J=9 Hz: 1H); 7.94 (d, J=9 Hz: 1H); 8.67 (broad s: 1H).

The ethyl 4-[3-(3-fluoro-6-methoxyquinolin-4-yl)propyl]piperidine-4-carboxylate was prepared as described in Example 11.

EXAMPLE 39

4-[3-(3-Fluoro-6-methoxyquinolin-4-yl)propyl]-1-(2-phenylthioethyl)piperidine-4-carboxylic Acid A mixture of 0.39 g of ethyl 4-[3-(3-fluoro-6-methoxyquinolin-4-yl)propyl]-1-(2-phenylthioethyl)piperidine-4-carboxylate in 3 cm$^3$ of dioxane, 3 cm$^3$ of methanol and 2.3 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C. The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.3 g of 4-[3-(3-fluoro-6-methoxyquinolin-4-yl)propyl]-1-(2-phenylthioethyl)piperidine-4-carboxylic acid was obtained in the form of a white solid.

$^1$H NMR Spectrum (400 MHz, $(CD_3)_2SO$-$d_6$ with addition of a few drops of $CF_3COOD$, δ in ppm): from 1.50 to 1.75 (mt: 6H); 2.20 (broad d, J=14 Hz: 2H); 2.87 (broad t, J=13 Hz: 2H); 3.16 (mt: 2H); 3.41 (s: 4H); 3.53 (broad d, J=13 Hz: 2H); 4.00 (s: 3H); 7.25 (broad t, J=7.5 Hz: 1H); from 7.30 to 7.45 (mt: 4H); 7.48 (d, J=2.5 Hz: 1H); 7.54 (dd, J=9 and 2.5 Hz: 1H); 8.07 (d, J=9 Hz: 1H); 8.97 (d, J=2 Hz: 1H).

Ethyl 4-[3-(3-fluoro-6-methoxyquinolin-4-yl)propyl]-1-(2-phenylthioethyl)piperidine-4-carboxylate A mixture of 0.4 g of ethyl 4-[3-(3-fluoro-6-methoxyquinolin-4-yl)propyl]piperidine-4-carboxylate, 0.28 g of 2-bromoethyl phenyl sulfide, 0.181 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.4 g of ethyl 4-[3-(3-fluoro-6-methoxyquinolin-4-yl)propyl]-1-(2-phenylthioethyl)piperidine-4-carboxylate was obtained.

$^1$H NMR Spectrum (500 MHz, $(CD_3)_2SO$-$d_6$, δ in ppm): 0.97 (t, J=7 Hz: 3H); 1.33 (broad t, J=12.5 Hz: 2H); from 1.45 to 1.65 (mt: 4H); from 1.85 to 2.00 (mt: 4H); from 2.30 to 2.70 (mt: 4H); 3.01 (mt: 4H); 3.92 (s: 3H); 3.94 (mt: 2H); 7.15 (mt: 1H); from 7.20 to 7.35 (mt: 5H); 7.37 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

EXAMPLE 40

4-[3-(3-Fluoro-6-methoxyquinolin-4-yl)propyl]-1-[2-(3-fluorophenylthio)ethyl]piperidine-4-carboxylic Acid A mixture of 0.2 g of ethyl 4-[3-(3-fluoro-6-methoxyquinolin-4-yl)propyl]-1-(2-phenylthioethyl)piperidine-4-carboxylate in 3 cm$^3$ of dioxane, 3 cm$^3$ of methanol and 1.1 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.18 g of 4-[3-(3-fluoro-6-methoxyquinolin-4-yl)propyl]-1-[2-(3-fluorophenylthio) ethyl]piperidine-4-carboxylic acid was obtained.

$^1$H NMR Spectrum (400 MHz, $(CD_3)_2SO$-$d_6$ with addition of a few drops of $CF_3COOD$, δ in ppm): from 1.50 to 1.75 (mt: 6H); 2.20 (broad d, J=14 Hz: 2H); 2.89 (broad t, J=12.5 Hz: 2H); 3.18 (mt: 2H); from 3.25 to 3.45 (mt: 4H); 3.54 (broad d, J=12.5 Hz: 2H); 3.99 (s: 3H); 7.05 (doubled triplet, J=9 and 2.5 Hz: 1H); from 7.15 to 7.30 (mt: 2H); 7.38 (mt: 1H); 7.48 (d, J=2.5 Hz: 1H); 7.55 (dd, J=9 and 2.5 Hz: 1H); 8.08 (d, J=9 Hz: 1H); 9.00 (d, J=2 Hz: 1H).

Ethyl 4-[3-(3-fluoro-6-methoxyquinolin-4-yl)propyl]-1-(2-phenylthioethyl)piperidine-4-carboxylate A mixture of 0.4 g of ethyl 4-[3-(3-fluoro-6-methoxyquinolin-4-yl)propyl]piperidine-4-carboxylate, 0.30 g of 3-fluoro-2-bromoethyl phenyl sulfide, 0.18 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure of argon, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.22 g of ethyl 4-[3-(3-fluoro-6-methoxyquinolin-4-yl)propyl]-1-(2-phenylthioethyl)piperidine-4-carboxylate was obtained.

$^1$H NMR Spectrum (500 MHz, $(CD_3)_2SO$-$d_6$, δ in ppm): 0.98 (t, J=7 Hz: 3H); 1.33 (broad t, J=12 Hz: 2H); from 1.45 to 1.65 (mt: 4H); from 1.85 to 2.00 (mt: 4H); from 2.30 to 2.70 (mt: 4H); 3.02 (mt: 2H); 3.07 (t, J=6.5 Hz: 2H); 3.92 (s: 3H); 3.94 (q, J=7 Hz: 2H); 6.94 (broad t, J=8.5 Hz: 1H); from 7.05 to 7.20 (mt: 2H); from 7.25 to 7.35 (mt: 2H); 7.37 (broad d, J=9 Hz: 1H); 7.94 (d, J=9 Hz: 1H); 8.66 (broad s: 1H).

The ethyl 4-[3-(3-fluoro-6-methoxyquinolin-4-yl)propyl] piperidine-4-carboxylate was prepared as described in Example 11.

The 3-fluoro-2-bromoethyl phenyl sulfide was prepared according to the method described in Example 14.

EXAMPLE 41

1-[2-(3,4-Difluorophenoxy)ethyl]-4-[3-(3-fluoro-6-methoxyquinolin-4-yl)propyl]piperidine-4-carboxylic Acid A mixture of 0.38 g of ethyl 1-[2-(3,4-difluorophenoxy) ethyl]-4-[3-(3-fluoro-6-methoxyquinolin-4-yl)propyl] piperidine-4-carboxylate in 3 cm$^3$ of dioxane, 3 cm$^3$ of methanol and 2.1 cm$^3$ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C. The residue was taken up in 5 cm$^3$ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a mixture of dichloromethane/methanol/aqueous ammonia (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.3 g of 1-[2-(3,4-difluoro-phenoxy)ethyl]-4-[3-(3-fluoro-6-methoxyquinolin-4-yl)-propyl]piperidine-4-carboxylic acid was obtained in the form of a white solid.

$^1$H NMR Spectrum (400 MHz, $(CD_3)_2SO$-$d_6$ with addition of a few drops of $CF_3COOD$, δ in ppm): from 1.50 to 1.75 (mt: 6H); 2.21 (broad d, J=14 Hz: 2H); 2.96 (broad t, J=13 Hz: 2H); 3.19 (broad t, J=6.5 Hz: 2H); from 3.50 to 3.65 (mt: 4H); 4.00 (s: 3H); 4.31 (t, J=5.5 Hz: 2H); 6.82 (mt: 1H); 7.11 (mt: 1H); 7.35 (mt: 1H); 7.50 (d, J=2.5 Hz: 1H); 7.57 (dd, J=9 and 2.5 Hz: 1H); 8.09 (d, J=9 Hz: 1H); 9.03 (d, J=2 Hz: 1H).

Ethyl 1-[2-(3,4-difluorophenoxy)ethyl]-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.3 g of 4-(2-bromoethoxy)-1,2-difluorobenzene, 0.18 g of potassium iodide and 0.74 g of potassium carbonate in 15 cm$^3$ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.4 g of ethyl 1-[2-(3,4-difluorophenoxy)ethyl]-4-[3-(3-fluoro-6-methoxyquinolin-4-yl)propyl]piperidine-4-carboxylate was obtained.

$^1$H NMR Spectrum (500 MHz, $(CD_3)_2SO$-$d_6$, δ in ppm): 0.98 (t, J=7 Hz: 3H); 1.36 (broad t, J=12 Hz: 2H); from 1.45 to 1.65 (mt: 4H); 1.93 (broad d, J=12 Hz: 2H); 2.00 (broad t, J=11.5 Hz: 2H); from 2.40 to 2.70 (mt: 4H); 3.02 (mt: 2H); 3.92 (s: 3H); 3.94 (q, J=7 Hz: 2H); 3.99 (mt: 2H); 6.73 (mt: 1H); 7.03 (mt: 1H); from 7.25 to 7.35 (mt: 2H); 7.37 (broad d, J=9 Hz: 1H); 7.93 (d, J=9 Hz: 1H); 8.66 (broad s,: 1H).

4-(2-Bromoethoxy)-1,2-difluorobenzene

A mixture of 15 g of 3,4-difluorophenol, 23.5 g of potassium carbonate and 60 cm$^3$ of 1,2-dibromoethane in 250 cm$^3$ of acetonitrile was stirred at a temperature in the region of 70° C. for 18 hours. After cooling to about 20° C., the reaction mixture was filtered through Celite and then concentrated to dryness under reduced pressure (2 kPa) at a temperature in the region of 40° C. The residue obtained was purified by chromatography under atmospheric pressure, on a column of silica gel (particle size 70–200μ; diameter 8 cm; mass 400 g), eluting with 40–60° C. petroleum ether. The fractions containing the product were combined and then concentrated to dryness under reduced pressure (2 kPa) in the region of 40° C. 15.7 g of 4-(2-bromoethoxy)-1,2-difluorobenzene were obtained in the form of an oil.

Infra-red spectrum ($CCl_4$): 1609; 1516; 1264; 1253; 1215; 1206; 1162; 1019; 854 and 834 cm$^{-1}$.

The ethyl 4-[3-(3-fluoro-6-methoxyquinolin-4-yl)propyl] piperidine-4-carboxylate was prepared as described in Example 11.

EXAMPLE 42

4-[3-(3-Fluoro-6-methoxyquinolin-4-yl)propyl]-1-(2-phenoxyethyl)piperidine-4-carboxylic Acid A mixture of 0.39 of ethyl 4-[3-(3-fluoro-6-methoxyquinolin-4-yl)propyl]-1-(2-phenoxyethyl)

piperidine-4-carboxylate in 3 cm³ of dioxane, 3 cm³ of methanol and 2.4 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a mixture of dichloromethane/methanol/aqueous ammonia (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.33 g of 4-[3-(3-fluoro-6-methoxyquinolin-4-yl)propyl]-1-(2-phenoxyethyl)piperidine-4-carboxylic acid was obtained in the form of a white solid.

¹H NMR Spectrum (300 MHz, $(CD_3)_2SO$-$d_6$ with addition of a few drops of $CF_3COOD$, δ in ppm): 1.36 (broad t, J=12.5 Hz: 2H); from 1.50 to 1.70 (mt: 4H); 1.96 (broad d, J=12.5 Hz: 2H); 2.08 (broad t, J=11.5 Hz: 2H); 2.62 (t, J=6 Hz: 2H); 2.71 (broad d, J=11.5 Hz: 2H); 3.05 (broad t, J=6.5 Hz: 2H); 3.97 (s: 3H); 4.03 (t, J=6 Hz: 2H); from 6.85 to 7.00 (mt: 3H); 7.29 (broad t, J=8 Hz: 2H); 7.35 (d, J=2.5 Hz: 1H); 7.40 (dd, J=9 and 2.5 Hz: 1H); 7.97 (d, J=9 Hz: 1H); 8.70 (broad s: 1H).

Ethyl 4-[3-(3-fluoro-6-methoxyquinolin-4-yl)propyl]-1-(2-phenoxyethyl)piperidine-4-carboxylate A mixture of 0.4 g of ethyl 4-[3-(3-fluoro-6-methoxyquinolin-4-yl)propyl]piperidine-4-carboxylate, 0.26 g of 2-bromoethyl phenyl ether, 0.181 g of potassium iodide and 0.737 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.4 g of ethyl 4-[3-(3-fluoro-6-methoxyquinolin-4-yl)propyl]-1-(2-phenoxyethyl)piperidine-4-carboxylate was obtained.

¹H NMR Spectrum (500 MHz, $(CD_3)_2SO$-$d_6$, δ in ppm): 0.99 (t, J=7 Hz: 3H); 1.37 (mt: 2H); from 1.45 to 1.65 (mt: 4H); from 1.85 to 2.10 (mt: 4H); from 2.35 to 2.75 (mt: 4H); 3.03 (mt: 2H); 3.93 (s: 3H); 3.96 (q, J=7 Hz: 2H); 4.02 (mt: 2H); 6.90 (mt: 3H); 7.26 (broad t, J=7.5 Hz: 2H); 7.32 (broad s: 1H); 7.38 (broad d, J=9 Hz: 1H); 7.95 (d, J=9 Hz: 1H); 8.68 (broad s: 1H).

The ethyl 4-[3-(3-fluoro-6-methoxyquinolin-4-yl)propyl] piperidine-4-carboxylate was prepared as described in Example 11.

EXAMPLE 43

4-[3-(3-Fluoro-6-methoxyquinolin-4-yl)propyl]-1-[2-(3-fluorophenoxy)ethyl]piperidine-4-carboxylic acid A mixture of 0.415 g of ethyl 4-[3-(3-fluoro-6-methoxyquinolin-4-yl)propyl]-1-[2-(3-fluorophenoxy)-ethyl]piperidine-4-carboxylate in 3 cm³ of dioxane, 3 cm³ of methanol and 2.4 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.34 g of 4-[3-(3-fluoro-6-methoxyquinolin-4-yl)propyl]-1-[2-(3-fluorophenoxy)ethyl]piperidine-4-carboxylic acid was obtained in the form of a white solid.

¹H NMR Spectrum (300 MHz, $(CD_3)_2SO$-$d_6$ with addition of a few drops of $CF_3COOD$, δ in ppm): 1.34 (broad t, J=12.5 Hz: 2H); from 1.50 to 1.70 (mt: 4H); 1.96 (broad d, J=12.5 Hz: 2H); 2.08 (broad t, J=11 Hz: 2H); 2.63 (t, J=6 Hz: 2H); 2.70 (broad d, J=11 Hz: 2H); 3.05 (broad t, J=6.5 Hz: 2H); 3.97 (s: 3H); 4.06 (t, J=6 Hz: 2H); from 6.70 to 6.90 (mt: 3H); from 7.25 to 7.40 (mt: 1H); 7.35 (d, J=2.5 Hz: 1H); 7.40 (dd, J=9 and 2.5 Hz: 1H); 7.97 (d, J=9 Hz: 1H); 8.70 (broad s: 1H).

Ethyl 4-[3-(3-fluoro-6-methoxyquinolin-4-yl)propyl]-1-[2-(3-fluorophenoxy)ethyl]piperidine-4-carboxylate A mixture of 0.4 g of ethyl 4-[3-(3-fluoro-6-methoxyquinolin-4-yl)propyl]piperidine-4-carboxylate, 0.281 g of 1-(2-bromoethoxy)-3-fluorobenzene, 0.181 g of potassium iodide and 0.737 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.43 g of ethyl 4-[3-(3-fluoro-6-methoxyquinolin-4-yl)propyl]-1-[2-(3-fluorophenoxy)ethyl]piperidine-4-carboxylate was obtained.

¹H NMR Spectrum (500 MHz, $(CD_3)_2SO$-$d_6$, δ in ppm): 0.98 (t, J=7 Hz: 3H); 1.35 (broad t, J=12 Hz: 2H); from 1.45 to 1.65 (mt: 4H); 1.92 (broad d, J=12 Hz: 2H); 2.00 (broad t, J=11.5 Hz: 2H); from 2.30 to 2.70 (mt: 4H); 3.02 (mt: 2H); 3.91 (s: 3H); 3.94 (q, J=7 Hz: 2H); 4.01 (mt: 2H); from 6.65 to 6.80 (mt: 3H); from 7.20 to 7.30 (mt: 1H); 7.28 (broad s: 1H); 7.36 (broad d, J=9 Hz: 1H); 7.93 (d, J=9 Hz: 1H); 8.65 (broad s: 1H).

1-(2-Bromoethoxy)-3-fluorobenzene

A mixture of 8.6 g of 3-fluorophenol, 15.3 g of potassium carbonate and 40.5 cm³ of 1,2-dibromoethane in 200 cm³ of acetonitrile was stirred, under an inert atmosphere, at a temperature in the region of 70° C. for 25 hours. After cooling to about 20° C., the suspension was filtered, the insoluble material was rinsed with 3 times 50 cm³ of acetonitrile and the filtrate was then concentrated to dryness under reduced pressure (2 kPa) at a temperature in the region of 40° C.

The residue obtained was taken up in 50 cm³ of diethyl ether and then filtered, and the filtration liquors were concentrated to dryness as under the previous conditions. The oil obtained by evaporation was purified by chromatography under a pressure of 50 kPa of argon on a column of silica gel (particle size 20–45μ; diameter 4.5 cm; height 22 cm), eluting with 40–60° C. petroleum ether. Fractions 8 to 60 were combined and then concentrated to dryness under reduced pressure (2 kPa) in the region of 40° C. 7.67 g of 1-(2-bromoethoxy)-3-fluorobenzene were obtained.

Infra-red spectrum (CCl₄): 1616; 1596; 1492; 1279; 1265; 1168; 1140; 1025; 853; 834 and 679 cm⁻¹.

The ethyl 4-[3-(3-fluoro-6-methoxyquinolin-4-yl)propyl] piperidine-4-carboxylate was prepared as described in Example 11.

EXAMPLE 44

1-[2-(2,6-Difluorophenoxy)ethyl]-4-[3-(3-fluoro-6-methoxyquinolin-4-yl)propyl]piperidine-4-carboxylic acid A mixture of 0.39 g of ethyl 1-[2-(2,6-difluorophenoxy) ethyl]-4-[3-(3-fluoro-6-methoxyquinolin-4-yl)propyl] piperidine-4-carboxylate in 3 cm³ of dioxane, 3 cm³ of methanol and 2.2 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C. The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.3 g of 1-[2-(2,6-difluorophenoxy)ethyl]-4-[3-(3-fluoro-6-methoxyquinolin-4-yl)propyl]piperidine-4-carboxylic acid was obtained in the form of a white solid.

¹H NMR Spectrum (300 MHz, (CD₃)₂SO-d₆, δ in ppm) 1.33 (broad t, J=12.5 Hz: 2H); from 1.50 to 1.65 (mt: 4H); 1.91 (broad d, J=12.5 Hz: 2H); 2.05 (broad t, J=11 Hz: 2H); 2.60 (t, J=6 Hz: 2H); 2.63 (mt: 2H); 3.05 (mt: 2H); 3.97 (s: 3H); 4.16 (t, J=6 Hz: 2H); from 7.05 to 7.20 (mt: 3H); 7.35 (d, J=2.5 Hz: 1H); 7.40 (dd, J=9 and 2.5 Hz: 1H); 7.97 (d, J=9 Hz: 1H); 8.70 (broad s: 1H).

Ethyl 1-[2-(2,6-difluorophenoxy)ethyl]-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.304 g of 1-(2-bromoethoxy)-3-fluorobenzene, 0.181 g of potassium iodide and 0.74 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C.

The evaporation residue was purified by chromatography under atmospheric pressure, on a cartridge of silica gel (Bond Elut; particle size 70–200μ; mass 10 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.4 g of ethyl 1-[2-(2,6-difluorophenoxy)ethyl]-4-[3-(3-fluoro-6-methoxyquinolin-4-yl)propyl]piperidine-4-carboxylate was obtained.

¹H NMR Spectrum (500 MHz, (CD₃)₂SO-d₆, δ in ppm): 0.97 (t, J=7 Hz: 3H); 1.26 (broad t, J=125 Hz: 2H); from 1.40 to 1.60 (mt: 4H); 1.88 (broad d, J=12 Hz: 2H); 1.98 (broad t, J=11 Hz: 2H); from 2.30 to 2.65 (mt: 4H); 3.00 (mt: 2H); 3.92 (s: 3H); 3.94 (mt: 2H); 4.11 (mt: 2H); from 6.95 to 7.10 (mt: 3H); 7.30 (broad s: 1H); 7.37 (broad d, J=9 Hz: 1H); 7.93 (d, J=9 Hz: 1H); 8.66 (broad s: 1H).

The ethyl 4-[3-(3-fluoro-6-methoxyquinolin-4-yl)propyl] piperidine-4-carboxylate was prepared as described in Example 11.

The 1-(2-bromoethoxy)-3-fluorobenzene was prepared according to the method described in Example 15.

EXAMPLE 45

1-[2-(2,3-Difluorophenoxy)ethyl]-4-[3-(3-fluoro-6-methoxyquinolin-4-yl)propyl]piperidine-4-carboxylic Acid A mixture of 0.42 g of ethyl 1-[2-(2,3-difluorophenoxy) ethyl]-4-[3-(3-fluoro-6-methoxyquinolin-4-yl)propyl] piperidine-4-carboxylate in 3 cm³ of dioxane, 3 cm³ of methanol and 2.4 cm³ of aqueous 5N sodium hydroxide solution was stirred at a temperature in the region of 70° C. for 17 hours. After cooling to about 20° C., the reaction mixture was concentrated to dryness under a pressure gradually reduced from 30 kPa to 2.5 kPa and at a temperature in the region of 45° C.

The residue was taken up in 5 cm³ of a dichloromethane/methanol/aqueous ammonia mixture (40/5/0.5 by volume) and was then purified by chromatography under atmospheric pressure, on a cartridge of silica gel (Bond Elut; particle size 70–200μ; mass 10 g), eluting with a dichloromethane/methanol/aqueous ammonia mixture (90/9/0.9 by volume) and then with a chloroform/methanol/aqueous ammonia mixture (77.5/19.5/3). The fractions containing the product were combined, concentrated to dryness under reduced pressure (2 kPa) at a temperature in the region of 40° C. and dried in a desiccator (10 kPa). 0.32 g of 1-[2-(2,3-difluorophenoxy)ethyl]-4-[3-(3-fluoro-6-methoxyquinolin-4-yl)propyl]piperidine-4-carboxylic acid was obtained in the form of a white solid.

¹H NMR Spectrum (300 MHz, (CD₃)₂SO-d₆, δ in ppm) 1.34 (broad t, J=12.5 Hz: 2H); from 1.50 to 1.70 (mt: 4H); 1.96 (broad d, J=12.5 Hz: 2H); 2.09 (broad t, J=11.5 Hz: 2H); 2.65 (t, J=6 Hz: 2H); 2.71 (broad d, J=11.5 Hz: 2H); 3.05 (mt: 2H); 3.97 (s: 3H); 4.16 (t, J=6 Hz: 2H); from 6.90 to 7.20 (mt: 3H); 7.34 (d, J=2.5 Hz: 1H); 7.40 (dd, J=9 and 2.5 Hz: 1H); 7.97 (d, J=9 Hz: 1H); 8.70 (broad s: 1H).

Ethyl 1-[2-(2,3-difluorophenoxy)ethyl]-4-[3-(3-fluoro-6-methoxyquinolin-4-yl)propyl]piperidine-4-carboxylate A mixture of 0.4 g of ethyl 4-[3-(3-fluoro-6-methoxyquinolin-4-yl)propyl]piperidine-4-carboxylate, 0.3 g of 1-(2-bromoethoxy)-2,3-difluorobenzene, 0.181 g of potassium iodide and 0.74 g of potassium carbonate in 15 cm³ of acetonitrile was stirred for 18 hours at a temperature in the region of 70° C. After cooling to about 20° C., the reaction mixture was concentrated to dryness under reduced pressure (5 kPa) at a temperature in the region of 40° C. The evaporation residue was purified by chromatography under atmospheric pressure, on a cartridge of silica gel (Bond Elut; particle size 70–200μ; mass 12 g), eluting with a mixture of ethyl acetate/40–60° C. petroleum ether (8/2 by volume). The fractions containing the product were combined and then concentrated to dryness under reduced pressure (2 kPa) at a temperature in the region of 40° C. 0.43 g of ethyl 1-[2-(2,3-difluorophenoxy)ethyl]-4-[3-(3-fluoro-6-methoxyquinolin-4-yl)propyl]piperidine-4-carboxylate was obtained.

¹H NMR Spectrum (500 MHz, (CD₃)₂SO-d₆, δ in ppm): 0.99 (mt: 3H); 1.34 (mt: 2H); from 1.40 to 1.60 (mt: 4H); 1.93 (broad d, J=12.5 Hz: 2H); from 1.95 to 2.10 (mt: 2H); from 2.45 to 2.70 (mt: 4H); 3.02 (mt: 2H); 3.93 (s: 3H); 3.95 (mt: 2H); 4.12 (mt: 2H); from 6.85 to 7.05 (mt: 2H); 7.09 (mt: 1H); 7.31 (broad s: 1H); 7.37 (broad d, J=9 Hz: 1H); 7.94 (d, J=9 Hz: 1H); 8.66 (broad s: 1H).

The ethyl 4-[3-(3-fluoro-6-methoxyquinolin-4-yl)propyl]piperidine-4-carboxylate was prepared as described in Example 11.

The 1-(2-bromoethoxy)-2,3-difluorobenzene was prepared as described in Example 17.

EXAMPLE 46

4-[3-(3-Fluoroquinolin-4-yl)propyl]-1-[2-(thien-2-yl)thioethyl]piperidine-4-carboxylic Acid A mixture of 1.29 g of ethyl 4-[3-(3-fluoroquinolin-4-yl)propyl]-1-[2-(thien-2-yl)thioethyl]piperidine-4-carboxylate in 65 cm³ of dioxane, 65 cm³ of methanol and 8 cm³ of aqueous 5N sodium hydroxide solution was stirred at a temperature in the region of 70° C. for 20 hours. 8 cm³ of aqueous 5N sodium hydroxide solution were added to the reaction mixture, which was stirred in the region of 70° C. for a further 6 hours. After cooling to about 20° C., the reaction mass was concentrated to dryness under reduced pressure (2 kPa) at a temperature in the region of 50° C. The residue was purified by chromatography under atmospheric pressure, on a column of silica gel (particle size 20–45μ; diameter 6 cm; height 30 cm), eluting with a chloroform/methanol/aqueous ammonia mixture (12/3/0.5 by volume) and collecting 100-cm³ fractions. Fractions 8 to 24 were combined and concentrated to dryness under reduced pressure (2 kPa) at a temperature in the region of 40° C. The white solid was taken up in 60 cm³ of diisopropyl ether and stirred for 18 hours at a temperature in the region of 20° C. The suspension was filtered, washed with 3 times 15 cm³ of diisopropyl ether, spin-filtered and then dried under reduced pressure (10 kPa) at about 50° C. 0.8 g of 4-[3-(3-fluoroquinolin-4-yl)propyl]-1-[2-(thien-2-yl)-thioethyl]piperidine-4-carboxylic acid was obtained in the form of a white solid melting at 180° C.

¹H NMR Spectrum (300 MHz, (CD₃)₂SO-d₆, δ in ppm): 1.27 (mt: 2H); 1.56 (mt: 4H); from 1.85 to 2.05 (mt: 4H); 2.44 (broad t, J=7 Hz: 2H); 2.57 (mt: 2H); 2.90 (broad t, J=7 Hz: 2H); 3.06 (unresolved peak: 2H); 7.04 (dd, J=5.5 and 3.5 Hz: 1H); 7.17 (dd, J=3.5 and 1.5 Hz: 1H); 7.60 (dd, J=5.5 and 1.5 Hz: 1H); 7.71 (broad t, J=7.5 Hz: 1H); 7.77 (broad t, J=7.5 Hz: 1H); 8.08 (broad d, J=7.5 Hz: 1H); 8.15 (broad d, J=7.5 Hz: 1H); 8.89 (d, J=1.5 Hz: 1H).

Ethyl 4-[3-(3-fluoroquinolin-4-yl)propyl]-1-[2-(thien-2-yl)thioethyl]piperidine-4-carboxylate A mixture of 1.8 g of ethyl 1-(2-chloroethyl)-4-[3-(3-fluoroquinolin-4-yl)propyl]piperidine-4-carboxylate monohydrochloride, 0.48 cm³ of thiophene-2-thiol, 2.8 g of potassium carbonate and 0.75 g of potassium iodide in 200 cm³ of anhydrous acetonitrile was stirred under an inert atmosphere for 18 hours at a temperature in the region of 70° C. After cooling to about 20° C., the suspension was filtered, washed with 3 times 30 cm³ of acetonitrile and the filtrate was then concentrated to dryness under reduced pressure (2 kPa) at a temperature in the region of 50° C. The evaporation residue was purified by chromatography under atmospheric pressure, on a column of silica gel (particle size 20–45μ; diameter 6 cm; height 30 cm), eluting with ethyl acetate and collecting 50-cm³ fractions. Fractions 25 to 52 were combined and then concentrated to dryness under reduced pressure (2 kPa) at a temperature in the region of 40° C. 1.3 g of ethyl 4-[3-(3-fluoroquinolin-4-yl)propyl]-1-[2-(thiophen-2-ylthio)ethyl]piperidine-4-carboxylate were obtained in the form of a viscous orange-colored oil.

¹H NMR Spectrum (300 MHz, (CD₃)₂SO-d₆, δ in ppm) 0.99 (t, J=7 Hz: 3H); 1.34 (very broad t, J=13 Hz: 2H); 1.56 (mt: 4H); from 1.85 to 2.00 (mt: 4H); 2.45 (broad t, J=7 Hz: 2H); 2.59 (broad d, J=11.5 Hz: 2H); 2.90 (broad t, J 7 Hz: 2H); 3.07 (broad t, J=6.5 Hz: 2H); 3.95 (q, J=7 Hz: 2H); 7.04 (dd, J=5.5 and 3.5 Hz: 1H); 7.17 (dd, J=3.5 and 1.5 Hz: 1H); 7.60 (dd, J=5.5 and 1.5 Hz: 1H); 7.70 (broad t, J=7.5 Hz: 1H); 7.77 (doubled triplet, J=7.5 and 1.5 Hz: 1H); 8.08 (broad d, J=7.5 Hz: 1H); 8.13 (broad d, J=7.5 Hz: 1H); 8.89 (d, J=1 Hz: 1H).

Ethyl 1-(2-chloroethyl)-4-[3-(3-fluoroquinolin-4-yl)propyl]piperidine-4-carboxylate Hydrochloride 1.2 cm³ of thionyl chloride in 5 cm³ of dichloromethane were added to a solution of 1.55 g of ethyl 4-[3-(3-fluoroquinolin-4-yl)propyl]-1-(2-hydroxy-ethyl)piperidine-4-carboxylate in 35 cm³ of dichloromethane, with stirring at a temperature in the region of 20° C. After stirring for 42 hours at a temperature in the region of 20° C., the reaction mixture was concentrated to dryness under reduced pressure (1.2 kPa) at about 50° C. The foam obtained was taken up in 3 times 100 cm³ of cyclohexane, concentrated to dryness under reduced pressure (2 kPa) at a temperature in the region of 40° C. and oven-dried under reduced pressure (10 kPa) at a temperature in the region of 20° C. 1.8 g of ethyl 1-(2-chloroethyl)-4-[3-(3-fluoroquinolin-4-yl)propyl]piperidine-4-carboxylate monohydrochloride were obtained in the form of a cream-colored solid.

¹H NMR Spectrum (300 MHz, (CD₃)₂SO-d₆, δ in ppm): 1.03 (t, J=7 Hz: 3H); from 1.45 to 2.10 (mt: 6H); 2.16 (broad d, J=14 Hz: 2H); from 2.70 to 3.00 (mt: 2H); 3.12 (mt: 2H); from 3.40 to 3.55 (mt: 4H); from 3.95 to 4.10 (mt: 4H); 7.72 (broad t, J=7.5 Hz: 1H); 7.79 (broad t, J=7.5 Hz: 1H); 8.09 (broad d, J=7.5 Hz: 1H); 8.18 (broad d, J=7.5 Hz: 1H); 8.92 (broad s: 1H); from 10.10 to 10.35 (unresolved peak: 1H).

Ethyl 4-[3-(3-fluoroquinolin-4-yl)propyl]-1-(²-hydroxyethyl)piperidine-4-carboxylate 1.14 cm³ of 2-iodoethanol and 1.9 g of potassium carbonate were added to a solution of 4.4 g of ethyl 4-[3-(3-fluoroquinolin-4-yl)propyl]piperidine-4-carboxylate in 100 cm³ of anhydrous acetonitrile, with vigorous stirring and under an inert atmosphere. The reaction mixture was stirred for 18 hours in the region of 20° C., filtered and washed with 3 times 30 cm³ of acetonitrile. The filtrate was concentrated to dryness under reduced pressure (2 kPa) at a temperature in the region of 50° C. The evaporation residue was purified by chromatography under atmospheric pressure, on a column of silica gel (particle size 20–45μ; diameter 5 cm; height 32 cm), eluting with dichloromethane/methanol/aqueous ammonia (40/5/0.5 by volume) and collecting 100-cm³ fractions. Fractions 8 to 12 were combined and then concentrated to dryness under reduced pressure (2 kPa) at a temperature in the region of 40° C. 3.5 g of ethyl 4-[3-(3-fluoroquinolin-4-yl)-propyl]-1-(2-hydroxyethyl)piperidine-4-carboxylate were obtained in the form of a viscous orange-colored oil.

¹H NMR Spectrum (300 MHz, (CD₃)₂SO-d₆, δ in ppm) 0.99 (t, J=7 Hz: 3H); 1.36 (mt: 2H); 1.57 (mt: 4H); from 1.85 to 2.05 (mt: 4H); 2.29 (t, J=6.5 Hz: 2H); 2.61 (d mt, J=12 Hz: 2H); 3.08 (broad t, J=6 Hz: 2H); 3.45 (mt: 2H); 3.96 (q, J=7 Hz: 2H); 4.31 (t, J=5.5 Hz: 1H); 7.70 (broad t, J=7.5 Hz: 1H); 7.77 (doubled triplet, J=7.5 and 1.5 Hz: 1H); 8.08 (dd, J=7.5 and 1.5 Hz: 1H); 8.14 (dd, J=7.5 and 1.5 Hz: 1H); 8.89 (d, J=1 Hz: 1H).

Ethyl 4-[3-(3-fluoroquinolin-4-yl)propyl]piperidine-4-carboxylate 50 cm$^3$ of a solution of hydrogen chloride in dioxane at a concentration of 4M were added cautiously to a solution of 8.7 g of ethyl 4-[3-(3-fluoroquinolin-4-yl)propyl]-1-(tert-butyloxycarbonyl)piperidine-4-carboxylate in 150 cm$^3$ of anhydrous dioxane, and the temperature was maintained below 30° C. during the addition. After stirring for 18 hours in the region of 20° C., the suspension was diluted with 250 cm$^3$ of diethyl ether, filtered and washed with 5 times 50 cm$^3$ of diethyl ether, and the solid was dried in a desiccator under reduced pressure (2 kPa) and at a temperature in the region of 20° C. The solid was taken up in 50 cm$^3$ of water and aqueous 5N sodium hydroxide solution was added so that the pH was at about 10, and the mixture was then extracted with 5 times 100 cm$^3$ of diethyl ether. The organic phases were combined, dried over magnesium sulfate, taken up with plant charcoal (3S), filtered and concentrated to dryness under reduced pressure (2 kPa) at a temperature in the region of 50° C. 4.7 g of ethyl 4-[3-(3-fluoroquinolin-4-yl)propyl]piperidine-4-carboxylate were obtained in the form of a viscous orange-colored oil.

Mass spectrum: EI m/z=344 M$^+$ m/z=288 $C_{17}H_{19}FNO_2^{+\cdot}$
m/z=184 $C_{10}H_{18}NO_2^+$
base peak m/z=161 $C_{10}H_8FN^+$ Ethyl 4-[3-(3-fluoroquinolin-4-yl)propyl]-1-(tert-butyloxycarbonyl)piperidine-4-carboxylate 17.7 g of ethyl 4-allyl-1-(tert-butyloxycarbonyl)piperidine-4-carboxylate in 200 cm$^3$ of tetrahydrofuran were cooled to a temperature in the region of −30° C. and 135 cm$^3$ of a 0.5M solution of 9-borabicyclo-[3.3.1]nonane in tetrahydrofuran were added with stirring and under an inert atmosphere. After the addition, the temperature of the mixture was returned to about 20° C. and the mixture was stirred for 2 hours. 14.8 g of 3-fluoro-4-iodoquinoline in 430 cm$^3$ of tetrahydrofuran, 1.3 g of palladium diphenylphosphinoferrocene chloride and 29.8 g of tribasic potassium phosphate were added. The reaction mixture was then heated at a temperature in the region of 70° C. for 20 hours. After cooling to a temperature in the region of 20° C., the reaction mass was filtered and washed with 3 times 100 cm$^3$ of tetrahydrofuran. The filtrate was concentrated to dryness under reduced pressure (2 kPa) at a temperature in the region of 40° C. The evaporation residue was taken up in 500 cm$^3$ of diethyl ether, the insoluble material was washed with 3 times 100 cm$^3$ of diethyl ether and the filtrate was concentrated to dryness under reduced pressure (2 kPa) at a temperature in the region of 40° C. The oil obtained was purified by chromatography under atmospheric pressure, on a column of silica gel (particle size 20–45μ; diameter 6 cm; height 45 cm), eluting with a dichloromethane/ethyl acetate mixture (90/10 by volume) and collecting 120-cm$^3$ fractions. Fractions 30 to 76 were combined and then concentrated to dryness under the same conditions as above. 13.7 g of ethyl 4-[3-(3-fluoroquinolin-4-yl)propyl]-1-(tert-butyloxycarbonyl)-piperidine-4-carboxylate were obtained in the form of a viscous orange-colored oil.

Mass spectrum: EI m/z=444 M$^{+\cdot}$ m/z=388 [M-tBu]$^{+\cdot}$
m/z=343 [M-BOC]$^+$
m/z=288 $C_{17}H_{19}FNO_2^{+\cdot}$ m/z=184 $C_{10}H_{18}NO_2^{+\cdot}$
m/z=161 $C_{10}H_8FN^+$ m/z=57 $C_4H_9^+$
3-Fluoro-4-iodoquinoline 17.3 cm$^3$ of diisopropylamine in 650 cm$^3$ of tetrahydrofuran were cooled to a temperature in the region of −75° C. and 76 cm$^3$ of a 1.6M solution of butyl lithium in hexane were added, with stirring and under an inert atmosphere, while maintaining the temperature at about −70° C. After stirring for 20 minutes at a temperature in the region of −75° C., a solution of 11.9 g of 3-fluoroquinoline in 200 cm$^3$ of tetrahydrofuran was added. The solution obtained was stirred for a further 4 hours at −75° C., followed by addition of a solution of 32.2 g of double-sublimed iodine in 150 cm$^3$ of tetrahydrofuran. After stirring for 2 hours at a temperature in the region of −40° C., the reaction mixture was hydrolyzed with 200 cm$^3$ of a tetrahydrofuran/water mixture (90/10 by volume) and then with 200 cm$^3$ of saturated sodium chloride solution. In the region of 20° C., the mixture was diluted with 300 cm$^3$ of ethyl acetate and washed with twice 250 cm$^3$ of saturated sodium chloride solution. The organic phase was dried over magnesium sulfate, filtered and concentrated to dryness under reduced pressure (2 kPa) at a temperature in the region of 50° C. The residue obtained was purified by chromatography under atmospheric pressure, on a column of silica gel (particle size 20–45μ; diameter 10 cm; height 30 cm), eluting with dichloromethane and collecting 100-cm$^3$ fractions. Fractions 45 to 80 were combined and then concentrated to dryness under reduced pressure (2 kPa) at a temperature in the region of 40° C. 15.1 g of 3-fluoro-4-iodoquinoline were obtained in the form of a cream-colored solid melting at 110° C.

Mass spectrum: EI m/z=273 M$^{+\cdot}$ base peak m/z 146 [M-I]$^+$
3-Fluoroquinoline 23.5 g of 3-aminoquinoline and 12.1 g of sodium nitrite in 20 cm$^3$ of distilled water were added cautiously to 100 cm$^3$ of tetrafluoroboric acid cooled to about 0° C., with vigorous stirring, and the reaction mixture was thus stirred for 30 minutes. The suspension was filtered, spin-filtered, washed with 3 times 30 cm$^3$ of ice-cold tetrafluoroboric acid, 50 cm$^3$ of ice-cold ethanol and 4 times 30 cm$^3$ of diethyl ether. The solid was dried in a desiccator (2 kPa) in the region of 20° C. and then taken up in 200 cm$^3$ of toluene and heated at a temperature in the region of 90° C. for 1 hour with stirring. After cooling to about 20° C., the phases of the reaction mass were separated by settling and the insoluble oil was washed with 3 times 100 cm$^3$ of toluene and taken up in 110 cm$^3$ of water, which was basified by slow addition of sodium hydrogen carbonate so that the pH was at about 8. The aqueous phase was extracted with 5 times 100 cm$^3$ of diethyl ether and the organic phases were combined, washed with twice 50 cm$^3$ of water, dried over magnesium sulfate and taken up with vegetable charcoal (3S), filtered and concentrated to dryness under reduced pressure (2 kPa) at a temperature in the region of 45° C. The oil was taken up in 50 cm$^3$ of a 40–60° C. petroleum ether/ethyl acetate mixture (90/10 by volume) and the insoluble material was filtered off, rinsed with twice 25 cm$^3$ of a 40–60° C. petroleum ether/ethyl acetate mixture (90/10 by volume) and dried in a desiccator under reduced pressure (2 kPa) at a temperature in the region of 20° C. The filtrate was concentrated to dryness under reduced pressure (2 kPa) at a temperature in the region of 40° C. The residue obtained was purified by chromatography under atmospheric pressure, on a column of silica gel (particle size 20–45μ; diameter 5 cm; height 45 cm), eluting with a 40–60° C. petroleum ether/ethyl acetate mixture (90/10 by volume) and collecting 100-cm$^3$ fractions. Fractions 20 to 31 were combined and then concentrated to dryness under reduced pressure (2 kPa) at a temperature in the region of 40° C. 13 g of 3-fluoroquinoline were obtained in the form of a colorless liquid.

Mass spectrum: EI m/z=147 M$^{+\cdot}$ base peak m/z=127 [M-HF]$^{+\cdot}$
m/z=120 [M-HCN]$^+$ The ethyl 4-allyl-1-(tert-butoxycarbonyl)-piperidine-4-carboxylate was prepared as described in Example 1.

EXAMPLE 47

Ethyl 4-[3-(3-chloro-6-methoxyquinolin-4-yl)-propyl]-1-[2-(pyridin-2-yloxy)ethyl]piperidine-4-carboxylate was prepared in the form of a viscous colorless oil.

$^1$H NMR Spectrum (300 MHz, $(CD_3)_2SO-d_6$, δ in ppm): 1.04 (t, J=7 Hz: 3H); 1.39 (very broad t, J=12 Hz: 2H); 1.51 (mt: 2H); 1.68 (mt: 2H); from 1.90 to 2.15 (mt: 4H); 2.60 (t, J=6 Hz: 2H); 2.70 (broad d, J=12 Hz: 2H); 3.16 (broad t, J=7.5 Hz: 2H); 3.95 (s: 3H); 3.99 (q, J=7 Hz: 2H); 4.31 (t, J=6 Hz: 2H); 6.78 (d, J=8 Hz: 1H); 6.96 (broad dd, J=7.5 and 5 Hz: 1H); 7.37 (d, J=2.5 Hz: 1H); 7.45 (dd, J=9 and 2.5 Hz: 1H); 7.69 (ddd, J=8–7.5 and 2 Hz: 1H); 7.96 (d, J=9 Hz: 1H); 8.14 (broad dd, J=5 and 2 Hz: 1H); 8.67 (s: 1H).

4-[3-(3-Chloro-6-methoxyquinolin-4-yl)propyl]-1-[2-(pyridin-2-yloxy)ethyl]piperidine-4-carboxylic Acid A mixture of 0.12 g of ethyl 4-[3-(3-chloro-6-methoxyquinolin-4-yl)propyl]-1-[2-(pyridin-2-yloxy)-ethyl]piperidine-4-carboxylate in 5 cm$^3$ of dioxane, 5 cm$^3$ of methanol and 1 cm$^3$ of aqueous 5N sodium hydroxide solution was stirred at a temperature in the region of 70° C. for 21 hours. After cooling to about 20° C., the reaction mass was concentrated to dryness under reduced pressure (5 kPa) at a temperature in the region of 60° C. The residue was taken up in 5 cm$^3$ of a dichloromethane/methanol/aqueous ammonia mixture (40/5/0.5 by volume) and then purified by chromatography under atmospheric pressure, on a column of silica gel (particle size 70–200μ; diameter 1.5 cm; mass 20 g), eluting with a dichloromethane/methanol/aqueous ammonia mixture (40/5/0.5 by volume). The fractions containing the product were combined and concentrated to dryness under reduced pressure (2 kPa) at a temperature in the region of 40° C. The foam was taken up in 2 cm$^3$ of methanol, filtered, washed with 1 cm$^3$ of methanol and 2 cm$^3$ of diethyl ether and then oven-dried under reduced pressure (10 kPa) at about 50° C. 0.115 g of 4-[3-(3-chloro-6-methoxyquinolin-4-yl)propyl]-1-[2-(pyridin-2-yloxy)ethyl]piperidine-4-carboxylic acid was obtained in the form of a white solid melting at about 70° C. and becoming sticky.

$^1$H NMR Spectrum (300 MHz, $(CD_3)_2SO-d_6$, δ in ppm) from 1.20 to 1.80 (mt: 6H); 1.98 (very broad d, J=13.5 Hz: 2H); 2.09 (very broad t, J=11 Hz: 2H); 2.60 (t, J=6 Hz: 2H); 2.67 (mt: 2H); 3.16 (mt: 2H); 3.98 (s: 3H); 4.32 (t, J=6 Hz: 2H); 6.80 (d, J=8 Hz: 1H); 6.96 (ddd, J=7.5–5 and 1 Hz: 1H); 7.39 (broad s: 1H); 7.45 (dd, J=9 and 2.5 Hz: 1H); 7.70 (ddd, J=8–7.5 and 2 Hz: 1H); 7.97 (d, J=9 Hz: 1H); 8.16 (broad dd, J=5 and 2 Hz: 1H); 8.67 (s: 1H).

EXAMPLE 48

4-[3-(3-Chloro-6-methoxyquinolin-4-yl)-3-(R,S)-fluoropropyl]-1-[2-(2,5-difluorophenylthio)ethyl]piperidine-4-carboxylic Acid A mixture of 0.07 g of methyl 4-[3-(3-chloro-6-methoxyquinolin-4-yl)-3-(R,S)-fluoropropyl]-1-[2-(2,5-difluorophenylthio)ethyl]piperidine-4-carboxylate in 3 cm$^3$ of dioxane, 3 cm$^3$ of methanol and 0.9 cm$^3$ of aqueous 5N sodium hydroxide solution was maintained at a temperature in the region of 70° C. for 4 hours. After cooling to about 20° C., the reaction mixture was concentrated to dryness under reduced pressure (2 kPa) at a temperature in the region of 40° C. The residue was chromatographed under atmospheric pressure, on a column of silica gel (particle size 70–200μ; mass 10 g), eluting with a dichloromethane/methanol/aqueous ammonia mixture (40/5/0.5 by volume). Fractions 10 to 15 were combined and then concentrated to dryness under the same conditions as above. 0.04 g of 4-[3-(3-chloro-6-methoxyquinolin-4-yl)-3-(R,S)-fluoropropyl]-1-[2-(2,5-difluorophenylthio)ethyl]-piperidine-4-carboxylic acid was obtained in the form of a white solid.

$^1$H NMR Spectrum (300 MHz, $(CD_3)_2SO-d_6$, δ in ppm): from 1.20 to 2.60 (mt: 12H); 2.66 (mt: 2H); 3.03 (t, J=7 Hz: 2H); 3.93 (s: 3H); 6.38 (mt, $J_{HF}$=48 Hz: 1H); 7.05 (mt: 1H); from 7.20 to 7.40 (mt: 2H); 7.52 (dd, J=9 and 2.5 Hz: 1H); 7.56 (d, J=2.5 Hz: 1H); 8.04 (d, J=9 Hz: 1H); 8.75 (broad s: 1H); from 12.30 to 12.70 (broad unresolved peak: 1H).

Methyl 4-[3-(3-chloro-6-methoxyquinolin-4-yl)-3-(R,S)-fluoropropyl]-1-[2-(2,5-difluorophenylthio)ethyl]-piperidine-4-carboxylate 0.1 cm$^3$ of diethylaminosulfur trifluoride was added to a solution of 0.25 g of methyl 4-[3-(3-chloro-6-methoxyquinolin-4-yl)-3-(R,S)-hydroxypropyl]-1-[2-(2,5-difluorophenylthio)ethyl]piperidine-4-carboxylate in 10 cm$^3$ of dichloromethane, with stirring and under an inert atmosphere, at a temperature in the region of 5° C. After stirring for 7 hours at a temperature in the region of 20° C., saturated sodium hydrogen carbonate solution was added to the reaction mixture. The aqueous phase was extracted with dichloromethane. The organic phase was dried over magnesium sulfate, filtered and then concentrated to dryness under reduced pressure (2 kPa) at a temperature in the region of 40° C. The residue obtained was purified by chromatography under atmospheric pressure, on a column of silica gel (particle size 70–200μ; mass: 15 g), eluting with 60 cm$^3$ of dichloromethane, then with 45 cm$^3$ of a mixture of ethyl acetate/dichloromethane (1/9 by volume), then with 30 cm$^3$ of a mixture of ethyl acetate/dichloromethane (2/8 by volume) and then with 210 cm$^3$ of a mixture of ethyl acetate/dichloromethane (3/7 by volume) and then with ethyl acetate. Fractions 24 to 26 were combined and then concentrated to dryness according to the same conditions as above. 0.08 g of methyl 4-[3-(3-chloro-6-methoxyquinolin-4-yl)-3-(R,S)-fluoropropyl]-1-[2-(2,5-difluorophenylthio)ethyl]piperidine-4-carboxylate was obtained in the form of a thick yellow oil.

$^1$H NMR Spectrum (400 MHz, $(CD_3)_2SO-d_6$, δ in ppm): from 1.20 to 2.60 (mt: 12H); from 2.55 to 2.75 (mt: 2H); 3.11 (t, J=7 Hz: 2H); 3.54 (s: 3H); 3.93 (s: 3H); 6.36 (mt, JHF=48 Hz: 1H); 7.05 (mt: 1H); from 7.15 to 7.35 (mt: 2H); from 7.45 to 7.55 (mt: 2H); 8.03 (d, J=9 Hz: 1H); 8.75 (s: 1H).

Methyl 4-[3-(3-chloro-6-methoxyquinolin-4-yl)-3-(R,S)-hydroxypropyl]-1-[2-(2,5-difluorophenylthio)ethyl]-piperidine-4-carboxylate A mixture of 1.75 g of ethyl 4-[3-(3-chloro-6-methoxyquinolin-4-yl)propyl]piperidine-4-carboxylate dihydrochloride, 0.95 g of 2-(2-bromoethylthio)-1,4-difluorobenzene, 0.622 g of potassium iodide and 3.11 g of potassium carbonate in 30 cm$^3$ of acetonitrile and 20 cm$^3$ of dimethylformamide was heated with stirring for 18 hours at a temperature in the region of 85° C. After cooling to about 20° C., the reaction mixture was filtered through Celite and the filtrate was then concentrated to dryness under reduced pressure (2 kPa) at a temperature in the region of 40° C. The residue obtained was taken up in water and diethyl ether. The organic phase was dried over magnesium sulfate, filtered and then concentrated to dryness as above. The residue obtained was purified by chromatography under atmospheric pressure, on a column of silica gel (particle size 70–200μ; diameter 4 cm), eluting with a dichloromethane/ methanol mixture (97.5/2.5 by volume). The fractions containing the product were combined and then concentrated to dryness according to the same conditions as above. 0.6 g of methyl 4-[3-(3-chloro-6-methoxyquinolin-4-yl)-3-(R,S)-hydroxypropyl]-1-[2-(2,5-difluorophenylthio)ethyl]piperidine-4-carboxylate was obtained.

$^1$H NMR Spectrum (300 MHz, (CD$_3$)$_2$SO-d$_6$, δ in ppm) from 1.20 to 2.15 (mt: 10H); from 2.45 to 2.55 (mt: 2H); 2.64 (mt: 2H); 3.12 (t, J=7 Hz: 2H); 3.47 (s: 3H); 3.87 (s: 3H); 5.41 (mt: 1H); 6.10 (unresolved peak: 1H); 7.04 (mt: 1H); from 7.15 to 7.35 (mt: 2H); 7.45 (dd, J=9 and 2.5 Hz: 1H); 7.97 (d, J=9 Hz: 1H); 8.13 (very broad d, J=2.5 Hz: 1H); 8.66 (s: 1H).

The 2-(2-bromoethylthio)-1,4-difluorobenzene may be obtained by applying the method described in Example 14.

The methyl 4-[3-(3-chloro-6-methoxyquinolin-4-yl)-3-(R,S)-hydroxypropyl]piperidine-4-carboxylate was prepared in Example 49.

EXAMPLE 49

4-[3-(3-Chloro-6-methoxyquinolin-4-yl)-3-(R,S)-fluoropropyl]-1-[2-(2,5-difluorophenoxy)ethyl]piperidine-4-carboxylic Acid A mixture of 0.15 g of ethyl 4-[3-(3-chloro-6-methoxyquinolin-4-yl)-3-(R,S)-fluoropropyl]-1-[2-(2,5-difluorophenoxy)ethyl]piperidine-4-carboxylate in 3 cm$^3$ of dioxane, 3 cm$^3$ of methanol and 1 cm$^3$ of aqueous 5N sodium hydroxide solution was maintained at a temperature in the region of 70° C. for 4 hours. After cooling to about 20° C., the reaction mixture was concentrated to dryness under reduced pressure (2 kPa) at a temperature in the region of 40° C. The residue was chromatographed under an atmospheric pressure of 60 kPa, on a Bond Elut of 60 cm$^3$ of silica gel (particle size 70–200μ; mass 25 g), eluting with 60 cm$^3$ of a dichloromethane/methanol/aqueous ammonia mixture (40/5/0.5 by volume) and then with a dichloromethane/methanol/aqueous ammonia mixture (40/5/2 by volume). The fractions containing the expected product were combined and then concentrated to dryness according to the same conditions as above. 0.04 g of 4-[3-(3-chloro-6-methoxyquinolin-4-yl)-3-(R,S)-fluoropropyl]-1-[2-(2,5-difluorophenoxy)ethyl]piperidine-4-carboxylic acid was obtained in the form of a white solid.

$^1$H NMR Spectrum (300 MHz, (CD$_3$)$_2$SO-d$_6$, δ in ppm): from 1.20 to 2.40 (mt: 10H); 2.65 (t, J=6 Hz: 2H); 2.72 (mt: 2H); 3.93 (s: 3H); 4.03 (t, J=6 Hz: 2H); 6.37 (mt, J$_{HF}$=48 Hz: 1H); 6.75 (mt: 1H); 7.14 (mt: 1H); 7.25 (mt: 1H); 7.52 (dd, J=9 and 2.5 Hz: 1H); 7.56 (d, J=2.5 Hz: 1H); 8.03 (d, J=9 Hz: 1H); 8.75 (d, J=1 Hz: 1H)

Methyl 4-[3-(3-chloro-6-methoxyquinolin-4-yl)-3-(R,S)-fluoropropyl]-1-[2-(2,5-difluorophenoxy)ethyl]-piperidine-4-carboxylate 0.2 cm$^3$ of diethylaminosulfur trifluoride was added to a solution of 0.5 g of methyl 4-[3-(3-chloro-6-methoxyquinolin-4-yl)-3-(R,S)-hydroxypropyl]-1-[2-(2,5-difluorophenoxy)ethyl]piperidine-4-carboxylate in 20 cm$^3$ of dichloromethane, with stirring and under an inert atmosphere, at a temperature in the region of 3° C. After stirring for 7 hours at a temperature in the region of 20° C., saturated sodium hydrogencarbonate solution was added to the reaction mixture. The aqueous phase was extracted with dichloromethane. The organic phase was dried over magnesium sulfate, filtered and then concentrated to dryness under reduced pressure (2 kPa) at a temperature in the region of 40° C. The residue obtained was purified by chromatography under atmospheric pressure, on a column of silica gel (particle size 70–200μ; diameter 1.5 cm; mass: 15 g), eluting with a mixture of ethyl acetate/petroleum ether (40–60° C.) (8/2 by volume). Fractions 9 to 11 were combined and then concentrated to dryness under the above conditions. 0.21 g of methyl 4-[3-(3-chloro-6-methoxyquinolin-4-yl)-3-(R,S)-fluoropropyl]-1-[2-(2,5-difluorophenoxy)ethyl]piperidine-4-carboxylate was obtained in the form of a thick yellow oil.

Mass spectrum: DCI m/z=551 MH$^+$

Presence of an impurity m'=532.

Methyl 4-[3-(3-chloro-6-methoxyquinolin-4-yl)-3-(R,S) hydroxypropyl]-1-[2-(2,5-difluorophenoxy)ethyl]-piperidine-4-carboxylate A mixture of 1.55 g of methyl 4-[3-(3-chloro-6-methoxyquinolin-4-yl)-3-hydroxypropyl]piperidine-4-carboxylate, 1.03 g of 1-(2-bromoethoxy)-2,5-difluorobenzene, 0.65 g of potassium iodide and 2.7 g of potassium carbonate in 30 cm$^3$ of acetonitrile and 20 cm$^3$ of dimethylformamide was heated with stirring at a temperature in the region of 85° C. for 17 hours. After cooling to a temperature in the region of 20° C., the suspension was filtered through Celite and the filtrate was concentrated to dryness under reduced pressure (2 kPa) in the region of 40° C.

The evaporation residue was taken up in dichloromethane and water. The organic phase was dried over magnesium sulfate, filtered and concentrated to dryness as under the above conditions. The residue was purified by chromatography under atmospheric pressure, on a column of silica gel (particle size 70–200μ; diameter 4 cm), eluting with a mixture of dichloromethane/methanol (97/3 by volume). The fractions containing the product were combined and then concentrated to dryness under reduced pressure (2 kPa), at a temperature in the region of 40° C. and under the same conditions as above. 0.5 g of methyl 4-[3-(3-chloro-6-methoxyquinolin-4-yl)-3-(R,S)hydroxypropyl]-1-[2-(2,5-difluorophenoxy)ethyl]piperidine-4-carboxylate was obtained.

$^1$H NMR Spectrum (300 MHz, (CD$_3$)$_2$SO-d$_6$, δ in ppm): from 1.20 to 2.20 (mt: 10H); from 2.60 to 2.80 (mt: 2H); 2.64 (t, J=6 Hz: 2H); 3.48 (s: 3H); 3.88 (s: 3H); 4.12 (t, J=6 Hz: 2H); 5.40 (mt: 1H); 6.10 (broad s: 1H); 6.74 (mt: 1H); 7.13 (mt: 1H); 7.24 (mt: 1H); 7.44 (dd, J=9 and 2.5 Hz: 1H); 7.96 (d, J=9 Hz: 1H); 8.14 (d, J=2.5 Hz: 1H); 8.66 (s: 1H).

Methyl 4-[3-(3-chloro-6-methoxyquinolin-4-yl)-3-(R,S) hydroxypropyl]piperidine-4-carboxylate A mixture of 2.95 g of methyl 4-[3-(3-chloro-6-methoxyquinolin-4-yl)-3-(R,S)hydroxypropyl]-(tert-butyloxycarbonyl)piperidine-carboxylate and 2.3 cm$^3$ of sulfuric acid in 100 cm$^3$ of methanol was heated at a temperature in the region of 80° C. for 1 and a half hours. After cooling, the reaction mixture was concentrated to dryness under reduced pressure (2 kPa) at a temperature in the region of 40° C. The residue was taken up in 10 cm$^3$ of water, basified to pH=11 with saturated sodium bicarbonate solution and then with saturated sodium carbonate solution and concentrated to dryness under reduced pressure (2 kPa) at a temperature in the region of 40° C. The residue obtained was purified by chromatography under atmospheric pressure, on a column of silica gel (particle size 20–45μ; diameter 2 cm; volume 80 cm$^3$), eluting with a mixture of chloroform/methanol/aqueous ammonia (12/3/0.5 by volume). Fractions 8 to 20 were combined and then concentrated to dryness under the same conditions as above. 1.37 g of methyl 4-[3-(3-chloro-6-methoxyquinolin-4-yl)-3-(R,S)-hydroxypropyl]piperidine-4-carboxylate were obtained in the form of a cream-colored foam.

H NMR Spectrum (300 MHz, (CD$_3$)$_2$SO-d$_6$, δ in ppm) from 1.10 to 1.45 (mt: 3H); from 1.55 to 1.75 (mt: 1H); from 1.80 to 2.05 (mt: 4H); 2.40 (mt: 2H); 2.72 (mt: 2H); 3.50 (s: 3H); 3.90 (s: 3H); 5.42 (broad t, J=6.5 Hz: 1H); 6.09 (mt: 1H); 7.45 (dd, J=9 and 3 Hz: 1H); 7.97 (d, J=9 Hz: 1H); 8.15 (d, J=3 Hz: 1H); 8.67 (s: 1H).

Methyl 4-[3-(3-chloro-6-methoxyquinolin-4-yl)-3-(R,S) hydroxypropyl]-(tert-butyloxycarbonyl)piperidine Carboxylate A solution of 5 g of ethyl 4-[3-(3-chloro-6-methoxyquinolin-4-yl)-propyl]-1-(tert-butyloxycarbonyl)-piperidine-4-carboxylate in 400 cm³ of dimethyl sulfoxide and 120 cm³ of tert-butanol was stirred under an oxygen-saturated atmosphere at a temperature in the region of 20° C. After 5 minutes, a solution of 2.8 g of potassium tert-butoxide in 30 cm³ of tert-butanol was added to the reaction mixture. After sparging with oxygen for 2 hours, 300 cm³ of ice-cold water and 3.5 cm³ of acetic acid were added cautiously. The aqueous phase was extracted with twice 200 cm³ of dichloromethane. The organic phases were combined and washed with 4 times 1 dm³ of water. The organic phase was concentrated to dryness under reduced pressure (2 kPa) at a temperature in the region of 40° C. The residue was taken up in 200 cm³ of diethyl ether, filtered, washed with 20 cm³ of diethyl ether and then dried in a dessicator under reduced pressure (0.1 kPa) at a temperature in the region of 40° C. 3 g of methyl 4-[3-(3-chloro-6-methoxyquinolin-4-yl)-3-(R,S)-hydroxypropyl]-(tert-butyloxycarbonyl) piperidine carboxylate were obtained in the form of a white solid melting at 222° C.

$^1$H NMR Spectrum (300 MHz, (CD$_3$)$_2$SO-d$_6$, δ in ppm) from 1.10 to 1.50 (mt: 3H); 1.39 (s: 9H); 1.70 (mt: 1H); from 1.80 to 2.10 (mt: 4H); 2.81 (mt: 2H); 3.69 (mt: 2H); 3.89 (s: 3H); 5.41 (dd, J=9 and 5 Hz: 1H); from 5.80 to 6.30 (broad unresolved peak: 1H); 7.44 (dd, J=9 and 3 Hz: 1H); 7.95 (d, J=9 Hz: 1H); 8.16 (d, J=3 Hz: 1H); 8.65 (s: 1H); from 12.00 to 12.90 (broad unresolved peak: 1H).

The 1-(2-bromoethoxy)-2,5-difluorobenzene was prepared as described in Example 16.

The ethyl 4-[3-(3-chloro-6-methoxyquinolinyl)-propyl]-1-(tert-butoxycarbonyl)piperidine-4-carboxylate was prepared as described in Example 5.

EXAMPLE 50

Ethyl 4-[3-(3-chloro-6-methoxyquinolin-4-yl)-propyl]-1-[2-(thiazol-2-yloxy)ethyl]piperidine-4-carboxylate was prepared.

$^1$H NMR Spectrum (300 MHz, (CD$_3$)$_2$SO-d$_6$, δ in ppm): 1.05 (t, J=7 Hz: 3H); 1.40 (very broad t, J=12 Hz: 2H); 1.53 (mt: 2H); 1.69 (mt: 2H); from 1.90 to 2.15 (mt: 4H); 2.64 (t, J=5.5 Hz: 2H); 2.70 (broad d, J=11.5 Hz: 2H); 3.16 (broad t, J=7.5 Hz: 2H); 3.96 (s: 3H); 4.01 (q, J=7 Hz: 2H); 4.42 (t, J=5.5 Hz: 2H); 7.04 (d, J=3.5 Hz: 1H); 7.17 (d, J=3.5 Hz: 1H); 7.37 (d, J=2.5 Hz: 1H); 7.46 (dd, J=9 and 2.5 Hz: 1H); 7.97 (d, J=9 Hz: 1H); 8.67 (s: 1H).

4-[3-(3-chloro-6-methoxyquinolin-4-yl)propyl]-1-[2-(thiazol-2-yloxy)ethyl]piperidine-4-carboxylic Acid A mixture of 0.68 g of ethyl 4-[3-(3-chloro-6-methoxyquinolin-4-yl)propyl]-1-[2-(thiazol-2-yloxy)-ethyl] piperidine-4-carboxylate in 7 cm³ of dioxane, 9 cm³ of methanol and 2 cm³ of aqueous 5N sodium hydroxide solution was maintained at a temperature in the region of 60° C. for 20 hours. After cooling to about 20° C., the reaction mass was concentrated to dryness under reduced pressure (2 kPa) at a temperature in the region of 40° C. The residue obtained was chromatographed under a pressure of 50 kPa of argon, on a column of silica gel (particle size 20–45μ; diameter 2.2 cm; mass 20 g), eluting with a mixture of dichloromethane/methanol (70/30 by volume). The fractions containing the expected product were combined and then concentrated to dryness under the above conditions. The residue obtained was taken up in 5 cm³ of ethyl acetate, stirred for 1 hour at room temperature and then filtered and rinsed with 3 times 3 cm³ of ethyl acetate and then 3 times 3 cm³ of pentane. 0.27 g of 4-[3-(3-chloro-6-methoxyquinolin-4-yl)propyl]-1-[2-(thiazol-2-yloxy)-ethyl] piperidine-4-carboxylic acid was obtained in the form of a white solid melting at 188° C.

$^1$H NMR Spectrum (300 MHz, (CD$_3$)$_2$SO-d$_6$, δ in ppm): 1.39 (broad t, J=12 Hz: 2H); from 1.50 to 1.65 (mt: 2H); 1.71 (mt: 2H); 1.98 (broad d, J=12 Hz: 2H); 2.12 (unresolved peak: 2H); from 2.60 to 2.85 (mt: 4H); 3.17 (broad t, J=7.5 Hz: 2H); 3.96 (s: 3H); 4.45 (very broad t, J=5.5 Hz: 2H); 7.05 (d, J=3.5 Hz: 1H); 7.18 (d, J=3.5 Hz: 1H); 7.37 (d, J=2.5 Hz: 1H); 7.46 (dd, J=9 and 2.5 Hz: 1H); 7.97 (d, J=9 Hz: 1H); 8.68 (s: 1H); from 11.80 to 12.70 (broad unresolved peak: 1H).

EXAMPLE 51

4-[3-(3-fluoro-6-methoxyquinolin-4-yl)propyl]-1-[2-(4,5-dihydrothiazol-2-ylthio)ethyl]piperidine-4-carboxylic Acid A mixture of 0.15 g of ethyl 4-[3-(3-fluoro-6-methoxyquinolin-4-yl)propyl]-1-[2-(4,5-dihydrothiazol-2-ylthio)ethyl]piperidine-4-carboxylate in 5 cm³ of dioxane, 5 cm³ of methanol and 1 cm³ of aqueous 5N sodium hydroxide solution was maintained at a temperature in the region of 75° C. for 20 hours. After cooling to about 20° C., the reaction mixture was concentrated to dryness under reduced pressure (2 kPa) at a temperature in the region of 40° C. The residue obtained was purified by chromatography under atmospheric pressure, on a column of silica gel (Bond Elut; particle size 70–200μ; mass 7 g), eluting with a mixture of dichloromethane/methanol/aqueous ammonia (40/5/0.5 by volume). The fractions containing the product were combined, concentrated to dryness under reduced pressure (2 kPa) at a temperature in the region of 40° C. and then oven-dried under reduced pressure (10 kPa) at about 50° C. 0.1 g of 4-[3-(3-fluoro-6-methoxyquinolin-4-yl)propyl]-1-[2-(4,5-dihydrothiazol-2-ylthio)ethyl]piperidine-4-carboxylic acid was obtained in the form of a white solid.

$^1$H NMR Spectrum (300 MHz, (CD$_3$)$_2$SO-d$_6$, δ in ppm): 1.33 (very broad t, J=11.5 Hz: 2H); 1.61 (mt: 4H); from 1.90 to 2.10 (mt: 4H); from 2.45 to 2.60 (mt: 2H); 2.63 (broad d, J=11.5 Hz: 2H); 3.05 (mt: 2H); 3.19 (t, J=6.5 Hz: 2H); 3.44 (t, J=8 Hz: 2H); 3.97 (s: 3H); 4.15 (t, J=8 Hz: 2H); 7.35 (broad s: 1H); 7.40 (broad d, J=9 Hz: 1H); 7.97 (broad d, J=9 Hz: 1H); 8.69 (broad s: 1H).

Ethyl 4-[3-(3-fluoro-6-methoxyquinolin-4-yl)propyl]-1-[2-(4,5-dihydrothiazol-2-ylthio)ethyl]piperidine-4-carboxylate A mixture of 0.7 g of ethyl 1-(2-chloroethyl)-4-[3-(3-fluoro-6-methoxyquinolin-4-yl)propyl]piperidine-4-carboxylate dihydrochloride, 0.18 g of 2-mercaptothiazoline and 0.63 cm³ of triethylamine in 10 cm³ of dimethylformamide was stirred under an inert atmosphere for 23 hours at a temperature in the region of 80° C. After cooling to about 20° C., the reaction mixture was taken up in water, extracted with ethyl acetate and washed with saturated sodium chloride solution. The organic phase was dried over magnesium sulfate, filtered and then concentrated to dryness under reduced pressure (2 kPa) at a temperature in the region of 40° C. The evaporation residue was added to a solution of 0.18 g of 2-mercaptothiazoline and 0.06 g of 10% sodium hydride in 10 cm³ of dimethylformamide, and the mixture was then heated at a temperature in the region of 80° C. for 15 hours. After cooling to about 20° C., the reaction mixture was taken up in water, extracted with ethyl acetate and washed with saturated sodium chloride solution. The organic phase was dried over magnesium sulfate, filtered and then concentrated to dryness under reduced pressure (2 kPa) at a temperature in the region of 40° C. The residue obtained was purified by chromatography under atmospheric pressure on a column of silica gel (particle size 70–200μ; diameter 2 cm; mass 40 g), eluting with a mixture of dichloromethane/ethanol (95/5 by volume) and collecting 10-cm³ fractions. Fractions 11 to 24 were combined and then concentrated to dryness under reduced pressure (2 kPa) at a temperature in the region of 40° C. 0.15 g of ethyl 4-[3-(3-fluoro-6-methoxyquinolin-4-yl)propyl]-1-[2-(4,5-dihydrothiazol-2-ylthio)ethyl]piperidine-4-carboxylate was obtained in the form of a brown oil.

¹H NMR Spectrum (300 MHz, (CD₃)₂SO-d₆, with addition of a few drops of CD₃COOD d4, δ in ppm): 1.06 (t, J=7 Hz: 3H); 1.41 (mt: 2H); from 1.50 to 1.70 (mt: 4H); 1.98 (broad d, J=13.5 Hz: 2H); 2.14 (broad t, J=11.5 Hz: 2H); 2.66 (t, J=7 Hz: 2H); 2.80 (very broad d, J=11.5 Hz: 2H); 3.04 (broad t, J=6.5 Hz: 2H); 3.21 (t, J=7 Hz: 2H); 3.42 (t, J=8 Hz: 2H); 3.94 (s: 3H); 3.97 (q, J=7 Hz: 2H); 4.12 (t, J=8 Hz: 2H); 7.32 (d, J=2.5 Hz: 1H); 7.38 (dd, J=9 and 2.5 Hz: 1H); 7.96 (d, J=9 Hz: 1H); 8.66 (d, J=1.5 Hz: 1H).

Ethyl 1-(2-chloroethyl)-4-[3-(3-fluoro-6-methoxyquinolin-4-yl)propyl]piperidine-4-carboxylate Dihydrochloride 5.73 cm³ of thionyl chloride were added dropwise to a suspension of 0.6 g of ethyl 4-[3-(3-fluoro-6-methoxyquinolin-4-yl)propyl]-1-(2-hydroxyethyl) piperidine-4-carboxylate in 10 cm³ of dichloromethane with stirring in the region of 20° C., and the mixture was stirred for 24 hours at a temperature in the region of 20° C. The reaction mixture was concentrated to dryness under reduced pressure (2 kPa) at a temperature in the region of 40° C. The residue was taken up in 3 times 30 cm³ of cyclohexane and evaporated to dryness as under the above conditions. 0.67 g of ethyl 1-(2-chloroethyl)-4-[3-(3-fluoro-6-methoxyquinolin-4-yl)propyl]piperidine-4-carboxylate dihydrochloride was obtained in the form of a beige-colored solid.

¹H NMR Spectrum (300 MHz, (CD₃)₂SO-d₆, δ in ppm): 1.05 (t, J=7 Hz: 3H); from 1.45 to 2.00 (mt: 6H); 2.19 (broad d, J=14 Hz: 2H); from 2.75 to 2.95 (mt: 2H); 3.09 (mt: 2H); from 3.40 to 3.60 (mt: 4H); from 3.95 to 4.15 (mt: 2H); 3.96 (s: 3H); 4.05 (q, J=7 Hz: 2H); 7.37 (d, J=2.5 Hz: 1H); 7.42 (dd, J=9 and 2.5 Hz: 1H); 7.99 (d, J=9 Hz: 1H); 8.73 (broad s: 1H); 10.00 (unresolved peak: 1H).

The ethyl 4-[3-(3-fluoro-6-methoxyquinolin-4-yl) propyl]-1-(2-hydroxyethyl)piperidine-4-carboxylate was prepared by analogy with the method described in Example 46.

EXAMPLE 52

4-[3-(3-fluoro-6-methoxyquinolin-4-yl)propyl]-1-[2-(3,4,5-trifluorophenoxy)ethyl]piperidine-4-carboxylic Acid A mixture of 0.8 g of ethyl 4-[3-(3-fluoro-6-methoxyquinolin-4-yl)propyl]-1-[2-(3,4,5-trifluorophenoxy)ethyl]piperidine-4-carboxylate in 50 cm³ of dioxane, 50 cm³ of methanol and 4.4 cm³ of aqueous 5N sodium hydroxide solution was stirred at a temperature in the region of 70° C. for 18 hours. A further 4.4 cm³ of aqueous 5N sodium hydroxide solution were added to the reaction mixture, which was stirred for 6 hours in the region of 70° C. After cooling to about 20° C., the reaction mass was concentrated to dryness under reduced pressure (1.1 kPa) at a temperature in the region of 5° C. The residue was purified by chromatography under atmospheric pressure, on a column of silica gel (particle size 20–45μ; diameter 4 cm; height 20 cm), eluting with a mixture of chloroform/methanol/aqueous ammonia (12/3/0.5 by volume) and collecting 60-cm³ fractions. Fractions 8 to 19 were combined, concentrated to dryness under reduced pressure (2 kPa) at a temperature in the region of 40° C. and oven-dried under reduced pressure (10 kPa) at about 50° C. 0.59 g of 4-[3-(3-fluoro-6-methoxyquinolin-4-yl)propyl]-1-[2-(3,4,5-trifluorophenoxy)ethyl]piperidine-4-carboxylic acid was obtained in the form of a white solid melting at about 120° C.

¹H NMR Spectrum (300 MHz, (CD₃)₂SO-d₆, δ in ppm) 1.32 (very broad t, J=12 Hz: 2H); 1.59 (mt: 4H); 1.95 (broad d, J=12 Hz: 2H); 2.07 (broad t, J=11 Hz: 2H); 2.59 (t, J=5.5 Hz: 2H); 2.68 (very broad d, J=11 Hz: 2H); 3.04 (mt: 2H); 3.95 (s: 3H); 4.03 (t, J=5.5 Hz: 2H); 6.97 (mt: 2H); 7.34 (d, J=2.5 Hz: 1H); 7.39 (dd, J=9 and 2.5 Hz: 1H); 7.96 (d, J=9 Hz: 1H); 8.69 (broad s: 1H).

Ethyl 4-[3-(3-fluoro-6-methoxyquinolin-4-yl)propyl]-1-[2-(3,4,5-trifluorophenoxy)ethyl]piperidine-4-carboxylate A mixture of 0.62 g of ethyl 4-[3-(3-fluoro-6-methoxyquinolin-4-yl)propyl]piperidine-4-carboxylate, 0.505 g of 5-(2-bromoethoxy)-1,2,3-trifluorobenzene, 0.34 g of potassium iodide and 1.14 g of potassium carbonate in 80 cm³ of acetonitrile was stirred under an inert atmosphere for 18 hours at a temperature in the region of 70° C. After cooling to about 20° C., the suspension was filtered and the insoluble material was washed with 3 times 30 cm³ of acetonitrile. The filtrate was concentrated to dryness under reduced pressure (2 kPa) at a temperature in the region of 40° C. The evaporation residue was purified by chromatography under atmospheric pressure, on a column of silica gel (particle size 20–45μ; diameter 3 cm; height 21 cm), eluting with ethyl acetate and collecting 40-cm³ fractions. Fractions 9 to 24 were combined and then concentrated to dryness under reduced pressure (2 kPa) at a temperature in the region of 40° C. 0.8 g of ethyl 4-[3-(3-fluoro-6-methoxyquinolin-4-yl)propyl]-1-[2-(3,4,5-trifluorophenoxy)ethyl]piperidine-4-carboxylate was obtained in the form of a pale yellow viscous oil.

¹H NMR Spectrum (300 MHz, (CD₃)₂SO-d₆, δ in ppm): 0.99 (t, J=7 Hz: 3H); 1.37 (very broad t, J=12 Hz: 2H); from 1.45 to 1.70 (mt: 4H); from 1.90 to 2.10 (mt: 4H); 2.59 (t, J=5.5 Hz: 2H); 2.69 (broad d, J=12 Hz: 2H); 3.04 (broad t, J=7 Hz: 2H); 3.94 (s: 3H); 3.97 (q, J=7 Hz: 2H); 4.03 (t, J=5.5 Hz: 2H); 6.97 (mt: 2H); 7.33 (d, J=2.5 Hz: 1H); 7.39 (dd, J=9 and 2.5 Hz: 1H); 7.97 (d, J=9 Hz: 1H); 8.69 (broad s: 1H).

The ethyl 4-[3-(3-fluoro-6-methoxyquinolin-4-yl)propyl] piperidine-4-carboxylate was prepared as described in Example 11.

The 5-(2-bromoethoxy)-1,2,3-trifluorobenzene was prepared by applying the method described in Example 13.

EXAMPLE 53

4-[3-(3-fluoro-6-methoxyquinolin-4-yl)propyl]-1-[2-(thiazol-2-ylthio)ethyl]piperidine-4-carboxylic Acid A mixture of 0.15 g of 4-[3-(3-fluoro-6-methoxyquinolin-4-yl)propyl]-1-[2-(thiazol-2-ylthio)ethyl]-piperidine-4-carboxylate in 3 cm³ of dioxane, 3 cm³ of methanol and 1 cm³ of aqueous 5N sodium hydroxide solution was stirred at a temperature in the region of 70° C. for 18 hours. After cooling to about 20° C., the reaction mass was concentrated to dryness under reduced pressure (2 kPa) at a temperature in the region of 50° C.

The residue was taken up in twice 20 cm³ of toluene and then concentrated to dryness as under the above conditions. The solid was purified by chromatography under atmospheric pressure, on a column of silica gel (Bond Elut; particle size 70–200μ; mass 7 g), eluting with a mixture of chloroform/methanol/aqueous ammonia (84/14/2 by volume) and collecting 5-cm³ fractions. Fractions 8 to 19 were combined, concentrated to dryness under reduced pressure (2 kPa) at a temperature in the region of 40° C. and then oven-dried under reduced pressure (to 10 kPa) at about 50° C. 0.114 g of 4-[3-(3-fluoro-6-methoxyquinolin-4-yl)propyl]-1-[2-(thiazol-2-ylthio)ethyl]piperidine-4-carboxylic acid was obtained in the form of a white solid.

¹H NMR Spectrum (300 MHz, $(CD_3)_2SO-d_6$, δ in ppm) 1.31 (broad t, J=12 Hz: 2H); 1.45 to 1.70 (mt: 4H); from 1.90 to 2.10 (mt: 4H); 2.58 (t, J=7 Hz: 2H); 2.65 (broad d, J=12 Hz: 2H); 3.04 (mt: 2H); from 3.25 to 3.45 (mt, 2H); 3.95 (s: 3H); 7.34 (d, J=2.5 Hz: 1H); 7.39 (dd, J=9 and 2.5 Hz: 1H); 7.63 (d, J=3.5 Hz: 1H); 7.71 (d, J=3.5 Hz: 1H); 7.96 (d, J=9 Hz: 1H); 8.68 (d, J=1 Hz: 1H).

Ethyl 4-[3-(3-fluoro-6-methoxyquinolin-4-yl)propyl]-1-[2-(thiazol-2-ylthio)ethyl]piperidine-4-carboxylate A mixture of 0.65 g of ethyl 1-(2-chloroethyl)-4-[3-(3-fluoro-6-methoxyquinolin-4-yl)propyl]piperidine-4-carboxylate dihydrochloride, 0.183 g of 2-mercaptothiazole, 0.21 g of potassium iodide and 0.88 g of potassium carbonate in 50 cm³ of acetonitrile was stirred under an inert atmosphere for 18 hours at a temperature in the region of 70° C. After cooling to about 20° C., the suspension was filtered and the insoluble material was washed with acetonitrile. The filtrate was concentrated to dryness under reduced pressure (2 kPa) at a temperature in the region of 40° C.

The evaporation residue was taken up in a mixture of ethyl acetate/40–60° C. petroleum ether (8/2 by volume) and filtered, and the filtrate was purified by chromatography under atmospheric pressure on a column of silica gel (particle size 70–200μ; diameter 1.5 cm; mass 100 g), eluting with ethyl acetate/40–60° C. petroleum ether (8/2 by volume) and collecting 15-cm³ fractions. The fractions 41 to 100 were combined and then concentrated to dryness under reduced pressure (2 kPa) at a temperature in the region of 40° C. 0.15 g of ethyl 4-[3-(3-fluoro-6-methoxyquinolin-4-yl)propyl]-1-[2-(thiazol-2-ylthio)ethyl]piperidine-4-carboxylate was obtained in the form of a thick yellow oil.

¹H NMR Spectrum (300 MHz, $(CD_3)_2SO-d_6$, δ in ppm) 1.00 (t, J=7 Hz: 3H); 1.36 (broad t, J=11.5 Hz: 2H); from 1.45 to 1.70 (mt: 4H); from 1.85 to 2.10 (mt: 4H); 2.59 (t, J=7 Hz: 2H); 2.68 (broad d, J=12 Hz: 2H); 3.05 (very broad t, J=7 Hz: 2H); 3.33 (mt: 2H); 3.96 (s: 3H); 3.98 (q, J=7 Hz: 2H); 7.35 (d, J=2.5 Hz: 1H); 7.40 (dd, J=9 and 2.5 Hz: 1H); 7.64 (d, J=3.5 Hz: 1H); 7.72 (d, J=3.5 Hz: 1H); 7.97 (d, J=9 Hz: 1H); 8.70 (d, J=1 Hz: 1H).

The ethyl 1-(2-chloroethyl)-4-[3-(3-fluoro-6-methoxyquinolin-4-yl)propyl]piperidine-4-carboxylate dihydrochloride was prepared as described in Example 51.

EXAMPLE 54

4-[3-(3-fluoro-6-methoxyquinolin-4-yl)propyl]-1-(3-phenylallyl)piperidine-4-carboxylic Acid A mixture of 0.13 g of ethyl 4-[3-(3-fluoro-6-methoxyquinolin-4-yl)propyl]-1-(3-phenylallyl)piperidine-4-carboxylate in 2 cm³ of dioxane, 2 cm³ of methanol and 1.32 cm³ of aqueous 5N sodium hydroxide solution was maintained at a temperature in the region of 70° C. for 18 hours. After cooling to about 20° C., the reaction mixture was concentrated to dryness under reduced pressure (2 kPa) at a temperature in the region of 40° C.

The residue obtained was taken up in 10 cm³ of water, acidified with acetic acid and extracted with ethyl acetate, allowed to separate by settling and then filtered and rinsed with twice 10 cm³ of ethanol. 0.12 g of 4-[3-(3-fluoro-6-methoxyquinolin-4-yl)propyl]-1-(3-phenylallyl)piperidine-4-carboxylic acid was obtained in the form of a white solid melting at 240° C.

¹H NMR Spectrum (300 MHz, $(CD_3)_2SO-d_6$, δ in ppm): 1.35 (broad t, J=11.5 Hz: 2H); from 1.50 to 1.75 (mt: 4H); from 1.85 to 2.10 (mt: 4H); 2.63 (broad d, J=11.5 Hz: 2H); from 2.95 to 3.15 (mt: 4H); 3.96 (s, 3H); 6.26 (dt, J=16 and 7 Hz: 1H); 6.50 (d, J=16 Hz: 1H); from 7.10 to 7.50 (mt: 7H); 8.06 (d, J=9 Hz: 1H); 8.69 (broad s: 1H).

Ethyl 4-[3-(3-fluoro-6-methoxyquinolin-4-yl)propyl]-1-(3-phenylallyl)piperidine-4-carboxylate 77 mg of borane-pyridine complex were added to a mixture of 0.31 g of ethyl 4-[3-(3-fluoro-6-methoxyquinolin-4-yl)propyl]piperidine-4-carboxylate and 0.1 cm³ of trans-cinnmaldehyde in 10 cm³ of ethanol. The reaction mixture was maintained at a temperature in the region of 77° C. for 22 hours. After cooling to about 20° C., the reaction mixture was concentrated to dryness under reduced pressure (2 kPa) at a temperature in the region of 40° C.

The residue obtained was taken up in 10 cm³ of water, extracted with twice 10 cm³ of dichloromethane, dried over magnesium sulfate, filtered and then concentrated to dryness under the above conditions. The residue obtained was chromatographed under a pressure of 60 kPa of argon, on a column of silica gel (particle size 70–200μ; diameter 2.5 cm; mass 20 g), eluting with 500 cm³ of a mixture of ethyl acetate/cyclohexane (40/60 by volume) and then of a mixture of dichloromethane/methanol (95/5 by volume). The fractions containing the expected product were combined and then concentrated to dryness under the above conditions. 0.13 g of ethyl 4-[3-(3-fluoro-6-methoxyquinolin-4-yl)propyl]-1-(3-phenylallyl)piperidine-4-carboxylate was obtained in the form of a viscous oil.

¹H NMR Spectrum (300 MHz, $(CD_3)_2SO-d_6$, δ in ppm) 1.01 (t, J=7 Hz: 3H); 1.40 (broad t, J=11.5 Hz: 2H); from 1.45 to 1.75 (mt: 4H); from 1.90 to 2.05 (mt: 4H); 2.65 (very broad d, J=12 Hz: 2H); 3.02 (d, J=7 Hz: 2H); 3.05 (mt: 2H); 3.96 (s: 3H); 3.97 (q, J=7 Hz: 2H); 6.25 (dt, J=16 and 7 Hz: 1H); 6.51 (d, J=16 Hz: 1H); from 7.15 to 7.50 (mt: 7H); 7.96 (d, J=9 Hz: 1H); 8.70 (d, J=1 Hz: 1H).

The ethyl 4-[3-(3-fluoro-6-methoxyquinolin-4-yl)propyl]piperidine-4-carboxylate was prepared as described in Example 11.

EXAMPLE 55

4-[3-(3-Chloro-6-methoxyquinolin-4-yl)propyl]-1-(3-phenylpropyl)piperidine-4-hydroxamic Acid A solution of 0.1 g of 4-[3-(3-chloro-6-methoxyquinolin-4-yl)propyl]-1-(3-phenylpropyl)piperidine-4-tert-butoxycarboxamide in 2 cm of trifluoroacetic acid was left for 60 days at a temperature in the region of 20° C. The solution was evaporated off under reduced pressure (2 kPa) at a temperature in the region of 40° C. and then purified by chromatography under atmospheric pressure on Bond Elut silica (particle size 70–200μ; volume 25 cm³), eluting with a mixture of dichloromethane/methanol/aqueous ammonia (40/5/0.3 by volume). The fractions containing the product were combined and then evaporated under the conditions described above. 0.036 g of 4-[3-(3-chloro-6-methoxyquinolin-4-yl)propyl]-1-(3-phenylpropyl) piperidine-4-hydroxamic acid was obtained in the form of a colorless oil.

$^1$H NMR Spectrum (300 MHz, $(CD_3)_2SO-d_6$, δ in ppm) 1.33 (mt: 2H); 1.51 (mt: 2H); from 1.60 to 1.80 (mt: 4H); from 1.90 to 2.10 (mt: 4H); 2.18 (t, J=7 Hz: 2H); from 2.45 to 2.65 (mt: 4H); 3.12 (broad t, J=7.5 Hz: 2H); 3.96 (s: 3H); from 7.15 to 7.25 (mt: 3H); 7.28 (t mt, J=7.5 Hz: 2H); 7.36 (d, J=2.5 Hz: 1H); 7.45 (dd, J=9 and 2.5 Hz: 1H); 7.96 (d, J=9 Hz: 1H); 8.56 (unresolved peak: 1H); 8.67 (s: 1H); 10.37 (unresolved peak: 1H).

4-[3-(3-Chloro-6-methoxyquinolin-4-yl)propyl]-1-(3-phenylpropyl)piperidine-4-tert-butoxyamide A mixture of 0.5 g of 4-[3-(3-chloro-6-methoxyquinolin-4-yl)propyl]-1-(3-phenylpropyl)piperidine-4-carboxylic acid, 0.175 g of 1-hydroxybenzotriazole hydrate, 0.498 g of 1-[3-(dimethylamino)propyl]-3-ethylcarbodiimide hydrochloride, 0.58 cm³ of triethylamine and 0.4 g of O-tert-butylhydroxylamine was stirred for 48 hours at a temperature in the region of 20° C. The reaction medium was diluted with 50 cm³ of water, stirred and the phases were then separated by settling. The aqueous phase was extracted with twice 25 cm³ of dichloromethane and the organic extracts were combined, dried over magnesium sulfate, filtered and then evaporated under reduced pressure (2 kPa) at a temperature in the region of 40° C.

The residue obtained was purified by chromatography under atmospheric pressure, on a column of silica gel (particle size 20–45μ; diameter 2.5 cm; mass 18 g), eluting with a mixture of dichloromethane/methanol/aqueous ammonia (40/5/0.2 by volume). The fractions containing the product were combined and then evaporated under the conditions described above. 0.27 g of 4-[3-(3-chloro-6-methoxyquinolin-4-yl)propyl]-1-(3-phenylpropyl) piperidine-4-tert-butoxyamide was obtained.

$^1$H NMR Spectrum (300 MHz, $(CD_3)_2SO-d_6$, δ in ppm) 1.09 (s: 9H); 1.35 (mt: 2H); 1.54 (mt: 2H); 1.67 (mt: 4H); 1.95 (broad t, J=11 Hz: 2H); 2.08 (broad d, J=13.5 Hz: 2H); 2.19 (t, J=7 Hz: 2H); from 2.50 to 2.65 (mt: 4H); 3.14 (broad t, J=7.5 Hz: 2H); 3.98 (s: 3H); from 7.10 to 7.25 (mt: 3H); 7.27 (broad t, J=7.5 Hz: 2H); 7.36 (d, J=2.5 Hz: 1H); 7.45 (dd, J=9 and 2.5 Hz: 1H); 7.96 (d, J=9 Hz: 1H); 8.68 (s: 1H); 10.06 (broad s: 1H).

Benzyl 4-[3-(3-chloro-6-methoxyquinolin-4-yl)-propyl]-1-(3-phenylpropyl)piperidine-4-carboxylate was prepared as described in Example 4.

EXAMPLE 56

4-[3-(3-Fluoro-6-methoxyquinolin-4-yl)propyl]-1-[3-(2,5-difluorophenyl)prop-2-enyl]piperidine-4-carboxylic Acid Hydrochloride Working in a manner analogous to that of Example 54, 4-[3-(3-fluoro-6-methoxyquinolin-4-yl)propyl]-1-[3-(2,5-difluorophenyl)prop-2-enyl]piperidine-4-carboxylic acid hydrochloride was prepared.

$^1$H NMR Spectrum (400 MHz, $(CD_3)_2SO-d_6$ with addition of a few drops of $CD_3COOD-d_4$ at a temperature of 383 K, δ in ppm): 1.73 (mt: 6H); 2.22 (broad d, J=14 Hz: 2H); 3.01 (unresolved peak: 2H); 3.11 (broad t, J=7 Hz: 2H); 3.42 (very broad d, J=12 Hz: 2H); 3.94 (d, J=7 Hz: 2H); 3.98 (s 3H); 6.48 (dt, J=16.5 and 7 Hz: 1H); 6.93 (d, J=16.5 Hz: 1H); from 7.10 to 7.30 (mt: 2H); 7.35 (broad s: 1H); 7.40 (dd, J=9 and 2.5 Hz: 1H); 7.44 (mt: 1H); 7.98 (d, J=9 Hz: 1H); 8.64 (broad s: 1H).

EXAMPLE 57

4-[3-(3-Fluoro-6-methoxyquinolin-4-yl)propyl]-1-[2-(2,5-difluorophenoxy)ethyl]piperidine-4-hydroxamic Acid Working in a manner analogous to that of Example 55, 4-[3-(3-fluoro-6-methoxyquinolin-4-yl)propyl]-1-[2-(2,5-difluorophenoxy)ethyl]piperidine-4-hydroxamic acid was prepared.

$^1$H NMR Spectrum (300 MHz, $(CD_3)_2SO-d_6$, δ in ppm): 1.31 (very broad t, J=12.5 Hz: 2H); from 1.45 to 1.70 (mt: 4H); 2.02 (broad d, J=12.5 Hz: 2H); 2.10 (broad t, J=11 Hz: 2H); from 2.55 to 2.75 (mt: 4H); 3.00 (mt: 2H); 3.97 (s: 3H); 4.12 (t, J=5.5 Hz: 2H); 6.75 (mt: 1H); 7.14 (mt: 1H) 7.24 (mt: 1H); 7.33 (d, J=3 Hz: 1H); 7.40 (dd, J=9 and 3 Hz: 1H); 7.96 (d, J=9 Hz: 1H); 8.63 (unresolved peak: 1H); 8.70 (d, J=0.5 Hz: 1H); 10.40 (unresolved peak: 1H).

EXAMPLE 58

1-Cinnamyl-4-[3-(3-fluoro-6-methoxyquinolin-4-yl) propyl]-piperidine-4-hydroxamic Acid Working in a manner analogous to that of Example 55, 1-cinnamyl-4-[3-(3-fluoro-6-methoxyquinolin-4-yl) propyl]-piperidine-4-hydroxamic acid was prepared.

$^1$H NMR Spectrum (400 MHz, $(CD_3)_2SO-d_6$ with addition of a few drops of $CD_3COOD-d_4$ at a temperature of 373 K, δ in ppm): from 1.50 to 1.75 (mt: 6H); 2.23 (broad d, J=14 Hz: 2H); 2.81 (broad t, J=11.5 Hz: 2H); 3.04 (mt: 2H); 3.22 (broad d, J=11.5 Hz: 2H); 3.69 (d, J=7 Hz: 2H); 3.97 (s: 3H); 6.24 (dt, J=16 and 7 Hz: 1H); 6.78 (d, J=16 Hz: 1H); from 7.20 to 7.50 (mt: 7H); 7.96 (d, J=9 Hz: 1H); 8.62 (broad s: 1H).

EXAMPLE 59

Sodium 4-[3-(3-chloro-6-trifluoromethylquinolin-4-yl) propyl]-1-[2-(2,5-difluorophenoxy)ethyl]piperidine-4-carboxylate Working in a manner analogous to that of Example 1, sodium 4-[3-(3-chloro-6-trifluoromethylquinolin-4-yl) propyl]-1-[2-(2,5-difluorophenoxy)ethyl]piperidine-4-carboxylate was prepared.

$^1$H NMR Spectrum (300 MHz, $(CD_3)_2SO-d_6$, δ in ppm): 1.09 (very broad t, J=11.5 Hz: 2H); from 1.40 to 1.70 (mt: 4H); 1.98 (broad d, J=11.5 Hz: 2H); 2.14 (t, J=10.5 Hz: 2H); from 2.50 to 2.70 (mt: 4H); 3.22 (broad t, J=7 Hz: 2H); 4.10 (t, J=5.5 Hz: 2H); 6.74 (mt: 1H); 7.12 (mt: 1H); 7.23 (mt: 1H); 8.06 (broad d, J=9 Hz: 1H); 8.26 (d, J=9 Hz: 1H); 8.26 (d, J=9 Hz: 1H); 8.54 (broad s: 1H); 9.00 (s: 1H).

The present invention also relates to pharmaceutical compositions containing at least one heterocyclylalkyl-piperidine derivative according to the invention, where appropriate in the form of a salt, in pure form, or in the form of a combination with one or more compatible and pharmaceutically acceptable diluents and/or adjuvants.

The compositions according to the invention may be used orally, parenterally, topically, rectally, or as aerosols.

Solid compositions for oral administration which were optionally used include tablets, pills, gel capsules, powders or granules. In these compositions, the active product according to the invention may optionally be mixed with one or more inert diluents or adjuvants, such as sucrose, lactose or starch. These compositions may comprise substances other than diluents, for example a lubricant such as magnesium stearate or a coating intended for controlled release.

Liquid compositions for oral administration which may be used include pharmaceutically acceptable solutions, suspensions, emulsions, syrups and elixirs containing inert diluents such as water or liquid paraffin. These compositions may also comprise substances other than diluents, for example wetting, sweetening or flavoring products.

The compositions for parenteral administration may be sterile solutions or emulsions. Solvents or vehicles which may be used include water, propylene glycol, a polyethylene glycol, plant oils, in particular olive oil, and injectable organic esters, for example ethyl oleate. These compositions may also contain adjuvants, in particular wetting agents, isotonic agents, emulsifiers, dispersants and stabilizers.

The sterilization may be carried out in several ways, for example using a bacteriological filter, by irradiation or by heating. The compositions may also be prepared in the form of sterile solid compositions which may be dissolved at the time of use in sterile water or any other injectable sterile medium.

The compositions for topical administration may be, for example, creams, ointments, lotions or aerosols.

The compositions for rectal administration were suppositories or rectal capsules which contain, besides the active principle, excipients such as cocoa butter, semi-synthetic glycerides or polyethylene glycols.

The compositions may also be aerosols. For use in the form of liquid aerosols, the compositions may be stable sterile solutions or solid compositions dissolved at the time of use in apyrogenic sterile water, in saline or any other pharmaceutically acceptable vehicle. For use in the form of dry aerosols intended to be inhaled directly, the active principle was finely divided and combined with a water-soluble solid diluent or vehicle with a particle size of from 30 to 80 µm, for example dextran, mannitol or lactose.

In human therapy, the novel heterocyclylalkyl-piperidine derivatives according to the invention were particularly useful in the treatment of infections of bacterial origin. The doses depend on the desired effect and on the duration of the treatment. The doctor will determine the dosage she or he considers most appropriate as a function of the treatment, depending on the age, weight, degree of infection and other factors specific to the individual to be treated. Generally, the doses were between 750 mg and 3 g of active product taken 2 or 3 times a day orally or between 400 mg and 1.2 g intravenously for an adult.

What is claimed is:

1. A compound of general formula (I):

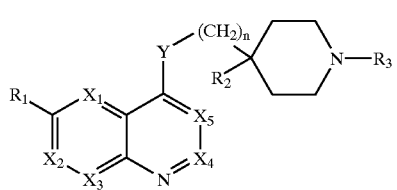

(I)

wherein:

$X_1$ is $>C-R'_1$;
$X_2$ is $>C-R'_2$;
$X_3$ is $>C-R'_3$;
$X_4$ is $>C-R'_4$;
$X_5$ is $>C-R'_5$;
and, optionally, one of $X_1$, $X_2$, $X_3$, $X_4$, and $X_5$ is a nitrogen atom;

$R_1, R'_1, R'_2, R'_3, R'_4$, and $R'_5$ are identical or different, and each independently is: a hydrogen or halogen atom or an alkyl, cycloalkyl, phenyl, phenylthio, mono- or bicyclic aromatic heterocyclyl or heterocyclylthio, hydroxyl, alkyloxy, trifluoromethoxy, alkylthio, trifluoromethylthio, cycloalkyloxy, cycloalkylthio cyano, carboxyl, alkyloxycarbonyl, cycloalkyloxycarbonyl, —NRaRb or —CONRaRb radical for which Ra and Rb are independently hydrogen, alkyl, cycloalkyl, phenyl, mono- or bicyclic aromatic heterocyclyl, or Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent and, when the additional heteroatom is S, the additional heteroatom optionally is sulfinyl or sulfonyl, or a methylene radical substituted with fluoro, hydroxyl, alkyloxy, alkylthio, cycloalkyloxy, cycloalkylthio, phenyl, mono- or bicyclic aromatic heterocyclyl, carboxyl, alkyloxycarbonyl, cycloalkyloxycarbonyl, —NRaRb or —CONRaRb for which Ra and Rb are defined as above, and are additionally chosen from phenoxy, heterocyclyloxy, benzyloxy, and heterocyclylmethyloxy, and, optionally, $R_1$ is difluoromethoxy, or a radical of structure $-C_mF_{2m+1}$, $-SC_mF_{2m+1}$, or $-OC_mF_{2m+1}$ wherein m is an integer from 1 to 6; and, optionally, $R'_5$ is trifluoroacetyl;

$R_2$ is:
carboxyl, alkyloxycarbonyl, cycloalkyloxycarbonyl, cyano, —CONRaRb, wherein
Ra and Rb are, independently, hydrogen, alkyl, cycloalkyl, phenyl, mono- or bicyclic aromatic heterocyclyl, and
optionally, one of Ra and Rb is hydroxyl, alkyloxy, or cycloalkyloxy, or
Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent and, when the additional heteroatom is S, the additional heteroatom optionally is sulfinyl or sulfonyl; or $R_2$ is hydroxymethyl, alkyl containing 1 or 2 carbon atoms substituted with carboxyl, alkyloxycarbonyl, cycloalkyloxycarbonyl, cyano, or —CONRaRb, wherein
Ra and Rb are, independently, hydrogen, alkyl, cycloalkyl, phenyl, mono- or bicyclic aromatic heterocyclyl, and
optionally one of Ra and Rb is hydroxyl, alkyloxy, or cycloalkyloxy, or
Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent, and, when the additional heteroatom is S, the additional heteroatom optionally is sulfinyl or sulfonyl; or R$_2$ is —CF$_2$—Rc, —C(CH$_3$)$_2$—Rc, —CO—Rc, —CHOH—Rc, —C(cycloalkyl)-Rc, or —CH═CH—Rc, wherein
Rc is carboxyl, alkyloxycarbonyl, cycloalkyloxycarbonyl, or —CONRaRb wherein Ra and Rb are, independently, hydrogen, alkyl, cycloalkyl, phenyl, mono- or bicyclic aromatic heterocyclyl, and optionally
one of Ra and Rb is hydroxyl, alkyloxy, or cycloalkyloxy, or
Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent, and, when the additional heteroatom is S, the additional heteroatom optionally is sulfinyl or sulfonyl;

R$_3$ is a phenyl, mono- or bicyclic aromatic heterocyclyl or alk-R°$_3$ radical, wherein
alk is an alkyl radical, and
R°$_3$ is hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)$_2$, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)$_2$, phenylalkyloxy, phenylalkylthio, phenylalkylsulfinyl, phenylalkylsulfonyl, phenylalkylamino, N-alkyl-N-phenylaminoalkyl, N-cycloalkyl-N-phenylalkylamino, benzoyl, mono- or bicyclic aromatic heterocyclyl, heterocyclyloxy, heterocyclylthio, heterocyclylsulfinyl, heterocyclylsulfonyl, heterocyclylamino, N-alkyl-N-heterocyclylamino, N-cycloalkyl-N-heterocyclylamino, heterocyclylcarbonyl, heterocyclylalkyloxy, heterocyclylalkylthio, heterocyclylalkylsulfinyl, heterocyclylalkylsulfonyl, heterocyclylalkylamino, N-alkyl-N-heterocyclylaminoalkyl, N-cycloalkyl-N-heterocyclylaminoalkyl, carboxyl, alkyloxycarbonyl, —NRaRb, or —CO—NRaRb, wherein Ra and Rb are, independently, hydrogen, alkyl, cycloalkyl, phenyl, mono- or bicyclic aromatic heterocyclyl, and optionally
one of Ra and Rb is hydroxyl, alkyloxy, or cycloalkyloxy, or
Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent, and, when the additional heteroatom is S, the additional heteroatom optionally is sulfinyl or sulfonyl, and
wherein any heterocyclyl mentioned above is mono- or bicyclic aromatic; or alternatively R°$_3$ is —CR'b═CR'c-R'a, wherein
R'a is phenyl, phenylalkyl, heterocyclyl, heterocyclylalkyl, phenoxyalkyl, phenylthioalkyl, phenylsulfinylalkyl, phenylsulfonylalkyl, phenylaminoalkyl, N-alkyl-N-phenylaminoalkyl, heterocyclyloxyalkyl, heterocyclylthioalkyl, heterocyclylsulfinylalkyl, heterocyclylsulfonylalkyl, heterocyclylaminoalkyl, N-alkyl-N-heterocyclylaminoalkyl, heterocyclylthio, heterocyclylsulfinyl, heterocyclylsulfonyl, phenylthio, phenylsulfinyl, or phenylsulfonyl,
wherein any heterocyclyl mentioned above is mono- or bicyclic aromatic, and
R'b and R'c are hydrogen, alkyl or cycloalkyl; or alternatively R°$_3$ is a radical —C≡C—Rd wherein
Rd is alkyl, phenyl, phenylalkyl, phenoxyalkyl, phenylthioalkyl, N-alkyl-N-phenylaminoalkyl, heterocyclyl, heterocyclylalkyl, heterocyclyloxyalkyl, heterocyclylthioalkyl, heterocyclylaminoalkyl, N-alkyl-N-heterocyclylaminoalkyl, wherein
any heterocyclyl mentioned above is mono- or bicyclic aromatic; or alternatively R°$_3$ is a —CF$_2$-phenyl, or mono- or bicyclic aromatic —CF$_2$-heterocyclyl radical;

Y is a radical >CH—Re, wherein
Re is hydrogen, fluoro, hydroxyl, alkyloxy, cycloalkyloxy, carboxyl, alkyloxycarbonyl, cycloalkyloxycarbonyl, —NRaRb or —CO—NRaRb, wherein Ra and Rb are, independently, hydrogen, alkyl, cycloalkyl, phenyl, mono- or bicyclic aromatic heterocyclyl, and optionally
one of Ra and Rb is hydroxyl, alkyloxy, or cycloalkyloxy, or
Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent, and, when the additional heteroatom is S, the additional heteroatom optionally is sulfinyl or sulfonyl,
or one of Ra and Rb is a hydrogen atom and the other is an alkyloxycarbonyl, acyl, cycloalkylcarbonyl, benzoyl or heterocyclylcarbonyl radical, wherein
any heterocyclyl portion is mono- or bicyclic aromatic; or alternatively Y is a difluoromethylene, carbonyl, hydroxyiminomethylene, alkyloxyiminomethylene, or cycloalkyloxyimino-methylene radical, or a 1,1-cycloalkylene radical containing 3 to 6 carbon atoms; and n is an integer from 0 to 4;
wherein any phenyl, benzyl, benzoyl or heterocyclyl radical or portion mentioned above are unsubstituted, or substituted on the ring with 1 to 4 substituents independently chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, phenyl, hydroxyalkyl, alkylthioalkyl, alkylsulfinylalkyl, alkylsulfonylalkyl, and —NRaRb wherein Ra and Rb are, independently, hydrogen, alkyl, cycloalkyl, phenyl, mono- or bicyclic aromatic heterocyclyl, and optionally one of Ra and Rb is hydroxyl, alkyloxy, or cycloalkyloxy, or Ra and Rb form, together with the nitrogen atom to which they are attached, a 5- or 6-membered heterocycle which can optionally contain an additional heteroatom chosen from O, S and N and, when the additional heteroatom is N, the additional heteroatom optionally is substituted with an alkyl, phenyl or mono- or bicyclic aromatic heterocyclyl substituent, and, when the additional heteroatom is S, the additional heteroatom optionally is sulfinyl or sulfonyl, or one of Ra and Rb is a hydrogen atom and the other is an alkyloxycarbonyl, acyl, cycloalkylcarbonyl, benzoyl or heterocyclylcarbonyl radical, wherein any heterocyclyl portion is mono- or bicyclic aromatic, wherein any alkyl or acyl radical or portion, unless otherwise indicated, comprises from 1 to 10 carbon atoms in a straight or branched chain, and any cycloalkyl radical comprises from 3 to 6 carbon atoms;

in any enantiomeric or diastereoisomeric form, in any syn or anti form, or any salt thereof.

2. A compound as claimed in claim 1, wherein $X_1$, $X_2$, $X_3$, $X_4$, and $X_5$ are, respectively, >C—$R'_1$ to >C—$R'_5$, or alternatively not more than one of them is a nitrogen atom;

$R_1$, $R'_1$, $R'_2$, $R'_3$, $R'_4$ and $R'_5$ are identical or different, and each is:
a hydrogen or halogen atom or an alkyl or alkyloxy radical, or is a methylene radical substituted with alkyloxy;

$R_2$ is carboxyl, alkyloxycarbonyl or —CONRaRb, wherein Ra is a hydrogen atom and Rb is a hydrogen atom or a hydroxyl radical; or $R_2$ is hydroxymethyl, alkyl containing 1 or 2 carbon atoms substituted with carboxyl, or alkyloxycarbonyl;

$R_3$ is a radical alk-$R°_3$ wherein
alk is an alkyl radical, and
$R°_3$ is hydrogen, cycloalkyl, cycloalkylthio, phenyl, phenoxy, phenylthio, phenylamino, heterocyclyloxy or heterocyclylthio, or alternatively
$R°_3$ is —CR'b=CR'c-R'a wherein R'a is phenyl, and wherein R'b and R'c are hydrogen;

Y is a radical >CH—Re, wherein
Re is hydrogen, fluoro, or hydroxyl;

n is an integer from 2 to 3;

wherein any phenyl or heterocyclyl radical or portion is unsubtituted, or is substituted on the ring with from 1 to 4 halogens, and wherein any alkyl or acyl radical or portion, unless otherwise indicated, comprises from 1 to 10 carbon atoms in a straight or branched chain, and any cycloalkyl radical comprises from 3 to 6 carbon atoms;

in any enantiomeric or diastereoisomeric form, in any syn or anti form, or any salt thereof, or mixture of any of the foregoing in any ratio.

3. 4-[3-(3-chloro-6-methoxyquinolin-4-yl)propyl]-1-[2-(thien-2-yl)thioethyl]piperidine-4-carboxylic acid, or any salt thereof.

4. 4-[3-(3-chloro-6-methoxyquinolin-4-yl)propyl]-1-[2-(3,5-difluorophenoxy)ethyl]piperidine-4-carboxylic acid, or any salt thereof.

5. 4-[3-(3-chloro-6-methoxyquinolin-4-yl)propyl]-1-(2-thiazol-2-thioethyl)piperidine-4-carboxylic acid, or any salt thereof.

6. 1-(2-cyclopentylthioethyl)-4-[3-(3-fluoro-6-methoxyquinolin-4-yl)propyl]piperidine-4-carboxylic acid, or any salt thereof.

7. 4-[3-(3-fluoro-6-methoxyquinolin-4-yl)propyl]-1-(3-phenylallyl)piperidine-4-carboxylic acid, or any salt thereof.

8. A process for preparing a compound as claimed in claim 1, comprising:

coupling a chain $R_3$ as defined in claim 1 with a compound of general formula (II):

(II)

wherein $X_1$, $X_2$, $X_3$, $X_4$, $X_5$, $R_1$, $R_2$, Y and n are as defined in claim 1;

optionally protecting $R_2$ when $R_2$ comprises a carboxyl or amino radical;

optionally removing said protection from $R_2$;

optionally separating any enantiomeric or diastereoisomeric form, any syn or anti form, or any salt thereof; and optionally converting a product obtained into a salt thereof.

9. A process as claimed in claim 8, wherein said coupling of a chain $R_3$ with a compound of general formula (II) occurs with a compound of general formula:

$$R_3—X$$

wherein $R_3$ is defined as above, and

X is a halogen atom, a methylsulfonyl radical, a trifluoromethylsulfonyl radical, or a p-toluenesulfonyl radical.

10. A process as claimed in claim 8, wherein
$R_3$ is a radical -alk-$R°_3$, wherein
alk is an alkyl radical, and
$R°_3$ is a radical —C≡C—Rd, wherein
Rd is phenyl, phenylalkyl, heterocyclyl or mono- or bicyclic aromatic heterocyclylalkyl;

comprising:
coupling an alkynyl halide, HC≡C-alk-X, wherein
alk is defined as above, and
X is a halogen atom; and
substituting the chain with a phenyl, phenylalkyl, heterocyclyl or heterocyclylalkyl radical.

11. A process as claimed in claim 9, wherein
$R_3$ is a radical -alk-$R°_3$, wherein
alk is an alkyl radical, and
$R°_3$ is a radical —C≡C—Rd, wherein
Rd is phenyl, phenylalkyl, heterocyclyl or mono- or bicyclic aromatic heterocyclylalkyl;

comprising:
  coupling an alkynyl halide, HC≡C-alk-X, wherein
    alk is defined as above, and
    X is a halogen atom; and
  substituting the chain with a phenyl, phenylalkyl, heterocyclyl or heterocyclylalkyl radical.

12. A process as claimed in claim 8, wherein:
  $R_3$ is a radical -alk-$R°_3$, wherein
    alk is an alkyl radical, and
    $R°_3$ is a phenoxy, phenylthio, phenylamino, heterocyclyloxy, heterocyclylthio or heterocyclylamino radical in which the heterocyclyl portion is aromatic;
comprising constructing the chain stepwise by:
  condensing a chain HO-alk-X wherein
    X is a halogen atom;
  obtaining a hydroxyalkyl chain;
  converting the hydroxyalkyl chain into a haloalkyl, methanesulfonylalkyl, or p-toluenesulfonylalkyl chain by known methods; and
  reacting the chain in basic medium with an aromatic derivative of structure Ar—ZH, wherein
    Ar is a phenyl or aromatic heterocyclyl radical, and
    Z is a sulfur, oxygen, or nitrogen atom.

13. A process as claimed in claim 9, wherein:
  $R_3$ is a radical -alk-$R°_3$, wherein
    alk is an alkyl radical, and
    $R°_3$ is a phenoxy, phenylthio, phenylamino, heterocyclyloxy, heterocyclylthio or heterocyclylamino radical in which the heterocyclyl portion is aromatic,
comprising constructing the chain stepwise by:
  condensing a chain HO-alk-X wherein
    X is a halogen atom;
  obtaining a hydroxyalkyl chain;
  converting the hydroxyalkyl chain into a haloalkyl, methanesulfonylalkyl, or p-toluenesulfonylalkyl chain by known methods; and
  reacting the chain in basic medium with an aromatic derivative of structure Ar—ZH, wherein
    Ar is a phenyl or aromatic heterocyclyl radical, and
    Z is a sulfur, oxygen, or nitrogen atom.

14. A pharmaceutical composition, comprising at least one compound according to claim 1, and one or more pharmaceutically acceptable adjuvants, diluents, or a mixture thereof.

15. A pharmaceutical composition, comprising at least one compound according to claim 3, and one or more pharmaceutically acceptable adjuvants, diluents, or a mixture thereof.

16. A pharmaceutical composition, comprising at least one compound according to claim 4, and one or more pharmaceutically acceptable adjuvants, diluents, or a mixture thereof.

17. A pharmaceutical composition, comprising at least one compound according to claim 5, and one or more pharmaceutically acceptable adjuvants, diluents, or a mixture thereof.

18. A pharmaceutical composition, comprising at least one compound according to claim 6, and one or more pharmaceutically acceptable adjuvants, diluents, or a mixture thereof.

19. A pharmaceutical composition, comprising at least one compound according to claim 7, and one or more pharmaceutically acceptable adjuvants, diluents, or a mixture thereof.

20. A composition comprising at least one compound of general formula (I) as claimed in claim 1, wherein the at least one compound is present as one or more enantiomeric forms, diastereoisomeric forms, syn forms, anti forms, or salts, or as a mixture of any of the foregoing.

* * * * *

UNITED STATES PATENT AND TRADEMARK OFFICE
CERTIFICATE OF CORRECTION

PATENT NO.   : 6,603,005 B2
DATED        : August 5, 2003
INVENTOR(S)  : Eric Bacqué et al.

It is certified that error appears in the above-identified patent and that said Letters Patent is hereby corrected as shown below:

Title page,
Item [75], Inventor, "Eric Baque", should read -- Eric Bacqué --.

Column 242,
Line 10, "cycloalkylthio" should read -- cycloalkylthio, --.

Signed and Sealed this

Twenty-first Day of October, 2003

JAMES E. ROGAN
*Director of the United States Patent and Trademark Office*